(12) United States Patent
Tamashima

(10) Patent No.: US 10,980,233 B2
(45) Date of Patent: Apr. 20, 2021

(54) OXADIAZOLE COMPOUND AND USE THEREOF AS PESTICIDES

(71) Applicant: Sumitomo Chemical Company, Limited, Tokyo (JP)

(72) Inventor: Hiroto Tamashima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/320,290

(22) PCT Filed: Aug. 9, 2017

(86) PCT No.: PCT/JP2017/028909
§ 371 (c)(1),
(2) Date: Jan. 24, 2019

(87) PCT Pub. No.: WO2018/030460
PCT Pub. Date: Feb. 15, 2018

(65) Prior Publication Data
US 2019/0230928 A1 Aug. 1, 2019

(30) Foreign Application Priority Data

Aug. 10, 2016 (JP) .............................. JP2016-157277

(51) Int. Cl.
| | | |
|---|---|---|
| *C07D 271/06* | (2006.01) | |
| *C07D 401/14* | (2006.01) | |
| *C07D 401/04* | (2006.01) | |
| *C07D 413/12* | (2006.01) | |
| *A01N 43/82* | (2006.01) | |

(52) U.S. Cl.
CPC ........... *A01N 43/82* (2013.01); *C07D 271/06* (2013.01); *C07D 401/04* (2013.01); *C07D 401/14* (2013.01); *C07D 413/12* (2013.01)

(58) Field of Classification Search
CPC .... A01N 43/82; C07D 271/06; C07D 401/04; C07D 401/15; C07D 413/12
See application file for complete search history.

(56) References Cited

U.S. PATENT DOCUMENTS

| | | |
|---|---|---|
| 6,271,226 B1 | 8/2001 | Kruger et al. |
| 10,653,146 B2 * | 5/2020 | Hoffman ................. A01N 43/82 |
| 2009/0221596 A1 | 9/2009 | Escher et al. |
| 2017/0144980 A1 | 5/2017 | Wieja et al. |
| 2018/0273494 A1 * | 9/2018 | Stierli .................. C07D 413/12 |
| 2018/0370927 A1 | 12/2018 | Hoffman et al. |

FOREIGN PATENT DOCUMENTS

| | | |
|---|---|---|
| DE | 19642864 A1 | 4/1998 |
| DE | 102005022384 A1 | 1/2007 |
| JP | 63-162680 A | 7/1988 |
| WO | 2000/32582 A1 | 6/2000 |
| WO | 2015/185485 A1 | 12/2015 |
| WO | 2017/109044 A1 | 6/2017 |

OTHER PUBLICATIONS

Int'l Preliminary Report on Patentability dated Feb. 12, 2019 in Int'l Application No. PCT/JP2017/028909.
Int'l Search Report dated Oct. 23, 2017 in Int'l Application No. PCT/JP2017/028909.

* cited by examiner

*Primary Examiner* — Rebecca L Anderson
(74) *Attorney, Agent, or Firm* — Panitch Schwarze Belisario & Nadel LLP

(57) ABSTRACT

Provided is a compound having excellent control efficacies against pests. Specifically, a compound represented by formula (I) is provided:

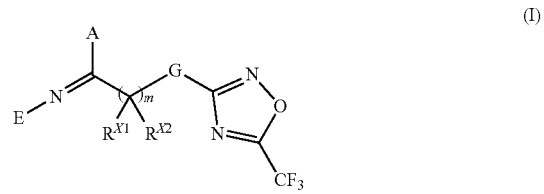

(I)

In the compound represented by formula (I), G represents a benzene ring or pyridine ring, etc.; A represents a hydrogen atom or a C1-C6 alkyl group, etc.; m represents 0, 1, 2, or 3; $R^{X1}$ represents a hydrogen atom, etc.; $R^{X2}$ represents a hydrogen atom, etc.; E represents a $OR^3$, etc.; and $R^3$ represents a hydrogen atom or a C1-C6 alkyl group, etc. The compound represented by formula (I) has excellent control efficacies against pests.

9 Claims, No Drawings

OXADIAZOLE COMPOUND AND USE THEREOF AS PESTICIDES

CROSS-REFERENCE TO RELATED APPLICATION

This application is a Section 371 of International Application No. PCT/JP2017/028909, filed Aug. 9, 2017, which was published in the English language on Feb. 15, 2018 under International Publication No. WO 2018/030460 A1, which claims priority under 35 U.S.C. § 119(b) to Japanese Application No. 2016-157277, filed Aug. 10, 2016, and the disclosures of which are incorporated herein by reference.

TECHNICAL FIELD

The present invention relates to an oxadiazole compound and use thereof.

BACKGROUND ART

Patent Literature 1 discloses a compound represented by the following formula as a synthetic intermediate compound of a medical use compound.

[Chem.1]

CITATION LIST

Patent Literature

PTL 1: WO 2000/032582 pamphlet

SUMMARY OF INVENTION

Technical Problem

An object of the present invention is to provide a compound having excellent control efficacies against pests.

Solution to Problem

The present inventor has studied to find out a compound having excellent control efficacies against pests. As a result, he has found out that a compound represented by the following formula (I) has excellent control efficacies against pests.

That is, the present invention provides the followings:
(1) A compound represented by formula (I):

[Chem.2]

(I)

(wherein:
G represents a benzene ring, a thiophene ring, a furan ring, a pyrazole ring, an imidazole ring, an oxazole ring, an isoxazole ring, a thiazole ring, an oxadiazole ring, a thiadiazole ring, a pyridine ring, a pyrazine ring, a pyrimidine ring, or a pyridazine ring (wherein said benzene ring, said thiophene ring, said furan ring, said pyrazole ring, said imidazole ring, said oxazole ring, said isoxazole ring, said thiazole ring, said pyridine ring, said pyrazine ring, said pyrimidine ring, and said pyridazine ring may optionally have one or more substituents selected from Group A);
A represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, a C1-C6 alkoxy group optionally having one or more substituents selected from Group C, a C1-C6 alkylthio group optionally having one or more substituents selected from Group C, a C1-C6 alkylsulfinyl group optionally having one or more substituents selected from Group C, a C1-C6 alkylsulfonyl group optionally having one or more substituents selected from Group C, a cyano group, or a $NR^1R^2$;
m represents 0, 1, 2, or 3;
$R^{X1}$ and $R^{X2}$ represent each independently a hydrogen atom, a halogen atom, a cyano group, a C1-C6 chain hydrocarbon group optionally having one or more substituents selected from Group B, a C1-C6 alkoxy group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, or a C3-C6 cycloalkyl group optionally having one or more substituents selected from Group C, wherein when m represents 2 or 3, two or more Rx and $R^{X2}$ may be identical to or different from each other;
E represents a $OR^3$, a $OC(O)R^4$, a $OC(X^1)NR^5R^6$, a $OC(X^2)OR^7$, a $OS(O)_2R^8$, a $NR^9R^{10}$ or a $S(O)_nR^{11}$;
n represents 1 or 2;
$R^1$, $R^5$, and $R^9$ represent each independently a hydrogen atom or a C1-C6 chain hydrocarbon group optionally having one or more substituents selected from Group B;
$R^2$ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, or a C1-C6 alkoxy group optionally having one or more substituents selected from Group C;

$R^3$, $R^6$, and $R^{10}$ represent each independently a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, or a C6-C10 aryl group optionally having one or more substituents selected from Group G;

$R^4$, $R^7$, $R^8$, and $R^{11}$ represent each independently a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, or a C6-C10 aryl group optionally having one or more substituents selected from Group G;

$R^1$ and $R^2$ may be combined with the nitrogen atom to which $R^1$ and $R^2$ are attached to form a 4 to 7 membered nonaromatic heterocyclic group (wherein said 4 to 7 membered nonaromatic heterocyclic group may optionally have one or more substituents selected from Group C);

$R^5$ and $R^6$ may be combined with the nitrogen atom to which $R^5$ and $R^6$ are attached to form a 4 to 7 membered nonaromatic heterocyclic group (wherein said 4 to 7 membered nonaromatic heterocyclic group may optionally have one or more substituents selected from Group C);

$R^9$ and $R^{10}$ may be combined with the nitrogen atom to which $R^9$ and $R^{10}$ are attached to form a 4 to 7 membered nonaromatic heterocyclic group (wherein said 4 to 7 membered nonaromatic heterocyclic group may optionally have one or more substituents selected from Group C);

$X^1$ and $X^2$ represent each independently an oxygen atom or a sulfur atom;

Group A: a group consisting of a C1-C6 alkyl group optionally having one or more substituents selected from Group D, a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a C1-C6 alkylsulfonyloxy group optionally having one or more halogen atoms, a halogen atom, a cyano group, and a nitro group;

Group B: a group consisting of a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, a C6-C10 aryl group optionally having one or more substituents selected from Group H, a $OR^{12}$, a $S(X^3)_tR^{13}$, a $C(X^4)R^{14}$, a $C(X^5)OR^{15}$, a $OC(X^6)R^{16}$, a $C(X^7)NR^{17}R^{18}$, a $S(X^8)_tNR^{19}R^{20}$, a $SC(O)R^{21}$, a $NR^{22}R^{23}$, a $NR^{24}C(X^9)R^{25}$, a $NR^{26}S(X^{10})_tR^{27}$, a $NR^{28}C(X^{11})OR^{29}$, a $OC(X^{12})NR^{30}R^{31}$, a $NR^{32}C(X^{13})NR^{33}R^{34}$, a $OC(X^{14})OR^{35}$, a $SC(X^{15})OR^{36}$, a $NC(O)R^{37}$, a $NC(O)OR^{38}$, a $NR^{39}$, a $NOR^{40}$, a $NR^{41}NR^{42}R^{43}$, a $NNR^{44}R^{45}$, a NCN, a $NNO_2$, an oxo group, a thioxo group, a halogen atom, a cyano group, a nitro group, a sulfanyl group, and a carboxy group;

Group C: a group consisting of a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, a C6-C10 aryl group optionally having one or more substituents selected from Group H, a $OR^{12}$, a $S(X^3)_tR^{13}$, a $C(X^4)R^{14}$, a $C(X^5)OR^{15}$, a $OC(X^6)R^{16}$, a $C(X^7)NR^{17}R^{18}$, a $S(X^8)_t$ $NR^{19}R^{20}$, a $SC(O)R^{21}$, a $NR^{22}R^{23}$, a $NR^{24}$ $C(X^9)R^{25}$, a $NR^{26}S(X^{10})_tR^{27}$, a $NR^{28}C(X^{11})OR^{29}$, a $OC(X^{12})NR^{30}R^{31}$, a $NR^{32}C(X^{13})NR^{33}R^{34}$, a $OC(X^{14})OR^{35}$, a $SC(X^{15})OR^{36}$, a $NC(O)R^{37}$, a $NC(O)OR^{38}$, a $NR^{39}$, a $NOR^{40}$, a $NR^{41}$ $NR^{42}R^{43}$, a $NNR^{44}R^{45}$, a NCN, a $NNO_2$, an oxo group, a thioxo group, a halogen atom, a cyano group, a nitro group, a sulfanyl group, and a carboxy group;

Group D: a group consisting of a halogen atom, a cyano group, a nitro group, and a C1-C6 alkoxy group optionally having one or more halogen atoms;

Group E: a group consisting of a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a halogen atom, an oxo group, a thioxo group, a cyano group, a nitro group, a hydroxy group, an amino group, a sulfanyl group, and a carboxy group;

Group F: a group consisting of a C1-C3 chain hydrocarbon group optionally having one or more halogen atoms, a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a halogen atom, an oxo group, a thioxo group, a cyano group, a nitro group, a hydroxy group, an amino group, a sulfanyl group, and a carboxy group;

Group G: a group consisting of a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, a C6-C10 aryl group optionally having one or more substituents selected from Group H, a $OR^{12}$, a $S(X^3)_tR^{13}$, a $C(X^4)R^{14}$, a $C(X^5)OR^{15}$, a $OC(X^6)R^6$, a $C(X^7)NR^{17}R^{18}$, a $S(X^8)_t$ $NR^{19}R^{20}$, a $SC(O)R^{21}$, a $NR^{22}R^{23}$, a $NR^{24}$ $C(X^9)R^{25}$, a $NR^{26}S(X^{10})_tR^{27}$, a $NR^{28}C(X^{11})OR^{29}$, a $OC(X^{12})NR^{30}R^{31}$, a $NR^{32}C(X^{13})NR^{33}R^{34}$, a $OC(X^{14})OR^{35}$, a $SC(X^{15})OR^{36}$, a $NC(O)R^{37}$, a $NC(O)OR^{38}$, a $NR^{39}$, a $NOR^{40}$, a $NR^{41}$ $NR^{42}R^{43}$, a $NNR^{44}R^{45}$, a NCN, a $NNO_2$, a halogen atom, a cyano group, a nitro group, a sulfanyl group, and a carboxy group;

Group H: a group consisting of a C1-C3 chain hydrocarbon group optionally having one or more halogen atoms, a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a halogen atom, a cyano group, a nitro group, a hydroxy group, an amino group, a sulfanyl group, and a carboxy group;

$R^{12}$, $R^{17}$, $R^{18}$, $R^{19}$, $R^{20}$, $R^{22}$, $R^{23}$, $R^{24}$, $R^{26}$, $R^{28}$, $R^{30}$, $R^{31}$, $R^{32}$, $R^{33}$, $R^{34}$, and $R^{40}$ represent each independently a hydrogen atom, a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, or a C6-C10 aryl group optionally having one or more substituents selected from Group H;

$R^{13}$, $R^{14}$, $R^{15}$, $R^{16}$, $R^{21}$, $R^{25}$, $R^{27}$, $R^{29}$, $R^{35}$, and $R^{36}$ represent each independently a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, or a C6-C10 aryl group optionally having one or more substituents selected from Group H;

$R^{37}$, $R^{38}$, and $R^{39}$ represent each independently a C1-C6 chain hydrocarbon group optionally having one or more substituents selected from Group E or a C3-C6 cycloalkyl group optionally having one or more substituents selected from Group F;

$R^{41}$, $R^{42}$, $R^{43}$, $R^{44}$, and $R^{45}$ represent each independently a hydrogen atom, a C1-C6 chain hydrocarbon group optionally having one or more substituents selected from Group E, or a C3-C6 cycloalkyl group optionally having one or more substituents selected from Group F;

t represents 0, 1, or 2;

$X^4$, $X^5$, $X^6$, $X^7$, $X^9$, $X^{11}$, $X^{12}$, $X^{13}$, $X^{14}$, and $X^{15}$ represent each independently an oxygen atom or a sulfur atom;

$X^3$, $X^8$, and $X^{10}$ represent each independently an oxygen atom, a NCN, a $NNO_2$, a $NC(O)R^{46}$, a $NC(O)OR^{47}$, or a $NR^{48}$, wherein when t represents 2, two $X^3$, two $X^8$, and two $X^{10}$ may be identical to or different from each other;

$R^{47}$ represents a C1-C3 chain hydrocarbon group optionally having one or more halogen atoms;

$R^{46}$ and $R^{48}$ represent each independently a hydrogen atom or a C1-C3 chain hydrocarbon group optionally having one or more halogen atoms;

$R^{17}$ and $R^{18}$ may be combined with the nitrogen atom to which $R^{17}$ and $R^{18}$ are attached to form a 4 to 7 membered nonaromatic heterocyclic group (wherein said 4 to 7 membered nonaromatic heterocyclic group may optionally have one or more substituents selected from Group F);

$R^{19}$ and $R^{20}$ may be combined with the nitrogen atom to which $R^{19}$ and $R^{20}$ are attached to form a 4 to 7 membered nonaromatic heterocyclic group (wherein said 4 to 7 membered nonaromatic heterocyclic group may optionally have one or more substituents selected from Group F);

$R^{22}$ and $R^{23}$ may be combined with the nitrogen atom to which $R^{22}$ and $R^{23}$ are attached to form a 4 to 7 membered nonaromatic heterocyclic group (wherein said 4 to 7 membered nonaromatic heterocyclic group may optionally have one or more substituents selected from Group F);

$R^{30}$ and $R^{31}$ may be combined with the nitrogen atom to which $R^{30}$ and $R^{31}$ are attached to form a 4 to 7 membered nonaromatic heterocyclic group (wherein said 4 to 7 membered nonaromatic heterocyclic group may optionally have one or more substituents selected from Group F);

$R^{33}$ and $R^{34}$ may be combined with the nitrogen atom to which $R^{33}$ and $R^{34}$ are attached to form a 4 to 7 membered nonaromatic heterocyclic group (wherein said 4 to 7 membered nonaromatic heterocyclic group may optionally have one or more substituents selected from Group F);

$R^{42}$ and $R^{43}$ may be combined with the nitrogen atom to which $R^{42}$ and $R^{43}$ are attached to form a 4 to 7 membered nonaromatic heterocyclic group (wherein said 4 to 7 membered nonaromatic heterocyclic group may optionally have one or more substituents selected from Group F); and $R^{44}$ and $R^{45}$ may be combined with the nitrogen atom to which $R^{44}$ and $R^{45}$ are attached to form a 4 to 7 membered nonaromatic heterocyclic group (wherein said 4 to 7 membered nonaromatic heterocyclic group may optionally have one or more substituents selected from Group F)) (hereinafter referred to as "compound of the present invention" or "Present compound").

(2) The compound according to (1), wherein
G represents a benzene ring;
$(CR^{X1}R^{X2})_m C(A)=N-E$ is attached to G at the meta position or the para position relative to the oxadiazole ring;
m represents 0 or 1;
$R^{X1}$ and $R^{X2}$ represent each independently a hydrogen atom; and
A represents a hydrogen atom, a C1-C6 alkyl group, a phenyl group, a C1-C6 alkoxy group, a C1-C6 alkylthio group, a cyano group, an amino group, a C1-C6 alkylamino group, a di(C1-C6 alkyl)amino group, or a 5 to 6 membered nonaromatic heterocyclic group.

(3) The compound according to (1), wherein
G represents a benzene ring optionally having one or more substituents selected from the group consisting of a fluorine atom and a methyl group;
$(CR^{X1}R^{X2})_m C(A)=N-E$ is attached to G at the meta position or the para position relative to the oxadiazole ring;
m represents 0; and
A represents a hydrogen atom, a C1-C6 alkyl group, a C3-C6 cycloalkyl group, a phenyl group, a C1-C6 alkoxy group, a C1-C6 alkylthio group, a cyano group, an amino group, a C1-C6 alkylamino group, or a di(C1-C6 alkyl)amino group.

(4) The compound according to (3), wherein
G represents a benzene ring;
$(CR^{X1}R^{X2})_m C(A)=N-E$ is attached to G at the para position relative to the oxadiazole ring; and
A represents a hydrogen atom, a methyl group, a methoxy group, a methylthio group, a cyano group, an amino group, a methylamino group, or a dimethylamino group.

(5) The compound according to (4), wherein A represents a hydrogen atom, a methoxy group, a cyano group, an amino group, a methylamino group, or a dimethylamino group.

(6) The compound according to any one of (1) to (5), wherein
E represents a $OR^3$, a $OC(O)R^4$, a $OC(X^1)NR^5R^6$, or a $OS(O)_2R^8$;
$R^3$ represents a hydrogen atom or a C1-C6 chain hydrocarbon group optionally having one or more substituents selected from Group D;

R⁴ represents a C1-C6 alkyl group optionally having one or more substituents selected from Group D, a phenyl group optionally having one or more substituents selected from Group D, or a 5 to 6 membered aromatic heterocyclic group optionally having one or more substituents selected from Group D;
R⁵ represents a hydrogen atom or a C1-C6 alkyl group optionally having one or more substituents selected from Group D;
R⁶ represents a phenyl group or a C1-C6 alkyl group optionally having one or more substituents selected from Group D;
R⁸ represents a C1-C6 alkyl group optionally having one or more substituents selected from Group D; and
X¹ represents an oxygen atom.
(7) The compound according to any one of (1) to (5), wherein
E represents a OR³, a OC(O)R⁴, or a OC(X¹)NR⁵R⁶;
R³ represents a C1-C6 chain hydrocarbon group optionally having one or more substituents selected from the group consisting of a cyano group and a C1-C6 alkoxy group, or a hydrogen atom;
R⁴ represents a C1-C6 alkyl group;
R⁵ and R⁶ represent each independently a C1-C6 alkyl group; and
X¹ represents an oxygen atom.
(8) An agent for controlling a pest comprising the compound according to any one of (1) to (7) (hereinafter also referred to as "control agent of the present invention").
(9) A method for controlling a pest, the method comprising applying an effective amount of the compound according to any one of (1) to (7) to a plant or a soil.
(10) Use of the compound according to any one of (1) to (7) for controlling a pest.

Advantageous Effects of Invention

The present invention can control pests.

DESCRIPTION OF EMBODIMENTS

The substituent(s) as described herein is/are explained as follows.
In the present description, when a substituent "optionally having one or more halogen atoms" has two or more halogen atoms, these halogen atoms may be identical to or different from each other.
The expression of "optionally having one or more substituents selected from Group X" (wherein "X" is any one of A to H) as described herein represents that when two or more substituents selected from Group X are present, these substituents may be identical to or different from each other.
The expression of "CX—CY" as described herein means that the number of carbon atom is X to Y. For example, the expression of "C1-C6" means that the number of carbon atom is 1 to 6.
The term of "halogen atom" represents fluorine atom, chlorine atom, bromine atom, or iodine atom.
Examples of "chain hydrocarbon group" include alkyl group, alkenyl group, and alkynyl group.
Examples of "alkyl group" include methyl group, ethyl group, n-propyl group, isopropyl group, 1,1-dimethylpropyl group, 1,2-dimethylpropyl group, 1-ethylpropyl group, n-butyl group, isobutyl group, tert-butyl group, pentyl group, and hexyl group.
Examples of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group.
Examples of "alkynyl group" include ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.
The term of "C3-C6 cycloalkyl group" represents cyclopropyl group, cyclobutyl group, cyclopentyl group, or cyclohexyl group.
The term of "C6-C10 aryl group" represents phenyl group or naphthyl group.
Examples of "3 to 8 membered nonaromatic heterocyclic group" include aziridinyl group, azetidinyl group, pyrrolidinyl group, piperidyl group, azepanyl group, azacy-clooctyl group, pyrazolidinyl group, imidazolidinyl group, oxazolidinyl group, thia-zolidinyl group, isoxazolidinyl group, morpholinyl group, thiomorpholinyl group, 1,2-oxazinyl group, 1,3-oxazinyl group, 1,3-thiazinyl group, piperazinyl group, tetrahydropyridazinyl group, hexahydropyridazinyl group, tetrahydropyrimidinyl group, hexahydropyrimidinyl group, and 1,4-thiazepanyl group.
Examples of "5 to 6 membered aromatic heterocyclic group" include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, thiadiazolyl group, pyridyl group, pyridazinyl group, pyrimidinyl group, and pyrazinyl group.
Examples of "C1-C6 alkylamino group" include methylamino group, ethylamino group, and hexylamino group.
Examples of "di(C1-C6 alkyl)amino group" include dimethylamino group, ethyl-methylamino group, diethylamino group, and dihexylamino group.
Examples of "C1-C6 alkylamino group optionally having one or more substituents selected from Group D" include methylamino group, 2,2,2-trifluoroethylamino group, 3-methoxypropylamino group, and 6-cyanohexylamino group.
Examples of "di(C1-C6 alkyl)amino group optionally having one or more substituents selected from Group D" include dimethylamino group, ethyltrifluo-romethylamino group, and dihexylamino group.
A compound wherein:
G represents a benzene ring, a pyridine ring, a pyrazine ring, a pyrimidine ring, or a pyridazine ring; and
(CR$^{X1}$R$^{X2}$)$_m$C(A)=N-E is attached to G at the meta position relative to the oxadiazole ring
is the compound represented by any one of the following formula (S-1) to formula (S-10).

[Chem. 3]

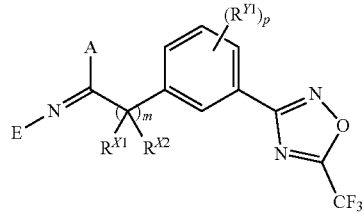

(S-1)

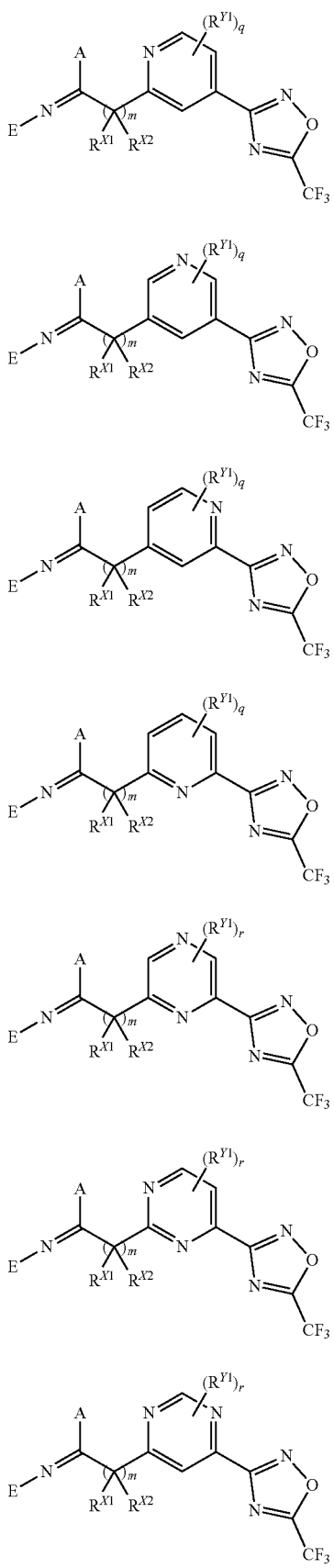

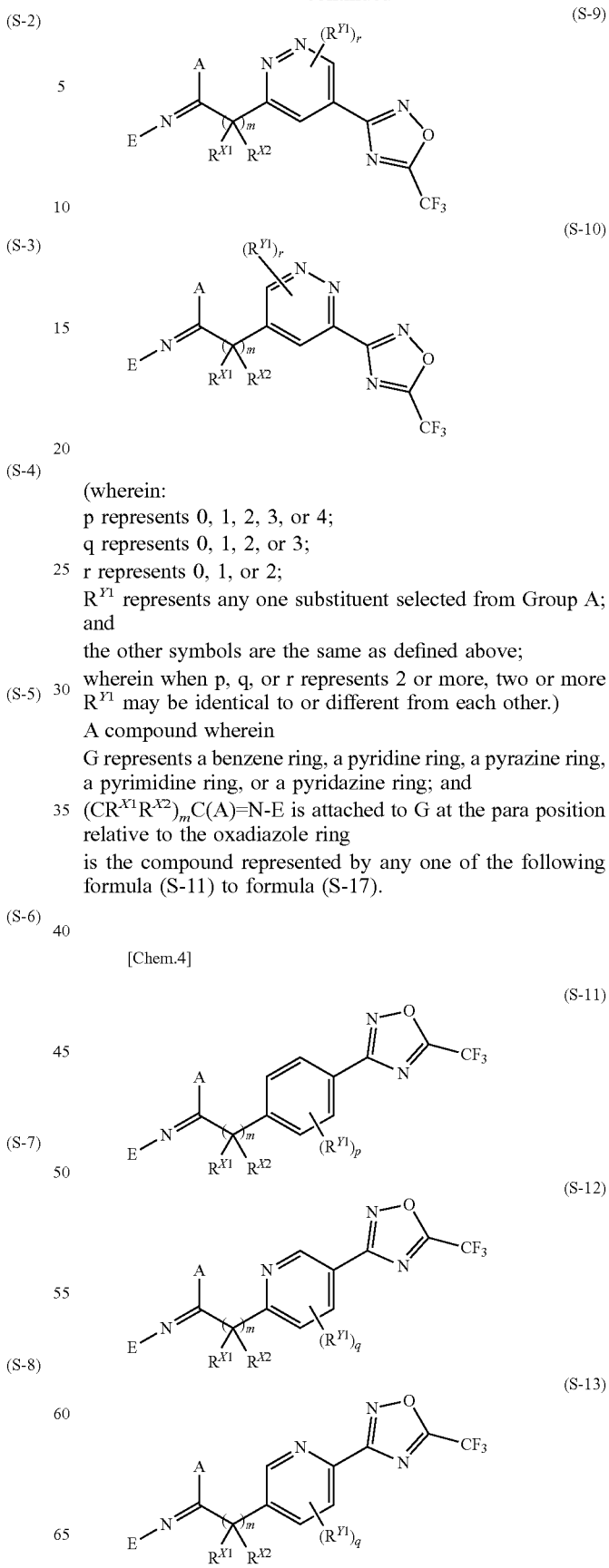

(wherein:
p represents 0, 1, 2, 3, or 4;
q represents 0, 1, 2, or 3;
r represents 0, 1, or 2;
$R^{Y1}$ represents any one substituent selected from Group A; and
the other symbols are the same as defined above;
wherein when p, q, or r represents 2 or more, two or more $R^{Y1}$ may be identical to or different from each other.)

A compound wherein
G represents a benzene ring, a pyridine ring, a pyrazine ring, a pyrimidine ring, or a pyridazine ring; and
$(CR^{X1}R^{X2})_m C(A)=N\text{-}E$ is attached to G at the para position relative to the oxadiazole ring
is the compound represented by any one of the following formula (S-11) to formula (S-17).

[Chem.4]

-continued

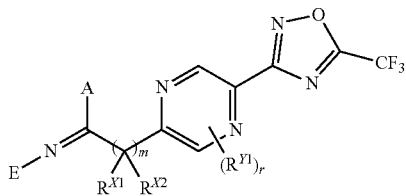
(S-14)

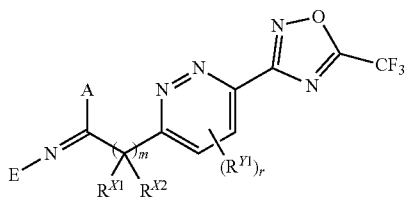
(S-15)

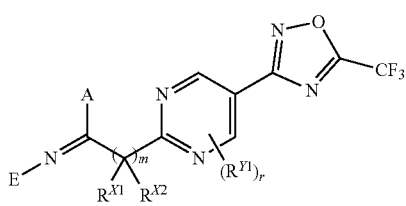
(S-16)

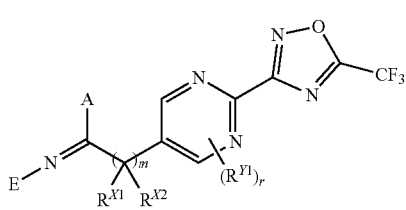
(S-17)

(wherein the symbols are the same as defined above;
wherein when p, q, or r represents 2 or more, two or more $R^{Y1}$ may be identical to or different from each other.)

When the compound of the present invention has one or more asymmetric centers, the compound of the present invention includes optical isomers each singly and any mixture composed of these isomers each in an arbitrary ratio of the respective isomer. Further, the compound of the present invention also includes two or more geometric isomers derived from carbon-carbon double bond or carbon-nitrogen double bond, and any mixture composed of these isomers each in an arbitrary ratio of the respective isomer.

The compound of the present invention may form an acid addition salt such as hydrochloride, sulfate, nitrate, phosphate, acetate, and benzoate by mixing the compound with an acid such as hydrochloric acid, sulfuric acid, nitric acid, phosphoric acid, acetic acid, and benzoic acid.

Embodiments of the compound of the present invention include the following compounds.

Embodiment 1

The compound of the present invention, wherein

G represents a pyridine ring, or a benzene ring optionally having one or more substituents selected from the group consisting of a fluorine atom and a methyl group; and $(CR^{X1}R^{X2})_m C(A)=N-E$ is attached to G at the meta position or the para position relative to the oxadiazole ring.

Embodiment 2

The compound of the present invention, wherein

G represents a pyridine ring, or a benzene ring optionally having one or more substituents selected from the group consisting of a fluorine atom and a methyl group; and $(CR^{X1}R^{X2})_m C(A)=N-E$ is attached to G at the para position relative to the oxadiazole ring.

Embodiment 3

The compound of the present invention, wherein
G represents a benzene ring or a pyridine ring; and
$(CR^{X1}R^{X2})_m C(A)=N-E$ is attached to G at the meta position or the para position relative to the oxadiazole ring.

Embodiment 4

The compound of the present invention, wherein
G represents a benzene ring or a pyridine ring; and
$(CR^{X1}R^{X2})_m C(A)=N-E$ is attached to G at the para position relative to the oxadiazole ring.

Embodiment 5

The compound of the present invention, wherein
G represents a benzene ring optionally having one or more substituents selected from the group consisting of a fluorine atom and a methyl group; and
$(CR^{X1}R^{X2})_m C(A)=N-E$ is attached to G at the meta position or the para position relative to the oxadiazole ring.

Embodiment 6

The compound of the present invention, wherein
G represents a benzene ring optionally having one or more substituents selected from the group consisting of a fluorine atom and a methyl group; and
$(CR^{X1}R^{X2})_m C(A)=N-E$ is attached to G at the para position relative to the oxadiazole ring.

Embodiment 7

The compound of the present invention, wherein
G represents a benzene ring; and
$(CR^{X1}R^{X2})_m C(A)=N-E$ is attached to G at the meta position or the para position relative to the oxadiazole ring.

Embodiment 8

The compound of the present invention, wherein
G represents a benzene ring; and
$(CR^{X1}R^{X2})_m C(A)=N-E$ is attached to G at the para position relative to the oxadiazole ring.

Embodiment 9

The compound of the present invention, wherein
A represents a hydrogen atom, a C1-C6 alkyl group optionally having one or more substituents selected from Group D, a C3-C6 cycloalkyl group optionally having one or more substituents selected from Group D, a phenyl group optionally having one or more substituents selected from Group D, a C1-C6 alkoxy group optionally having one or more substituents selected from Group D, a C1-C6 alkylthio group optionally having one or more substituents selected from Group D, a C1-C6 alkylsulfinyl group optionally having one or more substituents selected from Group D, a C1-C6 alkylsulfonyl group optionally having one or more substituents selected from Group D, a cyano group, an amino group, a pyrrolidinyl group, a piperidyl group, a morpholinyl group, a C1-C6 alkylamino group optionally having one or more substituents selected from Group D, or a di(C1-C6 alkyl)amino group optionally having one or more substituents selected from Group D.

Embodiment 10

The compound of the present invention, wherein
A represents a hydrogen atom, a methyl group, a methoxy group, a methylthio group, a cyano group, an amino group, a methylamino group, or a dimethylamino group.

Embodiment 11

The compound of the present invention, wherein
A represents a hydrogen atom, a methoxy group, a cyano group, an amino group, a methylamino group, or a dimethylamino group.

Embodiment 12

The compound of the present invention, wherein A represents a hydrogen atom.

Embodiment 13

The compound of the present invention, wherein A represents a cyano group.

Embodiment 14

The compound of the present invention, wherein A represents an amino group.

Embodiment 15

The compound of the present invention, wherein A represents a methylamino group.

Embodiment 16

The compound of the present invention, wherein A represents a dimethylamino group.

Embodiment 17

The compound of the present invention, wherein
E represents a $OR^3$, a $OC(O)R^4$, a $OC(X^1)NR^5R^6$, or a $OS(O)_2R^8$.

Embodiment 18

The compound of the present invention, wherein E represents a $OR^3$, a $OC(O)R^4$, or a $OC(X^1)NR^5R^6$.

Embodiment 19

The compound of the present invention, wherein E represents a $OR^3$.

Embodiment 20

The compound of the present invention, wherein E represents a $OC(O)R^4$.

Embodiment 21

The compound of the present invention, wherein E represents a $OC(X^1)NR^5R^6$.

Embodiment 22

The compound of the present invention, wherein
E represents a $OR^3$, a $OC(O)R^4$, a $OC(X^1)NR^5R^6$, or a $OS(O)_2R^8$;
$R^4$ and $R^5$ represent each independently a C1-C6 chain hydrocarbon group optionally having one or more substituents selected from Group B; and
$R^3$, $R^5$, and $R^6$ represent each independently a hydrogen atom, or a C1-C6 chain hydrocarbon group optionally having one or more substituents selected from Group B.

Embodiment 23

The compound of the present invention, wherein
E represents a $OR^3$, a $OC(O)R^4$, or a $OC(X^1)NR^5R^6$;
$R^4$ represents a C1-C6 chain hydrocarbon group optionally having one or more substituents selected from Group B; and
$R^3$, $R^5$, and $R^6$ represent each independently a hydrogen atom, or a C1-C6 chain hydrocarbon group optionally having one or more substituents selected from Group B.

Embodiment 24

The compound of the present invention, wherein
E represents a $OR^3$; and
$R^3$ represents a hydrogen atom, or a C1-C6 chain hydrocarbon group optionally having one or more substituents selected from Group B.

Embodiment 25

The compound of the present invention, wherein
E represents a $OC(O)R^4$; and
$R^4$ represents a C1-C6 chain hydrocarbon group optionally having one or more substituents selected from Group B.

Embodiment 26

The compound of the present invention, wherein
E represents a $OC(X^1)NR^5R^6$; and
$R^5$ and $R^6$ represent each independently a hydrogen atom, or a C1-C6 chain hydrocarbon group optionally having one or more substituents selected from Group B.

Embodiment 27

The compound of the present invention, wherein
E represents a $OR^3$, a $OC(O)R^4$, a $OC(X^1)NR^5R^6$, or a $OS(O)_2R^8$;
$R^4$ and $R^1$ represent each independently a C1-C6 chain hydrocarbon group optionally having one or more substituents selected from Group B; and
$R^3$, $R^5$, and $R^6$ represent each independently a C1-C6 chain hydrocarbon group optionally having one or more substituents selected from the group consisting of a cyano group and a C1-C6 alkoxy group, or a hydrogen atom.

Embodiment 28

The compound of the present invention, wherein
E represents a $OR^3$, a $OC(O)R^4$, or a $OC(X^1)NR^5R^6$;
$R^4$ represents a C1-C6 chain hydrocarbon group optionally having one or more substituents selected from Group B; and
$R^3$, $R^5$, and $R^6$ represent each independently a C1-C6 chain hydrocarbon group optionally having one or more substituents selected from the group consisting of a cyano group and a C1-C6 alkoxy group, or a hydrogen atom.

Embodiment 29

The compound of the present invention, wherein
E represents a $OR^3$; and
$R^3$ represents a C1-C6 chain hydrocarbon group optionally having one or more substituents selected from the group consisting of a cyano group and a C1-C6 alkoxy group, or a hydrogen atom.

Embodiment 30

The compound of the present invention, wherein
E represents a $OC(O)R^4$; and
$R^4$ represents a C1-C6 chain hydrocarbon group optionally having one or more substituents selected from the group consisting of a cyano group and a C1-C6 alkoxy group.

Embodiment 31

The compound of the present invention, wherein
E represents a $OC(X^1)NR^5R^6$; and
$R^5$ and $R^6$ represent each independently a C1-C6 chain hydrocarbon group optionally having one or more substituents selected from the group consisting of a cyano group and a C1-C6 alkoxy group, or a hydrogen atom.

Embodiment 32

The compound of the present invention, wherein
E represents a $OR^3$, a $OC(O)R^4$, a $OC(X^1)NR^5R^6$, or a $OS(O)_2R^8$; and
A represents a hydrogen atom, a methyl group, a methoxy group, a methylthio group, a cyano group, an amino group, a methylamino group, or a dimethylamino group.

Embodiment 33

The compound of the present invention, wherein
E represents a $OR^3$, a $OC(O)R^4$, or a $OC(X^1)NR^5R^6$; and
A represents a hydrogen atom, a methyl group, a methoxy group, a methylthio group, a cyano group, an amino group, a methylamino group, or a dimethylamino group.

Embodiment 34

The compound of the present invention, wherein
E represents a $OR^3$; and
A represents a hydrogen atom, a methyl group, a methoxy group, a methylthio group, a cyano group, an amino group, a methylamino group, or a dimethylamino group.

Embodiment 35

The compound of the present invention, wherein
E represents a $OC(O)R^4$; and
A represents a hydrogen atom, a methyl group, a methoxy group, a methylthio group, a cyano group, an amino group, a methylamino group, or a dimethylamino group.

Embodiment 36

The compound of the present invention, wherein
E represents a $OC(X^1)NR^5R^6$; and
A represents a hydrogen atom, a methyl group, a methoxy group, a methylthio group, a cyano group, an amino group, a methylamino group, or a dimethylamino group.

Embodiment 37

The compound of the present invention, wherein
E represents a $OR^3$, a $OC(O)R^4$, a $OC(X^1)NR^5R^6$, or a $OS(O)_2R^8$;
$R^4$ and $R^8$ represent each independently a C1-C6 chain hydrocarbon group optionally having one or more substituents selected from Group B;
$R^3$, $R^5$, and $R^6$ represent each independently a hydrogen atom, or a C1-C6 chain hydrocarbon group optionally having one or more substituents selected from Group B; and
A represents a hydrogen atom, a methyl group, a methoxy group, a methylthio group, a cyano group, an amino group, a methylamino group, or a dimethylamino group.

Embodiment 38

The compound of the present invention, wherein
E represents a $OR^3$, a $OC(O)R^4$, or a $OC(X^1)NR^5R^6$;
$R^4$ represents a C1-C6 chain hydrocarbon group optionally having one or more substituents selected from Group B;
$R^3$, $R^5$, and $R^6$ represent each independently a hydrogen atom, or a C1-C6 chain hydrocarbon group optionally having one or more substituents selected from Group B; and
A represents a hydrogen atom, a methyl group, a methoxy group, a methylthio group, a cyano group, an amino group, a methylamino group, or a dimethylamino group.

Embodiment 39

The compound of the present invention, wherein E represents a $OR^3$;
$R^3$ represents a hydrogen atom, or a C1-C6 chain hydrocarbon group optionally having one or more substituents selected from Group B; and
A represents a hydrogen atom, a methyl group, a methoxy group, a methylthio group, a cyano group, an amino group, a methylamino group, or a dimethylamino group.

Embodiment 40

The compound of the present invention, wherein
E represents a $OC(O)R^4$;
$R^4$ represents a C1-C6 chain hydrocarbon group optionally having one or more substituents selected from Group B; and
A represents a hydrogen atom, a methyl group, a methoxy group, a methylthio group, a cyano group, an amino group, a methylamino group, or a dimethylamino group.

Embodiment 41

The compound of the present invention, wherein
E represents a $OC(X^1)NR^5R^6$;
$R^5$ and $R^6$ represent each independently a hydrogen atom, or a C1-C6 chain hydrocarbon group optionally having one or more substituents selected from Group B; and
A represents a hydrogen atom, a methyl group, a methoxy group, a methylthio group, a cyano group, an amino group, a methylamino group, or a dimethylamino group.

Embodiment 42

The compound of the present invention, wherein
E represents a $OR^3$, a $OC(O)R^4$, a $OC(X^1)NR^5R^6$, or a $OS(O)_2R^8$;
$R^4$ and $R^5$ represent each independently a C1-C6 chain hydrocarbon group optionally having one or more substituents selected from Group B;
$R^3$, $R^5$, and $R^6$ represent each independently a C1-C6 chain hydrocarbon group optionally having one or more substituents selected from the group consisting of a cyano group and a C1-C6 alkoxy group, or a hydrogen atom; and A represents a hydrogen atom, a methyl group, a methoxy group, a methylthio group, a cyano group, an amino group, a methylamino group, or a dimethylamino group.

Embodiment 43

The compound of the present invention, wherein
E represents a $OR^3$, a $OC(O)R^4$, or a $OC(X^1)NR^5R^6$;
$R^4$ represents a C1-C6 chain hydrocarbon group optionally having one or more substituents selected from Group B;
$R^3$, $R^5$, and $R^6$ represent each independently a C1-C6 chain hydrocarbon group optionally having one or more substituents selected from the group consisting of a cyano group and a C1-C6 alkoxy group, or a hydrogen atom; and
A represents a hydrogen atom, a methyl group, a methoxy group, a methylthio group, a cyano group, an amino group, a methylamino group, or a dimethylamino group.

Embodiment 44

The compound of the present invention, wherein
E represents a $OR^3$;
$R^3$ represents a C1-C6 chain hydrocarbon group optionally having one or more substituents selected from the group consisting of a cyano group and a C1-C6 alkoxy group, or a hydrogen atom; and
A represents a hydrogen atom, a methyl group, a methoxy group, a methylthio group, a cyano group, an amino group, a methylamino group, or a dimethylamino group.

Embodiment 45

The compound of the present invention, wherein
E represents a $OC(O)R^4$;
$R^4$ represents a C1-C6 chain hydrocarbon group optionally having one or more substituents selected from the group consisting of a cyano group and a C1-C6 alkoxy group; and
A represents a hydrogen atom, a methyl group, a methoxy group, a methylthio group, a cyano group, an amino group, a methylamino group, or a dimethylamino group.

Embodiment 46

The compound of the present invention, wherein
E represents a $OC(X^1)NR^5R^6$;
$R^5$ and $R^6$ represent each independently a C1-C6 chain hydrocarbon group optionally having one or more substituents selected from the group consisting of a cyano group and a C1-C6 alkoxy group, or a hydrogen atom; and
A represents a hydrogen atom, a methyl group, a methoxy group, a methylthio group, a cyano group, an amino group, a methylamino group, or a dimethylamino group.

Embodiment 47

The compound according to any one of Embodiments 9 to 46, wherein
G represents a pyridine ring, or a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 48

The compound according to any one of Embodiments 9 to 46, wherein
G represents a pyridine ring, or a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 49

The compound according to any one of Embodiments 9 to 46, wherein
G represents a benzene ring or a pyridine ring; and
$(CR^{X1}R^{X2})_mC(A)=N$-E is attached to G at the meta position or the para position relative to the oxadiazole ring.

Embodiment 50

The compound according to any one of Embodiments 9 to 46, wherein
G represents a benzene ring or a pyridine ring; and
$(CR^{X1}R^{X2})_mC(A)=N$-E is attached to G at the para position relative to the oxadiazole ring.

Embodiment 51

The compound according to any one of Embodiments 9 to 46, wherein
G represents a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 52

The compound according to any one of Embodiments 9 to 46, wherein
G represents a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 53

The compound according to any one of Embodiments 9 to 46, wherein
G represents a benzene ring; and
$(CR^{X1}R^{X2})_mC(A)=N$-E is attached to G at the meta position or the para position relative to the oxadiazole ring.

Embodiment 54

The compound according to any one of Embodiments 9 to 46, wherein
G represents a benzene ring; and $(CR^{X1}R^{X2})_mC(A)=N$-E is attached to G at the para position relative to the oxadiazole ring.

Embodiment 55

The compound according to any one of Embodiments 9 to 46, wherein
m represents 0 or 1;
G represents a pyridine ring, or a benzene ring optionally having one or more substituents selected from the group consisting of a fluorine atom and a methyl group; and $(CR^{X1}R^{X2})_mC(A)=N$-E is attached to G at the meta position or the para position relative to the oxadiazole ring.

Embodiment 56

The compound according to any one of Embodiments 9 to 46, wherein
m represents 0 or 1;
G represents a pyridine ring, or a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 57

The compound according to any one of Embodiments 9 to 46, wherein
m represents 0 or 1;
G represents a benzene ring or a pyridine ring; and
$(CR^{X1}R^{X2})_mC(A)=N$-E is attached to G at the meta position or the para position relative to the oxadiazole ring.

Embodiment 58

The compound according to any one of Embodiments 9 to 46, wherein
m represents 0 or 1;
G represents a benzene ring or a pyridine ring; and
$(CR^{X1}R^{X2})_mC(A)=N$-E is attached to G at the para position relative to the oxadiazole ring.

Embodiment 59

The compound according to any one of Embodiments 9 to 46, wherein
m represents 0 or 1;
G represents a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 60

The compound according to any one of Embodiments 9 to 46, wherein
m represents 0 or 1;
G represents a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 61

The compound according to any one of Embodiments 9 to 46, wherein
m represents 0 or 1;
G represents a benzene ring; and
$(CR^{X1}R^{X2})_mC(A)=N$-E is attached to G at the meta position or the para position relative to the oxadiazole ring.

Embodiment 62

The compound according to any one of Embodiments 9 to 46, wherein
m represents 0 or 1;
G represents a benzene ring; and
$(CR^{X1}R^{X2})_mC(A)=N$-E is attached to G at the para position relative to the oxadiazole ring.

Embodiment 63

The compound according to any one of Embodiments 9 to 46, wherein
m represents 0;
G represents a pyridine ring, or a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 64

The compound according to any one of Embodiments 9 to 46, wherein
m represents 0;
G represents a pyridine ring, or a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 65

The compound according to any one of Embodiments 9 to 46, wherein
m represents 0;
G represents a benzene ring or a pyridine ring; and
$(CR^{X1}R^{X2})_mC(A)=N$-E is attached to G at the meta position or the para position relative to the oxadiazole ring.

Embodiment 66

The compound according to any one of Embodiments 9 to 46, wherein
m represents 0;
G represents a benzene ring or a pyridine ring; and
$(CR^{X1}R^{X2})_mC(A)=N$-E is attached to G at the para position relative to the oxadiazole ring.

Embodiment 67

The compound according to any one of Embodiments 9 to 46, wherein
m represents 0;
G represents a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 68

The compound according to any one of Embodiments 9 to 46, wherein
m represents 0;
G represents a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 69

The compound according to any one of Embodiments 9 to 46, wherein
m represents 0;
G represents a benzene ring; and
$(CR^{X1}R^{X2})_mC(A)=N$-E is attached to G at the meta position or the para position relative to the oxadiazole ring.

Embodiment 70

The compound according to any one of Embodiments 9 to 46, wherein
m represents 0;
G represents a benzene ring; and
$(CR^{X1}R^{X2})_mC(A)=N$-E is attached to G at the para position relative to the oxadiazole ring.

Embodiment 71

The compound of the present invention, wherein
m represents 0 or 1;
G represents a pyridine ring, or a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 72

The compound of the present invention, wherein
m represents 0 or 1;
G represents a pyridine ring, or a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 73

The compound of the present invention, wherein
m represents 0 or 1;
G represents a benzene ring or a pyridine ring; and
$(CR^{X1}R^{X2})_mC(A)=N$-E is attached to G at the meta position or the para position relative to the oxadiazole ring.

Embodiment 74

The compound of the present invention, wherein
m represents 0 or 1;
G represents a benzene ring or a pyridine ring; and
$(CR^{X1}R^{X2})_mC(A)=N$-E is attached to G at the para position relative to the oxadiazole ring.

Embodiment 75

The compound of the present invention, wherein
m represents 0 or 1;
G represents a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 76

The compound of the present invention, wherein
m represents 0 or 1;
G represents a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 77

The compound of the present invention, wherein
m represents 0 or 1;
G represents a benzene ring; and
$(CR^{X1}R^{X2})_mC(A)=N$-E is attached to G at the meta position or the para position relative to the oxadiazole ring.

Embodiment 78

The compound of the present invention, wherein
m represents 0 or 1;
G represents a benzene ring; and
$(CR^{X1}R^{X2})_mC(A)=N$-E is attached to G at the para position relative to the oxadiazole ring.

Embodiment 79

The compound of the present invention, wherein
m represents 0;
G represents a pyridine ring, or a benzene ring optionally having one or more substituents selected from the group consisting of a fluorine atom and a methyl group; and
$(CR^{X1}R^{X2})_mC(A)=N$-E is attached to G at the meta position or the para position relative to the oxadiazole ring.

Embodiment 80

The compound of the present invention, wherein
m represents 0;
G represents a pyridine ring, or a benzene ring optionally having one or more substituents selected from the group consisting of a fluorine atom and a methyl group; and
$(CR^{X1}R^{X2})_mC(A)=N$-E is attached to G at the para position relative to the oxadiazole ring.

Embodiment 81

The compound of the present invention, wherein
m represents 0;
G represents a benzene ring or a pyridine ring; and
$(CR^{X1}R^{X2})_mC(A)=N$-E is attached to G at the meta position or the para position relative to the oxadiazole ring.

Embodiment 82

The compound of the present invention, wherein
m represents 0;
G represents a benzene ring or a pyridine ring; and
$(CR^{X1}R^{X2})_mC(A)=N$-E is attached to G at the para position relative to the oxadiazole ring.

Embodiment 83

The compound of the present invention, wherein
m represents 0;
G represents a benzene ring optionally having one or more substituents selected from the group consisting of a fluorine atom and a methyl group; and Embodiment 84

The compound of the present invention, wherein
m represents 0;
G represents a benzene ring optionally having one or more substituents selected from the group consisting of a fluorine atom and a methyl group; and
$(CR^{X1}R^{X2})_m C(A)=N-E$ is attached to G at the para position relative to the oxadiazole ring.

Embodiment 85

The compound of the present invention, wherein
m represents 0;
G represents a benzene ring; and
$(CR^{X1}R^{X2})_m C(A)=N-E$ is attached to G at the meta position or the para position relative to the oxadiazole ring.

Embodiment 86

The compound of the present invention, wherein
m represents 0;
G represents a benzene ring; and
$(CR^{X1}R^{X2})_m C(A)=N-E$ is attached to G at the para position relative to the oxadiazole ring.

Embodiment 87

The compound according to any one of Embodiments 9 to 46, wherein
G represents a pyridine ring, a pyrazine ring, a pyrimidine ring, a pyridazine ring, or a benzene ring optionally having one or more substituents selected from the group consisting of a fluorine atom and a methyl group; and
$(CR^{X1}R^{X2})_m C(A)=N-E$ is attached to G at the meta position or the para position relative to the oxadiazole ring.

Embodiment 88

The compound according to any one of Embodiments 9 to 46, wherein
G represents a pyridine ring, a pyrazine ring, a pyrimidine ring, a pyridazine ring, or a benzene ring optionally having one or more substituents selected from the group consisting of a fluorine atom and a methyl group; and
$(CR^{X1}R^{X2})_m C(A)=N-E$ is attached to G at the para position relative to the oxadiazole ring.

Embodiment 89

The compound according to any one of Embodiments 9 to 46, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0 or 1; and
$(CR^{X1}R^{X2})_m C(A)=N-E$ is attached to G at the meta position or the para position relative to the oxadiazole ring.

Embodiment 90

The compound according to any one of Embodiments 9 to 46, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0 or 1; and
$(CR^{X1}R^{X2})_m C(A)=N-E$ is attached to G at the para position relative to the oxadiazole ring.

Embodiment 91

The compound according to any one of Embodiments 9 to 46, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0; and
$(CR^{X1}R^{X2})_m C(A)=N-E$ is attached to G at the meta position or the para position relative to the oxadiazole ring.

Embodiment 92

The compound according to any one of Embodiments 9 to 46, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0; and
$(CR^{X1}R^{X2})_m C(A)=N-E$ is attached to G at the para position relative to the oxadiazole ring.

Embodiment 93

The compound of the present invention, wherein
G represents a pyridine ring, a pyrazine ring, a pyrimidine ring, a pyridazine ring, or a benzene ring optionally having one or more substituents selected from the group consisting of a fluorine atom and a methyl group; and
$(CR^{X1}R^{X2})_m C(A)=N-E$ is attached to G at the meta position or the para position relative to the oxadiazole ring.

Embodiment 94

The compound of the present invention, wherein
G represents a pyridine ring, a pyrazine ring, a pyrimidine ring, a pyridazine ring, or a benzene ring optionally having one or more substituents selected from the group consisting of a fluorine atom and a methyl group; and
$(CR^{X1}R^{X2})_m C(A)=N-E$ is attached to G at the para position relative to the oxadiazole ring.

Embodiment 95

The compound of the present invention, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0 or 1; and
$(CR^{X1}R^{X2})_m C(A)=N-E$ is attached to G at the meta position or the para position relative to the oxadiazole ring.

Embodiment 96

The compound of the present invention, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0 or 1; and
$(CR^{X1}R^{X2})_m C(A)=N-E$ is attached to G at the para position relative to the oxadiazole ring.

Embodiment 97

The compound of the present invention, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0; and
$(CR^{X1}R^{X2})_m C(A)=N-E$ is attached to G at the meta position or the para position relative to the oxadiazole ring.

Embodiment 98

The compound of the present invention, wherein
G represents a pyridine ring, a pyrazine ring, a pyrimidine ring, a pyridazine ring, or a benzene ring optionally having one or more substituents selected from the group consisting of a fluorine atom and a methyl group;
m represents 0; and
$(CR^{X1}R^{X2})_m C(A)=N-E$ is attached to G at the para position relative to the oxadiazole ring.

Embodiment 99

The compound of the present invention, wherein
m represents 0;
G represents a benzene ring;
$(CR^{X1}R^{X2})_m C(A)=N-E$ is attached to G at the para position relative to the oxadiazole ring;
A represents a hydrogen atom, a C1-C6 alkoxy group, a cyano group, or a $NR^1R^2$;
$R^1$ and $R^2$ represent each independently a hydrogen atom or a C1-C6 alkyl group;
E represents a $OR^3$ or a $OC(O)NR^5R^6$;
$R^3$ represents a hydrogen atom, or a C1-C6 chain hydrocarbon group optionally having one or more substituents selected from the group consisting of a C1-C6 alkoxy group and a cyano group; and
$R^5$ and $R^6$ represent each independently a hydrogen atom or a C1-C6 alkyl group.

Embodiment 100

The compound of the present invention, wherein
m represents 0;
G represents a benzene ring;
$(CR^{X1}R^{X2})_m C(A)=N-E$ is attached to G at the para position relative to the oxadiazole ring;
A represents a hydrogen atom, a C1-C6 alkoxy group, a cyano group, or a $NR^1R^2$;
$R^1$ and $R^2$ represent each independently a hydrogen atom or a C1-C6 alkyl group;
E represents a $OR^3$; and
$R^3$ represents a hydrogen atom, or a C1-C6 chain hydrocarbon group optionally having one or more substituents selected from the group consisting of a C1-C6 alkoxy group and a cyano group.

Embodiment 101

The compound of the present invention, wherein
m represents 0;
G represents a benzene ring;
$(CR^{X1}R^{X2})_m C(A)=N-E$ is attached to G at the para position relative to the oxadiazole ring;
A represents a hydrogen atom, a C1-C6 alkoxy group, a cyano group, or a $NR^1R^2$;
$R^1$ and $R^2$ represent each independently a hydrogen atom or a C1-C6 alkyl group;
E represents a $OR^3$; and
$R^3$ represents a C1-C6 alkyl group optionally having one or more substituents selected from the group consisting of a C1-C6 alkoxy group and a cyano group.

Next, the process for preparing the compound of the present invention is described.

The compound of the present invention can be prepared, for example, according to the following processes.

Process A

The compound represented by formula (I-1) (hereinafter referred to as "Compound (I-1)") may be prepared by reacting the compound represented by formula (I-2) (hereinafter referred to as "Compound (1-2)") with the compound represented by formula (A1) (hereinafter referred to as "Compound (A1)") or a salt thereof in the presence of a base.

[Chem. 5]

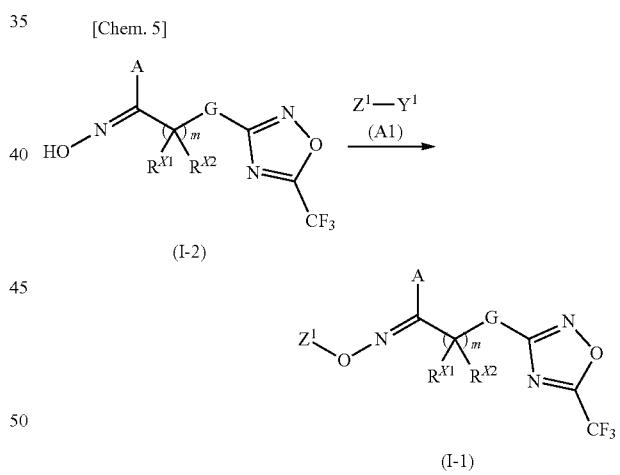

(wherein:
$Z^1$ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, a $C(O)R^4$, a $C(X^1)NR^5R^6$, a $C(X^2)OR^7$ or a $S(O)_2R^8$;
$Y^1$ represents a halogen atom; and
the other symbols are the same as defined above.)

The reaction is usually carried out in a solvent. Examples of the solvent to be used in the reaction include hydrocarbons such as n-hexane, cyclohexane, toluene, and xylene (hereinafter collectively referred to as "hydrocarbons"); ethers such as diethyl ether, tetrahydrofuran, 1,4-dioxane, ethylene glycol dimethyl ether, methyl tert-butyl ether (hereinafter referred to as "MTBE"), and diisopropyl ether (hereinafter collectively referred to as "ethers"); halogenated hydrocarbons such as chloroform, dichloromethane, and chlorobenzene (hereinafter collectively referred to as "halogenated hydrocarbons"); amides such as dimethylformamide (hereinafter referred to as "DMF"), 1,3-dimethyl-2-imidazolidinone, and N-methylpyrrolidone (hereinafter collectively referred to as "amides"); esters such as ethyl acetate and methyl acetate (hereinafter collectively referred to as "esters"); sulfoxides such as dimethyl sulfoxide (hereinafter collectively referred to as "sulfoxides"); nitriles such as acetonitrile and propionitrile (hereinafter collectively referred to as "nitriles"); and mixed solvents thereof.

Examples of the base to be used in the reaction include organic bases such as triethylamine, pyridine, 2,2'-bipyridine, and diazabicycloundecene (hereinafter collectively referred to as "organic bases"); alkali metal carbonates such as sodium carbonate and potassium carbonate (hereinafter collectively referred to as "alkali metal carbonates"); alkali metal hydrogen carbonates such as sodium hydrogen carbonate; alkali metal hydrides such as sodium hydride; and mixtures thereof.

Examples of the salt of the Compound (A1) include hydrochloride and hydrobromide. In the reaction, 1 to 10 mols of the Compound (A1) is usually used, and 1 to 20 mols of the base is usually used, per mol of the Compound (1-2).

The reaction temperature of the reaction is usually within a range of −20 to 150° C. The reaction period of the reaction is usually within a range of 0.1 to 120 hours.

When the reaction is completed, the reaction mixtures are mixed with water and then extracted with organic solvent(s), and the organic layers are worked up (for example, dried or concentrated) to isolate the Compound (I-1).

Process B

The compound represented by formula (I-3) (hereinafter referred to as "Compound (I-3)") may be prepared by reacting the compound represented by formula (A2) (hereinafter referred to as "Compound (A2)") with trifluoroacetic anhydride in the presence of a base.

[Chem. 6]

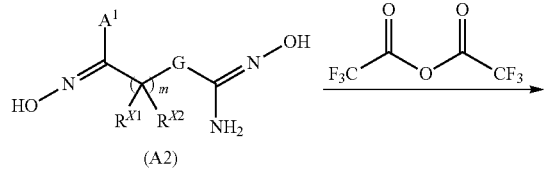

(A2)

(wherein:

$A^1$ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, or an amino group; and the other symbols are the same as defined above.)

The reaction is usually carried out in a solvent. Examples of the solvent to be used in the reaction include hydrocarbons, ethers, halogenated hydrocarbons, amides, esters, sulfoxides, nitriles, and mixed solvents thereof.

Examples of the base to be used in the reaction include organic bases and alkali metal carbonates.

When $A^1$ represents an amino group, 0.1 to 1.9 mols of the trifluoroacetic anhydride is usually used, and 0.1 to 5 mols of the base is usually used in the reaction, per mol of the Compound (A2).

When $A^1$ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, or a C6-C10 aryl group optionally having one or more substituents selected from Group G, 1 to 10 mols of the trifluoroacetic anhydride is usually used, and 1 to 10 mols of the base is usually used in the reaction, per mol of the Compound (A2).

The reaction temperature of the reaction is usually within a range of −20 to 150° C. The reaction period of the reaction is usually within a range of 0.1 to 120 hours.

When the reaction is completed, the reaction mixtures are mixed with water and then extracted with organic solvent(s), and the organic layers are worked up (for example, dried or concentrated) to isolate the Compound (1-3).

Process C

The compound represented by formula (I-4) (hereinafter referred to as "Compound (I-4)") may be prepared by reacting the compound represented by formula (A3) (hereinafter referred to as "Compound (A3)") with the compound represented by formula (A4) (hereinafter referred to as "Compound (A4)"). The reaction may be carried out in the presence of a base.

[Chem. 7]

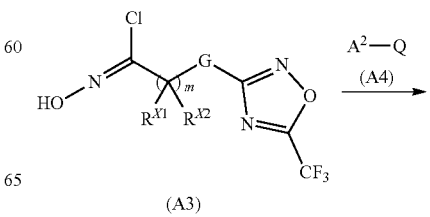

(A3)

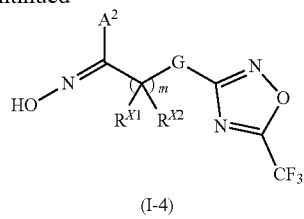

(I-4)

(wherein:

A² represents a C1-C6 alkoxy group optionally having one or more substituents selected from Group C, a C1-C6 alkylthio group optionally having one or more substituents selected from Group C, or a cyano group;

Q represents lithium, potassium, or sodium; and the other symbols are the same as defined above.)

The reaction may be carried out according to the process described in, for example, J. Agric. Food. Chem., 2008, 56, 6562-6566; U.S. Pat. No. 6,057,352 A; or Bioorg. Med. Chem. Lett., 2010, 20, 4693-4699.

The Compound (A4) is known, or may be prepared according to a known process.

Process D

The compound represented by formula (I-5) (hereinafter referred to as "Compound (I-5)") may be prepared by reacting the Compound (A3) with the compound represented by formula (A5) (hereinafter referred to as "Compound (A5)") or a salt thereof.

[Chem. 8]

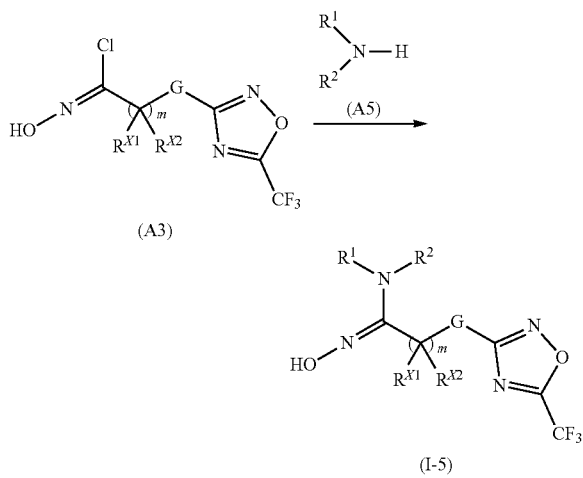

(wherein the symbols are the same as defined above.)

Examples of the salt of the Compound (A5) include hydrochloride and sulfate.

The reaction may be carried out according to the process described in, for example, WO 2007/30582 pamphlet or WO 2006/2099 pamphlet.

The Compound (A5) or a salt thereof is known, or may be prepared according to a known process.

Process E

The Compound (A3) may be prepared by reacting the compound represented by formula (I-6) (hereinafter referred to as "Compound (1-6)") with N-chlorosuccinimide.

[Chem.9]

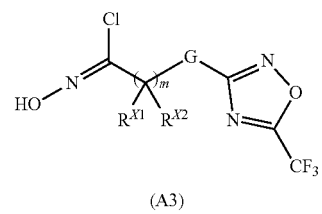

(I-6)

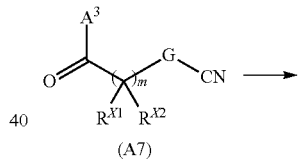

(A3)

(wherein the symbols are the same as defined above.)

The reaction may be carried out according to the process described in, for example, WO 2010/85581 pamphlet.

The Compound (1-6) may be prepared according to the process described in the Process B.

Process F

The compound represented by formula (A6) (hereinafter referred to as "Compound (A6)") may be prepared by reacting the compound represented by formula (A7) (hereinafter referred to as "Compound (A7)") with hydroxylamine.

[Chem.10]

(A7)

(A6)

(wherein:

A³ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, or a C6-C10 aryl group optionally having one or more substituents selected from Group G; and the other symbols are the same as defined above.)

The reaction may be carried out according to the process described in, for example, Tetrahedron, 2011, 67, 6352-6361.

The Compound (A7) is known, or may be prepared according to a known process.

Process G

The compound represented by formula (A8) (hereinafter referred to as "Compound (A8)") may be prepared by reacting the compound represented by formula (A9) (hereinafter referred to as "Compound (A9)") with hydroxylamine.

[Chem.11]

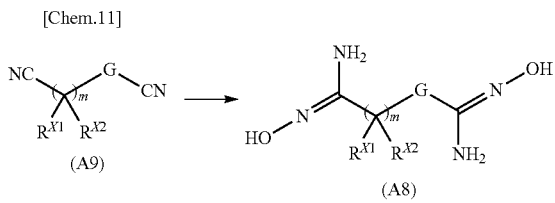

(wherein the symbols are the same as defined above.)

The reaction may be carried out according to the process described in, for example, J. Med. Chem., 1972, 15, 1194-1196.

The Compound (A9) is known, or may be prepared according to a known process.

Process H

The compound represented by formula (I-7) (hereinafter referred to as "Compound (I-7)") may be prepared by reacting the compound represented by formula (A10) (hereinafter referred to as "Compound (A10)") with the compound represented by formula (A11) (hereinafter referred to as "Compound (A11)") or a salt thereof.

[Chem. 12]

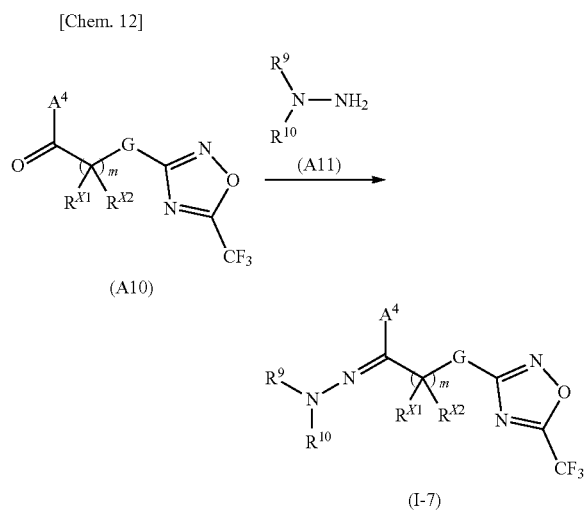

(wherein:
$A^4$ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, or a C1-C6 alkoxy group optionally having one or more substituents selected from Group C; and the other symbols are the same as defined above.)

Examples of the salt of the Compound (A11) include hydrochloride and sulfate. The reaction may be carried out according to the process described in, for example, Tetrahedron, 1981, 37, 4047-4058.

The Compound (A10) and the Compound (A11) are known, or may be prepared according to a known process (EP 2533783 A1).

Process I

The compound represented by formula (I-8) (hereinafter referred to as "Compound (I-8)") may be prepared by reacting the compound represented by formula (A12) (hereinafter referred to as "Compound (A12)") with the compound represented by formula (A13) (hereinafter referred to as "Compound (A13)") in the presence of a base.

[Chem. 13]

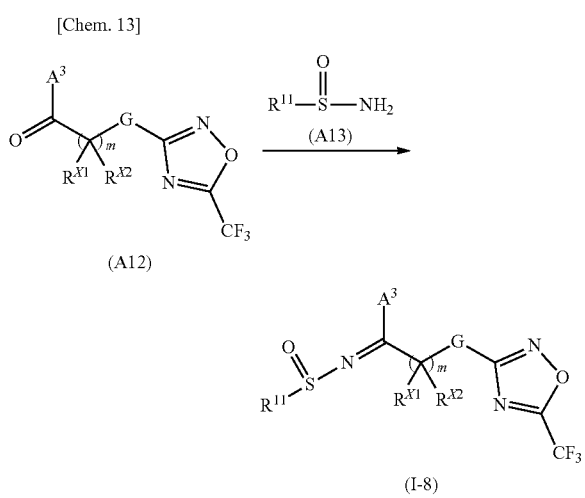

(wherein the symbols are the same as defined above.)

The reaction may be carried out according to the process described in, for example, WO 2015/116886 pamphlet.

The Compound (A12) and the Compound (A13) are known, or may be prepared according to a known process (EP 2533783 A1).

Process J

The compound represented by formula (I-9) (hereinafter referred to as "Compound (I-9)") may be prepared by reacting the Compound (A12) with the compound represented by formula (A14) (hereinafter referred to as "Compound (A14)") in the presence of a Lewis acid.

[Chem. 14]

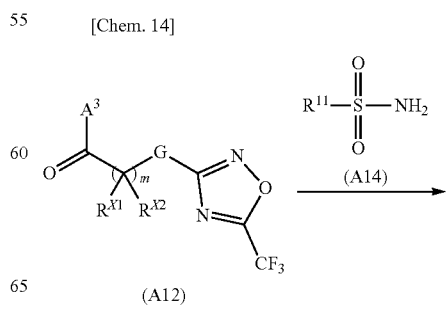

-continued

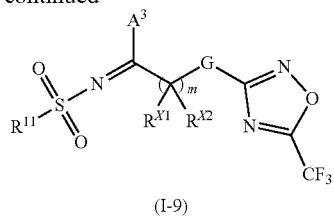

(I-9)

(wherein the symbols are the same as defined above.)

The reaction may be carried out according to the process described in, for example, Tetrahedron Asymmetry, 2011, 22, 1225-1230.

The Compound (A14) is known, or may be prepared according to a known process.

The control agent of the present invention is usually prepared by mixing the compound of the present invention with a solid carrier, a liquid carrier, a surfactant, and/or the others, and if necessary, adding auxiliary agents for formulation such as binders, dispersants, and stabilizers, to formulate into wettable powders, granular wettable powders, flowables, granules, dry flowables, emulsifiable concentrates, aqueous solutions, oil solutions, smoking agents, aerosols, microcapsules, poison baits, resin formulations, shampoo formulations, paste-like formulations, foams, carbon dioxide formulations, tablets, or the others. Such formulations may be processed into mosquito repellent coils, electric mosquito repellent mats, liquid mosquito formulations, smoking agents, fumigants, sheet formulations, spot-on formulations, or formulations for oral treatment. Such formulations comprise usually 0.1 to 99% by weight, and preferably 0.2 to 90% by weight of the compound of the present invention.

Examples of the solid carrier include fine powders or granules of clays (for example, kaolin, diatomaceous earth, synthetic hydrated silicon oxides, Fubasami clay, bentonite, or acid white clay), talcs, other inorganic minerals (for example, sericite, quartz powder, sulfur powder, active carbon, calcium carbonate, or hydrated silica), and the others.

Examples of the liquid carrier include water, alcohols, ketones (for example, acetone, methylethylketone, or cyclohexanone), aromatic hydrocarbons (for example, benzene, toluene, xylene, ethyl benzene, or methylnaphthalene), aliphatic hydrocarbons (for example, n-hexane or kerosene), esters, nitriles, ethers, amides, halogenated hydrocarbons, and the others.

Examples of the surfactant include alkyl sulfates, alkyl sulfonates, alkyl aryl sulfonates, alkyl aryl ethers and polyoxyethylated compounds thereof, polyoxyethylene glycol ethers, polyhydric alcohol esters, and sugar alcohol derivatives.

Examples of the other auxiliary agents for formulation include binders, dispersants, and stabilizers. Specific examples include casein, gelatin, polysaccharides (for example, starch, gum arabic, cellulose derivatives, or alginic acid), lignin derivatives, bentonite, saccharides, water-soluble synthetic polymers (for example, polyvinyl alcohol, polyvinyl pyrrolidone, or polyacrylic acids), acidic isopropyl phosphate, 2,6-di-tert-butyl-4-methylphenol, a mixture of 2-tert-butyl-4-methoxyphenol and 3-tert-butyl-4-methoxyphenol, vegetable oils, mineral oils, and fatty acids and esters thereof.

Also, the compound of the present invention may be mixed with an oil such as mineral oil and vegetable oil, a surfactant, or the others to use for controlling pests. Examples of the oil or the surfactant to be mixed with the compound of the present invention include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

Examples of base material of the resin formulation include polyvinyl chloride polymers, polyurethane, and the others, and plasticizers such as phthalate esters (for example, dimethyl phthalate or dioctyl phthalate), adipic acid esters, and stearic acid may be added to these base materials, if necessary. The resin formulation can be prepared by mixing the compound of the present invention with the above-mentioned base material, kneading the mixture in a conventional kneading apparatus, followed by molding it by injection molding, extrusion molding, pressure molding, or the like. The resultant resin formulation can be subjected to further molding, cutting procedure, or the like, if necessary, to be processed into shapes such as a plate, a film, a tape, a net, and a string shape. These resin formulations can be processed into animal collars, animal ear tags, sheet products, trap strings, gardening supports, or other products.

Examples of the base material for the poison baits include bait ingredients such as grain powders, vegetable oils, saccharides, and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor, and peanut oil, or the other ingredient.

The application dose of the compound of the present invention may be varied depending on a climate condition, a dosage form, an application period, an application method, an application site, a disease to be controlled, an insect to be controlled, a kind of crop to be applied, and the like. The amount of the compound of the present invention in the control agent of the present invention is usually within the range of 1 to 500 g, and preferably 2 to 200 g, per 1000 m$^2$. The emulsifiable concentrates, the wettable powders, or suspensions etc. are usually applied by diluting them with water, and then spreading them. In this case, the concentration of the compound of the present invention after dilution is usually 0.0005 to 2% by weight, and preferably 0.005 to 2% by weight. The dusts or the granules, etc., are usually applied as itself without diluting them.

The method for applying the compound of the present invention is not limited to a specific method as long as the compound of the present invention can be applied. Examples of the method include an application to a plant body such as a foliar application, an application to a cultivation area of plant such as a soil treatment, an application to seeds such as a seed disinfection, and an application to harmful arthropods. Also, a resin formulation processed into a sheet shape or a string shape may be wrapped around a crop, stretched near a crop, spread on a plant foot soil, or the like to apply the compound of the present invention.

When the compound of the present invention is applied to a foliage of a plant or a soil for cultivating a plant, the amount of the compound of the present invention is usually within the range of 1 to 500 g per 1000 m² of the soil. When the compound of the present invention is applied to seeds, the amount of the compound of the present invention in the control agent of the present invention is usually within the range of 0.001 to 100 g, and preferably 0.01 to 50 g per 1 Kg of seeds.

The emulsifiable concentrates, the wettable powders, or the flowables, etc., are usually applied by diluting them with water, and then spreading them. In this case, the concentration of the compound of the present invention is usually within the range of 0.0005 to 2% by weight. The dusts or the granules, etc., are usually applied as itself without diluting them.

When the compound of the present invention is used to control harmful arthropods that live inside a house, the application dose as an amount of the compound of the present invention is usually within a range from 0.01 to 1000 mg per 1 m² of an area to be treated, in the case of using it on a planar area. In the case of using it spatially, the application dose as an amount of the compound of the present invention is usually within a range from 0.01 to 500 mg per 1 m³ of the space to be treated. When the control agent of the present invention is formulated into emulsifiable concentrates, wettable powders, flowables, or the others, such formulations are usually applied after diluting it with water in such a way that the concentration of the compound of the present invention is within a range from 0.1 to 10000 ppm, and then sparging it. In the case of being formulated into oil solutions, aerosols, smoking agents, poison baits, or the others, such formulations are used as itself without diluting them.

When the compound of the present invention is used for controlling external parasites of livestock such as cows, horses, pigs, sheep, goats, and chickens, and small animals such as dogs, cats, rats, and mice, the compound of the present invention can be applied to the animals by a known method in the veterinary field. Specifically, when systemic control is intended, the compound of the present invention is administered to the animals as a tablet, a mixture with feed, or a suppository, or by injection (including intramuscular, subcutaneous, intravenous, and intraperitoneal injections), or the others. On the other hand, when non-systemic control is intended, the compound of the present invention is applied to the animals by means of spraying of an oil solution or an aqueous solution etc., a pour-on or spot-on treatment, or a washing of the animal with a shampoo formulation, or by putting a collar or an ear tag made of the resin formulations to the animal. In the case of administering to an animal body of the livestock or small animals, the dose of the compound of the present invention is usually within a range from 0.1 to 1000 mg per 1 kg of an animal body weight.

Also, the compound of the present invention may be used as an agent for controlling plant diseases in croplands such as fields, paddy fields, grasses, and orchards. The compound of the present invention can control cropland diseases in the croplands etc. for cultivating the following plant(s) etc. Further, the compound of the present invention can control harmful arthropods in the croplands.

Crops: corn, rice, wheat, barley, rye, oat, sorghum, cotton, soybean, peanut, buckwheat, beet, rapeseed, sunflower, sugar cane, tobacco, and the others;

Vegetables: solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, welsh onion, onion, garlic, or asparagus), ammiaceous vegetables (for example, carrot, parsley, celery, or parsnip), chenopo-diaceous vegetables (for example, spinach or Swiss chard), lamiaceous vegetables (for example, perilla, mint, or basil), strawberry, sweet potato, glutinous yarn, eddoe, and the others;

Flowers;

Foliage plants;

Fruits: pomaceous fruits (for example, apple, pear, Japanese pear, Chinese quince, or quince), stone fleshy fruits (for example, peach, plum, nectarine, Japanese apricot (*Prunus mume*), cherry fruit, apricot, or prune), citrus fruits (for example, Citrus unshiu, orange, lemon, lime, or grapefruit), nuts (for example, chestnuts, walnuts, hazelnuts, almond, pistachio, cashew nuts, or macadamia nuts), berry fruits (for example, blueberry, cranberry, blackberry, or raspberry), grapes, Japanese persimmon, olive, Japanese plum, banana, coffee, date palm, coconuts, and the others; and Trees other than fruit trees: tea, mulberry, flowering plants, roadside trees (for example, ash, birch, dogwood, eucalyptus, ginkgo (*Ginkgo biloba*), lilac, maple, oak (quercus), poplar, Judas tree, Formosan gum (*Liquidambar formosana*), plane tree, zelkova, Japanese arborvitae (*Thuja standishii*), fir wood, hemlock, juniper, pinus, picea, or yew (*Taxus cuspidate*)), and the others.

The above-mentioned "plant(s)" may include genetically modified plant(s).

Examples of the pest which may be controlled by the compound of the present invention include plant pathogens such as filamentous fungi and harmful arthropods, and more specifically include, but are not limited to, the followings.

Examples of the plant disease caused from plant pathogens include the followings. The scientific name of each pathogen which causes the disease is shown in parentheses.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium Head blight (*Fusarium graminearum, F. avenaceum, F. culmorum, Microdochium nivale*), rust (*Puccinia striiformis, P. graminis, P. recondita*), snow mold (*Micronectriella nivale, M. majus*), typhula snow blight (*Typhula sp.*), loose smut (*Ustilago tritici*), stinking smut (*Tilletia caries, T. controversa*), eyespot (*Pseudocercosporella herpotrichoides*), Septoria leaf blotch (*Septoria tritici*), glume blotch (*Stagonospora nodorum*), tan spot (*Pyrenophora tritici-repentis*), damping-off caused by rhizoctonia fungus (*Rhizoctonia solani*), and damping-off (*Gaeumannomyces graminis*);

Barley diseases: powdery mildew (*Erysiphe graminis*), scab (*Fusarium graminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramuraria disease (*Ramularia collo-cygni*), and damping-off caused by rhizoctonia fungus (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), Faeosufa area leaf spot disease (*Phaeosphaeria maydis*), Diplodia disease (*Stenocarpella maydis, Stenocarpella macrospora*), stalk rot disease (*Fusarium graminearum, Fusarium* verticilioides, *Colletotrichum graminicola*), and smut (*Ustilago maydis*);

Cotton diseases: anthracnose (*Colletotrichum gossypii*), Areolate mildew (*Ramuraria areola*), leaf spot (*Alternaria macrospora, A. gossypii*), and Black root rot caused by *Thielaviopsis* fungus (*Thielaviopsis basicola*);

Coffee diseases: rust (*Hemileia vastatrix*) and leaf spot (*Cercospora coffeicola*); Rapeseed diseases: sclerotinia rot (*Sclerotinia sclerotiorum*), alternaria leaf spot (*Alternaria brassicae*), and root rot (*Phoma lingam*);

Sugarcane diseases: rust (*Puccinia melanocephela, Puccinia kuehnii*) and smut (*Ustilago scitaminea*);

Sunflower diseases: rust (*Puccinia helianthi*) and downy mildew (*Plasmopara halstedii*);

Citrus diseases: melanose (*Diaporthe citri*), scab (*Elsinoe fawcetti*), fruit rot (*Penicillium digitatum, P. italicum*), and Phytophthora disease (*Phytophthora parasitica, Phytophthora citrophthora*);

Apple diseases: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophtora cactorum*);

Pear diseases: scab (*Venturia nashicola, V. pirina*), black spot (*Alternaria alternata* Japanese pear pathotype), and rust (*Gymnosporangium haraeanum*);

Peach diseases: brown rot (*Monilinia fructicola*), scab (*Cladosporium carpophilum*), and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of Cucurbitaceae: anthracnose (*Colletotrichum lagenarium*), powdery mildew (*Sphaerotheca fuliginea*), gummy stem blight (*Didymella bryoniae*), corynespora leaf spot (*Corynespora cassiicola*), Fusarium wilt (*Fusarium oxysporum*), downy mildew (*Pseudoperonospora cubensis*), Phytophthora rot (*Phytophthora* sp.), and damping-off (*Pythium* sp.);

Tomato diseases: early blight (*Alternaria solani*), leaf mold (*Cladosporium fulvum*), cercospora leaf mold (*Pseudocercospora fuligena*), late blight (*Phytophthora infestans*), and powdery mildew (*Leveillula taurica*);

Eggplant disease: brown spot (*Phomopsis vexans*) and powdery mildew (*Erysiphe cichoracearum*);

Diseases of brassica family: Alternaria leaf spot (*Alternaria japonica*), white spot (*Cercosporella brassicae*), clubroot (*Plasmodiophora brassicae*), and downy mildew (*Peronospora parasitica*);

Welsh onion diseases: rust (*Puccinia allii*);

Soybean diseases: purple stain (*Cercospora kikuchii*), Sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), Rhizoctonia rot (*Rhizoctonia solani*), septoria brown spot (*Septoria glycines*), Cercospora leaf spot (*Cercospora sojina*), sclerotinia rot (*Sclerotinia sclerotiorum*), powdery mildew (*Microsphaera diffusa*), phytophthora root and stem rot (*Phytophthora sojae*), downy mildew (*Peronospora manshurica*), and sudden death syndrome (*Fusarium virguliforme*);

Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemthianum*);

Peanut diseases: leaf spot (*Cercospora personata*), brown leaf spot (*Cercospora arachidicola*), and southern blight (*Sclerotium rolfsii*);

Garden pea diseases: powdery mildew (*Erysiphe pisi*);

Potato diseases: early blight (*Alternaria solani*), late blight (*Phytophthora infestans*), pink rot (*Phytophthora erythroseptica*), powdery scab (*Spongospora subterranean* f. sp. *subterranea*), and Verticillium wilt (*Verticillium albo-atrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theaesinensis*);

Tabacco diseases: brown spot (*Alternaria longipes*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*);

Rose diseases: blackspot (*Diplocarpon rosae*) and powdery mildew (*Sphaerotheca pannosa*);

Chrysanthemum and Asteraceae vegetable diseases: leaf blight (*Septoria chrysanthemi-indici*) and white rust (*Puccinia horiana*); Onion diseases: Botrytis leaf blight (*Botrytis cinerea, B. byssoidea, B. squamosa*), neck rot (*Botrytis allii*), and small sclerotial (*Botrytis squamosa*); Various plants diseases: gray mold (*Botrytis cinerea*) and Sclerotinia rot (*Sclerotinia sclerotiorum*);

Japanese radish diseases: Alternaria leaf spot (*Alternaria brassicicola*); Turfgrass diseases: dollar spot (*Sclerotinia homoeocarpa*) and brown patch and large patch (*Rhizoctonia solani*);

Banana diseases: Sigatoka disease (*Mycosphaerella fijiensis, Mycosphaerella musicola*);

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp., and the others;

Viral diseases of various plants mediated by *Polymixa* spp., *Olpidium* spp., or the others;

rice bacterial seedling blight (*Burkholderia plantarii*);

cucumber angular leaf spot (*Pseudomonas syringae* pv. *Lachrymans*);

eggplant bacterial wilt (*Ralstonia solanacearum*);

citrus canker (*Xanthomonas citiri*);

Chinese cabbage bacterial soft rot (*Erwinia carotovora*); and the others.

Examples of the harmful arthropods include the followings.

Hemiptera Pests:

Delphacidae (for example, *Laodelphax striatellus, Nilaparvata lugens, Sogatella furcifera, Peregrinus maidis, Javesella pellucida, Perkinsiella saccharicida*, or *Tagosodes orizicolus*);

Cicadellidae (for example, *Nephotettix cincticeps, Nephotettix virescens, Nephotettix nigropictus, Recilia dorsalis, Empoasca onukii, Empoasca fabae, Dalbulus maidis*, or *Cofana spectra*);

Cercopidae (for example, *Mahanarva posticata* or *Mahanarva fimbriolata*);

Aphididae (for example, *Aphis fabae, Aphis glycines, Aphis gossypii, Aphis pomi, Aphis spiraecola, Myzus persicae, Brachycaudus helichrysi, Brevicoryne brassicae, Dysaphis plantaginea* (Rosy apple aphid), *Lipaphis erysimi, Macrosiphum euphorbiae, Aulacorthum solani, Nasonovia ribisnigri, Rhopalosiphum padi, Rhopalosiphum maidis, Toxoptera citricidus, Hyalopterus pruni, Melanaphis sacchari, Tetraneura nigriabdominalis, Ceratovacuna lanigera*, or *Eriosoma lanigerum*); Phylloxeridae (for example, *Daktulosphaira vitifoliae, Phylloxera devastatrix* (Pecan *phylloxera*), *Phylloxera notabilis* (Pecan leaf *phylloxera*), or *Phylloxera russellae* (Southern pecan leaf *phylloxera*));

Adelgidae (for example, *Adelges tsugae, Adelges piceae*, or *Aphrastasia pectinatae*); Pentatomidae (for example, *Scotinophara lurida, Scotinophara coarctata* (Malayan rice black bug), *Nezara antennata, Eysarcoris aeneus, Eysarcoris lewisi, Eysarcoris ventralis, Eysarcoris annamita, Halyomorpha halys, Nezara viridula, Euschistus heros* (Brown stink bug), *Piezodorus guildinii* (Red banded stink bug), *Oebalus pugnax*, or *Dichelops melacanthus*);

Cydnidae (for example, *Scaptocoris castanea* (Burrower brown bug));

Alydidae (for example, *Riptortus pedestris, Leptocorisa chinensis*, or *Leptocorisa acuta*);

Coreidae (for example, *Cletus punctiger* or *Leptoglossus australis*);

Lygaeidae (for example, *Caverelius saccharivorus, Togo hemipterus*, or *Blissus leucopterus*);

Miridae (for example, *Trigonotylus caelestialium, Stenotus rubrovittatus, Stenodema calcarata*, or *Lygus lineolaris*);

Aleyrodidae (for example, *Trialeurodes vaporariorum, Bemisia tabaci, Dialeurodes citri, Aleurocanthus spiniferus, Aleurocanthus camelliae*, or *Pealius euryae*);

Diaspididae (for example, *Abgrallaspis cyanophylli, Aonidiella aurantii, Diaspidiotus perniciosus, Pseudaulacaspis pentagona, Unaspis yanonensis*, or *Unaspis citri*);

Coccidae (for example, *Ceroplastes rubens*);

Margarodidae (for example, *Icerya purchasi* or *Icerya seychellarum*);

Pseudococcidae (for example, *Phenacoccus solani, Phenacoccus solenopsis, Planococcus kraunhiae, Pseudococcus comstocki, Planococcus citri, Pseudococcus calceolariae, Pseudococcus longispinus*, or *Brevennia rehi*);

Psyllidae (for example, *Diaphorina citri, Trioza erytreae, Cacopsylla pyrisuga, Cacopsylla chinensis, Bactericera cockerelli*, or *Cacopsylla pyricola* (Pear *psylla*)); Tingidae (for example, *Corythucha ciliata, Corythucha marmorata, Stephanitis nashi*, or *Stephanitis pyrioides*);

Cimicidae (for example, *Cimex lectularius*);

Cicadidae (for example, *Quesada gigas* (Giant Cicada));

and the others.

Lepidoptera Pests:

Crambidae (for example, *Chilo suppressalis, Chilo polychrysus* (Darkheaded stem borer), *Scirpophaga innotata* (White stem borer), *Scirpophaga incertulas, Rupela albina, Cnaphalocrocis medinalis, Marasmia patnalis, Marasmia exigua, Notarcha derogata, Ostrinia furnacalis, Ostrinia nubilalis* (European corn borer), *Hellula undalis, Herpetogramma luctuosale, Pediasia teterrellus, Nymphula depunctalis*, or *Diatraea saccharalis* (Sugarcane borer));

Pyralidae (for example, *Elasmopalpus lignosellus* or *Plodia interpunctella*);

Noctuidae (for example, *Spodoptera litura, Spodoptera exigua, Mythimna separata, Mamestra brassicae, Sesamia inferens, Spodoptera mauritia, Naranga aenescens, Spodoptera frugiperda, Spodoptera exempta, Agrotis ipsilon, Autographa nigrisigna, Plusia festucae, Chrysodeixis includens* (Soybean looper), *Trichoplusia* spp., *Heliothis* spp. (for example, *Heliothis virescens*), *Helicoverpa* spp. (for example, *Helicoverpa armigera* or *Helicoverpa zea*), *Anticarsia gemmatalis* (Velvetbean caterpillar), *Alabama argillacea* (Cotton leafworm), or *Hydraecia immanis* (Hop vine borer));

Pieridae (for example, *Pieris rapae*);

Tortricidae (for example, *Grapholita molesta, Grapholita dimorpha, Leguminivora glycinivorella, Matsumuraeses azukivora, Adoxophyes orana fasciata, Adoxophyes honmai, Homona magnanima, Archips fuscocupreanus, Cydia pomonella, Tetramoera schistaceana, Epinotia aporema* (Bean Shoot Borer), or *Ecdytolopha aurantiana* (Citrus fruit borer));

Gracillariidae (for example, *Caloptilia theivora* or *Phyllonorycter ringoniella*);

Carposinidae (for example, *Carposina sasakii*);

Lyonetiidae (for example, *Leucoptera coffeela* (Coffee Leaf miner), *Lyonetia clerkella*, or *Lyonetia prunifoliella*);

Lymantriidae (for example, *Lymantria* spp. (for example, *Lymantria dispar*) or

*Euproctis* spp. (for example, *Euproctis pseudoconspersa*));

Plutellidae (for example, *Plutella xylostella*);

Gelechiidae (for example, *Anarsia lineatella, Helcystogramma triannulellum, Pectinophora gossypiella, Phthorimaea operculella*, or *Tuta absoluta*);

Arctiidae (for example, *Hyphantria cunea*);

Castniidae (for example, *Telchin licus* (Giant Sugarcane borer));

Cossidae (for example, *Cossus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis*);

Hesperiidae (for example, *Parnara guttata*);

and the others.

Thysanoptera Pests:

Thripidae (for example, *Frankliniella occidentalis, Thrips palmi, Scirtothrips dorsalis, Thrips tabaci, Frankliniella intonsa, Stenchaetothrips biformis*, or *Echinothrips americanus*);

Phlaeothripidae (for example, *Haplothrips aculeatus*);

and the others.

Diptera Pests:

Anthomyiidae (for example, *Delia platura* or *Delia antiqua*);

Ulidiidae (for example, *Tetanops myopaeformis*);

Agromyzidae (for example, *Agromyza oryzae, Liriomyza sativae, Liriomyza trifolii*, or *Chromatomyia horticola*);

Chloropidae (for example, *Chlorops oryzae*);

Tephritidae (for example, *Bactrocera cucurbitae, Bactrocera dorsalis, Bactrocera latifrons, Bactrocera oleae, Bactrocera tryoni*, or *Ceratitis capitata*);

Ephydridae (for example, *Hydrellia griseola, Hydrellia philippina*, or *Hydrellia sasakii*);

Drosophilidae (for example, *Drosophila suzukii*);
Phoridae (for example, *Megaselia spiracularis*);
Psychodidae (for example, *Clogmia albipunctata*);
Sciaridae (for example, *Bradysia difformis*);
Cecidomyiidae (for example, *Mayetiola destructor* or *Orseolia oryzae*);
Diopsidae (for example, *Diopsis macrophthalma*);
Tipulidae (for example, *Tipula aino*, *Tipula oleracea* (Common cranefly), or *Tipula paludosa* (European cranefly));
and the others.

Coleoptera Pests:
Chrysomelidae (for example, *Diabrotica virgifera virgifera*, *Diabrotica undecimpunctata howardi*, *Diabrotica barberi*, *Diabrotica virgifera zeae*, *Diabrotica balteata*, *Diabrotica speciosa* (Cucurbit Beetle), *Cerotoma trifurcata*, *Oulema melanopus*, *Aulacophora femoralis*, *Phyllotreta striolata*, *Phyllotreta cruciferae* (Cabbage flea beetle), *Phyllotreta pusilla* (Western black flea beetle), *Psylliodes chrysocephala* (Cabbage stem flea beetle), *Leptinotarsa decemlineata*, *Oulema oryzae*, *Colaspis brunnea*, *Chaetocnema pulicaria*, *Chaetocnema confinis*, *Epitrix cucumeris*, *Dicladispa armigera*, *Myochrous denticollis* (southern corn leaf beetle), *Laccoptera quadrimaculata*, or *Epitrix hirtipennis*);
Carabidae (for example, *Stenolophus lecontei* (Seedcorn beetle) or *Clivina impressifrons* (Slender seedcorn beetle));
Scarabaeidae (for example, *Anomala cuprea*, *Anomala rufocuprea*, *Anomala albopilosa*, *Popillia japonica*, *Heptophylla picea*, *Rhizotrogus majalis* (European Chafer), *Tomarus gibbosus*, *Holotrichia* spp., *Phyllophaga* spp. (for example, *Phyllophaga crinita*), or *Diloboderus* spp. (for example, *Diloboderus abderus*));
Curculionidae (for example, *Araecerus coffeae*, *Cylas formicarius*, *Euscepes postfasciatus*, *Hypera postica*, *Sitophilus zeamais*, *Echinocnemus squameus*, *Lissorhoptrus oryzophilus*, *Rhabdoscelus lineatocollis*, *Anthonomus grandis*, *Sphenophorus venatus*, *Sphenophorus callosus* (Southern Corn Billbug), *Sternechus subsignatus* (Soybean stalk weevil), *Sphenophorus levis* (Sugarcane weevil), *Scepticus griseus*, *Scepticus uniformis*, *Zabrotes subfasciatus*, *Tomicus piniperda*, *Hypothenemus hampei* (Coffee Berry Borer), *Aracanthus* spp. (for example, *Aracanthus mourei*), or *Eutinobothrus brasiliensis* (cotton root borer));
Tenebrionidae (for example, *Tribolium castaneum* or *Tribolium confusum*);
Coccinellidae (for example, *Epilachna vigintioctopunctata*);
Bostrychidae (for example, *Lyctus brunneus*);
Ptinidae;
Cerambycidae (for example, *Anoplophora malasiaca* or *Migdolus fryanus*); Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis*, *Agriotes fuscicollis*, *Melanotus legatus*, *Anchastus* spp., *Conoderus* spp., *Ctenicera* spp., *Limonius* spp., or *Aeolus* spp.);
Staphylinidae (for example, *Paederus fuscipes*);
and the others.

Orthoptera Pests:
Acrididae (for example, *Locusta migratoria*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Two striped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya japonica*, or *Patanga succincta*);
Gryllotalpidae (for example, *Gryllotalpa orientalis*);
Gryllidae (for example, *Acheta domesticus* or *Teleogryllus emma*);
Tettigoniidae (for example, *Anabrus simplex* (Mormon cricket));
and the others.

Hymenoptera Pests:
Tenthredinidae (for example, *Athalia rosae* or *Athalia japonica*); *Solenopsis* spp.;
Formicidae (for example, *Atta capiguara* (Brown leaf-cutting ant)); and the others.

Blattodea Pests:
Blattellidae (for example, *Blattella germanica*);
Blattidae (for example, *Periplaneta fuliginosa*, *Periplaneta americana*, *Periplaneta brunnea*, or *Blatta orientalis*);
Termitidae (for example, *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, or *Cornitermes cumulans*); and the others.

EXAMPLES

The following Examples including Preparation examples, Reference preparation examples, Formulation examples, and Test examples, serve to illustrate the present invention in more detail, which should not intend to limit the present invention.

In the present description, Me represents a methyl group, Et represents an ethyl group, Pr represents a propyl group, and Bn represents a benzyl group.

Preparation Example 1-1

To a mixture of the intermediate compound 1 described in the Reference preparation example 1-1 (7.2 g), DMF 80 mL, and pyridine 9.7 mL was added trifluoroacetic anhydride 1.7 mL at room temperature, and then the resulting mixture was heated at 80° C. with stirring for 3 hours. Then, to the resulting mixture was added water 1 L at room temperature, and the precipitates were collected by filtration, and the resulting precipitates were washed with water 200 mL, air-dried, and then subjected to silica gel column chromatography (n-hexane: ethyl acetate=4:1) to give the Present compound 1 represented by the following formula (4.9 g).

Present Compound 1

[Chem.15]

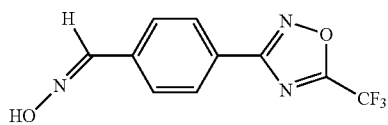

¹H-NMR (DMSO-D₆, 25° C.) δ: 11.62 (1H, s), 8.26 (1H, s), 8.10 (2H, d), 7.83 (2H, d).

Preparation Example 1-2

The compounds of the present invention prepared according to the process described in the Preparation example 1-1 and the physical properties thereof are shown below.
Present Compound 2

[Chem.16]

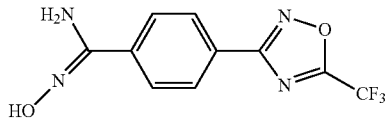

¹H-NMR (DMSO-D₆, 25° C.) δ: 9.94 (1H, s), 8.08 (2H, d), 7.93 (2H, d), 5.99 (2H, s).
Present Compound 23

[Chem.17]

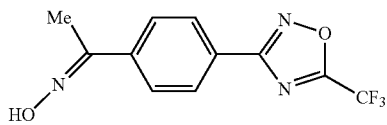

¹H-NMR (CDCl₃, 25° C.) δ: 8.17 (2H, d), 7.83 (2H, d), 7.77 (1H, s), 2.36 (3H, s).
Present Compound 24

[Chem.18]

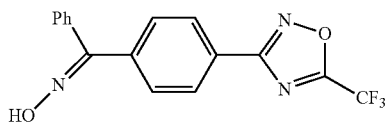

¹H-NMR (CDCl₃, 25° C.) δ: 8.26 (2H, d), 7.61 (2H, d), 7.53-7.35 (5H, m).
Present Compound 25

[Chem.19]

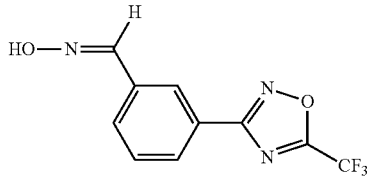

¹H-NMR (CDCl₃, 25° C.) δ: 8.36 (1H, s), 8.24 (1H, s), 8.17 (1H, d), 7.84 (1H, d), 7.59 (1H, t), 7.44 (1H, s).

Preparation Example 2-1

To a mixture of sodium hydride 56 mg and acetonitrile 20 mL was added the Present compound 1 (0.25 g), and the resulting mixture was stirred at room temperature for one hour. To the resulting mixture was added dropwise iodomethane 0.18 mL, and the mixture was stirred at room temperature overnight. To the reaction solution was added a saturated aqueous solution of ammonium chloride, and the mixture was extracted with ethyl acetate. The organic layers were washed with saturated brine, and then dried over anhydrous magnesium sulfate, and concentrated under reduced pressure. The resulting residues were subjected to silica gel column chromatography (n-hexane: ethyl acetate=9:1) to give the Present compound 3 represented by the following formula 0.21 g.
Present Compound 3

[Chem.20]

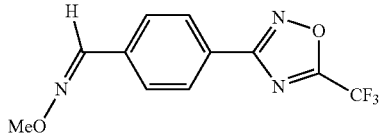

¹H-NMR (CDCl₃, 25° C.) δ: 8.13 (2H, d), 8.11 (1H, s), 7.74 (2H, d), 4.02 (3H, s).

Preparation Example 2-2

The compounds prepared according to the process described in the Preparation example 2-1 and the physical properties thereof are shown below.
The compound represented by formula (a)

[Chem.21]

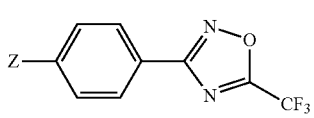

(a)

(wherein Z represents any one substituent indicated in Table 1 to Table 3).
In Table 1 to Table 3, the symbol "●" represents the point of attachment to the benzene ring.
For example, the Present compound 4 is the compound represented by the following formula.
Present Compound 4

[Chem.22]

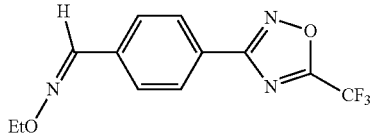

TABLE 1

| Present compound No. | Z | ¹H-NMR (CDCl₃, 25° C.) |
|---|---|---|
| 4 | ![H, N, EtO structure] | δ: 8.12 (2H, d), 8.11 (1H, s), 7.74 (2H, d), 4.27 (2H, q), 1.35 (3H, t). |

TABLE 1-continued

| Present compound No. | Z | ¹H-NMR (CDCl₃, 25° C.) |
|---|---|---|
| 5 | (PrO-CH=N-O-CH=, with H on C) | δ: 8.12 (2H, d), 8.12 (1H, s), 7.74 (2H, d), 4.17 (2H, t), 1.81-1.71 (2H, m), 0.99 (3H, t). |
| 6 | (NC-CH(H)-O-N=CH-) | δ: 8.20 (1H, s), 8.17 (2H, d), 7.78 (2H, d), 4.85 (2H, s). |
| 7 | (MeO-CH(H)-O-N=CH-) | δ: 8.23 (1H, s), 8.14 (2H, d), 7.79 (2H, d), 5.23 (2H, s), 3.51 (3H, s). |
| 8 | (HC≡C-CH(H)-O-N=CH-) | δ: 8.17 (1H, s), 8.14 (2H, d), 7.76 (2H, d), 4.82 (2H, d), 2.53 (1H, t). |
| 9 | (Et-N(Me)-C(=O)-O-N=CH-) | δ: 8.39 (1H, s), 8.18 (2H, d), 7.91 (2H, d), 3.47-3.37 (2H, m), 3.01 (3H, s), 1.21 (3H, t). |

TABLE 2

| Present compound No. | Z | ¹H-NMR (CDCl₃, 25° C.) |
|---|---|---|
| 10 | (H₂N-C(=N-OMe)-) | δ: 8.15 (2H, d), 7.81 (2H, d), 4.84 (2H, br s), 3.96 (3H, s). |
| 11 | (H₂N-C(=N-O-CH(H)-CN)-) | δ: 8.18 (2H, d), 7.82 (2H, d), 4.94 (2H, br s), 4.79 (2H, s). |
| 12 | (MeHN-C(=N-OMe)-) | δ: 8.17 (2H, d), 7.65 (2H, d), 5.26-5.16 (1H, br m), 3.89 (3H, s), 2.76 (3H, d). |
| 13 | (MeHN-C(=N-O-CH(H)-CN)-) | δ: 8.20 (2H, d), 7.66 (2H, d), 5.24-5.16 (1H, br m), 4.72 (2H, s), 2.79 (3H, d). |
| 14 | (Me₂N-C(=N-OMe)-) | δ: 8.17 (2H, d), 7.48 (2H, d), 3.68 (3H, s), 2.71 (6H, s). |
| 15 | (Me₂N-C(=N-O-CH(H)-CN)-) | δ: 8.20 (2H, d), 7.46 (2H, d), 4.50 (2H, s), 2.77 (6H, s). |
| 16 | (NC-C(=N-OMe)-) | δ: 8.21 (2H, d), 7.96 (2H, d), 4.27 (3H, s). |
| 17 | (NC-C(=N-O-CH(H)-CN)-) | δ: 8.26 (2H, d), 8.02 (2H, d), 5.07 (2H, s). |

Preparation Example 3-1

To a mixture of the Present compound 1 (0.18 g) and tetrahydrofuran 10 mL was added propionyl chloride 0.08 mL, and the resulting mixture was stirred at room temperature for 30 minutes. To the resulting mixture was added dropwise diisopropy-lethylamine 0.18 mL, and the mixture was stirred at room temperature overnight. To the reaction solution was added a saturated aqueous solution of sodium hydrogen carbonate, and the mixture was extracted with ethyl acetate. The organic layers were washed with saturated brine, and then dried over anhydrous magnesium sulfate, and concentrated under reduced pressure. The resulting residues were subjected to silica gel column chromatography (chloroform:methanol=99:1) to give the Present compound 18 represented by the following formula 0.10 g.

Present Compound 18

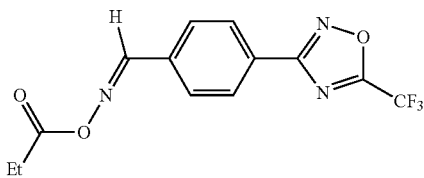
[Chem.23]

$^1$H-NMR (CDCl$_3$, 25° C.) δ: 8.42 (1H, s), 8.20 (2H, d), 7.91 (2H, d), 2.54 (2H, q), 1.28 (3H, t).

Preparation Example 4-1

To a mixture of the Present compound 1 (1.0 g) and DMF 3 mL was added N-chlorosuccinimide 0.52 g, and the resulting mixture was stirred at room temperature overnight. To the resulting reaction solution was added water, and the mixture was extracted with MTBE. The organic layers were washed with saturated brine, and then dried over anhydrous magnesium sulfate, and concentrated under reduced pressure. The resulting residues and DMF 8 mL were mixed, and to the resulting mixture was added 2.0 M solution of methylamine in tetrahydrofuran 15 mL, and the mixture was stirred at room temperature for one hour. To the reaction solution was added water, and the mixture was extracted with ethyl acetate. The organic layers were washed with saturated brine, and then dried over anhydrous magnesium sulfate, and concentrated under reduced pressure. The resulting residues were subjected to silica gel column chromatography (n-hexane: ethyl acetate=1:1) to give the Present compound 19 represented by the following formula 0.56 g.

Present Compound 19

[Chem.24]

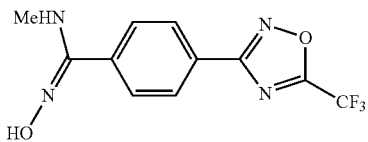

$^1$H-NMR (CDCl$_3$, 25° C.) δ: 8.18 (2H, d), 7.65 (2H, d), 5.30-5.22 (1H, br m), 2.79 (3H, d).

Preparation Example 4-2

The compounds of the present invention prepared according to the process described in the Preparation example 4-1 and the physical properties thereof are shown below.

TABLE 3

| Present compound No. | Z | $^1$H-NMR (CDCl$_3$, 25° C.) |
|---|---|---|
| 20 | Me$_2$N-C(=NOH)- | δ: 8.21 (2H, d), 7.55 (2H, d), 6.40 (1H, s), 2.71 (6H, s). |
| 26 | EtHN-C(=NOH)- | δ: 8.20 (1H, d), 7.68 (1H, d), 5.31-5.17 (1H, br m), 3.16-3.09 (1H, m), 1.15 (2H, t). |
| 27 | PrHN-C(=NOH)- | δ: 8.19 (2H, d), 7.68 (2H, d), 5.37-5.29 (1H, br m), 3.04 (2H, q), 1.57-1.45 (2H, m), 0.91 (3H, t). |
| 28 | iPr-NH-C(=NOH)- | δ: 8.20 (2H, d), 7.69 (2H, d), 5.23-5.02 (1H, br m), 3.58-3.40 (1H, m), 1.15 (6H, d). |
| 29 | cyclopropyl-NH-C(=NOH)- | δ: 8.20 (2H, d), 7.76 (2H, d), 5.64-5.54 (1H, br m), 2.57-2.49 (1H, m), 0.62-0.45 (4H, m). |
| 30 | BnHN-C(=NOH)- | δ: 8.17 (2H, d), 7.66 (2H, d), 7.38-7.30 (3H, m), 7.25-7.21 (2H, m), 5.74 (1H, s), 4.30 (2H, d). |
| 31 | MeO-CH$_2$CH$_2$-NH-C(=NOH)- | δ: 8.19 (2H, d), 7.69 (2H, d), 5.71-5.58 (1H, br m), 3.43 (2H, t), 3.38 (3H, s), 3.25 (2H, q). |
| 32 | MeEtN-C(=NOH)- | δ: 8.23 (2H, d), 7.58 (2H, d), 6.36 (1H, s), 3.01 (2H, q), 2.81 (3H, s), 1.04 (3H, t). |
| 33 | PhMeN-C(=NOH)- | δ: 8.11 (2H, d), 7.81 (1H, s), 7.74 (2H, d), 7.25 (2H, t), 6.90 (1H, t), 6.83 (2H, d), 3.35 (3H, s). |
| 34 | BnMeN-C(=NOH)- | δ: 8.24 (2H, d), 7.65 (2H, d), 7.41-7.31 (3H, m), 7.26-7.21 (2H, m), 4.19 (2H, s), 2.78 (3H, s). |

TABLE 3-continued

| Present compound No. | Z | ¹H-NMR (CDCl₃, 25° C.) |
|---|---|---|
| 35 | 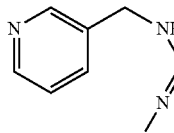 | δ: 8.57-8.53 (1H, m), 8.47-8.45 (1H, m), 8.17 (2H, d), 7.65 (2H, d), 7.60-7.54 (1H, m), 7.32-7.27 (1H, m), 5.81-5.73 (1H, br m), 4.33 (2H, d). |
| 36 | 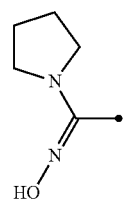 | δ: 8.23 (2H, d), 7.58 (2H, d), 6.49 (1H, s), 3.16 (4H, t), 1.90 (4H, t). |
| 37 | 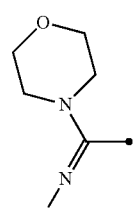 | δ: 8.17 (2H, d), 7.70 (2H, d), 7.44 (1H, br s), 3.79 (4H, t), 3.44 (4H, t). |

Preparation Example 5-1

To a mixture of the Present compound 1 (1.0 g) and DMF 3 mL was added N-chlorosuccinimide 0.52 g, and the resulting mixture was stirred at room temperature overnight. To the resulting reaction solution was added water, and the mixture was extracted with MTBE. The organic layers were washed with saturated brine, and then dried over anhydrous magnesium sulfate, and concentrated under reduced pressure. The resulting residues and DMF 5 mL were mixed, and to the resulting mixture was added a mixture of triethylamine 0.54 mL, sodium cyanide 0.23 g, and water 1 mL, and the mixture was stirred at room temperature overnight. To the reaction solution was added water, and the mixture was extracted with ethyl acetate. The organic layers were washed with saturated brine, and then dried over anhydrous magnesium sulfate, and concentrated under reduced pressure. The resulting residues were subjected to silica gel column chromatography (n-hexane: ethyl acetate=4:1) to give the Present compound 21 represented by the following formula 0.52 g.

Present Compound 21

[Chem.25]

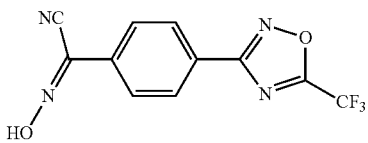

¹H-NMR (CDCl₃, 25° C.) δ: 9.39 (1H, br s), 8.22 (2H, d), 7.97 (2H, d).

Preparation Example 6-1

To a mixture of the Present compound 1 described in the Preparation example 1-1 (1.0 g) and DMF 3 mL was added N-chlorosuccinimide 0.52 g, and the resulting mixture was stirred at room temperature overnight. To the reaction solution was added water, and the mixture was extracted with MTBE. The organic layers were washed with saturated brine, and then dried over anhydrous magnesium sulfate, and concentrated under reduced pressure. The resulting residues and methanol 10 mL were mixed, and to the resulting mixture was added sodium methoxide 0.42 g, and the mixture was stirred at room temperature overnight. To the reaction solution was added a saturated aqueous solution of ammonium chloride, and the mixture was extracted with ethyl acetate. The organic layers were washed with saturated brine, and then dried over anhydrous magnesium sulfate, and concentrated under reduced pressure. The resulting residues were subjected to silica gel column chromatography (n-hexane: ethyl acetate=4:1) to give the Present compound 22 represented by the following formula 0.09 g.

Present Compound 22

[Chem.26]

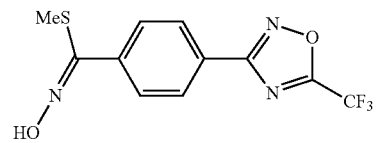

¹H-NMR (CDCl₃, 25° C.) δ: 8.15 (2H, d), 7.84 (2H, d), 6.92 (1H, s), 4.07 (3H, s).

Preparation Example 6-2

The compound of the present invention prepared according to the process described in the Preparation example 6-1 and the physical property thereof are shown below.

Present Compound 38

[Chem.27]

¹H-NMR (CDCl₃, 25° C.) δ: 8.23 (2H, d), 8.04 (1H, s), 7.69 (2H, d), 2.19 (3H, s).

Preparation Example 7-1

A mixture of the intermediate compound 5 (0.44 g), isopropyl alcohol 10 mL, and a 50% aqueous solution of hydroxylamine 0.27 mL was heated under reflux with stirring for 3 hours. The mixture was cooled to room temperature, and then concentrated under reduced pressure. The resulting residues were subjected to silica gel column chromatography (n-hexane: ethyl acetate=3:7) to give the Present compound 39 represented by the following formula 0.22 g.

Present Compound 39

[Chem.28]

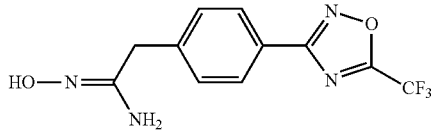

¹H-NMR (CDCl₃, 25° C.) δ: 8.12 (2H, d), 7.49 (2H, d), 6.43 (1H, br s), 4.52 (2H, br s), 3.57 (2H, s).

Reference Preparation Example 1-1

A mixture of 4-cyanobenzaldehyde 25 g, isopropyl alcohol 500 mL, and a 50% aqueous solution of hydroxylamine 37.5 mL was heated under reflux with stirring for 2 hours. The mixture was cooled to room temperature, and then water 1 L was added thereto, and the mixture was stirred at room temperature overnight. The precipitates were collected by filtration, and the resulting precipitates were washed with water 200 mL and ethanol 200 mL, and air-dried to give the intermediate compound 1 represented by the following formula 9.2 g.

Intermediate Compound 1

[Chem.29]

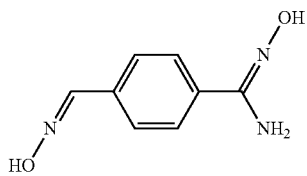

¹H-NMR (DMSO-D₆, 25° C.) δ: 11.27 (1H, s), 9.70 (1H, s), 8.12 (1H, s), 7.67 (2H, d), 7.55 (2H, d), 5.81 (2H, br s).

The intermediate compounds prepared according to the process described in the Reference preparation example 1-1 and the physical properties thereof are shown below.

Intermediate Compound 2

[Chem.30]

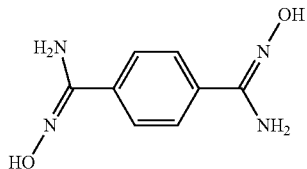

¹H-NMR (DMSO-D₆, 25° C.) δ: 9.68 (2H, s), 7.68-7.65 (4H, br m), 5.83 (4H, br s).

Intermediate Compound 3

[Chem.31]

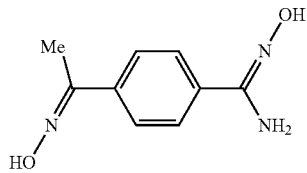

¹H-NMR (DMSO-D₆, 25° C.) δ: 11.24 (1H, s), 9.68 (1H, s), 7.72-7.61 (4H, m), 5.81 (2H, s), 2.16 (3H, s).

Intermediate Compound 4

[Chem.32]

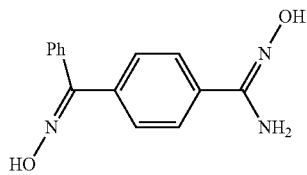

¹H-NMR (DMSO-D₆, 25° C.) δ: 9.92 (1H, s), 7.86 (2H, d), 7.74-7.55 (7H, m), 5.95 (2H, s).

Reference Preparation Example 2-1

A mixture of 4-cyanophenylacetonitrile 2.0 g, ethanol 15 mL, and a 50% aqueous solution of hydroxylamine 0.83 mL was heated under reflux with stirring for 2 hours. The mixture was cooled to room temperature, and then water 1 L was added thereto, and the mixture was stirred at room temperature overnight. The precipitates were collected by filtration, and the resulting precipitates were washed with ethanol 20 mL. A mixture of the resulting solids and ethyl acetate 200 mL was filtered, and the filtrate was concentrated under reduced pressure. To a mixture of the resulting residues 0.57 g, DMF 10 mL, and pyridine 0.79 mL was added trifluoroacetic anhydride 0.55 mL at room temperature, and then the mixture was heated at 80° C. with stirring for 7 hours. To the reaction solution was added water, and the mixture was extracted with ethyl acetate. The organic layers were washed with saturated brine, and then dried over anhydrous magnesium sulfate, and concentrated under reduced pressure. The resulting residues were subjected to silica gel column chromatography (n-hexane: ethyl acetate=7:3) to give the intermediate compound 5 represented by the following formula 0.44 g.

Intermediate Compound 5

[Chem.33]

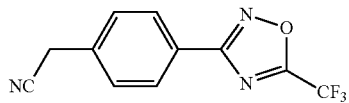

¹H-NMR (CDCl₃, 25° C.) δ: 8.17 (2H, d), 7.54 (2H, d), 3.88 (2H, s).

The compound represented by formula (T1)

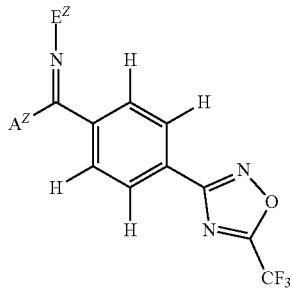

wherein the combination of $E^Z$ and $A^Z$ is any one combination described in the Substituent numbers ZA1 to ZA8896 (hereinafter the compounds represented by formula (T1) wherein the Substituent numbers are ZA1 to ZA8896 are referred to as "Present compounds ZA1 to ZA8896", and the "Present compounds ZA1 to ZA8896" are collectively referred to as "Present compound SX1") may be prepared according to the above processes.

Substituent number ZA1 to Substituent number ZA8896 represent combinations of $E^Z$ and $A^Z$ in the compound represented by formula (T1), the compound represented by formula (T2), the compound represented by formula (T3), the compound represented by formula (T4), the compound represented by formula (T5), the compound represented by formula (T6), the compound represented by formula (T7), the compound represented by formula (T8), the compound represented by formula (T9), the compound represented by formula (T10), the compound represented by formula (T11), the compound represented by formula (T12), the compound represented by formula (T13), or the compound represented by formula (T14), and are hereinafter referred to as [Substituent number; $E^Z,A^Z$].

For example, Substituent number ZA2 represents a combination wherein $E^Z$ represents a methoxy group and $A^Z$ represents a hydrogen atom.

In the following combinations of Substituent numbers ZA1 to ZA8896, H represents a hydrogen atom, O represents an oxygen atom, S represents a sulfur atom, N represents a nitrogen atom, Cl represents a chlorine atom, F represents a fluorine atom, Br represents a bromine atom, I represents an iodine atom, $OCH_3$ represents a methoxy group, $CF_3$ represents a trifluoromethyl group, $CH_2Ph$ represents a benzyl group, CN represents a cyano group, $NO_2$ represents a nitro group, OH represents a hydroxy group, SH represents a sulfanyl group, $NH_2$ represents an amino group, $OCH_2CH=CH_2$ represents an allyloxy group, $OCH_2C\equiv CH$ represents a propargyloxy group, α-Pr represents a cyclopropyl group, c-Bu represents a cyclobutyl group, c-Pen represents a cyclopentyl group, c-Hex represents a cyclohexyl group, Ph represents a phenyl group, 2-Py represents a 2-pyridyl group, 3-Py represents a 3-pyridyl group, 4-Py represents a 4-pyridyl group, Pyr represents a 1-pyrrolidinyl group, Pip represents a 1-piperidyl group, and Mor represents a morpholin-4-yl group.

[Substituent Number; $E^Z,A^Z$]:

[ZA1;OH,H], [ZA2;$OCH_3$,H], [ZA3;$OCH_2CH_3$,H], [ZA4;$OCH(CH_3)_2$,H], [ZA5;$O(CH_2)_2CH_3$,H], [ZA6;$O(CH_2)_3CH_3$,H], [ZA7;$O(CH_2)_4CH_3$,H], [ZA8;$O(CH_2)_5CH_3$,H], [ZA9;$OCH_2CH=CH_2$,H], [ZA10;$OCH_2C\equiv CH$,H], [ZA11;$OCH_2C\equiv CCH_3$,H], [ZA12;O-c-Pr,H], [ZA13;O-c-Bu,H], [ZA14;O-c-Pen,H], [ZA15;O-c-Hex,H], [ZA16;OPh,H], [ZA17;O(2-Py),H], [ZA18;O(3-Py),H], [ZA19;O(4-Py),H], [ZA20;$OCF_3$,H], [ZA21;$OCH_2Ph$,H], [ZA22;$OCH_2$(2-Py),H], [ZA23;$OCH_2$(3-Py),H], [ZA24;$OCH_2$(4-Py),H], [ZA25;$OCH_2CN$,H], [ZA26;$OCH_2NO_2$,H], [ZA27;$O(CH_2)_2$F,H], [ZA28;$O(CH_2)_2Cl$,H], [ZA29;$O(CH_2)_2Br$,H], [ZA30;$O(CH_2)_2I$,H], [ZA31;$O(CH_2)_2CF_3$,H], [ZA32;$O(CH_2)_2CN$,H], [ZA33;$O(CH_2)_2NO_2$,H], [ZA34;$O(CH_2)_2Ph$,H], [ZA35;$O(CH_2)_2$(2-Py),H], [ZA36;$O(CH_2)_2$(3-Py),H], [ZA37;$O(CH_2)_2$(4-Py),H], [ZA38;$O(CH_2)_2OH$,H], [ZA39;$O(CH_2)_2OCH_3$,H], [ZA40;$O(CH_2)_2SH$,H], [ZA41;$O(CH_2)_2SCH_3$,H], [ZA42;$O(CH_2)_2NH_2$,H], [ZA43;$O(CH_2)_2NHCH_3$,H], [ZA44;$O(CH_2)_2N(CH_3)_2$,H], [ZA45;$O(CH_2)_2NHPh$,H], [ZA46;$O(CH_2)_2NHCH_2Ph$,H], [ZA47;$O(CH_2)_2N(CH_3)CH_2Ph$,H], [ZA48;$O(CH_2)_2S(O)CH_3$,H], [ZA49;$O(CH_2)_2S(O)CH_2CH_3$,H], [ZA50;$O(CH_2)_2S(O)Ph$,H], [ZA51;$O(CH_2)_2S(O)_2CH_3$,H], [ZA52;$O(CH_2)_2S(O)_2CH_2CH_3$,H], [ZA53;$O(CH_2)_2S(O)_2Ph$,H], [ZA54;$O(CH_2)_2C(O)CH_3$,H], [ZA55;$O(CH_2)_2C(O)CH_2CH_3$,H], [ZA56;$O(CH_2)_2C(O)Ph$,H], [ZA57;$O(CH_2)_2C(S)CH_3$,H], [ZA58;$O(CH_2)_2C(S)CH_2CH_3$,H], [ZA59;$O(CH_2)_2C(S)Ph$,H], [ZA60;$O(CH_2)_2S(O)_2NHCH_3$,H], [ZA61;$O(CH_2)_2S(O)_2N(CH_3)_2$,H], [ZA62;$O(CH_2)_2S(O)_2NHPh$,H], [ZA63;$O(CH_2)_2S(O)_2N(CH_3)Ph$,H], [ZA64;$O(CH_2)_2C(O)NH_2$,H], [ZA65;$O(CH_2)_2C(O)NHCH_3$,H], [ZA66;$O(CH_2)_2C(O)N(CH_3)_2$,H], [ZA67;$O(CH_2)_2C(O)NHPh$,H], [ZA68;$O(CH_2)_2C(O)N(CH_3)Ph$,H], [ZA69;$O(CH_2)_2C(O)OCH_3$,H], [ZA70;$O(CH_2)_2C(O)OCH_2CH_3$,H], [ZA71;$O(CH_2)_2NHC(O)CH_3$,H], [ZA72;$O(CH_2)_2NHC(O)CH_2CH_3$,H], [ZA73;$O(CH_2)_2NHC(O)Ph$,H], [ZA74;$O(CH_2)_2NCH_3C(O)CH_3$,H], [ZA75;$O(CH_2)_2NCH_3C(O)CH_2CH_3$,H], [ZA76;$O(CH_2)_2NCH_3C(O)Ph$,H], [ZA77;$O(CH_2)_2NHC(O)OCH_3$,H], [ZA78;$O(CH_2)_2NHC(O)OCH_2CH_3$,H], [ZA79;$O(CH_2)_2NHC(O)OPh$,H], [ZA80;$O(CH_2)_2NCH_3C(O)OCH_3$,H], [ZA81;$O(CH_2)_2NCH_3C(O)OCH_2CH_3$,H], [ZA82;$O(CH_2)_2NCH_3C(O)OPh$,H], [ZA83;$O(CH_2)_2NHC(O)NHCH_3$,H], [ZA84;$O(CH_2)_2NHC(O)NHCH_2CH_3$,H], [ZA85;$O(CH_2)_2NHC(O)NHPh$,H], [ZA86;$O(CH_2)_2NHC(O)N(CH_3)_2$,H], [ZA87;$O(CH_2)_2NHC(O)N(CH_3)CH_2CH_3$,H], [ZA88;$O(CH_2)_2NHC(O)N(CH_3)Ph$,H], [ZA89;$O(CH_2)_2NHC(O)N(CH_2CH_3)_2$,H], [ZA90;$O(CH_2)_2NCH_3C(O)NHCH_3$,H], [ZA91;$O(CH_2)_2NCH_3C(O)NHCH_2CH_3$,H], [ZA92;$O(CH_2)_2NCH_3C(O)NHPh$,H], [ZA93;$O(CH_2)_2NCH_3C(O)N(CH_3)_2$,H], [ZA94;$O(CH_2)_2NCH_3C(O)N(CH_3)CH_2CH_3$,H], [ZA95;$O(CH_2)_2NCH_3C(O)N(CH_3)Ph$,H], [ZA96;$O(CH_2)_2NCH_3C(O)N(CH_2CH_3)_2$,H], [ZA97;$O(CH_2)_2OC(O)CH_3$,H], [ZA98;$O(CH_2)_2OC(O)CH_2CH_3$,H], [ZA99;$O(CH_2)_2OC(O)Ph$,H], [ZA100;$O(CH_2)_2OC(O)OCH_3$,H], [ZA101;$O(CH_2)_2OC(O)OCH_2CH_3$,H], [ZA102;$O(CH_2)_2OC(O)OPh$,H], [ZA103;$O(CH_2)_2OC(O)NHCH_3$,H], [ZA104;$O(CH_2)_2OC(O)NHCH_2CH_3$,H], [ZA105;$O(CH_2)_2OC(O)NHPh$,H], [ZA106;$O(CH_2)_2OC(O)N(CH_3)_2$,H], [ZA107;$O(CH_2)_2OC(O)N(CH_3)CH_2CH_3$,H], [ZA108;$O(CH_2)_2OC(O)N(CH_3)Ph$,H], [ZA109;$O(CH_2)_2OC(O)N(CH_2CH_3)_2$,H], [ZA110;$O(CH_2)_2SC(O)CH_3$,H], [ZA111;$O(CH_2)_2SC(O)CH_2CH_3$,H], [ZA112;$O(CH_2)_2SC(O)Ph$,H], [ZA113;$O(CH_2)_2SC(O)OCH_3$,H], [ZA114;$O(CH_2)_2SC(O)OCH_2CH_3$,H], [ZA115;$O(CH_2)_2SC(O)OPh$,H], [ZA116;$O(CH_2)_2S(O)_2NHCH_3$,H], [ZA117;$O(CH_2)_2S(O)_2NHCH_2CH_3$,H], [ZA118;$O(CH_2)_2S(O)_2NHPh$,H], [ZA119;$O(CH_2)_2S(O)_2N(CH_3)_2$,H], [ZA120;$O(CH_2)_2S(O)_2N(CH_3)CH_2CH_3$,H], [ZA121;$O(CH_2)_2S(O)_2N(CH_3)Ph$,H], [ZA122;$O(CH_2)_2S(O)_2N(CH_2CH_3)_2$,H], [ZA123;$O(CH_2)_3F$,H], [ZA124;$O(CH_2)_3Cl$,H], [ZA125;$O(CH_2)_3Br$,H], [ZA126;$O(CH_2)_3I$,H], [ZA127;$O(CH_2)_3CF_3$,H], [ZA128;$O(CH_2)_3CN$,H], [ZA129;$O(CH_2)_3NO_2$,H],

[ZA130;O(CH$_2$)$_3$Ph,H], [ZA131;O(CH$_2$)$_3$(2-Py),H], [ZA132;O(CH$_2$)$_3$(3-Py),H], [ZA133;O(CH$_2$)$_3$(4-Py),H], [ZA134;O(CH$_2$)$_3$OH,H], [ZA135;O(CH$_2$)$_3$OCH$_3$,H], [ZA136;O(CH$_2$)$_3$OCH$_2$CH$_3$,H], [ZA137;O(CH$_2$)$_3$SH,H], [ZA138;O(CH$_2$)$_3$SCH$_3$,H], [ZA139;O(CH$_2$)$_3$SCH$_2$CH$_3$,H], [ZA140;O(CH$_2$)$_3$NH$_2$,H], [ZA141;O(CH$_2$)$_3$NHCH$_3$,H], [ZA142;O(CH$_2$)$_3$N(CH$_3$)$_2$,H], [ZA143;O(CH$_2$)$_4$F,H], [ZA144;O(CH$_2$)$_4$Cl,H], [ZA145;O(CH$_2$)$_4$CF$_3$,H], [ZA146;O(CH$_2$)$_4$CN,H], [ZA147;O(CH$_2$)$_4$NO$_2$,H], [ZA148;O(CH$_2$)$_4$Ph,H], [ZA149;O(CH$_2$)$_4$OH,H], [ZA150;O(CH$_2$)$_4$OCH$_3$,H], [ZA151;O(CH$_2$)$_4$SH,H], [ZA152;O(CH$_2$)$_4$SCH$_3$,H], [ZA153;O(CH$_2$)$_4$NH$_2$,H], [ZA154;O(CH$_2$)$_4$NHCH$_3$,H], [ZA155;O(CH$_2$)$_4$N(CH$_3$)$_2$,H], [ZA156;O(CH$_2$)$_5$F,H], [ZA157;O(CH$_2$)$_5$Cl,H], [ZA158;O(CH$_2$)$_5$CF$_3$,H], [ZA159;O(CH$_2$)$_5$CN,H], [ZA160;O(CH$_2$)$_5$NO$_2$,H], [ZA161;O(CH$_2$)$_5$Ph,H], [ZA162;O(CH$_2$)$_5$OH,H], [ZA163;O(CH$_2$)$_5$OCH$_3$,H], [ZA164;O(CH$_2$)$_5$SH,H], [ZA165;O(CH$_2$)$_5$SCH$_3$,H], [ZA166;O(CH$_2$)$_5$NH$_2$,H], [ZA167;O(CH$_2$)$_5$NHCH$_3$,H], [ZA168;O(CH$_2$)$_5$N(CH$_3$)$_2$,H], [ZA169;O(CH$_2$)$_6$F,H], [ZA170;O(CH$_2$)$_6$Cl,H], [ZA171;O(CH$_2$)$_6$CF$_3$,H], [ZA172;O(CH$_2$)$_6$CN,H], [ZA173;O(CH$_2$)$_6$NO$_2$,H], [ZA174;O(CH$_2$)$_6$Ph,H], [ZA175;O(CH$_2$)$_6$OH,H], [ZA176;O(CH$_2$)$_6$OCH$_3$,H], [ZA177;O(CH$_2$)$_6$SH,H], [ZA178;O(CH$_2$)$_6$SCH$_3$,H], [ZA179;O(CH$_2$)$_6$NH$_2$,H], [ZA180;O(CH$_2$)$_6$NHCH$_3$,H], [ZA181;O(CH$_2$)$_6$N(CH$_3$)$_2$,H], [ZA182;OC(O)CH$_3$,H], [ZA183;OC(O)CH$_2$CH$_3$,H], [ZA184;OC(O)CH(CH$_3$)$_2$,H], [ZA185;OC(O)(CH$_2$)$_2$CH$_3$,H], [ZA186;OC(O)(CH$_2$)$_3$CH$_3$,H], [ZA187;OC(O)(CH$_2$)$_4$CH$_3$,H], [ZA188;OC(O)(CH$_2$)$_5$CH$_3$,H], [ZA189;OC(O)CH$_2$CH=CH$_2$,H], [ZA190;OC(O)CH$_2$C≡CH,H], [ZA191;OC(O)CH$_2$C≡CCH$_3$,H], [ZA192;OC(O)c-Pr,H], [ZA193;OC(O)c-Bu,H], [ZA194;OC(O)c-Pen,H], [ZA195;OC(O)c-Hex,H], [ZA196;OC(O)Ph,H], [ZA197;OC(O)(2-Py),H], [ZA198;OC(O)(3-Py),H], [ZA199;OC(O)(4-Py),H], [ZA200;OC(O)CF$_3$,H], [ZA201;OC(O)CH$_2$Ph,H], [ZA202;OC(O)CH$_2$(2-Py),H], [ZA203;OC(O)CH$_2$(3-Py),H], [ZA204;OC(O)CH$_2$(4-Py),H], [ZA205;OC(O)CH$_2$CN,H], [ZA206;OC(O)CH$_2$NO$_2$,H], [ZA207;OC(O)(CH$_2$)$_2$F,H], [ZA208;OC(O)(CH$_2$)$_2$Cl,H], [ZA209;OC(O)(CH$_2$)$_2$CF$_3$,H], [ZA210;OC(O)(CH$_2$)$_2$CN,H], [ZA211;OC(O)(CH$_2$)$_2$NO$_2$,H], [ZA212;OC(O)(CH$_2$)$_2$Ph,H], [ZA213;OC(O)(CH$_2$)$_2$OCH$_3$,H], [ZA214;OC(O)(CH$_2$)$_3$F,H], [ZA215;OC(O)(CH$_2$)$_3$Cl,H], [ZA216;OC(O)(CH$_2$)$_3$CF$_3$,H], [ZA217;OC(O)(CH$_2$)$_3$CN,H], [ZA218;OC(O)(CH$_2$)$_3$NO$_2$,H], [ZA219;OC(O)(CH$_2$)$_3$Ph,H], [ZA220;OC(O)(CH$_2$)$_3$OCH$_3$,H], [ZA221;OC(O)(CH$_2$)$_4$F,H], [ZA222;OC(O)(CH$_2$)$_4$Cl,H], [ZA223;OC(O)(CH$_2$)$_4$CF$_3$,H], [ZA224;OC(O)(CH$_2$)$_4$CN,H], [ZA225;OC(O)(CH$_2$)$_4$NO$_2$,H], [ZA226;OC(O)(CH$_2$)$_4$Ph,H], [ZA227;OC(O)(CH$_2$)$_4$OCH$_3$,H], [ZA228;OC(O)(CH$_2$)$_5$F,H], [ZA229;OC(O)(CH$_2$)$_5$Cl,H], [ZA230;OC(O)(CH$_2$)$_5$CF$_3$,H], [ZA231;OC(O)(CH$_2$)$_5$CN,H], [ZA232;OC(O)(CH$_2$)$_5$NO$_2$,H], [ZA233;OC(O)(CH$_2$)$_5$Ph,H], [ZA234;OC(O)(CH$_2$)$_5$OCH$_3$,H], [ZA235;OC(O)(CH$_2$)$_6$F,H], [ZA236;OC(O)(CH$_2$)$_6$Cl,H], [ZA237;OC(O)(CH$_2$)$_6$CF$_3$,H], [ZA238;OC(O)(CH$_2$)$_6$CN,H], [ZA239;OC(O)(CH$_2$)$_6$NO$_2$,H], [ZA240;OC(O)(CH$_2$)$_6$Ph,H], [ZA241;OC(O)(CH$_2$)$_6$OCH$_3$,H], [ZA242;OC(O)NH$_2$,H], [ZA243;OC(O)NHCH$_3$,H], [ZA244;OC(O)NHCH$_2$CH$_3$,H], [ZA245;OC(O)NH(CH$_2$)$_2$CH$_3$,H], [ZA246;OC(O)NH(CH$_2$)$_3$CH$_3$,H], [ZA247;OC(O)NH(CH)$_4$CH$_3$,H], [ZA248;OC(O)NH(CH$_2$)$_5$CH$_3$,H], [ZA249;OC(O)NHCH(CH$_3$)$_2$,H], [ZA250;OC(O)NHCH$_2$F,H], [ZA251;OC(O)NHCH$_2$Cl,H], [ZA252;OC(O)NHCH$_2$CN,H], [ZA253;OC(O)NHCH$_2$OCH$_3$,H], [ZA254;OC(O)NHCH$_2$Ph,H], [ZA255;OC(O)NH(CH$_2$)$_2$F,H], [ZA256;OC(O)NH(CH$_2$)$_2$Cl,H], [ZA257;OC(O)NH(CH$_2$)$_2$CN,H], [ZA258;OC(O)NH(CH$_2$)$_2$OCH$_3$,H], [ZA259;OC(O)NH(CH$_2$)$_2$Ph,H], [ZA260;OC(O)NH(CH$_2$)$_3$F,H], [ZA261;OC(O)NH(CH$_2$)$_3$Cl,H], [ZA262;OC(O)NH(CH$_2$)$_3$CN,H], [ZA263;OC(O)NH(CH$_2$)$_3$OCH$_3$,H], [ZA264;OC(O)NH(CH$_2$)$_3$Ph,H], [ZA265;OC(O)NH(CH$_2$)$_4$F,H], [ZA266;OC(O)NH(CH$_2$)$_4$Cl,H], [ZA267;OC(O)NH(CH$_2$)$_4$CN,H], [ZA268;OC(O)NH(CH$_2$)$_4$OCH$_3$,H], [ZA269;OC(O)NH(CH$_2$)$_4$Ph,H], [ZA270;OC(O)NHPh,H], [ZA271;OC(O)NH(2-Py),H], [ZA272;OC(O)NH(3-Py),H], [ZA273;OC(O)NH(4-Py),H], [ZA274;OC(O)N(CH$_3$)$_2$,H], [ZA275;OC(O)N(CH$_3$)CH$_2$CH$_3$,H], [ZA276;OC(O)N(CH$_3$)(CH$_2$)$_2$CH$_3$,H], [ZA277;OC(O)N(CH$_3$)(CH$_2$)$_3$CH$_3$,H], [ZA278;OC(O)N(CH$_3$)(CH$_2$)$_4$CH$_3$,H], [ZA279;OC(O)N(CH$_3$)(CH$_2$)$_5$CH$_3$,H], [ZA280;OC(O)N(CH$_3$)CH(CH$_3$)$_2$,H], [ZA281;OC(O)N(CH$_3$)CH$_2$F,H], [ZA282;OC(O)N(CH$_3$)CH$_2$Cl,H], [ZA283;OC(O)N(CH$_3$)CH$_2$CN,H], [ZA284;OC(O)N(CH$_3$)CH$_2$OCH$_3$,H], [ZA285;OC(O)N(CH$_3$)CH$_2$Ph,H], [ZA286;OC(O)N(CH$_3$)(CH$_2$)$_2$F,H], [ZA287;OC(O)N(CH$_3$)(CH$_2$)$_2$Cl,H], [ZA288;OC(O)N(CH$_3$)(CH$_2$)$_2$CN,H], [ZA289;OC(O)N(CH$_3$)(CH$_2$)$_2$OCH$_3$,H], [ZA290;OC(O)N(CH$_3$)(CH$_2$)$_2$Ph,H], [ZA291;OC(O)N(CH$_3$)(CH$_2$)$_3$F,H], [ZA292;OC(O)N(CH$_3$)(CH$_2$)$_3$Cl,H], [ZA293;OC(O)N(CH$_3$)(CH$_2$)$_3$CN,H], [ZA294;OC(O)N(CH$_3$)(CH$_2$)$_3$OCH$_3$,H], [ZA295;OC(O)N(CH$_3$)(CH$_2$)$_3$Ph,H], [ZA296;OC(O)N(CH$_3$)(CH$_2$)$_4$F,H], [ZA297;OC(O)N(CH$_3$)(CH$_2$)$_4$Cl,H], [ZA298;OC(O)N(CH$_3$)(CH$_2$)$_4$CN,H], [ZA299;OC(O)N(CH$_3$)(CH$_2$)$_4$OCH$_3$,H], [ZA300;OC(O)N(CH)(CH$_2$)$_4$Ph,H], [ZA31;OC(O)N(CH$_3$)Ph,H], [ZA302;OC(O)N(CH$_3$)(2-Py),H], [ZA303;OC(O)N(CH$_3$)(3-Py),H], [ZA304;OC(O)N(CH$_3$)(4-Py),H], [ZA305;OC(O)N(CH$_2$CH$_3$)$_2$,H], [ZA306;OC(O)(Pyr),H], [ZA307;OC(O)(Pip),H], [ZA308;OC(O)(Mor),H], [ZA309;OC(O)OCH$_3$,H], [ZA310;OC(O)OCH$_2$CH$_3$,H], [ZA311;OC(O)OCH(CH$_3$)$_2$,H], [ZA312;OC(O)O(CH$_2$)$_2$CH$_3$,H], [ZA313;OC(O)O(CH$_2$)$_3$CH$_3$,H], [ZA314;OC(O)O(CH$_2$)$_4$CH$_3$,H], [ZA315;OC(O)O(CH$_2$)$_5$CH$_3$,H], [ZA316;OC(O)OCH$_2$CH=CH$_2$,H], [ZA317;OC(O)OCH$_2$C≡CH,H], [ZA318;OC(O)OCH$_2$C≡CCH$_3$,H], [ZA319;OC(O)O-c-Pr,H], [ZA320;OC(O)O-c-Bu,H], [ZA321;OC(O)O-c-Pen,H], [ZA322;OC(O)O-c-Hex,H], [ZA323;OC(O)OPh,H], [ZA324;OC(O)O(2-Py),H], [ZA325;OC(O)O(3-Py),H], [ZA326;OC(O)O(4-Py),H], [ZA327;OC(O)OCF$_3$,H], [ZA328;OC(O)OCH$_2$Ph,H], [ZA329;OC(O)OCH$_2$(2-Py),H], [ZA330;OC(O)OCH$_2$(3-Py),H], [ZA331;OC(O)OCH$_2$(4-Py),H], [ZA332;OC(O)OCH$_2$CN,H], [ZA333;OC(O)OCH$_2$NO$_2$,H], [ZA334;OC(O)O(CH$_2$)$_2$F,H], [ZA335;OC(O)O(CH$_2$)$_2$Cl,H], [ZA336;OC(O)O(CH$_2$)$_2$CF$_3$,H], [ZA337;OC(O)O(CH$_2$)$_2$CN,H], [ZA338;OC(O)O(CH$_2$)$_2$NO$_2$,H], [ZA339;OC(O)O(CH$_2$)$_2$Ph,H], [ZA340;OC(O)O(CH$_2$)$_2$OCH$_3$,H], [ZA341;OC(O)O(CH$_2$)$_3$F,H], [ZA342;OC(O)O(CH$_2$)$_3$Cl,H], [ZA343;OC(O)O(CH$_2$)$_3$CF$_3$,H], [ZA344;OC(O)O(CH$_2$)$_3$CN,H], [ZA345;OC(O)O(CH$_2$)$_3$NO$_2$,H], [ZA346;OC(O)O(CH$_2$)$_3$Ph,H], [ZA347;OC(O)O(CH$_2$)$_3$OCH$_3$,H], [ZA348;OC(O)O(CH$_2$)$_4$F,H], [ZA349;OC(O)O(CH$_2$)$_4$Cl,H], [ZA350;OC(O)O(CH$_2$)$_4$CF$_3$,H], [ZA351;OC(O)O(CH$_2$)$_4$CN,H], [ZA352;OC(O)O(CH$_2$)$_4$NO$_2$,H], [ZA353;OC(O)O(CH$_2$)$_4$Ph,H], [ZA354;OC(O)O(CH$_2$)$_4$OCH$_3$,H], [ZA355;OC(O)O(CH$_2$)$_5$F,H], [ZA356;OC(O)O(CH$_2$)$_5$Cl,H], [ZA357;OC(O)O(CH$_2$)$_5$CF$_3$,H], [ZA358;OC(O)O(CH$_2$)$_5$CN,H], [ZA359;OC(O)O(CH$_2$)$_5$NO$_2$,H], [ZA360;OC(O)O(CH$_2$)$_5$Ph,H], [ZA361;OC(O)O(CH$_2$)$_5$OCH$_3$,H], [ZA362;OC(O)O(CH$_2$)$_6$F,H], [ZA363;OC(O)O(CH$_2$)$_6$Cl,H], [ZA364;OC(O)O(CH$_2$)$_6$CF$_3$,H], [ZA365;OC(O)O(CH$_2$)$_6$CN,H], [ZA366;OC(O)O(CH$_2$)$_6$NO$_2$,H], [ZA367;OC(O)O(CH$_2$)$_6$Ph,H], [ZA368;OC(O)O(CH$_2$)$_6$OCH$_3$,H], [ZA369;OS(O)$_2$CH$_3$,H], [ZA370;OS(O)$_2$CH$_2$CH$_3$,H], [ZA371;OS(O)$_2$CH(CH$_3$)$_2$,H], [ZA372;OS(O)$_2$(CH$_2$)$_2$CH$_3$,H], [ZA373;OS(O)$_2$(CH$_2$)$_3$CH$_3$,H], [ZA374;OS(O)$_2$(CH$_2$)$_4$CH$_3$,H], [ZA375;OS(O)$_2$ (CH₂)₅CH₃,H], [ZA376;OS(O)₂CH₂CH=CH₂,H], [ZA377;OS(O)₂CH₂C≡CH,H], [ZA378;OS(O)₂CH₂C≡CCH₃,H], [ZA379;OS(O)₂-c-Pr,H], [ZA380;OS(O)₂-c-Bu,H], [ZA381;OS(O)₂-c-Pen,H], [ZA382;OS(O)₂-c-Hex,H], [ZA383;OS(O)₂Ph,H], [ZA384;OS(O)₂(2-Py),H], [ZA385;OS(O)₂(3-Py),H], [ZA386;OS(O)₂(4-Py),H], [ZA387;OS(O)₂CF₃,H], [ZA388;OS(O)₂CH₂Ph,H], [ZA389;OS(O)₂CH₂(2-Py),H], [ZA390;OS(O)₂CH₂(3-Py),H], [ZA391;OS(O)₂CH₂(4-Py),H], [ZA392;OS(O)₂CH₂CN,H], [ZA393;OS(O)₂CH₂NO₂,H], [ZA394;OS(O)₂(CH₂)₂F,H], [ZA395;OS(O)₂(CH₂)₂Cl,H], [ZA396;OS(O)₂(CH₂)₂CF₃,H], [ZA397;OS(O)₂(CH₂)₂CN,H], [ZA398;OS(O)₂(CH₂)₂NO₂,H], [ZA399;OS(O)₂(CH₂)₂Ph,H], [ZA400;OS(O)₂(CH₂)₂OCH₃,H], [ZA401;OS(O)₂(CH₂)₃F,H], [ZA402;OS(O)₂(CH₂)₃Cl,H], [ZA403;OS(O)₂(CH₂)₃CF₃,H], [ZA404;OS(O)₂(CH₂)₃CN,H], [ZA405;OS(O)₂(CH₂)₃NO₂,H], [ZA406;OS(O)₂(CH₂)₃Ph,H], [ZA407;OS(O)₂(CH₂)₃OCH₃,H], [ZA408;OS(O)₂(CH₂)₄F,H], [ZA409;OS(O)₂(CH₂)₄Cl,H], [ZA410;OS(O)₂(CH₂)₄CF₃,H], [ZA411;OS(O)₂(CH₂)₄CN,H], [ZA412;OS(O)₂(CH₂)₄NO₂,H], [ZA413;OS(O)₂(CH₂)₄Ph,H], [ZA414;OS(O)₂(CH₂)₄OCH₃,H], [ZA415;OS(O)₂(CH₂)₅F,H], [ZA416;OS(O)₂(CH₂)₅Cl,H], [ZA417;OS(O)₂(CH₂)₅CF₃,H], [ZA418;OS(O)₂(CH₂)₅CN,H], [ZA419;OS(O)₂(CH₂)₅NO₂,H], [ZA420;OS(O)₂(CH₂)₅Ph,H], [ZA421;OS(O)₂(CH₂)₅OCH₃,H], [ZA422;OS(O)₂(CH₂)₆F,H], [ZA423;OS(O)₂(CH₂)₆Cl,H], [ZA424;OS(O)₂(CH₂)₆CF₃,H], [ZA425;OS(O)₂(CH₂)₆CN,H], [ZA426;OS(O)₂(CH₂)₆NO₂,H], [ZA427;OS(O)₂(CH₂)₆Ph,H], [ZA428;OS(O)₂(CH₂)₆OCH₃,H], [ZA429;NH₂,H], [ZA430;NHCH₃,H], [ZA431;NHCH₂CH₃,H], [ZA432;NH(CH₂)₂CH₃,H], [ZA433;NH(CH₂)₃CH₃,H], [ZA434;NH(CH₂)₄CH₃,H], [ZA435;NH(CH₂)₅CH₃,H], [ZA436;NHCH(CH₃)₂,H], [ZA437;NHCH₂F,H], [ZA438;NHCH₂CN,H], [ZA439;NHCH₂OCH₃,H], [ZA440;NHCH₂Ph,H], [ZA441;NH(CH₂)₂F,H], [ZA442;NH(CH₂)₂CN,H], [ZA443;NH(CH₂)₂OCH₃,H], [ZA444;NH(CH₂)₂Ph,H], [ZA445;NH(CH₂)₃F,H], [ZA446;NH(CH₂)₃Cl,H], [ZA447;NH(CH₂)₃CN,H], [ZA448;NH(CH₂)₃OCH₃,H], [ZA449;NH(CH₂)₃Ph,H], [ZA450;NH(CH₂)₄F,H], [ZA451;NH(CH₂)₄CN,H], [ZA452;NH(CH₂)₄OCH₃,H], [ZA453;NH(CH₂)₄Ph,H], [ZA454;NHPh,H], [ZA455;NH(2-Py),H], [ZA456;NH(3-Py),H], [ZA457;NH(4-Py),H], [ZA458;N(CH₃)₂,H], [ZA459;N(CH₃)CH₂CH₃,H], [ZA460;N(CH₃)(CH₂)₂CH₃,H], [ZA461;N(CH₃)(CH₂)₃CH₃,H], [ZA462;(CH₃)(CH₂)₄CH₃,H], [ZA463;(CH₃)(CH₂)₅CH₃,H], [ZA464;N(CH₃)CH(CH₃)₂,H], [ZA465;N(CH₃)CH₂F,H], [ZA466;N(CH₃)CH₂CN,H], [ZA467;N(CH₃)CH₂OCH₃,H], [ZA468;N(CH₃)CH₂Ph,H], [ZA469;N(CH₃)(CH₂)₂F,H], [ZA470;N(CH₃)(CH₂)₂CN,H], [ZA471;N(CH₃)(CH₂)₂OCH₃,H], [ZA472;N(CH₃)(CH₂)₂Ph,H], [ZA473;N(CH₃)(CH₂)₃F,H], [ZA474;N(CH₃)(CH₂)₃CN,H], [ZA475;N(CH₃)(CH₂)₃OCH₃,H], [ZA476;N(CH₃)(CH₂)₃Ph,H], [ZA477;N(CH₃)(CH₂)₄F,H], [ZA478;N(CH₃)(CH₂)₄CN,H], [ZA479;N(CH₃)(CH₂)₄OCH₃,H], [ZA480;N(CH₃)(CH₂)₄Ph,H], [ZA481;N(CH₃)Ph,H], [ZA482;N(CH₃)(2-Py),H], [ZA483;N(CH₃)(3-Py),H], [ZA484;N(CH₃)(4-Py),H], [ZA485;N(CH₂CH₃)₂,H], [ZA486;Pyr,H], [ZA487;Pip,H], [ZA488;Mor,H], [ZA489;S(O)₂CH₃,H], [ZA490;S(O)₂CH₂CH₃,H], [ZA491;S(O)₂CH(CH₃)₂,H], [ZA492;S(O)₂(CH₂)₂CH₃,H], [ZA493;S(O)₂(CH₂)₃CH₃,H], [ZA494;S(O)₂(CH₂)₄CH₃,H], [ZA495;S(O)₂(CH₂)₅CH₃,H], [ZA496;S(O)₂CH₂CH=CH₂,H], [ZA497;S(O)₂CH₂C≡CH,H], [ZA498;S(O)₂CH₂C≡CCH₃,H], [ZA499;S(O)₂-c-Pr,H], [ZA500;S(O)₂-c-Bu,H], [ZA501;S(O)₂-c-Pen,H], [ZA502;S(O)₂-c-Hex,H], [ZA503;S(O)₂Ph,H], [ZA504;S(O)₂(2-Py),H], [ZA505;S(O)₂(3-Py),H], [ZA506;S(O)₂(4-Py),H], [ZA507;S(O)₂CF₃,H], [ZA508;S(O)₂CH₂Ph,H], [ZA509;S(O)₂CH₂(2-Py),H], [ZA510;S(O)₂CH₂(3-Py),H], [ZA511;S(O)₂CH₂(4-Py),H], [ZA512;S(O)₂CH₂CN,H], [ZA513;S(O)₂CH₂NO₂,H], [ZA514;S(O)₂(CH₂)₂F,H], [ZA515;S(O)₂(CH₂)₂Cl,H], [ZA516;S(O)₂(CH₂)₂CF₃,H], [ZA517;S(O)₂(CH₂)₂CN,H], [ZA518;S(O)₂(CH₂)₂NO₂,H], [ZA519;S(O)₂(CH₂)₂Ph,H], [ZA520;S(O)₂(CH₂)₂OCH₃,H], [ZA521;S(O)₂(CH₂)₃F,H], [ZA522;S(O)₂(CH₂)₃Cl,H], [ZA523;S(O)₂(CH₂)₃CF₃,H], [ZA524;S(O)₂(CH₂)₃CN,H], [ZA525;S(O)₂(CH₂)₃NO₂,H], [ZA526;S(O)₂(CH₂)₃Ph,H], [ZA527;S(O)₂(CH₂)₃OCH₃,H], [ZA528;S(O)₂(CH₂)₄F,H], [ZA529;S(O)₂(CH₂)₄Cl,H], [ZA530;S(O)₂(CH₂)₄CF₃,H], [ZA531;S(O)₂(CH₂)₄CN,H], [ZA532;S(O)₂(CH₂)₄NO₂,H], [ZA533;S(O)₂(CH₂)₄Ph,H], [ZA534;S(O)₂(CH₂)₄OCH₃,H], [ZA535;S(O)₂(CH₂)₅F,H], [ZA536;S(O)₂(CH₂)₅Cl,H], [ZA537;S(O)₂(CH₂)₅CF₃,H], [ZA538;S(O)₂(CH₂)₅CN,H], [ZA539;S(O)₂(CH₂)₅NO₂,H], [ZA540;S(O)₂(CH₂)₅Ph,H], [ZA541;S(O)₂(CH₂)₅OCH₃,H], [ZA542;S(O)₂(CH₂)₆F,H], [ZA543;S(O)₂(CH₂)₆Cl,H], [ZA544;S(O)₂(CH₂)₆CF₃,H], [ZA545;S(O)₂(CH₂)₆CN,H], [ZA546;S(O)₂(CH₂)₆NO₂,H], [ZA547;S(O)₂(CH₂)₆Ph,H], [ZA548;S(O)₂(CH₂)₆OCH₃,H], [ZA549;S(O)CH₃,H], [ZA550;S(O)CH₂CH₃,H], [ZA551;S(O)CH(CH₃)₂,H], [ZA552;S(O)(CH₂)₂CH₃,H], [ZA553;S(O)(CH₂)₃CH₃,H], [ZA554;S(O)(CH₂)₄CH₃,H], [ZA555;S(O)(CH₂)₅CH₃,H], [ZA556;S(O)CH₂CH=CH₂,H], [ZA557;S(O)CH₂C≡CH,H], [ZA558;S(O)CH₂C≡CCH₃,H], [ZA559;S(O)c-Pr,H], [ZA560;S(O)c-Bu,H], [ZA561;S(O)c-Pen,H], [ZA562;S(O)c-Hex,H], [ZA563;S(O)Ph,H], [ZA564;S(O)(2-Py),H], [ZA565;S(O)(3-Py),H], [ZA566;S(O)(4-Py),H], [ZA567;S(O)CF₃,H], [ZA568;S(O)CH₂Ph,H], [ZA569;S(O)CH₂(2-Py),H], [ZA570;S(O)CH₂(3-Py),H], [ZA571;S(O)CH₂(4-Py),H], [ZA572;S(O)CH₂CN,H], [ZA573;S(O)CH₂NO₂,H], [ZA574;S(O)(CH₂)₂F,H], [ZA575;S(O)(CH₂)₂Cl,H], [ZA576;S(O)(CH₂)₂CF₃,H], [ZA577;S(O)(CH₂)₂CN,H], [ZA578;S(O)(CH₂)₂NO₂,H], [ZA579;S(O)(CH₂)₂Ph,H], [ZA580;S(O)(CH₂)₂OCH₃,H], [ZA581;S(O)(CH₂)₃F,H], [ZA582;S(O)(CH₂)₃Cl,H], [ZA583;S(O)(CH₂)₃CF₃,H], [ZA584;S(O)(CH₂)₃CN,H], [ZA585;S(O)(CH₂)₃NO₂,H], [ZA586;S(O)(CH₂)₃Ph,H], [ZA587;S(O)(CH₂)₃OCH₃,H], [ZA588;S(O)(CH₂)₄F,H], [ZA589;S(O)(CH₂)₄Cl,H], [ZA590;S(O)(CH₂)₄CF₃,H], [ZA591;S(O)(CH₂)₄CN,H], [ZA592;S(O)(CH₂)₄NO₂,H], [ZA593;S(O)(CH₂)₄Ph,H], [ZA594;S(O)(CH₂)₄OCH₃,H], [ZA595;S(O)(CH₂)₅F,H], [ZA596;S(O)(CH₂)₅Cl,H], [ZA597;S(O)(CH₂)₅CF₃,H], [ZA598;S(O)(CH₂)₅CN,H], [ZA599;S(O)(CH₂)₅NO₂,H], [ZA600;S(O)(CH₂)₅Ph,H], [ZA61;S(O)(CH₂)₅OCH₃,H], [ZA602;S(O)(CH₂)₆F,H], [ZA603;S(O)(CH₂)₆Cl,H], [ZA604;S(O)(CH₂)₆CF₃,H], [ZA605;S(O)(CH₂)₆CN,H], [ZA606;S(O)(CH₂)₆NO₂,H], [ZA607;S(O)(CH₂)₆Ph,H], [ZA608;S(O)(CH₂)₆OCH₃,H], [ZA609;OH,CH₃], [ZA610;OCH₃,CH₃], [ZA611;OCH₂CH₃,CH₃], [ZA612;OCH(CH₃)₂,CH₃], [ZA613;O(CH₂)₂CH₃,CH₃], [ZA614;O(CH₂)₃CH₃,CH₃], [ZA615;O(CH₂)₄CH₃,CH₃], [ZA616;O(CH₂)₅CH₃,CH₃], [ZA617;OCH₂CH=CH₂,CH₃], [ZA618;OCH₂C≡CH,CH₃], [ZA619;OCH₂C≡CCH₃,CH₃], [ZA620;O-c-Pr,CH₃], [ZA621;O-c-Bu,CH₃], [ZA622;O-c-Pen,CH₃], [ZA623;O-c-Hex,CH₃], [ZA624;OPh,CH₃], [ZA625;O(2-Py),CH₃], [ZA626;O(3-Py),CH₃], [ZA627;O(4-Py),CH₃], [ZA628;OCF₃,CH₃], [ZA629;OCH₂Ph,CH₃], [ZA630;OCH₂(2-Py),CH₃], [ZA631;OCH₂(3-Py),CH₃], [ZA632;OCH₂(4-Py),CH₃], [ZA633;OCH₂CN,CH₃], [ZA634;OCH₂NO₂,CH₃], [ZA635;O(CH₂)₂F,CH₃], [ZA636;O(CH₂)₂Cl,CH₃], [ZA637;O(CH₂)₂Br,CH₃], [ZA638;(CH₂)₂I,CH₃], [ZA639;O(CH₂)₂CF₃,CH₃], [ZA640;O(CH₂)₂CN,CH₃], [ZA641;(CH₂)₂NO₂,CH₃], [ZA642;O(CH₂)₂Ph,CH₃], [ZA643;O(CH₂)₂(2-Py),CH₃],

[ZA644;O(CH₂)₂(3-Py),CH₃], [ZA645;O(CH₂)₂(4-Py),CH₃], [ZA646;O(CH₂)₂OH,CH₃], [ZA647;O(CH₂)₂OCH₃,CH₃], [ZA648;O(CH₂)₂SH,CH₃], [ZA649;O(CH₂)₂SCH₃,CH₃], [ZA650;O(CH₂)₂NH₂,CH₃], [ZA651;O(CH₂)₂NHCH₃,CH₃], [ZA652;O(CH₂)₂N(CH₃)₂,CH₃], [ZA653;O(CH₂)₂ NHPh,CH₃], [ZA654;O(CH₂)₂NHCH₂Ph,CH₃], [ZA655;O(CH₂)₂N(CH₃)CH₂Ph,CH₃], [ZA656;O(CH₂)₂S(O)CH₃,CH₃], [ZA657;O(CH₂)₂S(O)CH₂CH₃,CH₃], [ZA658;(CH₂)₂ S(O)Ph,CH₃], [ZA659;O(CH₂)₂S(O)₂CH₃,CH₃], [ZA660;O(CH₂)₂S(O)₂CH₂CH₃,CH₃], [ZA661;O(CH₂)₂S(O)₂Ph,CH₃], [ZA662;O(CH₂)₂C(O)CH₃,CH₃], [ZA663;O(CH₂)₂ C(O)CH₂CH₃,CH₃], [ZA664;O(CH₂)₂C(O)Ph,CH₃], [ZA665;O(CH₂)₂C(S)CH₃,CH₃], [ZA666;O(CH₂)₂C(S)CH₂CH₃,CH₃], [ZA667;O(CH₂)₂C(S)Ph,CH₃], [ZA668;O(CH₂)₂ S(O)₂NHCH₃,CH₃], [ZA669;O(CH₂)₂S(O)₂N(CH₃)₂,CH₃], [ZA670;O(CH₂)₂S(O)₂ NHPh,CH₃], [ZA671;O(CH₂)₂S(O)₂N(CH₃)Ph,CH₃], [ZA672;O(CH₂)₂C(O)NH₂,CH₃], [ZA673;O(CH₂)₂C(O)NHCH₃,CH₃], [ZA674;O(CH₂)₂C(O)N(CH₃)₂,CH₃], [ZA675;O(CH₂)₂C(O)NHPh,CH₃], [ZA676;O(CH₂)₂C(O)N(CH₃)Ph,CH₃], [ZA677;O(CH₂)₂C(O)OCH₃,CH₃], [ZA678;O(CH₂)₂C(O)OCH₂CH₃,CH₃], [ZA679;O(CH₂)₂NHC(O)CH₃,CH₃], [ZA680;O(CH₂)₂NHC(O)CH₂CH₃,CH₃], [ZA681;O(CH₂)₂NHC(O)Ph,CH₃], [ZA682;O(CH₂)₂NCH₃C(O)CH₃,CH₃], [ZA683;O(CH₂)₂NCH₃C(O)CH₂CH₃,CH₃], [ZA684;O(CH₂)₂NCH₃C(O)Ph,CH₃], [ZA685;O(CH₂)₂NHC(O)OCH₃,CH₃], [ZA686;O(CH₂)₂NHC(O)OCH₂CH₃,CH₃], [ZA687;O(CH₂)₂ NHC(O)OPh,CH₃], [ZA688;(CH₂)₂NCH₃C(O)OCH₃,CH₃], [ZA689;O(CH₂)₂NCH₃ C(O)OCH₂CH₃,CH₃], [ZA690;O(CH₂)₂NCH₃C(O)OPh,CH₃], [ZA691;(CH₂)₂ NHC(O)NHCH₃,CH₃], [ZA692;O(CH₂)₂NHC(O)NHCH₂CH₃,CH₃], [ZA693;O(CH₂)₂ NHC(O)NHPh,CH₃], [ZA694;O(CH₂)₂NHC(O)N(CH₃)₂,CH₃], [ZA695;O(CH₂)₂ NHC(O)N(CH₃)CH₂CH₃,CH₃], [ZA696;O(CH₂)₂NHC(O)N(CH₃)Ph,CH₃], [ZA697;O(CH₂)₂NHC(O)N(CH₂CH₃)₂,CH₃], [ZA698;O(CH₂)₂NCH₃C(O)NHCH₃,CH₃], [ZA699;O(CH₂)₂NCH₃C(O)NHCH₂CH₃,CH₃], [ZA700;O(CH₂)₂NCH₃C(O)NHPh,CH₃], [ZA701;O(CH₂)₂NCH₃C(O)N(CH₃)₂,CH₃], [ZA702;O(CH₂)₂NCH₃C(O)N(CH₃)CH₂CH₃,CH₃], [ZA703;O(CH₂)₂NCH₃C(O)N(CH₃)Ph,CH₃], [ZA704;O(CH₂)₂NCH₃ C(O)N(CH₂CH₃)₂,CH₃], [ZA705;O(CH₂)₂OC(O)CH₃,CH₃], [ZA706;O(CH₂)₂OC(O)CH₂CH₃,CH₃], [ZA707;O(CH₂)₂OC(O)Ph,CH₃], [ZA708;O(CH₂)₂OC(O)OCH₃,CH₃], [ZA709;O(CH₂)₂OC(O)OCH₂CH₃,CH₃], [ZA710;(CH₂)₂OC(O)OPh,CH₃], [ZA711;O(CH₂)₂OC(O)NHCH₃,CH₃], [ZA712;O(CH₂)₂OC(O)NHCH₂CH₃,CH₃], [ZA713;O(CH₂)₂OC(O)NHPh,CH₃], [ZA714;O(CH₂)₂OC(O)N(CH₃)₂,CH₃], [ZA715;O(CH₂)₂OC(O)N(CH₃)CH₂CH₃,CH₃], [ZA716;O(CH₂)₂OC(O)N(CH₃)Ph,CH₃], [ZA717;O(CH₂)₂OC(O)N(CH₂CH₃)₂,CH₃], [ZA718;O(CH₂)₂SC(O)CH₃,CH₃], [ZA719;O(CH₂)₂SC(O)CH₂CH₃,CH₃], [ZA720;O(CH₂)₂SC(O)Ph,CH₃], [ZA721;O(CH₂)₂SC(O)OCH₃,CH₃], [ZA722;O(CH₂)₂SC(O)OCH₂CH₃,CH₃], [ZA723;O(CH₂)₂ SC(O)OPh,CH₃], [ZA724;O(CH₂)₂S(O)₂NHCH₃,CH₃], [ZA725;O(CH₂)₂S(O)₂NHCH₂ CH₃,CH₃], [ZA726;O(CH₂)₂S(O)₂NHPh,CH₃], [ZA727;O(CH₂)₂S(O)₂N(CH₃)₂,CH₃], [ZA728;O(CH₂)₂S(O)₂N(CH₃)CH₂CH₃,CH₃], [ZA729;O(CH₂)₂S(O)₂N(CH₃)Ph,CH₃], [ZA730;O(CH₂)₂S(O)₂N(CH₂CH₃)₂,CH₃], [ZA731;O(CH₂)₃F,CH₃], [ZA732;O(CH₂)₃ Cl,CH₃], [ZA733;O(CH₂)₃Br,CH₃], [ZA734;O(CH₂)₃I,CH₃], [ZA735;O(CH₂)₃CF₃,CH₃], [ZA736;O(CH₂)₃CN,CH₃], [ZA737;O(CH₂)₃NO₂,CH₃], [ZA738;O(CH₂)₃Ph,CH₃], [ZA739;O(CH₂)₃(2-Py),CH₃], [ZA740;O(CH₂)₃(3-Py),CH₃], [ZA741;O(CH₂)₃ (4-Py),CH₃], [ZA742;O(CH₂)₃OH,CH₃], [ZA743;O(CH₂)₃OCH₃,CH₃], [ZA744;O(CH₂)₃OCH₂CH₃,CH₃], [ZA745;O(CH₂)₃SH,CH₃], [ZA746;O(CH₂)₃SCH₃,CH₃], [ZA747;O(CH₂)₃SCH₂CH₃,CH₃], [ZA748;O(CH₂)₃NH₂,CH₃], [ZA749;O(CH₂)₃NHCH₃,CH₃], [ZA750;O(CH₂)₃N(CH₃)₂,CH₃], [ZA751;O(CH₂)₄F,CH₃], [ZA752;O(CH₂)₄ Cl,CH₃], [ZA753;O(CH₂)₄CF₃,CH₃], [ZA754;O(CH₂)₄CN,CH₃], [ZA755;O(CH₂)₄NO₂,CH₃], [ZA756;O(CH₂)₄Ph,CH₃], [ZA757;O(CH₂)₄OH,CH₃], [ZA758;(CH₂)₄OCH₃,CH₃], [ZA759;O(CH₂)₄SH,CH₃], [ZA760;O(CH₂)₄SCH₃,CH₃], [ZA761;(CH₂)₄NH₂,CH₃], [ZA762;O(CH₂)₄NHCH₃,CH₃], [ZA763;O(CH₂)₄N(CH₃)₂,CH₃], [ZA764;O(CH₂)₅F,CH₃], [ZA765;O(CH₂)₅Cl,CH₃], [ZA766;O(CH₂)₅CF₃,CH₃], [ZA767;O(CH₂)₅ CN,CH₃], [ZA768;O(CH₂)₅NO₂,CH₃], [ZA769;O(CH₂)₅Ph,CH₃], [ZA770;O(CH₂)₅ OH,CH₃], [ZA771;(CH₂)₅OCH₃,CH₃], [ZA772;O(CH₂)₅SH,CH₃], [ZA773;O(CH₂)₅ SCH₃,CH₃], [ZA774;O(CH₂)₅NH₂,CH₃], [ZA775;O(CH₂)₅NHCH₃,CH₃], [ZA776;O(CH₂)₅N(CH₃)₂,CH₃], [ZA777;O(CH₂)₆F,CH₃], [ZA778;O(CH₂)₆Cl,CH₃], [ZA779;O(CH₂)₆ CF₃,CH₃], [ZA780;O(CH₂)₆CN,CH₃], [ZA781;O(CH₂)₆NO₂,CH₃], [ZA782;O(CH₂)₆ Ph,CH₃], [ZA783;O(CH₂)₆OH,CH₃], [ZA784;O(CH₂)₆OCH₃,CH₃], [ZA785;O(CH₂)₆ SH,CH₃], [ZA786;O(CH₂)₆SCH₃,CH₃], [ZA787;O(CH₂)₆NH₂,CH₃], [ZA788;O(CH₂)₆ NHCH₃,CH₃], [ZA789;O(CH₂)₆N(CH₃)₂,CH₃], [ZA790;OC(O)CH₃,CH₃], [ZA791;OC(O)CH₂CH₃,CH₃], [ZA792;OC(O)CH(CH₃)₂,CH₃], [ZA793;OC(O)(CH₂)₂ CH₃,CH₃], [ZA794;OC(O)(CH₂)₃CH₃,CH₃], [ZA795;OC(O)(CH₂)₄ CH₃,CH₃], [ZA796;OC(O)(CH₂)₅CH₃,CH₃], [ZA797;OC(O)CH₂CH=CH₂,CH₃], [ZA798;OC(O)CH₂C≡CH,CH₃], [ZA799;OC(O)CH₂C≡CCH₃,CH₃], [ZA800;OC(O)c-Pr,CH₃], [ZA81;OC(O)c-Bu,CH₃], [ZA802;OC(O)c-Pen,CH₃], [ZA803;OC(O)c-Hex,CH₃], [ZA804;OC(O)Ph,CH₃], [ZA805;OC(O)(2-Py),CH₃], [ZA806;OC(O)(3-Py),CH₃], [ZA807;OC(O)(4-Py),CH₃], [ZA808;OC(O)CF₃,CH₃], [ZA809;OC(O)CH₂Ph,CH₃], [ZA81;OC(O)CH₂(2-Py),CH₃], [ZA811;OC(O)CH₂ (3-Py),CH₃], [ZA812;OC(O)CH₂(4-Py),CH₃], [ZA813;OC(O)CH₂CN,CH₃], [ZA814;OC(O)CH₂NO₂,CH₃], [ZA815;OC(O)(CH₂)₂F,CH₃], [ZA816;OC(O)(CH₂)₂ Cl,CH₃], [ZA817;OC(O)(CH₂)₂CF₃,CH₃], [ZA818;OC(O)(CH₂)₂CN,CH₃], [ZA819;OC(O)(CH₂)₂NO₂,CH₃], [ZA820;OC(O)(CH₂)₂Ph,CH₃], [ZA821;OC(O)(CH₂)₂ OCH₃,CH₃], [ZA822;OC(O)(CH₂)₃F,CH₃], [ZA823;OC(O)(CH₂)₃Cl,CH₃], [ZA824;OC(O)(CH₂)₃CF₃,CH₃], [ZA825;OC(O)(CH₂)₃CN,CH₃], [ZA826;OC(O)(CH₂)₃ NO₂,CH₃], [ZA827;OC(O)(CH₂)₃Ph,CH₃], [ZA828;OC(O)(CH₂)₃OCH₃,CH₃], [ZA829;OC(O)(CH₂)₄F,CH₃], [ZA830;OC(O)(CH₂)₄Cl,CH₃], [ZA831;OC(O)(CH₂)₄CF₃,CH₃], [ZA832;OC(O)(CH₂)₄CN,CH₃], [ZA833;OC(O)(CH₂)₄NO₂,CH₃], [ZA834;OC(O)(CH₂)₄Ph,CH₃], [ZA835;OC(O)(CH₂)₄OCH₃,CH₃], [ZA836;OC(O)(CH₂)₅F,CH₃], [ZA837;OC(O)(CH₂)₅Cl,CH₃], [ZA838;OC(O)(CH₂)₅CF₃,CH₃], [ZA839;OC(O)(CH₂)₅CN,CH₃], [ZA840;OC(O)(CH₂)₅NO₂,CH₃], [ZA841;OC(O)(CH₂)₅Ph,CH₃], [ZA842;OC(O)(CH₂)₅ OCH₃,CH₃], [ZA843;OC(O)(CH₂)₆F,CH₃], [ZA844;OC(O)(CH₂)₆Cl,CH₃], [ZA845;OC(O)(CH₂)₆CF₃,CH₃], [ZA846;OC(O)(CH₂)₆CN,CH₃], [ZA847;OC(O)(CH₂)₆ NO₂,CH₃], [ZA848;OC(O)(CH₂)₆Ph,CH₃], [ZA849;OC(O)(CH)₆OCH₃,CH₃], [ZA850;OC(O)NH₂,CH₃], [ZA851;OC(O)NHCH₃,CH₃], [ZA852;OC(O)NHCH₂CH₃,CH₃], [ZA853;OC(O)NH(CH₂)₂CH₃,CH₃], [ZA854;OC(O)NH(CH₂)₃CH₃,CH₃], [ZA855;OC(O)NH(CH₂)₄CH₃,CH₃], [ZA856;OC(O)NH(CH₂)₅CH₃,CH₃], [ZA857;OC(O)NHCH(CH₃)₂,CH₃], [ZA858;OC(O)NHCH₂F,CH₃], [ZA859;OC(O)NHCH₂Cl,CH₃], [ZA860;OC(O)NHCN,CH₃], [ZA861;OC(O)NHCH₂Ph,CH₃], [ZA862;OC(O)NHCH₂Ph,CH₃], [ZA863;OC(O)NH(CH)₂F,CH₃], [ZA864;OC(O)NH(CH₂)₂Cl,CH₃], [ZA865;OC(O)NH(CH₂)₂CN,CH₃], [ZA866;OC(O)NH(CH₂)₂OCH₃,

CH₃], [ZA867;OC(O)NH(CH₂)₂Ph,CH₃], [ZA868;OC(O)NH(CH₂)₃F,CH₃], [ZA869;OC(O)NH(CH₂)₃Cl,CH₃], [ZA870;OC(O)NH(CH₂)₃CN,CH₃], [ZA871;OC(O)NH(CH₂)₃OCH₃,CH₃], [ZA872;OC(O)NH(CH₂)₃Ph,CH₃], [ZA873;OC(O)NH(CH₂)₄F,CH₃], [ZA874;OC(O)NH(CH₂)₄Cl,CH₃], [ZA875;OC(O)NH(CH₂)₄CN,CH₃], [ZA876;OC(O)NH(CH₂)₄OCH₃,CH₃], [ZA877;OC(O)NH(CH₂)₄Ph,CH₃], [ZA878;OC(O)NHPh,CH₃], [ZA879;OC(O)NH(2-Py),CH₃], [ZA880;OC(O)NH(3-Py),CH₃], [ZA881;OC(O)NH(4-Py),CH₃], [ZA882;OC(O)N(CH₃)₂,CH₃], [ZA883;OC(O)N(CH₃)CH₂CH₃,CH₃], [ZA884;OC(O)N(CH₃)(CH₂)₂CH₃,CH₃], [ZA885;OC(O)N(CH₃)(CH₂)₃CH₃,CH₃], [ZA886;OC(O)N(CH₃)(CH)₄CH₃,CH₃], [ZA887;OC(O)N(CH₃)(CH₂)₅CH₃,CH₃], [ZA888;OC(O)N(CH₃)CH(CH₃)₂,CH₃], [ZA889;OC(O)N(CH₃)CH₂F,CH₃], [ZA890;OC(O)N(CH₃)CH₂Cl,CH₃], [ZA891;OC(O)N(CH₃)CH₂CN,CH₃], [ZA892;OC(O)N(CH)CH₂OCH₃,CH₃], [ZA893;OC(O)N(CH₃)CH₂Ph,CH₃], [ZA894;OC(O)N(CH₃)(CH₂)F,CH₃], [ZA895;OC(O)N(CH₃)(CH₂)₂Cl,CH₃], [ZA896;OC(O)N(CH₃)(CH₂)₂CN,CH₃], [ZA897;OC(O)N(CH₃)(CH₂)₂OCH₃,CH₃], [ZA898;OC(O)N(CH₃)(CH₂)₂Ph,CH₃], [ZA899;OC(O)N(CH₃)(CH₂)₃F,CH₃], [ZA900;OC(O)N(CH₃)(CH₂)₃Cl,CH₃], [ZA91;OC(O)N(CH₃)(CH₂)₃CN,CH₃], [ZA902;OC(O)N(CH₃)(CH₂)₃OCH₃,CH₃], [ZA903;OC(O)N(CH₃)(CH₂)₃Ph,CH₃], [ZA904;OC(O)N(CH₃)(CH₂)₄F,CH₃], [ZA905;OC(O)N(CH₃)(CH₂)₄Cl,CH₃], [ZA906;OC(O)N(CH)(CH₂)₄CN,CH₃], [ZA907;OC(O)N(CH₃)(CH₂)₄OCH₃,CH₃], [ZA908;OC(O)N(CH₃)(CH₂)₄Ph,CH₃], [ZA909;OC(O)N(CH₃)Ph,CH₃], [ZA91;OC(O)N(CH₃)(2-Py),CH₃], [ZA911;OC(O)N(CH₃)(3-Py),CH₃], [ZA912;OC(O)N(CH₃)(4-Py),CH₃], [ZA913;OC(O)N(CH₂CH₃)₂,CH₃], [ZA914;OC(O)(Pyr),CH₃], [ZA915;OC(O)(Pip),CH₃], [ZA916;OC(O)(Mor),CH₃], [ZA917;OC(O)OCH₃,CH₃], [ZA918;OC(O)OCH₂CH₃,CH₃], [ZA919;OC(O)OCH(CH₃)₂,CH₃], [ZA920;OC(O)O(CH₂)₂CH₃,CH₃], [ZA921;OC(O)O(CH₂)₃CH₃,CH₃], [ZA922;OC(O)O(CH₂)₄CH₃,CH₃], [ZA923;OC(O)O(CH₂)₅CH₃,CH₃], [ZA924;OC(O)OCH₂CH=CH₂,CH₃], [ZA925;OC(O)OCH₂C≡CH,CH₃], [ZA926;OC(O)OCH₂C≡CCH₃,CH₃], [ZA927;OC(O)O-c-Pr,CH₃], [ZA928;OC(O)O-c-Bu,CH₃], [ZA929;OC(O)O-c-Pen,CH₃], [ZA930;OC(O)O-c-Hex,CH₃], [ZA931;OC(O)OPh,CH₃], [ZA932;OC(O)O(2-Py),CH₃], [ZA933;OC(O)O(3-Py),CH₃], [ZA934;OC(O)O(4-Py),CH₃], [ZA935;OC(O)OCF₃,CH₃], [ZA936;OC(O)OCH₂Ph,CH₃], [ZA937;OC(O)OCH₂(2-Py),CH₃], [ZA938;OC(O)OCH₂(3-Py),CH₃], [ZA939;OC(O)OCH₂(4-Py),CH₃], [ZA940;OC(O)OCH₂CN,CH₃], [ZA941;OC(O)OCH₂NO₂,CH₃], [ZA942;OC(O)O(CH₂)₂F,CH₃], [ZA943;OC(O)O(CH₂)₂Cl,CH₃], [ZA944;OC(O)O(CH₂)₂CF₃,CH₃], [ZA945;OC(O)O(CH₂)₂CN,CH₃], [ZA946;OC(O)O(CH₂)₂NO₂,CH₃], [ZA947;OC(O)O(CH₂)₂Ph,CH₃], [ZA948;OC(O)O(CH₂)₂OCH₃,CH₃], [ZA949;OC(O)O(CH₂)₃F,CH₃], [ZA950;OC(O)O(CH₂)₃Cl,CH₃], [ZA951;OC(O)O(CH₂)₃CF₃,CH₃], [ZA952;OC(O)O(CH₂)₃CN,CH₃], [ZA953;OC(O)O(CH₂)₃NO₂,CH₃], [ZA954;OC(O)O(CH₂)₃Ph,CH₃], [ZA955;OC(O)O(CH₂)₃OCH₃,CH₃], [ZA956;OC(O)O(CH₂)₄F,CH₃], [ZA957;OC(O)O(CH₂)₄Cl,CH₃], [ZA958;OC(O)O(CH₂)₄CF₃,CH₃], [ZA959;OC(O)O(CH₂)₄CN,CH₃], [ZA960;OC(O)O(CH₂)₄NO₂,CH₃], [ZA961;OC(O)O(CH₂)₄Ph,CH₃], [ZA962;OC(O)O(CH₂)₄OCH₃,CH₃], [ZA963;OC(O)O(CH₂)₅F,CH₃], [ZA964;OC(O)O(CH₂)₅Cl,CH₃], [ZA965;OC(O)O(CH₂)₅CF₃,CH₃], [ZA966;OC(O)O(CH₂)₅CN,CH₃], [ZA967;OC(O)O(CH₂)₅NO₂,CH₃], [ZA968;OC(O)O(CH₂)₅Ph,CH₃], [ZA969;OC(O)O(CH₂)₅OCH₃,CH₃], [ZA970;OC(O)O(CH₂)₆F,CH₃], [ZA971;OC(O)O(CH₂)₆Cl,CH₃], [ZA972;OC(O)O(CH₂)₆CF₃,CH₃], [ZA973;OC(O)O(CH₂)₆CN,CH₃], [ZA974;OC(O)O(CH₂)₆NO₂,CH₃], [ZA975;OC(O)O(CH₂)₆Ph,CH₃], [ZA976;OC(O)O(CH₂)₆OCH₃,CH₃], [ZA977;OS(O)₂CH₃,CH₃], [ZA978;OS(O)₂CH₂CH₃,CH₃], [ZA979;OS(O)₂CH(CH₃)₂,CH₃], [ZA980;OS(O)₂(CH₂)₂CH₃,CH₃], [ZA981;OS(O)₂(CH₂)₃CH₃,CH₃], [ZA982;OS(O)₂(CH₂)₄CH₃,CH₃], [ZA983;OS(O)₂(CH₂)₅CH₃,CH₃], [ZA984;OS(O)₂CH₂CH=CH₂,CH₃], [ZA985;OS(O)₂CH₂C=CH,CH₃], [ZA986;OS(O)₂CH₂C≡CCH₃,CH₃], [ZA987;OS(O)₂-c-Pr,CH₃], [ZA988;OS(O)₂-c-Bu,CH₃], [ZA989;OS(O)₂-c-Pen,CH₃], [ZA990;OS(O)₂-c-Hex,CH₃], [ZA991;OS(O)₂Ph,CH₃], [ZA992;OS(O)₂(2-Py),CH₃], [ZA993;OS(O)₂(3-Py),CH₃], [ZA994;OS(O)₂(4-Py),CH₃], [ZA995;OS(O)₂CF₃,CH₃], [ZA996;OS(O)₂CH₂Ph,CH₃], [ZA997;OS(O)₂CH₂(2-Py),CH₃], [ZA998;OS(O)₂CH₂(3-Py),CH₃], [ZA999;OS(O)₂CH₂(4-Py),CH₃], [ZA1000;OS(O)₂CH₂CN,CH₃], [ZA1001;OS(O)₂CH₂NO₂,CH₃], [ZA1002;OS(O)₂(CH₂)₂F,CH₃], [ZA1003;OS(O)₂(CH₂)₂Cl,CH₃], [ZA1004;OS(O)₂(CH₂)₂CF₃,CH₃], [ZA1005;OS(O)₂(CH₂)₂CN,CH₃], [ZA1006;OS(O)₂(CH₂)₂NO₂,CH₃], [ZA1007;OS(O)₂(CH₂)₂Ph,CH₃], [ZA1008;OS(O)₂(CH₂)₂OCH₃,CH₃], [ZA1009;OS(O)₂(CH₂)₃F,CH₃], [ZA1010;OS(O)₂(CH₂)₃Cl,CH₃], [ZA1011;OS(O)₂(CH₂)₃CF₃,CH₃], [ZA1012;OS(O)₂(CH₂)₃CN,CH₃], [ZA1013;OS(O)₂(CH₂)₃NO₂,CH₃], [ZA1014;OS(O)₂(CH₂)₃Ph,CH₃], [ZA1015;OS(O)₂(CH₂)₃OCH₃,CH₃], [ZA1016;OS(O)₂(CH₂)₄F,CH₃], [ZA1017;OS(O)₂(CH₂)₄Cl,CH₃], [ZA1018;OS(O)₂(CH₂)₄CF₃,CH₃], [ZA1019;OS(O)₂(CH₂)₄CN,CH₃], [ZA1020;OS(O)₂(CH₂)₄NO₂,CH₃], [ZA1021;OS(O)₂(CH₂)₄Ph,CH₃], [ZA1022;OS(O)₂(CH₂)₄OCH₃,CH₃], [ZA1023;OS(O)₂(CH₂)₅F,CH₃], [ZA1024;OS(O)₂(CH₂)₅Cl,CH₃], [ZA1025;OS(O)₂(CH₂)₅CF₃,CH₃], [ZA1026;OS(O)₂(CH₂)₅CN,CH₃], [ZA1027;OS(O)₂(CH₂)₅NO₂,CH₃], [ZA1028;OS(O)₂(CH₂)₅Ph,CH₃], [ZA1029;OS(O)₂(CH₂)₅OCH₃,CH₃], [ZA1030;OS(O)₂(CH₂)₆F,CH₃], [ZA1031;OS(O)₂(CH₂)₆Cl,CH₃], [ZA1032;OS(O)₂(CH₂)₆CF₃,CH₃], [ZA1033;OS(O)₂(CH₂)₆CN,CH₃], [ZA1034;OS(O)₂(CH₂)₆NO₂,CH₃], [ZA1035;OS(O)₂(CH₂)₆Ph,CH₃], [ZA1036;OS(O)₂(CH₂)₆OCH₃,CH₃], [ZA1037;NH₂,CH₃], [ZA1038;NHCH₃,CH₃], [ZA1039;NHCH₂CH₃,CH₃], [ZA1040;NH(CH₂)₂CH₃,CH₃], [ZA1041;NH(CH₂)₃CH₃,CH₃], [ZA1042;NH(CH₂)₄CH₃,CH₃], [ZA1043;NH(CH₂)₅CH₃,CH₃], [ZA1044;NHCH(CH₃)₂,CH₃], [ZA1045;NHCH₂F,CH₃], [ZA1046;NHCH₂CN,CH₃], [ZA1047;NHCH₂OCH₃,CH₃], [ZA1048;NHCH₂Ph,CH₃], [ZA1049;NH(CH₂)₂F,CH₃], [ZA1050;NH(CH₂)₂CN,CH₃], [ZA1051;NH(CH₂)₂OCH₃,CH₃], [ZA1052;NH(CH₂)₂Ph,CH₃], [ZA1053;NH(CH₂)₃F,CH₃], [ZA1054;NH(CH₂)₃Cl,CH₃], [ZA1055;NH(CH₂)₃CN,CH₃], [ZA1056;NH(CH₂)₃OCH₃,CH₃], [ZA1057;NH(CH₂)₃Ph,CH₃], [ZA1058;NH(CH₂)₄F,CH₃], [ZA1059;NH(CH₂)₄CN,CH₃], [ZA1060;NH(CH₂)₄OCH₃,CH₃], [ZA1061;NH(CH₂)₄Ph,CH₃], [ZA1062;NHPh,CH₃], [ZA1063;NH(2-Py),CH₃], [ZA1064;NH(3-Py),CH₃], [ZA1065;NH(4-Py),CH₃], [ZA1066;N(CH₃)₂,CH₃], [ZA1067;N(CH₃)CH₂CH₃,CH₃], [ZA1068;N(CH₃)(CH₂)₂CH₃,CH₃], [ZA1069;N(CH₃)(CH₂)₃CH₃,CH₃], [ZA1070;(CH₃)(CH₂)₄CH₃,CH₃], [ZA1071;(CH₃)(CH₂)₅CH₃,CH₃], [ZA1072;N(CH₃)CH(CH₃)₂,CH₃], [ZA1073;N(CH₃)CH₂F,CH₃], [ZA1074;N(CH₃)CH₂CN,CH₃], [ZA1075;N(CH₃)CH₂OCH₃,CH₃], [ZA1076;N(CH₃)CH₂Ph,CH₃], [ZA1077;N(CH₃)(CH₂)₂F,CH₃], [ZA1078;N(CH₃)(CH₂)₂CN,CH₃], [ZA1079;N(CH₃)(CH₂)₂OCH₃,CH₃], [ZA1080;N(CH₃)(CH₂)₂Ph,CH₃], [ZA1081;N(CH₃)(CH₂)₃F,CH₃], [ZA1082;N(CH₃)(CH₂)₃CN,CH₃], [ZA1083;N(CH₃)(CH₂)₃OCH₃,CH₃], [ZA1084;N(CH₃)(CH₂)₃Ph,CH₃], [ZA1085;N(CH₃)(CH₂)₄F,CH₃], [ZA1086;N(CH₃)(CH₂)₄CN,CH₃], [ZA1087;N(CH₃)(CH₂)₄OCH₃,CH₃], [ZA1088;N(CH₃)

(CH₂)₄Ph,CH₃], [ZA1089;N(CH₃)Ph,CH₃], [ZA1090;N(CH₃)(2-Py),CH₃], [ZA1091;N(CH₃)(3-Py),CH₃], [ZA1092;N(CH₃)(4-Py),CH₃], [ZA1093;N(CH₂CH₃)₂,CH₃], [ZA1094;Pyr,CH₃], [ZA1095;Pip,CH₃], [ZA1096;Mor,CH₃], [ZA1097;S(O)₂CH₃,CH₃], [ZA1098;S(O)₂CH₂CH₃,CH₃], [ZA1099;S(O)₂CH(CH₃)₂,CH₃], [ZA1100;S(O)₂(CH₂)₂ CH₃,CH₃], [ZA1101;S(O)₂(CH₂)₃CH₃,CH₃], [ZA1102;S(O)₂(CH₂)₄CH₃,CH₃], [ZA1103;S(O)₂(CH₂)₅CH₃,CH₃], [ZA1104;S(O)₂CH₂CH=CH₂,CH₃], [ZA1105;S(O)₂ CH₂C≡CH,CH₃], [ZA1106;S(O)₂CH₂C≡CCH₃,CH₃], [ZA1107;S(O)₂-c-Pr,CH₃], [ZA1108;S(O)₂-c-Bu,CH₃], [ZA1109;S(O)₂-c-Pen,CH₃], [ZA1110;S(O)₂-c-Hex,CH₃], [ZA1111;S(O)₂Ph,CH₃], [ZA1112;S(O)₂(2-Py),CH₃], [ZA1113;S(O)₂(3-Py),CH₃], [ZA1114;S(O)₂(4-Py),CH₃], [ZA1115;S(O)₂CF₃,CH₃], [ZA1116;S(O)₂CH₂Ph,CH₃], [ZA1117;S(O)₂CH₂(2-Py),CH₃], [ZA1118;S(O)₂CH₂(3-Py),CH₃], [ZA1119;S(O)₂CH₂(4-Py),CH₃], [ZA1120;S(O)₂CH₂CN,CH₃], [ZA1121;S(O)₂CH₂NO₂,CH₃], [ZA1122;S(O)₂(CH₂)₂F,CH₃], [ZA1123;S(O)₂(CH₂)₂Cl,CH₃], [ZA1124;S(O)₂(CH₂)₂CF₃,CH₃], [ZA1125;S(O)₂(CH₂)₂CN,CH₃], [ZA1126;S(O)₂(CH₂)₂NO₂,CH₃], [ZA1127;S(O)₂(CH₂)₂Ph,CH₃], [ZA1128;S(O)₂(CH₂)₂OCH₃,CH₃], [ZA1129;S(O)₂(CH₂)₃F,CH₃], [ZA1130;S(O)₂(CH₂)₃Cl,CH₃], [ZA1131;S(O)₂(CH₂)₃CF₃,CH₃], [ZA1132;S(O)₂(CH₂)₃ CN,CH₃], [ZA1133;S(O)₂(CH₂)₃NO₂,CH₃], [ZA1134;S(O)₂(CH₂)₃Ph,CH₃], [ZA1135;S(O)₂(CH₂)₃OCH₃,CH₃], [ZA1136;S(O)₂(CH₂)₄F,CH₃], [ZA1137;S(O)₂(CH₂)₄Cl,CH₃], [ZA1138;S(O)₂(CH₂)₄CF₃,CH₃], [ZA1139;S(O)₂(CH₂)₄CN,CH₃], [ZA1140;S(O)₂(CH₂)₄NO₂,CH₃], [ZA1141;S(O)₂(CH₂)₄Ph,CH₃], [ZA1142;S(O)₂(CH₂)₄OCH₃,CH₃], [ZA1143;S(O)₂(CH₂)₅F,CH₃], [ZA1144;S(O)₂(CH₂)₅Cl,CH₃], [ZA1145;S(O)₂(CH₂)₅CF₃,CH₃], [ZA1146;S(O)₂(CH₂)₅CN,CH₃], [ZA1147;S(O)₂(CH₂)₅ NO₂,CH₃], [ZA1148;S(O)₂(CH₂)₅Ph,CH₃], [ZA1149;S(O)₂(CH₂)₅OCH₃,CH₃], [ZA1150;S(O)₂(CH₂)₆F,CH₃], [ZA1151;S(O)₂(CH₂)₆Cl,CH₃], [ZA1152;S(O)₂(CH₂)₆CF₃,CH₃], [ZA1153;S(O)₂(CH₂)₆CN,CH₃], [ZA1154;S(O)₂(CH₂)₆NO₂,CH₃], [ZA1155;S(O)₂(CH₂)₆Ph,CH₃], [ZA1156;S(O)₂(CH₂)₆ OCH₃,CH₃], [ZA1157;S(O)CH₃,CH₃], [ZA1158;S(O)CH₂CH₃,CH₃], [ZA1159;S(O)CH(CH₃)₂,CH₃], [ZA1160;S(O)(CH₂)₂CH₃,CH₃], [ZA1161;S(O)(CH₂)₃ CH₃,CH₃], [ZA1162;S(O)(CH₂)₄CH₃,CH₃], [ZA1163;S(O)(CH₂)₅CH₃,CH₃], [ZA1164;S(O)CH₂CH=CH₂,CH₃], [ZA1165;S(O)CH₂C≡CH,CH₃], [ZA1166;S(O)CH₂ C≡CCH₃,CH₃], [ZA1167;S(O)c-Pr,CH₃], [ZA1168;S(O)c-Bu,CH₃], [ZA1169;S(O)c-Pen,CH₃], [ZA1170;S(O)c-Hex,CH₃], [ZA1171;S(O)Ph,CH₃], [ZA1172;S(O)(2-Py),CH₃], [ZA1173;S(O)(3-Py),CH₃], [ZA1174;S(O)(4-Py),CH₃], [ZA1175;S(O)CF₃,CH₃], [ZA1176;S(O)CH₂Ph,CH₃], [ZA1177;S(O)CH₂(2-Py),CH₃], [ZA1178;S(O)CH₂(3-Py),CH₃], [ZA1179;S(O)CH₂(4-Py),CH₃], [ZA1180;S(O)CH₂ CN,CH₃], [ZA1181;S(O)CH₂NO₂,CH₃], [ZA1182;S(O)(CH₂)₂F,CH₃], [ZA1183;S(O)(CH₂)₂Cl,CH₃], [ZA1184;S(O)(CH₂)₂CF₃,CH₃], [ZA1185;S(O)(CH₂)₂ CN,CH₃], [ZA1186;S(O)(CH₂)₂NO₂,CH₃], [ZA1187;S(O)(CH₂)₂Ph,CH₃], [ZA1188;S(O)(CH₂)₂OCH₃,CH₃], [ZA1189;S(O)(CH₂)₃F,CH₃], [ZA1190;S(O)(CH₂)₃ Cl,CH₃], [ZA1191;S(O)(CH₂)₃CF₃,CH₃], [ZA1192;S(O)(CH₂)₃CN,CH₃], [ZA1193;S(O)(CH₂)₃NO₂,CH₃], [ZA1194;S(O)(CH₂)₃Ph,CH₃], [ZA1195;S(O)(CH₂)₃ OCH₃,CH₃], [ZA1196;S(O)(CH₂)₄F,CH₃], [ZA1197;S(O)(CH₂)₄Cl,CH₃], [ZA1198;S(O)(CH₂)₄CF₃,CH₃], [ZA1199;S(O)(CH₂)₄CN,CH₃], [ZA1200;S(O)(CH₂)₄ NO₂,CH₃], [ZA1201;S(O)(CH₂)₄Ph,CH₃], [ZA1202;S(O)(CH₂)₄OCH₃,CH₃], [ZA1203;S(O)(CH₂)₅F,CH₃], [ZA1204;S(O)(CH₂)₅Cl,CH₃], [ZA1205;S(O)(CH₂)₅CF₃,CH₃], [ZA1206;S(O)(CH₂)₅CN,CH₃], [ZA1207;S(O)(CH₂)₅NO₂,CH₃], [ZA1208;S(O)(CH₂)₅Ph,CH₃], [ZA1209;S(O)(CH₂)₅OCH₃,CH₃], [ZA1210;S(O)(CH₂)₆ F,CH₃], [ZA1211;S(O)(CH₂)₆Cl,CH₃], [ZA1212;S(O)(CH₂)₆CF₃,CH₃], [ZA1213;S(O)(CH₂)₆CN,CH₃], [ZA1214;S(O)(CH₂)₆NO₂,CH₃], [ZA1215;S(O)(CH₂)₆Ph,CH₃], [ZA1216;S(O)(CH₂)₆OCH₃,CH₃], [ZA1217;OH,OCH₃], [ZA1218;OCH₃,OCH₃], [ZA1219;OCH₂CH₃,OCH₃], [ZA1220;OCH(CH₃)₂,OCH₃], [ZA1221;O(CH₂)₂ CH₃,OCH₃], [ZA1222;O(CH₂)₃CH₃,OCH₃], [ZA1223;O(CH₂)₄CH₃,OCH₃], [ZA1224;O(CH₂)₅CH₃,OCH₃], [ZA1225;OCH₂CH=CH₂,OCH₃], [ZA1226;OCH₂ C≡CH,OCH₃], [ZA1227;OCH₂C≡CCH₃,OCH₃], [ZA1228;O-c-Pr,OCH₃], [ZA1229;O-c-Bu,OCH₃], [ZA1230;O-c-Pen,OCH₃], [ZA1231;O-c-Hex,OCH₃], [ZA1232;OPh,OCH₃], [ZA1233;O(2-Py),OCH₃], [ZA1234;O(3-Py),OCH₃], [ZA1235;O(4-Py),OCH₃], [ZA1236;OCF₃,OCH₃], [ZA1237;OCH₂Ph,OCH₃], [ZA1238;OCH₂(2-Py),OCH₃], [ZA1239;OCH₂(3-Py),OCH₃], [ZA1240;OCH₂ (4-Py),OCH₃], [ZA1241;OCH₂CN,OCH₃], [ZA1242;OCH₂NO₂,OCH₃], [ZA1243;O(CH₂)₂F,OCH₃], [ZA1244;O(CH₂)₂Cl,OCH₃], [ZA1245;O(CH₂)₂Br,OCH₃], [ZA1246;O(CH₂)₂I,OCH₃], [ZA1247;O(CH₂)₂CF₃,OCH₃], [ZA1248;O(CH₂)₂ CN,OCH₃], [ZA1249;O(CH₂)₂NO₂,OCH₃], [ZA1250;O(CH₂)₂Ph,OCH₃], [ZA1251;O(CH₂)₂ (2-Py),OCH₃], [ZA1252;O(CH₂)₂(3-Py),OCH₃], [ZA1253;O(CH₂)₂(4-Py),OCH₃], [ZA1254;O(CH₂)₂OH,OCH₃], [ZA1255;O(CH₂)₂ OCH₃,OCH₃], [ZA1256;O(CH₂)₂ SH,OCH₃], [ZA1257;O(CH₂)₂SCH₃,OCH₃], [ZA1258;O(CH₂)₂NH₂,OCH₃], [ZA1259;O(CH₂)₂NHCH₃,OCH₃], [ZA1260;O(CH₂)₂N(CH₃)₂,OCH₃], [ZA1261;O(CH₂)₂NHPh,OCH₃], [ZA1262;O(CH₂)₂NHCH₂Ph,OCH₃], [ZA1263;O(CH₂)₂N(CH₃)CH₂Ph,OCH₃], [ZA1264;O(CH₂)₂S(O)CH₃,OCH₃], [ZA1265;O(CH₂)₂S(O)CH₂CH₃,OCH₃], [ZA1266;O(CH₂)₂S(O)Ph,OCH₃], [ZA1267;O(CH₂)₂S(O)₂CH₃,OCH₃], [ZA1268;O(CH₂)₂S(O)₂CH₂CH₃,OCH₃], [ZA1269;O(CH₂)₂S(O)₂Ph,OCH₃], [ZA1270;O(CH₂)₂C(O)CH₃,OCH₃], [ZA1271;O(CH₂)₂C(O)CH₂CH₃,OCH₃], [ZA1272;O(CH₂)₂C(O)Ph,OCH₃], [ZA1273;O(CH₂)₂C(S)CH₃,OCH₃], [ZA1274;O(CH₂)₂C(S)CH₂CH₃,OCH₃], [ZA1275;O(CH₂)₂C(S)Ph,OCH₃], [ZA1276;O(CH₂)₂S(O)₂NHCH₃,OCH₃], [ZA1277;O(CH₂)₂S(O)₂N(CH₃)₂,OCH₃], [ZA1278;O(CH₂)₂S(O)₂NHPh,OCH₃], [ZA1279;O(CH₂)₂S(O)₂N(CH₃)Ph,OCH₃], [ZA1280;O(CH₂)₂C(O)NH₂,OCH₃], [ZA1281;O(CH₂)₂C(O)NHCH₃,OCH₃], [ZA1282;O(CH₂)₂C(O)N(CH₃)₂,OCH₃], [ZA1283;O(CH₂)₂C(O)NHPh,OCH₃], [ZA1284;O(CH₂)₂C(O)N(CH₃)Ph,OCH₃], [ZA1285;O(CH₂)₂C(O)OCH₃,OCH₃], [ZA1286;O(CH₂)₂C(O)OCH₂CH₃,OCH₃], [ZA1287;O(CH₂)₂NHC(O)CH₃,OCH₃], [ZA1288;O(CH₂)₂NHC(O)CH₂CH₃,OCH₃], [ZA1289;O(CH₂)₂NHC(O)Ph,OCH₃], [ZA1290;O(CH₂)₂NCH₃C(O)CH₃,OCH₃], [ZA1291;O(CH₂)₂NCH₃C(O)CH₂CH₃,OCH₃], [ZA1292;O(CH₂)₂NCH₃C(O)Ph,OCH₃], [ZA1293;O(CH₂)₂NHC(O)OCH₃,OCH₃], [ZA1294;O(CH₂)₂NHC(O)OCH₂CH₃,OCH₃], [ZA1295;O(CH₂)₂NHC(O)OPh,OCH₃], [ZA1296;O(CH₂)₂NCH₃C(O)OCH₃,OCH₃], [ZA1297;O(CH₂)₂NCH₃C(O)OCH₂CH₃,OCH₃], [ZA1298;O(CH₂)₂NCH₃C(O)OPh,OCH₃], [ZA1299;O(CH₂)₂NHC(O)NHCH₃,OCH₃], [ZA1300;O(CH₂)₂ NHC(O)NHCH₂CH₃,OCH₃], [ZA1301;O(CH₂)₂NHC(O)NHPh,OCH₃], [ZA1302;O(CH₂)₂NHC(O)N(CH₃)₂,OCH₃], [ZA1303;O(CH₂)₂NHC(O)N(CH₃)CH₂CH₃,OCH₃], [ZA1304;O(CH₂)₂NHC(O)N(CH₃)Ph,OCH₃], [ZA1305;O(CH₂)₂NHC(O)N(CH₂CH₃)₂,OCH₃], [ZA1306;O(CH₂)₂NCH₃C(O)NHCH₃,OCH₃], [ZA1307;O(CH₂)₂NCH₃ C(O)NHCH₂CH₃,OCH₃], [ZA1308;O(CH₂)₂NCH₃C(O)NHPh,OCH₃], [ZA1309;O(CH₂)₂NCH₃C(O)N(CH₃)₂,OCH₃], [ZA1310;O(CH₂)₂

NCH₃C(O)N(CH₃)CH₂CH₃,OCH₃], [ZA1311;O(CH₂)₂NCH₃ C(O)N(CH₃)Ph,OCH₃], [ZA1312;O(CH₂)₂NCH₃C(O)N(CH₂CH₃)₂,OCH₃], [ZA1313;O(CH₂)₂OC(O)CH₃,OCH₃], [ZA1314;O(CH₂)₂OC(O)CH₂CH₃,OCH₃], [ZA1315;O(CH₂)₂OC(O)Ph,OCH₃], [ZA1316;O(CH₂)₂OC(O)OCH₃,OCH₃], [ZA1317;O(CH₂)₂OC(O)OCH₂CH₃,OCH₃], [ZA1318;O(CH₂)₂OC(O)OPh,OCH₃], [ZA1319;O(CH₂)₂OC(O)NHCH₃,OCH₃], [ZA1320;O(CH₂)₂OC(O)NHCHCH₃,OCH₃], [ZA1321;O(CH₂)₂OC(O)NHPh,OCH₃], [ZA1322;O(CH₂)₂OC(O)N(CH₃)₂,OCH₃], [ZA1323;O(CH₂)₂OC(O)N(CH₃)CH₂CH₃,OCH₃], [ZA1324;O(CH₂)₂OC(O)N(CH₃)Ph,OCH₃], [ZA1325;O(CH₂)₂OC(O)N(CH₂CH₃)₂,OCH₃], [ZA1326;O(CH₂)₂SC(O)CH₃,OCH₃], [ZA1327;O(CH₂)₂SC(O)CH₂CH₃,OCH₃], [ZA1328;O(CH₂)₂SC(O)Ph,OCH₃], [ZA1329;O(CH₂)₂SC(O)OCH₃,OCH₃], [ZA1330;O(CH₂)₂SC(O)OCH₂CH₃,OCH₃], [ZA1331;O(CH₂)₂SC(O)OPh,OCH₃], [ZA1332;O(CH₂)₂S(O)₂NHCH₃,OCH₃], [ZA1333;O(CH₂)₂S(O)₂NHCH₂CH₃,OCH₃], [ZA1334;O(CH₂)₂S(O)₂NHPh,OCH₃], [ZA1335;O(CH₂)₂S(O)₂N(CH₃)₂,OCH₃], [ZA1336;O(CH₂)₂S(O)₂N(CH₃)CH₂CH₃,OCH₃], [ZA1337;O(CH₂)₂S(O)₂N(CH₃)Ph,OCH₃], [ZA1338;O(CH₂)₂S(O)₂N(CH₂CH₃)₂,OCH₃], [ZA1339;O(CH₂)₃F,OCH₃], [ZA1340;O(CH₂)₃Cl,OCH₃], [ZA1341;O(CH₂)₃Br,OCH₃], [ZA1342;O(CH₂)₃I,OCH₃], [ZA1343;O(CH₂)₃CF₃,OCH₃], [ZA1344;O(CH₂)₃CN,OCH₃], [ZA1345;O(CH₂)₃NO₂,OCH₃], [ZA1346;O(CH₂)₃Ph,OCH₃], [ZA1347;O(CH₂)₃(2-Py),OCH₃], [ZA1348;O(CH₂)₃(3-Py),OCH₃], [ZA1349;O(CH₂)₃ (4-Py),OCH₃], [ZA1350;O(CH₂)₃OH,OCH₃], [ZA1351;O(CH₂)₃OCH₃,OCH₃], [ZA1352;O(CH₂)₃OCH₂CH₃,OCH₃], [ZA1353;O(CH₂)₃SH,OCH₃], [ZA1354;O(CH₂)₃ SCH₃,OCH₃], [ZA1355;O(CH₂)₃SCH₂CH₃,OCH₃], [ZA1356;O(CH₂)₃NH₂,OCH₃], [ZA1357;O(CH₂)₃NHCH₃,OCH₃], [ZA1358;O(CH₂)₃N(CH₃)₂,OCH₃], [ZA1359;O(CH₂)₄F,OCH₃], [ZA1360;O(CH₂)₄Cl,OCH₃], [ZA1361;O(CH₂)₄CF₃,OCH₃], [ZA1362;O(CH₂)₄CN,OCH₃], [ZA1363;O(CH₂)₄NO₂,OCH₃], [ZA1364;O(CH₂)₄ Ph,OCH₃], [ZA1365;O(CH₂)₄OH,OCH₃], [ZA1366;O(CH₂)₄OCH₃,OCH₃], [ZA1367;O(CH₂)₄ SH,OCH₃], [ZA1368;O(CH₂)₄SCH₃,OCH₃], [ZA1369;O(CH₂)₄NH₂,OCH₃], [ZA1370;O(CH₂)₄NHCH₃,OCH₃], [ZA1371;O(CH₂)₄N(CH₃)₂,OCH₃], [ZA1372;O(CH₂)₅F,OCH₃], [ZA1373;O(CH₂)₅Cl,OCH₃], [ZA1374;O(CH₂)₅CF₃,OCH₃], [ZA1375;O(CH₂)₅CN,OCH₃], [ZA1376;O(CH₂)₅NO₂,OCH₃], [ZA1377;O(CH₂)₅Ph,OCH₃], [ZA1378;O(CH₂)₅OH,OCH₃], [ZA1379;O(CH₂)₅OCH₃,OCH₃], [ZA1380;O(CH₂)₅SH,OCH₃], [ZA1381;O(CH₂)₅SCH₃,OCH₃], [ZA1382;O(CH₂)₅NH₂,OCH₃], [ZA1383;O(CH₂)₅NHCH₃,OCH₃], [ZA1384;O(CH₂)₅N(CH₃)₂,OCH₃], [ZA1385;O(CH₂)₆F,OCH₃], [ZA1386;O(CH₂)₆Cl,OCH₃], [ZA1387;O(CH₂)₆CF₃,OCH₃], [ZA1388;O(CH₂)₆CN,OCH₃], [ZA1389;O(CH₂)₆NO₂,OCH₃], [ZA1390;O(CH₂)₆ Ph,OCH₃], [ZA1391;O(CH₂)₆OH,OCH₃], [ZA1392;O(CH₂)₆OCH₃,OCH₃], [ZA1393;O(CH₂)₆SH,OCH₃], [ZA1394;O(CH₂)₆SCH₃,OCH₃], [ZA1395;O(CH₂)₆NH₂,OCH₃], [ZA1396;O(CH₂)₆NHCH₃,OCH₃], [ZA1397;O(CH₂)₆N(CH₃)₂,OCH₃], [ZA1398;OC(O)CH₃,OCH₃], [ZA1399;OC(O)CH₂CH₃,OCH₃], [ZA1400;OC(O)CH(CH₃)₂,OCH₃], [ZA1401;OC(O)(CH₂)₂CH₃,OCH₃], [ZA1402;OC(O)(CH₂)₃CH₃,OCH₃], [ZA1403;OC(O)(CH₂)₄CH₃,OCH₃], [ZA1404;OC(O)(CH₂)₅CH₃,OCH₃], [ZA1405;OC(O)CH₂CH=CH₂,OCH₃], [ZA1406;OC(O)CH₂C=CH,OCH₃], [ZA1407;OC(O)CH₂C≡CCH₃,OCH₃], [ZA1408;OC(O)c-Pr,OCH₃], [ZA1409;OC(O)c-Bu,OCH₃], [ZA1410;OC(O)c-Pen,OCH₃], [ZA1411;OC(O)c-Hex,OCH₃], [ZA1412;OC(O)Ph,OCH₃], [ZA1413;OC(O)(2-Py),OCH₃], [ZA1414;OC(O)(3-Py),OCH₃], [ZA1415;OC(O)(4-Py),OCH₃], [ZA1416;OC(O)CF₃,OCH₃], [ZA1417;OC(O)CH₂Ph,OCH₃], [ZA1418;OC(O)CH₂(2-Py),OCH₃], [ZA1419;OC(O)CH₂(3-Py),OCH₃], [ZA1420;OC(O)CH₂(4-Py),OCH₃], [ZA1421;OC(O)CH₂CN,OCH₃], [ZA1422;OC(O)CH₂NO₂,OCH₃], [ZA1423;OC(O)(CH₂)₂F,OCH₃], [ZA1424;OC(O)(CH₂)₂Cl,OCH₃], [ZA1425;OC(O)(CH₂)₂CF₃,OCH₃], [ZA1426;OC(O)(CH₂)₂CN,OCH₃], [ZA1427;OC(O)(CH₂)₂NO₂,OCH₃], [ZA1428;OC(O)(CH₂)₂Ph,OCH₃], [ZA1429;OC(O)(CH₂)₂OCH₃,OCH₃], [ZA1430;OC(O)(CH₂)₃F,OCH₃], [ZA1431;OC(O)(CH₂)₃Cl,OCH₃], [ZA1432;OC(O)(CH₂)₃CF₃,OCH₃], [ZA1433;OC(O)(CH₂)₃CN,OCH₃], [ZA1434;OC(O)(CH₂)₃NO₂,OCH₃], [ZA1435;OC(O)(CH₂)₃Ph,OCH₃], [ZA1436;OC(O)(CH₂)₃OCH₃,OCH₃], [ZA1437;OC(O)(CH₂)₄F,OCH₃], [ZA1438;OC(O)(CH₂)₄Cl,OCH₃], [ZA1439;OC(O)(CH₂)₄CF₃,OCH₃], [ZA1440;OC(O)(CH₂)₄ CN,OCH₃], [ZA1441;OC(O)(CH₂)₄NO₂,OCH₃], [ZA1442;OC(O)(CH₂)₄Ph,OCH₃], [ZA1443;OC(O)(CH₂)₄OCH₃,OCH₃], [ZA1444;OC(O)(CH₂)₅F,OCH₃], [ZA1445;OC(O)(CH₂)₅Cl,OCH₃], [ZA1446;OC(O)(CH₂)₅CF₃,OCH₃], [ZA1447;OC(O)(CH₂)₅CN,OCH₃], [ZA1448;OC(O)(CH₂)₅NO₂,OCH₃], [ZA1449;OC(O)(CH₂)₅Ph,OCH₃], [ZA1450;OC(O)(CH₂)₅OCH₃,OCH₃], [ZA1451;OC(O)(CH₂)₆F,OCH₃], [ZA1452;OC(O)(CH₂)₆Cl,OCH₃], [ZA1453;OC(O)(CH₂)₆CF₃,OCH₃], [ZA1454;OC(O)(CH₂)₆ CN,OCH₃], [ZA1455;OC(O)(CH₂)₆NO₂,OCH₃], [ZA1456;OC(O)(CH₂)₆Ph,OCH₃], [ZA1457;OC(O)(CH₂)₆OCH₃, OCH₃], [ZA1458;OC(O)NH₂,OCH₃], [ZA1459;OC(O)NHCH₃,OCH₃], [ZA1460;OC(O)NHCH₂CH₃,OCH₃], [ZA1461;OC(O)NH(CH₂)₂CH₃,OCH₃], [ZA1462;OC(O)NH(CH₂)₃CH₃,OCH₃], [ZA1463;OC(O)NH(CH₂)₄CH₃,OCH₃], [ZA1464;OC(O)NH(CH₂)₅CH₃,OCH₃], [ZA1465;OC(O)NHCH(CH₃)₂,OCH₃], [ZA1466;OC(O)NHCH₂F,OCH₃], [ZA1467;OC(O)NHCH₂Cl,OCH₃], [ZA1468;OC(O)NHCH₂CN,OCH₃], [ZA1469;OC(O)NHCH₂OCH₃,OCH₃], [ZA1470;OC(O)NHCH₂Ph,OCH₃], [ZA1471;OC(O)NH(CH₂)₂F,OCH₃], [ZA1472;OC(O)NH(CH₂)₂Cl,OCH₃], [ZA1473;OC(O)NH(CH₂)₂CN,OCH₃], [ZA1474;OC(O)NH(CH₂)₂OCH₃,OCH₃], [ZA1475;OC(O)NH(CH₂)₂ Ph,OCH₃], [ZA1476;OC(O)NH(CH₂)₃F,OCH₃], [ZA1477;OC(O)NH(CH₂)₃Cl,OCH₃], [ZA1478;OC(O)NH(CH₂)₃CN,OCH₃], [ZA1479;OC(O)NH(CH₂)₃OCH₃,OCH₃], [ZA1480;OC(O)NH(CH₂)₃Ph,OCH₃], [ZA1481;OC(O)NH(CH₂)₄F,OCH₃], [ZA1482;OC(O)NH(CH₂)₄Cl,OCH₃], [ZA1483;OC(O)NH(CH₂)₄CN,OCH₃], [ZA1484;OC(O)NH(CH₂)₄OCH₃,OCH₃], [ZA1485;OC(O)NH(CH₂)₄ Ph,OCH₃], [ZA1486;OC(O)NHPh,OCH₃], [ZA1487;OC(O)NH(2-Py),OCH₃], [ZA1488;OC(O)NH(3-Py),OCH₃], [ZA1489;OC(O)NH(4-Py),OCH₃], [ZA1490;OC(O)N(CH₃)₂,OCH₃], [ZA1491;OC(O)N(CH₃)CH₂CH₃,OCH₃], [ZA1492;OC(O)N(CH₃)(CH₂)₂CH₃,OCH₃], [ZA1493;OC(O)N(CH₃)(CH₂)₃CH₃,OCH₃], [ZA1494;OC(O)N(CH₃)(CH₂)₄CH₃,OCH₃], [ZA1495;OC(O)N(CH₃)(CH₂)₅CH₃,OCH₃], [ZA1496;OC(O)N(CH₃)CH(CH₃)₂,OCH₃], [ZA1497;OC(O)N(CH₃)CH₂F,OCH₃], [ZA1498;OC(O)N(CH₃)CH₂Cl,OCH₃], [ZA1499;OC(O)N(CH₃)CH₂CN,OCH₃], [ZA1500;OC(O)N(CH₃)CH₂OCH₃,OCH₃],
[ZA1501;OC(O)N(CH₃)CH₂Ph,OCH₃], [ZA1502;OC(O)N(CH₃)(CH₂)₂F,OCH₃], [ZA1503;OC(O)N(CH₃)(CH₃)(CH₂)₂Cl,OCH₃], [ZA1504;OC(O)N(CH₃)(CH₂)₂CN,OCH₃], [ZA1505;OC(O)N(CH₃)(CH₂)₂OCH₃,OCH₃], [ZA1506;OC(O)N(CH₃)(CH₂)₂Ph,OCH₃], [ZA1507;OC(O)N(CH₃)(CH₂)₃F,OCH₃], [ZA1508;OC(O)N(CH₃)(CH₂)₃ Cl,OCH₃], [ZA1509;OC(O)N(CH₃)(CH₂)₃CN,OCH₃], [ZA1510;OC(O)N(CH₃)(CH₂)₃OCH₃,OCH₃], [ZA1511;OC(O)N(CH₃)(CH₂)₃Ph,OCH₃], [ZA1512;OC(O)

N(CH₃)(CH₂)₄F,OCH₃], [ZA1513;OC(O)N(CH₃)(CH₂)₄Cl, OCH₃], [ZA1514;OC(O)N(CH₃)(CH₂)₄CN,OCH₃], [ZA1515;OC(O)N(CH₃)(CH₂)₄OCH₃,OCH₃], [ZA1516; OC(O)N(CH₃)(CH₂)₄Ph,OCH₃], [ZA1517;OC(O)N(CH₃) Ph,OCH₃], [ZA1518;OC(O)N(CH₃)(2-Py),OCH₃], [ZA1519;OC(O)N(CH₃)(3-Py),OCH₃], [ZA1520;OC(O)N (CH₃)(4-Py),OCH₃], [ZA1521;OC(O)N(CH₂CH₃)₂,OCH₃], [ZA1522;OC(O)(Pyr),OCH₃], [ZA1523;OC(O)(Pip), OCH₃], [ZA1524;OC(O)(Mor),OCH₃], [ZA1525;OC(O) OCH₃,OCH₃], [ZA1526;OC(O)OCH₂CH₃,OCH₃], [ZA1527;OC(O)OCH(CH₃)₂,OCH₃], [ZA1528;OC(O)O (CH₂)₂CH₃,OCH₃], [ZA1529;OC(O)O(CH₂)₃CH₃,OCH₃], [ZA1530;OC(O)O(CH₂)₄CH₃,OCH₃], [ZA1531;OC(O)O (CH₂)₅CH₃,OCH₃], [ZA1532;OC(O)OCH₂CH=CH₂, OCH₃], [ZA1533;OC(O)OCH₂C≡CH,OCH₃], [ZA1534;OC (O)OCH₂C≡CCH₃,OCH₃], [ZA1535;OC(O)O-c-Pr,OCH₃], [ZA1536;OC(O)O-c-Bu,OCH₃], [ZA1537;OC(O)O-c-Pen, OCH₃], [ZA1538;OC(O)O-c-Hex,OCH₃], [ZA1539;OC(O) OPh,OCH₃], [ZA1540;OC(O)O(2-Py),OCH₃], [ZA1541; OC(O)O(3-Py),OCH₃], [ZA1542;OC(O)O(4-Py),OCH₃], [ZA1543;OC(O)OCF₃,OCH₃], [ZA1544;OC(O)OCH₂Ph, OCH₃], [ZA1545;OC(O)OCH₂(2-Py),OCH₃], [ZA1546;OC (O)OCH₂(3-Py),OCH₃], [ZA1547;OC(O)OCH₂(4-Py), OCH₃], [ZA1548;OC(O)OCH₂CN,OCH₃], [ZA1549;OC (O)OCH₂NO₂,OCH₃], [ZA1550;OC(O)O(CH₂)₂F,OCH₃], [ZA1551;OC(O)O(CH₂)₂Cl,OCH₃], [ZA1552;OC(O)O (CH₂)₂CF₃,OCH₃], [ZA1553;OC(O)O(CH₂)₂CN, OCH₂CN,OCH₃], [ZA1554;OC(O)O(CH₂)₂NO₂,OCH₃], [ZA1555;OC(O)O(CH₂)₂Ph,OCH₃], [ZA1556;OC(O)O (CH₂)₂OCH₃,OCH₃], [ZA1557;OC(O)O(CH₂)₃F,OCH₃], [ZA1558;OC(O)O(CH₂)₃Cl,OCH₃], [ZA1559;OC(O)O (CH₂)₃CF₃,OCH₃], [ZA1560;OC(O)O(CH₂)₃CN,OCH₃], [ZA1561;OC(O)O(CH₂)₃NO₂,OCH₃], [ZA1562;OC(O)O (CH₂)₃Ph,OCH₃], [ZA1563;OC(O)O(CH₂)₃OCH₃,OCH₃], [ZA1564;OC(O)O(CH₂)₄F,OCH₃], [ZA1565;OC(O)O (CH₂)₄Cl,OCH₃], [ZA1566;OC(O)O(CH₂)₄CF₃,OCH₃], [ZA1567;OC(O)O(CH₂)₄CN,OCH₃], [ZA1568;OC(O)O (CH₂)₄NO₂,OCH₃], [ZA1569;OC(O)O(CH₂)₄Ph,OCH₃], [ZA1570;OC(O)O(CH₂)₄OCH₃,OCH₃], [ZA1571;OC(O)O (CH₂)₅F,OCH₃], [ZA1572;OC(O)O(CH₂)₅Cl,OCH₃], [ZA1573;OC(O)O(CH₂)₅CF₃,OCH₃], [ZA1574;OC(O)O (CH₂)₅CN,OCH₃], [ZA1575;OC(O)O(CH₂)₅NO₂,OCH₃], [ZA1576;OC(O)O(CH₂)₅Ph,OCH₃], [ZA1577;OC(O)O (CH₂)₅OCH₃,OCH₃], [ZA1578;OC(O)O(CH₂)₆F,OCH₃], [ZA1579;OC(O)O(CH₂)₆Cl,OCH₃], [ZA1580;OC(O)O (CH₂)₆CF₃,OCH₃], [ZA1581;OC(O)O(CH₂)₆CN,OCH₃], [ZA1582;OC(O)O(CH₂)₆NO₂,OCH₃], [ZA1583;OC(O)O (CH₂)₆Ph,OCH₃], [ZA1584;OC(O)O(CH₂)₆OCH₃,OCH₃], [ZA1585;OS(O)₂CH₃,OCH₃], [ZA1586;OS(O)₂CH₂CH₃, OCH₃], [ZA1587;OS(O)₂CH(CH₃)₂,OCH₃], [ZA1588;OS (O)₂(CH₂)₂CH₃,OCH₃], [ZA1589;OS(O)₂(CH₂)₃CH₃, OCH₃], [ZA1590;OS(O)₂(CH₂)₄CH₃,OCH₃], [ZA1591;OS (O)₂(CH₂)₅CH₃,OCH₃], [ZA1592;OS(O)₂CH₂CH=CH₂, OCH₃], [ZA1593;OS(O)₂CH₂C≡CH,OCH₃], [ZA1594;OS (O)₂CH₂C≡CCH₃,OCH₃], [ZA1595;OS(O)₂-c-Pr,OCH₃], [ZA1596;OS(O)₂-c-Bu,OCH₃], [ZA1597;OS(O)₂-c-Pen, OCH₃], [ZA1598;OS(O)₂-c-Hex,OCH₃], [ZA1599;OS(O)₂ Ph,OCH₃], [ZA1600;OS(O)₂(2-Py),OCH₃], [ZA1601;OS (O)₂ (3-Py),OCH₃], [ZA1602;OS(O)₂(4-Py),OCH₃], [ZA1603;OS(O)₂CF₃,OCH₃], [ZA1604;OS(O)₂CH₂Ph, OCH₃], [ZA1605;OS(O)₂CH₂(2-Py),OCH₃], [ZA1606;OS (O)₂ CH₂(3-Py),OCH₃], [ZA1607;OS(O)₂CH₂(4-Py), OCH₃], [ZA1608;OS(O)₂CH₂CN,OCH₃], [ZA1609;OS(O)₂ CH₂NO₂,OCH₃], [ZA1610;OS(O)₂(CH₂)₂F,OCH₃], [ZA1611;OS(O)₂(CH₂)₂Cl,OCH₃], [ZA1612;OS(O)₂ (CH₂)₂ CF₃,OCH₃], [ZA1613;OS(O)₂(CH₂)₂ CN,OCH₃], [ZA1614;OS(O)₂(CH₂)₂NO₂,OCH₃], [ZA1615;OS(O)₂ (CH₂)₂Ph,OCH₃], [ZA1616;OS(O)₂(CH₂)₂OCH₃,OCH₃], [ZA1617;OS(O)₂(CH₂)₃F,OCH₃], [ZA1618;OS(O)₂(CH₂)₃ Cl,OCH₃], [ZA1619;OS(O)₂(CH₂)₃CF₃,OCH₃], [ZA1620; OS(O)₂(CH₂)₃CN,OCH₃], [ZA1621;OS(O)₂(CH₂)₃NO₂, OCH₃], [ZA1622;OS(O)₂(CH₂)₃Ph,OCH₃], [ZA1623;OS (O)₂(CH₂)₃OCH₃,OCH₃], [ZA1624;OS(O)₂(CH₂)₄F, OCH₃], [ZA1625;OS(O)₂(CH₂)₄Cl,OCH₃], [ZA1626;OS (O)₂ (CH₂)₄CF₃,OCH₃], [ZA1627;OS(O)₂(CH₂)₄CN OCH₃], [ZA1628;OS(O)₂(CH₂)₄NO₂,OCH₃], [ZA1629;OS (O)₂(CH₂)₄Ph,OCH₃], [ZA1630;OS(O)₂(CH₂)₄OCH₃, OCH₃], [ZA1631;OS(O)₂(CH₂)₅F,OCH₃], [ZA1632;OS (O)₂ (CH₂)₅Cl,OCH₃], [ZA1633;OS(O)₂ (CH₂)₅CF₃, OCH₃], [ZA1634;OS(O)₂(CH₂)₅CN,OCH₃], [ZA1635;OS (O)₂(CH₂)₅NO₂,OCH₃], [ZA1636;OS(O)₂(CH₂)₅Ph, OCH₃], [ZA1637;OS(O)₂(CH₂)₅OCH₃,OCH₃], [ZA1638; OS(O)₂(CH₂)₆F,OCH₃], [ZA1639;OS(O)₂(CH₂)₆Cl, OCH₃], [ZA1640;OS(O)₂ (CH₂)₆CF₃,OCH₃], [ZA1641;OS (O)₂(CH₂)₆CN,OCH₃], [ZA1642;OS(O)₂(CH₂)₆NO₂, OCH₃], [ZA1643;OS(O)₂(CH₂)₆Ph,OCH₃], [ZA1644;OS (O)₂(CH₂)₆OCH₃,OCH₃], [ZA1645;NH₂,OCH₃], [ZA1646; NHCH₃,OCH₃], [ZA1647;NHCH₂CH₃,OCH₃], [ZA1648; NH(CH₂)₂CH₃,OCH₃], [ZA1649;NH(CH₂)₃CH₃,OCH₃], [ZA1650;NH(CH₂)₄ CH₃,OCH₃], [ZA1651;NH(CH₂)₅CH₃, OCH₃], [ZA1652;NHCH(CH₃)₂,OCH₃], [ZA1653; NHCH₂F,OCH₃], [ZA1654;NHCH₂CN,OCH₃], [ZA1655; NHCH₂OCH₃,OCH₃], [ZA1656;NHCH₂Ph,OCH₃], [ZA1657;NH(CH₂)₂F,OCH₃], [ZA1658;NH(CH₂)₂CN, OCH₃], [ZA1659;NH(CH₂)₂OCH₃,OCH₃], [ZA1660;NH (CH₂)₂Ph,OCH₃], [ZA1661;NH(CH₂)₃F,OCH₃], [ZA1662; NH(CH₂)₃Cl,OCH₃], [ZA1663;NH(CH₂)₃ CN,OCH₃], [ZA1664;NH(CH₂)₃OCH₃,OCH₃], [ZA1665;NH(CH₂)₃Ph, OCH₃], [ZA1666;NH(CH₂)₄F,OCH₃], [ZA1667;NH(CH₂)₄ CN,OCH₃], [ZA1668;NH(CH₂)₄ OCH₃,OCH₃], [ZA1669; NH(CH₂)₄Ph,OCH₃], [ZA1670;NHPh,OCH₃], [ZA1671; NH(2-Py),OCH₃], [ZA1672;NH(3-Py),OCH₃], [ZA1673; NH(4-Py),OCH₃], [ZA1674;N(CH₃)₂,OCH₃], [ZA1675;N (CH₃)CH₂CH₃,OCH₃], [ZA1676;N(CH₃)(CH₂)₂ CH₃, OCH₃], [ZA1677;N(CH₃)(CH₂)₃CH₃,OCH₃], [ZA1678; (CH₃)(CH₂)₄CH₃,OCH₃], [ZA1679;(CH₃)(CH₂)₅CH₃, OCH₃], [ZA1680;N(CH₃)CH(CH₃)₂,OCH₃], [ZA1681;N (CH₃)CH₂F,OCH₃], [ZA1682;N(CH₃)CH₂CN,OCH₃], [ZA1683;N(CH₃)CH₂ OCH₃,OCH₃], [ZA1684;N(CH₃) CH₂Ph,OCH₃], [ZA1685;N(CH₃)(CH₂)₂F,OCH₃], [ZA1686;N(CH₃)(CH₂)₂CN,OCH₃], [ZA1687;N(CH₃) (CH₂)₂OCH₃,OCH₃], [ZA1688;N(CH₃)(CH₂)₂Ph,OCH₃], [ZA1689;N(CH₃)(CH₂)₃F,OCH₃], [ZA1690;N(CH₃)(CH₂)₃ CN,OCH₃], [ZA1691;N(CH₃)(CH₂)₃OCH₃,OCH₃], [ZA1692;N(CH₃)(CH₂)₃ Ph,OCH₃], [ZA1693;N(CH₃) (CH₂)₄F,OCH₃], [ZA1694;N(CH₃)(CH₂)₄CN,OCH₃], [ZA1695;N(CH₃)(CH₂)₄OCH₃,OCH₃], [ZA1696;N(CH₃) (CH₂)₄Ph,OCH₃], [ZA1697;N(CH₃)Ph,OCH₃], [ZA1698;N (CH₃)(2-Py),OCH₃], [ZA1699;N(CH₃)(3-Py),OCH₃], [ZA1700;N(CH₃)(4-Py),OCH₃], [ZA1701;N(CH₂CH₃)₂, OCH₃], [ZA1702;Pyr,OCH₃], [ZA1703;Pip,OCH₃], [ZA1704;Mor,OCH₃], [ZA1705;S(O)₂CH₃,OCH₃], [ZA1706;S(O)₂CH₂CH₃,OCH₃], [ZA1707;S(O)₂CH (CH₃)₂,OCH₃], [ZA1708;S(O)₂(CH₂)₂CH₃,OCH₃], [ZA1709;S(O)₂(CH₂)₃CH₃,OCH₃], [ZA1710;S(O)₂ (CH₂)₄ CH₃,OCH₃], [ZA1711;S(O)₂(CH₂)₅CH₃,OCH₃], [ZA1712; S(O)₂CH₂CH=CH₂,OCH₃], [ZA1713;S(O)₂ CH₂C≡CH, OCH₃], [ZA1714;S(O)₂CH₂C≡CCH₃,OCH₃], [ZA1715;S (O)₂-c-Pr,OCH₃], [ZA1716;S(O)₂-c-Bu,OCH₃], [ZA1717;S (O)₂-c-Pen,OCH₃], [ZA1718;S(O)₂-c-Hex,OCH₃], [ZA1719;S(O)₂Ph,OCH₃], [ZA1720;S(O)₂ (2-Py),OCH₃], [ZA1721;S(O)₂(3-Py),OCH₃], [ZA1722;S(O)₂(4-Py), OCH₃], [ZA1723;S(O)₂CF₃,OCH₃], [ZA1724;S(O)₂ CH₂Ph,OCH₃], [ZA1725;S(O)₂CH₂ (2-Py),OCH₃],

[ZA1726;S(O)₂CH₂(3-Py),OCH₃], [ZA1727;S(O)₂CH₂(4-Py),OCH₃], [ZA1728;S(O)₂CH₂CN,OCH₃], [ZA1729;S(O)₂CH₂NO₂,OCH₃], [ZA1730;S(O)₂(CH₂)₂F,OCH₃], [ZA1731;S(O)₂(CH₂)₂Cl,OCH₃], [ZA1732;S(O)₂(CH₂)₂CF₃,OCH₃], [ZA1733;S(O)₂(CH₂)₂CN,OCH₃], [ZA1734;S(O)₂(CH₂)₂NO₂,OCH₃], [ZA1735;S(O)₂(CH₂)₂Ph,OCH₃], [ZA1736;S(O)₂(CH₂)₂OCH₃,OCH₃], [ZA1737;S(O)₂(CH₂)₃F,OCH₃], [ZA1738;S(O)₂(CH₂)₃Cl,OCH₃], [ZA1739;S(O)₂(CH₂)₃CF₃,OCH₃], [ZA1740;S(O)₂(CH₂)₃CN,OCH₃], [ZA1741;S(O)₂(CH₂)₃NO₂,OCH₃], [ZA1742;S(O)₂(CH₂)₃Ph,OCH₃], [ZA1743;S(O)₂(CH₂)₃OCH₃,OCH₃], [ZA1744;S(O)₂(CH₂)₄F,OCH₃], [ZA1745;S(O)₂(CH₂)₄Cl,OCH₃], [ZA1746;S(O)₂(CH₂)₄CF₃,OCH₃], [ZA1747;S(O)₂(CH₂)₄CN,OCH₃], [ZA1748;S(O)₂(CH₂)₄NO₂,OCH₃], [ZA1749;S(O)₂(CH₂)₄Ph,OCH₃], [ZA1750;S(O)₂(CH₂)₄OCH₃,OCH₃], [ZA1751;S(O)₂(CH₂)₅F,OCH₃], [ZA1752;S(O)₂(CH₂)₅Cl,OCH₃], [ZA1753;S(O)₂(CH₂)₅CF₃,OCH₃], [ZA1754;S(O)₂(CH₂)₅CN,OCH₃], [ZA1755;S(O)₂(CH₂)₅NO₂,OCH₃], [ZA1756;S(O)₂(CH₂)₅Ph,OCH₃], [ZA1757;S(O)₂(CH₂)₅OCH₃,OCH₃], [ZA1758;S(O)₂(CH₂)₆F,OCH₃], [ZA1759;S(O)₂(CH₂)₆Cl,OCH₃], [ZA1760;S(O)₂(CH₂)₆CF₃,OCH₃], [ZA1761;S(O)₂(CH₂)₆CN,OCH₃], [ZA1762;S(O)₂(CH₂)₆NO₂,OCH₃], [ZA1763;S(O)₂(CH₂)₆Ph,OCH₃], [ZA1764;S(O)₂(CH₂)₆OCH₃,OCH₃], [ZA1765;S(O)CH₃,OCH₃], [ZA1766;S(O)CH₂CH₃,OCH₃], [ZA1767;S(O)CH(CH₃)₂,OCH₃], [ZA1768;S(O)(CH₂)₂CH₃,OCH₃], [ZA1769;S(O)(CH₂)₃CH₃,OCH₃], [ZA1770;S(O)(CH₂)₄CH₃,OCH₃], [ZA1771;S(O)(CH₂)₅CH₃,OCH₃], [ZA1772;S(O)CH₂CH=CH₂,OCH₃], [ZA1773;S(O)CH₂C≡CH,OCH₃], [ZA1774;S(O)CH₂C≡CCH₃,OCH₃], [ZA1775;S(O)c-Pr,OCH₃], [ZA1776;S(O)c-Bu,OCH₃], [ZA1777;S(O)c-Pen,OCH₃], [ZA1778;S(O)c-Hex,OCH₃], [ZA1779;S(O)Ph,OCH₃], [ZA1780;S(O)(2-Py),OCH₃], [ZA1781;S(O)(3-Py),OCH₃], [ZA1782;S(O)(4-Py),OCH₃], [ZA1783;S(O)CF₃,OCH₃], [ZA1784;S(O)CH₂Ph,OCH₃], [ZA1785;S(O)CH₂(2-Py),OCH₃], [ZA1786;S(O)CH₂(3-Py),OCH₃], [ZA1787;S(O)CH₂(4-Py),OCH₃], [ZA1788;S(O)CH₂CN,OCH₃], [ZA1789;S(O)CH₂NO₂,OCH₃], [ZA1790;S(O)(CH₂)₂F,OCH₃], [ZA1791;S(O)(CH₂)₂Cl,OCH₃], [ZA1792;S(O)(CH₂)₂CF₃,OCH₃], [ZA1793;S(O)(CH₂)₂CN,OCH₃], [ZA1794;S(O)(CH₂)₂NO₂,OCH₃], [ZA1795;S(O)(CH₂)₂Ph,OCH₃], [ZA1796;S(O)(CH₂)₂OCH₃,OCH₃], [ZA1797;S(O)(CH₂)₃F,OCH₃], [ZA1798;S(O)(CH₂)₃Cl,OCH₃], [ZA1799;S(O)(CH₂)₃CF₃,OCH₃], [ZA1800;S(O)(CH₂)₃CN,OCH₃], [ZA1801;S(O)(CH₂)₃NO₂,OCH₃], [ZA1802;S(O)(CH₂)₃Ph,OCH₃], [ZA1803;S(O)(CH₂)₃OCH₃,OCH₃], [ZA1804;S(O)(CH₂)₄F,OCH₃], [ZA1805;S(O)(CH₂)₄Cl,OCH₃], [ZA1806;S(O)(CH₂)₄CF₃,OCH₃], [ZA1807;S(O)(CH₂)₄CN,OCH₃], [ZA1808;S(O)(CH₂)₄NO₂,OCH₃], [ZA1809;S(O)(CH₂)₄Ph,OCH₃], [ZA1810;S(O)(CH₂)₄OCH₃,OCH₃], [ZA1811;S(O)(CH₂)₅F,OCH₃], [ZA1812;S(O)(CH₂)₅Cl,OCH₃], [ZA1813;S(O)(CH₂)₅CF₃,OCH₃], [ZA1814;S(O)(CH₂)₅CN,OCH₃], [ZA1815;S(O)(CH₂)₅NO₂,OCH₃], [ZA1816;S(O)(CH₂)₅Ph,OCH₃], [ZA1817;S(O)(CH₂)₅OCH₃,OCH₃], [ZA1818;S(O)(CH₂)₆F,OCH₃], [ZA1819;S(O)(CH₂)₆Cl,OCH₃], [ZA1820;S(O)(CH₂)₆CF₃,OCH₃], [ZA1821;S(O)(CH₂)₆CN,OCH₃], [ZA1822;S(O)(CH₂)₆NO₂,OCH₃], [ZA1823;S(O)(CH₂)₆Ph,OCH₃], [ZA1824;S(O)(CH₂)₆OCH₃,OCH₃], [ZA1825;OH,SCH₃], [ZA1826;OCH₃,SCH₃], [ZA1827;OCH₂CH₃,SCH₃], [ZA1828;OCH(CH₃)₂,SCH₃], [ZA1829;O(CH₂)₂CH₃,SCH₃], [ZA1830;O(CH₂)₃CH₃,SCH₃], [ZA1831;O(CH₂)₄CH₃,SCH₃], [ZA1832;O(CH₂)₅CH₃,SCH₃], [ZA1833;OCH₂CH=CH₂,SCH₃], [ZA1834;OCH₂C≡CH,SCH₃], [ZA1835;OCH₂C≡CCH₃,SCH₃], [ZA1836;O-c-Pr,SCH₃], [ZA1837;O-c-Bu,SCH₃], [ZA1838;O-c-Pen,SCH₃], [ZA1839;O-c-Hex,SCH₃], [ZA1840;OPh,SCH₃], [ZA1841;O(2-Py),SCH₃], [ZA1842;O(3-Py),SCH₃], [ZA1843;O(4-Py),SCH₃], [ZA1844;OCF₃,SCH₃], [ZA1845;OCH₂Ph,SCH₃], [ZA1846;OCH₂(2-Py),SCH₃], [ZA1847;OCH₂(3-Py),SCH₃], [ZA1848;OCH₂(4-Py),SCH₃], [ZA1849;OCH₂CN,SCH₃], [ZA1850;OCH₂NO₂,SCH₃], [ZA1851;O(CH₂)₂F,SCH₃], [ZA1852;O(CH₂)₂Cl,SCH₃], [ZA1853;O(CH₂)₂Br,SCH₃], [ZA1854;O(CH₂)₂I,SCH₃], [ZA1855;O(CH₂)₂CF₃,SCH₃], [ZA1856;O(CH₂)₂CN,SCH₃], [ZA1857;O(CH₂)₂NO₂,SCH₃], [ZA1858;O(CH₂)₂Ph,SCH₃], [ZA1859;O(CH₂)₂(2-Py),SCH₃], [ZA1860;O(CH₂)₂(3-Py),SCH₃], [ZA1861;O(CH₂)₂(4-Py),SCH₃], [ZA1862;O(CH₂)₂OH,SCH₃], [ZA1863;O(CH₂)₂OCH₃,SCH₃], [ZA1864;O(CH₂)₂SH,SCH₃], [ZA1865;O(CH₂)₂SCH₃,SCH₃], [ZA1866;O(CH₂)₂NH₂,SCH₃], [ZA1867;O(CH₂)₂NHCH₃,SCH₃], [ZA1868;O(CH₂)₂N(CH₃)₂,SCH₃], [ZA1869;O(CH₂)₂NHPh,SCH₃], [ZA1870;O(CH₂)₂NHCH₂Ph,SCH₃], [ZA1871;O(CH₂)₂N(CH₃)CH₂Ph,SCH₃], [ZA1872;O(CH₂)₂S(O)CH₃,SCH₃], [ZA1873;O(CH₂)₂S(O)CH₂CH₃,SCH₃], [ZA1874;O(CH₂)₂S(O)Ph,SCH₃], [ZA1875;O(CH₂)₂S(O)₂CH₃,SCH₃], [ZA1876;O(CH₂)₂S(O)₂CH₂CH₃,SCH₃], [ZA1877;O(CH₂)₂S(O)₂Ph,SCH₃], [ZA1878;O(CH₂)₂C(O)CH₃,SCH₃], [ZA1879;O(CH₂)₂C(O)CH₂CH₃,SCH₃], [ZA1880;O(CH₂)₂C(O)Ph,SCH₃], [ZA1881;O(CH₂)₂C(S)CH₃,SCH₃], [ZA1882;O(CH₂)₂C(S)CH₂CH₃,SCH₃], [ZA1883;O(CH₂)₂C(S)Ph,SCH₃], [ZA1884;O(CH₂)₂S(O)₂NHCH₃,SCH₃], [ZA1885;O(CH₂)₂S(O)₂N(CH₃)₂,SCH₃], [ZA1886;O(CH₂)₂S(O)₂NHPh,SCH₃], [ZA1887;O(CH₂)₂S(O)₂N(CH₃)Ph,SCH₃], [ZA1888;O(CH₂)₂C(O)NH₂,SCH₃], [ZA1889;O(CH₂)₂C(O)NHCH₃,SCH₃], [ZA1890;O(CH₂)₂C(O)N(CH₃)₂,SCH₃], [ZA1891;O(CH₂)₂C(O)NHPh,SCH₃], [ZA1892;O(CH₂)₂C(O)N(CH₃)Ph,SCH₃], [ZA1893;O(CH₂)₂C(O)OCH₃,SCH₃], [ZA1894;O(CH₂)₂C(O)OCH₂CH₃,SCH₃], [ZA1895;O(CH₂)₂NHC(O)CH₃,SCH₃], [ZA1896;O(CH₂)₂NHC(O)CH₂CH₃,SCH₃], [ZA1897;O(CH₂)₂NHC(O)Ph,SCH₃], [ZA1898;O(CH₂)₂NCH₃C(O)CH₃,SCH₃], [ZA1899;O(CH₂)₂NCH₃C(O)CH₂CH₃,SCH₃], [ZA1900;O(CH₂)₂NCH₃C(O)Ph,SCH₃], [ZA1901;O(CH₂)₂NHC(O)OCH₃,SCH₃], [ZA1902;O(CH₂)₂NHC(O)OCH₂CH₃,SCH₃], [ZA1903;O(CH₂)₂NHC(O)OPh,SCH₃], [ZA1904;O(CH₂)₂NCH₃C(O)OCH₃,SCH₃], [ZA1905;O(CH₂)₂NCH₃C(O)OCH₂CH₃,SCH₃], [ZA1906;O(CH₂)₂NCH₃C(O)OPh,SCH₃], [ZA1907;O(CH₂)₂NHC(O)NHCH₃,SCH₃], [ZA1908;O(CH₂)₂NHC(O)NHCH₂CH₃,SCH₃], [ZA1909;O(CH₂)₂NHC(O)NHPh,SCH₃], [ZA1910;O(CH₂)₂NHC(O)N(CH₃)₂,SCH₃], [ZA1911;O(CH₂)₂NHC(O)N(CH₃)CH₂CH₃,SCH₃], [ZA1912;O(CH₂)₂NHC(O)N(CH₃)Ph,SCH₃], [ZA1913;O(CH₂)₂NHC(O)N(CH₂CH₃)₂,SCH₃], [ZA1914;O(CH₂)₂NCH₃C(O)NHCH₃,SCH₃], [ZA1915;O(CH₂)₂NCH₃C(O)NHCH₂CH₃,SCH₃], [ZA1916;O(CH₂)₂NCH₃C(O)NHPh,SCH₃], [ZA1917;O(CH₂)₂NCH₃C(O)N(CH₃)₂,SCH₃], [ZA1918;O(CH₂)₂NCH₃C(O)N(CH₃)CH₂CH₃,SCH₃], [ZA1919;O(CH₂)₂NCH₃C(O)NCHH₃)Ph,SCH₃], [ZA1920;O(CH₂)₂NCH₃C(O)N(CH₂CH₃)₂,SCH₃], [ZA1921;O(CH₂)₂OC(O)CH₃,SCH₃], [ZA1922;O(CH₂)₂OC(O)CH₂CH₃,SCH₃], [ZA1923;O(CH₂)₂OC(O)Ph,SCH₃], [ZA1924;O(CH₂)₂OC(O)OCH₃,SCH₃], [ZA1925;O(CH₂)₂OC(O)OCH₂CH₃,SCH₃], [ZA1926;O(CH₂)₂OC(O)OPh,SCH₃], [ZA1927;O(CH₂)₂OC(O)NHCH₃,SCH₃], [ZA1928;O(CH₂)₂OC(O)NHCH₂CH₃,SCH₃], [ZA1929;O(CH₂)₂OC(O)NHPh,SCH₃], [ZA1930;O(CH₂)₂OC(O)N(CH₃)₂,SCH₃], [ZA1931;O(CH₂)₂OC(O)N(CH₃)CH₂CH₃,SCH₃], [ZA1932;O(CH₂)₂OC(O)N(CH₃)Ph,SCH₃], [ZA1933;O(CH₂)₂OC(O)N(CH₂CH₃)₂,SCH₃], [ZA1934;O(CH₂)₂SC(O)CH₃,SCH₃], [ZA1935;O(CH₂)₂SC(O)

CH₂CHCH₃,SCH₃], [ZA1936;O(CH₂)₂SC(O)Ph,SCH₃], [ZA1937;O(CH₂)₂SC(O)OCH₃,SCH₃], [ZA1938; O(CH₂)₂SC(O)OCH₂CH₃,SCH₃], [ZA1939;O(CH₂)₂SC(O) OPh,SCH₃], [ZA1940;O(CH₂)₂S(O)₂NHCH₃,SCH₃], [ZA1941;O(CH₂)₂S(O)₂NHCH₂CH₃,SCH₃], [ZA1942;O (CH₂)₂S(O)₂NHPh,SCH₃], [ZA1943;O(CH₂)₂S(O)₂N (CH₃)₂,SCH₃], [ZA1944;O(CH₂)₂S(O)₂N(CH₃)CH₂CH₃, SCH₃], [ZA1945;O(CH₂)₂S(O)₂N(CH₃)Ph,SCH₃], [ZA1946;O(CH₂)₂S(O)₂N(CH₂CH₃)₂,SCH₃], [ZA1947;O (CH₂)₃F,SCH₃], [ZA1948;O(CH₂)₃Cl,SCH₃], [ZA1949;O (CH₂)₃Br,SCH₃], [ZA1950;O(CH₂)₃I,SCH₃], [ZA1951;O (CH₂)₃CF₃,SCH₃], [ZA1952;O(CH₂)₃CN,SCH₃], [ZA1953;O(CH₂)₃NO₂,SCH₃], [ZA1954;O(CH₂)₃Ph, SCH₃], [ZA1955;O(CH₂)₃(2-Py),SCH₃], [ZA1956; O(CH₂)₃(3-Py),SCH₃], [ZA1957;O(CH₂)₃(4-Py),SCH₃], [ZA1958;O(CH₂)₃ OH,SCH₃], [ZA1959;O(CH₂)₃OCH₃, SCH₃], [ZA1960;O(CH₂)₃OCH₂CH₃,SCH₃], [ZA1961;O (CH₂)₃SH,SCH₃], [ZA1962;O(CH₂)₃SCH₃,SCH₃], [ZA1963;O(CH₂)₃SCH₂ CH₃,SCH₃], [ZA1964; O(CH₂)₃NH₂,SCH₃], [ZA1965;O(CH₂)₃NHCH₃,SCH₃], [ZA1966;O(CH₂)₃N(CH₃)₂,SCH₃], [ZA1967;O(CH₂)₄F, SCH₃], [ZA1968;O(CH₂)₄ Cl,SCH₃], [ZA1969;O(CH₂)₄ CF₃,SCH₃], [ZA1970;O(CH₂)₄CN,SCH₃], [ZA1971;O (CH₂)₄NO₂,SCH₃], [ZA1972;O(CH₂)₄Ph,SCH₃], [ZA1973; O(CH₂)₄OH,SCH₃], [ZA1974;O(CH₂)₄OCH₃,SCH₃], [ZA1975;O(CH₂)₄SH,SCH₃], [ZA1976;O(CH₂)₄SCH₃, SCH₃], [ZA1977;O(CH₂)₄NH₂,SCH₃], [ZA1978; O(CH₂)₄NHCH₃,SCH₃], [ZA1979;O(CH₂)₄N(CH₃)₂, SCH₃], [ZA1980;O(CH₂)₅F,SCH₃], [ZA1981;O(CH₂)₅ Cl,SCH₃], [ZA1982;O(CH₂)₅CF₃,SCH₃], [ZA1983; O(CH₂)₅CN,SCH₃], [ZA1984;O(CH₂)₅NO₂,SCH₃], [ZA1985;O(CH₂)₅Ph,SCH₃], [ZA1986;O(CH₂)₅OH, SCH₃], [ZA1987;O(CH₂)₅OCH₃,SCH₃], [ZA1988; O(CH₂)₅SH,SCH₃], [ZA1989;O(CH₂)₅SCH₃,SCH₃], [ZA1990;O(CH₂)₅NH₂,SCH₃], [ZA1991;O(CH₂)₅NHCH₃, SCH₃], [ZA1992;O(CH₂)₅N(CH₃)₂,SCH₃], [ZA1993;O (CH₂)₆F,SCH₃], [ZA1994;O(CH₂)₆ Cl,SCH₃], [ZA1995;O (CH₂)₆CF₃,SCH₃], [ZA1996;O(CH₂)₆CN,SCH₃], [ZA1997;O(CH 2)₆NO₂,SCH₃], [ZA1998;O(CH₂)₆Ph, SCH₃], [ZA1999;O(CH₂)₆OH,SCH₃], [ZA2000; O(CH₂)₆OCH₃,SCH₃],

[ZA2001;O(CH₂)₆SH,SCH₃], [ZA2002;O(CH₂)₆SCH₃, SCH₃], [ZA2003;O(CH₂)₆NH₂,SCH₃], [ZA2004; O(CH₂)₆NHCH₃,SCH₃], [ZA2005;O(CH₂)₆N(CH₃)₂, SCH₃], [ZA2006;OC(O)CH₃,SCH₃], [ZA2007;OC(O) CH₂CH₃,SCH₃], [ZA2008;OC(O)CH(CH₃)₂,SCH₃], [ZA2009;OC(O)(CH₂)₂CH₃,SCH₃], [ZA2010;OC(O) (CH₂)₃CH₃,SCH₃], [ZA2011;OC(O)(CH₂)₄CH₃,SCH₃], [ZA2012;OC(O)(CH₂)₅CH₃,SCH₃], [ZA2013;OC(O) CH₂CH=CH₂,SCH₃], [ZA2014;OC(O)CH₂C≡CH,SCH₃], [ZA2015;OC(O)CH₂C≡CCH₃,SCH₃], [ZA2016;OC(O)c-Pr,SCH₃], [ZA2017;OC(O)c-Bu,SCH₃], [ZA2018;OC(O)c-Pen,SCH₃], [ZA2019;OC(O)c-Hex,SCH₃], [ZA2020;OC (O)Ph,SCH₃], [ZA2021;OC(O)(2-Py),SCH₃], [ZA2022;OC (O)(3-Py),SCH₃], [ZA2023;OC(O)(4-Py),SCH₃], [ZA2024; OC(O)CF₃,SCH₃], [ZA2025;OC(O)CH₂ Ph,SCH₃], [ZA2026;OC(O)CH₂(2-Py),SCH₃], [ZA2027;OC(O)CH₂ (3-Py),SCH₃], [ZA2028;OC(O)CH₂(4-Py),SCH₃], [ZA2029;OC(O)CH₂CN,SCH₃], [ZA2030;OC(O)CH₂NO₂, SCH₃], [ZA2031;OC(O)(CH₂)₂F,SCH₃], [ZA2032;OC(O) (CH₂)₂Cl,SCH₃], [ZA2033;OC(O)(CH₂)₂CF₃,SCH₃], [ZA2034;OC(O)(CH₂)₂CN,SCH₃], [ZA2035;OC(O) (CH₂)₂NO₂,SCH₃], [ZA2036;OC(O)(CH₂)₂Ph,SCH₃], [ZA2037;OC(O)(CH₂)₂OCH₃,SCH₃], [ZA2038;OC(O) (CH₂)₃F,SCH₃], [ZA2039;OC(O)(CH₂)₃Cl,SCH₃], [ZA2040;OC(O)(CH₂)₃CF₃,SCH₃], [ZA2041;OC(O) (CH₂)₃CN,SCH₃], [ZA2042;OC(O)(CH₂)₃NO₂,SCH₃], [ZA2043;OC(O)(CH₂)₃Ph,SCH₃], [ZA2044;OC(O)(CH₂)₃ OCH₃,SCH₃], [ZA2045;OC(O)(CH₂)₄F,SCH₃], [ZA2046; OC(O)(CH₂)₄Cl,SCH₃], [ZA2047;OC(O)(CH₂)₄CF₃, SCH₃], [ZA2048;OC(O)(CH₂)₄CN,SCH₃], [ZA2049;OC (O)(CH₂)₄NO₂,SCH₃], [ZA2050;OC(O)(CH₂)₄Ph,SCH₃], [ZA2051;OC(O)(CH₂)₄OCH₃,SCH₃], [ZA2052;OC(O) (CH₂)₅F,SCH₃], [ZA2053;OC(O)(CH₂)₅Cl,SCH₃], [ZA2054;OC(O)(CH₂)₅CF₃,SCH₃], [ZA2055;OC(O) (CH₂)₅CN,SCH₃], [ZA2056;OC(O)(CH₂)₅NO₂,SCH₃], [ZA2057;OC(O)(CH₂)₅Ph,SCH₃], [ZA2058;OC(O)(CH₂)₅ OCH₃,SCH₃], [ZA2059;OC(O)(CH₂)₆F,SCH₃], [ZA2060; OC(O)(CH₂)₆Cl,SCH₃], [ZA2061;OC(O)(CH₂)₆CF₃, SCH₃], [ZA2062;OC(O)(CH₂)₆CN,SCH₃], [ZA2063;OC (O)(CH₂)₆NO₂,SCH₃], [ZA2064;OC(O)(CH₂)₆Ph,SCH₃], [ZA2065;OC(O)(CH₂)₆OCH₃,SCH₃], [ZA2066;OC(O) NH₂,SCH₃], [ZA2067;OC(O)NHCH₃,SCH₃], [ZA2068;OC (O)NHCH₂ CH₃,SCH₃], [ZA2069;OC(O)NH(CH₂)₂CH₃, SCH₃], [ZA2070;OC(O)NH(CH₂)₃CH₃,SCH₃], [ZA2071; OC(O)NH(CH₂)₄CH₃,SCH₃], [ZA2072;OC(O)NH(CH)₅ CH₃,SCH₃], [ZA2073;OC(O)NHCH(CH₃)₂,SCH₃], [ZA2074;OC(O)NHCH₂F,SCH₃], [ZA2075;OC(O) NHCH₂Cl,SCH₃], [ZA2076;OC(O)NHCH₂CN,SCH₃], [ZA2077;OC(O)NHCH₂OCH₃,SCH₃], [ZA2078;OC(O) NHCH₂Ph,SCH₃], [ZA2079;OC(O)NH(CH₂)₂F,SCH₃], [ZA2080;OC(O)NH(CH₂)₂Cl,SCH₃], [ZA2081;OC(O)NH (CH₂)₂CN,SCH₃], [ZA2082;OC(O)NH(CH₂)₂OCH₃, SCH₃], [ZA2083;OC(O)NH(CH₂)₂Ph,SCH₃], [ZA2084;OC (O)NH(CH₂)₃F,SCH₃], [ZA2085;OC(O)NH(CH₂)₃Cl, SCH₃], [ZA2086;OC(O)NH(CH₂)₃CN,SCH₃], [ZA2087; OC(O)NH(CH₂)₃OCH₃,SCH₃], [ZA2088;OC(O)NH(CH)₃ Ph,SCH₃], [ZA2089;OC(O)NH(CH₂)₄F,SCH₃], [ZA2090; OC(O)NH(CH₂)₄Cl,SCH₃], [ZA2091;OC(O)NH(CH₂)₄CN, SCH₃], [ZA2092;OC(O)NH(CH₂)₄OCH₃,SCH₃], [ZA2093; OC(O)NH(CH₂)₄Ph,SCH₃], [ZA2094;OC(O)NHPh,SCH₃], [ZA2095;OC(O)NH(2-Py),SCH₃], [ZA2096;OC(O)NH(3-Py),SCH₃], [ZA2097;OC(O)NH(4-Py),SCH₃], [ZA2098; OC(O)N(CH₃)₂,SCH₃], [ZA2099;OC(O)N(CH₃)CH₂CH₃, SCH₃], [ZA2100;OC(O)N(CH₃)(CH₂)₂CH₃,SCH₃], [ZA2101;OC(O)N(CH₃)(CH₂)₃CH₃,SCH₃], [ZA2102;OC (O)N(CH₃)(CH₂)₄CH₃,SCH₃], [ZA2103;OC(O)N(CH₃) (CH₂)₅CH₃,SCH₃], [ZA2104;OC(O)N(CH₃)CH(CH₃)₂, SCH₃], [ZA2105;OC(O)N(CH₃)CH₂F,SCH₃], [ZA2106;OC (O)N(CH₃)CH₂Cl,SCH₃], [ZA2107;OC(O)N(CH₃)CH₂CN, SCH₃], [ZA2108;OC(O)N(CH₃)CH₂OCH₃,SCH₃], [ZA2109;OC(O)N(CH₃)CH₂Ph,SCH₃], [ZA2110;OC(O)N (CH₃)(CH₂)₂F,SCH₃], [ZA2111;OC(O)N(CH₃)(CH₂)₂Cl, SCH₃], [ZA2112;OC(O)N(CH₃)(CH₂)₂CN,SCH₃], [ZA2113;OC(O)N(CH₃)(CH₂)₂OCH₃,SCH₃], [ZA2114;OC (O)N(CH₃)(CH₂)₂Ph,SCH₃], [ZA2115;OC(O)N(CH₃) (CH₂)₃F,SCH₃], [ZA2116;OC(O)N(CH₃)(CH₂)₃Cl,SCH₃], [ZA2117;OC(O)N(CH₃)(CH₂)₃CN,SCH₃], [ZA2118;OC (O)N(CH₃)(CH₂)₃OCH₃,SCH₃], [ZA2119;OC(O)N(CH₃) (CH₂)₃Ph,SCH₃], [ZA2120;OC(O)N(CH₃)(CH₂)₄F,SCH₃], [ZA2121;OC(O)N(CH₃)(CH₂)₄Cl,SCH₃], [ZA2122;OC(O) N(CH₃)(CH₂)₄CN,SCH₃], [ZA2123;OC(O)N(CH₃)(CH₂)₄ OCH₃,SCH₃], [ZA2124;OC(O)N(CH₃)(CH₂)₄Ph,SCH₃], [ZA2125;OC(O)N(CH₃)Ph,SCH₃], [ZA2126;OC(O)N (CH₃)(2-Py),SCH₃], [ZA2127;OC(O)N(CH₃)(3-Py),SCH₃], [ZA2128;OC(O)N(CH₃)(4-Py),SCH₃], [ZA2129;OC(O)N (CH₂CH₃)₂,SCH₃], [ZA2130;OC(O)(Pyr),SCH₃], [ZA2131;OC(O)(Pip),SCH₃], [ZA2132;OC(O)(Mor), SCH₃], [ZA2133;OC(O)OCH₃,SCH₃], [ZA2134;OC(O) OCH₂CH₃,SCH₃], [ZA2135;OC(O)OCH(CH₃)₂,SCH₃], [ZA2136;OC(O)O(CH₂)₂CH₃,SCH₃], [ZA2137;OC(O)O (CH₂)₃CH₃,SCH₃], [ZA2138;OC(O)O(CH₂)₄CH₃,SCH₃], [ZA2139;OC(O)O(CH₂)₅CH₃,SCH₃], [ZA2140;OC(O) OCH₂CH=CH₂,SCH₃], [ZA2141;OC(O)OCH₂C≡CH, SCH₃], [ZA2142;OC(O)OCH₂C≡CCH₃,SCH₃], [ZA2143; OC(O)O-c-Pr,SCH₃], [ZA2144;OC(O)O-c-Bu,SCH₃],

[ZA2145;OC(O)O-c-Pen,SCH₃], [ZA2146;OC(O)O-c-Hex,SCH₃], [ZA2147;OC(O)OPh,SCH₃], [ZA2148;OC(O)O(2-Py),SCH₃], [ZA2149;OC(O)O(3-Py),SCH₃], [ZA2150;OC(O)O(4-Py),SCH₃], [ZA2151;OC(O)OCF₃,SCH₃], [ZA2152;OC(O)OCH₂Ph,SCH₃], [ZA2153;OC(O)OCH₂(2-Py),SCH₃], [ZA2154;OC(O)OCH₂(3-Py),SCH₃], [ZA2155;OC(O)OCH₂(4-Py),SCH₃], [ZA2156;OC(O)OCH₂CN,SCH₃], [ZA2157;OC(O)OCH₂NO₂,SCH₃], [ZA2158;OC(O)O(CH₂)₂F,SCH₃], [ZA2159;OC(O)O(CH₂)₂Cl,SCH₃], [ZA2160;OC(O)O(CH₂)₂CF₃,SCH₃], [ZA2161;OC(O)O(CH₂)₂CN,SCH₃], [ZA2162;OC(O)O(CH₂)₂NO₂,SCH₃], [ZA2163;OC(O)O(CH₂)₂Ph,SCH₃], [ZA2164;OC(O)O(CH₂)₂OCH₃,SCH₃], [ZA2165;OC(O)O(CH₂)₃F,SCH₃], [ZA2166;OC(O)O(CH₂)₃Cl,SCH₃], [ZA2167;OC(O)O(CH₂)₃CF₃,SCH₃], [ZA2168;OC(O)O(CH₂)₃CN,SCH₃], [ZA2169;OC(O)O(CH₂)₃NO₂,SCH₃], [ZA2170;OC(O)O(CH₂)₃Ph,SCH₃], [ZA2171;OC(O)O(CH₂)₃OCH₃,SCH₃], [ZA2172;OC(O)O(CH₂)₄F,SCH₃], [ZA2173;OC(O)O(CH₂)₄Cl,SCH₃], [ZA2174;OC(O)O(CH₂)₄CF₃,SCH₃], [ZA2175;OC(O)O(CH₂)₄CN,SCH₃], [ZA2176;OC(O)O(CH₂)₄NO₂,SCH₃], [ZA2177;OC(O)O(CH₂)₄Ph,SCH₃], [ZA2178;OC(O)O(CH₂)₄OCH₃,SCH₃], [ZA2179;OC(O)O(CH₂)₅F,SCH₃], [ZA2180;OC(O)O(CH₂)₅Cl,SCH₃], [ZA2181;OC(O)O(CH₂)₅CF₃,SCH₃], [ZA2182;OC(O)O(CH₂)₅CN,SCH₃], [ZA2183;OC(O)O(CH₂)₅NO₂,SCH₃], [ZA2184;OC(O)O(CH₂)₅Ph,SCH₃], [ZA2185;OC(O)O(CH₂)₅OCH₃,SCH₃], [ZA2186;OC(O)O(CH₂)₆F,SCH₃], [ZA2187;OC(O)O(CH₂)₆Cl,SCH₃], [ZA2188;OC(O)O(CH₂)₆CF₃,SCH₃], [ZA2189;OC(O)O(CH₂)₆CN,SCH₃], [ZA2190;OC(O)O(CH₂)₆NO₂,SCH₃], [ZA2191;OC(O)O(CH₂)₆Ph,SCH₃], [ZA2192;OC(O)O(CH₂)₆OCH₃,SCH₃], [ZA2193;OS(O)₂CH₃,SCH₃], [ZA2194;OS(O)₂CH₂CH₃,SCH₃], [ZA2195;OS(O)₂CH(CH₃)₂,SCH₃], [ZA2196;OS(O)₂(CH₂)₂CH₃,SCH₃], [ZA2197;OS(O)₂(CH₂)₃CH₃,SCH₃], [ZA2198;OS(O)₂(CH₂)₄CH₃,SCH₃], [ZA2199;OS(O)₂(CH₂)₅CH₃,SCH₃], [ZA2200;OS(O)₂CH₂CH=CH₂,SCH₃], [ZA2201;OS(O)₂CH₂C≡CH,SCH₃], [ZA2202;OS(O)₂CH₂C≡CCH₃,SCH₃], [ZA2203;OS(O)₂-c-Pr,SCH₃], [ZA2204;OS(O)₂-c-Bu,SCH₃], [ZA2205;OS(O)₂-c-Pen,SCH₃], [ZA2206;OS(O)₂-c-Hex,SCH₃], [ZA2207;OS(O)₂Ph,SCH₃], [ZA2208;OS(O)₂(2-Py),SCH₃], [ZA2209;OS(O)₂(3-Py),SCH₃], [ZA221;OS(O)₂(4-Py),SCH₃], [ZA2211;OS(O)₂CF₃,SCH₃], [ZA2212;OS(O)₂CH₂Ph,SCH₃], [ZA2213;OS(O)₂CH₂(2-Py),SCH₃], [ZA2214;OS(O)₂CH₂(3-Py),SCH₃], [ZA2215;OS(O)₂CH₂(4-Py),SCH₃], [ZA2216;OS(O)₂CH₂CN,SCH₃], [ZA2217;OS(O)₂CH₂NO₂,SCH₃], [ZA2218;OS(O)₂(CH₂)₂F,SCH₃], [ZA2219;OS(O)₂(CH₂)₂Cl,SCH₃], [ZA2220;OS(O)₂(CH₂)₂CF₃,SCH₃], [ZA2221;OS(O)₂(CH₂)₂CN,SCH₃], [ZA2222;OS(O)₂(CH₂)₂NO₂,SCH₃], [ZA2223;OS(O)₂(CH₂)₂Ph,SCH₃], [ZA2224;OS(O)₂(CH₂)₂OCH₃,SCH₃], [ZA2225;OS(O)₂(CH₂)₃F,SCH₃], [ZA2226;OS(O)₂(CH₂)₃Cl,SCH₃], [ZA2227;OS(O)₂(CH₂)₃CF₃,SCH₃], [ZA2228;OS(O)₂(CH₂)₃CN,SCH₃], [ZA2229;OS(O)₂(CH₂)₃NO₂,SCH₃], [ZA2230;OS(O)₂(CH₂)₃Ph,SCH₃], [ZA2231;OS(O)₂(CH₂)₃OCH₃,SCH₃], [ZA2232;OS(O)₂(CH₂)₄F,SCH₃], [ZA2233;OS(O)₂(CH₂)₄Cl,SCH₃], [ZA2234;OS(O)₂(CH)₄CF₃,SCH₃], [ZA2235;OS(O)₂(CH₂)₄CN,SCH₃], [ZA2236;OS(O)₂(CH₂)₄NO₂,SCH₃], [ZA2237;OS(O)₂(CH₂)₄Ph,SCH₃], [ZA2238;OS(O)₂(CH₂)₄OCH₃,SCH₃], [ZA2239;OS(O)₂(CH₂)₅F,SCH₃], [ZA2240;OS(O)₂(CH₂)₅Cl,SCH₃], [ZA2241;OS(O)₂(CH₂)₅CF₃,SCH₃], [ZA2242;OS(O)₂(CH₂)₅CN,SCH₃], [ZA2243;OS(O)₂(CH₂)₅NO₂,SCH₃], [ZA2244;OS(O)₂(CH₂)₅Ph,SCH₃], [ZA2245;OS(O)₂(CH₂)₅OCH₃,SCH₃], [ZA2246;OS(O)₂(CH₂)₆F,SCH₃], [ZA2247;OS(O)₂(CH₂)₆Cl,SCH₃], [ZA2248;OS(O)₂(CH₂)₆CF₃,SCH₃], [ZA2249;OS(O)₂(CH₂)₆CN,SCH₃], [ZA2250;OS(O)₂(CH₂)₆NO₂,SCH₃], [ZA2251;OS(O)₂(CH₂)₆Ph,SCH₃], [ZA2252;OS(O)₂(CH₂)₆OCH₃,SCH₃], [ZA2253;NH₂,SCH₃], [ZA2254;NHCH₃,SCH₃], [ZA2255;NHCH₂CH₃,SCH₃], [ZA2256;NH(CH₂)₂CH₃,SCH₃], [ZA2257;NH(CH₂)₃CH₃,SCH₃], [ZA2258;NH(CH₂)₄CH₃,SCH₃], [ZA2259;NH(CH₂)₅CH₃,SCH₃], [ZA2260;NHCH(CH₃)₂,SCH₃], [ZA2261;NHCH₂F,SCH₃], [ZA2262;NHCH₂CN,SCH₃], [ZA2263;NHCH₂OCH₃,SCH₃], [ZA2264;NHCH₂Ph,SCH₃], [ZA2265;NH(CH₂)₂F,SCH₃], [ZA2266;NH(CH₂)₂CN,SCH₃], [ZA2267;NH(CH₂)₂OCH₃,SCH₃], [ZA2268;NH(CH₂)₂Ph,SCH₃], [ZA2269;NH(CH₂)₃F,SCH₃], [ZA2270;NH(CH₂)₃Cl,SCH₃], [ZA2271;NH(CH₂)₃CN,SCH₃], [ZA2272;NH(CH₂)₃OCH₃,SCH₃], [ZA2273;NH(CH₂)₃Ph,SCH₃], [ZA2274;NH(CH₂)₄F,SCH₃], [ZA2275;NH(CH₂)₄CN,SCH₃], [ZA2276;NH(CH₂)₄OCH₃,SCH₃], [ZA2277;NH(CH₂)₄Ph,SCH₃], [ZA2278;NHPh,SCH₃], [ZA2279;NH(2-Py),SCH₃], [ZA228;NH(3-Py),SCH₃], [ZA2281;NH(4-Py),SCH₃], [ZA2282;N(CH₃)₂,SCH₃], [ZA2283;N(CH₃)CH₂CH₃,SCH₃], [ZA2284;N(CH₃)(CH₂)₂CH₃,SCH₃], [ZA2285;N(CH₃)(CH₂)₃CH₃,SCH₃], [ZA2286;(CH₃)(CH₂)₄CH₃,SCH₃], [ZA2287;(CH₃)(CH₂)₅CH₃,SCH₃], [ZA2288;N(CH₃)CH(CH₃)₂,SCH₃], [ZA2289;N(CH₃)CH₂F,SCH₃], [ZA2290;N(CH₃)CH₂CN,SCH₃], [ZA2291;N(CH₃)CH₂OCH₃,SCH₃], [ZA2292;N(CH₃)CH₂Ph,SCH₃], [ZA2293;N(CH₃)(CH₂)₂F,SCH₃], [ZA2294;N(CH₃)(CH₂)₂CN,SCH₃], [ZA2295;N(CH₃)(CH₂)₂OCH₃,SCH₃], [ZA2296;N(CH₃)(CH₂)₂Ph,SCH₃], [ZA2297;N(CH₃)(CH₂)₃F,SCH₃], [ZA2298;N(CH₃)(CH₂)₃CN,SCH₃], [ZA2299;N(CH₃)(CH₂)₃OCH₃,SCH₃], [ZA2300;N(CH₃)(CH₂)₃Ph,SCH₃], [ZA2301;N(CH₃)(CH₂)₄F,SCH₃], [ZA2302;N(CH₃)(CH₂)₄CN,SCH₃], [ZA2303;N(CH₃)(CH₂)₄OCH₃,SCH₃], [ZA2304;N(CH₃)(CH₂)₄Ph,SCH₃], [ZA2305;N(CH₃)Ph,SCH₃], [ZA2306;N(CH₃)(2-Py),SCH₃], [ZA2307;N(CH₃)(3-Py),SCH₃], [ZA2308;N(CH₃)(4-Py),SCH₃], [ZA2309;N(CH₂CH₃)₂,SCH₃], [ZA2310;Pyr,SCH₃], [ZA2311;Pip,SCH₃], [ZA2312;Mor,SCH₃], [ZA2313;S(O)₂CH₃,SCH₃], [ZA2314;S(O)₂CH₂CH₃,SCH₃], [ZA2315;S(O)₂CH(CH₃)₂,SCH₃], [ZA2316;S(O)₂(CH₂)₂CH₃,SCH₃], [ZA2317;S(O)₂(CH₂)₃CH₃,SCH₃], [ZA2318;S(O)₂(CH₂)₄CH₃,SCH₃], [ZA2319;S(O)₂(CH₂)₅CH₃,SCH₃], [ZA2320;S(O)₂CH₂CH=CH₂,SCH₃], [ZA2321;S(O)₂CH₂C≡CH,SCH₃], [ZA2322;S(O)₂CH₂C≡CCH₃,SCH₃], [ZA2323;S(O)₂-c-Pr,SCH₃], [ZA2324;S(O)₂-c-Bu,SCH₃], [ZA2325;S(O)₂-c-Pen,SCH₃], [ZA2326;S(O)₂-c-Hex,SCH₃], [ZA2327;S(O)₂Ph,SCH₃], [ZA2328;S(O)₂(2-Py),SCH₃], [ZA2329;S(O)₂(3-Py),SCH₃], [ZA2330;S(O)₂(4-Py),SCH₃], [ZA2331;S(O)₂CF₃,SCH₃], [ZA2332;S(O)₂CH₂Ph,SCH₃], [ZA2333;S(O)₂CH₂(2-Py),SCH₃], [ZA2334;S(O)₂CH₂(3-Py),SCH₃], [ZA2335;S(O)₂CH₂(4-Py),SCH₃], [ZA2336;S(O)₂CH₂CN,SCH₃], [ZA2337;S(O)₂CH₂NO₂,SCH₃], [ZA2338;S(O)₂(CH₂)₂F,SCH₃], [ZA2339;S(O)₂(CH₂)₂Cl,SCH₃], [ZA2340;S(O)₂(CH₂)₂CF₃,SCH₃], [ZA2341;S(O)₂(CH₂)₂CN,SCH₃], [ZA2342;S(O)₂(CH₂)₂NO₂,SCH₃], [ZA2343;S(O)₂(CH₂)₂Ph,SCH₃], [ZA2344;S(O)₂(CH₂)₂OCH₃,SCH₃], [ZA2345;S(O)₂(CH₂)₃F,SCH₃], [ZA2346;S(O)₂(CH₂)₃Cl,SCH₃], [ZA2347;S(O)₂(CH₂)₃CF₃,SCH₃], [ZA2348;S(O)₂(CH₂)₃CN,SCH₃], [ZA2349;S(O)₂(CH₂)₃NO₂,SCH₃], [ZA2350;S(O)₂(CH₂)₃Ph,SCH₃], [ZA2351;S(O)₂(CH₂)₃OCH₃,SCH₃], [ZA2352;S(O)₂(CH₂)₄F,SCH₃], [ZA2353;S(O)₂(CH₂)₄Cl,SCH₃], [ZA2354;S(O)₂(CH₂)₄CF₃,SCH₃], [ZA2355;S(O)₂(CH₂)₄CN,SCH₃], [ZA2356;S(O)₂(CH₂)₄NO₂,SCH₃], [ZA2357;S(O)₂(CH₂)₄Ph,SCH₃], [ZA2358;S(O)₂(CH₂)₄OCH₃,SCH₃], [ZA2359;S(O)₂(CH₂)₅F,SCH₃], [ZA2360;S(O)₂(CH₂)₅Cl,SCH₃], [ZA2361;S(O)₂(CH₂)₅CF₃,SCH₃], [ZA2362;S(O)₂(CH₂)₅CN,SCH₃], [ZA2363;S(O)₂(CH₂)₅NO₂,SCH₃], [ZA2364;S(O)₂(CH₂)₅Ph,SCH₃], [ZA2365;S (O)₂(CH₂)₅OCH₃,SCH₃], [ZA2366;S(O)₂(CH₂)₆F,SCH₃], [ZA2367;S(O)₂(CH₂)₆Cl,SCH₃], [ZA2368;S(O)₂(CH₂)₆CF₃,SCH₃], [ZA2369;S(O)₂(CH₂)₆CN,SCH₃], [ZA2370;S(O)₂(CH₂)₆NO₂,SCH₃], [ZA2371;S(O)₂(CH₂)₆Ph,SCH₃], [ZA2372;S(O)₂(CH₂)₆OCH₃,SCH₃], [ZA2373;S(O)CH₃,SCH₃], [ZA2374;S(O)CH₂CH₃,SCH₃], [ZA2375;S(O)CH(CH₃)₂,SCH₃], [ZA2376;S(O)(CH₂)₂CH₃,SCH₃], [ZA2377;S(O)(CH₂)₃CH₃,SCH₃], [ZA2378;S(O)(CH₂)₄CH₃,SCH₃], [ZA2379;S(O)(CH₂)₅CH₃,SCH₃], [ZA2380;S(O)CH₂CH=CH₂,SCH₃], [ZA2381;S(O)CH₂C≡CH,SCH₃], [ZA2382;S(O)CH₂C≡CCH₃,SCH₃], [ZA2383;S(O)c-Pr,SCH₃], [ZA2384;S(O)c-Bu,SCH₃], [ZA2385;S(O)c-Pen,SCH₃], [ZA2386;S(O)c-Hex,SCH₃], [ZA2387;S(O)Ph,SCH₃], [ZA2388;S(O)(2-Py),SCH₃], [ZA2389;S(O)(3-Py),SCH₃], [ZA2390;S(O)(4-Py),SCH₃], [ZA2391;S(O)CF₃,SCH₃], [ZA2392;S(O)CH₂Ph,SCH₃], [ZA2393;S(O)CH₂(2-Py),SCH₃], [ZA2394;S(O)CH₂(3-Py),SCH₃], [ZA2395;S(O)CH₂(4-Py),SCH₃], [ZA2396;S(O)CH₂CN,SCH₃], [ZA2397;S(O)CH₂NO₂,SCH₃], [ZA2398;S(O)(CH₂)₂F,SCH₃], [ZA2399;S(O)(CH₂)₂Cl,SCH₃], [ZA2400;S(O)(CH₂)₂CF₃,SCH₃], [ZA2401;S(O)(CH₂)₂CN,SCH₃], [ZA2402;S(O)(CH₂)₂NO₂,SCH₃], [ZA2403;S(O)(CH₂)₂Ph,SCH₃], [ZA2404;S(O)(CH₂)₂OCH₃,SCH₃], [ZA2405;S(O)(CH₂)₃F,SCH₃], [ZA2406;S(O)(CH₂)₃Cl,SCH₃], [ZA2407;S(O)(CH₂)₃CF₃,SCH₃], [ZA2408;S(O)(CH₂)₃CN,SCH₃], [ZA2409;S(O)(CH₂)₃NO₂,SCH₃], [ZA2410;S(O)(CH₂)₃Ph,SCH₃], [ZA2411;S(O)(CH₂)₃OCH₃,SCH₃], [ZA2412;S(O)(CH₂)₄F,SCH₃], [ZA2413;S(O)(CH₂)₄Cl,SCH₃], [ZA2414;S(O)(CH₂)₄CF₃,SCH₃], [ZA2415;S(O)(CH₂)₄CN,SCH₃], [ZA2416;S(O)(CH₂)₄NO₂,SCH₃], [ZA2417;S(O)(CH₂)₄Ph,SCH₃], [ZA2418;S(O)(CH₂)₄OCH₃,SCH₃], [ZA2419;S(O)(CH₂)₅F,SCH₃], [ZA2420;S(O)(CH₂)₅Cl,SCH₃], [ZA2421;S(O)(CH₂)₅CF₃,SCH₃], [ZA2422;S(O)(CH₂)₅CN,SCH₃], [ZA2423;S(O)(CH₂)₅NO₂,SCH₃], [ZA2424;S(O)(CH₂)₅Ph,SCH₃], [ZA2425;S(O)(CH₂)₅OCH₃,SCH₃], [ZA2426;S(O)(CH₂)₆F,SCH₃], [ZA2427;S(O)(CH₂)₆Cl,SCH₃], [ZA2428;S(O)(CH₂)₆CF₃,SCH₃], [ZA2429;S(O)(CH₂)₆CN,SCH₃], [ZA2430;S(O)(CH₂)₆NO₂,SCH₃], [ZA2431;S(O)(CH₂)₆Ph,SCH₃], [ZA2432;S(O)(CH)₆OCH₃,SCH₃], [ZA2433;OH,CN], [ZA2434;OCH₃,CN], [ZA2435;OCH₂CH₃,CN], [ZA2436;OCH(CH₃)₂,CN], [ZA2437;O(CH₂)₂CH₃,CN], [ZA2438;(CH₂)₃CH₃,CN], [ZA2439;O(CH₂)₄CH₃,CN], [ZA2440;O(CH₂)₅CH₃,CN], [ZA2441;OCH₂CH=CH₂,CN], [ZA2442;OCH₂C≡CH,CN], [ZA2443;OCH₂C≡CCH₃,CN], [ZA2444;O-c-Pr,CN], [ZA2445;O-c-Bu,CN], [ZA2446;O-c-Pen,CN], [ZA2447;O-c-Hex,CN], [ZA2448;OPh,CN], [ZA2449;O(2-Py),CN], [ZA2450;O(3-Py),CN], [ZA2451;O(4-Py),CN], [ZA2452;OCF₃,CN], [ZA2453;OCH₂Ph,CN], [ZA2454;OCH₂(2-Py),CN], [ZA2455;OCH₂(3-Py),CN], [ZA2456;OCH₂(4-Py),CN], [ZA2457;OCH₂CN,CN], [ZA2458;OCH₂NO₂,CN], [ZA2459;O(CH₂)₂F,CN], [ZA2460;O(CH₂)₂Cl,CN], [ZA2461;(CH₂)₂Br,CN], [ZA2462;O(CH₂)₂I,CN], [ZA2463;O(CH₂)₂CF₃,CN], [ZA2464;O(CH₂)₂CN,CN], [ZA2465;O(CH₂)₂NO₂,CN], [ZA2466;O(CH₂)₂Ph,CN], [ZA2467;O(CH₂)₂(2-Py),CN], [ZA2468;O(CH₂)₂(3-Py),CN], [ZA2469;O(CH₂)₂(4-Py),CN], [ZA2470;O(CH₂)₂OH,CN], [ZA2471;(CH₂)₂OCH₃,CN], [ZA2472;O(CH₂)₂SH,CN], [ZA2473;O(CH₂)₂SCH₃,CN], [ZA2474;O(CH₂)₂NH₂,CN], [ZA2475;O(CH₂)₂NHCH₃,CN], [ZA2476;O(CH₂)₂N(CH₃)₂,CN], [ZA2477;O(CH₂)₂NHPh,CN], [ZA2478;(CH₂)₂NHCH₂Ph,CN], [ZA2479;O(CH₂)₂N(CH₃)CH₂Ph,CN], [ZA2480;O(CH₂)₂S(O)CH₃,CN], [ZA2481;(CH₂)₂S(O)CH₂CH₃,CN], [ZA2482;O(CH₂)₂S(O)Ph,CN], [ZA2483;O(CH₂)₂S(O)₂CH₃,CN], [ZA2484;O(CH₂)₂S(O)₂CH₂CH₃,CN], [ZA2485;O(CH₂)₂S(O)₂Ph,CN], [ZA2486;O(CH₂)₂C(O)CH₃,CN], [ZA2487;O(CH₂)₂C(O)CH₂CH₃,CN], [ZA2488;O(CH₂)₂C(O)Ph,CN], [ZA2489;O(CH₂)₂C(S)CH₃,CN], [ZA2490;O(CH₂)₂C(S)CH₂CH₃,CN], [ZA2491;(CH₂)₂C(S)Ph,CN], [ZA2492;O(CH₂)₂S(O)₂NHCH₃,CN], [ZA2493;O(CH₂)₂S(O)₂N(CH₃)₂,CN], [ZA2494;O(CH₂)₂S(O)₂NHPh,CN], [ZA2495;O(CH₂)₂S(O)₂N(CH₃)Ph,CN], [ZA2496;O(CH₂)₂C(O)NH₂,CN], [ZA2497;O(CH₂)₂C(O)NHCH₃,CN], [ZA2498;O(CH₂)₂C(O)N(CH₃)₂,CN], [ZA2499;O(CH₂)₂C(O)NHPh,CN], [ZA2500;O(CH₂)₂C(O)N(CH3)Ph,CN], [ZA2501;(CH₂)₂C(O)OCH₃,CN], [ZA2502;O(CH₂)₂C(O)OCH₂CH₃,CN], [ZA2503;O(CH₂)₂NHC(O)CH₃,CN], [ZA2504;O(CH₂)₂NHC(O)CH₂CH₃,CN], [ZA2505;O(CH₂)₂NHC(O)Ph,CN], [ZA2506;O(CH₂)₂NCH₃C(O)CH₃,CN], [ZA2507;O(CH₂)₂NCH₃C(O)CH₂CH₃,CN], [ZA2508;O(CH₂)₂NCH₃C(O)Ph,CN], [ZA2509;O(CH₂)₂NHC(O)OCH₃,CN], [ZA2510;O(CH₂)₂NHC(O)OCH₂CH₃,CN], [ZA2511;O(CH₂)₂NHC(O)OPh,CN], [ZA2512;O(CH₂)₂NCH₃C(O)OCH₃,CN], [ZA2513;O(CH₂)₂NCH₃C(O)OCH₂CH₃,CN], [ZA2514;O(CH₂)₂NCH₃C(O)OPh,CN], [ZA2515;O(CH₂)₂NHC(O)NHCH₃,CN], [ZA2516;O(CH₂)₂NHC(O)NHCH₂CH₃,CN], [ZA2517;O(CH₂)₂NHC(O)NHPh,CN], [ZA2518;O(CH₂)₂NHC(O)N(CH₃)₂,CN], [ZA2519;O(CH₂)₂NHC(O)N(CH₃)CH₂CH₃,CN], [ZA2520;O(CH₂)₂NHC(O)N(CH₃)Ph,CN], [ZA2521;(CH₂)₂NHC(O)N(CH₂CH₃)₂,CN], [ZA2522;O(CH₂)₂NCH₃C(O)NHCH₃,CN], [ZA2523;O(CH₂)₂NCH₃C(O)NHCH₂CH₃,CN], [ZA2524;O(CH₂)₂NCH₃C(O)NHPh,CN], [ZA2525;O(CH₂)₂NCH₃C(O)N(CH₃)₂,CN], [ZA2526;O(CH₂)₂NCH₃C(O)N(CH₃)CH₂CH₃,CN], [ZA2527;O(CH₂)₂NCH₃C(O)N(CH₃)Ph,CN], [ZA2528;O(CH₂)₂NCH₃C(O)N(CH₂CH₃)₂,CN], [ZA2529;O(CH₂)₂OC(O)CH₃,CN], [ZA2530;O(CH₂)₂OC(O)CH₂CH₃,CN], [ZA2531;(CH₂)₂OC(O)Ph,CN], [ZA2532;O(CH₂)₂OC(O)OCH₃,CN], [ZA2533;O(CH₂)₂OC(O)OCH₂CH₃,CN], [ZA2534;O(CH₂)₂OC(O)OPh,CN], [ZA2535;O(CH₂)₂OC(O)NHCH₃,CN], [ZA2536;O(CH₂)₂OC(O)NHCH₂CH₃,CN], [ZA2537;O(CH₂)₂OC(O)NHPh,CN], [ZA2538;O(CH₂)₂OC(O)N(CH₃)₂,CN], [ZA2539;O(CH₂)₂OC(O)N(CH₃)CH₂CH₃,CN], [ZA2540;O(CH₂)₂OC(O)N(CH₃)Ph,CN], [ZA2541;(CH₂)₂OC(O)N(CH₂CH₃)₂,CN], [ZA2542;O(CH₂)₂SC(O)CH₃,CN], [ZA2543;O(CH)₂SC(O)CH₂CH₃,CN], [ZA2544;O(CH₂)₂SC(O)Ph,CN], [ZA2545;O(CH₂)₂SC(O)OCH₃,CN], [ZA2546;O(CH₂)₂SC(O)OCH₂CH₃,CN], [ZA2547;O(CH₂)₂SC(O)OPh,CN], [ZA2548;O(CH₂)₂S(O)₂NHCH₃,CN], [ZA2549;O(CH₂)₂S(O)₂NHCH₂CH₃,CN], [ZA2550;O(CH₂)₂S(O)₂NHPh,CN], [ZA2551;(CH₂)₂S(O)₂N(CH₃)₂,CN], [ZA2552;O(CH₂)₂S(O)₂N(CH₃)CH₂CH₃,CN], [ZA2553;O(CH₂)₂S(O)₂N(CH₃)Ph,CN], [ZA2554;O(CH₂)₂S(O)₂N(CH₂CH₃)₂,CN], [ZA2555;O(CH₂)₃F,CN], [ZA2556;O(CH₂)₃Cl,CN], [ZA2557;O(CH₂)₃Br,CN], [ZA2558;(CH₂)₃I,CN], [ZA2559;O(CH₂)₃CF₃,CN], [ZA2560;O(CH₂)₃CN,CN], [ZA2561;(CH₂)₃NO₂,CN], [ZA2562;O(CH₂)₃Ph,CN], [ZA2563;O(CH₂)₃(2-Py),CN], [ZA2564;O(CH₂)₃(3-Py),CN], [ZA2565;O(CH₂)₃(4-Py),CN], [ZA2566;O(CH₂)₃OH,CN], [ZA2567;O(CH₂)₃OCH₃,CN], [ZA2568;O(CH₂)₃OCH₂CH₃,CN], [ZA2569;O(CH₂)₃SH,CN], [ZA2570;O(CH₂)₃SCH₃,CN], [ZA2571;(CH₂)₃SCH₂CH₃,CN], [ZA2572;O(CH₂)₃NH₂,CN], [ZA2573;O(CH₂)₃NHCH₃,CN], [ZA2574;O(CH₂)₃N(CH₃)₂,CN], [ZA2575;O(CH₂)₄F,CN], [ZA2576;O(CH₂)₄Cl,CN], [ZA2577;O(CH₂)₄CF₃,CN], [ZA2578;O(CH₂)₄CN,CN], [ZA2579;O(CH₂)₄NO₂,CN], [ZA2580;O(CH₂)₄Ph,CN], [ZA2581;O(CH₂)₄OH,CN], [ZA2582;O(CH₂)₄OCH₃,CN], [ZA2583;O(CH₂)₄SH,CN], [ZA2584;O(CH₂)₄SCH₃,CN], [ZA2585;O(CH₂)₄NH₂,CN], [ZA2586;O(CH₂)₄NHCH₃,CN], [ZA2587;O(CH₂)₄N(CH₃)₂,CN], [ZA2588;O(CH₂)₅F,CN], [ZA2589;O(CH₂)₅Cl,CN],

[ZA2590;O(CH₂)₅CF₃,CN], [ZA2591;(CH₂)₅CN,CN], [ZA2592;O(CH₂)₅NO₂,CN], [ZA2593;O(CH₂)₅Ph,CN], [ZA2594;O(CH₂)₅OH,CN], [ZA2595;O(CH₂)₅OCH₃,CN], [ZA2596;O(CH₂)₅SH,CN], [ZA2597;O(CH₂)₅SCH₃,CN], [ZA2598;O(CH₂)₅NH₂,CN], [ZA2599;O(CH₂)₅NHCH₃, CN], [ZA2600;O(CH₂)₅N(CH₃)₂,CN], [ZA2601;(CH₂)₆F, CN], [ZA2602;O(CH₂)₆Cl,CN], [ZA2603;O(CH₂)₆CF₃, CN], [ZA2604;O(CH₂)₆CN,CN], [ZA2605;O(CH₂)₆NO₂, CN], [ZA2606;O(CH₂)₆Ph,CN], [ZA2607;O(CH₂)₆OH, CN], [ZA2608;O(CH₂)₆OCH₃,CN], [ZA2609;O(CH₂)₆SH, CN], [ZA2610;O(CH₂)₆SCH₃,CN], [ZA2611;O(CH₂)₆NH₂, CN], [ZA2612;O(CH₂)₆NHCH₃,CN], [ZA2613;O(CH₂)₆N(CH₃)₂,CN], [ZA2614;OC(O)CH₃,CN], [ZA2615;OC(O)CH₂ CH₃,CN], [ZA2616;OC(O)CH(CH₃)₂,CN], [ZA2617;OC(O)(CH₂)₂CH₃,CN], [ZA2618;OC(O)(CH₂)₃CH₃,CN], [ZA2619;OC(O)(CH₂)₄CH₃,CN], [ZA2620;OC(O)(CH₂)₅CH₃,CN], [ZA2621;OC(O)CH₂CH=CH₂,CN], [ZA2622;OC(O)CH₂C≡CH,CN], [ZA2623;OC(O)CH₂C≡CCH₃,CN], [ZA2624;OC(O)c-Pr,CN], [ZA2625;OC(O)c-Bu,CN], [ZA2626;OC(O)c-Pen,CN], [ZA2627;OC(O)c-Hex,CN], [ZA2628;OC(O)Ph,CN], [ZA2629;OC(O)(2-Py),CN], [ZA2630;OC(O)(3-Py),CN], [ZA2631;OC(O)(4-Py),CN], [ZA2632;OC(O)CF₃,CN], [ZA2633;OC(O)CH₂Ph,CN], [ZA2634;OC(O)CH₂(2-Py),CN], [ZA2635;OC(O)CH₂(3-Py),CN], [ZA2636;OC(O)CH₂(4-Py),CN], [ZA2637;OC(O)CH₂CN,CN], [ZA2638;OC(O)CH₂NO₂,CN], [ZA2639;OC(O)(CH₂)₂F,CN], [ZA2640;OC(O)(CH₂)₂ Cl,CN], [ZA2641;OC(O)(CH₂)₂CF₃,CN], [ZA2642;OC(O)(CH₂)₂CN,CN], [ZA2643;OC(O)(CH₂)₂NO₂,CN], [ZA2644;OC(O)(CH₂)₂Ph,CN], [ZA2645;OC(O)(CH₂)₂OCH₃,CN], [ZA2646;OC(O)(CH₂)₃F,CN], [ZA2647;OC(O)(CH₂)₃Cl, CN], [ZA2648;OC(O)(CH₂)₃CF₃,CN], [ZA2649;OC(O)(CH₂)₃CN,CN], [ZA2650;OC(O)(CH₂)₃NO₂,CN], [ZA2651;OC(O)(CH₂)₃Ph,CN], [ZA2652;OC(O)(CH₂)₃OCH₃,CN], [ZA2653;OC(O)(CH₂)₄F,CN], [ZA2654;OC(O)(CH₂)₄Cl,CN], [ZA2655;OC(O)(CH₂)₄CF₃,CN], [ZA2656;OC(O)(CH₂)₄CN,CN], [ZA2657;OC(O)(CH₂)₄NO₂,CN], [ZA2658;OC(O)(CH₂)₄Ph,CN], [ZA2659;OC(O)(CH₂)₄OCH₃,CN], [ZA2660;OC(O)(CH₂)₅F,CN], [ZA2661;OC(O)(CH₂)₅Cl,CN], [ZA2662;OC(O)(CH₂)₅CF₃,CN], [ZA2663;OC(O)(CH₂)₅CN,CN], [ZA2664;OC(O)(CH₂)₅NO₂,CN], [ZA2665;OC(O)(CH₂)₅Ph,CN], [ZA2666;OC(O)(CH₂)₅OCH₃,CN], [ZA2667;OC(O)(CH₂)₆ F,CN], [ZA2668;OC(O)(CH₂)₆Cl,CN], [ZA2669;OC(O)(CH₂)₆CF₃,CN], [ZA2670;OC(O)(CH₂)₆CN,CN], [ZA2671;OC(O)(CH₂)₆NO₂,CN], [ZA2672;OC(O)(CH₂)₆Ph,CN], [ZA2673;OC(O)(CH₂)₆OCH₃,CN], [ZA2674;OC(O)NH₂,CN], [ZA2675;OC(O)NHCH₃,CN], [ZA2676;OC(O)NHCH₂CH₃,CN], [ZA2677;OC(O)NH(CH₂)₂CH₃,CN], [ZA2678;OC(O)NH(CH₂)₃CH₃,CN], [ZA2679;OC(O)NH(CH₂)₄CH₃,CN], [ZA2680;OC(O)NH(CH₂)₅CH₃,CN], [ZA2681;OC(O)NHCH(CH₃)₂,CN], [ZA2682;OC(O)NHCH₂F,CN], [ZA2683;OC(O)NHCH₂Cl,CN], [ZA2684;OC(O)NHCH₂CN,CN], [ZA2685;OC(O)NHCH₂OCH₃, CN], [ZA2686;OC(O)NHCH₂Ph,CN], [ZA2687;OC(O)NH(CH₂)₂F,CN], [ZA2688;OC(O)NH(CH₂)₂Cl,CN], [ZA2689;OC(O)NH(CH₂)₂CN,CN], [ZA2690;OC(O)NH(CH₂)₂OCH₃,CN], [ZA2691;OC(O)NH(CH₂)₂Ph,CN], [ZA2692;OC(O)NH(CH₂)₃F,CN], [ZA2693;OC(O)NH(CH₂)₃Cl,CN], [ZA2694;OC(O)NH(CH₂)₃CN,CN], [ZA2695;OC(O)NH(CH₂)₃OCH₃,CN], [ZA2696;OC(O)NH(CH₂)₃Ph,CN], [ZA2697;OC(O)NH(CH₂)₄F,CN], [ZA2698;OC(O)NH(CH₂)₄Cl,CN], [ZA2699;OC(O)NH(CH₂)₄CN,CN], [ZA2700;OC(O)NH(CH₂)₄OCH₃,CN], [ZA2701;OC(O)NH(CH₂)₄Ph,CN], [ZA2702;OC(O)NHPh, CN], [ZA2703;OC(O)NH(2-Py),CN], [ZA2704;OC(O)NH(3-Py),CN], [ZA2705;OC(O)NH(4-Py),CN], [ZA2706;OC(O)N(CH₃)₂,CN], [ZA2707;OC(O)N(CH₃)CH₂CH₃,CN], [ZA2708;OC(O)N(CH₃)(CH₂)₂CH₃,CN], [ZA2709;OC(O)N(CH₃)(CH₂)₃CH₃,CN], [ZA271;OC(O)N(CH₃)(CH₂)₄ CN], [ZA2711;OC(O)N(CH₃)(CH₂)₅ CH₃,CN], [ZA2712;OC(O)N(CH₃)CH(CH₃)₂,CN], [ZA2713;OC(O)N(CH₃)CH₂F,CN], [ZA2714;OC(O)N(CH₃)CH₂Cl,CN], [ZA2715;OC(O)N(CH₃)CH₂CN,CN], [ZA2716;OC(O)N(CH₃)CH₂OCH₃,CN], [ZA2717;OC(O)N(CH₃)CH₂Ph, CN], [ZA2718;OC(O)N(CH₃)(CH₂)₂F,CN], [ZA2719;OC(O)N(CH₃)(CH₂)₂Cl,CN], [ZA2720;OC(O)N(CH)(CH₂)₂CN,CN], [ZA2721;OC(O)N(CH₃)(CH₂)₂OCH₃,CN], [ZA2722;OC(O)N(CH₃)(CH₂)₂Ph,CN], [ZA2723;OC(O)N(CH₃)(CH₂)₃F,CN], [ZA2724;OC(O)N(CH₃)(CH₂)₃Cl, CN], [ZA2725;OC(O)N(CH₃)(CH₂)₃CN,CN], [ZA2726;OC(O)N(CH₃)(CH₂)₃OCH₃,CN], [ZA2727;OC(O)N(CH₃)(CH₂)₃Ph,CN], [ZA2728;OC(O)N(CH₃)(CH₂)₄F,CN], [ZA2729;OC(O)N(CH₃)(CH₂)₄Cl,CN], [ZA2730;OC(O)N(CH₃)(CH₂)₄CN,CN], [ZA2731;OC(O)N(CH₃)(CH₂)₄OCH₃,CN], [ZA2732;OC(O)N(CH₃)(CH₂)₄Ph,CN], [ZA2733;OC(O)N(CH₃)Ph,CN], [ZA2734;OC(O)N(CH₃)(2-Py),CN], [ZA2735;OC(O)N(CH₃)(3-Py),CN], [ZA2736;OC(O)N(CH₃)(4-Py),CN], [ZA2737;OC(O)N(CH₂CH₃)₂, CN], [ZA2738;OC(O)(Pyr),CN], [ZA2739;OC(O)(Pip), CN], [ZA2740;OC(O)(Mor),CN], [ZA2741;OC(O)OCH₃, CN], [ZA2742;OC(O)OCH₂CH₃,CN], [ZA2743;OC(O)OCH(CH₃)₂,CN], [ZA2744;OC(O)O(CH₂)₂CH₃,CN], [ZA2745;OC(O)O(CH₂)₃CH₃,CN], [ZA2746;OC(O)O(CH₂)₄CH₃,CN], [ZA2747;OC(O)O(CH₂)₅CH₃,CN], [ZA2748;OC(O)OCH₂CH=CH₂,CN], [ZA2749;OC(O)OCH₂C≡CH,CN], [ZA2750;OC(O)OCH₂C≡CCH₃,CN], [ZA2751;OC(O)O-c-Pr,CN], [ZA2752;OC(O)O-c-Bu,CN], [ZA2753;OC(O)O-c-Pen,CN], [ZA2754;OC(O)O-c-Hex, CN], [ZA2755;OC(O)OPh,CN], [ZA2756;OC(O)O(2-Py), CN], [ZA2757;OC(O)O(3-Py),CN], [ZA2758;OC(O)O(4-Py),CN], [ZA2759;OC(O)OCF₃,CN], [ZA2760;OC(O)OCH₂Ph,CN], [ZA2761;OC(O)OCH₂(2-Py),CN], [ZA2762;OC(O)OCH₂(3-Py),CN], [ZA2763;OC(O)OCH₂(4-Py),CN], [ZA2764;OC(O)OCH₂CN,CN], [ZA2765;OC(O)OCH₂NO₂,CN], [ZA2766;OC(O)O(CH₂)₂F,CN], [ZA2767;OC(O)O(CH₂)₂Cl,CN], [ZA2768;OC(O)O(CH₂)₂CF₃,CN], [ZA2769;OC(O)O(CH₂)₂CN,CN], [ZA2770;OC(O)O(CH₂)₂NO₂,CN], [ZA2771;OC(O)O(CH₂)₂Ph,CN], [ZA2772;OC(O)O(CH₂)₂OCH₃,CN], [ZA2773;OC(O)O(CH₂)₃F,CN], [ZA2774;OC(O)O(CH₂)₃Cl,CN], [ZA2775;OC(O)O(CH₂)₃CF₃,CN], [ZA2776;OC(O)O(CH₂)₃CN, CN], [ZA2777;OC(O)O(CH₂)₃NO₂,CN], [ZA2778;OC(O)O(CH₂)₃Ph,CN], [ZA2779;OC(O)O(CH₂)₃OCH₃,CN], [ZA2780;OC(O)O(CH₂)₄F,CN], [ZA2781;OC(O)O(CH₂)₄Cl,CN], [ZA2782;OC(O)O(CH₂)₄CF₃,CN], [ZA2783;OC(O)O(CH₂)₄CN,CN], [ZA2784;OC(O)O(CH₂)₄NO₂,CN], [ZA2785;OC(O)O(CH₂)₄Ph,CN], [ZA2786;OC(O)O(CH₂)₄ OCH₃,CN], [ZA2787;OC(O)O(CH₂)₅F,CN], [ZA2788;OC(O)O(CH₂)₅Cl,CN], [ZA2789;OC(O)O(CH₂)₅CF₃,CN], [ZA2790;OC(O)O(CH₂)₅CN,CN], [ZA2791;OC(O)O(CH₂)₅ NO₂,CN], [ZA2792;OC(O)O(CH₂)₅Ph,CN], [ZA2793;OC(O)O(CH₂)₅OCH₃,CN], [ZA2794;OC(O)O(CH₂)₆F,CN], [ZA2795;OC(O)O(CH₂)₆Cl,CN], [ZA2796;OC(O)O(CH₂)₆CF₃,CN], [ZA2797;OC(O)O(CH₂)₆CN, CN], [ZA2798;OC(O)O(CH₂)₆NO₂,CN], [ZA2799;OC(O)O(CH₂)₆Ph,CN], [ZA2800;OC(O)O(CH₂)₆OCH₃,CN], [ZA2801;OS(O)₂CH₃,CN], [ZA2802;OS(O)₂CH₂ CH₃, CN], [ZA2803;OS(O)₂CH(CH₃)₂,CN], [ZA2804;OS(O)₂(CH₂)₂CH₃,CN], [ZA2805;OS(O)₂(CH₂)₃CH₃,CN], [ZA2806;OS(O)₂(CH₂)₄CH₃,CN], [ZA2807;OS(O)₂(CH₂)₅ CH₃,CN], [ZA2808;OS(O)₂CH₂CH=CH₂,CN], [ZA2809;OS(O)₂CH₂C≡CH,CN], [ZA281;OS(O)₂CH₂C≡CCH₃,CN], [ZA2811;OS(O)₂-c-Pr,CN], [ZA2812;

OS(O)₂-c-Bu,CN], [ZA2813;OS(O)₂-c-Pen,CN], [ZA2814; OS(O)₂-c-Hex,CN], [ZA2815;OS(O)₂Ph,CN], [ZA2816;OS(O)₂(2-Py),CN], [ZA2817;OS(O)₂(3-Py),CN], [ZA2818;OS(O)₂(4-Py),CN], [ZA2819;OS(O)₂CF₃,CN], [ZA2820;OS(O)₂CH₂Ph,CN], [ZA2821;OS(O)₂CH₂(2-Py),CN], [ZA2822;OS(O)₂CH₂(3-Py),CN], [ZA2823;OS(O)₂CH₂(4-Py),CN], [ZA2824;OS(O)₂CH₂CN,CN], [ZA2825;OS(O)₂CH₂NO₂,CN], [ZA2826;OS(O)₂(CH₂)₂F,CN], [ZA2827;OS(O)₂(CH₂)₂Cl,CN], [ZA2828;OS(O)₂(CH₂)₂CF₃,CN], [ZA2829;OS(O)₂(CH₂)₂CN,CN], [ZA2830;OS(O)₂(CH₂)₂NO₂,CN], [ZA2831;OS(O)₂(CH₂)₂Ph,CN], [ZA2832;OS(O)₂(CH₂)₂OCH₃,CN], [ZA2833;OS(O)₂(CH₂)₃F,CN], [ZA2834;OS(O)₂(CH₂)₃Cl,CN], [ZA2835;OS(O)₂(CH₂)₃CF₃,CN], [ZA2836;OS(O)₂(CH₂)₃CN,CN], [ZA2837;OS(O)₂(CH₂)₃NO₂,CN], [ZA2838;OS(O)₂(CH₂)₃Ph,CN], [ZA2839;OS(O)₂(CH₂)₃OCH₃,CN], [ZA2840;OS(O)₂(CH₂)₄F,CN], [ZA2841;OS(O)₂(CH₂)₄Cl,CN], [ZA2842;OS(O)₂(CH₂)₄CF₃,CN], [ZA2843;OS(O)₂(CH₂)₄CN,CN], [ZA2844;OS(O)₂(CH₂)₄NO₂,CN], [ZA2845;OS(O)₂(CH₂)₄Ph,CN], [ZA2846;OS(O)₂(CH₂)₄OCH₃,CN], [ZA2847;OS(O)₂(CH₂)₅F,CN], [ZA2848;OS(O)₂(CH₂)₅Cl,CN], [ZA2849;OS(O)₂(CH₂)₅CF₃,CN], [ZA2850;OS(O)₂(CH₂)₅CN,CN], [ZA2851;OS(O)₂(CH₂)₅NO₂,CN], [ZA2852;OS(O)₂(CH₂)₅Ph,CN], [ZA2853;OS(O)₂(CH₂)₅OCH₃,CN], [ZA2854;OS(O)₂(CH₂)₆F,CN], [ZA2855;OS(O)₂(CH₂)₆Cl,CN], [ZA2856;OS(O)₂(CH₂)₆CF₃,CN], [ZA2857;OS(O)₂(CH₂)₆CN,CN], [ZA2858;OS(O)₂(CH₂)₆NO₂,CN], [ZA2859;OS(O)₂(CH₂)₆Ph,CN], [ZA2860;OS(O)₂(CH₂)₆OCH₃,CN], [ZA2861;NH₂,CN], [ZA2862;NHCH₃,CN], [ZA2863;NHCH₂CH₃,CN], [ZA2864;NH(CH₂)₂CH₃,CN], [ZA2865;NH(CH₂)₃CH₃,CN], [ZA2866;NH(CH₂)₄CH₃,CN], [ZA2867;NH(CH₂)₅CH₃,CN], [ZA2868;NHCH(CH₃)₂,CN], [ZA2869;NHCH₂F,CN], [ZA2870;NHCH₂CN,CN], [ZA2871;NHCH₂OCH₃,CN], [ZA2872;NHCH₂Ph,CN], [ZA2873;NH(CH₂)₂F,CN], [ZA2874;NH(CH₂)₂CN,CN], [ZA2875;NH(CH₂)₂OCH₃,CN], [ZA2876;NH(CH₂)₂Ph,CN], [ZA2877;NH(CH₂)₃F,CN], [ZA2878;NH(CH₂)₃Cl,CN], [ZA2879;NH(CH₂)₃CN,CN], [ZA2880;NH(CH₂)₃OCH₃,CN], [ZA2881;NH(CH₂)₃Ph,CN], [ZA2882;NH(CH₂)₄F,CN], [ZA2883;NH(CH₂)₄CN,CN], [ZA2884;NH(CH₂)₄OCH₃,CN], [ZA2885;NH(CH₂)₄Ph,CN], [ZA2886;NHPh,CN], [ZA2887;NH(2-Py),CN], [ZA2888;NH(3-Py),CN], [ZA2889;NH(4-Py),CN], [ZA2890;N(CH₃)₂,CN], [ZA2891;N(CH₃)CH₂CH₃,CN], [ZA2892;N(CH₃)(CH₂)₂CH₃,CN], [ZA2893;N(CH₃)(CH₂)₃CH₃,CN], [ZA2894;(CH₃)(CH₂)₄CH₃,CN], [ZA2895;(CH₃)(CH₂)₅CH₃,CN], [ZA2896;N(CH₃)CH(CH₃)₂,CN], [ZA2897;N(CH₃)CH₂F,CN], [ZA2898;N(CH₃)CH₂CN,CN], [ZA2899;N(CH₃)CH₂OCH₃,CN], [ZA2900;N(CH₃)CH₂Ph,CN], [ZA2901;N(CH₃)(CH₂)₂F,CN], [ZA2902;N(CH₃)(CH₂)₂CN,CN], [ZA2903;N(CH₃)(CH₂)₂OCH₃,CN], [ZA2904;N(CH₃)(CH₂)₂Ph,CN], [ZA2905;N(CH₃)(CH₂)₃F,CN], [ZA2906;N(CH₃)(CH₂)₃CN,CN], [ZA2907;N(CH₃)(CH₂)₃OCH₃,CN], [ZA2908;N(CH₃)(CH₂)₃Ph,CN], [ZA2909;N(CH₃)(CH₂)₄F,CN], [ZA2910;N(CH₃)(CH₂)₄CN,CN], [ZA2911;N(CH₃)(CH₂)₄OCH₃,CN], [ZA2912;N(CH₃)(CH₂)₄Ph,CN], [ZA2913;N(CH₃)Ph,CN], [ZA2914;N(CH₃)(2-Py),CN], [ZA2915;N(CH₃)(3-Py),CN], [ZA2916;N(CH₃)(4-Py),CN], [ZA2917;N(CH₂CH₃)₂,CN], [ZA2918;Pyr,CN], [ZA2919;Pip,CN], [ZA2920;Mor,CN], [ZA2921;S(O)₂CH₃,CN], [ZA2922;S(O)₂CH₂CH₃,CN], [ZA2923;S(O)₂CH(CH₃)₂,CN], [ZA2924;S(O)₂(CH₂)₂CH₃,CN], [ZA2925;S(O)₂(CH₂)₃CH₃,CN], [ZA2926;S(O)₂(CH₂)₄CH₃,CN], [ZA2927;S(O)₂(CH₂)₅CH₃,CN], [ZA2928;S(O)₂CH₂CH=CH₂,CN], [ZA2929;S(O)₂CH₂C≡CH,CN], [ZA2930;S(O)₂CH₂C≡CCH₃,CN], [ZA2931;S(O)₂-c-Pr,CN], [ZA2932;S(O)₂-c-Bu,CN], [ZA2933;S(O)₂-c-Pen,CN], [ZA2934;S(O)₂-c-Hex,CN], [ZA2935;S(O)₂Ph,CN], [ZA2936;S(O)₂(2-Py),CN], [ZA2937;S(O)₂(3-Py),CN], [ZA2938;S(O)₂(4-Py),CN], [ZA2939;S(O)₂CF₃,CN], [ZA2940;S(O)₂CH₂Ph,CN], [ZA2941;S(O)₂CH₂(2-Py),CN], [ZA2942;S(O)₂CH₂(3-Py),CN], [ZA2943;S(O)₂CH₂(4-Py),CN], [ZA2944;S(O)₂CH₂CN,CN], [ZA2945;S(O)₂CH₂NO₂,CN], [ZA2946;S(O)₂(CH₂)₂F,CN], [ZA2947;S(O)₂(CH₂)₂Cl,CN], [ZA2948;S(O)₂(CH₂)₂CF₃,CN], [ZA2949;S(O)₂(CH₂)₂CN,CN], [ZA2950;S(O)₂(CH₂)₂NO₂,CN], [ZA2951;S(O)₂(CH₂)₂Ph,CN], [ZA2952;S(O)₂(CH₂)₂OCH₃,CN], [ZA2953;S(O)₂(CH₂)₃F,CN], [ZA2954;S(O)₂(CH₂)₃Cl,CN], [ZA2955;S(O)₂(CH₂)₃CF₃,CN], [ZA2956;S(O)₂(CH₂)₃CN,CN], [ZA2957;S(O)₂(CH₂)₃NO₂,CN], [ZA2958;S(O)₂(CH₂)₃Ph,CN], [ZA2959;S(O)₂(CH₂)₃OCH₃,CN], [ZA2960;S(O)₂(CH₂)₄F,CN], [ZA2961;S(O)₂(CH₂)₄Cl,CN], [ZA2962;S(O)₂(CH₂)₄CF₃,CN], [ZA2963;S(O)₂(CH₂)₄CN,CN], [ZA2964;S(O)₂(CH₂)₄NO₂,CN], [ZA2965;S(O)₂(CH₂)₄Ph,CN], [ZA2966;S(O)₂(CH₂)₄OCH₃,CN], [ZA2967;S(O)₂(CH₂)₅F,CN], [ZA2968;S(O)₂(CH₂)₅Cl,CN], [ZA2969;S(O)₂(CH₂)₅CF₃,CN], [ZA2970;S(O)₂(CH₂)₅CN,CN], [ZA2971;S(O)₂(CH₂)₅NO₂,CN], [ZA2972;S(O)₂(CH₂)₅Ph,CN], [ZA2973;S(O)₂(CH₂)₅OCH₃,CN], [ZA2974;S(O)₂(CH₂)₆F,CN], [ZA2975;S(O)₂(CH₂)₆Cl,CN], [ZA2976;S(O)₂(CH₂)₆CF₃,CN], [ZA2977;S(O)₂(CH₂)₆CN,CN], [ZA2978;S(O)₂(CH₂)₆NO₂,CN], [ZA2979;S(O)₂(CH₂)₆Ph,CN], [ZA2980;S(O)₂(CH₂)₆OCH₃,CN], [ZA2981;S(O)CH₃,CN], [ZA2982;S(O)CH₂CH₃,CN], [ZA2983;S(O)CH(CH₃)₂,CN], [ZA2984;S(O)(CH₂)₂CH₃,CN], [ZA2985;S(O)(CH₂)₃CH₃,CN], [ZA2986;S(O)(CH₂)₄CH₃,CN], [ZA2987;S(O)(CH₂)₅CH₃,CN], [ZA2988;S(O)CH₂CH=CH₂,CN], [ZA2989;S(O)CH₂C≡CH,CN], [ZA2990;S(O)CH₂C≡CCH₃,CN], [ZA2991;S(O)c-Pr,CN], [ZA2992;S(O)c-Bu,CN], [ZA2993;S(O)c-Pen,CN], [ZA2994;S(O)c-Hex,CN], [ZA2995;S(O)Ph,CN], [ZA2996;S(O)(2-Py),CN], [ZA2997;S(O)(3-Py),CN], [ZA2998;S(O)(4-Py),CN], [ZA2999;S(O)CF₃,CN], [ZA3000;S(O)CH₂Ph,CN], [ZA3001;S(O)CH₂(2-Py),CN], [ZA3002;S(O)CH₂(3-Py),CN], [ZA3003;S(O)CH₂(4-Py),CN], [ZA3004;S(O)CH₂CN,CN], [ZA3005;S(O)CH₂NO₂,CN], [ZA3006;S(O)(CH₂)₂F,CN], [ZA3007;S(O)(CH₂)₂Cl,CN], [ZA3008;S(O)(CH₂)₂CF₃,CN], [ZA3009;S(O)(CH₂)₂CN,CN], [ZA3010;S(O)(CH₂)₂NO₂,CN], [ZA3011;S(O)(CH₂)₂Ph,CN], [ZA3012;S(O)(CH₂)₂OCH₃,CN], [ZA3013;S(O)(CH₂)₃F,CN], [ZA3014;S(O)(CH₂)₃Cl,CN], [ZA3015;S(O)(CH₂)₃CF₃,CN], [ZA316;S(O)(CH₂)₃CN,CN], [ZA3017;S(O)(CH₂)₃NO₂,CN], [ZA3018;S(O)(CH₂)₃Ph,CN], [ZA3019;S(O)(CH₂)₃OCH₃,CN], [ZA3020;S(O)(CH₂)₄F,CN], [ZA3021;S(O)(CH₂)₄Cl,CN], [ZA3022;S(O)(CH₂)₄CF₃,CN], [ZA3023;S(O)(CH₂)₄CN,CN], [ZA3024;S(O)(CH₂)₄NO₂,CN], [ZA3025;S(O)(CH₂)₄Ph,CN], [ZA3026;S(O)(CH₂)₄OCH₃,CN], [ZA3027;S(O)(CH₂)₅F,CN], [ZA3028;S(O)(CH₂)₅Cl,CN], [ZA3029;S(O)(CH₂)₅CF₃,CN], [ZA3030;S(O)(CH₂)₅CN,CN], [ZA3031;S(O)(CH₂)₅NO₂,CN], [ZA3032;S(O)(CH₂)₅Ph,CN], [ZA3033;S(O)(CH₂)₅OCH₃,CN], [ZA3034;S(O)(CH₂)₆F,CN], [ZA3035;S(O)(CH₂)₆Cl,CN], [ZA3036;S(O)(CH₂)₆CF₃,CN], [ZA3037;S(O)(CH₂)₆CN,CN], [ZA3038;S(O)(CH₂)₆NO₂,CN], [ZA3039;S(O)(CH₂)₆Ph,CN], [ZA3040;S(O)(CH₂)₆OCH₃,CN], [ZA3041;OH,NH₂], [ZA3042;OCH₃,NH₂], [ZA3043;OCH₂CH₃,NH₂], [ZA3044;OCH(CH₃)₂,NH₂], [ZA3045;O(CH₂)₂CH₃,NH₂], [ZA3046;O(CH₂)₃CH₃,NH₂], [ZA3047;O(CH₂)₄CH₃,NH₂], [ZA3048;O(CH₂)₅CH₃,NH₂], [ZA3049;OCH₂CH=CH₂,NH₂], [ZA3050;OCH₂C≡CH,NH₂], [ZA3051;OCH₂C≡CCH₃,NH₂], [ZA3052;O-c-Pr,NH₂], [ZA3053;O-c-Bu,NH₂], [ZA3054;O-c-Pen,NH₂], [ZA3055;O-c-Hex,NH₂], [ZA3056;OPh,NH₂], [ZA3057;O (2-Py),NH₂], [ZA3058;O(3-Py),NH₂], [ZA3059;O(4-Py),NH₂], [ZA3060;OCF₃,NH₂], [ZA3061;OCH₂Ph,NH₂], [ZA3062;OCH₂(2-Py),NH₂], [ZA3063;OCH₂(3-Py),NH₂], [ZA3064;OCH₂(4-Py),NH₂], [ZA3065;OCH₂CN,NH₂], [ZA3066;OCH₂NO₂,NH₂], [ZA3067;O(CH₂)₂F,NH₂], [ZA3068;O(CH₂)₂Cl,NH₂], [ZA3069;O(CH₂)₂Br,NH₂], [ZA3070;O(CH₂)₂I,NH₂], [ZA3071;(CH₂)₂CF₃,NH₂], [ZA3072;O(CH₂)₂CN,NH₂], [ZA3073;O(CH₂)₂NO₂,NH₂], [ZA3074;O(CH₂)₂Ph,NH₂], [ZA3075;O(CH₂)₂(2-Py),NH₂], [ZA3076;O(CH₂)₂(3-Py),NH₂], [ZA3077;O(CH₂)₂(4-Py),NH₂], [ZA3078;O(CH₂)₂OH,NH₂], [ZA3079;O(CH₂)₂OCH₃,NH₂], [ZA3080;O(CH₂)₂SH,NH₂], [ZA3081;(CH₂)₂SCH₃,NH₂], [ZA3082;O(CH₂)₂NH₂,NH₂], [ZA3083;O(CH)₂NHCH₃,NH₂], [ZA3084;O(CH₂)₂N(CH₃)₂,NH₂], [ZA3085;O(CH₂)₂NHPh,NH₂], [ZA3086;O(CH₂)₂NHCH₂Ph,NH₂], [ZA3087;O(CH₂)₂N(CH₃)CH₂Ph,NH₂], [ZA3088;(CH₂)₂S(O)CH₃,NH₂], [ZA3089;O(CH₂)₂S(O)CH₂CH₃,NH₂], [ZA3090;O(CH₂)₂S(O)Ph,NH₂], [ZA3091;(CH₂)₂S(O)₂CH₃,NH₂], [ZA3092;O(CH₂)₂S(O)₂CH₂CH₃,NH₂], [ZA3093;O(CH₂)₂S(O)₂Ph,NH₂], [ZA3094;O(CH₂)₂C(O)CH₃,NH₂], [ZA3095;O(CH₂)₂C(O)CH₂CH₃,NH₂], [ZA3096;O(CH₂)₂C(O)Ph,NH₂], [ZA3097;O(CH₂)₂C(S)CH₃,NH₂], [ZA3098;O(CH₂)₂C(S)CH₂CH₃,NH₂], [ZA3099;O(CH₂)₂C(S)Ph,NH₂], [ZA3100;O(CH₂)₂S(O)₂NHCH₃,NH₂], [ZA3101;O(CH₂)₂S(O)₂N(CH₃)₂,NH₂], [ZA3102;O(CH₂)₂S(O)₂NHPh,NH₂], [ZA3103;O(CH₂)₂S(O)₂N(CH₃)Ph,NH₂], [ZA3104;O(CH₂)₂C(O)NH₂,NH₂], [ZA3105;O(CH₂)₂C(O)NHCH₃,NH₂], [ZA3106;O(CH₂)₂C(O)N(CH₃)₂,NH₂], [ZA3107;O(CH₂)₂C(O)NHPh,NH₂], [ZA3108;O(CH₂)₂C(O)N(CH₃)Ph,NH₂], [ZA3109;O(CH₂)₂C(O)OCH₃,NH₂], [ZA3110;O(CH₂)₂C(O)OCH₂CH₃,NH₂], [ZA3111;O(CH₂)₂NHC(O)CH₃,NH₂], [ZA3112;O(CH₂)₂NHC(O)CH₂CH₃,NH₂], [ZA3113;O(CH₂)₂NHC(O)Ph,NH₂], [ZA3114;O(CH₂)₂NCH₃C(O)CH₃,NH₂], [ZA3115;O(CH₂)₂NCH₃C(O)CH₂CH₃,NH₂], [ZA3116;O(CH₂)₂NCH₃C(O)Ph,NH₂], [ZA3117;O(CH₂)₂NHC(O)OCH₃,NH₂], [ZA3118;O(CH₂)₂NHC(O)OCH₂CH₃,NH₂], [ZA3119;O(CH₂)₂NHC(O)OPh,NH₂], [ZA3120;O(CH₂)₂NCH₃C(O)OCH₃,NH₂], [ZA3121;O(CH₂)₂NCH₃C(O)OCH₂CH₃,NH₂], [ZA3122;O(CH₂)₂NCH₃C(O)OPh,NH₂], [ZA3123;O(CH₂)₂NHC(O)NHCH₃,NH₂], [ZA3124;O(CH₂)₂NHC(O)NHCH₂CH₃,NH₂], [ZA3125;O(CH₂)₂NHC(O)NHPh,NH₂], [ZA3126;O(CH₂)₂NHC(O)N(CH₃)₂,NH₂], [ZA3127;O(CH₂)₂NHC(O)N(CH₃)CH₂CH₃,NH₂], [ZA3128;O(CH₂)₂NHC(O)N(CH₃)Ph,NH₂], [ZA3129;O(CH₂)₂NHC(O)N(CH₂CH₃)₂,NH₂], [ZA3130;O(CH₂)₂NCH₃C(O)NHCH₃,NH₂], [ZA3131;O(CH₂)₂NCH₃C(O)NHCH₂CH₃,NH₂], [ZA3132;O(CH₂)₂NCH₃C(O)NHPh,NH₂], [ZA3133;O(CH₂)₂NCH₃C(O)N(CH₃)₂,NH₂], [ZA3134;O(CH₂)₂NCH₃C(O)N(CH₃)CH₂CH₃,NH₂], [ZA3135;O(CH₂)₂NCH₃C(O)N(CH₃)Ph,NH₂], [ZA3136;O(CH₂)₂NCH₃C(O)N(CH₂CH₃)₂,NH₂], [ZA3137;O(CH₂)₂OC(O)CH₃,NH₂], [ZA3138;O(CH₂)₂OC(O)CH₂CH₃,NH₂], [ZA3139;O(CH₂)₂OC(O)Ph,NH₂], [ZA3140;O(CH₂)₂OC(O)OCH₃,NH₂], [ZA3141;O(CH₂)₂OC(O)OCH₂CH₃,NH₂], [ZA3142;O(CH₂)₂OC(O)OPh,NH₂], [ZA3143;O(CH₂)₂OC(O)NHCH₃,NH₂], [ZA3144;O(CH₂)₂OC(O)NHCH₂CH₃,NH₂], [ZA3145;O(CH₂)₂OC(O)NHPh,NH₂], [ZA3146;O(CH₂)₂OC(O)N(CH₃)₂,NH₂], [ZA3147;O(CH₂)₂OC(O)N(CH₃)CH₂CH₃,NH₂], [ZA3148;O(CH₂)₂OC(O)N(CH₃)Ph,NH₂], [ZA3149;O(CH₂)₂OC(O)N(CH₂CH₃)₂,NH₂], [ZA3150;O(CH₂)₂SC(O)CH₃,NH₂], [ZA3151;O(CH₂)₂SC(O)CH₂CH₃,NH₂], [ZA3152;O(CH₂)₂SC(O)Ph,NH₂], [ZA3153;O(CH₂)₂SC(O)OCH₃,NH₂], [ZA3154;O(CH₂)₂SC(O)OCH₂CH₃,NH₂], [ZA3155;O(CH₂)₂SC(O)OPh,NH₂], [ZA3156;O(CH₂)₂S(O)₂NHCH₃,NH₂], [ZA3157;O(CH₂)₂S(O)₂NHCH₂CH₃,NH₂], [ZA3158;O(CH₂)₂S(O)₂NHPh,NH₂], [ZA3159;O(CH₂)₂S(O)₂N(CH₃)₂,NH₂], [ZA3160;O(CH₂)₂S(O)₂N(CH₃)CH₂CH₃,NH₂], [ZA3161;O(CH₂)₂S(O)₂N(CH₃)Ph,NH₂], [ZA3162;O(CH₂)₂S(O)₂N(CH₂CH₃)₂,NH₂], [ZA3163;O(CH₂)₃F,NH₂], [ZA3164;O(CH₂)₃Cl,NH₂], [ZA3165;O(CH₂)₃Br,NH₂], [ZA3166;O(CH₂)₃I,NH₂], [ZA3167;O(CH₂)₃CF₃,NH₂], [ZA3168;O(CH₂)₃CN,NH₂], [ZA3169;O(CH₂)₃NO₂,NH₂], [ZA3170;O(CH₂)₃Ph,NH₂], [ZA3171;O(CH₂)₃(2-Py),NH₂], [ZA3172;O(CH₂)₃ (3-Py),NH₂], [ZA3173;O(CH₂)₃(4-Py),NH₂], [ZA3174;O(CH₂)₃OH,NH₂], [ZA3175;O(CH₂)₃OCH₃,NH₂], [ZA3176;O(CH₂)₃OCH₂CH₃,NH₂], [ZA3177;O(CH₂)₃ SH,NH₂], [ZA3178;O(CH₂)₃SCH₃,NH₂], [ZA3179;O(CH₂)₃SCH₂CH₃,NH₂], [ZA3180;O(CH₂)₃NH₂,NH₂], [ZA3181;O(CH₂)₃NHCH₃,NH₂], [ZA3182;O(CH₂)₃N(CH₃)₂,NH₂], [ZA3183;O(CH₂)₄F,NH₂], [ZA3184;O(CH₂)₄Cl,NH₂], [ZA3185;O(CH₂)₄CF₃,NH₂], [ZA3186;O(CH₂)₄CN,NH₂], [ZA3187;O(CH₂)₄NO₂,NH₂], [ZA3188;O(CH₂)₄ Ph,NH₂], [ZA3189;O(CH₂)₄OH,NH₂], [ZA3190;O(CH₂)₄OCH₃,NH₂], [ZA3191;O(CH₂)₄SH,NH₂], [ZA3192;O(CH₂)₄SCH₃,NH₂], [ZA3193;O(CH₂)₄NH₂,NH₂], [ZA3194;O(CH)₄NHCH₃,NH₂], [ZA3195;O(CH₂)₄N(CH₃)₂,NH₂], [ZA3196;O(CH₂)₅F,NH₂], [ZA3197;O(CH₂)₅Cl,NH₂], [ZA3198;O(CH₂)₅CF₃,NH₂], [ZA3199;O(CH₂)₅CN,NH₂], [ZA3200;O(CH₂)₅NO₂,NH₂], [ZA3201;(CH₂)₅Ph,NH₂], [ZA3202;O(CH₂)₅OH,NH₂], [ZA3203;O(CH₂)₅OCH₃,NH₂], [ZA3204;O(CH₂)₅SH,NH₂], [ZA3205;O(CH₂)₅SCH₃,NH₂], [ZA3206;O(CH₂)₅NH₂,NH₂], [ZA3207;O(CH₂)₅NHCH₃,NH₂], [ZA3208;O(CH₂)₅N(CH₃)₂,NH₂], [ZA3209;O(CH₂)₆F,NH₂], [ZA3210;O(CH₂)₆Cl,NH₂], [ZA3211;O(CH₂)₆CF₃,NH₂], [ZA3212;O(CH₂)₆CN,NH₂], [ZA3213;O(CH₂)₆NO₂,NH₂], [ZA3214;O(CH₂)₆Ph,NH₂], [ZA3215;O(CH₂)₆OH,NH₂], [ZA3216;O(CH₂)₆OCH₃,NH₂], [ZA3217;O(CH₂)₆SH,NH₂], [ZA3218;O(CH₂)₆SCH₃,NH₂], [ZA3219;O(CH₂)₆NH₂,NH₂], [ZA3220;O(CH₂)₆NHCH₃,NH₂], [ZA3221;(CH₂)₆N(CH₃)₂,NH₂], [ZA3222;OC(O)CH₃,NH₂], [ZA3223;OC(O)CH₂CH₃,NH₂], [ZA3224;OC(O)CH(CH₃)₂,NH₂], [ZA3225;OC(O)(CH₂)₂CH₃,NH₂], [ZA3226;OC(O)(CH₂)₃CH₃,NH₂], [ZA3227;OC(O)(CH₂)₄CH₃,NH₂], [ZA3228;OC(O)(CH₂)₅CH₃,NH₂], [ZA3229;OC(O)CH₂CH=CH₂,NH₂], [ZA3230;OC(O)CH₂C≡CH,NH₂], [ZA3231;OC(O)CH₂C≡CCH₃,NH₂], [ZA3232;OC(O)c-Pr,NH₂], [ZA3233;OC(O)c-Bu,NH₂], [ZA3234;OC(O)c-Pen,NH₂], [ZA3235;OC(O)c-Hex,NH₂], [ZA3236;OC(O)Ph,NH₂], [ZA3237;OC(O)(2-Py),NH₂], [ZA3238;OC(O)(3-Py),NH₂], [ZA3239;OC(O)(4-Py),NH₂], [ZA3240;OC(O)CF₃,NH₂], [ZA3241;OC(O)CH₂Ph,NH₂], [ZA3242;OC(O)CH₂(2-Py),NH₂], [ZA3243;OC(O)CH₂(3-Py),NH₂], [ZA3244;OC(O)CH₂(4-Py),NH₂], [ZA3245;OC(O)CH₂CN,NH₂], [ZA3246;OC(O)CH₂ NO₂,NH₂], [ZA3247;OC(O)(CH₂)₂F,NH₂], [ZA3248;OC(O)(CH₂)₂Cl,NH₂], [ZA3249;OC(O)(CH₂)₂CF₃,NH₂], [ZA3250;OC(O)(CH₂)₂CN,NH₂], [ZA3251;OC(O)(CH₂)₂NO₂,NH₂], [ZA3252;OC(O)(CH₂)₂Ph,NH₂], [ZA3253;OC(O)(CH₂)₂OCH₃,NH₂], [ZA3254;OC(O)(CH₂)₃F,NH₂], [ZA3255;OC(O)(CH₂)₃Cl,NH₂], [ZA3256;OC(O)(CH)₃CF₃,NH₂], [ZA3257;OC(O)(CH₂)₃CN,NH₂], [ZA3258;OC(O)(CH₂)₃NO₂,NH₂], [ZA3259;OC(O)(CH₂)₃Ph,NH₂], [ZA3260;OC(O)(CH₂)₃OCH₃,NH₂], [ZA3261;OC(O)(CH₂)₄F,NH₂], [ZA3262;OC(O)(CH₂)₄Cl,NH₂], [ZA3263;OC(O)(CH₂)₄CF₃,NH₂], [ZA3264;OC(O)(CH₂)₄CN,NH₂], [ZA3265;OC(O)(CH₂)₄NO₂,NH₂], [ZA3266;OC(O)(CH₂)₄Ph,NH₂], [ZA3267;OC(O)(CH₂)₄OCH₃,NH₂], [ZA3268;OC(O)(CH₂)₅F,NH₂], [ZA3269;OC(O)(CH₂)₅Cl,NH₂], [ZA3270;OC(O)(CH₂)₅CF₃,NH₂], [ZA3271;OC(O)(CH₂)₅CN,NH₂], [ZA3272;OC(O)(CH₂)₅ NO₂,NH₂], [ZA3273;OC(O)(CH₂)₅Ph,NH₂], [ZA3274;OC(O)(CH₂)₅

OCH₃,NH₂], [ZA3275;OC(O)(CH₂)₆F,NH₂], [ZA3276;OC(O)(CH₂)₆Cl,NH₂], [ZA3277;OC(O)(CH₂)₆CF₃,NH₂], [ZA3278;OC(O)(CH₂)₆CN,NH₂], [ZA3279;OC(O)(CH₂)₆NO₂,NH₂], [ZA3280;OC(O)(CH₂)₆Ph,NH₂], [ZA3281;OC(O)(CH₂)₆OCH₃,NH₂], [ZA3282;OC(O)NH₂,NH₂], [ZA3283;OC(O)NHCH₃,NH₂], [ZA3284;OC(O)NHCH₂CH₃,NH₂], [ZA3285;OC(O)NH(CH₂)₂CH₃,NH₂], [ZA3286;OC(O)NH(CH₂)₃CH₃,NH₂], [ZA3287;OC(O)NH(CH₂)₄CH₃,NH₂], [ZA3288;OC(O)NH(CH₂)₅CH₃,NH₂], [ZA3289;OC(O)NHCH(CH)₂,NH₂], [ZA3290;OC(O)NHCH₂F,NH₂], [ZA3291;OC(O)NHCH₂Cl,NH₂], [ZA3292;OC(O)NHCH₂CN,NH₂], [ZA3293;OC(O)NHCH₂OCH₃,NH₂], [ZA3294;OC(O)NHCH₂Ph,NH₂], [ZA3295;OC(O)NH(CH₂)₂F,NH₂], [ZA3296;OC(O)NH(CH₂)₂Cl,NH₂], [ZA3297;OC(O)NH(CH₂)₂CN,NH₂], [ZA3298;OC(O)NH(CH₂)₂OCH₃,NH₂], [ZA3299;OC(O)NH(CH₂)₂Ph,NH₂], [ZA3300;OC(O)NH(CH₂)₃F,NH₂], [ZA3301;OC(O)NH(CH₂)₃Cl,NH₂], [ZA3302;OC(O)NH(CH₂)₃CN,NH₂], [ZA3303;OC(O)NH(CH₂)₃OCH₃,NH₂], [ZA3304;OC(O)NH(CH)₃Ph,NH₂], [ZA3305;OC(O)NH(CH₂)₄F,NH₂], [ZA3306;OC(O)NH(CH₂)₄Cl,NH₂], [ZA3307;OC(O)NH(CH₂)₄CN,NH₂], [ZA3308;OC(O)NH(CH₂)₄OCH₃,NH₂], [ZA3309;OC(O)NH(CH)₄Ph,NH₂], [ZA3310;OC(O)NHPh,NH₂], [ZA3311;OC(O)NH(2-Py),NH₂], [ZA3312;OC(O)NH(3-Py),NH₂], [ZA3313;OC(O)NH(4-Py),NH₂], [ZA3314;OC(O)N(CH₃)₂,NH₂], [ZA3315;OC(O)N(CH₃)CH₂CH₃,NH₂], [ZA3316;OC(O)N(CH₃)(CH₂)₂CH₃,NH₂], [ZA3317;OC(O)N(CH₃)(CH₂)₃CH₃,NH₂], [ZA3318;OC(O)N(CH₃)(CH₂)₄CH₃,NH₂], [ZA3319;OC(O)N(CH₃)(CH₂)₅CH₃,NH₂], [ZA3320;OC(O)N(CH)CH(CH₃)₂,NH₂], [ZA3321;OC(O)N(CH₃)CH₂F,NH₂], [ZA3322;OC(O)N(CH₃)CH₂Cl,NH₂], [ZA3323;OC(O)N(CH₃)CH₂CN,NH₂], [ZA3324;OC(O)N(CH₃)CH₂OCH₃,NH₂], [ZA3325;OC(O)N(CH₃)CH₂Ph,NH₂], [ZA3326;OC(O)N(CH₃)(CH₂)₂F,NH₂], [ZA3327;OC(O)N(CH₃)(CH₂)₂Cl,NH₂], [ZA3328;OC(O)N(CH₃)(CH₂)₂CN,NH₂], [ZA3329;OC(O)N(CH₃)(CH₂)₂OCH₃,NH₂], [ZA3330;OC(O)N(CH₃)(CH₂)₂Ph,NH₂], [ZA3331;OC(O)N(CH₃)(CH₂)₃F,NH₂], [ZA3332;OC(O)N(CH₃)(CH₂)₃Cl,NH₂], [ZA3333;OC(O)N(CH₃)(CH₂)₃CN,NH₂], [ZA3334;OC(O)N(CH₃)(CH₂)₃OCH₃,NH₂], [ZA3335;OC(O)N(CH₃)(CH₂)₃Ph,NH₂], [ZA3336;OC(O)N(CH₃)(CH₂)₄F,NH₂], [ZA3337;OC(O)N(CH₃)(CH₂)₄Cl,NH₂], [ZA3338;OC(O)N(CH₃)(CH₂)₄CN,NH₂], [ZA3339;OC(O)N(CH₃)(CH₂)₄OCH₃,NH₂], [ZA3340;OC(O)N(CH₃)(CH₂)₄Ph,NH₂], [ZA3341;OC(O)N(CH₃)Ph,NH₂], [ZA3342;OC(O)N(CH₃)(2-Py),NH₂], [ZA3343;OC(O)N(CH₃)(3-Py),NH₂], [ZA3344;OC(O)N(CH₃)(4-Py),NH₂], [ZA3345;OC(O)N(CH₂CH₃)₂,NH₂], [ZA3346;OC(O)(Pyr),NH₂], [ZA3347;OC(O)(Pip),NH₂], [ZA3348;OC(O)(Mor),NH₂], [ZA3349;OC(O)OCH₃,NH₂], [ZA3350;OC(O)OCH₂CH₃,NH₂], [ZA3351;OC(O)OCH(CH₃)₂,NH₂], [ZA3352;OC(O)O(CH₂)₂CH₃,NH₂], [ZA3353;OC(O)O(CH₂)₃CH₃,NH₂], [ZA3354;OC(O)O(CH₂)₄CH₃,NH₂], [ZA3355;OC(O)O(CH₂)₅CH₃,NH₂], [ZA3356;OC(O)OCH₂CH=CH₂,NH₂], [ZA3357;OC(O)OCH₂C≡CH,NH₂], [ZA3358;OC(O)OCH₂C≡CCH₃,NH₂], [ZA3359;OC(O)O-c-Pr,NH₂], [ZA3360;OC(O)O-c-Bu,NH₂], [ZA3361;OC(O)O-c-Pen,NH₂], [ZA3362;OC(O)O-c-Hex,NH₂], [ZA3363;OC(O)OPh,NH₂], [ZA3364;OC(O)O(2-Py),NH₂], [ZA3365;OC(O)O(3-Py),NH₂], [ZA3366;OC(O)O(4-Py),NH₂], [ZA3367;OC(O)OCF₃,NH₂], [ZA3368;OC(O)OCH₂Ph,NH₂], [ZA3369;OC(O)OCH₂(2-Py),NH₂], [ZA3370;OC(O)OCH₂(3-Py),NH₂], [ZA3371;OC(O)OCH₂(4-Py),NH₂], [ZA3372;OC(O)OCH₂CN,NH₂], [ZA3373;OC(O)OCH₂NO₂,NH₂], [ZA3374;OC(O)O(CH₂)₂F,NH₂], [ZA3375;OC(O)O(CH₂)₂Cl,NH₂], [ZA3376;OC(O)O(CH₂)₂CF₃,NH₂], [ZA3377;OC(O)O(CH₂)₂CN,NH₂], [ZA3378;OC(O)O(CH₂)₂NO₂,NH₂], [ZA3379;OC(O)O(CH₂)₂Ph,NH₂], [ZA3380;OC(O)O(CH₂)₂OCH₃,NH₂], [ZA3381;OC(O)O(CH₂)₃F,NH₂], [ZA3382;OC(O)O(CH₂)₃Cl,NH₂], [ZA3383;OC(O)O(CH₂)₃CF₃,NH₂], [ZA3384;OC(O)O(CH₂)₃CN,NH₂], [ZA3385;OC(O)O(CH₂)₃NO₂,NH₂], [ZA3386;OC(O)O(CH₂)₃Ph,NH₂], [ZA3387;OC(O)O(CH₂)₃OCH₃,NH₂], [ZA3388;OC(O)O(CH₂)₄F,NH₂], [ZA3389;OC(O)O(CH₂)₄Cl,NH₂], [ZA3390;OC(O)O(CH₂)₄CF₃,NH₂], [ZA3391;OC(O)O(CH₂)₄CN,NH₂], [ZA3392;OC(O)O(CH₂)₄NO₂,NH₂], [ZA3393;OC(O)O(CH₂)₄Ph,NH₂], [ZA3394;OC(O)O(CH₂)₄OCH₃,NH₂], [ZA3395;OC(O)O(CH₂)₅F,NH₂], [ZA3396;OC(O)O(CH₂)₅Cl,NH₂], [ZA3397;OC(O)O(CH₂)₅CF₃,NH₂], [ZA3398;OC(O)O(CH₂)₅CN,NH₂], [ZA3399;OC(O)O(CH₂)₅NO₂,NH₂], [ZA3400;OC(O)O(CH₂)₅Ph,NH₂], [ZA3401;OC(O)O(CH₂)₅OCH₃,NH₂], [ZA3402;OC(O)O(CH₂)₆F,NH₂], [ZA3403;OC(O)O(CH₂)₆Cl,NH₂], [ZA3404;OC(O)O(CH₂)₆CF₃,NH₂], [ZA3405;OC(O)O(CH₂)₆CN,NH₂], [ZA3406;OC(O)O(CH₂)₆NO₂,NH₂], [ZA3407;OC(O)O(CH₂)₆Ph,NH₂], [ZA3408;OC(O)O(CH₂)₆OCH₃,NH₂], [ZA3409;OS(O)₂CH₃,NH₂], [ZA3410;OS(O)₂CH₂CH₃,NH₂], [ZA3411;OS(O)₂CH(CH₃)₂,NH₂], [ZA3412;OS(O)₂(CH₂)₂CH₃,NH₂], [ZA3413;OS(O)₂(CH₂)₃CH₃,NH₂], [ZA3414;OS(O)₂(CH₂)₄CH₃,NH₂], [ZA3415;OS(O)₂(CH₂)₅CH₃,NH₂], [ZA3416;OS(O)₂CH₂CH=CH₂,NH₂], [ZA3417;OS(O)₂CH₂C≡CH,NH₂], [ZA3418;OS(O)₂CH₂C≡CCH₃,NH₂], [ZA3419;OS(O)₂-c-Pr,NH₂], [ZA3420;OS(O)₂-c-Bu,NH₂], [ZA3421;OS(O)₂-c-Pen,NH₂], [ZA3422;OS(O)₂-c-Hex,NH₂], [ZA3423;OS(O)₂Ph,NH₂], [ZA3424;OS(O)₂(2-Py),NH₂], [ZA3425;OS(O)₂(3-Py),NH₂], [ZA3426;OS(O)₂(4-Py),NH₂], [ZA3427;OS(O)₂CF₃,NH₂], [ZA3428;OS(O)₂CH₂Ph,NH₂], [ZA3429;OS(O)₂CH₂(2-Py),NH₂], [ZA3430;OS(O)₂CH₂(3-Py),NH₂], [ZA3431;OS(O)₂CH₂(4-Py),NH₂], [ZA3432;OS(O)₂CH₂CN,NH₂], [ZA3433;OS(O)₂CH₂NO₂,NH₂], [ZA3434;OS(O)₂(CH₂)₂F,NH₂], [ZA3435;OS(O)₂(CH₂)₂Cl,NH₂], [ZA3436;OS(O)₂(CH₂)₂CF₃,NH₂], [ZA3437;OS(O)₂(CH₂)₂CN,NH₂], [ZA3438;OS(O)₂(CH₂)₂NO₂,NH₂], [ZA3439;OS(O)₂(CH₂)₂Ph,NH₂], [ZA3440;OS(O)₂(CH₂)₂OCH₃,NH₂], [ZA3441;OS(O)₂(CH₂)₃F,NH₂], [ZA3442;OS(O)₂(CH₂)₃Cl,NH₂], [ZA3443;OS(O)₂(CH₂)₃CF₃,NH₂], [ZA3444;OS(O)₂(CH₂)₃CN,NH₂], [ZA3445;OS(O)₂(CH₂)₃NO₂,NH₂], [ZA3446;OS(O)₂(CH₂)₃Ph,NH₂], [ZA3447;OS(O)₂(CH₂)₃OCH₃,NH₂], [ZA3448;OS(O)₂(CH₂)₄F,NH₂], [ZA3449;OS(O)₂(CH₂)₄Cl,NH₂], [ZA3450;OS(O)₂(CH₂)₄CF₃,NH₂], [ZA3451;OS(O)₂(CH₂)₄CN,NH₂], [ZA3452;OS(O)₂(CH₂)₄NO₂,NH₂], [ZA3453;OS(O)₂(CH₂)₄Ph,NH₂], [ZA3454;OS(O)₂(CH₂)₄OCH₃,NH₂], [ZA3455;OS(O)₂(CH₂)₅F,NH₂], [ZA3456;OS(O)₂(CH₂)₅Cl,NH₂], [ZA3457;OS(O)₂(CH₂)₅CF₃,NH₂], [ZA3458;OS(O)₂(CH₂)₅CN,NH₂], [ZA3459;OS(O)₂(CH₂)₅NO₂,NH₂], [ZA3460;OS(O)₂(CH₂)₅Ph,NH₂], [ZA3461;OS(O)₂(CH₂)₅OCH₃,NH₂], [ZA3462;OS(O)₂(CH₂)₆F,NH₂], [ZA3463;OS(O)₂(CH₂)₆Cl,NH₂], [ZA3464;OS(O)₂(CH₂)₆CF₃,NH₂], [ZA3465;OS(O)₂(CH₂)₆CN,NH₂], [ZA3466;OS(O)₂(CH₂)₆NO₂,NH₂], [ZA3467;OS(O)₂(CH₂)₆Ph,NH₂], [ZA3468;OS(O)₂(CH₂)₆OCH₃,NH₂], [ZA3469;NH₂,NH₂], [ZA3470;NHCH₃,NH₂], [ZA3471;NHCH₂CH₃,NH₂], [ZA3472;NH(CH₂)₂CH₃,NH₂], [ZA3473;NH(CH₂)₃CH₃,NH₂], [ZA3474;NH(CH₂)₄CH₃,NH₂], [ZA3475;NH(CH₂)₅CH₃,NH₂], [ZA3476;NHCH(CH₃)₂,NH₂], [ZA3477;NHCH₂F,NH₂], [ZA3478;NHCH₂CN,NH₂], [ZA3479;NHCH₂OCH₃,NH₂], [ZA3480;NHCH₂Ph,NH₂], [ZA3481;NH(CH₂)₂F,NH₂], [ZA3482;NH(CH₂)₂CN,NH₂], [ZA3483;NH(CH₂)₂OCH₃,NH₂], [ZA3484;NH(CH₂)₂Ph,NH₂], [ZA3485;NH(CH₂)₃F,NH₂], [ZA3486;NH(CH₂)₃Cl,NH₂], [ZA3487;NH (CH₂)₃CN,NH₂], [ZA3488;NH(CH₂)₃OCH₃,NH₂], [ZA3489;NH(CH₂)₃ Ph,NH₂], [ZA3490;NH(CH₂)₄F,NH₂], [ZA3491;NH(CH₂)₄CN,NH₂], [ZA3492;NH(CH₂)₄OCH₃, NH₂], [ZA3493;NH(CH₂)₄Ph,NH₂], [ZA3494;NHPh,NH₂], [ZA3495;NH(2-Py),NH₂], [ZA3496;NH(3-Py),NH₂], [ZA3497;NH(4-Py),NH₂], [ZA3498;N(CH₃)₂,NH₂], [ZA3499;N(CH₃)CH₂CH₃,NH₂], [ZA3500;N(CH₃)(CH₂)₂CH₃, NH₂],

[ZA3501;N(CH₃)(CH₂)₃CH₃,NH₂], [ZA3502;(CH₃)(CH₂)₄CH₃,NH₂], [ZA3503;(CH₃)(CH₂)₅CH₃,NH₂], [ZA3504;N(CH₃)CH(CH₃)₂,NH₂], [ZA3505;N(CH₃)CH₂F, NH₂], [ZA3506;N(CH₃)CH₂CN,NH₂], [ZA3507;N(CH₃)CH₂OCH₃,NH₂], [ZA3508;N(CH₃)CH₂Ph,NH₂], [ZA3509; N(CH₃)(CH₂)₂F,NH₂], [ZA3510;N(CH₃)(CH₂)₂CN,NH₂], [ZA3511;N(CH₃)(CH₂)₂OCH₃,NH₂], [ZA3512;N(CH₃)(CH₂)₂Ph,NH₂], [ZA3513;N(CH₃)(CH₂)₃F,NH₂], [ZA3514; N(CH₃)(CH₂)₃CN,NH₂], [ZA3515;N(CH₃)(CH₂)₃OCH₃, NH₂], [ZA3516;N(CH₃)(CH₂)₃Ph,NH₂], [ZA3517;N(CH₃)(CH₂)₄F,NH₂], [ZA3518;N(CH₃)(CH₂)₄CN,NH₂], [ZA3519;N(CH₃)(CH₂)₄OCH₃,NH₂], [ZA3520;N(CH₃)(CH₂)₄Ph,NH₂], [ZA3521;N(CH₃)Ph,NH₂], [ZA3522;N(CH₃)(2-Py),NH₂], [ZA3523;N(CH₃)(3-Py),NH₂], [ZA3524;N(CH₃)(4-Py),NH₂], [ZA3525;N(CH₂CH₃)₂, NH₂], [ZA3526;Pyr,NH₂], [ZA3527;Pip,NH₂], [ZA3528; Mor,NH₂], [ZA3529;S(O)₂CH₃,NH₂], [ZA3530;S(O)₂CH₂CH₃,NH₂], [ZA3531;S(O)₂CH(CH₃)₂,NH₂], [ZA3532; S(O)₂(CH₂)₂CH₃,NH₂], [ZA3533;S(O)₂(CH₂)₃ CH₃,NH₂], [ZA3534;S(O)₂(CH₂)₄CH₃,NH₂], [ZA3535;S(O)₂(CH₂)₅CH₃,NH₂], [ZA3536;S(O)₂CH₂CH=CH₂,NH₂], [ZA3537; S(O)₂ CH₂C≡CH,NH₂], [ZA3538;S(O)₂ CH₂C≡CCH₃, NH₂], [ZA3539;S(O)₂-c-Pr,NH₂], [ZA3540;S(O)₂-c-Bu, NH₂], [ZA3541;S(O)₂-c-Pen,NH₂], [ZA3542;S(O)₂-c-Hex, NH₂], [ZA3543;S(O)₂Ph,NH₂], [ZA3544;S(O)₂(2-Py), NH₂], [ZA3545;S(O)₂(3-Py),NH₂], [ZA3546;S(O)₂(4-Py), NH₂], [ZA3547;S(O)₂CF₃,NH₂], [ZA3548;S(O)₂CH₂Ph, NH₂], [ZA3549;S(O)₂CH₂(2-Py),NH₂], [ZA3550;S(O)₂CH₂(3-Py),NH₂], [ZA3551;S(O)₂CH₂ (4-Py),NH₂], [ZA3552;S(O)₂CH₂CN,NH₂], [ZA3553;S(O)₂CH₂NO₂, NH₂], [ZA3554;S(O)₂(CH₂)₂F,NH₂], [ZA3555;S(O)₂(CH₂)₂ Cl,NH₂], [ZA3556;S(O)₂(CH₂)₂CF₃,NH₂], [ZA3557;S(O)₂ (CH₂)₂CN,NH₂], [ZA3558;S(O)₂(CH₂)₂NO₂,NH₂], [ZA3559;S(O)₂(CH₂)₂Ph,NH₂], [ZA3560;S(O)₂ (CH₂)₂OCH₃,NH₂], [ZA3561;S(O)₂(CH₂)₃F,NH₂], [ZA3562;S(O)₂(CH₂)₃Cl,NH₂], [ZA3563;S(O)₂(CH₂)₃CF₃, NH₂], [ZA3564;S(O)₂(CH₂)₃CN,NH₂], [ZA3565;S(O)₂(CH₂)₃NO₂,NH₂], [ZA3566;S(O)₂(CH₂)₃Ph,NH₂], [ZA3567;S(O)₂(CH₂)₃OCH₃,NH₂], [ZA3568;S(O)₂(CH₂)₄F,NH₂], [ZA3569;S(O)₂(CH₂)₄Cl,NH₂], [ZA3570;S(O)₂(CH₂)₄CF₃,NH₂], [ZA3571;S(O)₂(CH₂)₄ CN,NH₂], [ZA3572;S(O)₂(CH₂)₄NO₂,NH₂], [ZA3573;S(O)₂(CH₂)₄Ph,NH₂], [ZA3574;S(O)₂(CH)₄OCH₃,NH₂], [ZA3575;S(O)₂ (CH₂)₅F,NH₂], [ZA3576;S(O)₂(CH₂)₅Cl,NH₂], [ZA3577;S(O)₂(CH₂)₅CF₃,NH₂], [ZA3578;S(O)₂(CH₂)₅CN,NH₂], [ZA3579;S(O)₂(CH₂)₅NO₂,NH₂], [ZA3580;S(O)₂ (CH₂)₅Ph,NH₂], [ZA3581;S(O)₂(CH₂)₅ OCH₃,NH₂], [ZA3582;S(O)₂(CH₂)₆F,NH₂], [ZA3583;S(O)₂(CH₂)₆Cl, NH₂], [ZA3584;S(O)₂(CH₂)₆CF₃,NH₂], [ZA3585;S(O)₂(CH₂)₆CN,NH₂], [ZA3586;S(O)₂(CH₂)₆ NO₂,NH₂], [ZA3587;S(O)₂(CH₂)₆Ph,NH₂], [ZA3588;S(O)₂(CH₂)₆OCH₃,NH₂], [ZA3589;S(O)CH₃,NH₂], [ZA3590;S(O)CH₂CH₃,NH₂], [ZA3591;S(O)CH(CH₃)₂,NH₂], [ZA3592;S(O)(CH₂)₂CH₃,NH₂], [ZA3593;S(O)(CH₂)₃CH₃,NH₂], [ZA3594;S(O)(CH₂)₄ CH₃,NH₂], [ZA3595;S(O)(CH₂)₅CH₃,NH₂], [ZA3596;S(O)CH₂CH=CH₂,NH₂], [ZA3597;S(O)CH₂C≡CH,NH₂], [ZA3598;S(O)CH₂C≡CCH₃,NH₂], [ZA3599;S(O)c-Pr,NH₂], [ZA3600;S(O)c-Bu,NH₂], [ZA3601;S(O)c-Pen,NH₂], [ZA3602;S(O)c-Hex,NH₂],

[ZA3603;S(O)Ph,NH₂], [ZA3604;S(O)(2-Py),NH₂], [ZA3605;S(O)(3-Py),NH₂], [ZA3606;S(O)(4-Py),NH₂], [ZA3607;S(O)CF₃,NH₂], [ZA3608;S(O)CH₂Ph,NH₂], [ZA3609;S(O)CH₂(2-Py),NH₂], [ZA3610;S(O)CH₂ (3-Py), NH₂], [ZA3611;S(O)CH₂(4-Py),NH₂], [ZA3612;S(O)CH₂CN,NH₂], [ZA3613;S(O)CH₂NO₂,NH₂], [ZA3614;S(O)(CH₂)₂F,NH₂], [ZA3615;S(O)(CH₂)₂ Cl,NH₂], [ZA3616;S(O)(CH₂)₂CF₃,NH₂], [ZA3617;S(O)(CH₂)₂CN, NH₂], [ZA3618;S(O)(CH₂)₂NO₂,NH₂], [ZA3619;S(O)(CH₂)₂Ph,NH₂], [ZA3620;S(O)(CH₂)₂ OCH₃,NH₂], [ZA3621;S(O)(CH₂)₃F,NH₂], [ZA3622;S(O)(CH₂)₃Cl, NH₂], [ZA3623;S(O)(CH₂)₃CF₃,NH₂], [ZA3624;S(O)(CH₂)₃CN,NH₂], [ZA3625;S(O)(CH₂)₃ NO₂,NH₂], [ZA3626;S(O)(CH₂)₃Ph,NH₂], [ZA3627;S(O)(CH₂)₃OCH₃,NH₂], [ZA3628;S(O)(CH₂)₄F,NH₂], [ZA3629;S(O)(CH₂)₄Cl,NH₂], [ZA3630;S(O)(CH₂)₄CF₃,NH₂], [ZA3631; S(O)(CH₂)₄CN,NH₂], [ZA3632;S(O)(CH₂)₄NO₂,NH₂], [ZA3633;S(O)(CH₂)₄Ph,NH₂], [ZA3634;S(O)(CH₂)₄OCH₃,NH₂], [ZA3635;S(O)(CH₂)₅ F,NH₂], [ZA3636;S(O)(CH₂)₅Cl,NH₂], [ZA3637;S(O)(CH₂)₅CF₃,NH₂], [ZA3638; S(O)(CH₂)₅CN,NH₂], [ZA3639;S(O)(CH₂)₅NO₂,NH₂], [ZA3640;S(O)(CH₂)₅ Ph,NH₂], [ZA3641;S(O)(CH₂)₅OCH₃,NH₂], [ZA3642;S(O)(CH₂)₆F,NH₂], [ZA3643;S(O)(CH₂)₆Cl,NH₂], [ZA3644;S(O)(CH₂)₆CF₃,NH₂], [ZA3645; S(O)(CH₂)₆ CN,NH₂], [ZA3646;S(O)(CH₂)₆NO₂,NH₂], [ZA3647;S(O)(CH₂)₆Ph,NH₂], [ZA3648;S(O)(CH₂)₆OCH₃,NH₂], [ZA3649;OH,NHCH₃], [ZA3650;OCH₃, NHCH₃], [ZA3651;OCH₂CH₃,NHCH₃], [ZA3652;OCH(CH₃)₂,NHCH₃], [ZA3653;(CH₂)₂CH₃,NHCH₃], [ZA3654; O(CH₂)₃CH₃,NHCH₃], [ZA3655;O(CH₂)₄CH₃,NHCH₃], [ZA3656;(CH₂)₅CH₃,NHCH₃], [ZA3657;OCH₂CH=CH₂, NHCH₃], [ZA3658;OCH₂ C≡CH,NHCH₃], [ZA3659; OCH₂C≡CCH₃,NHCH₃], [ZA3660;O-c-Pr,NHCH₃], [ZA3661;O-c-Bu,NHCH₃], [ZA3662;O-c-Pen,NHCH₃], [ZA3663;O-c-Hex,NHCH₃], [ZA3664;OPh,NHCH₃], [ZA3665;O(2-Py),NHCH₃], [ZA3666;O(3-Py),NHCH₃], [ZA3667;O(4-Py),NHCH₃], [ZA3668;OCF₃,NHCH₃], [ZA3669;OCH₂Ph,NHCH₃], [ZA3670;OCH₂(2-Py), NHCH₃], [ZA3671;OCH₂ (3-Py),NHCH₃], [ZA3672;OCH₂ (4-Py),NHCH₃], [ZA3673;OCH₂CN,NHCH₃], [ZA3674; OCH₂NO₂,NHCH₃], [ZA3675;O(CH₂)₂F,NHCH₃], [ZA3676;O(CH₂)₂ Cl,NHCH₃], [ZA3677;O(CH₂)₂Br, NHCH₃], [ZA3678;(CH₂)₂I,NHCH₃], [ZA3679;O(CH₂)₂CF₃,NHCH₃], [ZA3680;O(CH₂)₂CN,NHCH₃], [ZA3681;(CH₂)₂NO₂,NHCH₃], [ZA3682;O(CH₂)₂Ph,NHCH₃], [ZA3683;O(CH₂)₂(2-Py),NHCH₃], [ZA3684;O(CH₂)₂(3-Py),NHCH₃], [ZA3685;O(CH₂)₂(4-Py),NHCH₃], [ZA3686; O(CH₂)₂OH,NHCH₃], [ZA3687;O(CH₂)₂OCH₃,NHCH₃], [ZA3688;O(CH₂)₂SH,NHCH₃], [ZA3689;O(CH₂)₂SCH₃, NHCH₃], [ZA3690;O(CH₂)₂NH₂,NHCH₃], [ZA3691; (CH₂)₂ NHCH₃,NHCH₃], [ZA3692;O(CH₂)₂N(CH₃)₂, NHCH₃], [ZA3693;O(CH₂)₂ NHPh,NHCH₃], [ZA3694;O(CH₂)₂NHCH₂Ph,NHCH₃], [ZA3695;O(CH₂)₂N(CH₃)CH₂Ph,NHCH₃], [ZA3696;O(CH₂)₂S(O)CH₃,NHCH₃], [ZA3697;O(CH₂)₂S(O)CH₂CH₃,NHCH₃], [ZA3698;O(CH₂)₂S(O)Ph,NHCH₃], [ZA3699;O(CH₂)₂S(O)₂CH₃, NHCH₃], [ZA3700;O(CH₂)₂S(O)₂CH₂CH₃,NHCH₃], [ZA3701;(CH₂)₂S(O)₂Ph,NHCH₃], [ZA3702;O(CH)₂C(O)CH₃,NHCH₃], [ZA3703;O(CH₂)₂C(O)CH₂CH₃,NHCH₃], [ZA3704;O(CH₂)₂C(O)Ph,NHCH₃], [ZA3705;O(CH₂)₂C(S)CH₃,NHCH₃], [ZA3706;O(CH₂)₂C(S)CH₂CH₃, NHCH₃], [ZA3707;O(CH₂)C(S)Ph,NHCH₃], [ZA3708;O(CH₂)₂S(O)₂NHCH₃,NHCH₃], [ZA3709;O(CH₂)₂S(O)₂N(CH₃)₂,NHCH₃], [ZA3710;O(CH₂)₂S(O)₂NHPh,NHCH₃], [ZA3711;O(CH₂)₂S(O)₂N(CH₃)Ph,NHCH₃], [ZA3712;O(CH₂)₂C(O)NH₂,NHCH₃], [ZA3713;O(CH₂)₂C(O)NHCH₃, NHCH₃], [ZA3714;O(CH₂)₂C(O)N(CH₃)₂,NHCH₃],

[ZA3715;O(CH₂)₂C(O)NHPh,NHCH₃], [ZA3716;O(CH₂)₂C(O)N(CH₃)Ph,NHCH₃], [ZA3717;O(CH₂)₂C(O)OCH₃,NHCH₃], [ZA3718;O(CH₂)₂C(O)OCH₂CH₃,NHCH₃], [ZA3719;O(CH₂)₂NHC(O)CH₃,NHCH₃], [ZA3720;O(CH₂)₂NHC(O)CH₂CH₃,NHCH₃], [ZA3721;(CH₂)₂NHC(O)Ph,NHCH₃], [ZA3722;O(CH₂)₂NCH₃C(O)CH₃,NHCH₃], [ZA3723;O(CH₂)₂NCH₃C(O)CH₂CH₃,NHCH₃], [ZA3724;O(CH₂)₂NCH₃C(O)Ph,NHCH₃], [ZA3725;O(CH₂)₂NHC(O)OCH₃,NHCH₃], [ZA3726;O(CH₂)₂NHC(O)OCH₂CH₃,NHCH₃], [ZA3727;O(CH₂)₂NHC(O)OPh,NHCH₃], [ZA3728;O(CH₂)₂NCH₃C(O)OCH₃,NHCH₃], [ZA3729;O(CH₂)₂NCH₃C(O)OCH₂CH₃,NHCH₃], [ZA3730;O(CH)₂NCH₃C(O)OPh,NHCH₃], [ZA3731;(CH₂)₂NHC(O)NHCH₃,NHCH₃], [ZA3732;O(CH₂)₂NHC(O)NHCH₂CH₃,NHCH₃], [ZA3733;O(CH)₂NHC(O)NHPh,NHCH₃], [ZA3734;O(CH₂)₂NHC(O)N(CH₃)₂,NHCH₃], [ZA3735;O(CH₂)₂NHC(O)N(CH₃)CH₂CH₃,NHCH₃], [ZA3736;O(CH₂)₂ NHC(O)N(CH₃)Ph,NHCH₃], [ZA3737;O(CH₂)₂NHC(O)N(CH₂CH₃)₂,NHCH₃], [ZA3738;O(CH₂)₂ NCH₃C(O)NHCH₃,NHCH₃], [ZA3739;O(CH₂)₂NCH₃C(O)NHCH₂ CH₃,NHCH₃], [ZA3740;O(CH₂)₂NCH₃C(O)NHPh,NHCH₃], [ZA3741;(CH₂)₂NCH₃C(O)N(CH₃)₂,NHCH₃], [ZA3742;O(CH₂)₂NCH₃C(O)N(CH₃)CH₂CH₃,NHCH₃], [ZA3743;O(CH₂)₂NCH₃C(O)N(CH₃)Ph,NHCH₃], [ZA3744;O(CH₂)₂NCH₃C(O)N(CH₂CH₃)₂,NHCH₃], [ZA3745;O(CH₂)₂OC(O)CH₃,NHCH₃], [ZA3746;O(CH₂)₂OC(O)CH₂ CH₃,NHCH₃], [ZA3747;O(CH₂)₂OC(O)Ph,NHCH₃], [ZA3748;O(CH₂)₂OC(O)OCH₃,NHCH₃], [ZA3749;O(CH₂)₂OC(O)OCH₂CH₃,NHCH₃], [ZA3750;O(CH₂)₂ OC(O)OPh,NHCH₃], [ZA3751;(CH₂)₂OC(O)NHCH₃,NHCH₃], [ZA3752;O(CH₂)₂ OC(O)NHCH₂CH₃,NHCH₃], [ZA3753;O(CH₂)₂OC(O)NHPh,NHCH₃], [ZA3754;O(CH₂)₂OC(O)N(CH₃)₂,NHCH₃], [ZA3755;O(CH₂)₂OC(O)N(CH)CH₂CH₃,NHCH₃], [ZA3756;(CH₂)₂OC(O)N(CH₃)Ph,NHCH₃], [ZA3757;O(CH₂)₂OC(O)N(CH₂CH₃)₂,NHCH₃], [ZA3758;O(CH₂)₂SC(O)CH₃,NHCH₃], [ZA3759;O(CH₂)₂SC(O)CH₂CH₃,NHCH₃], [ZA3760;O(CH₂)₂SC(O)Ph,NHCH₃], [ZA3761;(CH₂)₂SC(O)OCH₃,NHCH₃], [ZA3762;O(CH₂)₂SC(O)OCH₂CH₃,NHCH₃], [ZA3763;O(CH₂)₂SC(O)OPh,NHCH₃], [ZA3764;O(CH₂)₂S(O)₂NHCH₃,NHCH₃], [ZA3765;O(CH₂)₂S(O)₂NHCH₂CH₃,NHCH₃], [ZA3766;O(CH₂)₂S(O)₂NHPh,NHCH₃], [ZA3767;O(CH₂)₂S(O)₂N(CH₃)₂,NHCH₃], [ZA3768;O(CH₂)₂S(O)₂N(CH₃)CH₂CH₃,NHCH₃], [ZA3769;O(CH₂)₂S(O)₂N(CH₃)Ph,NHCH₃], [ZA3770;O(CH₂)₂S(O)₂N(CH₂CH₃)₂,NHCH₃], [ZA3771;(CH₂)₃ F,NHCH₃], [ZA3772;O(CH₂)₃Cl,NHCH₃], [ZA3773;O(CH₂)₃Br,NHCH₃], [ZA3774;O(CH₂)₃I,NHCH₃], [ZA3775;O(CH₂)₃CF₃,NHCH₃], [ZA3776;O(CH₂)₃ CN,NHCH₃], [ZA3777;O(CH₂)₃NO₂,NHCH₃], [ZA3778;(CH₂)₃Ph,NHCH₃], [ZA3779;O(CH₂)₃(2-Py),NHCH₃], [ZA3780;O(CH₂)₃(3-Py),NHCH₃], [ZA3781;(CH₂)₃(4-Py),NHCH₃], [ZA3782;O(CH₂)₃OH,NHCH₃], [ZA3783;O(CH₂)₃OCH₃,NHCH₃], [ZA3784;O(CH₂)₃OCH₂CH₃,NHCH₃], [ZA3785;O(CH₂)₃SH,NHCH₃], [ZA3786;O(CH)₃SCH₃,NHCH₃], [ZA3787;O(CH₂)₃SCH₂CH₃,NHCH₃], [ZA3788;O(CH₂)₃NH₂,NHCH₃], [ZA3789;O(CH₂)₃NHCH₃,NHCH₃], [ZA3790;O(CH₂)₃N(CH₃)₂,NHCH₃], [ZA3791;(CH₂)₄F,NHCH₃], [ZA3792;O(CH₂)₄Cl,NHCH₃], [ZA3793;O(CH₂)₄CF₃,NHCH₃], [ZA3794;O(CH₂)₄CN,NHCH₃], [ZA3795;O(CH₂)₄NO₂,NHCH₃], [ZA3796;O(CH₂)₄Ph,NHCH₃], [ZA3797;O(CH₂)₄ OH,N HCH₃], [ZA3798;O(CH₂)₄OCH₃,NHCH₃], [ZA3799;O(CH₂)₄SH,NHCH₃], [ZA3800;O(CH₂)₄SCH₃,NHCH₃], [ZA3801;O(CH₂)₄NH₂,NHCH₃], [ZA3802;O(CH₂)₄ NHCH₃,NHCH₃], [ZA3803;O(CH₂)₄N(CH₃)₂,NHCH₃], [ZA3804;O(CH₂)₅F,NHCH₃], [ZA3805;O(CH₂)₅Cl,NHCH₃], [ZA3806;O(CH₂)₅CF₃,NHCH₃], [ZA3807;O(CH₂)₅ CN,NHCH₃], [ZA3808;O(CH₂)₅NO₂,NHCH₃], [ZA3809;O(CH₂)₅Ph,NHCH₃], [ZA3810;O(CH₂)₅ OH,NHCH₃], [ZA3811;O(CH₂)₅OCH₃,NHCH₃], [ZA3812;O(CH₂)₅ SH,NHCH₃], [ZA3813;O(CH₂)₅SCH₃,NHCH₃], [ZA3814;O(CH₂)₅NH₂,NHCH₃], [ZA3815;O(CH₂)₅NHCH₃,NHCH₃], [ZA3816;O(CH₂)₅N(CH₃)₂,NHCH₃], [ZA3817;O(CH₂)₆F,NHCH₃], [ZA3818;O(CH₂)₆Cl,NHCH₃], [ZA3819;O(CH₂)₆CF₃,NHCH₃], [ZA3820;O(CH₂)₆CN,NHCH₃], [ZA3821;O(CH₂)₆NO₂,NHCH₃], [ZA3822;O(CH₂)₆Ph,NHCH₃], [ZA3823;O(CH₂)₆OH,NHCH₃], [ZA3824;O(CH₂)₆OCH₃,NHCH₃], [ZA3825;O(CH₂)₆SH,NHCH₃], [ZA3826;O(CH₂)₆SCH₃,NHCH₃], [ZA3827;O(CH₂)₆NH₂,NHCH₃], [ZA3828;O(CH₂)₆NHCH₃,NHCH₃], [ZA3829;O(CH₂)₆N(CH₃)₂,NHCH₃], [ZA3830;OC(O)CH₃,NHCH₃], [ZA3831;OC(O)CH₂CH₃,NHCH₃], [ZA3832;OC(O)CH(CH₃)₂,NHCH₃], [ZA3833;OC(O)(CH₂)₂CH₃,NHCH₃], [ZA3834;OC(O)(CH₂)₃CH₃,NHCH₃], [ZA3835;OC(O)(CH₂)₄CH₃,NHCH₃], [ZA3836;OC(O)(CH₂)₅CH₃,NHCH₃], [ZA3837;OC(O)CH₂CH=CH₂,NHCH₃], [ZA3838;OC(O)CH₂C≡CH,NHCH₃], [ZA3839;OC(O)CH₂C≡CCH₃,NHCH₃], [ZA3840;OC(O)c-Pr,NHCH₃], [ZA3841;OC(O)c-Bu,NHCH₃], [ZA3842;OC(O)c-Pen,NHCH₃], [ZA3843;OC(O)c-Hex,NHCH₃], [ZA3844;OC(O)Ph,NHCH₃], [ZA3845;OC(O)(2-Py),NHCH₃], [ZA3846;OC(O)(3-Py),NHCH₃], [ZA3847;OC(O)(4-Py),NHCH₃], [ZA3848;OC(O)CF₃,NHCH₃], [ZA3849;OC(O)CH₂Ph,NHCH₃], [ZA3850;OC(O)CH₂(2-Py),NHCH₃], [ZA3851;OC(O)CH₂(3-Py),NHCH₃], [ZA3852;OC(O)CH₂(4-Py),NHCH₃], [ZA3853;OC(O)CH₂CN,NHCH₃], [ZA3854;OC(O)CH₂NO₂,NHCH₃], [ZA3855;OC(O)(CH₂)₂F,NHCH₃], [ZA3856;OC(O)(CH)₂Cl,NHCH₃], [ZA3857;OC(O)(CH₂)₂CF₃,NHCH₃], [ZA3858;OC(O)(CH₂)₂CN,NHCH₃], [ZA3859;OC(O)(CH₂)₂NO₂,NHCH₃], [ZA3860;OC(O)(CH₂)₂Ph,NHCH₃], [ZA3861;OC(O)(CH₂)₂OCH₃,NHCH₃], [ZA3862;OC(O)(CH₂)₃F,NHCH₃], [ZA3863;OC(O)(CH₂)₃Cl,NHCH₃], [ZA3864;OC(O)(CH₂)₃CF₃,NHCH₃], [ZA3865;OC(O)(CH₂)₃CN,NHCH₃], [ZA3866;OC(O)(CH₂)₃NO₂,NHCH₃], [ZA3867;OC(O)(CH₂)₃Ph,NHCH₃], [ZA3868;OC(O)(CH₂)₃OCH₃,NHCH₃], [ZA3869;OC(O)(CH₂)₄F,NHCH₃], [ZA3870;OC(O)(CH₂)₄Cl,NHCH₃], [ZA3871;OC(O)(CH₂)₄CF₃,NHCH₃], [ZA3872;OC(O)(CH₂)₄CN,NHCH₃], [ZA3873;OC(O)(CH₂)₄NO₂,NHCH₃], [ZA3874;OC(O)(CH₂)₄Ph,NHCH₃], [ZA3875;OC(O)(CH₂)₄OCH₃,NHCH₃], [ZA3876;OC(O)(CH₂)₅F,NHCH₃], [ZA3877;OC(O)(CH₂)₅Cl,NHCH₃], [ZA3878;OC(O)(CH₂)₅ CF₃,NHCH₃], [ZA3879;OC(O)(CH₂)₅CN,NHCH₃], [ZA3880;OC(O)(CH₂)₅NO₂,NHCH₃], [ZA3881;OC(O)(CH₂)₅Ph,NHCH₃], [ZA3882;OC(O)(CH₂)₅OCH₃,NHCH₃], [ZA3883;OC(O)(CH₂)₆F,NHCH₃], [ZA3884;OC(O)(CH₂)₆Cl,NHCH₃], [ZA3885;OC(O)(CH₂)₆CF₃,NHCH₃], [ZA3886;OC(O)(CH₂)₆CN,NHCH₃], [ZA3887;OC(O)(CH₂)₆NO₂,NHCH₃], [ZA3888;OC(O)(CH₂)₆Ph,NHCH₃], [ZA3889;OC(O)(CH₂)₆OCH₃,NHCH₃], [ZA3890;OC(O)NH₂,NHCH₃], [ZA3891;OC(O)NHCH₃,NHCH₃], [ZA3892;OC(O)NHCH₂CH₃,NHCH₃], [ZA3893;OC(O)NH(CH₂)₂CH₃,NHCH₃], [ZA3894;OC(O)NH(CH₂)₃ CH₃,NHCH₃], [ZA3895;OC(O)NH(CH₂)₄CH₃,NHCH₃], [ZA3896;OC(O)NH(CH₂)₅CH₃,NHCH₃], [ZA3897;OC(O)NHCH(CH)₂,NHCH₃], [ZA3898;OC(O)NHCH₂F,NHCH₃], [ZA3899;OC(O)NHCH₂Cl,NHCH₃], [ZA3900;OC(O)NHCH₂CN,NHCH₃], [ZA3901;OC(O)NHCH₂OCH₃,NHCH₃], [ZA3902;OC(O)NHCH₂Ph,NHCH₃], [ZA3903;OC(O)NH(CH₂)₂F,NHCH₃], [ZA3904;OC(O)NH(CH₂)₂Cl,NHCH₃], [ZA3905;OC(O)NH(CH₂)₂CN,NHCH₃], [ZA3906;OC(O)NH(CH)₂OCH₃,NHCH₃],

[ZA3907;OC(O)NH(CH₂)₂Ph,NHCH₃], [ZA3908;OC(O)NH(CH₂)₃F,NHCH₃], [ZA3909;OC(O)NH(CH₂)₃Cl,NHCH₃], [ZA391;OC(O)NH(CH₂)₃CN,NHCH₃], [ZA3911;OC(O)NH(CH₂)₃OCH₃,NHCH₃], [ZA3912;OC(O)NH(CH₂)₃Ph,NHCH₃], [ZA3913;OC(O)NH(CH₂)₄F,NHCH₃], [ZA3914;OC(O)NH(CH₂)₄Cl,NHCH₃], [ZA3915;OC(O)NH(CH₂)₄CN,NHCH₃], [ZA3916;OC(O)NH(CH₂)₄OCH₃,NHCH₃], [ZA3917;OC(O)NH(CH₂)₄Ph,NHCH₃], [ZA3918;OC(O)NHPh,NHCH₃], [ZA3919;OC(O)NH(2-Py),NHCH₃], [ZA3920;OC(O)NH(3-Py),NHCH₃], [ZA3921;OC(O)NH(4-Py),NHCH₃], [ZA3922;OC(O)N(CH₃)₂,NHCH₃], [ZA3923;OC(O)N(CH₃)CH₂CH₃,NHCH₃], [ZA3924;OC(O)N(CH₃)(CH₂)₂CH₃,NHCH₃], [ZA3925;OC(O)N(CH₃)(CH₂)₃CH₃,NHCH₃], [ZA3926;OC(O)N(CH₃)(CH₂)₄CH₃,NHCH₃], [ZA3927;OC(O)N(CH₃)(CH₂)₅CH₃,NHCH₃], [ZA3928;OC(O)N(CH₃)CH(CH₃)₂,NHCH₃], [ZA3929;OC(O)N(CH₃)CH₂F,NHCH₃], [ZA3930;OC(O)N(CH₃)CH₂Cl,NHCH₃], [ZA3931;OC(O)N(CH₃)CH₂CN,NHCH₃], [ZA3932;OC(O)N(CH₃)CH₂OCH₃,NHCH₃], [ZA3933;OC(O)N(CH₃)CH₂Ph,NHCH₃], [ZA3934;OC(O)N(CH₃)(CH₂)₂F,NHCH₃], [ZA3935;OC(O)N(CH₃)(CH₂)₂Cl,NHCH₃], [ZA3936;OC(O)N(CH₃)(CH₂)₂CN,NHCH₃], [ZA3937;OC(O)N(CH₃)(CH₂)₂OCH₃,NHCH₃], [ZA3938;OC(O)N(CH₃)(CH₂)₂Ph,NHCH₃], [ZA3939;OC(O)N(CH₃)(CH)₃F,NHCH₃], [ZA3940;OC(O)N(CH₃)(CH₂)₃Cl,NHCH₃], [ZA3941;OC(O)N(CH₃)(CH₂)₃CN,NHCH₃], [ZA3942;OC(O)N(CH₃)(CH₂)₃OCH₃,NHCH₃], [ZA3943;OC(O)N(CH₃)(CH₂)₃Ph,NHCH₃], [ZA3944;OC(O)N(CH₃)(CH)₄F,NHCH₃], [ZA3945;OC(O)N(CH₃)(CH₂)₄Cl,NHCH₃], [ZA3946;OC(O)N(CH₃)(CH₂)₄CN,NHCH₃], [ZA3947;OC(O)N(CH₃)(CH₂)₄OCH₃,NHCH₃], [ZA3948;OC(O)N(CH₃)(CH₂)₄Ph,NHCH₃], [ZA3949;OC(O)N(CH₃)Ph,NHCH₃], [ZA3950;OC(O)N(CH₃)(2-Py),NHCH₃], [ZA3951;OC(O)N(CH₃)(3-Py),NHCH₃], [ZA3952;OC(O)N(CH₃)(4-Py),NHCH₃], [ZA3953;OC(O)N(CH₂CH₃)₂,NHCH₃], [ZA3954;OC(O)(Pyr),NHCH₃], [ZA3955;OC(O)(Pip),NHCH₃], [ZA3956;OC(O)(Mor),NHCH₃], [ZA3957;OC(O)OCH₃,NHCH₃], [ZA3958;OC(O)OCH₂CH₃,NHCH₃], [ZA3959;OC(O)OCH(CH₃)₂,NHCH₃], [ZA3960;OC(O)O(CH)₂CH₃,NHCH₃], [ZA3961;OC(O)O(CH₂)₃CH₃,NHCH₃], [ZA3962;OC(O)O(CH₂)₄CH₃,NHCH₃], [ZA3963;OC(O)O(CH₂)₅CH₃,NHCH₃], [ZA3964;OC(O)OCH₂CH=CH₂,NHCH₃], [ZA3965;OC(O)OCH₂C≡CH,NHCH₃], [ZA3966;OC(O)OCH₂C≡CCH₃,NHCH₃], [ZA3967;OC(O)O-c-Pr,NHCH₃], [ZA3968;OC(O)O-c-Bu,NHCH₃], [ZA3969;OC(O)O-c-Pen,NHCH₃], [ZA3970;OC(O)O-c-Hex,NHCH₃], [ZA3971;OC(O)OPh,NHCH₃], [ZA3972;OC(O)O(2-Py),NHCH₃], [ZA3973;OC(O)O(3-Py),NHCH₃], [ZA3974;OC(O)O(4-Py),NHCH₃], [ZA3975;OC(O)OCF₃,NHCH₃], [ZA3976;OC(O)OCH₂Ph,NHCH₃], [ZA3977;OC(O)OCH₂(2-Py),NHCH₃], [ZA3978;OC(O)OCH₂(3-Py),NHCH₃], [ZA3979;OC(O)OCH₂(4-Py),NHCH₃], [ZA3980;OC(O)OCH₂CN,NHCH₃], [ZA3981;OC(O)OCH₂NO₂,NHCH₃], [ZA3982;OC(O)O(CH₂)₂F,NHCH₃], [ZA3983;OC(O)O(CH₂)₂Cl,NHCH₃], [ZA3984;OC(O)O(CH₂)₂CF₃,NHCH₃], [ZA3985;OC(O)O(CH)₂CN,NHCH₃], [ZA3986;OC(O)O(CH)₂NO₂,NHCH₃], [ZA3987;OC(O)O(CH₂)₂Ph,NHCH₃], [ZA3988;OC(O)O(CH₂)₂OCH₃,NHCH₃], [ZA3989;OC(O)O(CH₂)₃F,NHCH₃], [ZA3990;OC(O)O(CH₂)₃Cl,NHCH₃], [ZA3991;OC(O)O(CH₂)₃CF₃,NHCH₃], [ZA3992;OC(O)O(CH₂)₃CN,NHCH₃], [ZA3993;OC(O)O(CH₂)₃NO₂,NHCH₃], [ZA3994;OC(O)O(CH₂)₃Ph,NHCH₃], [ZA3995;OC(O)O(CH₂)₃OCH₃,NHCH₃], [ZA3996;OC(O)O(CH)₄F,NHCH₃], [ZA3997;OC(O)O(CH₂)₄Cl,NHCH₃], [ZA3998;OC(O)O(CH₂)₄CF₃,NHCH₃], [ZA3999;OC(O)O(CH₂)₄CN,NHCH₃], [ZA4000;OC(O)O(CH₂)₄NO₂,NHCH₃], [ZA4001;OC(O)O(CH₂)₄Ph,NHCH₃], [ZA4002;OC(O)O(CH₂)₄OCH₃,NHCH₃], [ZA4003;OC(O)O(CH₂)₅F,NHCH₃], [ZA4004;OC(O)O(CH₂)₅Cl,NHCH₃], [ZA4005;OC(O)O(CH₂)₅CF₃,NHCH₃], [ZA4006;OC(O)O(CH₂)₅CN,NHCH₃], [ZA4007;OC(O)O(CH₂)₅NO₂,NHCH₃], [ZA4008;OC(O)O(CH₂)₅Ph,NHCH₃], [ZA4009;OC(O)O(CH₂)₅OCH₃,NHCH₃], [ZA4010;OC(O)O(CH₂)₆F,NHCH₃], [ZA4011;OC(O)O(CH₂)₆Cl,NHCH₃], [ZA4012;OC(O)O(CH₂)₆CF₃,NHCH₃], [ZA4013;OC(O)O(CH₂)₆CN,NHCH₃], [ZA4014;OC(O)O(CH₂)₆NO₂,NHCH₃], [ZA4015;OC(O)O(CH₂)₆Ph,NHCH₃], [ZA4016;OC(O)O(CH₂)₆OCH₃,NHCH₃], [ZA4017;OS(O)₂CH₃,NHCH₃], [ZA4018;OS(O)₂CH₂CH₃,NHCH₃], [ZA4019;OS(O)₂CH(CH₃)₂,NHCH₃], [ZA4020;OS(O)₂(CH₂)₂CH₃,NHCH₃], [ZA4021;OS(O)₂(CH₂)₃CH₃,NHCH₃], [ZA4022;OS(O)₂(CH₂)₄CH₃,NHCH₃], [ZA4023;OS(O)₂(CH₂)₅CH₃,NHCH₃], [ZA4024;OS(O)₂CH₂CH=CH₂,NHCH₃], [ZA4025;OS(O)₂CH₂C≡CH,NHCH₃], [ZA4026;OS(O)₂CH₂C≡CCH₃,NHCH₃], [ZA4027;OS(O)₂-c-Pr,NHCH₃], [ZA4028;OS(O)₂-c-Bu,NHCH₃], [ZA4029;OS(O)₂-c-Pen,NHCH₃], [ZA4030;OS(O)₂-c-Hex,NHCH₃], [ZA4031;OS(O)₂Ph,NHCH₃], [ZA4032;OS(O)₂(2-Py),NHCH₃], [ZA4033;OS(O)₂(3-Py),NHCH₃], [ZA4034;OS(O)₂(4-Py),NHCH₃], [ZA4035;OS(O)₂CF₃,NHCH₃], [ZA4036;OS(O)₂CH₂Ph,NHCH₃], [ZA4037;OS(O)₂CH₂(2-Py),NHCH₃], [ZA4038;OS(O)₂CH₂(3-Py),NHCH₃], [ZA4039;OS(O)₂CH₂(4-Py),NHCH₃], [ZA4040;OS(O)₂CH₂CN,NHCH₃], [ZA4041;OS(O)₂CH₂NO₂,NHCH₃], [ZA4042;OS(O)₂(CH₂)₂F,NHCH₃], [ZA4043;OS(O)₂(CH₂)₂Cl,NHCH₃], [ZA4044;OS(O)₂(CH₂)₂CF₃,NHCH₃], [ZA4045;OS(O)₂(CH₂)₂CN,NHCH₃], [ZA4046;OS(O)₂(CH₂)₂NO₂,NHCH₃], [ZA4047;OS(O)₂(CH₂)₂Ph,NHCH₃], [ZA4048;OS(O)₂(CH₂)₂OCH₃,NHCH₃], [ZA4049;OS(O)₂(CH₂)₃F,NHCH₃], [ZA4050;OS(O)₂(CH)₃Cl,NHCH₃], [ZA4051;OS(O)₂(CH₂)₃CF₃,NHCH₃], [ZA4052;OS(O)₂(CH₂)₃CN,NHCH₃], [ZA4053;OS(O)₂(CH₂)₃NO₂,NHCH₃], [ZA4054;OS(O)₂(CH₂)₃Ph,NHCH₃], [ZA4055;OS(O)₂(CH₂)₃OCH₃,NHCH₃], [ZA4056;OS(O)₂(CH₂)₄F,NHCH₃], [ZA4057;OS(O)₂(CH₂)₄Cl,NHCH₃], [ZA4058;OS(O)₂(CH₂)₄CF₃,NHCH₃], [ZA4059;OS(O)₂(CH₂)₄CN,NHCH₃], [ZA4060;OS(O)₂(CH₂)₄NO₂,NHCH₃], [ZA4061;OS(O)₂(CH₂)₄Ph,NHCH₃], [ZA4062;OS(O)₂(CH₂)₄OCH₃,NHCH₃], [ZA4063;OS(O)₂(CH₂)₅F,NHCH₃], [ZA4064;OS(O)₂(CH₂)₅Cl,NHCH₃], [ZA4065;OS(O)₂(CH₂)₅CF₃,NHCH₃], [ZA4066;OS(O)₂(CH₂)₅CN,NHCH₃], [ZA4067;OS(O)₂(CH₂)₅NO₂,NHCH₃], [ZA4068;OS(O)₂(CH₂)₅Ph,NHCH₃], [ZA4069;OS(O)₂(CH₂)₅OCH₃,NHCH₃], [ZA4070;OS(O)₂(CH₂)₆F,NHCH₃], [ZA4071;OS(O)₂(CH₂)₆Cl,NHCH₃], [ZA4072;OS(O)₂(CH₂)₆CF₃,NHCH₃], [ZA4073;OS(O)₂(CH₂)₆CN,NHCH₃], [ZA4074;OS(O)₂(CH₂)₆NO₂,NHCH₃], [ZA4075;OS(O)₂(CH₂)₆Ph,NHCH₃], [ZA4076;OS(O)₂(CH₂)₆OCH₃,NHCH₃], [ZA4077;NH₂,NHCH₃], [ZA4078;NHCH₃,NHCH₃], [ZA4079;NHCH₂CH₃,NHCH₃], [ZA4080;NH(CH₂)₂CH₃,NHCH₃], [ZA4081;NH(CH₂)₃CH₃,NHCH₃], [ZA4082;NH(CH₂)₄CH₃,NHCH₃], [ZA4083;NH(CH₂)₅CH₃,NHCH₃], [ZA4084;NHCH(CH₃)₂,NHCH₃], [ZA4085;NHCH₂F,NHCH₃], [ZA4086;NHCH₂CN,NHCH₃], [ZA4087;NHCH₂OCH₃,NHCH₃], [ZA4088;NHCH₂Ph,NHCH₃], [ZA4089;NH(CH₂)₂F,NHCH₃], [ZA4090;NH(CH₂)₂CN,NHCH₃], [ZA4091;NH(CH₂)₂OCH₃,NHCH₃], [ZA4092;NH(CH₂)₂Ph,NHCH₃], [ZA4093;NH(CH₂)₃F,NHCH₃], [ZA4094;NH(CH₂)₃Cl,NHCH₃], [ZA4095;NH(CH₂)₃CN,NHCH₃], [ZA4096;NH(CH₂)₃OCH₃,NHCH₃], [ZA4097;NH(CH₂)₃Ph,NHCH₃], [ZA4098;NH(CH₂)₄F,NHCH₃], [ZA4099;NH(CH₂)₄CN,

NHCH₃], [ZA4100;NH(CH₂)₄ OCH₃,NHCH₃], [ZA4101; NH(CH₂)₄Ph,NHCH₃], [ZA4102;NHPh,NHCH₃], [ZA4103;NH(2-Py),NHCH₃], [ZA4104;NH(3-Py), NHCH₃], [ZA4105;NH(4-Py),NHCH₃], [ZA4106;N(CH₃)₂, NHCH₃], [ZA4107;N(CH₃)CH₂CH₃,NHCH₃], [ZA4108;N (CH₃)(CH₂)₂CH₃,NHCH₃], [ZA4109;N(CH₃)(CH₂)₃CH₃, NHCH₃], [ZA4110;(CH₃)(CH₂)₄CH₃,NHCH₃], [ZA4111; (CH₃)(CH₂)₅CH₃,NHCH₃], [ZA4112;N(CH₃)CH(CH₃)₂, NHCH₃], [ZA4113;N(CH₃)CH₂F,NHCH₃], [ZA4114;N (CH₃)CH₂CN,NHCH₃], [ZA4115;N(CH₃)CH₂OCH₃, NHCH₃], [ZA4116;N(CH₃)CH₂Ph,NHCH₃], [ZA4117;N (CH₃)(CH₂)₂F,NHCH₃], [ZA4118;N(CH₃)(CH₂)₂CN, NHCH₃], [ZA4119;N(CH₃)(CH₂)₂OCH₃,NHCH₃], [ZA4120;N(CH₃)(CH₂)₂ Ph,NHCH₃], [ZA4121;N(CH₃) (CH₂)₃F,NHCH₃], [ZA4122;N(CH₃)(CH₂)₃CN,NHCH₃], [ZA4123;N(CH₃)(CH₂)₃OCH₃,NHCH₃], [ZA4124;N(CH₃) (CH₂)₃Ph,NHCH₃], [ZA4125;N(CH₃)(CH₂)₄F,NHCH₃], [ZA4126;N(CH₃)(CH₂)₄CN,NHCH₃], [ZA4127;N(CH₃) (CH₂)₄OCH₃,NHCH₃], [ZA4128;N(CH₃)(CH₂)₄Ph, NHCH₃], [ZA4129;N(CH₃)Ph,NHCH₃], [ZA4130;N(CH₃) (2-Py),NHCH₃], [ZA4131;N(CH₃)(3-Py),NHCH₃], [ZA4132;N(CH₃)(4-Py),NHCH₃], [ZA4133;N(CH₂CH₃)₂, NHCH₃], [ZA4134;Pyr,NHCH₃], [ZA4135;Pip,NHCH₃], [ZA4136;Mor,NHCH₃], [ZA4137;S(O)₂CH₃,NHCH₃], [ZA4138;S(O)₂CH₂CH₃,NHCH₃], [ZA4139;S(O)₂CH (CH₃)₂,NHCH₃], [ZA4140;S(O)₂(CH₂)₂CH₃,NHCH₃], [ZA4141;S(O)₂(CH₂)₃CH₃,NHCH₃], [ZA4142;S(O)₂ (CH₂)₄ CH₃,NHCH₃], [ZA4143;S(O)₂(CH₂)₅CH₃, NHCH₃], [ZA4144;S(O)₂CH₂CH=CH₂,NHCH₃], [ZA4145;S(O)₂CH₂C≡CH,NHCH₃], [ZA4146;S(O)₂ CH₂C≡CCH₃,NHCH₃], [ZA4147;S(O)₂-c-Pr,NHCH₃], [ZA4148;S(O)₂-c-Bu,NHCH₃], [ZA4149;S(O)₂-c-Pen, NHCH₃], [ZA4150;S(O)₂-c-Hex,NHCH₃], [ZA4151; S(O)₂Ph,NHCH₃], [ZA4152;S(O)₂(2-Py),NHCH₃], [ZA4153;S(O)₂ (3-Py),NHCH₃], [ZA4154;S(O)₂(4-Py), NHCH₃], [ZA4155;S(O)₂CF₃,NHCH₃], [ZA4156;S(O)₂ CH₂Ph,NHCH₃], [ZA4157;S(O)₂CH₂(2-Py),NHCH₃], [ZA4158;S(O)₂ CH₂(3-Py),NHCH₃], [ZA4159;S(O)₂CH₂ (4-Py),NHCH₃], [ZA4160;S(O)₂CH₂ CN,NHCH₃], [ZA4161;S(O)₂CH₂NO₂,NHCH₃], [ZA4162;S(O)₂(CH₂)₂F, NHCH₃], [ZA4163;S(O)₂(CH₂)₂Cl,NHCH₃], [ZA4164;S (O)₂(CH₂)₂CF₃,NHCH₃], [ZA4165;S(O)₂ (CH₂)₂CN, NHCH₃], [ZA4166;S(O)₂(CH₂)₂NO₂,NHCH₃], [ZA4167;S (O)₂(CH₂)₂ Ph,NHCH₃], [ZA4168;S(O)₂(CH₂)₂OCH₃, NHCH₃], [ZA4169;S(O)₂(CH₂)₃F,NHCH₃], [ZA4170; S(O)₂(CH₂)₃Cl,NHCH₃], [ZA4171;S(O)₂(CH₂)₃CF₃, NHCH₃], [ZA4172;S(O)₂ (CH₂)₃CN,NHCH₃], [ZA4173;S (O)₂(CH₂)₃NO₂,NHCH₃], [ZA4174;S(O)₂(CH₂)₃ Ph,NHCH₃], [ZA4175;S(O)₂(CH₂)₃OCH₃,NHCH₃], [ZA4176;S(O)₂(CH₂)₄F,NHCH₃], [ZA4177;S(O)₂ (CH₂)₄Cl,NHCH₃], [ZA4178;S(O)₂(CH₂)₄CF₃,NHCH₃], [ZA4179;S(O)₂ (CH₂)₄CN,NHCH₃], [ZA4180;S(O)₂ (CH₂)₄NO₂,NHCH₃], [ZA4181;S(O)₂(CH₂)₄ Ph,NHCH₃], [ZA4182;S(O)₂(CH₂)₄OCH₃,NHCH₃], [ZA4183;S(O)₂ (CH₂)₅F,NHCH₃], [ZA4184;S(O)₂(CH₂)₅Cl,NHCH₃], [ZA4185;S(O)₂(CH₂)₅CF₃,NHCH₃], [ZA4186;S(O)₂ (CH₂)₅CN,NHCH₃], [ZA4187;S(O)₂(CH₂)₅NO₂,NHCH₃], [ZA4188;S(O)₂(CH₂)₅ Ph,NHCH₃], [ZA4189;S(O)₂ (CH₂)₅OCH₃,NHCH₃], [ZA4190;S(O)₂(CH₂)₆F,NHCH₃], [ZA4191;S(O)₂(CH₂)₆Cl,NHCH₃], [ZA4192;S(O)₂ (CH₂)₆CF₃,NHCH₃], [ZA4193;S(O)₂ (CH₂)₆CN,NHCH₃], [ZA4194;S(O)₂(CH₂)₆NO₂,NHCH₃], [ZA4195;S(O)₂ (CH₂)₆ Ph,NHCH₃], [ZA4196;S(O)₂(CH₂)₆OCH₃,NHCH₃], [ZA4197;S(O)CH₃,NHCH₃], [ZA4198;S(O)CH₂CH₃, NHCH₃], [ZA4199;S(O)CH(CH₃)₂,NHCH₃], [ZA4200;S (O)(CH₂)₂CH₃,NHCH₃], [ZA4201;S(O)(CH₂)₃CH₃, NHCH₃], [ZA4202;S(O)(CH₂)₄CH₃,NHCH₃], [ZA4203;S (O)(CH₂)₅CH₃,NHCH₃], [ZA4204;S(O)CH₂CH=CH₂, NHCH₃], [ZA4205;S(O)CH₂C≡CH,NHCH₃], [ZA4206;S (O)CH₂C≡CCH₃,NHCH₃], [ZA4207;S(O)c-Pr,NHCH₃], [ZA4208;S(O)c-Bu,NHCH₃], [ZA4209;S(O)c-Pen, NHCH₃], [ZA421;S(O)c-Hex,NHCH₃], [ZA4211;S(O)Ph, NHCH₃], [ZA4212;S(O)(2-Py),NHCH₃], [ZA4213;S(O)(3-Py),NHCH₃], [ZA4214;S(O)(4-Py),NHCH₃], [ZA4215;S (O)CF₃,NHCH₃], [ZA4216;S(O)CH₂ Ph,NHCH₃], [ZA4217;S(O)CH₂(2-Py),NHCH₃], [ZA4218;S(O)CH₂(3-Py),NHCH₃], [ZA4219;S(O)CH₂(4-Py),NHCH₃], [ZA4220;S(O)CH₂CN,NHCH₃], [ZA4221;S(O)CH₂NO₂, NHCH₃], [ZA4222;S(O)(CH₂)₂F,NHCH₃], [ZA4223;S(O) (CH₂)₂Cl,NHCH₃], [ZA4224;S(O)(CH₂)₂CF₃,NHCH₃], [ZA4225;S(O)(CH₂)₂CN,NHCH₃], [ZA4226;S(O)(CH₂)₂ NO₂,NHCH₃], [ZA4227;S(O)(CH₂)₂Ph,NHCH₃], [ZA4228;S(O)(CH₂)₂OCH₃,NHCH₃], [ZA4229;S(O) (CH₂)₃ F,NHCH₃], [ZA4230;S(O)(CH₂)₃Cl,NHCH₃], [ZA4231;S(O)(CH₂)₃CF₃,NHCH₃], [ZA4232;S(O)(CH₂)₃ CN,NHCH₃], [ZA4233;S(O)(CH₂)₃NO₂,NHCH₃], [ZA4234;S(O)(CH)₃Ph,NHCH₃], [ZA4235;S(O)(CH₂)₃ OCH₃,NHCH₃], [ZA4236;S(O)(CH₂)₄F,NHCH₃], [ZA4237;S(O)(CH₂)₄Cl,NHCH₃], [ZA4238;S(O)(CH₂)₄ CF₃,NHCH₃], [ZA4239;S(O)(CH₂)₄CN,NHCH₃], [ZA4240;S(O)(CH₂)₄NO₂,NHCH₃], [ZA4241;S(O)(CH₂)₄ Ph,NHCH₃], [ZA4242;S(O)(CH₂)₄OCH₃,NHCH₃], [ZA4243;S(O)(CH₂)₅F,NHCH₃], [ZA4244;S(O)(CH₂)₅Cl, NHCH₃], [ZA4245;S(O)(CH₂)₅CF₃,NHCH₃], [ZA4246;S (O)(CH₂)₅CN,NHCH₃], [ZA4247;S(O)(CH)₅NO₂, NHCH₃], [ZA4248;S(O)(CH₂)₅Ph,NHCH₃], [ZA4249;S(O) (CH₂)₅OCH₃,NHCH₃], [ZA4250;S(O)(CH₂)₆F,NHCH₃], [ZA4251;S(O)(CH₂)₆Cl,NHCH₃], [ZA4252;S(O)(CH₂)₆ CF₃,NHCH₃], [ZA4253;S(O)(CH₂)₆CN,NHCH₃], [ZA4254;S(O)(CH₂)₆NO₂,NHCH₃], [ZA4255;S(O)(CH₂)₆ Ph,NHCH₃], [ZA4256;S(O)(CH₂)₆OCH₃,NHCH₃], [ZA4257;OH,N(CH₃)₂], [ZA4258;OCH₃,N(CH₃)₂], [ZA4259;OCH₂CH₃,N(CH₃)₂], [ZA4260;OCH(CH₃)₂,N (CH₃)₂], [ZA4261;(CH₂)₂CH₃,N(CH₃)₂], [ZA4262;O(CH₂)₃ CH₃,N(CH₃)₂], [ZA4263;O(CH₂)₄CH₃,N(CH₃)₂], [ZA4264; O(CH)₅CH₃,N(CH₃)₂], [ZA4265;OCH₂CH=CH₂,N (CH₃)₂], [ZA4266;OCH₂C≡CH,N(CH₃)₂], [ZA4267;OCH₂ C≡CCH₃,N(CH₃)₂], [ZA4268;O-c-Pr,N(CH₃)₂], [ZA4269; O-c-Bu,N(CH₃)₂], [ZA4270;O-c-Pen,N(CH₃)₂], [ZA4271; O-c-Hex,N(CH₃)₂], [ZA4272;OPh,N(CH₃)₂], [ZA4273;O (2-Py),N(CH₃)₂], [ZA4274;O(3-Py),N(CH₃)₂], [ZA4275;O (4-Py),N(CH₃)₂], [ZA4276;OCF₃,N(CH₃)₂], [ZA4277; OCH₂Ph,N(CH₃)₂], [ZA4278;OCH₂(2-Py),N(CH₃)₂], [ZA4279;OCH₂(3-Py),N(CH₃)₂], [ZA4280;OCH₂(4-Py),N (CH)₂], [ZA4281;OCH₂ CN,N(CH₃)₂], [ZA4282; OCH₂NO₂,N(CH)₂], [ZA4283;O(CH₂)₂F,N(CH₃)₂], [ZA4284;O(CH₂)₂C,N(CH)₂], [ZA4285;O(CH₂)₂Br,N (CH)₂], [ZA4286;O(CH₂)₂ I,N(CH₃)₂], [ZA4287;O (CH₂)₂CF₃,N(CH₃)₂], [ZA4288;O(CH₂)₂CN,N(CH₃)₂], [ZA4289;O(CH₂)₂NO₂,N(CH₃)₂], [ZA4290;O(CH₂)₂Ph,N (CH₃)₂], [ZA4291;(CH₂)₂ (2-Py),N(CH₃)₂], [ZA4292;O (CH)₂(3-Py),N(CH₃)₂], [ZA4293;O(CH₂)₂(4-Py), N(CH₃)₂], [ZA4294;O(CH₂)₂OH,N(CH₃)₂], [ZA4295;O (CH₂)₂OCH₃,N(CH)₂], [ZA4296;O(CH₂)₂SH,N(CH)₂], [ZA4297;O(CH₂)₂SCH₃,N(CH)₂], [ZA4298;O(CH₂)₂NH₂, N(CH₃)₂], [ZA4299;O(CH₂)₂NHCH₃,N(CH₃)₂], [ZA4300; O(CH₂)₂N(CH₃)₂,N(CH)₂], [ZA4301;(CH₂)₂NHPh,N (CH₃)₂], [ZA4302;O(CH₂)₂NHCH₂Ph,N(CH₃)₂], [ZA4303; O(CH₂)₂N(CH₃)CH₂Ph,N(CH₃)₂], [ZA4304;O(CH₂)₂S(O) CH₃,N(CH₃)₂], [ZA4305;O(CH₂)₂ S(O)CH₂CH₃,N(CH₃)₂], [ZA4306;O(CH₂)₂S(O)Ph,N(CH₃)₂], [ZA4307;O(CH₂)₂S (O)₂ CH₃,N(CH₃)₂], [ZA4308;O(CH₂)₂S(O)₂CH₂CH₃,N (CH₃)₂], [ZA4309;O(CH₂)₂S(O)₂ Ph,N(CH₃)₂], [ZA4310; (CH₂)₂C(O)CH₃,N(CH₃)₂], [ZA4311;O(CH₂)₂C(O)

CH₂CH₃,N(CH₃)₂], [ZA4312;O(CH₂)₂C(O)Ph,N(CH₃)₂], [ZA4313;O(CH₂)₂C(S)CH₃,N(CH₃)₂], [ZA4314;O(CH₂)₂C(S)CH₂CH₃,N(CH)₂], [ZA4315;O(CH₂)₂C(S)Ph,N(CH₃)₂], [ZA4316;O(CH₂)₂S(O)₂NHCH₃,N(CH₃)₂], [ZA4317;O(CH₂)₂S(O)₂N(CH₃)₂,N(CH₃)₂], [ZA4318;O(CH₂)₂S(O)₂NHPh,N(CH₃)₂], [ZA4319;O(CH₂)₂S(O)₂N(CH₃)Ph,N(CH₃)₂], [ZA4320;O(CH₂)₂C(O)NH₂,N(CH₃)₂], [ZA4321;(CH₂)₂C(O)NHCH₃,N(CH₃)₂], [ZA4322;O(CH₂)₂C(O)N(CH₃)₂,N(CH₃)₂], [ZA4323;O(CH₂)₂C(O)NHPh,N(CH₃)₂], [ZA4324;O(CH₂)₂C(O)N(CH₃)Ph,N(CH₃)₂], [ZA4325;O(CH₂)₂C(O)OCH₃,N(CH)₂], [ZA4326;O(CH₂)₂C(O)OCH₂CH₃,N(CH)₂], [ZA4327;O(CH₂)₂NHC(O)CH₃,N(CH₃)₂], [ZA4328;O(CH₂)₂NHC(O)CH₂CH₃,N(CH)₂], [ZA4329;O(CH₂)₂NHC(O)Ph,N(CH₃)₂], [ZA4330;O(CH₂)₂NCH₃C(O)CH₃,N(CH)₂], [ZA4331;(CH₂)₂NCH₃C(O)CH₂CH₃,N(CH)₂], [ZA4332;O(CH₂)₂NCH₃C(O)Ph,N(CH₃)₂], [ZA4333;O(CH₂)₂NHC(O)OCH₃,N(CH)₂], [ZA4334;O(CH₂)₂NHC(O)OCH₂CH₃,N(CH)₂], [ZA4335;O(CH₂)₂NHC(O)OPh,N(CH₃)₂], [ZA4336;O(CH₂)₂NCH₃C(O)OCH₃,N(CH₃)₂], [ZA4337;O(CH₂)₂NCH₃C(O)OCH₂CH₃,N(CH)₂], [ZA4338;(CH₂)₂NCH₃C(O)OPh,N(CH)₂], [ZA4339;O(CH₂)₂NHC(O)NHCH₃,N(CH₃)₂], [ZA4340;O(CH₂)₂NHC(O)NHCH₂CH₃,N(CH₃)₂], [ZA4341;(CH₂)₂NHC(O)NHPh,N(CH₃)₂], [ZA4342;O(CH₂)₂NHC(O)N(CH₃)₂,N(CH₃)₂], [ZA4343;O(CH₂)₂NHC(O)N(CH₃)CH₂CH₃,N(CH)₂], [ZA4344;O(CH₂)₂NHC(O)N(CH₃)Ph,N(CH₃)₂], [ZA4345;O(CH₂)₂NHC(O)N(CH₂CH₃)₂,N(CH₃)₂], [ZA4346;O(CH₂)₂NCH₃C(O)NHCH₃,N(CH₃)₂], [ZA4347;O(CH₂)₂NCH₃C(O)NHCH₂CH₃,N(CH)₂], [ZA4348;O(CH₂)₂NCH₃C(O)NHPh,N(CH)₂], [ZA4349;O(CH₂)₂NCH₃C(O)N(CH₃)₂,N(CH₃)₂], [ZA4350;O(CH₂)₂NCH₃C(O)N(CH₃)CH₂CH₃,N(CH)₂], [ZA4351;(CH₂)₂NCH₃C(O)N(CH₃)Ph,N(CH₃)₂], [ZA4352;O(CH)₂NCH₃C(O)N(CH₂CH₃)₂,N(CH₃)₂], [ZA4353;(CH₂)₂OC(O)CH₃,N(CH₃)₂], [ZA4354;O(CH₂)₂OC(O)CH₂CH₃,N(CH₃)₂], [ZA4355;(CH₂)₂OC(O)Ph,N(CH₃)₂], [ZA4356;(CH₂)₂OC(O)OCH₃,N(CH₃)₂], [ZA4357;O(CH₂)₂OC(O)OCH₂CH₃,N(CH₃)₂], [ZA4358;(CH₂)₂OC(O)OPh,N(CH₃)₂], [ZA4359;O(CH₂)₂OC(O)NHCH₃,N(CH)₂], [ZA4360;O(CH₂)₂OC(O)NHCH₂CH₃,N(CH₃)₂], [ZA4361;(CH₂)₂OC(O)NHPh,N(CH₃)₂], [ZA4362;O(CH₂)₂OC(O)N(CH₃)₂,N(CH₃)₂], [ZA4363;O(CH₂)₂OC(O)N(CH₃)CH₂CH₃,N(CH₃)₂], [ZA4364;O(CH₂)₂OC(O)N(CH₃)Ph,N(CH)₂], [ZA4365;O(CH₂)₂OC(O)N(CH₂CH₃)₂,N(CH)₂], [ZA4366;O(CH₂)₂SC(O)CH₃,N(CH)₂], [ZA4367;O(CH₂)₂SC(O)CH₂CH₃,N(CH₃)₂], [ZA4368;O(CH₂)₂SC(O)Ph,N(CH)₂], [ZA4369;O(CH₂)₂SC(O)OCH₃,N(CH₃)₂], [ZA4370;O(CH₂)₂SC(O)OCH₂CH₃,N(CH)₂], [ZA4371;(CH₂)₂SC(O)OPh,N(CH₃)₂], [ZA4372;O(CH₂)₂S(O)₂NHCH₃,N(CH₃)₂], [ZA4373;O(CH₂)₂S(O)₂NHCH₂CH₃,N(CH)₂], [ZA4374;O(CH₂)₂S(O)₂NHPh,N(CH₃)₂], [ZA4375;O(CH₂)₂S(O)₂N(CH₃)₂,N(CH)₂], [ZA4376;O(CH₂)₂S(O)₂N(CH₃)CH₂CH₃,N(CH₃)₂], [ZA4377;O(CH₂)₂S(O)₂N(CH₃)Ph,N(CH₃)₂], [ZA4378;(CH₂)₂S(O)₂N(CH₂CH₃)₂,N(CH₃)₂], [ZA4379;O(CH₂)₃F,N(CH₃)₂], [ZA4380;O(CH₂)₃Cl,N(CH₃)₂], [ZA4381;O(CH₂)₃Br,N(CH₃)₂], [ZA4382;O(CH₂)₃,N(CH)₂], [ZA4383;O(CH₂)₃CF₃,N(CH₃)₂], [ZA4384;O(CH₂)₃CN,N(CH₃)₂], [ZA4385;O(CH₂)₃NO₂,N(CH₃)₂], [ZA4386;O(CH₂)₃Ph,N(CH₃)₂], [ZA4387;O(CH₂)₃(2-Py),N(CH₃)₂], [ZA4388;O(CH₂)₃(3-Py),N(CH₃)₂], [ZA4389;O(CH₂)₃(4-Py),N(CH₃)₂], [ZA4390;O(CH₂)₃OH,N(CH₃)₂], [ZA4391;(CH₂)₃OCH₃,N(CH₃)₂], [ZA4392;O(CH₂)₃OCH₂CH₃,N(CH₃)₂], [ZA4393;O(CH₂)₃SH,N(CH)₂], [ZA4394;O(CH₂)₃SCH₃,N(CH₃)₂], [ZA4395;O(CH₂)₃SCH₂CH₃,N(CH₃)₂], [ZA4396;O(CH₂)₃NH₂,N(CH)₂], [ZA4397;O(CH₂)₃NHCH₃,N(CH₃)₂], [ZA4398;O(CH₂)₃N(CH₃)₂,N(CH)₂], [ZA4399;O(CH₂)₄F,N(CH₃)₂], [ZA4400;O(CH₂)₄Cl,N(CH₃)₂], [ZA4401;(CH₂)₄CF₃,N(CH)₂], [ZA4402;O(CH₂)₄CN,N(CH₃)₂], [ZA4403;O(CH₂)₄NO₂,N(CH₃)₂], [ZA4404;O(CH₂)₄Ph,N(CH)₂], [ZA4405;O(CH₂)₄OH,N(CH₃)₂], [ZA4406;O(CH₂)₄OCH₃,N(CH₃)₂], [ZA4407;O(CH₂)₄SH,N(CH₃)₂], [ZA4408;O(CH₂)₄SCH₃,N(CH)₂], [ZA4409;O(CH₂)₄NH₂,N(CH₃)₂], [ZA4410;(CH₂)₄NHCH₃,N(CH₃)₂], [ZA4411;O(CH₂)₄N(CH₃)₂,N(CH)₂], [ZA4412;O(CH₂)₅F,N(CH₃)₂], [ZA4413;O(CH₂)₅Cl,N(CH₃)₂], [ZA4414;O(CH₂)₅CF₃,N(CH₃)₂], [ZA4415;O(CH₂)₅CN,N(CH₃)₂], [ZA4416;O(CH₂)₅NO₂,N(CH)₂], [ZA4417;O(CH₂)₅Ph,N(CH)₂], [ZA4418;O(CH₂)₅OH,N(CH₃)₂], [ZA4419;O(CH₂)₅OCH₃,N(CH₃)₂], [ZA4420;O(CH₂)₅SH,N(CH₃)₂], [ZA4421;(CH₂)₅SCH₃,N(CH)₂], [ZA4422;O(CH₂)₅NH₂,N(CH)₂], [ZA4423;O(CH₂)₅NHCH₃,N(CH₃)₂], [ZA4424;O(CH₂)₅N(CH₃)₂,N(CH)₂], [ZA4425;O(CH₂)₆F,N(CH)₂], [ZA4426;O(CH₂)₆C,N(CH)₂], [ZA4427;O(CH₂)₆CF₃,N(CH₃)₂], [ZA4428;O(CH₂)₆CN,N(CH)₂], [ZA4429;O(CH₂)₆NO₂,N(CH)₂], [ZA4430;O(CH₂)₆Ph,N(CH₃)₂], [ZA4431;(CH₂)₆OH,N(CH₃)₂], [ZA4432;O(CH₂)₆OCH₃,N(CH)₂], [ZA4433;O(CH₂)₆SH,N(CH₃)₂], [ZA4434;O(CH₂)₆SCH₃,N(CH₃)₂], [ZA4435;O(CH₂)₆NH₂,N(CH₃)₂], [ZA4436;O(CH₂)₆NHCH₃,N(CH₃)₂], [ZA4437;O(CH₂)₆N(CH₃)₂,N(CH)₂], [ZA4438;OC(O)CH₃,N(CH)₂], [ZA4439;OC(O)CH₂CH₃,N(CH)₂], [ZA4440;OC(O)CH(CH)₂,N(CH)₂], [ZA4441;OC(O)(CH₂)₂CH₃,N(CH)₂], [ZA4442;OC(O)(CH₂)₃CH₃,N(CH₃)₂], [ZA4443;OC(O)(CH₂)₄CH₃,N(CH₃)₂], [ZA4444;OC(O)(CH₂)₅CH₃,N(CH₃)₂], [ZA4445;OC(O)CH₂CH=CH₂,N(CH₃)₂], [ZA4446;OC(O)CH₂C≡CH,N(CH₃)₂], [ZA4447;OC(O)CH₂C≡CCH₃,N(CH₃)₂], [ZA4448;OC(O)c-Pr,N(CH₃)₂], [ZA4449;OC(O)c-Bu,N(CH₃)₂], [ZA4450;OC(O)c-Pen,N(CH₃)₂], [ZA4451;OC(O)c-Hex,N(CH₃)₂], [ZA4452;OC(O)Ph,N(CH₃)₂], [ZA4453;OC(O)(2-Py),N(CH₃)₂], [ZA4454;OC(O)(3-Py),N(CH₃)₂], [ZA4455;OC(O)(4-Py),N(CH₃)₂], [ZA4456;OC(O)CF₃,N(CH₃)₂], [ZA4457;OC(O)CH₂Ph,N(CH₃)₂], [ZA4458;OC(O)CH₂(2-Py),N(CH₃)₂], [ZA4459;OC(O)CH₂(3-Py),N(CH₃)₂], [ZA4460;OC(O)CH₂(4-Py),N(CH₃)₂], [ZA4461;OC(O)CH₂CN,N(CH₃)₂], [ZA4462;OC(O)CH₂NO₂,N(CH₃)₂], [ZA4463;OC(O)(CH₂)₂F,N(CH₃)₂], [ZA4464;OC(O)(CH₂)₂Cl,N(CH₃)₂], [ZA4465;OC(O)(CH₂)₂CF₃,N(CH₃)₂], [ZA4466;OC(O)(CH₂)₂CN,N(CH₃)₂], [ZA4467;OC(O)(CH₂)₂NO₂,N(CH₃)₂], [ZA4468;OC(O)(CH₂)₂Ph,N(CH₃)₂], [ZA4469;OC(O)(CH₂)₂OCH₃,N(CH₃)₂], [ZA4470;OC(O)(CH₂)₃F,N(CH₃)₂], [ZA4471;OC(O)(CH₂)₃Cl,N(CH₃)₂], [ZA4472;OC(O)(CH₂)₃CF₃,N(CH₃)₂], [ZA4473;OC(O)(CH₂)₃CN,N(CH₃)₂], [ZA4474;OC(O)(CH₂)₃NO₂,N(CH₃)₂], [ZA4475;OC(O)(CH₂)₃Ph,N(CH₃)₂], [ZA4476;OC(O)(CH₂)₃OCH₃,N(CH₃)₂], [ZA4477;OC(O)(CH₂)₄F,N(CH₃)₂], [ZA4478;OC(O)(CH₂)₄Cl,N(CH₃)₂], [ZA4479;OC(O)(CH₂)₄CF₃,N(CH₃)₂], [ZA4480;OC(O)(CH₂)₄CN,N(CH₃)₂], [ZA4481;OC(O)(CH₂)₄NO₂,N(CH₃)₂], [ZA4482;OC(O)(CH₂)₄Ph,N(CH₃)₂], [ZA4483;OC(O)(CH₂)₄OCH₃,N(CH₃)₂], [ZA4484;OC(O)(CH₂)₅F,N(CH₃)₂], [ZA4485;OC(O)(CH₂)₅Cl,N(CH₃)₂], [ZA4486;OC(O)(CH₂)₅CF₃,N(CH₃)₂], [ZA4487;OC(O)(CH₂)₅CN,N(CH₃)₂], [ZA4488;OC(O)(CH₂)₅NO₂,N(CH₃)₂], [ZA4489;OC(O)(CH₂)₅Ph,N(CH₃)₂], [ZA4490;OC(O)(CH₂)₅OCH₃,N(CH₃)₂], [ZA4491;OC(O)(CH₂)₆F,N(CH₃)₂], [ZA4492;OC(O)(CH₂)₆Cl,N(CH₃)₂], [ZA4493;OC(O)(CH₂)₆CF₃,N(CH₃)₂], [ZA4494;OC(O)(CH₂)₆CN,N(CH₃)₂], [ZA4495;OC(O)(CH₂)₆NO₂,N(CH₃)₂], [ZA4496;OC(O)(CH₂)₆Ph,N(CH₃)₂], [ZA4497;OC(O)(CH₂)₆OCH₃,N(CH₃)₂], [ZA4498;OC(O)NH₂,N(CH₃)₂], [ZA4499;OC(O)NHCH₃,N(CH₃)₂], [ZA4500;OC(O)NHCH₂CH₃,N(CH₃)₂],

[ZA4501;OC(O)NH(CH₂)₂CH₃,N(CH₃)₂], [ZA4502;OC(O)NH(CH₂)₃CH₃,N(CH₃)₂], [ZA4503;OC(O)NH(CH₂)₄CH₃,N(CH₃)₂], [ZA4504;OC(O)NH(CH₂)₅CH₃,N(CH₃)₂], [ZA4505;OC(O)NHCH(CH₃)₂,N(CH₃)₂], [ZA4506;OC(O)NHCH₂F,N(CH₃)₂], [ZA4507;OC(O)NHCH₂Cl,N(CH₃)₂], [ZA4508;OC(O)NHCH₂CN,N(CH₃)₂], [ZA4509;OC(O)NHCH₂OCH₃,N(CH₃)₂], [ZA4510;OC(O)NHCH₂Ph,N(CH₃)₂], [ZA4511;OC(O)NH(CH₂)₂F,N(CH₃)₂], [ZA4512;OC(O)NH(CH₂)₂Cl,N(CH₃)₂], [ZA4513;OC(O)NH(CH₂)₂CN,N(CH₃)₂], [ZA4514;OC(O)NH(CH₂)₂OCH₃,N(CH₃)₂], [ZA4515;OC(O)NH(CH₂)₂Ph,N(CH₃)₂], [ZA4516;OC(O)NH(CH₂)₃F,N(CH₃)₂], [ZA4517;OC(O)NH(CH₂)₃Cl,N(CH₃)₂], [ZA4518;OC(O)NH(CH₂)₃CN,N(CH₃)₂], [ZA4519;OC(O)NH(CH₂)₃OCH₃,N(CH₃)₂], [ZA4520;OC(O)NH(CH₂)₃Ph,N(CH₃)₂], [ZA4521;OC(O)NH(CH₂)₄F,N(CH₃)₂], [ZA4522;OC(O)NH(CH₂)₄Cl,N(CH₃)₂], [ZA4523;OC(O)NH(CH₂)₄CN,N(CH₃)₂], [ZA4524;OC(O)NH(CH₂)₄OCH₃,N(CH₃)₂], [ZA4525;OC(O)NH(CH₂)₄Ph,N(CH₃)₂], [ZA4526;OC(O)NHPh,N(CH₃)₂], [ZA4527;OC(O)NH(2-Py),N(CH₃)₂], [ZA4528;OC(O)NH(3-Py),N(CH₃)₂], [ZA4529;OC(O)NH(4-Py),N(CH₃)₂], [ZA4530;OC(O)N(CH₃)₂,N(CH₃)₂], [ZA4531;OC(O)N(CH₃)CH₂CH₃,N(CH₃)₂], [ZA4532;OC(O)N(CH₃)(CH₂)₂CH₃,N(CH₃)₂], [ZA4533;OC(O)N(CH₃)(CH₂)₃CH₃,N(CH₃)₂], [ZA4534;OC(O)N(CH₃)(CH₂)₄CH₃,N(CH₃)₂], [ZA4535;OC(O)N(CH₃)(CH₂)₅CH₃,N(CH₃)₂], [ZA4536;OC(O)N(CH₃)CH(CH₃)₂,N(CH₃)₂], [ZA4537;OC(O)N(CH₃)CH₂F,N(CH₃)₂], [ZA4538;OC(O)N(CH₃)CH₂Cl,N(CH)₂], [ZA4539;OC(O)N(CH₃)CH₂CN,N(CH₃)₂], [ZA4540;OC(O)N(CH₃)CH₂OCH₃,N(CH)₂], [ZA4541;OC(O)N(CH₃)CH₂Ph,N(CH₃)₂], [ZA4542;OC(O)N(CH₃)(CH₂)₂F,N(CH₃)₂], [ZA4543;OC(O)N(CH₃)(CH₂)₂Cl,N(CH₃)₂], [ZA4544;OC(O)N(CH₃)(CH₂)₂CN,N(CH₃)₂], [ZA4545;OC(O)N(CH₃)(CH₂)₂OCH₃,N(CH₃)₂], [ZA4546;OC(O)N(CH₃)(CH₂)₂Ph,N(CH₃)₂], [ZA4547;OC(O)N(CH₃)(CH₂)₃F,N(CH₃)₂], [ZA4548;OC(O)N(CH₃)(CH₂)₃Cl,N(CH₃)₂], [ZA4549;OC(O)N(CH₃)(CH₂)₃CN,N(CH₃)₂], [ZA4550;OC(O)N(CH₃)(CH₂)₃OCH₃,N(CH₃)₂], [ZA4551;OC(O)N(CH₃)(CH₂)₃Ph,N(CH₃)₂], [ZA4552;OC(O)N(CH₃)(CH₂)₄F,N(CH₃)₂], [ZA4553;OC(O)N(CH₃)(CH₂)₄Cl,N(CH)₂], [ZA4554;OC(O)N(CH₃)(CH₂)₄CN,N(CH₃)₂], [ZA4555;OC(O)N(CH₃)(CH₂)₄OCH₃,N(CH₃)₂], [ZA4556;OC(O)N(CH₃)(CH₂)₄Ph,N(CH₃)₂], [ZA4557;OC(O)N(CH₃)Ph,N(CH₃)₂], [ZA4558;OC(O)N(CH₃)(2-Py),N(CH₃)₂], [ZA4559;OC(O)N(CH₃)(3-Py),N(CH₃)₂], [ZA4560;OC(O)N(CH₃)(4-Py),N(CH₃)₂], [ZA4561;OC(O)N(CH₂CH₃)₂,N(CH)₂], [ZA4562;OC(O)(Pyr),N(CH₃)₂], [ZA4563;OC(O)(Pip),N(CH₃)₂], [ZA4564;OC(O)(Mor),N(CH₃)₂], [ZA4565;OC(O)OCH₃,N(CH₃)₂], [ZA4566;OC(O)OCH₂CH₃,N(CH₃)₂], [ZA4567;OC(O)OCH(CH₃)₂,N(CH₃)₂], [ZA4568;OC(O)O(CH₂)₂CH₃,N(CH₃)₂], [ZA4569;OC(O)O(CH₂)₃CH₃,N(CH)₂], [ZA4570;OC(O)O(CH₂)₄CH₃,N(CH₃)₂], [ZA4571;OC(O)O(CH₂)₅CH₃,N(CH₃)₂], [ZA4572;OC(O)OCH₂CH=CH₂,N(CH₃)₂], [ZA4573;OC(O)OCH₂C≡CH,N(CH₃)₂], [ZA4574;OC(O)OCH₂C≡CCH₃,N(CH₃)₂], [ZA4575;OC(O)O-c-Pr,N(CH₃)₂], [ZA4576;OC(O)O-c-Bu,N(CH₃)₂], [ZA4577;OC(O)O-c-Pen,N(CH₃)₂], [ZA4578;OC(O)O-c-Hex,N(CH₃)₂], [ZA4579;OC(O)OPh,N(CH₃)₂], [ZA4580;OC(O)O(2-Py),N(CH₃)₂], [ZA4581;OC(O)O(3-Py),N(CH₃)₂], [ZA4582;OC(O)O(4-Py),N(CH₃)₂], [ZA4583;OC(O)OCF₃,N(CH₃)₂], [ZA4584;OC(O)OCH₂Ph,N(CH)₂], [ZA4585;OC(O)OCH₂(2-Py),N(CH₃)₂], [ZA4586;OC(O)OCH₂(3-Py),N(CH₃)₂], [ZA4587;OC(O)OCH₂(4-Py),N(CH₃)₂], [ZA4588;OC(O)OCH₂CN,N(CH₃)₂], [ZA4589;OC(O)OCH₂NO₂,N(CH₃)₂], [ZA4590;OC(O)O(CH₂)₂F,N(CH₃)₂], [ZA4591;OC(O)O(CH₂)₂Cl,N(CH)₂], [ZA4592;OC(O)O(CH₂)₂CF₃,N(CH)₂], [ZA4593;OC(O)O(CH₂)₂CN,N(CH₃)₂], [ZA4594;OC(O)O(CH₂)₂NO₂,N(CH₃)₂], [ZA4595;OC(O)O(CH₂)₂Ph,N(CH₃)₂], [ZA4596;OC(O)O(CH₂)₂OCH₃,N(CH₃)₂], [ZA4597;OC(O)O(CH₂)₃F,N(CH)₂], [ZA4598;OC(O)O(CH₂)₃Cl,N(CH₃)₂], [ZA4599;OC(O)O(CH₂)₃CF₃,N(CH)₂], [ZA4600;OC(O)O(CH₂)₃CN,N(CH₃)₂], [ZA4601;OC(O)O(CH₂)₃NO₂,N(CH)₂], [ZA4602;OC(O)O(CH₂)₃Ph,N(CH)₂], [ZA4603;OC(O)O(CH₂)₃OCH₃,N(CH)₂], [ZA4604;OC(O)O(CH₂)₄F,N(CH)₂], [ZA4605;OC(O)O(CH₂)₄Cl,N(CH₃)₂], [ZA4606;OC(O)O(CH₂)₄CF₃,N(CH₃)₂], [ZA4607;OC(O)O(CH₂)₄CN,N(CH)₂], [ZA4608;OC(O)O(CH₂)₄NO₂,N(CH₃)₂], [ZA4609;OC(O)O(CH₂)₄Ph,N(CH₃)₂], [ZA461;OC(O)O(CH₂)₄OCH₃,N(CH₃)₂], [ZA4611;OC(O)O(CH₂)₅F,N(CH₃)₂], [ZA4612;OC(O)O(CH₂)₅Cl,N(CH)₂], [ZA4613;OC(O)O(CH₂)₅CF₃,N(CH)₂], [ZA4614;OC(O)O(CH₂)₅CN,N(CH₃)₂], [ZA4615;OC(O)O(CH₂)₅NO₂,N(CH₃)₂], [ZA4616;OC(O)O(CH₂)₅Ph,N(CH₃)₂], [ZA4617;OC(O)O(CH₂)₅OCH₃,N(CH₃)₂], [ZA4618;OC(O)O(CH₂)₆F,N(CH₃)₂], [ZA4619;OC(O)O(CH₂)₆Cl,N(CH)₂], [ZA4620;OC(O)O(CH₂)₆CF₃,N(CH₃)₂], [ZA4621;OC(O)O(CH₂)₆CN,N(CH₃)₂], [ZA4622;OC(O)O(CH₂)₆NO₂,N(CH₃)₂], [ZA4623;OC(O)O(CH₂)₆Ph,N(CH₃)₂], [ZA4624;OC(O)O(CH₂)₆OCH₃,N(CH₃)₂], [ZA4625;OS(O)₂CH₃,N(CH₃)₂], [ZA4626;OS(O)₂CH₂CH₃,N(CH₃)₂], [ZA4627;OS(O)₂CH(CH₃)₂,N(CH₃)₂], [ZA4628;OS(O)₂(CH₂)₂CH₃,N(CH₃)₂], [ZA4629;OS(O)₂(CH₂)₃CH₃,N(CH₃)₂], [ZA4630;OS(O)₂(CH₂)₄CH₃,N(CH₃)₂], [ZA4631;OS(O)₂(CH₂)₅CH₃,N(CH)₂], [ZA4632;OS(O)₂CH₂CH=CH₂,N(CH)₂], [ZA4633;OS(O)₂CH₂C≡CH,N(CH₃)₂], [ZA4634;OS(O)₂CH₂C≡CCH₃,N(CH₃)₂], [ZA4635;OS(O)₂-c-Pr,N(CH₃)₂], [ZA4636;OS(O)₂-c-Bu,N(CH₃)₂], [ZA4637;OS(O)₂-c-Pen,N(CH₃)₂], [ZA4638;OS(O)₂-c-Hex,N(CH₃)₂], [ZA4639;OS(O)₂Ph,N(CH₃)₂], [ZA4640;OS(O)₂(2-Py),N(CH₃)₂], [ZA4641;OS(O)₂(3-Py),N(CH₃)₂], [ZA4642;OS(O)₂(4-Py),N(CH₃)₂], [ZA4643;OS(O)₂CF₃,N(CH)₂], [ZA4644;OS(O)₂CH₂Ph,N(CH₃)₂], [ZA4645;OS(O)₂CH₂(2-Py),N(CH₃)₂], [ZA4646;OS(O)₂CH₂(3-Py),N(CH₃)₂], [ZA4647;OS(O)₂CH₂(4-Py),N(CH₃)₂], [ZA4648;OS(O)₂CH₂CN,N(CH)₂], [ZA4649;OS(O)₂CH₂NO₂,N(CH)₂], [ZA4650;OS(O)₂(CH₂)₂F,N(CH)₂], [ZA4651;OS(O)₂(CH₂)₂Cl,N(CH)₂], [ZA4652;OS(O)₂(CH₂)₂CF₃,N(CH₃)₂], [ZA4653;OS(O)₂(CH₂)₂CN,N(CH₃)₂], [ZA4654;OS(O)₂(CH₂)₂NO₂,N(CH₃)₂], [ZA4655;OS(O)₂(CH₂)₂Ph,N(CH₃)₂], [ZA4656;OS(O)₂(CH₂)₂OCH₃,N(CH₃)₂], [ZA4657;OS(O)₂(CH₂)₃F,N(CH₃)₂], [ZA4658;OS(O)₂(CH₂)₃Cl,N(CH)₂], [ZA4659;OS(O)₂(CH₂)₃CF₃,N(CH₃)₂], [ZA4660;OS(O)₂(CH₂)₃CN,N(CH)₂], [ZA4661;OS(O)₂(CH₂)₃NO₂,N(CH₃)₂], [ZA4662;OS(O)₂(CH₂)₃Ph,N(CH₃)₂], [ZA4663;OS(O)₂(CH₂)₃OCH₃,N(CH₃)₂], [ZA4664;OS(O)₂(CH₂)₄F,N(CH₃)₂], [ZA4665;OS(O)₂(CH₂)₄Cl,N(CH)₂], [ZA4666;OS(O)₂(CH₂)₄CF₃,N(CH₃)₂], [ZA4667;OS(O)₂(CH₂)₄CN,N(CH₃)₂], [ZA4668;OS(O)₂(CH₂)₄NO₂,N(CH₃)₂], [ZA4669;OS(O)₂(CH₂)₄Ph,N(CH₃)₂], [ZA4670;OS(O)₂(CH₂)₄OCH₃,N(CH₃)₂], [ZA4671;OS(O)₂(CH₂)₅F,N(CH₃)₂], [ZA4672;OS(O)₂(CH₂)₅Cl,N(CH)₂], [ZA4673;OS(O)₂(CH₂)₅CF₃,N(CH₃)₂], [ZA4674;OS(O)₂(CH₂)₅CN,N(CH)₂], [ZA4675;OS(O)₂(CH₂)₅N₂,N(CH)₂], [ZA4676;OS(O)₂(CH₂)₅Ph,N(CH)₂], [ZA4677;OS(O)₂(CH₂)₅OCH₃,N(CH)₂], [ZA4678;OS(O)₂(CH₂)₆F,N(CH₃)₂], [ZA4679;OS(O)₂(CH₂)₆Cl,N(CH₃)₂], [ZA4680;OS(O)₂(CH₂)₆CF₃,N(CH)₂], [ZA4681;OS(O)₂(CH₂)₆CN,N(CH₃)₂], [ZA4682;OS(O)₂(CH₂)₆NO₂,N(CH₃)₂], [ZA4683;OS(O)₂(CH₂)₆Ph,N(CH₃)₂], [ZA4684;OS(O)₂(CH₂)₆OCH₃,N(CH₃)₂], [ZA4685;NH₂,N(CH₃)₂], [ZA4686;NHCH₃,N(CH₃)₂], [ZA4687;NHCH₂CH₃,N(CH)₂], [ZA4688;NH(CH₂)₂CH₃,N(CH)₂], [ZA4689;NH (CH$_2$)$_3$CH$_3$,N(CH$_3$)$_2$], [ZA4690;NH(CH$_2$)$_4$CH$_3$,N(CH$_3$)$_2$], [ZA4691;NH(CH$_2$)$_5$CH$_3$,N(CH$_3$)$_2$], [ZA4692;NHCH(CH$_3$)$_2$,N(CH$_3$)$_2$], [ZA4693;NHCH$_2$F,N(CH$_3$)$_2$], [ZA4694;NHCH$_2$ CN,N(CH$_3$)$_2$], [ZA4695;NHCH$_2$OCH$_3$,N(CH$_3$)$_2$], [ZA4696;NHCH$_2$Ph,N(CH$_3$)$_2$], [ZA4697;NH(CH$_2$)$_2$F,N(CH$_3$)$_2$], [ZA4698;NH(CH$_2$)$_2$CN,N(CH$_3$)$_2$], [ZA4699;NH(CH$_2$)$_2$ OCH$_3$,N(CH$_3$)$_2$], [ZA4700;NH(CH$_2$)$_2$Ph,N(CH$_3$)$_2$], [ZA4701;NH(CH$_2$)$_3$F,N(CH$_3$)$_2$], [ZA4702;NH(CH$_2$)$_3$Cl,N(CH)$_2$], [ZA4703;NH(CH$_2$)$_3$CN,N(CH$_3$)$_2$], [ZA4704;NH(CH$_2$)$_3$OCH$_3$,N(CH$_3$)$_2$], [ZA4705;NH(CH$_2$)$_3$Ph,N(CH$_3$)$_2$], [ZA4706;NH(CH$_2$)$_4$F,N(CH$_3$)$_2$], [ZA4707;NH(CH$_2$)$_4$CN,N(CH$_3$)$_2$], [ZA4708;NH(CH$_2$)$_4$OCH$_3$,N(CH$_3$)$_2$], [ZA4709;NH(CH$_2$)$_4$Ph,N(CH$_3$)$_2$], [ZA471;NHPh,N(CH$_3$)$_2$], [ZA4711;NH(2-Py),N(CH$_3$)$_2$], [ZA4712;NH(3-Py),N(CH$_3$)$_2$], [ZA4713;NH(4-Py),N(CH$_3$)$_2$], [ZA4714;N(CH$_3$)$_2$,N(CH$_3$)$_2$], [ZA4715;N(CH$_3$)CH$_2$CH$_3$,N(CH$_3$)$_2$], [ZA4716;N(CH$_3$)(CH$_2$)$_2$CH$_3$,N(CH$_3$)$_2$], [ZA4717;N(CH$_3$)(CH$_2$)$_3$CH$_3$,N(CH$_3$)$_2$], [ZA4718;(CH$_3$)(CH$_2$)$_4$CH$_3$,N(CH$_3$)$_2$], [ZA4719;(CH$_3$)(CH$_2$)$_5$CH$_3$,N(CH$_3$)$_2$], [ZA4720;N(CH$_3$)CH(CH$_3$)$_2$,N(CH)$_2$], [ZA4721;N(CH$_3$)CH$_2$F,N(CH)$_2$], [ZA4722;N(CH$_3$)CH$_2$CN,N(CH$_3$)$_2$], [ZA4723;N(CH$_3$)CH$_2$OCH$_3$,N(CH$_3$)$_2$], [ZA4724;N(CH$_3$)CH$_2$Ph,N(CH$_3$)$_2$], [ZA4725;N(CH$_3$)(CH$_2$)$_2$F,N(CH$_3$)$_2$], [ZA4726;N(CH$_3$)(CH$_2$)$_2$CN,N(CH$_3$)$_2$], [ZA4727;N(CH$_3$)(CH$_2$)$_2$OCH$_3$,N(CH$_3$)$_2$], [ZA4728;N(CH$_3$)(CH$_2$)$_2$Ph,N(CH$_3$)$_2$], [ZA4729;N(CH$_3$)(CH$_2$)$_3$F,N(CH$_3$)$_2$], [ZA4730;N(CH$_3$)(CH$_2$)$_3$CN,N(CH$_3$)$_2$], [ZA4731;N(CH$_3$)(CH$_2$)$_3$OCH$_3$,N(CH$_3$)$_2$], [ZA4732;N(CH$_3$)(CH$_2$)$_3$Ph,N(CH$_3$)$_2$], [ZA4733;N(CH$_3$)(CH$_2$)$_4$F,N(CH$_3$)$_2$], [ZA4734;N(CH$_3$)(CH$_2$)$_4$CN,N(CH$_3$)$_2$], [ZA4735;N(CH$_3$)(CH$_2$)$_4$OCH$_3$,N(CH$_3$)$_2$], [ZA4736;N(CH$_3$)(CH$_2$)$_4$Ph,N(CH$_3$)$_2$], [ZA4737;N(CH$_3$)Ph,N(CH$_3$)$_2$], [ZA4738;N(CH$_3$)(2-Py),N(CH$_3$)$_2$], [ZA4739;N(CH$_3$)(3-Py),N(CH$_3$)$_2$], [ZA4740;N(CH$_3$)(4-Py),N(CH$_3$)$_2$], [ZA4741;N(CH$_2$CH$_3$)$_2$,N(CH$_3$)$_2$], [ZA4742;Pyr,N(CH$_3$)$_2$], [ZA4743;Pip,N(CH$_3$)$_2$], [ZA4744;Mor,N(CH$_3$)$_2$], [ZA4745;S(O)$_2$CH$_3$,N(CH)$_2$], [ZA4746;S(O)$_2$CH$_2$CH$_3$,N(CH$_3$)$_2$], [ZA4747;S(O)$_2$CH(CH$_3$)$_2$,N(CH)$_2$], [ZA4748;S(O)$_2$(CH$_2$)$_2$CH$_3$,N(CH)$_2$], [ZA4749;S(O)$_2$(CH$_2$)$_3$CH$_3$,N(CH$_3$)$_2$], [ZA4750;S(O)$_2$(CH$_2$)$_4$CH$_3$,N(CH$_3$)$_2$], [ZA4751;S(O)$_2$(CH$_2$)$_5$CH$_3$,N(CH$_3$)$_2$], [ZA4752;S(O)$_2$CH$_2$CH=CH$_2$,N(CH$_3$)$_2$], [ZA4753;S(O)$_2$CH$_2$C≡CH,N(CH$_3$)$_2$], [ZA4754;S(O)$_2$CH$_2$C≡CCH$_3$,N(CH$_3$)$_2$], [ZA4755;S(O)$_2$-c-Pr,N(CH$_3$)$_2$], [ZA4756;S(O)$_2$-c-Bu,N(CH$_3$)$_2$], [ZA4757;S(O)$_2$-c-Pen,N(CH$_3$)$_2$], [ZA4758;S(O)$_2$-c-Hex,N(CH$_3$)$_2$], [ZA4759;S(O)$_2$Ph,N(CH)$_2$], [ZA4760;S(O)$_2$(2-Py),N(CH)$_2$], [ZA4761;S(O)$_2$ (3-Py),N(CH$_3$)$_2$], [ZA4762;S(O)$_2$(4-Py),N(CH$_3$)$_2$], [ZA4763;S(O)$_2$CF$_3$,N(CH$_3$)$_2$], [ZA4764;S(O)$_2$CH$_2$Ph,N(CH)$_2$], [ZA4765;S(O)$_2$CH$_2$(2-Py),N(CH)$_2$], [ZA4766;S(O)$_2$ CH$_2$(3-Py),N(CH$_3$)$_2$], [ZA4767;S(O)$_2$CH$_2$(4-Py),N(CH$_3$)$_2$], [ZA4768;S(O)$_2$CH$_2$ CN,N(CH$_3$)$_2$], [ZA4769;S(O)$_2$CH$_2$NO$_2$,N(CH$_3$)$_2$], [ZA4770;S(O)$_2$(CH$_2$)$_2$F,N(CH)$_2$], [ZA4771;S(O)$_2$(CH$_2$)$_2$Cl,N(CH)$_2$], [ZA4772;S(O)$_2$(CH$_2$)$_2$CF$_3$,N(CH$_3$)$_2$], [ZA4773;S(O)$_2$(CH$_2$)$_2$CN,N(CH)$_2$], [ZA4774;S(O)$_2$(CH$_2$)$_2$NO$_2$,N(CH)$_2$], [ZA4775;S(O)$_2$(CH$_2$)$_2$ Ph,N(CH$_3$)$_2$], [ZA4776;S(O)$_2$(CH$_2$)$_2$OCH$_3$,N(CH$_3$)$_2$], [ZA4777;S(O)$_2$(CH$_2$)$_3$F,N(CH$_3$)$_2$], [ZA4778;S(O)$_2$(CH$_2$)$_3$Cl,N(CH)$_2$], [ZA4779;S(O)$_2$(CH$_2$)$_3$CF$_3$,N(CH$_3$)$_2$], [ZA4780;S(O)$_2$(CH$_2$)$_3$CN,N(CH$_3$)$_2$], [ZA4781;S(O)$_2$(CH$_2$)$_3$NO$_2$,N(CH$_3$)$_2$], [ZA4782;S(O)$_2$(CH$_2$)$_3$ Ph,N(CH$_3$)$_2$], [ZA4783;S(O)$_2$(CH$_2$)$_3$OCH$_3$,N(CH)$_2$], [ZA4784;S(O)$_2$(CH$_2$)$_4$F,N(CH$_3$)$_2$], [ZA4785;S(O)$_2$(CH$_2$)$_4$Cl,N(CH)$_2$], [ZA4786;S(O)$_2$(CH)$_4$CF$_3$,N(CH$_3$)$_2$], [ZA4787;S(O)$_2$(CH$_2$)$_4$CN,N(CH$_3$)$_2$], [ZA4788;S(O)$_2$(CH$_2$)$_4$NO$_2$,N(CH)$_2$], [ZA4789;S(O)$_2$(CH$_2$)$_4$ Ph,N(CH$_3$)$_2$], [ZA4790;S(O)$_2$(CH$_2$)$_4$OCH$_3$,N(CH$_3$)$_2$], [ZA4791;S(O)$_2$(CH$_2$)$_5$F,N(CH)$_2$], [ZA4792;S(O)$_2$(CH$_2$)$_5$Cl,N(CH)$_2$], [ZA4793;S(O)$_2$(CH$_2$)$_5$CF$_3$,N(CH$_3$)$_2$], [ZA4794;S(O)$_2$(CH$_2$)$_5$CN,N(CH)$_2$], [ZA4795;S(O)$_2$(CH$_2$)$_5$NO$_2$,N(CH)$_2$], [ZA4796;S(O)$_2$(CH$_2$)$_5$ Ph,N(CH$_3$)$_2$], [ZA4797;S(O)$_2$(CH$_2$)$_5$OCH$_3$,N(CH)$_2$], [ZA4798;S(O)$_2$(CH$_2$)$_6$F,N(CH)$_2$], [ZA4799;S(O)$_2$(CH$_2$)$_6$Cl,N(CH)$_2$], [ZA4800;S(O)$_2$(CH$_2$)$_6$CF$_3$,N(CH$_3$)$_2$], [ZA4801;S(O)$_2$(CH$_2$)$_6$CN,N(CH$_3$)$_2$], [ZA4802;S(O)$_2$(CH$_2$)$_6$NO$_2$,N(CH$_3$)$_2$], [ZA4803;S(O)$_2$(CH$_2$)$_6$ Ph,N(CH$_3$)$_2$], [ZA4804;S(O)$_2$(CH$_2$)$_6$OCH$_3$,N(CH$_3$)$_2$], [ZA4805;S(O)CH$_3$,N(CH$_3$)$_2$], [ZA4806;S(O)CH$_2$CH$_3$,N(CH$_3$)$_2$], [ZA4807;S(O)CH(CH$_3$)$_2$,N(CH$_3$)$_2$], [ZA4808;S(O)(CH$_2$)$_2$CH$_3$,N(CH$_3$)$_2$], [ZA4809;S(O)(CH$_2$)$_3$CH$_3$,N(CH$_3$)$_2$], [ZA4810;S(O)(CH$_2$)$_4$CH$_3$,N(CH$_3$)$_2$], [ZA4811;S(O)(CH$_2$)$_5$CH$_3$,N(CH$_3$)$_2$], [ZA4812;S(O)CH$_2$CH=CH$_2$,N(CH$_3$)$_2$], [ZA4813;S(O)CH$_2$C≡CH,N(CH$_3$)$_2$], [ZA4814;S(O)CH$_2$C≡CCH$_3$,N(CH)$_2$], [ZA4815;S(O)c-Pr,N(CH$_3$)$_2$], [ZA4816;S(O)c-Bu,N(CH$_3$)$_2$], [ZA4817;S(O)c-Pen,N(CH$_3$)$_2$], [ZA4818;S(O)c-Hex,N(CH$_3$)$_2$], [ZA4819;S(O)Ph,N(CH$_3$)$_2$], [ZA4820;S(O)(2-Py),N(CH$_3$)$_2$], [ZA4821;S(O)(3-Py),N(CH$_3$)$_2$], [ZA4822;S(O)(4-Py),N(CH$_3$)$_2$], [ZA4823;S(O)CF$_3$,N(CH$_3$)$_2$], [ZA4824;S(O)CH$_2$ Ph,N(CH$_3$)$_2$], [ZA4825;S(O)CH$_2$(2-Py),N(CH$_3$)$_2$], [ZA4826;S(O)CH$_2$(3-Py),N(CH$_3$)$_2$], [ZA4827;S(O)CH$_2$(4-Py),N(CH$_3$)$_2$], [ZA4828;S(O)CH$_2$CN,N(CH$_3$)$_2$], [ZA4829;S(O)CH$_2$NO$_2$,N(CH$_3$)$_2$], [ZA4830;S(O)(CH$_2$)$_2$F,N(CH)$_2$], [ZA4831;S(O)(CH$_2$)$_2$Cl,N(CH$_3$)$_2$], [ZA4832;S(O)(CH$_2$)$_2$CF$_3$,N(CH$_3$)$_2$], [ZA4833;S(O)(CH$_2$)$_2$CN,N(CH$_3$)$_2$], [ZA4834;S(O)(CH$_2$)$_2$NO$_2$,N(CH)$_2$], [ZA4835;S(O)(CH$_2$)$_2$ Ph,N(CH$_3$)$_2$], [ZA4836;S(O)(CH$_2$)$_2$OCH$_3$,N(CH$_3$)$_2$], [ZA4837;S(O)(CH$_2$)$_3$F,N(CH$_3$)$_2$], [ZA4838;S(O)(CH$_2$)$_3$Cl,N(CH$_3$)$_2$], [ZA4839;S(O)(CH$_2$)$_3$CF$_3$,N(CH$_3$)$_2$], [ZA4840;S(O)(CH$_2$)$_3$CN,N(CH$_3$)$_2$], [ZA4841;S(O)(CH$_2$)$_3$NO$_2$,N(CH$_3$)$_2$], [ZA4842;S(O)(CH$_2$)$_3$Ph,N(CH)$_2$], [ZA4843;S(O)(CH$_2$)$_3$OCH$_3$,N(CH$_3$)$_2$], [ZA4844;S(O)(CH$_2$)$_4$F,N(CH$_3$)$_2$], [ZA4845;S(O)(CH$_2$)$_4$Cl,N(CH$_3$)$_2$], [ZA4846;S(O)(CH$_2$)$_4$CF$_3$,N(CH)$_2$], [ZA4847;S(O)(CH$_2$)$_4$CN,N(CH$_3$)$_2$], [ZA4848;S(O)(CH$_2$)$_4$NO$_2$,N(CH$_3$)$_2$], [ZA4849;S(O)(CH$_2$)$_4$ Ph,N(CH$_3$)$_2$], [ZA4850;S(O)(CH$_2$)$_4$OCH$_3$,N(CH$_3$)$_2$], [ZA4851;S(O)(CH$_2$)$_5$F,N(CH$_3$)$_2$], [ZA4852;S(O)(CH$_2$)$_5$Cl,N(CH$_3$)$_2$], [ZA4853;S(O)(CH$_2$)$_5$CF$_3$,N(CH$_3$)$_2$], [ZA4854;S(O)(CH)$_5$CN,N(CH$_3$)$_2$], [ZA4855;S(O)(CH$_2$)$_5$NO$_2$,N(CH$_3$)$_2$], [ZA4856;S(O)(CH$_2$)$_5$Ph,N(CH$_3$)$_2$], [ZA4857;S(O)(CH$_2$)$_5$OCH$_3$,N(CH$_3$)$_2$], [ZA4858;S(O)(CH$_2$)$_6$F,N(CH$_3$)$_2$], [ZA4859;S(O)(CH$_2$)$_6$Cl,N(CH$_3$)$_2$], [ZA4860;S(O)(CH$_2$)$_6$CF$_3$,N(CH$_3$)$_2$], [ZA4861;S(O)(CH$_2$)$_6$CN,N(CH$_3$)$_2$], [ZA4862;S(O)(CH$_2$)$_6$NO$_2$,N(CH)$_2$], [ZA4863;S(O)(CH$_2$)$_6$Ph,N(CH$_3$)$_2$], [ZA4864;S(O)(CH$_2$)$_6$OCH$_3$,N(CH$_3$)$_2$], [ZA4865;OH,CH$_2$CH$_3$], [ZA4866;OCH$_3$,CH$_2$CH$_3$], [ZA4867;OCH$_2$CH$_3$,CH$_2$CH$_3$], [ZA4868;OCH(CH$_3$)$_2$,CH$_2$CH$_3$], [ZA4869;O(CH$_2$)$_2$ CH$_3$,CH$_2$CH$_3$], [ZA4870;O(CH$_2$)$_3$CH$_3$,CH$_2$CH$_3$], [ZA4871;(CH$_2$)$_4$CH$_3$,CH$_2$CH$_3$], [ZA4872;O(CH$_2$)$_5$CH$_3$,CH$_2$CH$_3$], [ZA4873;OCH$_2$CH=CH$_2$,CH$_2$CH$_3$], [ZA4874;OCH$_2$ C≡CH,CH$_2$CH$_3$], [ZA4875;OCH$_2$C≡CCH$_3$,CH$_2$CH$_3$], [ZA4876;O-c-Pr,CH$_2$CH$_3$], [ZA4877;O-c-Pen,CH$_2$CH$_3$], [ZA4878;O-c-Hex,CH$_2$CH$_3$], [ZA4879;OPh,CH$_2$CH$_3$], [ZA4880;OCH$_2$Ph,CH$_2$CH$_3$], [ZA4881;OCH$_2$(2-Py),CH$_2$CH$_3$], [ZA4882;OCH$_2$ (3-Py),CH$_2$CH$_3$], [ZA4883;OCH$_2$(4-Py),CH$_2$CH$_3$], [ZA4884;OCH$_2$CN,CH$_2$CH$_3$], [ZA4885;OCH$_2$NO$_2$,CH$_2$CH$_3$], [ZA4886;O(CH$_2$)$_2$F,CH$_2$CH$_3$], [ZA4887;O(CH$_2$)$_2$ CN,CH$_2$CH$_3$], [ZA4888;O(CH$_2$)$_2$Ph,CH$_2$CH$_3$], [ZA4889;O(CH$_2$)$_2$OCH$_3$,CH$_2$CH$_3$], [ZA4890;O(CH$_2$)$_3$F,CH$_2$CH$_3$], [ZA4891;(CH$_2$)$_3$CN,CH$_2$CH$_3$], [ZA4892;O(CH$_2$)$_3$NO$_2$,CH$_2$CH$_3$], [ZA4893;O(CH$_2$)$_3$Ph,CH$_2$CH$_3$], [ZA4894;O(CH$_2$)$_3$OCH$_3$,CH$_2$CH$_3$], [ZA4895;O(CH$_2$)$_4$ F,CH$_2$CH$_3$], [ZA4896;O(CH$_2$)$_4$CN,CH$_2$CH$_3$], [ZA4897;O(CH$_2$)$_4$NO$_2$,CH$_2$CH$_3$], [ZA4898;O(CH$_2$)$_4$Ph,CH$_2$CH$_3$], [ZA4899;O(CH$_2$)$_4$OCH$_3$,CH$_2$CH$_3$], [ZA4900;O(CH$_2$)$_5$ F,CH$_2$CH$_3$], [ZA4901;(CH$_2$)$_5$CN,CH$_2$CH$_3$], [ZA4902;O(CH$_2$)$_5$NO$_2$,CH$_2$CH$_3$], [ZA4903;O(CH$_2$)$_5$Ph,

CH₂CH₃], [ZA4904;O(CH₂)₅OCH₃,CH₂CH₃], [ZA4905;O(CH₂)₆F,CH₂CH₃], [ZA4906;O(CH₂)₆CN,CH₂CH₃], [ZA4907;O(CH₂)₆NO₂,CH₂CH₃], [ZA4908;O(CH₂)₆Ph,CH₂CH₃], [ZA4909;O(CH₂)₆OCH₃,CH₂CH₃], [ZA4910;OC(O)CH₃,CH₂CH₃], [ZA4911;OC(O)CH₂CH₃,CH₂CH₃], [ZA4912;OC(O)CH(CH₃)₂,CH₂CH₃], [ZA4913;OC(O)(CH₂)₂CH₃,CH₂CH₃], [ZA4914;OC(O)(CH₂)₃CH₃,CH₂CH₃], [ZA4915;OC(O)(CH₂)₄CH₃,CH₂CH₃], [ZA4916;OC(O)(CH₂)₅CH₃,CH₂CH₃], [ZA4917;OC(O)CH₂CH=CH₂,CH₂CH₃], [ZA4918;OC(O)CH₂C≡CH,CH₂CH₃], [ZA4919;OC(O)CH₂C≡CCH₃,CH₂CH₃], [ZA4920;OC(O)c-Pr,CH₂CH₃], [ZA4921;OC(O)c-Pen,CH₂CH₃], [ZA4922;OC(O)c-Hex,CH₂CH₃], [ZA4923;OC(O)Ph,CH₂CH₃], [ZA4924;OC(O)(2-Py),CH₂CH₃], [ZA4925;OC(O)(3-Py),CH₂CH₃], [ZA4926;OC(O)(4-Py),CH₂CH₃], [ZA4927;OC(O)CH₂Ph,CH₂CH₃], [ZA4928;OC(O)CH₂(2-Py),CH₂CH₃], [ZA4929;OC(O)CH₂(3-Py),CH₂CH₃], [ZA4930;OC(O)CH₂(4-Py),CH₂CH₃], [ZA4931;OC(O)CH₂CN,CH₂CH₃], [ZA4932;OC(O)CH₂NO₂,CH₂CH₃], [ZA4933;OC(O)(CH₂)₂F,CH₂CH₃], [ZA4934;OC(O)(CH₂)₂CN,CH₂CH₃], [ZA4935;OC(O)(CH₂)₂NO₂,CH₂CH₃], [ZA4936;OC(O)(CH₂)₂Ph,CH₂CH₃], [ZA4937;OC(O)(CH₂)₂OCH₃,CH₂CH₃], [ZA4938;OC(O)(CH₂)₃F,CH₂CH₃], [ZA4939;OC(O)(CH₂)₃CN,CH₂CH₃], [ZA4940;OC(O)(CH₂)₃N₂,CH₂CH₃], [ZA4941;OC(O)(CH₂)₃OCH₃,CH₂CH₃], [ZA4942;OC(O)NH₂,CH₂CH₃], [ZA4943;OC(O)NHCH₃,CH₂CH₃], [ZA4944;OC(O)NHCH₂CH₃,CH₂CH₃], [ZA4945;OC(O)NH(CH₂)₂CH₃,CH₂CH₃], [ZA4946;OC(O)NH(CH₂)₃CH₃,CH₂CH₃], [ZA4947;OC(O)NH(CH)₄CH₃,CH₂CH₃], [ZA4948;OC(O)NH(CH₂)₅CH₃,CH₂CH₃], [ZA4949;OC(O)NHCH(CH₃)₂,CH₂CH₃], [ZA4950;OC(O)NHCH₂F,CH₂CH₃], [ZA4951;OC(O)NHCH₂CN,CH₂CH₃], [ZA4952;OC(O)NHCH₂OCH₃,CH₂CH₃], [ZA4953;OC(O)NHCH₂Ph,CH₂CH₃], [ZA4954;OC(O)NH(CH₂)₂F,CH₂CH₃], [ZA4955;OC(O)NH(CH₂)₂CN,CH₂CH₃], [ZA4956;OC(O)NH(CH₂)₂OCH₃,CH₂CH₃], [ZA4957;OC(O)NH(CH₂)₃F,CH₂CH₃], [ZA4958;OC(O)NH(CH)₃CN,CH₂CH₃], [ZA4959;OC(O)NH(CH₂)₃OCH₃,CH₂CH₃], [ZA4960;OC(O)NH(CH₂)₄F,CH₂CH₃], [ZA4961;OC(O)NH(CH₂)₄CN,CH₂CH₃], [ZA4962;OC(O)NH(CH₂)₄OCH₃,CH₂CH₃], [ZA4963;OC(O)NHPh,CH₂CH₃], [ZA4964;OC(O)NH(2-Py),CH₂CH₃], [ZA4965;OC(O)NH(3-Py),CH₂CH₃], [ZA4966;OC(O)NH(4-Py),CH₂CH₃], [ZA4967;OC(O)N(CH₃)₂,CH₂CH₃], [ZA4968;OC(O)N(CH₃)CH₂CH₃,CH₂CH₃], [ZA4969;OC(O)N(CH₃)(CH₂)₂CH₃,CH₂CH₃], [ZA4970;OC(O)N(CH₃)(CH₂)₃CH₃,CH₂CH₃], [ZA4971;OC(O)N(CH₃)CH(CH₃)₂,CH₂CH₃], [ZA4972;OC(O)N(CH₃)CH₂F,CH₂CH₃], [ZA4973;OC(O)N(CH₃)CH₂CN,CH₂CH₃], [ZA4974;OC(O)N(CH₃)CH₂OCH₃,CH₂CH₃], [ZA4975;OC(O)N(CH₃)CH₂Ph,CH₂CH₃], [ZA4976;OC(O)N(CH₃)(CH₂)₂F,CH₂CH₃], [ZA4977;OC(O)N(CH₃)(CH₂)₂CN,CH₂CH₃], [ZA4978;OC(O)N(CH₃)(CH₂)₂OCH₃,CH₂CH₃], [ZA4979;OC(O)N(CH₃)Ph,CH₂CH₃], [ZA4980;OC(O)N(CH₃)(2-Py),CH₂CH₃], [ZA4981;OC(O)N(CH₃)(3-Py),CH₂CH₃], [ZA4982;OC(O)N(CH₃)(4-Py),CH₂CH₃], [ZA4983;OC(O)N(CH₂CH₃)₂,CH₂CH₃], [ZA4984;OC(O)(Pyr),CH₂CH₃], [ZA4985;OC(O)(Pip),CH₂CH₃], [ZA4986;OC(O)(Mor),CH₂CH₃], [ZA4987;OC(O)OCH₃,CH₂CH₃], [ZA4988;OC(O)OCH₂CH₃,CH₂CH₃], [ZA4989;OC(O)OCH(CH₃)₂,CH₂CH₃], [ZA4990;OC(O)O(CH₂)₂CH₃,CH₂CH₃], [ZA4991;OC(O)O(CH₂)₃CH₃,CH₂CH₃], [ZA4992;OC(O)O(CH₂)₄CH₃,CH₂CH₃], [ZA4993;OC(O)O(CH₂)₅CH₃,CH₂CH₃], [ZA4994;OC(O)OCH₂CH=CH₂,CH₂CH₃], [ZA4995;OC(O)OCH₂C≡CH,CH₂CH₃], [ZA4996;OC(O)OCH₂C≡CCH₃,CH₂CH₃], [ZA4997;OC(O)O-c-Pr,CH₂CH₃], [ZA4998;OC(O)O-c-Pen,CH₂CH₃], [ZA4999;OC(O)O-c-Hex,CH₂CH₃], [ZA5000;OC(O)OPh,CH₂CH₃], [ZA5001;OC(O)O(2-Py),CH₂CH₃], [ZA5002;OC(O)O(3-Py),CH₂CH₃], [ZA5003;OC(O)O(4-Py),CH₂CH₃], [ZA5004;OC(O)OCF₃,CH₂CH₃], [ZA5005;OC(O)OCH₂Ph,CH₂CH₃], [ZA5006;OC(O)OCH₂(2-Py),CH₂CH₃], [ZA5007;OC(O)OCH₂(3-Py),CH₂CH₃], [ZA5008;OC(O)OCH₂(4-Py),CH₂CH₃], [ZA5009;OC(O)OCH₂CN,CH₂CH₃], [ZA501;OC(O)OCH₂NO₂,CH₂CH₃], [ZA5011;OC(O)O(CH₂)₂F,CH₂CH₃], [ZA5012;OC(O)O(CH₂)₂CN,CH₂CH₃], [ZA5013;OC(O)O(CH₂)₂OCH₃,CH₂CH₃], [ZA5014;OC(O)O(CH₂)₃F,CH₂CH₃], [ZA5015;OC(O)O(CH₂)₃CN,CH₂CH₃], [ZA5016;OC(O)O(CH₂)₃OCH₃,CH₂CH₃], [ZA5017;OS(O)₂CH₃,CH₂CH₃], [ZA5018;OS(O)₂CH₂CH₃,CH₂CH₃], [ZA5019;OS(O)₂CH(CH₃)₂,CH₂CH₃], [ZA5020;OS(O)₂(CH₂)₂CH₃,CH₂CH₃], [ZA5021;OS(O)₂(CH₂)₃CH₃,CH₂CH₃], [ZA5022;OS(O)₂(CH₂)₄CH₃,CH₂CH₃], [ZA5023;OS(O)₂(CH₂)₅CH₃,CH₂CH₃], [ZA5024;OS(O)₂-c-Pr,CH₂CH₃], [ZA5025;OS(O)₂-c-Pen,CH₂CH₃], [ZA5026;OS(O)₂-c-Hex,CH₂CH₃], [ZA5027;OS(O)₂Ph,CH₂CH₃], [ZA5028;OS(O)₂(2-Py),CH₂CH₃], [ZA5029;OS(O)₂(3-Py),CH₂CH₃], [ZA5030;OS(O)₂(4-Py),CH₂CH₃], [ZA5031;OS(O)₂CF₃,CH₂CH₃], [ZA5032;OS(O)₂CH₂Ph,CH₂CH₃], [ZA5033;OH,(CH₂)₂CH₃], [ZA5034;OCH₃,(CH₂)₂CH₃], [ZA5035;OCH₂CH₃,(CH₂)₂CH₃], [ZA5036;OCH(CH₃)₂,(CH₂)₂CH₃], [ZA5037;O(CH₂)₂CH₃,(CH₂)₂CH₃], [ZA5038;O(CH₂)₃CH₃,(CH₂)₂CH₃], [ZA5039;O(CH₂)₄CH₃,(CH₂)₂CH₃], [ZA5040;O(CH₂)₅CH₃,(CH₂)₂CH₃], [ZA5041;OCH₂CH=CH₂,(CH₂)₂CH₃], [ZA5042;OCH₂C≡CH,(CH₂)₂CH₃], [ZA5043;OCH₂C≡CCH₃,(CH₂)₂CH₃], [ZA5044;O-c-Pr,(CH₂)₂CH₃], [ZA5045;O-c-Pen,(CH₂)₂CH₃], [ZA5046;O-c-Hex,(CH₂)₂CH₃], [ZA5047;OPh,(CH₂)₂CH₃], [ZA5048;OCH₂Ph,(CH₂)₂CH₃], [ZA5049;OCH₂(2-Py),(CH₂)₂CH₃], [ZA5050;OCH₂(3-Py),(CH₂)₂CH₃], [ZA5051;OCH₂(4-Py),(CH₂)₂CH₃], [ZA5052;OCH₂CN,(CH₂)₂CH₃], [ZA5053;OCH₂NO₂,(CH₂)₂CH₃], [ZA5054;O(CH₂)₂F,(CH₂)₂CH₃], [ZA5055;(CH₂)₂CN,(CH₂)₂CH₃], [ZA5056;(CH₂)₂Ph,(CH₂)₂CH₃], [ZA5057;O(CH₂)₂OCH₃,(CH₂)₂CH₃], [ZA5058;(CH₂)₃F,(CH₂)₂CH₃], [ZA5059;O(CH₂)₃CN,(CH₂)₂CH₃], [ZA5060;O(CH₂)₃NO₂,(CH₂)₂CH₃], [ZA5061;(CH₂)₃Ph,(CH₂)₂CH₃], [ZA5062;O(CH₂)₃OCH₃,(CH₂)₂CH₃], [ZA5063;O(CH₂)₄F,(CH₂)₂CH₃], [ZA5064;O(CH)₄CN,(CH₂)₂CH₃], [ZA5065;O(CH₂)₄NO₂,(CH₂)₂CH₃], [ZA5066;O(CH₂)₄Ph,(CH₂)₂CH₃], [ZA5067;O(CH₂)₄OCH₃,(CH₂)₂CH₃], [ZA5068;O(CH₂)₅F,(CH₂)₂CH₃], [ZA5069;O(CH₂)₅CN,(CH₂)₂CH₃], [ZA5070;O(CH₂)₅NO₂,(CH₂)₂CH₃], [ZA5071;O(CH)₅Ph,(CH₂)₂CH₃], [ZA5072;O(CH₂)₅OCH₃,(CH₂)₂CH₃], [ZA5073;O(CH₂)₆F,(CH₂)₂CH₃], [ZA5074;O(CH₂)₆CN,(CH₂)₂CH₃], [ZA5075;O(CH₂)₆NO₂,(CH₂)₂CH₃], [ZA5076;O(CH₂)₆Ph,(CH₂)₂CH₃], [ZA5077;O(CH₂)₆OCH₃,(CH₂)₂CH₃], [ZA5078;OC(O)CH₃,(CH₂)₂CH₃], [ZA5079;OC(O)CH₂CH₃,(CH₂)₂CH₃], [ZA5080;OC(O)CH(CH₃)₂,(CH₂)₂CH₃], [ZA5081;OC(O)(CH₂)₂CH₃,(CH₂)₂CH₃], [ZA5082;OC(O)(CH₂)₃CH₃,(CH₂)₂CH₃], [ZA5083;OC(O)(CH₂)₄CH₃,(CH₂)₂CH₃], [ZA5084;OC(O)(CH₂)₅CH₃,(CH₂)₂CH₃], [ZA5085;OC(O)CH₂CH=CH₂,(CH₂)₂CH₃], [ZA5086;OC(O)CH₂C≡CH,(CH₂)₂CH₃], [ZA5087;OC(O)CH₂C≡CCH₃,(CH₂)₂CH₃], [ZA5088;OC(O)c-Pr,(CH₂)₂CH₃], [ZA5089;OC(O)c-Pen,(CH₂)₂CH₃], [ZA5090;OC(O)c-Hex,(CH₂)₂CH₃], [ZA5091;OC(O)Ph,(CH₂)₂CH₃], [ZA5092;OC(O)(2-Py),(CH₂)₂CH₃], [ZA5093;OC(O)(3-Py),(CH₂)₂CH₃], [ZA5094;OC(O)(4-Py),(CH₂)₂CH₃], [ZA5095;OC(O)CH₂Ph,(CH₂)₂CH₃], [ZA5096;OC(O)CH₂(2-Py),(CH₂)₂CH₃], [ZA5097;OC(O)CH₂(3-Py),(CH₂)₂CH₃], [ZA5098;OC(O)CH₂(4-Py), (CH₂)₂ CH₃], [ZA5099;OC(O)CH₂CN,(CH₂)₂CH₃], [ZA5100;OC(O)CH₂NO₂,(CH₂)₂CH₃], [ZA5101;OC(O)(CH₂)₂F,(CH₂)₂CH₃], [ZA5102;OC(O)(CH₂)₂CN,(CH₂)₂CH₃], [ZA5103;OC(O)(CH₂)₂NO₂,(CH₂)₂CH₃], [ZA5104;OC(O)(CH₂)₂Ph,(CH₂)₂CH₃], [ZA5105;OC(O)(CH₂)₂OCH₃,(CH₂)₂CH₃], [ZA5106;OC(O)(CH₂)₃F,(CH₂)₂CH₃], [ZA5107;OC(O)(CH₂)₃CN,(CH₂)₂CH₃], [ZA5108;OC(O)(CH₂)₃NO₂,(CH₂)₂CH₃], [ZA5109;OC(O)(CH₂)₃OCH₃,(CH₂)₂CH₃], [ZA5110;OC(O)NH₂,(CH₂)₂CH₃], [ZA5111;OC(O)NHCH₃,(CH₂)₂CH₃], [ZA5112;OC(O)NHCH₂CH₃,(CH₂)₂CH₃], [ZA5113;OC(O)NH(CH₂)₂CH₃,(CH₂)₂CH₃], [ZA5114;OC(O)NH(CH₂)₃CH₃,(CH₂)₂CH₃], [ZA5115;OC(O)NH(CH₂)₄CH₃,(CH₂)₂CH₃], [ZA5116;OC(O)NH(CH₂)₅CH₃,(CH₂)₂CH₃], [ZA5117;OC(O)NHCH(CH₃)₂,(CH₂)₂ CH₃], [ZA5118;OC(O)NHCH₂F,(CH₂)₂CH₃], [ZA5119;OC(O)NHCH₂CN,(CH₂)₂CH₃], [ZA5120;OC(O)NHCH₂OCH₃,(CH₂)₂CH₃], [ZA5121;OC(O)NHCH₂Ph,(CH₂)₂CH₃], [ZA5122;OC(O)NH(CH₂)₂F,(CH₂)₂CH₃], [ZA5123;OC(O)NH(CH₂)₂CN,(CH₂)₂CH₃], [ZA5124;OC(O)NH(CH₂)₂OCH₃,(CH₂)₂CH₃], [ZA5125;OC(O)NH(CH₂)₃F,(CH₂)₂CH₃], [ZA5126;OC(O)NH(CH₂)₃ CN,(C H₂)₂CH₃], [ZA5127;OC(O)NH(CH₂)₃OCH₃,(CH₂)₂ CH₃], [ZA5128;OC(O)NH(CH₂)₄ F,(CH₂)₂CH₃], [ZA5129;OC(O)NH(CH₂)₄CN,(CH₂)₂CH₃], [ZA5130;OC(O)NH(CH₂)₄ OCH₃,(CH₂)₂CH₃], [ZA5131; OC(O)NHPh,(CH₂)₂CH₃], [ZA5132;OC(O)NH(2-Py),(CH₂)₂CH₃], [ZA5133;OC(O)NH(3-Py),(CH₂)₂CH₃], [ZA5134;OC(O)NH(4-Py),(CH₂)₂CH₃], [ZA5135;OC(O)N(CH₃)₂,(CH₂)₂ CH₃], [ZA5136;OC(O)N(CH₃)CH₂CH₃,(CH₂)₂CH₃], [ZA5137;OC(O)N(CH₃)(CH₂)₂CH₃,(CH₂)₂CH₃], [ZA5138;OC(O)N(CH₃)(CH₂)₃CH₃,(CH₂)₂CH₃], [ZA5139;OC(O)N(CH₃)CH(CH₃)₂,(CH₂)₂CH₃], [ZA5140;OC(O)N(CH₃)CH₂F,(CH₂)₂CH₃], [ZA5141;OC(O)N(CH₃)CH₂CN,(CH₂)₂CH₃], [ZA5142;OC(O)N(CH₃)CH₂OCH₃,(CH₂)₂CH₃], [ZA5143;OC(O)N(CH₃)CH₂Ph,(CH₂)₂CH₃], [ZA5144;OC(O)N(CH₃)(CH₂)₂ F,(CH₂)₂CH₃], [ZA5145;OC(O)N(CH₃)(CH₂)₂CN,(CH₂)₂CH₃], [ZA5146;OC(O)N(CH₃)(CH₂)₂OCH₃,(CH₂)₂CH₃], [ZA5147;OC(O)N(CH₃)Ph,(CH₂)₂CH₃], [ZA5148;OC(O)N(CH₃)(2-Py),(CH₂)₂CH₃], [ZA5149;OC(O)N(CH₃)(3-Py),(CH₂)₂CH₃], [ZA5150;OC(O)N(CH₃)(4-Py),(CH₂)₂CH₃], [ZA5151;OC(O)N(CH₂CH₃)₂,(CH₂)₂CH₃], [ZA5152;OC(O)(Pyr),(CH₂)₂ CH₃], [ZA5153;OC(O)(Pip),(CH₂)₂CH₃], [ZA5154;OC(O)(Mor),(CH₂)₂CH₃], [ZA5155;OC(O)OCH₃,(CH₂)₂CH₃], [ZA5156;OC(O)OCH₂CH₃,(CH₂)₂CH₃], [ZA5157;OC(O)OCH(CH₃)₂,(CH₂)₂CH₃], [ZA5158;OC(O)O(CH₂)₂CH₃,(CH₂)₂CH₃], [ZA5159;OC(O)O(CH₂)₃CH₃,(CH₂)₂CH₃], [ZA5160;OC(O)O(CH₂)₄CH₃,(CH₂)₂CH₃], [ZA5161;OC(O)O(CH₂)₅CH₃,(CH₂)₂CH₃], [ZA5162;OC(O)OCH₂CH=CH₂,(CH₂)₂CH₃], [ZA5163;OC(O)OCH₂C≡CH,(CH₂)₂CH₃], [ZA5164;OC(O)OCH₂C≡CCH₃,(CH₂)₂CH₃], [ZA5165;OC(O)O-c-Pr,(CH₂)₂CH₃], [ZA5166;OC(O)O-c-Pen,(CH₂)₂CH₃], [ZA5167;OC(O)O-c-Hex,(CH₂)₂CH₃], [ZA5168;OC(O)OPh,(CH₂)₂CH₃], [ZA5169;OC(O)O(2-Py),(CH₂)₂CH₃], [ZA5170;OC(O)O(3-Py),(CH₂)₂CH₃], [ZA5171;OC(O)O(4-Py),(CH₂)₂CH₃], [ZA5172;OC(O)OCF₃,(CH₂)₂CH₃], [ZA5173;OC(O)OCH₂Ph,(CH₂)₂CH₃], [ZA5174;OC(O)OCH₂(2-Py),(CH₂)₂ CH₃], [ZA5175;OC(O)OCH₂(3-Py),(CH₂)₂CH₃], [ZA5176;OC(O)OCH₂(4-Py),(CH₂)₂CH₃], [ZA5177;OC(O)OCH₂CN,(CH₂)₂CH₃], [ZA5178;OC(O)OCH₂NO₂,(CH₂)₂CH₃], [ZA5179;OC(O)O(CH₂)₂F,(CH₂)₂CH₃], [ZA5180;OC(O)O(CH₂)₂CN,(CH₂)₂CH₃], [ZA5181;OC(O)O(CH₂)₂OCH₃,(CH₂)₂CH₃], [ZA5182;OC(O)O(CH₂)₃F,(CH₂)₂CH₃], [ZA5183;OC(O)O(CH₂)₃CN,(CH₂)₂CH₃], [ZA5184;OC(O)O(CH₂)₃OCH₃,(CH₂)₂CH₃], [ZA5185;OS(O)₂CH₃,(CH₂)₂CH₃], [ZA5186;OS(O)₂CH₂CH₃,(CH₂)₂CH₃], [ZA5187;OS(O)₂CH(CH₃)₂,(CH₂)₂CH₃], [ZA5188;OS(O)₂(CH₂)₂CH₃,(CH₂)₂CH₃], [ZA5189;OS(O)₂(CH₂)₃CH₃,(CH₂)₂CH₃], [ZA5190;OS(O)₂(CH₂)₄CH₃,(CH₂)₂CH₃], [ZA5191;OS(O)₂(CH₂)₅CH₃,(CH₂)₂CH₃], [ZA5192;OS(O)₂-c-Pr,(CH₂)₂CH₃], [ZA5193;OS(O)₂-c-Pen,(CH₂)₂CH₃], [ZA5194;OS(O)₂-c-Hex,(CH₂)₂CH₃], [ZA5195;OS(O)₂Ph,(CH₂)₂CH₃], [ZA5196;OS(O)₂(2-Py),(CH₂)₂CH₃], [ZA5197;OS(O)₂(3-Py),(CH₂)₂CH₃], [ZA5198;OS(O)₂(4-Py),(CH₂)₂CH₃], [ZA5199;OS(O)₂ CF₃,(CH₂)₂CH₃], [ZA5200;OS(O)₂CH₂Ph,(CH₂)₂CH₃], [ZA5201;OH,c-Pr], [ZA5202;OCH₃,c-Pr], [ZA5203;OCH₂CH₃,c-Pr], [ZA5204;OCH(CH₃)₂,c-Pr], [ZA5205;O(CH₂)₂CH₃,c-Pr], [ZA5206;O(CH₂)₃CH₃,c-Pr], [ZA5207;O(CH₂)₄CH₃,c-Pr], [ZA5208;O(CH₂)₅CH₃,c-Pr], [ZA5209;OCH₂CH=CH₂,c-Pr], [ZA5210;OCH₂C≡CH,c-Pr], [ZA5211;OCH₂C≡CCH₃,c-Pr], [ZA5212;O-c-Pr,c-Pr], [ZA5213;O-c-Pen,c-Pr], [ZA5214;O-c-Hex,c-Pr], [ZA5215;OPh,c-Pr], [ZA5216;OCH₂Ph,c-Pr], [ZA5217;OCH₂(2-Py),c-Pr], [ZA5218;OCH₂(3-Py),c-Pr], [ZA5219;OCH₂(4-Py),c-Pr], [ZA5220;OCH₂CN,c-Pr], [ZA5221;OCH₂NO₂,c-Pr], [ZA5222;O(CH₂)₂F,c-Pr], [ZA5223;O(CH₂)₂CN,c-Pr], [ZA5224;O(CH₂)₂Ph,c-Pr], [ZA5225;O(CH₂)₂OCH₃,c-Pr], [ZA5226;O(CH₂)₃F,c-Pr], [ZA5227;O(CH₂)₃CN,c-Pr], [ZA5228;O(CH₂)₃NO₂,c-Pr], [ZA5229;O(CH₂)₃Ph,c-Pr], [ZA5230;O(CH₂)₃OCH₃,c-Pr], [ZA5231;(CH₂)₄F,c-Pr], [ZA5232;O(CH₂)₄CN,c-Pr], [ZA5233;O(CH₂)₄NO₂,c-Pr], [ZA5234;O(CH₂)₄Ph,c-Pr], [ZA5235;O(CH₂)₄OCH₃,c-Pr], [ZA5236;O(CH₂)₅F,c-Pr], [ZA5237;O(CH₂)₅CN,c-Pr], [ZA5238;O(CH₂)₅NO₂,c-Pr], [ZA5239;O(CH₂)₅Ph,c-Pr], [ZA5240;O(CH₂)₅OCH₃,c-Pr], [ZA5241;(CH₂)₆ F,c-Pr], [ZA5242;O(CH₂)₆CN,c-Pr], [ZA5243;O(CH₂)₆NO₂,c-Pr], [ZA5244;O(CH₂)₆ Ph,c-Pr], [ZA5245;O(CH₂)₆OCH₃,c-Pr], [ZA5246;OC(O)CH₃,c-Pr], [ZA5247;OC(O)CH₂CH₃,c-Pr], [ZA5248;OC(O)CH(CH₃)₂,c-Pr], [ZA5249;OC(O)(CH₂)₂CH₃,c-Pr], [ZA5250;OC(O)(CH₂)₃CH₃,c-Pr], [ZA5251;OC(O)(CH₂)₄CH₃,c-Pr], [ZA5252;OC(O)(CH₂)₅CH₃,c-Pr], [ZA5253;OC(O)CH₂CH=CH₂,c-Pr], [ZA5254;OC(O)CH₂C≡CH,c-Pr], [ZA5255;OC(O)CH₂C≡CCH₃,c-Pr], [ZA5256;OC(O)c-Pr,c-Pr], [ZA5257;OC(O)c-Pen,c-Pr], [ZA5258;OC(O)c-Hex,c-Pr], [ZA5259;OC(O)Ph,c-Pr], [ZA5260;OC(O)(2-Py),c-Pr], [ZA5261;OC(O)(3-Py),c-Pr], [ZA5262;OC(O)(4-Py),c-Pr], [ZA5263;OC(O)CH₂Ph,c-Pr], [ZA5264;OC(O)CH₂ (2-Py),c-Pr], [ZA5265;OC(O)CH₂(3-Py),c-Pr], [ZA5266;OC(O)CH₂(4-Py),c-Pr], [ZA5267;OC(O)CH₂CN,c-Pr], [ZA5268;OC(O)CH₂NO₂,c-Pr], [ZA5269;OC(O)(CH₂)₂ F,c-Pr], [ZA5270;OC(O)(CH₂)₂ CN,c-Pr], [ZA5271;OC(O)(CH₂)₂NO₂,c-Pr], [ZA5272;OC(O)(CH₂)₂Ph,c-Pr], [ZA5273;OC(O)(CH₂)₂OCH₃,c-Pr], [ZA5274;OC(O)(CH₂)₃F,c-Pr], [ZA5275;OC(O)(CH₂)₃CN,c-Pr], [ZA5276;OC(O)(CH₂)₃NO₂,c-Pr], [ZA5277;OC(O)(CH₂)₃OCH₃,c-Pr], [ZA5278;OC(O)NH₂,c-Pr], [ZA5279;OC(O)NHCH₃,c-Pr], [ZA5280;OC(O)NHCH₂CH₃,c-Pr], [ZA5281;OC(O)NH(CH₂)₂CH₃,c-Pr], [ZA5282;OC(O)NH(CH₂)₃CH₃,c-Pr], [ZA5283;OC(O)NH(CH₂)₄CH₃,c-Pr], [ZA5284;OC(O)NH(CH₂)₅CH₃,c-Pr], [ZA5285;OC(O)NHCH(CH₃)₂,c-Pr], [ZA5286;OC(O)NHCH₂F,c-Pr], [ZA5287;OC(O)NHCH₂CN,c-Pr], [ZA5288;OC(O)NHCH₂OCH₃,c-Pr], [ZA5289;OC(O)NHCH₂Ph,c-Pr], [ZA5290;OC(O)NH(CH₂)₂F,c-Pr], [ZA5291;OC(O)NH(CH₂)₂CN,c-Pr], [ZA5292;OC(O)NH(CH₂)₂OCH₃,c-Pr], [ZA5293;OC(O)NH(CH₂)₃F,c-Pr], [ZA5294;OC(O)NH(CH₂)₃CN,c-Pr], [ZA5295;OC(O)NH(CH₂)₃OCH₃,c-Pr], [ZA5296;OC(O)NH(CH₂)₄F,c-Pr], [ZA5297;OC(O)NH(CH₂)₄CN,c-Pr], [ZA5298;OC(O)NH(CH₂)₄OCH₃,c-Pr], [ZA5299;OC(O)NHPh,c-Pr], [ZA5300;OC(O)NH(2-Py),c-Pr], [ZA5301;OC(O)NH(3-Py),c-Pr], [ZA5302;OC(O)NH(4-Py),c-Pr], [ZA5303;OC(O)N(CH₃)₂, c-Pr], [ZA5304;OC(O)N(CH₃)CH₂CH₃,c-Pr], [ZA5305;OC(O)N(CH₃)(CH₂)₂CH₃,c-Pr], [ZA5306;OC(O)N(CH₃)(CH₂)₃CH₃,c-Pr], [ZA5307;OC(O)N(CH₃)CH(CH₃)₂,c-Pr], [ZA5308;OC(O)N(CH₃)CH₂F,c-Pr], [ZA5309;OC(O)N(CH₃)CH₂CN,c-Pr], [ZA5310;OC(O)N(CH₃)CH₂OCH₃,c-Pr], [ZA5311;OC(O)N(CH₃)CH₂Ph,c-Pr], [ZA5312;OC(O)N(CH₃)(CH₂)₂F,c-Pr], [ZA5313;OC(O)N(CH₃)(CH₂)₂CN,c-Pr], [ZA5314;OC(O)N(CH₃)(CH₂)₂OCH₃,c-Pr], [ZA5315;OC(O)N(CH₃)Ph,c-Pr], [ZA5316;OC(O)N(CH₃)(2-Py),c-Pr], [ZA5317;OC(O)N(CH₃)(3-Py),c-Pr], [ZA5318;OC(O)N(CH₃)(4-Py),c-Pr], [ZA5319;OC(O)N(CH₂CH₃)₂,c-Pr], [ZA5320;OC(O)(Pyr),c-Pr], [ZA5321;OC(O)(Pip),c-Pr], [ZA5322;OC(O)(Mor),c-Pr], [ZA5323;OC(O)OCH₃,c-Pr], [ZA5324;OC(O)OCH₂CH₃,c-Pr], [ZA5325;OC(O)OCH(CH₃)₂,c-Pr], [ZA5326;OC(O)O(CH₂)₂CH₃,c-Pr], [ZA5327;OC(O)O(CH₂)₃CH₃,c-Pr], [ZA5328;OC(O)O(CH₂)₄CH₃,c-Pr], [ZA5329;OC(O)O(CH₂)₅CH₃,c-Pr], [ZA5330;OC(O)OCH₂CH=CH₂,c-Pr], [ZA5331;OC(O)OCH₂C≡CH,c-Pr], [ZA5332;OC(O)OCH₂C≡CCH₃,c-Pr], [ZA5333;OC(O)O-c-Pr,c-Pr], [ZA5334;OC(O)O-c-Pen,c-Pr], [ZA5335;OC(O)O-c-Hex,c-Pr], [ZA5336;OC(O)OPh,c-Pr], [ZA5337;OC(O)O(2-Py),c-Pr], [ZA5338;OC(O)O(3-Py),c-Pr], [ZA5339;OC(O)O(4-Py),c-Pr], [ZA5340;OC(O)OCF₃,c-Pr], [ZA5341;OC(O)OCH₂Ph,c-Pr], [ZA5342;OC(O)OCH₂(2-Py),c-Pr], [ZA5343;OC(O)OCH₂(3-Py),c-Pr], [ZA5344;OC(O)OCH₂(4-Py),c-Pr], [ZA5345;OC(O)OCH₂CN,c-Pr], [ZA5346;OC(O)OCH₂NO₂,c-Pr], [ZA5347;OC(O)O(CH₂)₂F,c-Pr], [ZA5348;OC(O)O(CH₂)₂CN,c-Pr], [ZA5349;OC(O)O(CH₂)₂OCH₃,c-Pr], [ZA5350;OC(O)O(CH₂)₃F,c-Pr], [ZA5351;OC(O)O(CH₂)₃CN,c-Pr], [ZA5352;OC(O)O(CH₂)₃OCH₃,c-Pr], [ZA5353;OS(O)₂CH₃,c-Pr], [ZA5354;OS(O)₂CH₂CH₃,c-Pr], [ZA5355;OS(O)₂CH(CH₃)₂,c-Pr], [ZA5356;OS(O)₂(CH₂)₂CH₃,c-Pr], [ZA5357;OS(O)₂(CH₂)₃CH₃,c-Pr], [ZA5358;OS(O)₂(CH₂)₄CH₃,c-Pr], [ZA5359;OS(O)₂(CH₂)₅CH₃,c-Pr], [ZA5360;OS(O)₂-c-Pr,c-Pr], [ZA5361;OS(O)₂-c-Pen,c-Pr], [ZA5362;OS(O)₂-c-Hex,c-Pr], [ZA5363;OS(O)₂Ph,c-Pr], [ZA5364;OS(O)₂(2-Py),c-Pr], [ZA5365;OS(O)₂(3-Py),c-Pr], [ZA5366;OS(O)₂(4-Py),c-Pr], [ZA5367;OS(O)₂CF₃,c-Pr], [ZA5368;OS(O)₂CH₂Ph,c-Pr], [ZA5369;OH,CH₂Ph], [ZA5370;OCH₃,CH₂Ph], [ZA5371;OCH₂CH₃,CH₂Ph], [ZA5372;OCH(CH₃)₂,CH₂Ph], [ZA5373;O(CH₂)₂CH₃,CH₂Ph], [ZA5374;O(CH₂)₃CH₃,CH₂Ph], [ZA5375;O(CH₂)₄CH₃,CH₂Ph], [ZA5376;O(CH₂)₅CH₃,CH₂Ph], [ZA5377;OCH₂CH=CH₂,CH₂Ph], [ZA5378;OCH₂C≡CH,CH₂Ph], [ZA5379;OCH₂C≡CCH₃,CH₂Ph], [ZA5380;O-c-Pr,CH₂Ph], [ZA5381;O-c-Pen,CH₂Ph], [ZA5382;O-c-Hex,CH₂Ph], [ZA5383;OPh,CH₂Ph], [ZA5384;OCH₂Ph,CH₂Ph], [ZA5385;OCH₂(2-Py),CH₂Ph], [ZA5386;OCH₂(3-Py),CH₂Ph], [ZA5387;OCH₂(4-Py),CH₂Ph], [ZA5388;OCH₂CN,CH₂Ph], [ZA5389;OCH₂NO₂,CH₂Ph], [ZA5390;O(CH₂)₂F,CH₂Ph], [ZA5391;O(CH₂)₂CN,CH₂Ph], [ZA5392;O(CH₂)₂Ph,CH₂Ph], [ZA5393;O(CH₂)₂OCH₃,CH₂Ph], [ZA5394;O(CH₂)₃F,CH₂Ph], [ZA5395;O(CH₂)₃CN,CH₂Ph], [ZA5396;O(CH₂)₃NO₂,CH₂Ph], [ZA5397;O(CH₂)₃Ph,CH₂Ph], [ZA5398;O(CH₂)₃OCH₃,CH₂Ph], [ZA5399;O(CH₂)₄F,CH₂Ph], [ZA5400;O(CH₂)₄CN,CH₂Ph], [ZA5401;(CH₂)₄NO₂,CH₂Ph], [ZA5402;O(CH₂)₄Ph,CH₂Ph], [ZA5403;O(CH₂)₄OCH₃,CH₂Ph], [ZA5404;O(CH₂)₅F,CH₂Ph], [ZA5405;O(CH₂)₅CN,CH₂Ph], [ZA5406;O(CH₂)₅NO₂,CH₂Ph], [ZA5407;O(CH₂)₅Ph,CH₂Ph], [ZA5408;O(CH₂)₅OCH₃,CH₂Ph], [ZA5409;O(CH₂)₆F,CH₂Ph], [ZA5410;(CH₂)₆CN,CH₂Ph], [ZA5411;O(CH₂)₆NO₂,CH₂Ph], [ZA5412;O(CH₂)₆Ph,CH₂Ph], [ZA5413;O(CH₂)₆OCH₃,CH₂Ph], [ZA5414;OC(O)CH₃,CH₂Ph], [ZA5415;OC(O)CH₂CH₃,CH₂Ph], [ZA5416;OC(O)CH(CH₃)₂,CH₂Ph], [ZA5417;OC(O)(CH₂)₂CH₃,CH₂Ph], [ZA5418;OC(O)(CH₂)₃CH₃,CH₂Ph], [ZA5419;OC(O)(CH₂)₄CH₃,CH₂Ph], [ZA5420;OC(O)(CH₂)₅CH₃,CH₂Ph], [ZA5421;OC(O)CH₂CH=CH₂,CH₂Ph], [ZA5422;OC(O)CH₂C≡CH,CH₂Ph], [ZA5423;OC(O)CH₂C≡CCH₃,CH₂Ph], [ZA5424;OC(O)c-Pr,CH₂Ph], [ZA5425;OC(O)c-Pen,CH₂Ph], [ZA5426;OC(O)c-Hex,CH₂Ph], [ZA5427;OC(O)Ph,CH₂Ph], [ZA5428;OC(O)(2-Py),CH₂Ph], [ZA5429;OC(O)(3-Py),CH₂Ph], [ZA5430;OC(O)(4-Py),CH₂Ph], [ZA5431;OC(O)CH₂Ph,CH₂Ph], [ZA5432;OC(O)CH₂(2-Py),CH₂Ph], [ZA5433;OC(O)CH₂(3-Py),CH₂Ph], [ZA5434;OC(O)CH₂(4-Py),CH₂Ph], [ZA5435;OC(O)CH₂CN,CH₂Ph], [ZA5436;OC(O)CH₂NO₂,CH₂Ph], [ZA5437;OC(O)(CH₂)₂F,CH₂Ph], [ZA5438;OC(O)(CH₂)₂CN,CH₂Ph], [ZA5439;OC(O)(CH₂)₂NO₂,CH₂Ph], [ZA5440;OC(O)(CH₂)₂Ph,CH₂Ph], [ZA5441;OC(O)(CH₂)₂OCH₃,CH₂Ph], [ZA5442;OC(O)(CH₂)₃F,CH₂Ph], [ZA5443;OC(O)(CH₂)₃CN,CH₂Ph], [ZA5444;OC(O)(CH₂)₃NO₂,CH₂Ph], [ZA5445;OC(O)(CH₂)₃OCH₃,CH₂Ph], [ZA5446;OC(O)NH₂,CH₂Ph], [ZA5447;OC(O)NHCH₃,CH₂Ph], [ZA5448;OC(O)NHCH₂CH₃,CH₂Ph], [ZA5449;OC(O)NH(CH₂)₂CH₃,CH₂Ph], [ZA5450;OC(O)NH(CH₂)₃CH₃,CH₂Ph], [ZA5451;OC(O)NH(CH₂)₄CH₃,CH₂Ph], [ZA5452;OC(O)NH(CH₂)₅CH₃,CH₂Ph], [ZA5453;OC(O)NHCH(CH₃)₂,CH₂Ph], [ZA5454;OC(O)NHCH₂F,CH₂Ph], [ZA5455;OC(O)NHCH₂CN,CH₂Ph], [ZA5456;OC(O)NHCH₂OCH₃,CH₂Ph], [ZA5457;OC(O)NHCH₂Ph,CH₂Ph], [ZA5458;OC(O)NH(CH₂)₂F,CH₂Ph], [ZA5459;OC(O)NH(CH₂)₂CN,CH₂Ph], [ZA5460;OC(O)NH(CH₂)₂OCH₃,CH₂Ph], [ZA5461;OC(O)NH(CH₂)₃F,CH₂Ph], [ZA5462;OC(O)NH(CH₂)₃CN,CH₂Ph], [ZA5463;OC(O)NH(CH₂)₃OCH₃,CH₂Ph], [ZA5464;OC(O)NH(CH₂)₄F,CH₂Ph], [ZA5465;OC(O)NH(CH₂)₄CN,CH₂Ph], [ZA5466;OC(O)NH(CH₂)₄OCH₃,CH₂Ph], [ZA5467;OC(O)NHPh,CH₂Ph], [ZA5468;OC(O)NH(2-Py),CH₂Ph], [ZA5469;OC(O)NH(3-Py),CH₂Ph], [ZA5470;OC(O)NH(4-Py),CH₂Ph], [ZA5471;OC(O)N(CH₃)₂,CH₂Ph], [ZA5472;OC(O)N(CH₃)CH₂CH₃,CH₂Ph], [ZA5473;OC(O)N(CH₃)(CH₂)₂CH₃,CH₂Ph], [ZA5474;OC(O)N(CH₃)(CH₂)₃CH₃,CH₂Ph], [ZA5475;OC(O)N(CH₃)CH(CH₃)₂,CH₂Ph], [ZA5476;OC(O)N(CH₃)CH₂F,CH₂Ph], [ZA5477;OC(O)N(CH₃)CH₂CN,CH₂Ph], [ZA5478;OC(O)N(CH₃)CH₂OCH₃,CH₂Ph], [ZA5479;OC(O)N(CH₃)CH₂Ph,CH₂Ph], [ZA5480;OC(O)N(CH₃)(CH₂)₂F,CH₂Ph], [ZA5481;OC(O)N(CH)(CH₂)₂CN,CH₂Ph], [ZA5482;OC(O)N(CH₃)(CH₂)₂OCH₃,CH₂Ph], [ZA5483;OC(O)N(CH₃)Ph,CH₂Ph], [ZA5484;OC(O)N(CH₃)(2-Py),CH₂Ph], [ZA5485;OC(O)N(CH₃)(3-Py),CH₂Ph], [ZA5486;OC(O)N(CH₃)(4-Py),CH₂Ph], [ZA5487;OC(O)N(CH₂CH₃)₂,CH₂Ph], [ZA5488;OC(O)(Pyr),CH₂Ph], [ZA5489;OC(O)(Pip),CH₂Ph], [ZA5490;OC(O)(Mor),CH₂Ph], [ZA5491;OC(O)OCH₃,CH₂Ph], [ZA5492;OC(O)OCH₂CH₃,CH₂Ph], [ZA5493;OC(O)OCH(CH₃)₂,CH₂Ph], [ZA5494;OC(O)O(CH₂)₂CH₃,CH₂Ph], [ZA5495;OC(O)O(CH₂)₃CH₃,CH₂Ph], [ZA5496;OC(O)O(CH₂)₄CH₃,CH₂Ph], [ZA5497;OC(O)O(CH₂)₅CH₃,CH₂Ph], [ZA5498;OC(O)OCH₂CH=CH₂,CH₂Ph], [ZA5499;OC(O)OCH₂C≡CH,CH₂Ph], [ZA5500;OC(O)OCH₂C≡CCH₃,CH₂Ph],

[ZA5501;OC(O)O-c-Pr,CH₂Ph], [ZA5502;OC(O)O-c-Pen,CH₂Ph], [ZA5503;OC(O)O-c-Hex,CH₂Ph], [ZA5504;OC(O)OPh,CH₂Ph], [ZA5505;OC(O)O(2-Py),CH₂Ph], [ZA5506;OC(O)O(3-Py),CH₂Ph], [ZA5507;OC(O)O(4-Py),CH₂Ph], [ZA5508;OC(O)OCF₃,CH₂Ph], [ZA5509;OC(O)OCH₂Ph,CH₂Ph], [ZA5510;OC(O)OCH₂(2-Py),CH₂Ph], [ZA5511;OC(O)OCH₂(3-Py),CH₂Ph], [ZA5512;OC(O)OCH₂(4-Py),CH₂Ph], [ZA5513;OC(O)OCH₂CN,CH₂Ph], [ZA5514;OC(O)OCH₂NO₂,CH₂Ph], [ZA5515;OC (O)O(CH$_2$)$_2$F,CH$_2$Ph], [ZA5516;OC(O)O(CH$_2$)$_2$CN,CH$_2$Ph], [ZA5517;OC(O)O(CH$_2$)$_2$OCH$_3$,CH$_2$Ph], [ZA5518;OC(O)O(CH$_2$)$_3$F,CH$_2$Ph], [ZA5519;OC(O)O(CH$_2$)$_3$CN,CH$_2$Ph], [ZA5520;OC(O)O(CH$_2$)$_3$OCH$_3$,CH$_2$Ph], [ZA5521;OS(O)$_2$CH$_3$,CH$_2$Ph], [ZA5522;OS(O)$_2$CH$_2$CH$_3$,CH$_2$Ph], [ZA5523;OS(O)$_2$CH(CH$_3$)$_2$,CH$_2$Ph], [ZA5524;OS(O)$_2$(CH$_2$)$_2$CH$_3$,CH$_2$Ph], [ZA5525;OS(O)$_2$(CH$_2$)$_3$CH$_3$,CH$_2$Ph], [ZA5526;OS(O)$_2$(CH$_2$)$_4$CH$_3$,CH$_2$Ph], [ZA5527;OS(O)$_2$(CH$_2$)$_5$CH$_3$,CH$_2$Ph], [ZA5528;OS(O)$_2$-c-Pr,CH$_2$Ph], [ZA5529;OS(O)$_2$-c-Pen,CH$_2$Ph], [ZA5530;OS(O)$_2$-c-Hex,CH$_2$Ph], [ZA5531;OS(O)$_2$Ph,CH$_2$Ph], [ZA5532;OS(O)$_2$(2-Py),CH$_2$Ph], [ZA5533;OS(O)$_2$(3-Py),CH$_2$Ph], [ZA5534;OS(O)$_2$(4-Py),CH$_2$Ph], [ZA5535;OS(O)$_2$CF$_3$,CH$_2$Ph], [ZA5536;OS(O)$_2$CH$_2$Ph,CH$_2$Ph], [ZA5537;OH,Ph], [ZA5538;OCH$_3$,Ph], [ZA5539;OCH$_2$CH$_3$,Ph], [ZA5540;OCH(CH$_3$)$_2$,Ph], [ZA5541;O(CH$_2$)$_2$CH$_3$,Ph], [ZA5542;O(CH$_2$)$_3$CH$_3$,Ph], [ZA5543;O(CH$_2$)$_4$CH$_3$,Ph], [ZA5544;O(CH$_2$)$_5$CH$_3$,Ph], [ZA5545;OCH$_2$CH=CH$_2$,Ph], [ZA5546;OCH$_2$C≡CH,Ph], [ZA5547;OCH$_2$C≡CCH$_3$,Ph], [ZA5548;O-c-Pr,Ph], [ZA5549;O-c-Pen,Ph], [ZA5550;O-c-Hex,Ph], [ZA5551;OPh,Ph], [ZA5552;OCH$_2$Ph,Ph], [ZA5553;OCH$_2$(2-Py),Ph], [ZA5554;OCH$_2$(3-Py),Ph], [ZA5555;OCH$_2$(4-Py),Ph], [ZA5556;OCH$_2$CN,Ph], [ZA5557;OCH$_2$NO$_2$,Ph], [ZA5558;O(CH$_2$)$_2$F,Ph], [ZA5559;O(CH$_2$)$_2$CN,Ph], [ZA5560;O(CH$_2$)$_2$Ph,Ph], [ZA5561;O(CH$_2$)$_2$OCH$_3$,Ph], [ZA5562;O(CH$_2$)$_3$F,Ph], [ZA5563;O(CH$_2$)$_3$CN,Ph], [ZA5564;O(CH$_2$)$_3$NO$_2$,Ph], [ZA5565;O(CH$_2$)$_3$Ph,Ph], [ZA5566;O(CH$_2$)$_3$OCH$_3$,Ph], [ZA5567;O(CH$_2$)$_4$F,Ph], [ZA5568;O(CH$_2$)$_4$CN,Ph], [ZA5569;O(CH$_2$)$_4$NO$_2$,Ph], [ZA5570;O(CH$_2$)$_4$Ph,Ph], [ZA5571;O(CH$_2$)$_4$OCH$_3$,Ph], [ZA5572;O(CH$_2$)$_5$F,Ph], [ZA5573;O(CH$_2$)$_5$CN,Ph], [ZA5574;O(CH$_2$)$_5$NO$_2$,Ph], [ZA5575;O(CH$_2$)$_5$Ph,Ph], [ZA5576;O(CH$_2$)$_5$OCH$_3$,Ph], [ZA5577;O(CH$_2$)$_6$F,Ph], [ZA5578;O(CH$_2$)$_6$CN,Ph], [ZA5579;O(CH$_2$)$_6$NO$_2$,Ph], [ZA5580;O(CH$_2$)$_6$Ph,Ph], [ZA5581;O(CH$_2$)$_6$OCH$_3$,Ph], [ZA5582;OC(O)CH$_3$,Ph], [ZA5583;OC(O)CH$_2$CH$_3$,Ph], [ZA5584;OC(O)CH(CH$_3$)$_2$,Ph], [ZA5585;OC(O)(CH$_2$)$_2$CH$_3$,Ph], [ZA5586;OC(O)(CH$_2$)$_3$CH$_3$,Ph], [ZA5587;OC(O)(CH$_2$)$_4$CH$_3$,Ph], [ZA5588;OC(O)(CH$_2$)$_5$CH$_3$,Ph], [ZA5589;OC(O)CH$_2$CH=CH$_2$,Ph], [ZA5590;OC(O)CH$_2$C≡CH,Ph], [ZA5591;OC(O)CH$_2$C≡CCH$_3$,Ph], [ZA5592;OC(O)c-Pr,Ph], [ZA5593;OC(O)c-Pen,Ph], [ZA5594;OC(O)c-Hex,Ph], [ZA5595;OC(O)Ph,Ph], [ZA5596;OC(O)(2-Py),Ph], [ZA5597;OC(O)(3-Py),Ph], [ZA5598;OC(O)(4-Py),Ph], [ZA5599;OC(O)CH$_2$Ph,Ph], [ZA5600;OC(O)CH$_2$(2-Py),Ph], [ZA5601;OC(O)CH$_2$(3-Py),Ph], [ZA5602;OC(O)CH$_2$(4-Py),Ph], [ZA5603;OC(O)CH$_2$CN,Ph], [ZA5604;OC(O)CH$_2$NO$_2$,Ph], [ZA5605;OC(O)(CH$_2$)$_2$F,Ph], [ZA5606;OC(O)(CH$_2$)$_2$CN,Ph], [ZA5607;OC(O)(CH$_2$)$_2$NO$_2$,Ph], [ZA5608;OC(O)(CH$_2$)$_2$Ph,Ph], [ZA5609;OC(O)(CH$_2$)$_2$OCH$_3$,Ph], [ZA5610;OC(O)(CH$_2$)$_3$F,Ph], [ZA5611;OC(O)(CH$_2$)$_3$CN,Ph], [ZA5612;OC(O)(CH$_2$)$_3$NO$_2$,Ph], [ZA5613;OC(O)(CH$_2$)$_3$OCH$_3$,Ph], [ZA5614;OC(O)NH$_2$,Ph], [ZA5615;OC(O)NHCH$_3$,Ph], [ZA5616;OC(O)NHCH$_2$CH$_3$,Ph], [ZA5617;OC(O)NH(CH$_2$)$_2$CH$_3$,Ph], [ZA5618;OC(O)NH(CH$_2$)$_3$CH$_3$,Ph], [ZA5619;OC(O)NH(CH$_2$)$_4$CH$_3$,Ph], [ZA5620;OC(O)NH(CH$_2$)$_5$CH$_3$,Ph], [ZA5621;OC(O)NHCH(CH$_3$)$_2$,Ph], [ZA5622;OC(O)NHCH$_2$F,Ph], [ZA5623;OC(O)NHCH$_2$CN,Ph], [ZA5624;OC(O)NHCH$_2$OCH$_3$,Ph], [ZA5625;OC(O)NHCH$_2$Ph,Ph], [ZA5626;OC(O)NH(CH$_2$)$_2$F,Ph], [ZA5627;OC(O)NH(CH$_2$)$_2$CN,Ph], [ZA5628;OC(O)NH(CH$_2$)$_2$OCH$_3$,Ph], [ZA5629;OC(O)NH(CH$_2$)$_3$F,Ph], [ZA5630;OC(O)NH(CH$_2$)$_3$CN,Ph], [ZA5631;OC(O)NH(CH$_2$)$_3$OCH$_3$,Ph], [ZA5632;OC(O)NH(CH$_2$)$_4$F,Ph], [ZA5633;OC(O)NH(CH$_2$)$_4$CN,Ph], [ZA5634;OC(O)NH(CH$_2$)$_4$OCH$_3$,Ph], [ZA5635;OC(O)NHPh,Ph], [ZA5636;OC(O)NH(2-Py),Ph], [ZA5637;OC(O)NH(3-Py),Ph], [ZA5638;OC(O)NH(4-Py),Ph], [ZA5639;OC(O)N(CH$_3$)$_2$,Ph], [ZA5640;OC(O)N(CH$_3$)CH$_2$CH$_3$,Ph], [ZA5641;OC(O)N(CH$_3$)(CH$_2$)$_2$CH$_3$,Ph], [ZA5642;OC(O)N(CH$_3$)(CH$_2$)$_3$CH$_3$,Ph], [ZA5643;OC(O)N(CH$_3$)CH(CH$_3$)$_2$,Ph], [ZA5644;OC(O)N(CH$_3$)CH$_2$F,Ph], [ZA5645;OC(O)N(CH$_3$)CH$_2$CN,Ph], [ZA5646;OC(O)N(CH$_3$)CH$_2$OCH$_3$,Ph], [ZA5647;OC(O)N(CH$_3$)CH$_2$Ph,Ph], [ZA5648;OC(O)N(CH$_3$)(CH$_2$)$_2$F,Ph], [ZA5649;OC(O)N(CH$_3$)(CH$_2$)$_2$CN,Ph], [ZA5650;OC(O)N(CH$_3$)(CH$_2$)$_2$OCH$_3$,Ph], [ZA5651;OC(O)N(CH$_3$)Ph,Ph], [ZA5652;OC(O)N(CH$_3$)(2-Py),Ph], [ZA5653;OC(O)N(CH$_3$)(3-Py),Ph], [ZA5654;OC(O)N(CH$_3$)(4-Py),Ph], [ZA5655;OC(O)N(CH$_2$CH$_3$)$_2$,Ph], [ZA5656;OC(O)(Pyr),Ph], [ZA5657;OC(O)(Pip),Ph], [ZA5658;OC(O)(Mor),Ph], [ZA5659;OC(O)OCH$_3$,Ph], [ZA5660;OC(O)OCH$_2$CH$_3$,Ph], [ZA5661;OC(O)OCH(CH$_3$)$_2$,Ph], [ZA5662;OC(O)O(CH$_2$)$_2$CH$_3$,Ph], [ZA5663;OC(O)O(CH$_2$)$_3$CH$_3$,Ph], [ZA5664;OC(O)O(CH$_2$)$_4$CH$_3$,Ph], [ZA5665;OC(O)O(CH$_2$)$_5$CH$_3$,Ph], [ZA5666;OC(O)OCH$_2$CH=CH$_2$,Ph], [ZA5667;OC(O)OCH$_2$C≡CH,Ph], [ZA5668;OC(O)OCH$_2$C≡CCH$_3$,Ph], [ZA5669;OC(O)O-c-Pr,Ph], [ZA5670;OC(O)O-c-Pen,Ph], [ZA5671;OC(O)O-c-Hex,Ph], [ZA5672;OC(O)OPh,Ph], [ZA5673;OC(O)O(2-Py),Ph], [ZA5674;OC(O)O(3-Py),Ph], [ZA5675;OC(O)O(4-Py),Ph], [ZA5676;OC(O)OCF$_3$,Ph], [ZA5677;OC(O)OCH$_2$Ph,Ph], [ZA5678;OC(O)OCH$_2$(2-Py),Ph], [ZA5679;OC(O)OCH$_2$(3-Py),Ph], [ZA5680;OC(O)OCH$_2$(4-Py),Ph], [ZA5681;OC(O)OCH$_2$CN,Ph], [ZA5682;OC(O)OCH$_2$NO$_2$,Ph], [ZA5683;OC(O)O(CH$_2$)$_2$F,Ph], [ZA5684;OC(O)O(CH$_2$)$_2$CN,Ph], [ZA5685;OC(O)O(CH$_2$)$_2$OCH$_3$,Ph], [ZA5686;OC(O)O(CH$_2$)$_3$F,Ph], [ZA5687;OC(O)O(CH$_2$)$_3$CN,Ph], [ZA5688;OC(O)O(CH$_2$)$_3$OCH$_3$,Ph], [ZA5689;OS(O)$_2$CH$_3$,Ph], [ZA5690;OS(O)$_2$CH$_2$CH$_3$,Ph], [ZA5691;OS(O)$_2$CH(CH$_3$)$_2$,Ph], [ZA5692;OS(O)$_2$(CH$_2$)$_2$CH$_3$,Ph], [ZA5693;OS(O)$_2$(CH$_2$)$_3$CH$_3$,Ph], [ZA5694;OS(O)$_2$(CH$_2$)$_4$CH$_3$,Ph], [ZA5695;OS(O)$_2$(CH$_2$)$_5$CH$_3$,Ph], [ZA5696;OS(O)$_2$-c-Pr,Ph], [ZA5697;OS(O)$_2$-c-Pen,Ph], [ZA5698;OS(O)$_2$-c-Hex,Ph], [ZA5699;OS(O)$_2$Ph,Ph], [ZA5700;OS(O)$_2$(2-Py),Ph], [ZA5701;OS(O)$_2$(3-Py),Ph], [ZA5702;OS(O)$_2$(4-Py),Ph], [ZA5703;OS(O)$_2$CF$_3$,Ph], [ZA5704;OS(O)$_2$CH$_2$Ph,Ph], [ZA5705;OH,2-Py], [ZA5706;OCH$_3$,2-Py], [ZA5707;OCH$_2$CH$_3$,2-Py], [ZA5708;OCH(CH$_3$)$_2$,2-Py], [ZA5709;O(CH$_2$)$_2$CH$_3$,2-Py], [ZA5710;O(CH$_2$)$_3$CH$_3$,2-Py], [ZA5711;O(CH$_2$)$_4$CH$_3$,2-Py], [ZA5712;O(CH$_2$)$_5$CH$_3$,2-Py], [ZA5713;OCH$_2$CH=CH$_2$,2-Py], [ZA5714;OCH$_2$C≡CH,2-Py], [ZA5715;OCH$_2$C≡CCH$_3$,2-Py], [ZA5716;O-c-Pr,2-Py], [ZA5717;O-c-Pen,2-Py], [ZA5718;O-c-Hex,2-Py], [ZA5719;OPh,2-Py], [ZA5720;OCH$_2$Ph,2-Py], [ZA5721;OCH$_2$(2-Py),2-Py], [ZA5722;OCH$_2$(3-Py),2-Py], [ZA5723;OCH$_2$(4-Py),2-Py], [ZA5724;OCH$_2$CN,2-Py], [ZA5725;OCH$_2$NO$_2$,2-Py], [ZA5726;O(CH$_2$)$_2$F,2-Py], [ZA5727;O(CH$_2$)$_2$CN,2-Py], [ZA5728;O(CH$_2$)$_2$Ph,2-Py], [ZA5729;O(CH$_2$)$_2$OCH$_3$,2-Py], [ZA5730;O(CH$_2$)$_3$F,2-Py], [ZA5731;(CH$_2$)$_3$CN,2-Py], [ZA5732;O(CH$_2$)$_3$NO$_2$,2-Py], [ZA5733;O(CH$_2$)$_3$Ph,2-Py], [ZA5734;O(CH$_2$)$_3$OCH$_3$,2-Py], [ZA5735;O(CH$_2$)$_4$F,2-Py], [ZA5736;O(CH$_2$)$_4$CN,2-Py], [ZA5737;O(CH$_2$)$_4$NO$_2$,2-Py], [ZA5738;O(CH$_2$)$_4$Ph,2-Py], [ZA5739;O(CH$_2$)$_4$OCH$_3$,2-Py], [ZA5740;O(CH$_2$)$_5$F,2-Py], [ZA5741;(CH$_2$)$_5$CN,2-Py], [ZA5742;O(CH$_2$)$_5$NO$_2$,2-Py], [ZA5743;O(CH$_2$)$_5$Ph,2-Py], [ZA5744;O(CH$_2$)$_5$OCH$_3$,2-Py], [ZA5745;O(CH$_2$)$_6$F,2-Py], [ZA5746;O(CH$_2$)$_6$CN,2-Py], [ZA5747;O(CH$_2$)$_6$NO$_2$,2-Py], [ZA5748;O(CH$_2$)$_6$Ph,2-Py], [ZA5749;O(CH$_2$)$_6$OCH$_3$,2-Py], [ZA5750;OC(O)CH$_3$,2-Py], [ZA5751;OC(O)CH$_2$CH$_3$,2-Py], [ZA5752;OC(O)CH(CH$_3$)$_2$,2-Py], [ZA5753;OC(O)(CH$_2$)$_2$CH$_3$,2-Py], [ZA5754;OC(O)(CH$_2$)$_3$CH$_3$,2-Py], [ZA5755;OC(O)(CH$_2$)$_4$CH$_3$,2-

Py], [ZA5756;OC(O)(CH$_2$)$_5$CH$_3$,2-Py], [ZA5757;OC(O)CH$_2$CH=CH$_2$,2-Py], [ZA5758;OC(O)CH$_2$C≡CH,2-Py], [ZA5759;OC(O)CH$_2$C≡CCH$_3$,2-Py], [ZA5760;OC(O)c-Pr,2-Py], [ZA5761;OC(O)c-Pen,2-Py], [ZA5762;OC(O)c-Hex,2-Py], [ZA5763;OC(O)Ph,2-Py], [ZA5764;OC(O)(2-Py),2-Py], [ZA5765;OC(O)(3-Py),2-Py], [ZA5766;OC(O)(4-Py),2-Py], [ZA5767;OC(O)CH$_2$Ph,2-Py], [ZA5768;OC(O)CH$_2$(2-Py),2-Py], [ZA5769;OC(O)CH$_2$(3-Py),2-Py], [ZA577;OC(O)CH$_2$(4-Py),2-Py], [ZA5771;OC(O)CH$_2$CN,2-Py], [ZA5772;OC(O)CH$_2$NO$_2$,2-Py], [ZA5773;OC(O)(CH$_2$)$_2$F,2-Py], [ZA5774;OC(O)(CH)$_2$CN,2-Py], [ZA5775;OC(O)(CH$_2$)$_2$NO$_2$,2-Py], [ZA5776;OC(O)(CH$_2$)$_2$Ph,2-Py], [ZA5777;OC(O)(CH$_2$)$_2$OCH$_3$,2-Py], [ZA5778;OC(O)(CH$_2$)$_3$F,2-Py], [ZA5779;OC(O)(CH$_2$)$_3$CN,2-Py], [ZA5780;OC(O)(CH$_2$)$_3$NO$_2$,2-Py], [ZA5781;OC(O)(CH$_2$)$_3$OCH$_3$,2-Py], [ZA5782;OC(O)NH$_2$,2-Py], [ZA5783;OC(O)NHCH$_3$,2-Py], [ZA5784;OC(O)NHCH$_2$CH$_3$,2-Py], [ZA5785;OC(O)NH(CH$_2$)$_2$CH$_3$,2-Py], [ZA5786;OC(O)NH(CH$_2$)$_3$CH$_3$,2-Py], [ZA5787;OC(O)NH(CH$_2$)$_4$CH$_3$,2-Py], [ZA5788;OC(O)NH(CH$_2$)$_5$CH$_3$,2-Py], [ZA5789;OC(O)NHCH(CH$_3$)$_2$,2-Py], [ZA5790;OC(O)NHCH$_2$F,2-Py], [ZA5791;OC(O)NHCH$_2$CN,2-Py], [ZA5792;OC(O)NHCH$_2$OCH$_3$,2-Py], [ZA5793;OC(O)NHCH$_2$Ph,2-Py], [ZA5794;OC(O)NH(CH$_2$)$_2$F,2-Py], [ZA5795;OC(O)NH(CH$_2$)$_2$CN,2-Py], [ZA5796;OC(O)NH(CH$_2$)$_2$OCH$_3$,2-Py], [ZA5797;OC(O)NH(CH$_2$)$_2$F,2-Py], [ZA5798;OC(O)NH(CH$_2$)$_3$CN,2-Py], [ZA5799;OC(O)NH(CH$_2$)$_3$OCH$_3$,2-Py], [ZA5800;OC(O)NH(CH$_2$)$_4$F,2-Py], [ZA5801;OC(O)NH(CH$_2$)$_4$CN,2-Py], [ZA5802;OC(O)NH(CH$_2$)$_4$OCH$_3$,2-Py], [ZA5803;OC(O)NHPh,2-Py], [ZA5804;OC(O)NH(2-Py),2-Py], [ZA5805;OC(O)NH(3-Py),2-Py], [ZA5806;OC(O)NH(4-Py),2-Py], [ZA5807;OC(O)N(CH$_3$)$_2$,2-Py], [ZA5808;OC(O)N(CH$_3$)CH$_2$CH$_3$,2-Py], [ZA5809;OC(O)N(CH$_3$)(CH$_2$)$_2$CH$_3$,2-Py], [ZA5810;OC(O)N(CH$_3$)(CH$_2$)$_3$CH$_3$,2-Py], [ZA5811;OC(O)N(CH$_3$)CH(CH$_3$)$_2$,2-Py], [ZA5812;OC(O)N(CH$_3$)CH$_2$F,2-Py], [ZA5813;OC(O)N(CH$_3$)CH$_2$CN,2-Py], [ZA5814;OC(O)N(CH$_3$)CH$_2$OCH$_3$,2-Py], [ZA5815;OC(O)N(CH$_3$)CH$_2$Ph,2-Py], [ZA5816;OC(O)N(CH$_3$)(CH$_2$)$_2$F,2-Py], [ZA5817;OC(O)N(CH$_3$)(CH$_2$)$_2$CN,2-Py], [ZA5818;OC(O)N(CH$_3$)(CH$_2$)$_2$OCH$_3$,2-Py], [ZA5819;OC(O)N(CH$_3$)Ph,2-Py], [ZA5820;OC(O)N(CH$_3$)(2-Py),2-Py], [ZA5821;OC(O)N(CH$_3$)(3-Py),2-Py], [ZA5822;OC(O)N(CH$_3$)(4-Py),2-Py], [ZA5823;OC(O)N(CH$_2$CH$_3$)$_2$,2-Py], [ZA5824;OC(O)(Pyr),2-Py], [ZA5825;OC(O)(Pip),2-Py], [ZA5826;OC(O)(Mor),2-Py], [ZA5827;OC(O)OCH$_3$,2-Py], [ZA5828;OC(O)OCH$_2$CH$_3$,2-Py], [ZA5829;OC(O)OCH(CH$_3$)$_2$,2-Py], [ZA5830;OC(O)O(CH$_2$)$_2$CH$_3$,2-Py], [ZA5831;OC(O)O(CH$_2$)$_3$CH$_3$,2-Py], [ZA5832;OC(O)O(CH$_2$)$_4$CH$_3$,2-Py], [ZA5833;OC(O)O(CH$_2$)$_5$CH$_3$,2-Py], [ZA5834;OC(O)OCH$_2$CH$_2$CH=CH$_2$,2-Py], [ZA5835;OC(O)OCH$_2$C≡CH,2-Py], [ZA5836;OC(O)OCH$_2$C≡CCH$_3$,2-Py], [ZA5837;OC(O)O-c-Pr,2-Py], [ZA5838;OC(O)O-c-Pen,2-Py], [ZA5839;OC(O)O-c-Hex,2-Py], [ZA5840;OC(O)OPh,2-Py], [ZA5841;OC(O)O(2-Py),2-Py], [ZA5842;OC(O)O(3-Py),2-Py], [ZA5843;OC(O)O(4-Py),2-Py], [ZA5844;OC(O)OCF$_3$,2-Py], [ZA5845;OC(O)OCH$_2$Ph,2-Py], [ZA5846;OC(O)OCH$_2$(2-Py),2-Py], [ZA5847;OC(O)OCH$_2$(3-Py),2-Py], [ZA5848;OC(O)OCH$_2$(4-Py),2-Py], [ZA5849;OC(O)OCH$_2$CN,2-Py], [ZA5850;OC(O)OCH$_2$NO$_2$,2-Py], [ZA5851;OC(O)O(CH$_2$)$_2$F,2-Py], [ZA5852;OC(O)O(CH$_2$)$_2$CN,2-Py], [ZA5853;OC(O)O(CH$_2$)$_2$OCH$_3$,2-Py], [ZA5854;OC(O)O(CH$_2$)$_3$F,2-Py], [ZA5855;OC(O)O(CH$_2$)$_3$CN,2-Py], [ZA5856;OC(O)O(CH$_2$)$_3$OCH$_3$,2-Py], [ZA5857;OS(O)$_2$CH$_3$,2-Py], [ZA5858;OS(O)$_2$CH$_2$CH$_3$,2-Py], [ZA5859;OS(O)$_2$(CH$_3$)$_2$,2-Py], [ZA5860;OS(O)$_2$(CH$_2$)$_2$CH$_3$,2-Py], [ZA5861;OS(O)$_2$(CH$_2$)$_3$CH$_3$,2-Py], [ZA5862;OS(O)$_2$(CH$_2$)$_4$CH$_3$,2-Py], [ZA5863;OS(O)$_2$(CH$_2$)$_5$CH$_3$,2-Py], [ZA5864;OS(O)$_2$-c-Pr,2-Py], [ZA5865;OS(O)$_2$-c-Pen,2-Py], [ZA5866;OS(O)$_2$-c-Hex,2-Py], [ZA5867;OS(O)$_2$Ph,2-Py], [ZA5868;OS(O)$_2$(2-Py),2-Py], [ZA5869;OS(O)$_2$(3-Py),2-Py], [ZA5870;OS(O)$_2$(4-Py),2-Py], [ZA5871;OS(O)$_2$CF$_3$,2-Py], [ZA5872;OS(O)$_2$CH$_2$Ph,2-Py], [ZA5873;OH,3-Py], [ZA5874;OCH$_3$,3-Py], [ZA5875;OCH$_2$CH$_3$,3-Py], [ZA5876;OCH(CH$_3$)$_2$,3-Py], [ZA5877;O(CH$_2$)$_2$CH$_3$,3-Py], [ZA5878;O(CH$_2$)$_3$CH$_3$,3-Py], [ZA5879;O(CH$_2$)$_4$CH$_3$,3-Py], [ZA5880;O(CH$_2$)$_5$CH$_3$,3-Py], [ZA5881;OCH$_2$CH=CH$_2$,3-Py], [ZA5882;OCH$_2$C≡CH,3-Py], [ZA5883;OCH$_2$C≡CCH$_3$,3-Py], [ZA5884;O-c-Pr,3-Py], [ZA5885;O-c-Pen,3-Py], [ZA5886;O-c-Hex,3-Py], [ZA5887;OPh,3-Py], [ZA5888;OCH$_2$Ph,3-Py], [ZA5889;OCH$_2$(2-Py),3-Py], [ZA5890;OCH$_2$(3-Py),3-Py], [ZA5891;OCH$_2$(4-Py),3-Py], [ZA5892;OCH$_2$CN,3-Py], [ZA5893;OCH$_2$NO$_2$,3-Py], [ZA5894;O(CH$_2$)$_2$F,3-Py], [ZA5895;O(CH$_2$)$_2$CN,3-Py], [ZA5896;O(CH$_2$)$_2$Ph,3-Py], L[ZA5897;O(CH$_2$)$_2$OCH$_3$,3-Py], [ZA5898;O(CH$_2$)$_3$F,3-Py], [ZA5899;O(CH$_2$)$_3$CN,3-Py], [ZA5900;O(CH$_2$)$_3$NO$_2$,3-Py], [ZA5901;(CH$_2$)$_3$Ph,3-Py], [ZA5902;O(CH$_2$)$_3$OCH$_3$,3-Py], [ZA5903;O(CH$_2$)$_4$F,3-Py], [ZA5904;O(CH$_2$)$_4$CN,3-Py], [ZA5905;O(CH$_2$)$_4$NO$_2$,3-Py], [ZA5906;O(CH$_2$)$_4$Ph,3-Py], [ZA5907;O(CH$_2$)$_4$OCH$_3$,3-Py], [ZA5908;O(CH$_2$)$_5$F,3-Py], [ZA5909;O(CH$_2$)$_5$CN,3-Py], [ZA5910;O(CH$_2$)$_5$NO$_2$,3-Py], [ZA5911;O(CH$_2$)$_5$Ph,3-Py], [ZA5912;O(CH$_2$)$_5$OCH$_3$,3-Py], [ZA5913;O(CH$_2$)$_6$F,3-Py], [ZA5914;O(CH$_2$)$_6$CN,3-Py], [ZA5915;O(CH$_2$)$_6$NO$_2$,3-Py], [ZA5916;O(CH$_2$)$_6$Ph,3-Py], [ZA5917;O(CH$_2$)$_6$OCH$_3$,3-Py], [ZA5918;OC(O)CH$_3$,3-Py], [ZA5919;OC(O)CH$_2$CH$_3$,3-Py], [ZA5920;OC(O)CH(CH$_3$)$_2$,3-Py], [ZA5921;OC(O)(CH$_2$)$_2$CH$_3$,3-Py], [ZA5922;OC(O)(CH$_2$)$_3$CH$_3$,3-Py], [ZA5923;OC(O)(CH$_2$)$_4$CH$_3$,3-Py], [ZA5924;OC(O)(CH$_2$)$_5$CH$_3$,3-Py], [ZA5925;OC(O)CH$_2$CH=CH$_2$,3-Py], [ZA5926;OC(O)CH$_2$C≡CH,3-Py], [ZA5927;OC(O)CH$_2$C≡CCH$_3$,3-Py], [ZA5928;OC(O)c-Pr,3-Py], [ZA5929;OC(O)c-Pen,3-Py], [ZA5930;OC(O)c-Hex,3-Py], [ZA5931;OC(O)Ph,3-Py], [ZA5932;OC(O)(2-Py),3-Py], [ZA5933;OC(O)(3-Py),3-Py], [ZA5934;OC(O)(4-Py),3-Py], [ZA5935;OC(O)CH$_2$Ph,3-Py], [ZA5936;OC(O)CH$_2$(2-Py),3-Py], [ZA5937;OC(O)CH$_2$(3-Py),3-Py], [ZA5938;OC(O)CH$_2$(4-Py),3-Py], [ZA5939;OC(O)CH$_2$CN,3-Py], [ZA5940;OC(O)CH$_2$NO$_2$,3-Py], [ZA5941;OC(O)(CH$_2$)$_2$F,3-Py], [ZA5942;OC(O)(CH$_2$)$_2$CN,3-Py], [ZA5943;OC(O)(CH$_2$)$_2$NO$_2$,3-Py], [ZA5944;OC(O)(CH$_2$)$_2$Ph,3-Py], [ZA5945;OC(O)(CH$_2$)$_2$OCH$_3$,3-Py], [ZA5946;OC(O)(CH$_2$)$_3$F,3-Py], [ZA5947;OC(O)(CH$_2$)$_3$CN,3-Py], [ZA5948;OC(O)(CH$_2$)$_3$NO$_2$,3-Py], [ZA5949;OC(O)(CH$_2$)$_3$OCH$_3$,3-Py], [ZA5950;OC(O)NH$_2$,3-Py], [ZA5951;OC(O)NHCH$_3$,3-Py], [ZA5952;OC(O)NHCH$_2$CH$_3$,3-Py], [ZA5953;OC(O)NH(CH$_2$)$_2$CH$_3$,3-Py], [ZA5954;OC(O)NH(CH$_2$)$_3$CH$_3$,3-Py], [ZA5955;OC(O)NH(CH$_2$)$_4$CH$_3$,3-Py], [ZA5956;OC(O)NH(CH$_2$)$_5$CH$_3$,3-Py], [ZA5957;OC(O)NHCH(CH$_3$)$_2$,3-Py], [ZA5958;OC(O)NHCH$_2$F,3-Py], [ZA5959;OC(O)NHCH$_2$CN,3-Py], [ZA5960;OC(O)NHCH$_2$OCH$_3$,3-Py], [ZA5961;OC(O)NHCH$_2$Ph,3-Py], [ZA5962;OC(O)NH(CH$_2$)$_2$F,3-Py], [ZA5963;OC(O)NH(CH$_2$)$_2$CN,3-Py], [ZA5964;OC(O)NH(CH$_2$)$_2$OCH$_3$,3-Py], [ZA5965;OC(O)NH(CH$_2$)$_3$F,3-Py], [ZA5966;OC(O)NH(CH$_2$)$_3$CN,3-Py], [ZA5967;OC(O)NH(CH$_2$)$_3$OCH$_3$,3-Py], [ZA5968;OC(O)NH(CH$_2$)$_4$F,3-Py], [ZA5969;OC(O)NH(CH$_2$)$_4$CN,3-Py], [ZA5970;OC(O)NH(CH)$_4$OCH$_3$,3-Py], [ZA5971;OC(O)NHPh,3-Py], [ZA5972;OC(O)NH(2-Py),3-Py], [ZA5973;OC(O)NH(3-Py),3-Py], [ZA5974;OC(O)NH(4-Py),3-Py], [ZA5975;OC(O)N(CH$_3$)$_2$,3-Py], [ZA5976;OC(O)N(CH$_3$)CH$_2$CH$_3$,3-Py], [ZA5977;OC(O)N(CH$_3$)(CH$_2$)$_2$CH$_3$,3-Py], [ZA5978;OC(O)N(CH$_3$)(CH$_2$)$_3$CH$_3$,3-Py], [ZA5979;OC(O)N(CH$_3$)CH(CH$_3$)$_2$,3-Py], [ZA5980;OC(O)N(CH$_3$)CH$_2$F,3-Py],

[ZA5981;OC(O)N(CH₃)CH₂CN,3-Py], [ZA5982;OC(O)N(CH₃)CH₂OCH₃,3-Py], [ZA5983;OC(O)N(CH₃)CH₂Ph,3-Py], [ZA5984;OC(O)N(CH)(CH₂)₂F,3-Py], [ZA5985;OC(O)N(CH₃)(CH₂)₂CN,3-Py], [ZA5986;OC(O)N(CH₃)(CH₂)₂OCH₃,3-Py], [ZA5987;OC(O)N(CH₃)Ph,3-Py], [ZA5988;OC(O)N(CH₃)(2-Py),3-Py], [ZA5989;OC(O)N(CH₃)(3-Py),3-Py], [ZA5990;OC(O)N(CH₃)(4-Py),3-Py], [ZA5991;OC(O)N(CH₂CH₃)₂,3-Py], [ZA5992;OC(O)(Pyr),3-Py], [ZA5993;OC(O)(Pip),3-Py], [ZA5994;OC(O)(Mor),3-Py], [ZA5995;OC(O)OCH₃,3-Py], [ZA5996;OC(O)OCH₂CH₃,3-Py], [ZA5997;OC(O)OCH(CH₃)₂,3-Py], [ZA5998;OC(O)O(CH₂)₂CH₃,3-Py], [ZA5999;OC(O)O(CH₂)₃CH₃,3-Py], [ZA6000;OC(O)O(CH₂)₄CH₃,3-Py], [ZA6001;OC(O)O(CH₂)₅CH₃,3-Py], [ZA6002;OC(O)OCH₂CH=CH₂,3-Py], [ZA6003;OC(O)OCH₂C≡CH,3-Py], [ZA6004;OC(O)OCH₂C≡CCH₃,3-Py], [ZA6005;OC(O)O-c-Pr,3-Py], [ZA6006;OC(O)O-c-Pen,3-Py], [ZA6007;OC(O)O-c-Hex,3-Py], [ZA6008;OC(O)OPh,3-Py], [ZA6009;OC(O)O(2-Py),3-Py], [ZA6010;OC(O)O(3-Py),3-Py], [ZA6011;OC(O)O(4-Py),3-Py], [ZA6012;OC(O)OCF₃,3-Py], [ZA6013;OC(O)OCH₂ Ph,3-Py], [ZA6014;OC(O)OCH₂(2-Py),3-Py], [ZA6015;OC(O)OCH₂(3-Py),3-Py], [ZA6106;OC(O)OCH₂(4-Py),3-Py], [ZA6017;OC(O)OCH₂CN,3-Py], [ZA6018;OC(O)OCH₂NO₂,3-Py], [ZA6019;OC(O)O(CH₂)₂F,3-Py], [ZA6020;OC(O)O(CH₂)₂CN,3-Py], [ZA6021;OC(O)O(CH₂)₂OCH₃,3-Py], [ZA6022;OC(O)O(CH₂)₃F,3-Py], [ZA6023;OC(O)O(CH₂)₃CN,3-Py], [ZA6024;OC(O)O(CH₂)₃OCH₃,3-Py], [ZA6025;OS(O)₂CH₃,3-Py], [ZA6026;OS(O)₂CH₂CH₃,3-Py], [ZA6027;OS(O)₂CH(CH₃)₂,3-Py], [ZA6028;OS(O)₂(CH₂)₂CH₃,3-Py], [ZA6029;OS(O)₂(CH₂)₃CH₃,3-Py], [ZA6030;OS(O)₂(CH₂)₄CH₃,3-Py], [ZA6031;OS(O)₂(CH₂)₅CH₃,3-Py], [ZA6032;OS(O)₂-c-Pr,3-Py], [ZA6033;OS(O)₂-c-Pen,3-Py], [ZA6034;OS(O)₂-c-Hex,3-Py], [ZA6035;OS(O)₂Ph,3-Py], [ZA6036;OS(O)₂ (2-Py),3-Py], [ZA6037;OS(O)₂(3-Py),3-Py], [ZA6038;OS(O)₂(4-Py),3-Py], [ZA6039;OS(O)₂CF₃,3-Py], [ZA6040;OS(O)₂CH₂Ph,3-Py], [ZA6041;OH,4-Py], [ZA6042;OCH₃,4-Py], [ZA6043;OCH₂CH₃,4-Py], [ZA6044;OCH(CH₃)₂,4-Py], [ZA6045;O(CH₂)₂CH₃,4-Py], [ZA6046;O(CH₂)₃CH₃,4-Py], [ZA6047;O(CH₂)₄CH₃,4-Py], [ZA6048;O(CH₂)₅CH₃,4-Py], [ZA6049;OCH₂CH=CH₂,4-Py], [ZA6050;OCH₂ C≡CH,4-Py], [ZA6051;OCH₂C≡CCH₃,4-Py], [ZA6052;O-c-Pr,4-Py], [ZA6053;O-c-Pen,4-Py], [ZA6054;O-c-Hex,4-Py], [ZA6055;OPh,4-Py], [ZA6056;OCH₂Ph,4-Py], [ZA6057;OCH₂(2-Py),4-Py], [ZA6058;OCH₂(3-Py),4-Py], [ZA6059;OCH₂(4-Py),4-Py], [ZA6060;OCH₂CN,4-Py], [ZA6061;OCH₂NO₂,4-Py], [ZA6062;O(CH₂)₂F,4-Py], [ZA6063;O(CH₂)₂CN,4-Py], [ZA6064;O(CH₂)₂Ph,4-Py], [ZA6065;O(CH₂)₂OCH₃,4-Py], [ZA6066;O(CH₂)₃F,4-Py], [ZA6067;O(CH₂)₃CN,4-Py], [ZA6068;O(CH₂)₃NO₂,4-Py], [ZA6069;O(CH₂)₃Ph,4-Py], [ZA6070;O(CH₂)₃OCH₃,4-Py], [ZA6071;(CH₂)₄F,4-Py], [ZA6072;O(CH₂)₄CN,4-Py], [ZA6073;O(CH₂)₄NO₂,4-Py], [ZA6074;O(CH₂)₄Ph,4-Py], [ZA6075;O(CH₂)₄OCH₃,4-Py], [ZA6076;O(CH₂)₅ F,4-Py], [ZA6077;O(CH₂)₅CN,4-Py], [ZA6078;O(CH₂)₅NO₂,4-Py], [ZA6079;O(CH₂)₅ Ph,4-Py], [ZA6080;O(CH₂)₅OCH₃,4-Py], [ZA6081;(CH₂)₆F,4-Py], [ZA6082;O(CH₂)₆ CN,4-Py], [ZA6083;O(CH₂)₆NO₂,4-Py], [ZA6084;O(CH₂)₆Ph,4-Py], [ZA6085;O(CH₂)₆OCH₃,4-Py], [ZA6086;OC(O)CH₃,4-Py], [ZA6087;OC(O)CH₂CH₃,4-Py], [ZA6088;OC(O)CH(CH₃)₂,4-Py], [ZA6089;OC(O)(CH₂)₂CH₃,4-Py], [ZA6090;OC(O)(CH₂)₃CH₃,4-Py], [ZA6091;OC(O)(CH₂)₄CH₃,4-Py], [ZA6092;OC(O)(CH₂)₅CH₃,4-Py], [ZA6093;OC(O)CH₂CH=CH₂,4-Py], [ZA6094;OC(O)CH₂C≡CH,4-Py], [ZA6095;OC(O)CH₂C≡CCH₃,4-Py], [ZA6096;OC(O)c-Pr,4-Py], [ZA6097;OC(O)c-Pen,4-Py], [ZA6098;OC(O)c-Hex,4-Py], [ZA6099;OC(O)Ph,4-Py], [ZA6100;OC(O)(2-Py),4-Py], [ZA6101;OC(O)(3-Py),4-Py], [ZA6102;OC(O)(4-Py),4-Py], [ZA6103;OC(O)CH₂ Ph,4-Py], [ZA6104;OC(O)CH₂(2-Py),4-Py], [ZA6105;OC(O)CH₂(3-Py),4-Py], [ZA6106;OC(O)CH₂(4-Py),4-Py], [ZA6107;OC(O)CH₂CN,4-Py], [ZA6108;OC(O)CH₂NO₂,4-Py], [ZA6109;OC(O)(CH₂)₂F,4-Py], [ZA6110;OC(O)(CH₂)₂CN,4-Py], [ZA6111;OC(O)(CH₂)₂NO₂,4-Py], [ZA6112;OC(O)(CH₂)₂Ph,4-Py], [ZA6113;OC(O)(CH₂)₂OCH₃,4-Py], [ZA6114;OC(O)(CH₂)₃F,4-Py], [ZA6115;OC(O)(CH₂)₃CN,4-Py], [ZA6116;OC(O)(CH₂)₃NO₂,4-Py], [ZA6117;OC(O)(CH₂)₃OCH₃,4-Py], [ZA6118;OC(O)NH₂,4-Py], [ZA6119;OC(O)NHCH₃,4-Py], [ZA6120;OC(O)NHCH₂CH₃,4-Py], [ZA6121;OC(O)NH(CH₂)₂CH₃,4-Py], [ZA6122;OC(O)NH(CH₂)₃CH₃,4-Py], [ZA6123;OC(O)NH(CH₂)₄CH₃,4-Py], [ZA6124;OC(O)NH(CH₂)₅CH₃,4-Py], [ZA6125;OC(O)NHCH(CH₃)₂,4-Py], [ZA6126;OC(O)NHCH₂F,4-Py], [ZA6127;OC(O)NHCH₂CN,4-Py], [ZA6128;OC(O)NHCH₂OCH₃,4-Py], [ZA6129;OC(O)NHCH₂Ph,4-Py], [ZA6130;OC(O)NH(CH₂)₂F,4-Py], [ZA6131;OC(O)NH(CH₂)₂CN,4-Py], [ZA6132;OC(O)NH(CH₂)₂OCH₃,4-Py], [ZA6133;OC(O)NH(CH₂)₃F,4-Py], [ZA6134;OC(O)NH(CH₂)₃CN,4-Py], [ZA6135;OC(O)NH(CH₂)₃OCH₃,4-Py], [ZA6136;OC(O)NH(CH₂)₄F,4-Py], [ZA6137;OC(O)NH(CH₂)₄CN,4-Py], [ZA6138;OC(O)NH(CH₂)₄OCH₃,4-Py], [ZA6139;OC(O)NHPh,4-Py], [ZA6140;OC(O)NH(2-Py),4-Py], [ZA6141;OC(O)NH(3-Py),4-Py], [ZA6142;OC(O)NH(4-Py),4-Py], [ZA6143;OC(O)N(CH₃)₂,4-Py], [ZA6144;OC(O)N(CH₃)CH₂CH₃,4-Py], [ZA6145;OC(O)N(CH₃)(CH₂)₂CH₃,4-Py], [ZA6146;OC(O)N(CH₃)(CH₂)₃CH₃,4-Py], [ZA6147;OC(O)N(CH₃)CH(CH₃)₂,4-Py], [ZA6148;OC(O)N(CH₃)CH₂F,4-Py], [ZA6149;OC(O)N(CH₃)CH₂CN,4-Py], [ZA6150;OC(O)N(CH₃)CH₂OCH₃,4-Py], [ZA6151;OC(O)N(CH₃)CH₂Ph,4-Py], [ZA6152;OC(O)N(CH₃)(CH₂)₂F,4-Py], [ZA6153;OC(O)N(CH₃)(CH₂)₂CN,4-Py], [ZA6154;OC(O)N(CH₃)(CH₂)₂OCH₃,4-Py], [ZA6155;OC(O)N(CH₃)Ph,4-Py], [ZA6156;OC(O)N(CH₃)(2-Py),4-Py], [ZA6157;OC(O)N(CH₃)(3-Py),4-Py], [ZA6158;OC(O)N(CH₃)(4-Py),4-Py], [ZA6159;OC(O)N(CH₂CH₃)₂,4-Py], [ZA6160;OC(O)(Pyr),4-Py], [ZA6161;OC(O)(Pip),4-Py], [ZA6162;OC(O)(Mor),4-Py], [ZA6163;OC(O)OCH₃,4-Py], [ZA6164;OC(O)OCH₂CH₃,4-Py], [ZA6165;OC(O)OCH(CH₃)₂,4-Py], [ZA6166;OC(O)O(CH₂)₂CH₃,4-Py], [ZA6167;OC(O)O(CH₂)₃CH₃,4-Py], [ZA6168;OC(O)O(CH₂)₄CH₃,4-Py], [ZA6169;OC(O)O(CH₂)₅CH₃,4-Py], [ZA6170;OC(O)OCH₂CH=CH₂,4-Py], [ZA6171;OC(O)OCH₂C≡CH,4-Py], [ZA6172;OC(O)OCH₂C≡CCH₃,4-Py], [ZA6173;OC(O)O-c-Pr,4-Py], [ZA6174;OC(O)O-c-Pen,4-Py], [ZA6175;OC(O)O-c-Hex,4-Py], [ZA6176;OC(O)OPh,4-Py], [ZA6177;OC(O)O(2-Py),4-Py], [ZA6178;OC(O)O(3-Py),4-Py], [ZA6179;OC(O)O(4-Py),4-Py], [ZA6180;OC(O)OCF₃,4-Py], [ZA6181;OC(O)OCH₂Ph,4-Py], [ZA6182;OC(O)OCH₂(2-Py),4-Py], [ZA6183;OC(O)OCH₂(3-Py),4-Py], [ZA6184;OC(O)OCH₂(4-Py),4-Py], [ZA6185;OC(O)OCH₂CN,4-Py], [ZA6186;OC(O)OCH₂NO₂,4-Py], [ZA6187;OC(O)O(CH₂)₂F,4-Py], [ZA6188;OC(O)O(CH₂)₂CN,4-Py], [ZA6189;OC(O)O(CH₂)₂OCH₃,4-Py], [ZA6190;OC(O)O(CH₂)₃F,4-Py], [ZA6191;OC(O)O(CH₂)₃CN,4-Py], [ZA6192;OC(O)O(CH₂)₃OCH₃,4-Py], [ZA6193;OS(O)₂CH₃,4-Py], [ZA6194;OS(O)₂CH₂CH₃,4-Py], [ZA6195;OS(O)₂CH(CH₃)₂,4-Py], [ZA6196;OS(O)₂(CH₂)₂CH₃,4-Py], [ZA6197;OS(O)₂(CH₂)₃CH₃,4-Py], [ZA6198;OS(O)₂(CH₂)₄CH₃,4-Py], [ZA6199;OS(O)₂(CH₂)₅CH₃,4-Py], [ZA6200;OS(O)₂-c-Pr,4-Py], [ZA6201;OS(O)₂-c-Pen,4-Py], [ZA6202;OS(O)₂-c-Hex,4-Py], [ZA6203;OS(O)₂Ph,4-Py], [ZA6204;OS(O)₂(2-Py),4-Py], [ZA6205;OS(O)₂(3-Py),4-Py], [ZA6206;OS(O)₂(4-Py),4-Py], [ZA6207;

OS(O)₂CF₃,4-Py], [ZA6208;OS(O)₂CH₂Ph,4-Py], [ZA6209;OH,OCH₂CH₃], [ZA6210;OCH₃,OCH₂CH₃], [ZA6211;OCH₂CH₃,OCH₂CH₃], [ZA6212;OCH(CH₃)₂, OCH₂CH₃], [ZA6213;O(CH₂)₂ CH₃,OCH₂CH₃], [ZA6214; O(CH₂)₃CH₃,OCH₂CH₃], [ZA6215;O(CH₂)₄CH₃, OCH₂CH₃], [ZA6216;O(CH₂)₅CH₃,OCH₂ CH₃], [ZA6217; OCH₂CH=CH₂,OCH₂CH₃], [ZA6218;OCH₂C≡CH, OCH₂CH₃], [ZA6219;OCH₂C≡CCH₃,OCH₂CH₃], [ZA6220;O-c-Pr,OCH₂CH₃], [ZA6221;O-c-Pen, OCH₂CH₃], [ZA6222;O-c-Hex,OCH₂CH₃], [ZA6223;OPh OCH₂CH₃], [ZA6224;OCH₂Ph,OCH₂CH₃], [ZA6225; OCH₂(2-Py),OCH₂CH₃], [ZA6226;OCH₂ (3-Py), OCH₂CH₃], [ZA6227;OCH₂(4-Py),OCH₂CH₃], [ZA6228; OCH₂CN,OCH₂CH₃], [ZA6229;OCH₂NO₂,OCH₂CH₃], [ZA6230;O(CH₂)₂F,OCH₂CH₃], [ZA6231;(CH₂)₂ CN,OCH₂CH₃], [ZA6232;O(CH₂)₂Ph,OCH₂CH₃], [ZA6233;O(CH₂)₂OCH₃,OCH₂CH₃], [ZA6234;O(CH₂)₃F, OCH₂CH₃], [ZA6235;O(CH₂)₃CN,OCH₂CH₃], [ZA6236;O (CH₂)₃ NO₂,OCH₂CH₃], [ZA6237;O(CH₂)₃Ph,OCH₂CH₃], [ZA6238;O(CH₂)₃OCH₃,OCH₂CH₃], [ZA6239;O(CH₂)₄F, OCH₂CH₃], [ZA6240;O(CH₂)₄CN,OCH₂CH₃], [ZA6241; (CH₂)₄NO₂,OCH₂CH₃], [ZA6242;O(CH₂)₄Ph,OCH₂CH₃], [ZA6243;O(CH₂)₄OCH₃,OCH₂CH₃], [ZA6244;O(CH₂)₅F, OCH₂CH₃], [ZA6245;O(CH₂)₅CN,OCH₂CH₃], [ZA6246;O (CH₂)₅NO₂,OCH₂CH₃], [ZA6247;O(CH₂)₅Ph,OCH₂CH₃], [ZA6248;O(CH₂)₅OCH₃,OCH₂CH₃], [ZA6249;O(CH₂)₆F, OCH₂CH₃], [ZA6250;O(CH₂)₆CN,OCH₂CH₃], [ZA6251; (CH₂)₆NO₂,OCH₂CH₃], [ZA6252;O(CH₂)₆Ph,OCH₂CH₃], [ZA6253;(CH₂)₆OCH₃,OCH₂CH₃], [ZA6254;OC(O)CH₃, OCH₂CH₃], [ZA6255;OC(O)CH₂CH₃,OCH₂CH₃], [ZA6256;OC(O)CH(CH₃)₂OCH₂CH₃], [ZA6257;OC(O) (CH₂)₂CH₃,OCH₂CH₃], [ZA6258;OC(O)(CH₂)₃CH₃, OCH₂CH₃], [ZA6259;OC(O)(CH₂)₄CH₃,OCH₂CH₃], [ZA6260;OC(O)(CH₂)₅CH₃,OCH₂CH₃], [ZA6261;OC(O) CH₂CH=CH₂,OCH₂CH₃], [ZA6262;OC(O)CH₂C≡CH, OCH₂CH₃], [ZA6263;OC(O)CH₂C≡CCH₃,OCH₂CH₃], [ZA6264;OC(O)c-Pr,OCH₂CH₃], [ZA6265;OC(O)c-Pen, OCH₂CH₃], [ZA6266;OC(O)c-Hex,OCH₂CH₃], [ZA6267; OC(O)Ph,OCH₂CH₃], [ZA6268;OC(O)(2-Py),OCH₂CH₃], [ZA6269;OC(O)(3-Py),OCH₂CH₃], [ZA6270;OC(O)(4-Py),OCH₂CH₃], [ZA6271;OC(O)CH₂Ph,OCH₂CH₃], [ZA6272;OC(O)CH₂(2-Py),OCH₂CH₃], [ZA6273;OC(O) CH₂(3-Py),OCH₂CH₃], [ZA6274;OC(O)CH₂(4-Py), OCH₂CH₃], [ZA6275;OC(O)CH₂CN,OCH₂CH₃], [ZA6276;OC(O)CH₂NO₂,OCH₂CH₃], [ZA6277;OC(O) (CH₂)₂F,OCH₂CH₃], [ZA6278;OC(O)(CH₂)₂CN, OCH₂CH₃], [ZA6279;OC(O)(CH₂)₂NO₂,OCH₂CH₃], [ZA6280;OC(O)(CH₂)₂Ph,OCH₂CH₃], [ZA6281;OC(O) (CH₂)₂OCH₃,OCH₂CH₃], [ZA6282;OC(O)(CH₂)₃F, OCH₂CH₃], [ZA6283;OC(O)(CH₂)₃CN,OCH₂CH₃], [ZA6284;OC(O)(CH₂)₃NO₂,OCH₂CH₃], [ZA6285;OC(O) (CH₂)₃OCH₃,OCH₂CH₃], [ZA6286;OC(O)NH₂, OCH₂CH₃], [ZA6287;OC(O)NHCH₃,OCH₂CH₃], [ZA6288;OC(O)NHCH₂CH₃,OCH₂CH₃], [ZA6289;OC(O) NH(CH₂)₂CH₃,OCH₂CH₃], [ZA6290;OC(O)NH(CH₂)₃ CH₃,OCH₂CH₃], [ZA6291;OC(O)NH(CH₂)₄CH₃, OCH₂CH₃], [ZA6292;OC(O)NH(CH₂)₅CH₃,OCH₂CH₃], [ZA6293;OC(O)NHCH(CH₃)₂,OCH₂CH₃], [ZA6294;OC (O)NHCH₂F,OCH₂CH₃], [ZA6295;OC(O)NHCH₂CN, OCH₂CH₃], [ZA6296;OC(O)NHCH₂OCH₃,OCH₂CH₃], [ZA6297;OC(O)NHCH₂Ph,OCH₂CH₃], [ZA6298;OC(O) NH(CH₂)₂F,OCH₂CH₃], [ZA6299;OC(O)NH(CH₂)₂CN, OCH₂CH₃], [ZA6300;OC(O)NH(CH₂)₂OCH₃,OCH₂CH₃], [ZA6301;OC(O)NH(CH₂)₃F,OCH₂CH₃], [ZA6302;OC(O) NH(CH₂)₃CN,OCH₂CH₃], [ZA6303;OC(O)NH(CH₂)₃ OCH₃,OCH₂CH₃], [ZA6304;OC(O)NH(CH₂)₄F, OCH₂CH₃], [ZA6305;OC(O)NH(CH₂)₄CN,OCH₂CH₃], [ZA6306;OC(O)NH(CH₂)₄OCH₃,OCH₂CH₃], [ZA6307; OC(O)NHPh,OCH₂CH₃], [ZA6308;OC(O)NH(2-Py), OCH₂CH₃], [ZA6309;OC(O)NH(3-Py),OCH₂CH₃], [ZA6310;OC(O)NH(4-Py),OCH₂CH₃], [ZA6311;OC(O)N (CH₃),OCH₂CH₃], [ZA6312;OC(O)N(CH₃)CH₂CH₃, OCH₂CH₃], [ZA6313;OC(O)N(CH₃)(CH₂)₂CH₃, OCH₂CH₃], [ZA6314;OC(O)N(CH₃)(CH₂)₃CH₃, OCH₂CH₃], [ZA6315;OC(O)N(CH₃)CH(CH₃)₂, OCH₂CH₃], [ZA6316;OC(O)N(CH₃)CH₂F,OCH₂CH₃], [ZA6317;OC(O)N(CH₃)CH₂ CN,OCH₂CH₃], [ZA6318;OC (O)N(CH₃)CH₂OCH₃,OCH₂CH₃], [ZA6319;OC(O)N (CH₃)CH₂Ph,OCH₂CH₃], [ZA6320;OC(O)N(CH₃)(CH₂)₂ F,OCH₂CH₃], [ZA6321;OC(O)N(CH₃)(CH₂)₂CN, OCH₂CH₃], [ZA6322;OC(O)N(CH₃)(CH₂)₂OCH₃, OCH₂CH₃], [ZA6323;OC(O)N(CH₃)Ph,OCH₂CH₃], [ZA6324;OC(O)N(CH₃)(2-Py),OCH₂CH₃], [ZA6325;OC (O)N(CH₃)(3-Py),OCH₂CH₃], [ZA6326;OC(O)N(CH₃)(4-Py),OCH₂CH₃], [ZA6327;OC(O)N(CH₂CH₃)₂,OCH₂CH₃], [ZA6328;OC(O)(Pyr),OCH₂CH₃], [ZA6329;OC(O)(Pip), OCH₂CH₃], [ZA6330;OC(O)(Mor),OCH₂CH₃], [ZA6331; OC(O)OCH₃,OCH₂CH₃], [ZA6332;OC(O)OCH₂CH₃, OCH₂CH₃], [ZA6333;OC(O)OCH(CH₃)₂,OCH₂CH₃], [ZA6334;OC(O)O(CH₂)₂CH₃,OCH₂CH₃], [ZA6335;OC (O)O(CH₂)₃CH₃,OCH₂CH₃], [ZA6336;OC(O)O(CH₂)₄ CH₃,OCH₂CH₃], [ZA6337;OC(O)O(CH₂)₅CH₃, OCH₂CH₃], [ZA6338;OC(O)OCH₂CH=CH₂,OCH₂CH₃], [ZA6339;OC(O)OCH₂C≡CH,OCH₂CH₃], [ZA6340;OC(O) OCH₂C≡CCH₃,OCH,CH₃], [ZA6341;OC(O)O-c-Pr, OCH₂CH₃], [ZA6342;OC(O)O-c-Pen,OCH₂CH₃], [ZA6343;OC(O)O-c-Hex,OCH₂CH₃], [ZA6344;OC(O) OPh,OCH₂CH₃], [ZA6345;OC(O)O(2-Py),OCH₂CH₃], [ZA6346;OC(O)O(3-Py),OCH₂CH₃], [ZA6347;OC(O)O(4-Py),OCH₂CH₃], [ZA6348;OC(O)OCF₃,OCH₂CH₃], [ZA6349;OC(O)OCH₂Ph,OCH₂CH₃], [ZA6350;OC(O) OCH₂(2-Py),OCH₂CH₃], [ZA6351;OC(O)OCH₂(3-Py), OCH₂CH₃], [ZA6352;OC(O)OCH₂(4-Py),OCH₂CH₃], [ZA6353;OC(O)OCH₂CN,OCH₂CH₃], [ZA6354;OC(O) OCH₂NO₂,OCH₂CH₃], [ZA6355;OC(O)O(CH₂)₂F,OCH₂ CH₃], [ZA6356;OC(O)O(CH₂)₂CN,OCH₂CH₃], [ZA6357; OC(O)O(CH₂)₂OCH₃,OCH CH₃], [ZA6358;OC(O)O(CH₂)₃ F,OCH₂CH₃], [ZA6359;OC(O)O(CH₂)₃CN,OCH₂CH₃], [ZA6360;OC(O)O(CH₂)₃OCH₃,OCH₂CH₃], [ZA6361;OS (O)₂ CH₃,OCH₂CH₃], [ZA6362;OS(O)₂CH₂CH₃, OCH₂CH₃], [ZA6363;OS(O)₂CH(CH₃)₂,OCH₂CH₃], [ZA6364;OS(O)₂(CH₂)₂CH₃, OCH₂CH₃], [ZA6365;OS (O)₂ (CH₂)₃CH₃,OCH₂CH₃], [ZA6366;OS(O)₂(CH₂)₄CH₃, OCH₂CH₃], [ZA6367;OS(O)₂(CH₂)₅CH₃,OCH₂CH₃], [ZA6368;OS(O)₂-c-Pr,OCH₂CH₃], [ZA6369;OS(O)₂-c-Pen,OCH₂CH₃], [ZA6370;OS(O)₂-c-Hex,OCH₂CH₃], [ZA6371;OS(O)₂Ph,OCH₂CH₃], [ZA6372;OS(O)₂ (2-Py), OCH₂CH₃], [ZA6373;OS(O)₂(3-Py),OCH₂CH₃], [ZA6374; OS(O)₂(4-Py),OCH₂ CH₃], [ZA6375;OS(O)₂CF₃, OCH₂CH₃], [ZA6376;OS(O)₂CH₂Ph,OCH₂CH₃], [ZA6377;OH,SCH₂CH₃], [ZA6378;OCH₃,SCH₂CH₃], [ZA6379;OCH₂CH₃,SCH₂CH₃], [ZA6380;OCH(CH₃)₂, SCH₂CH₃], [ZA6381;O(CH₂)₂CH₃,SCH₂CH₃], [ZA6382;O (CH₂)₃ CH₃,SCH₂CH₃], [ZA6383;O(CH₂)₄CH₃, SCH₂CH₃], [ZA6384;O(CH₂)₅CH₃,SCH₂CH₃], [ZA6385; OCH₂CH=CH₂,SCH₂CH₃], [ZA6386;OCH₂C≡CH, SCH₂CH₃], [ZA6387;OCH₂C≡CCH₃,SCH₂CH₃], [ZA6388;O-c-Pr,SCH₂CH₃], [ZA6389;O-c-Pen,SCH₂CH₃], [ZA6390;O-c-Hex,SCH₂CH₃], [ZA6391;OPh,SCH₂CH₃], [ZA6392;OCH₂Ph,SCH₂CH₃], [ZA6393;OCH₂(2-Py), SCH₂CH₃], [ZA6394;OCH₂ (3-Py),SCH₂CH₃], [ZA6395; OCH₂(4-Py),SCH₂CH₃], [ZA6396;OCH₂CN,SCH₂CH₃], [ZA6397;OCH₂NO₂,SCH₂CH₃], [ZA6398;O(CH₂)₂F, SCH₂CH₃], [ZA6399;O(CH₂)₂ CN,SCH₂CH₃], [ZA6400;O (CH₂)₂Ph,SCH₂CH₃], [ZA6401;(CH₂)₂OCH₃,SCH₂CH₃], [ZA6402;O(CH₂)₃F,SCH₂CH₃], [ZA6403;O(CH₂)₃CN, SCH₂CH₃], [ZA6404;O(CH₂)₃ NO₂,SCH₂CH₃], [ZA6405; O(CH₂)₃Ph,SCH₂CH₃], [ZA6406;O(CH₂)₃OCH₃, SCH₂CH₃], [ZA6407;O(CH₂)₄F,SCH₂CH₃], [ZA6408;O (CH₂)₄CN,SCH₂CH₃], [ZA6409;O(CH₂)₄ NO₂,SCH₂CH₃], [ZA6410;(CH₂)₄Ph,SCH₂CH₃], [ZA6411;O(CH₂)₄OCH₃, SCH₂CH₃], [ZA6412;O(CH₂)₅F,SCH₂CH₃], [ZA6413;O (CH₂)₅CN,SCH₂CH₃], [ZA6414;O(CH₂)₅ NO₂,SCH₂CH₃], [ZA6415;O(CH₂)₅Ph,SCH₂CH₃], [ZA6416;O(CH₂)₅OCH₃, SCH₂CH₃], [ZA6417;O(CH₂)₆F,SCH₂CH₃], [ZA6418;O (CH₂)₆CN,SCH₂CH₃], [ZA6419;O(CH₂)₆ NO₂,SCH₂CH₃], [ZA6420;O(CH₂)₆Ph,SCH₂CH₃], [ZA6421;(CH₂)₆OCH₃, SCH₂CH₃], [ZA6422;OC(O)CH₃,SCH₂CH₃], [ZA6423;OC (O)CH₂CH₃,SCH₂CH₃], [ZA6424;OC(O)CH(CH₃)₂, SCH₂CH₃], [ZA6425;OC(O)(CH₂)₂CH₃,SCH₂CH₃], [ZA6426;OC(O)(CH₂)₃CH₃,SCH₂CH₃], [ZA6427;OC(O) (CH₂)₄CH₃,SCH₂CH₃], [ZA6428;OC(O)(CH₂)₅CH₃, SCH₂CH₃], [ZA6429;OC(O)CH₂CH=CH₂,SCH₂CH₃], [ZA6430;OC(O)CH₂C≡CH,SCH₂CH₃], [ZA6431;OC(O) CH₂C≡CCH₃,SCH₂CH₃], [ZA6432;OC(O)c-Pr,SCH₂CH₃], [ZA6433;OC(O)c-Pen,SCH₂CH₃], [ZA6434;OC(O)c-Hex, SCH₂CH₃], [ZA6435;OC(O)Ph,SCH₂CH₃], [ZA6436;OC (O)(2-Py),SCH₂CH₃], [ZA6437;OC(O)(3-Py),SCH₂CH₃], [ZA6438;OC(O)(4-Py),SCH₂CH₃], [ZA6439;OC(O) CH₂Ph,SCH₂CH₃], [ZA6440;OC(O)CH₂(2-Py),SCH₂CH₃], [ZA6441;OC(O)CH₂(3-Py),SCH₂CH₃], [ZA6442;OC(O) CH₂(4-Py),SCH₂CH₃], [ZA6443;OC(O)CH₂CN, SCH₂CH₃], [ZA6444;OC(O)CH₂NO₂,SCH₂CH₃], [ZA6445;OC(O)(CH₂)₂F,SCH₂CH₃], [ZA6446;OC(O) (CH₂)₂CN,SCH₂CH₃], [ZA6447;OC(O)(CH₂)₂NO₂, SCH₂CH₃], [ZA6448;OC(O)(CH₂)₂Ph,SCH₂CH₃], [ZA6449;OC(O)(CH₂)₂OCH₃,SCH₂CH₃], [ZA6450;OC(O) (CH₂)₃F,SCH₂CH₃], [ZA6451;OC(O)(CH₂)₃CN, SCH₂CH₃], [ZA6452;OC(O)(CH₂)₃NO₂,SCH₂CH₃], [ZA6453;OC(O)(CH₂)₃OCH₃,SCH₂CH₃], [ZA6454;OC(O) NH₂,SCH₂CH₃], [ZA6455;OC(O)NHCH₃,SCH₂CH₃], [ZA6456;OC(O)NHCH₂CH₃,SCH₂CH₃], [ZA6457;OC(O) NH(CH₂)₂CH₃,SCH₂CH₃], [ZA6458;OC(O)NH(CH₂)₃ CH₃,SCH₂CH₃], [ZA6459;OC(O)NH(CH₂)₄CH₃, SCH₂CH₃], [ZA6460;OC(O)NH(CH₂)₅CH₃,SCH₂CH₃], [ZA6461;OC(O)NHCH(CH₃)₂,SCH₂CH₃], [ZA6462;OC (O)NHCH₂F,SCH₂CH₃], [ZA6463;OC(O)NHCH₂CN, SCH₂CH₃], [ZA6464;OC(O)NHCH₂OCH₃,SCH₂CH₃], [ZA6465;OC(O)NHCH₂Ph,SCH₂CH₃], [ZA6466;OC(O) NH(CH₂)₂F,SCH₂CH₃], [ZA6467;OC(O)NH(CH₂)₂CN, SCH₂CH₃], [ZA6468;OC(O)NH(CH₂)₂OCH₃,SCH₂CH₃], [ZA6469;OC(O)NH(CH₂)₂F,SCH₂CH₃], [ZA6470;OC(O) NH(CH₂)₃CN,SCH₂CH₃], [ZA6471;OC(O)NH(CH₂)₃ OCH₃,SCH₂CH₃], [ZA6472;OC(O)NH(CH₂)₄F, SCH₂CH₃], [ZA6473;OC(O)NH(CH₂)₄CN,SCH₂CH₃], [ZA6474;OC(O)NH(CH₂)₄OCH₃,SCH₂CH₃], [ZA6475;OC (O)NHPh,SCH₂CH₃], [ZA6476;OC(O)NH(2-Py), SCH₂CH₃], [ZA6477;OC(O)NH(3-Py),SCH₂CH₃], [ZA6478;OC(O)NH(4-Py),SCH₂CH₃], [ZA6479;OC(O)N (CH₃),SCH₂CH₃], [ZA6480;OC(O)N(CH₃)CH₂CH₃, SCH₂CH₃], [ZA6481;OC(O)N(CH₃)(CH₂)₂CH₃,SCH₂ CH₃], [ZA6482;OC(O)N(CH₃)(CH₂)₃CH₃,SCH₂CH₃], [ZA6483;OC(O)N(CH₃)CH(CH₃)₂,SCH₂CH₃], [ZA6484; OC(O)N(CH₃)CH₂F,SCH₂CH₃], [ZA6485;OC(O)N(CH₃) CH₂ CN,SCH₂CH₃], [ZA6486;OC(O)N(CH₃)CH₂OCH₃, SCH₂CH₃], [ZA6487;OC(O)N(CH₃)CH₂Ph,SCH₂CH₃], [ZA6488;OC(O)N(CH₃)(CH₂)₂F,SCH₂CH₃], [ZA6489;OC (O)N(CH₃)(CH₂)₂CN,SCH₂CH₃], [ZA6490;OC(O)N(CH₃) (CH₂)₂OCH₃,SCH₂CH₃], [ZA6491;OC(O)N(CH₃)Ph, SCH₂CH₃], [ZA6492;OC(O)N(CH₃)(2-Py),SCH₂CH₃], [ZA6493;OC(O)N(CH₃)(3-Py),SCH₂ CH₃], [ZA6494;OC (O)N(CH₃)(4-Py),SCH₂CH₃], [ZA6495;OC(O)N (CH₂CH₃)₂ SCH₂ CH₃], [ZA6496;OC(O)(Pyr),SCH₂CH₃], [ZA6497;OC(O)(Pip),SCH₂CH₃], [ZA6498;OC(O)(Mor), SCH₂CH₃], [ZA6499;OC(O)OCH₃,SCH₂CH₃], [ZA6500; OC(O)OCH₂CH₃,SCH₂CH₃], [ZA6501;OC(O)OCH(CH₃)₂,SCH₂CH₃], [ZA6502;OC (O)O(CH₂)₂CH₃,SCH₂CH₃], [ZA6503;OC(O)O(CH₂)₃ CH₃,SCH₂CH₃], [ZA6504;OC(O)O(CH₂)₄CH₃,SCH₂CH₃], [ZA6505;OC(O)O(CH₂)CH₃,SCH₂CH₃], [ZA6506;OC(O) OCH₂CH=CH₂,SCH₂CH₃], [ZA6507;OC(O)OCH₂C≡CH, SCH₂CH₃], [ZA6508;OC(O)OCH₂C≡CCH₃,SCH₂CH₃], [ZA6509;OC(O)O-c-Pr,SCH₂CH₃], [ZA6510;OC(O)O-c-Pen,SCH₂CH₃], [ZA6511;OC(O)O-c-Hex,SCH₂CH₃], [ZA6512;OC(O)OPh,SCH₂CH₃], [ZA6513;OC(O)O(2-Py), SCH₂CH₃], [ZA6514;OC(O)O(3-Py),SCH₂CH₃], [ZA6515; OC(O)O(4-Py),SCH₂CH₃], [ZA6516;OC(O)OCF₃, SCH₂CH₃], [ZA6517;OC(O)OCH₂Ph,SCH₂CH₃], [ZA6518;OC(O)OCH₂(2-Py),SCH₂CH₃], [ZA6519;OC(O) OCH₂(3-Py),SCH₂CH₃], [ZA6520;OC(O)OCH₂(4-Py), SCH₂CH₃], [ZA6521;OC(O)OCH₂CN,SCH₂CH₃], [ZA6522;OC(O)OCH₂NO₂,SCH₂CH₃], [ZA6523;OC(O)O (CH₂)₂F,SCH₂CH₃], [ZA6524;OC(O)O(CH₂)₂CN, SCH₂CH₃], [ZA6525;OC(O)O(CH₂)₂OCH₃,SCH₂CH₃], [ZA6526;OC(O)O(CH₂)₂F,SCH₂CH₃], [ZA6527;OC(O)O (CH₂)₃CN,SCH₂CH₃], [ZA6528;OC(O)O(CH₂)₃OCH₃, SCH₂CH₃], [ZA6529;OS(O)₂CH₃,SCH₂CH₃], [ZA6530; OS(O)₂CH₂CH₃,SCH₂CH₃], [ZA6531;OS(O)₂CH(CH₃)₂ SCH₂CH₃], [ZA6532;OS(O)₂(CH₂)₂CH₃,SCH₂CH₃], [ZA6533;OS(O)₂(CH₂)₃CH₃,SCH₂CH₃], [ZA6534;OS(O)₂ (CH₂)₄CH₃,SCH₂CH₃], [ZA6535;OS(O)₂(CH₂)₅CH₃, SCH₂CH₃], [ZA6536;OS(O)₂-c-Pr,SCH₂CH₃], [ZA6537; OS(O)₂-c-Pen,SCH₂CH₃], [ZA6538;OS(O)₂-c-Hex, SCH₂CH₃], [ZA6539;OS(O)₂Ph,SCH₂CH₃], [ZA6540;OS (O)₂(2-Py),SCH₂CH₃], [ZA6541;OS(O)₂ (3-Py), SCH₂CH₃], [ZA6542;OS(O)₂(4-Py),SCH₂CH₃], [ZA6543; OS(O)₂CF₃,SCH₂CH₃], [ZA6544;OS(O)₂CH₂Ph, SCH₂CH₃], [ZA6545;OH,NHCH₂CH₃], [ZA6546;OCH₃, NHCH₂CH₃], [ZA6547;OCH₂CH₃,NHCH₂CH₃], [ZA6548; OCH(CH₃)₂,NHCH₂CH₃], [ZA6549;O(CH₂)₂CH₃, NHCH₂CH₃], [ZA6550;O(CH₂)₃CH₃,NHCH₂CH₃], [ZA6551;O(CH₂)₄CH₃,NHCH₂CH₃], [ZA6552;O(CH₂)₅ CH₃,NHCH₂CH₃], [ZA6553;OCH₂CH=CH₂, NHCH₂CH₃], [ZA6554;OCH₂C≡CH,NHCH₂CH₃], [ZA6555;OCH₂C≡CCH₃,NHCH₂CH₃], [ZA6556;O-c-Pr, NHCH₂CH₃], [ZA6557;O-c-Pen,NHCH₂CH₃], [ZA6558; O-c-Hex,NHCH₂CH₃], [ZA6559;OPh,NHCH₂CH₃], [ZA6560;OCH₂Ph,NHCH₂CH₃], [ZA6561;OCH₂ (2-Py), NHCH₂CH₃], [ZA6562;OCH₂(3-Py),NHCH₂CH₃], [ZA6563;OCH₂ (4-Py),NHCH₂CH₃], [ZA6564;OCH₂CN, NHCH₂CH₃], [ZA6565;OCH₂NO₂,NHCH₂CH₃], [ZA6566;O(CH₂)₂F,NHCH₂CH₃], [ZA6567;O(CH₂)CN, NHCH₂CH₃], [ZA6568;O(CH₂)₂Ph,NHCH₂CH₃], [ZA6569;O(CH₂)₂OCH₃,NHCH₂CH₃], [ZA6570;O(CH₂)₃ F,NHCH₂CH₃], [ZA6571;(CH₂)₃CN,NHCH₂CH₃], [ZA6572;O(CH 2)₃NO₂,NHCH₂CH₃], [ZA6573;O(CH₂)₃ Ph,NHCH₂CH₃], [ZA6574;O(CH₂)₃OCH₃,NHCH₂CH₃], [ZA6575;O(CH₂)₄F,NHCH₂CH₃], [ZA6576;O(CH₂)₄CN, NHCH₂CH₃], [ZA6577;O(CH₂)₄NO₂,NHCH₂CH₃], [ZA6578;(CH₂)₄Ph,NHCH₂CH₃], [ZA6579;O(CH₂)₄ OCH₃,NHCH₂CH₃], [ZA6580;O(CH₂)₅F,NHCH₂CH₃], [ZA6581;(CH₂)₅CN,NHCH₂CH₃], [ZA6582;O(CH₂)₅NO₂, NHCH₂CH₃], [ZA6583;O(CH₂)₅Ph,NHCH₂CH₃], [ZA6584;O(CH₂)₅OCH₃,NHCH₂CH₃], [ZA6585;O(CH₂)₆ F,NHCH₂CH₃], [ZA6586;O(CH₂)₆CN,NHCH₂CH₃], [ZA6587;O(CH₂)₆NO₂,NHCH₂CH₃], [ZA6588;O(CH₂)₆ Ph,NHCH₂CH₃], [ZA6589;O(CH₂)₆OCH₃,NHCH₂CH₃], [ZA6590;OC(O)CH₃,NHCH₂CH₃], [ZA6591;OC(O)

CH$_2$CH$_3$,NHCH$_2$CH$_3$], [ZA6592;OC(O)CH(CH$_3$)$_2$, NHCH$_2$CH$_3$], [ZA6593;OC(O)(CH$_2$)$_2$CH$_3$,NHCH$_2$CH$_3$], [ZA6594;OC(O)(CH$_2$)$_3$CH$_3$,NHCH$_2$CH$_3$], [ZA6595;OC(O)(CH$_2$)$_4$CH$_3$,NHCH$_2$CH$_3$], [ZA6596;OC(O)(CH$_2$)$_5$CH$_3$,NHCH$_2$CH$_3$], [ZA6597;OC(O)CH$_2$CH=CH$_2$, NHCH$_2$CH$_3$], [ZA6598;OC(O)CH$_2$C≡CH,NHCH$_2$CH$_3$], [ZA6599;OC(O)CH$_2$C≡CCH$_3$,NHCH$_2$CH$_3$], [ZA6600;OC(O)c-Pr,NHCH$_2$CH$_3$], [ZA6601;OC(O)c-Pen,NHCH$_2$CH$_3$], [ZA6602;OC(O)c-Hex,NHCH$_2$CH$_3$], [ZA6603;OC(O)Ph, NHCH$_2$CH$_3$], [ZA6604;OC(O)(2-Py),NHCH$_2$CH$_3$], [ZA6605;OC(O)(3-Py),NHCH$_2$CH$_3$], [ZA6606;OC(O)(4-Py),NHCH$_2$CH$_3$], [ZA6607;OC(O)CH$_2$Ph,NHCH$_2$CH$_3$], [ZA6608;OC(O)CH$_2$(2-Py),NHCH$_2$CH$_3$], [ZA6609;OC(O)CH$_2$(3-Py),NHCH$_2$CH$_3$], [ZA6610;OC(O)CH$_2$(4-Py), NHCH$_2$CH$_3$], [ZA6611;OC(O)CH$_2$CN,NHCH$_2$CH$_3$], [ZA6612;OC(O)CH$_2$NO$_2$,NHCH$_2$CH$_3$], [ZA6613;OC(O)(CH$_2$)$_2$F,NHCH$_2$CH$_3$], [ZA6614;OC(O)(CH$_2$)$_2$CN, NHCH$_2$CH$_3$], [ZA6615;OC(O)(CH$_2$)$_2$NO$_2$,NHCH$_2$CH$_3$], [ZA6616;OC(O)(CH$_2$)$_2$Ph,NHCH$_2$CH$_3$], [ZA6617;OC(O)(CH$_2$)$_2$OCH$_3$,NHCH$_2$CH$_3$], [ZA6618;OC(O)(CH$_2$)$_3$F, NHCH$_2$CH$_3$], [ZA6619;OC(O)(CH$_2$)$_3$CN,NHCH$_2$CH$_3$], [ZA6620;OC(O)(CH$_2$)$_3$NO$_2$,NHCH$_2$CH$_3$], [ZA6621;OC(O)(CH$_2$)$_3$OCH$_3$,NHCH$_2$CH$_3$], [ZA6622;OC(O)NH$_2$, NHCH$_2$CH$_3$], [ZA6623;OC(O)NHCH$_3$,NHCH$_2$CH$_3$], [ZA6624;OC(O)NHCH$_2$CH$_3$,NHCH$_2$CH$_3$], [ZA6625;OC(O)NH(CH$_2$)$_2$CH$_3$,NHCH$_2$CH$_3$], [ZA6626;OC(O)NH(CH$_2$)$_3$CH$_3$,NHCH$_2$CH$_3$], [ZA6627;OC(O)NH(CH$_2$)$_4$CH$_3$, NHCH$_2$CH$_3$], [ZA6628;OC(O)NH(CH$_2$)$_5$CH$_3$,NHCH$_2$CH$_3$], [ZA6629;OC(O)NHCH(CH$_3$)$_2$,NHCH$_2$CH$_3$], [ZA6630;OC(O)NHCH$_2$F,NHCH$_2$CH$_3$], [ZA6631;OC(O)NHCH$_2$CN,NHCH$_2$CH$_3$], [ZA6632;OC(O)NHCH$_2$OCH$_3$, NHCH$_2$CH$_3$], [ZA6633;OC(O)NHCH$_2$Ph,NHCH$_2$CH$_3$], [ZA6634;OC(O)NH(CH$_2$)$_2$F,NHCH$_2$CH$_3$], [ZA6635;OC(O)NH(CH$_2$)$_2$CN,NHCH$_2$CH$_3$], [ZA6636;OC(O)NH(CH$_2$)$_2$OCH$_3$,NHCH$_2$CH$_3$], [ZA6637;OC(O)NH(CH$_2$)$_3$F, NHCH$_2$CH$_3$], [ZA6638;OC(O)NH(CH$_2$)$_3$CN,NHCH$_2$CH$_3$], [ZA6639;OC(O)NH(CH$_2$)$_3$OCH$_3$,NHCH$_2$CH$_3$], [ZA6640;OC(O)NH(CH$_2$)$_4$F,NHCH$_2$CH$_3$], [ZA6641;OC(O)NH(CH$_2$)$_4$CN,NHCH$_2$CH$_3$], [ZA6642;OC(O)NH(CH$_2$)$_4$OCH$_3$, NHCH$_2$CH$_3$], [ZA6643;OC(O)NHPh,NHCH$_2$CH$_3$], [ZA6644;OC(O)NH(2-Py),NHCH$_2$CH$_3$], [ZA6645;OC(O)NH(3-Py),NHCH$_2$CH$_3$], [ZA6646;OC(O)NH(4-Py), NHCH$_2$CH$_3$], [ZA6647;OC(O)N(CH$_3$)$_2$,NHCH$_2$CH$_3$], [ZA6648;OC(O)N(CH$_3$)CH$_2$CH$_3$,NHCH$_2$CH$_3$], [ZA6649;OC(O)N(CH$_3$)(CH$_2$)$_2$CH$_3$,NHCH$_2$CH$_3$], [ZA6650;OC(O)N(CH$_3$)(CH$_2$)$_3$CH$_3$,NHCH$_2$CH$_3$], [ZA6651;OC(O)N(CH$_3$)CH(CH$_3$)$_2$,NHCH$_2$CH$_3$], [ZA6652;OC(O)N(CH$_3$)CH$_2$F, NHCH$_2$CH$_3$], [ZA6653;OC(O)N(CH$_3$)CH$_2$CN, NHCH$_2$CH$_3$], [ZA6654;OC(O)N(CH$_3$)CH$_2$OCH$_3$, NHCH$_2$CH$_3$], [ZA6655;OC(O)N(CH$_3$)CH$_2$Ph,NHCH$_2$CH$_3$], [ZA6656;OC(O)N(CH$_3$)(CH$_2$)$_2$F, NHCH$_2$CH$_3$], [ZA6657;OC(O)N(CH$_3$)(CH$_2$)$_2$CN, NHCH$_2$CH$_3$], [ZA6658;OC(O)N(CH$_3$)(CH$_2$)$_2$OCH$_3$, NHCH$_2$CH$_3$], [ZA6659;OC(O)N(CH$_3$)Ph,NHCH$_2$CH$_3$], [ZA6660;OC(O)N(CH$_3$)(2-Py),NHCH$_2$CH$_3$], [ZA6661;OC(O)N(CH$_3$)(3-Py),NHCH$_2$CH$_3$], [ZA6662;OC(O)N(CH$_3$)(4-Py),NHCH$_2$CH$_3$], [ZA6663;OC(O)N(CH$_2$CH$_3$)$_2$, NHCH$_2$CH$_3$], [ZA6664;OC(O)(Pyr),NHCH$_2$CH$_3$], [ZA6665;OC(O)(Pip),NHCH$_2$CH$_3$], [ZA6666;OC(O)(Mor),NHCH$_2$CH$_3$], [ZA6667;OC(O)OCH$_3$,NHCH$_2$CH$_3$], [ZA6668;OC(O)OCH$_2$CH$_3$,NHCH$_2$CH$_3$], [ZA6669;OC(O)OCH(CH$_3$)$_2$,NHCH$_2$CH$_3$], [ZA6670;OC(O)O(CH$_2$)$_2$CH$_3$, NHCH$_2$CH$_3$], [ZA6671;OC(O)O(CH$_2$)$_3$CH$_3$,NHCH$_2$CH$_3$], [ZA6672;OC(O)O(CH$_2$)$_4$CH$_3$,NHCH$_2$CH$_3$], [ZA6673;OC(O)O(CH$_2$)$_5$CH$_3$,NHCH$_2$CH$_3$], [ZA6674;OC(O)OCH$_2$CH=CH$_2$,NHCH$_2$CH$_3$], [ZA6675;OC(O)OCH$_2$C≡CH,NHCH$_2$CH$_3$], [ZA6676;OC(O)OCH$_2$C≡CCH$_3$,NHCH$_2$CH$_3$], [ZA6677;OC(O)O-c-Pr, NHCH$_2$CH$_3$], [ZA6678;OC(O)O-c-Pen,NHCH$_2$CH$_3$], [ZA6679;OC(O)O-c-Hex,NHCH$_2$CH$_3$], [ZA6680;OC(O)OPh,NHCH$_2$CH$_3$], [ZA6681;OC(O)O(2-Py),NHCH$_2$CH$_3$], [ZA6682;OC(O)O(3-Py),NHCH$_2$CH$_3$], [ZA6683;OC(O)O(4-Py),NHCH$_2$CH$_3$], [ZA6684;OC(O)OCF$_3$,NHCH$_2$CH$_3$], [ZA6685;OC(O)OCH$_2$Ph,NHCH$_2$CH$_3$], [ZA6686;OC(O)OCH$_2$(2-Py),NHCH$_2$CH$_3$], [ZA6687;OC(O)OCH$_2$(3-Py), NHCH$_2$CH$_3$], [ZA6688;OC(O)OCH$_2$(4-Py),NHCH$_2$CH$_3$], [ZA6689;OC(O)OCH$_2$CN,NHCH$_2$CH$_3$], [ZA6690;OC(O)OCH$_2$NO$_2$,NHCH$_2$CH$_3$], [ZA6691;OC(O)O(CH$_2$)$_2$F, NHCH$_2$CH$_3$], [ZA6692;OC(O)O(CH$_2$)$_2$CN,NHCH$_2$CH$_3$], [ZA6693;OC(O)O(CH$_2$)$_2$OCH$_3$,NHCH$_2$CH$_3$], [ZA6694;OC(O)O(CH$_2$)$_3$F,NHCH$_2$CH$_3$], [ZA6695;OC(O)O(CH$_2$)$_3$CN,NHCH$_2$CH$_3$], [ZA6696;OC(O)O(CH$_2$)$_3$OCH$_3$, NHCH$_2$CH$_3$], [ZA6697;OS(O)$_2$CH$_3$,NHCH$_2$CH$_3$], [ZA6698;OS(O)$_2$CH$_2$CH$_3$,NHCH$_2$CH$_3$], [ZA6699;OS(O)$_2$CH(CH$_3$)$_2$,NHCH$_2$CH$_3$], [ZA6700;OS(O)$_2$(CH$_2$)$_2$CH$_3$, NHCH$_2$CH$_3$], [ZA6701;OS(O)$_2$(CH$_2$)$_3$CH$_3$,NHCH$_2$CH$_3$], [ZA6702;OS(O)$_2$(CH$_2$)$_4$CH$_3$,NHCH$_2$CH$_3$], [ZA6703;OS(O)$_2$(CH$_2$)$_5$CH$_3$,NHCH$_2$CH$_3$], [ZA6704;OS(O)$_2$-c-Pr, NHCH$_2$CH$_3$], [ZA6705;OS(O)$_2$-c-Pen,NHCH$_2$CH$_3$], [ZA6706;OS(O)$_2$-c-Hex,NHCH$_2$CH$_3$], [ZA6707;OS(O)$_2$Ph,NHCH$_2$CH$_3$], [ZA6708;OS(O)$_2$(2-Py),NHCH$_2$CH$_3$], [ZA6709;OS(O)$_2$(3-Py),NHCH$_2$CH$_3$], [ZA6710;OS(O)$_2$(4-Py),NHCH$_2$CH$_3$], [ZA6711;OS(O)$_2$CF$_3$,NHCH$_2$CH$_3$], [ZA6712;OS(O)$_2$CH$_2$Ph,NHCH$_2$CH$_3$], [ZA6713;OH,NH(CH$_2$)$_2$CH$_3$], [ZA6714;OCH$_3$,NH(CH$_2$)$_2$CH$_3$], [ZA6715;OCH$_2$CH$_3$,NH(CH$_2$)$_2$CH$_3$], [ZA6716;OCH(CH$_3$)$_2$,NH(CH$_2$)$_2$CH$_3$], [ZA6717;O(CH$_2$)$_2$CH$_3$,NH(CH$_2$)$_2$CH$_3$], [ZA6718;O(CH$_2$)$_3$CH$_3$,NH(CH$_2$)$_2$CH$_3$], [ZA6719;O(CH$_2$)$_4$CH$_3$,NH(CH$_2$)$_2$CH$_3$], [ZA6720;O(CH$_2$)$_5$CH$_3$,NH(CH$_2$)$_2$CH$_3$], [ZA6721;OCH$_2$CH=CH$_2$,NH(CH$_2$)$_2$CH$_3$], [ZA6722;OCH$_2$C≡CH,NH(CH$_2$)$_2$CH$_3$], [ZA6723;OCH$_2$C≡CCH$_3$,NH(CH$_2$)$_2$CH$_3$], [ZA6724;O-c-Pr,NH(CH$_2$)$_2$CH$_3$], [ZA6725;O-c-Pen,NH(CH$_2$)$_2$CH$_3$], [ZA6726;O-c-Hex,NH(CH$_2$)$_2$CH$_3$], [ZA6727;OPh,NH(CH$_2$)$_2$CH$_3$], [ZA6728;OCH$_2$Ph,NH(CH$_2$)$_2$CH$_3$], [ZA6729;OCH$_2$(2-Py), NH(CH$_2$)$_2$CH$_3$], [ZA6730;OCH$_2$(3-Py),NH(CH$_2$)$_2$CH$_3$], [ZA6731;OCH$_2$(4-Py),NH(CH$_2$)$_2$CH$_3$], [ZA6732;OCH$_2$CN,NH(CH$_2$)$_2$CH$_3$], [ZA6733;OCH$_2$NO$_2$,NH(CH$_2$)$_2$CH$_3$], [ZA6734;O(CH$_2$)$_2$F,NH(CH$_2$)$_2$CH$_3$], [ZA6735;O(CH$_2$)$_2$CN,NH(CH$_2$)$_2$CH$_3$], [ZA6736;O(CH$_2$)$_2$Ph,NH(CH$_2$)$_2$CH$_3$], [ZA6737;O(CH$_2$)$_2$OCH$_3$,NH(CH$_2$)$_2$CH$_3$], [ZA6738;(CH$_2$)$_3$F,NH(CH$_2$)$_2$CH$_3$], [ZA6739;O(CH$_2$)$_3$CN,NH(CH$_2$)$_2$CH$_3$], [ZA6740;O(CH$_2$)$_3$NO$_2$,NH(CH$_2$)$_2$CH$_3$], [ZA6741;(CH$_2$)$_3$Ph,NH(CH$_2$)$_2$CH$_3$], [ZA6742;O(CH$_2$)$_3$OCH$_3$,NH(CH$_2$)$_2$CH$_3$], [ZA6743;O(CH$_2$)$_4$F,NH(CH$_2$)$_2$CH$_3$], [ZA6744;O(CH$_2$)$_4$CN,NH(CH$_2$)$_2$CH$_3$], [ZA6745;O(CH$_2$)$_4$NO$_2$,NH(CH$_2$)$_2$CH$_3$], [ZA6746;O(CH$_2$)$_4$Ph,NH(CH$_2$)$_2$CH$_3$], [ZA6747;O(CH$_2$)$_4$OCH$_3$,NH(CH$_2$)$_2$CH$_3$], [ZA6748;O(CH$_2$)$_5$F,NH(CH$_2$)$_2$CH$_3$], [ZA6749;O(CH$_2$)$_5$CN,NH(CH$_2$)$_2$CH$_3$], [ZA6750;O(CH$_2$)$_5$NO$_2$,NH(CH$_2$)$_2$CH$_3$], [ZA6751;(CH$_2$)$_5$Ph,NH(CH$_2$)$_2$CH$_3$], [ZA6752;O(CH$_2$)$_5$OCH$_3$,NH(CH$_2$)$_2$CH$_3$], [ZA6753;(CH$_2$)$_6$F,NH(CH$_2$)$_2$CH$_3$], [ZA6754;O(CH$_2$)$_6$CN,NH(CH$_2$)$_2$CH$_3$], [ZA6755;(CH$_2$)$_6$NO$_2$,NH(CH$_2$)$_2$CH$_3$], [ZA6756;(CH$_2$)$_6$Ph,NH(CH$_2$)$_2$CH$_3$], [ZA6757;O(CH$_2$)$_6$OCH$_3$,NH(CH$_2$)$_2$CH$_3$], [ZA6758;OC(O)CH$_3$,NH(CH$_2$)$_2$CH$_3$], [ZA6759;OC(O)CH$_2$CH$_3$,NH(CH$_2$)$_2$CH$_3$], [ZA6760;OC(O)CH(CH$_3$)$_2$,NH(CH$_2$)$_2$CH$_3$], [ZA6761;OC(O)(CH$_2$)$_2$CH$_3$,NH(CH$_2$)$_2$CH$_3$], [ZA6762;OC(O)(CH$_2$)$_3$CH$_3$,NH(CH$_2$)$_2$CH$_3$], [ZA6763;OC(O)(CH$_2$)$_4$CH$_3$,NH(CH$_2$)$_2$CH$_3$], [ZA6764;OC(O)(CH$_2$)$_5$CH$_3$,NH(CH$_2$)$_2$CH$_3$], [ZA6765;OC(O)CH$_2$CH=CH$_2$,NH(CH$_2$)$_2$CH$_3$], [ZA6766;OC(O)CH$_2$C≡CH,NH(CH$_2$)$_2$CH$_3$], [ZA6767;OC(O)CH$_2$C≡CCH$_3$,NH(CH$_2$)$_2$CH$_3$], [ZA6768;OC(O)c-Pr,NH(CH)$_2$CH$_3$], [ZA6769;OC(O)c-Pen,NH (CH₂)₂CH₃], [ZA6770;OC(O)c-Hex,NH(CH₂)₂CH₃], [ZA6771;OC(O)Ph,NH(CH₂)₂CH₃], [ZA6772;OC(O)(2-Py),NH(CH₂)₂CH₃], [ZA6773;OC(O)(3-Py),NH(CH₂)₂CH₃], [ZA6774;OC(O)(4-Py),NH(CH₂)₂CH₃], [ZA6775;OC(O)CH₂Ph,NH(CH₂)₂CH₃], [ZA6776;OC(O)CH₂(2-Py),NH(CH₂)₂CH₃], [ZA6777;OC(O)CH₂(3-Py),NH(CH₂)₂CH₃], [ZA6778;OC(O)CH₂(4-Py),NH(CH₂)₂CH₃], [ZA6779;OC(O)CH₂CN,NH(CH₂)₂CH₃], [ZA6780;OC(O)CH₂NO₂,NH(CH₂)₂CH₃], [ZA6781;OC(O)(CH₂)₂F,NH(CH₂)₂CH₃], [ZA6782;OC(O)(CH₂)₂CN,NH(CH₂)₂CH₃], [ZA6783;OC(O)(CH₂)₂NO₂,NH(CH₂)₂CH₃], [ZA6784;OC(O)(CH₂)₂Ph,NH(CH₂)₂CH₃], [ZA6785;OC(O)(CH₂)₂OCH₃,NH(CH₂)₂CH₃], [ZA6786;OC(O)(CH₂)₃F,NH(CH₂)₂CH₃], [ZA6787;OC(O)(CH₂)₃CN,NH(CH₂)₂CH₃], [ZA6788;OC(O)(CH₂)₃NO₂,NH(CH₂)₂CH₃], [ZA6789;OC(O)(CH₂)₃OCH₃,NH(CH₂)₂CH₃], [ZA6790;OC(O)NH₂,NH(CH₂)₂CH₃], [ZA6791;OC(O)NHCH₃,NH(CH₂)₂CH₃], [ZA6792;OC(O)NHCH₂CH₃,NH(CH₂)₂CH₃], [ZA6793;OC(O)NH(CH₂)₂CH₃,NH(CH₂)₂CH₃], [ZA6794;OC(O)NH(CH₂)₃CH₃,NH(CH₂)₂CH₃], [ZA6795;OC(O)NH(CH₂)₄CH₃,NH(CH₂)₂CH₃], [ZA6796;OC(O)NH(CH₂)₅CH₃,NH(CH₂)₂CH₃], [ZA6797;OC(O)NHCH(CH₃)₂,NH(CH₂)₂CH₃], [ZA6798;OC(O)NHCH₂F,NH(CH₂)₂CH₃], [ZA6799;OC(O)NHCH₂CN,NH(CH₂)₂CH₃], [ZA6800;OC(O)NHCH₂OCH₃,NH(CH₂)₂CH₃], [ZA6801;OC(O)NHCH₂Ph,NH(CH₂)₂CH₃], [ZA6802;OC(O)NH(CH₂)₂F,NH(CH₂)₂CH₃], [ZA6803;OC(O)NH(CH₂)₂CN,NH(CH₂)₂CH₃], [ZA6804;OC(O)NH(CH₂)₂OCH₃,NH(CH₂)₂CH₃], [ZA6805;OC(O)NH(CH₂)₃F,NH(CH₂)₂CH₃], [ZA6806;OC(O)NH(CH₂)₃CN,NH(CH₂)₂CH₃], [ZA6807;OC(O)NH(CH₂)₃OCH₃,NH(CH₂)₂CH₃], [ZA6808;OC(O)NH(CH₂)₄F,NH(CH)₂CH₃], [ZA6809;OC(O)NH(CH₂)₄CN,NH(CH₂)₂CH₃], [ZA681;OC(O)NH(CH₂)₄OCH₃,NH(CH₂)₂CH₃], [ZA6811;OC(O)NHPh,NH(CH₂)₂CH₃], [ZA6812;OC(O)NH(2-Py),NH(CH₂)₂CH₃], [ZA6813;OC(O)NH(3-Py),NH(CH₂)₂CH₃], [ZA6814;OC(O)NH(4-Py),NH(CH₂)₂CH₃], [ZA6815;OC(O)N(CH₃)₂,NH(CH₂)₂CH₃], [ZA6816;OC(O)N(CH₃)CH₂CH₃,NH(CH)₂CH₃], [ZA6817;OC(O)N(CH₃)(CH₂)₂CH₃,NH(CH₂)₂CH₃], [ZA6818;OC(O)N(CH₃)(CH)₃CH₃,NH(CH₂)₂CH₃], [ZA6819;OC(O)N(CH₃)CH(CH₃)₂,NH(CH₂)₂CH₃], [ZA6820;OC(O)N(CH₃)CH₂F,NH(CH₂)₂CH₃], [ZA6821;OC(O)N(CH₃)CH₂CN,NH(CH₂)₂CH₃], [ZA6822;OC(O)N(CH₃)CH₂OCH₃,NH(CH₂)₂CH₃], [ZA6823;OC(O)N(CH₃)CH₂Ph,NH(CH₂)₂CH₃], [ZA6824;OC(O)N(CH₃)(CH₂)₂F,NH(CH₂)₂CH₃], [ZA6825;OC(O)N(CH₃)(CH₂)₂CN,NH(CH₂)₂CH₃], [ZA6826;OC(O)N(CH₃)(CH₂)₂OCH₃,NH(CH₂)₂CH₃], [ZA6827;OC(O)N(CH₃)Ph,NH(CH₂)₂CH₃], [ZA6828;OC(O)N(CH₃)(2-Py),NH(CH₂)₂CH₃], [ZA6829;OC(O)N(CH₃)(3-Py),NH(CH₂)₂CH₃], [ZA6830;OC(O)N(CH₃)(4-Py),NH(CH₂)₂CH₃], [ZA6831;OC(O)N(CH₂CH₃)₂,NH(CH₂)₂CH₃], [ZA6832;OC(O)(Pyr),NH(CH₂)₂CH₃], [ZA6833;OC(O)(Pip),NH(CH₂)₂CH₃], [ZA6834;OC(O)(Mor),NH(CH₂)₂CH₃], [ZA6835;OC(O)OCH₃,NH(CH₂)₂CH₃], [ZA6836;OC(O)OCH₂CH₃,NH(CH₂)₂CH₃], [ZA6837;OC(O)OCH(CH₃)₂,NH(CH₂)₂CH₃], [ZA6838;OC(O)O(CH₂)₂CH₃,NH(CH₂)₂CH₃], [ZA6839;OC(O)O(CH₂)₃CH₃,NH(CH₂)₂CH₃], [ZA6840;OC(O)O(CH₂)₄CH₃,NH(CH₂)₂CH₃], [ZA6841;OC(O)O(CH₂)₅CH₃,NH(CH₂)₂CH₃], [ZA6842;OC(O)OCH₂CH=CH₂,NH(CH₂)₂CH₃], [ZA6843;OC(O)OCH₂C≡CH,NH(CH₂)₂CH₃], [ZA6844;OC(O)OCH₂C≡CCH₃,NH(CH₂)₂CH₃], [ZA6845;OC(O)O-c-Pr,NH(CH₂)₂CH₃], [ZA6846;OC(O)O-c-Pen,NH(CH₂)₂CH₃], [ZA6847;OC(O)O-c-Hex,NH(CH₂)₂CH₃], [ZA6848;OC(O)OPh,NH(CH₂)₂CH₃], [ZA6849;OC(O)O(2-Py),NH(CH₂)₂CH₃], [ZA6850;OC(O)O(3-Py),NH(CH)₂CH₃], [ZA6851;OC(O)O(4-Py),NH(CH₂)₂CH₃], [ZA6852;OC(O)OCF₃,NH(CH₂)₂CH₃], [ZA6853;OC(O)OCH₂Ph,NH(CH₂)₂CH₃], [ZA6854;OC(O)OCH₂(2-Py),NH(CH₂)₂CH₃], [ZA6855;OC(O)OCH₂(3-Py),NH(CH₂)₂CH₃], [ZA6856;OC(O)OCH₂(4-Py),NH(CH₂)₂CH₃], [ZA6857;OC(O)OCH₂CN,NH(CH₂)₂CH₃], [ZA6858;OC(O)OCH₂NO₂,NH(CH₂)₂CH₃], [ZA6859;OC(O)O(CH₂)₂F,NH(CH₂)₂CH₃], [ZA6860;OC(O)O(CH₂)₂CN,NH(CH₂)₂CH₃], [ZA6861;OC(O)O(CH₂)₂OCH₃,NH(CH₂)₂CH₃], [ZA6862;OC(O)O(CH₂)₃F,NH(CH₂)₂CH₃], [ZA6863;OC(O)O(CH₂)₃CN,NH(CH₂)₂CH₃], [ZA6864;OC(O)O(CH)₃OCH₃,NH(CH₂)₂CH₃], [ZA6865;OS(O)₂CH₃,NH(CH₂)₂CH₃], [ZA6866;OS(O)₂CH₂CH₃,NH(CH₂)₂CH₃], [ZA6867;OS(O)₂CH(CH₃)₂,NH(CH₂)₂CH₃], [ZA6868;OS(O)₂(CH₂)₂CH₃,NH(CH₂)₂CH₃], [ZA6869;OS(O)₂(CH₂)₃CH₃,NH(CH₂)₂CH₃], [ZA6870;OS(O)₂(CH₂)₄CH₃,NH(CH₂)₂CH₃], [ZA6871;OS(O)₂(CH₂)₅CH₃,NH(CH₂)₂CH₃], [ZA6872;OS(O)₂-c-Pr,NH(CH₂)₂CH₃], [ZA6873;OS(O)₂-c-Pen,NH(CH₂)₂CH₃], [ZA6874;OS(O)₂-c-Hex,NH(CH₂)₂CH₃], [ZA6875;OS(O)₂Ph,NH(CH₂)₂CH₃], [ZA6876;OS(O)₂(2-Py),NH(CH₂)₂CH₃], [ZA6877;OS(O)₂(3-Py),NH(CH₂)₂CH₃], [ZA6878;OS(O)₂(4-Py),NH(CH₂)₂CH₃], [ZA6879;OS(O)₂CF₃,NH(CH₂)₂CH₃], [ZA6880;OS(O)₂CH₂Ph,NH(CH₂)₂CH₃], [ZA6881;OH,N(CH₂CH₃)₂], [ZA6882;OCH₃,N(CH₂CH₃)₂], [ZA6883;OCH₂CH₃,N(CH₂CH₃)₂], [ZA6884;OCH(CH₃)₂,N(CH₂CH₃)₂], [ZA6885;O(CH₂)₂CH₃,N(CH₂CH)₂], [ZA6886;O(CH₂)₃CH₃,N(CH₂CH)₂], [ZA6887;O(CH₂)₄CH₃,N(CH₂CH₃)₂], [ZA6888;O(CH₂)₅CH₃,N(CH₂CH)₂], [ZA6889;OCH₂CH=CH₂,N(CH₂CH₃)₂], [ZA6890;OCH₂C≡CH,N(CH₂CH₃)₂], [ZA6891;OCH₂C≡CCH₃,N(CH₂CH)₂], [ZA6892;O-c-Pr,N(CH₂CH₃)₂], [ZA6893;O-c-Pen,N(CH₂CH₃)₂], [ZA6894;O-c-Hex,N(CH₂CH₃)₂], [ZA6895;OPh,N(CH₂CH₃)₂], [ZA6896;OCH₂Ph,N(CH₂CH₃)₂], [ZA6897;OCH₂(2-Py),N(CH₂CH₃)₂], [ZA6898;OCH₂(3-Py),N(CH₂CH₃)₂], [ZA6899;OCH₂(4-Py),N(CH₂CH)₂], [ZA6900;OCH₂CN,N(CH₂CH)₂], [ZA6901;OCH₂NO₂,N(CH₂CH₃)₂], [ZA6902;O(CH₂)₂F,N(CH₂CH₃)₂], [ZA6903;O(CH₂)₂CN,N(CH₂CH₃)₂], [ZA6904;O(CH₂)₂Ph,N(CH₂CH₃)₂], [ZA6905;O(CH₂)₂OCH₃,N(CH₂CH₃)₂], [ZA6906;O(CH₂)₃F,N(CH₂CH)₂], [ZA6907;O(CH₂)₃CN,N(CH₂CH)₂], [ZA6908;O(CH₂)₃NO₂,N(CH₂CH₃)₂], [ZA6909;O(CH₂)₃Ph,N(CH₂CH₃)₂], [ZA6910;(CH₂)₃OCH₃,N(CH₂CH)₂], [ZA6911;O(CH₂)₄F,N(CH₂CH₃)₂], [ZA6912;O(CH₂)₄CN,N(CH₂CH₃)₂], [ZA6913;O(CH₂)₄NO₂,N(CH₂CH₃)₂], [ZA6914;O(CH₂)₄Ph,N(CH₂CH₃)₂], [ZA6915;O(CH₂)₄OCH₃,N(CH₂CH₃)₂], [ZA6916;O(CH₂)₅F,N(CH₂CH)₂], [ZA6917;O(CH₂)₅CN,N(CH₂CH₃)₂], [ZA6918;O(CH₂)₅NO₂,N(CH₂CH)₂], [ZA6919;O(CH₂)₅Ph,N(CH₂CH)₂], [ZA6920;O(CH₂)₅OCH₃,N(CH₂CH)₂], [ZA6921;(CH₂)₆F,N(CH₂CH₃)₂], [ZA6922;O(CH₂)₆CN,N(CH₂CH₃)₂], [ZA6923;O(CH₂)₆NO₂,N(CH₂CH₃)₂], [ZA6924;O(CH₂)₆Ph,N(CH₂CH)₂], [ZA6925;O(CH₂)₆OCH₃,N(CH₂CH₃)₂], [ZA6926;OC(O)CH₃,N(CH₂CH)₂], [ZA6927;OC(O)CH₂CH₃,N(CH₂CH₃)₂], [ZA6928;OC(O)CH(CH₃)₂,N(CH₂CH)₂], [ZA6929;OC(O)(CH₂)₂CH₃,N(CH₂CH)₂], [ZA6930;OC(O)(CH₂)₃CH₃,N(CH₂CH₃)₂], [ZA6931;OC(O)(CH₂)₄CH₃,N(CH₂CH₃)₂], [ZA6932;OC(O)(CH₂)₅CH₃,N(CH₂CH₃)₂], [ZA6933;OC(O)CH₂CH=CH₂,N(CH₂CH₃)₂], [ZA6934;OC(O)CH₂C≡CH,N(CH₂CH₃)₂], [ZA6935;OC(O)CH₂C≡CCH₃,N(CH₂CH₃)₂], [ZA6936;OC(O)c-Pr,N(CH₂CH₃)₂], [ZA6937;OC(O)c-Pen,N(CH₂CH₃)₂], [ZA6938;OC(O)c-Hex,N(CH₂CH₃)₂], [ZA6939;OC(O)Ph,N(CH₂CH₃)₂], [ZA6940;OC(O)(2-Py),N(CH₂CH₃)₂], [ZA6941;OC(O)(3-Py),N(CH₂CH)₂], [ZA6942;OC(O)(4-Py),N(CH₂CH₃)₂], [ZA6943;OC(O)CH₂Ph,N(CH₂CH)₂], [ZA6944;OC(O)CH₂(2-Py),N(CH₂CH)₂], [ZA6945;OC(O)CH₂(3-Py),N (CH₂CH₃)₂], [ZA6946;OC(O)CH₂(4-Py),N(CH₂CH₃)₂], [ZA6947;OC(O)CH₂CN,N(CH₂CH₃)₂], [ZA6948;OC(O)CH₂NO₂,N(CH₂CH)₂], [ZA6949;OC(O)(CH₂)₂F,N(CH₂CH₃)₂], [ZA6950;OC(O)(CH₂)₂CN,N(CH₂CH₃)₂], [ZA6951;OC(O)(CH₂)₂NO₂,N(CH₂CH)₂], [ZA6952;OC(O)(CH₂)₂Ph,N(CH₂CH₃)₂], [ZA6953;OC(O)(CH₂)₂OCH₃,N(CH₂CH₃)₂], [ZA6954;OC(O)(CH₂)₃F,N(CH₂CH₃)₂], [ZA6955;OC(O)(CH₂)₃CN,N(CH₂CH)₂], [ZA6956;OC(O)(CH₂)₃NO₂,N(CH₂CH)₂], [ZA6957;OC(O)(CH₂)₃OCH₃,N(CH₂CH₃)₂], [ZA6958;OC(O)NH₂,N(CH₂CH₃)₂], [ZA6959;OC(O)NHCH₃,N(CH₂CH₃)₂], [ZA6960;OC(O)NHCH₂CH₃,N(CH₂CH₃)₂], [ZA6961;OC(O)NH(CH₂)₂CH₃,N(CH₂CH₃)₂], [ZA6962;OC(O)NH(CH₂)₃CH₃,N(CH₂CH)₂], [ZA6963;OC(O)NH(CH₂)₄CH₃,N(CH₂CH₃)₂], [ZA6964;OC(O)NH(CH₂)₅CH₃,N(CH₂CH₃)₂], [ZA6965;OC(O)NHCH(CH₃)₂,N(CH₂CH)₂], [ZA6966;OC(O)NHCH₂F,N(CH₂CH₃)₂], [ZA6967;OC(O)NHCH₂CN,N(CH₂CH)₂], [ZA6968;OC(O)NHCH₂OCH₃,N(CH₂CH₃)₂], [ZA6969;OC(O)NHCH₂Ph,N(CH₂CH₃)₂], [ZA6970;OC(O)NH(CH₂)₂F,N(CH₂CH₃)₂], [ZA6971;OC(O)NH(CH₂)₂CN,N(CH₂CH₃)₂], [ZA6972;OC(O)NH(CH₂)₂OCH₃,N(CH₂CH₃)₂], [ZA6973;OC(O)NH(CH₂)₃F,N(CH₂CH₃)₂], [ZA6974;OC(O)NH(CH₂)₃CN,N(CH₂CH)₂], [ZA6975;OC(O)NH(CH₂)₃OCH₃,N(CH₂CH₃)₂], [ZA6976;OC(O)NH(CH₂)₄F,N(CH₂CH)₂], [ZA6977;OC(O)NH(CH₂)₄CN,N(CH₂CH₃)₂], [ZA6978;OC(O)NH(CH₂)₄OCH₃,N(CH₂CH₃)₂], [ZA6979;OC(O)NHPh,N(CH₂CH₃)₂], [ZA6980;OC(O)NH(2-Py),N(CH₂CH)₂], [ZA6981;OC(O)NH(3-Py),N(CH₂CH₃)₂], [ZA6982;OC(O)NH(4-Py),N(CH₂CH)₂], [ZA6983;OC(O)N(CH₃)₂,N(CH₂CH)₂], [ZA6984;OC(O)N(CH₃)CH₂CH₃,N(CH₂CH₃)₂], [ZA6985;OC(O)N(CH₃)(CH₂)₂CH₃,N(CH₂CH)₂], [ZA6986;OC(O)N(CH₃)(CH₂)₃CH₃,N(CH₂CH₃)₂], [ZA6987;OC(O)N(CH₃)CH(CH₃)₂,N(CH₂CH₃)₂], [ZA6988;OC(O)N(CH₃)CH₂F,N(CH₂CH₃)₂], [ZA6989;OC(O)N(CH₃)CH₂CN,N(CH₂CH₃)₂], [ZA6990;OC(O)N(CH₃)CH₂OCH₃,N(CH₂CH)₂], [ZA6991;OC(O)N(CH₃)CH₂Ph,N(CH₂CH₃)₂], [ZA6992;OC(O)N(CH₃)(CH₂)₂F,N(CH₂CH₃)₂], [ZA6993;OC(O)N(CH₃)(CH₂)₂CN,N(CH₂CH₃)₂], [ZA6994;OC(O)N(CH₃)(CH₂)₂OCH₃,N(CH₂CH₃)₂], [ZA6995;OC(O)N(CH₃)Ph,N(CH₂CH)₂], [ZA6996;OC(O)N(CH₃)(2-Py),N(CH₂CH₃)₂], [ZA6997;OC(O)N(CH₃)(3-Py),N(CH₂CH₃)₂], [ZA6998;OC(O)N(CH₃)(4-Py),N(CH₂CH₃)₂], [ZA6999;OC(O)N(CH₂CH₃)₂,N(CH₂CH)₂], [ZA7000;OC(O)(Pyr),N(CH₂CH₃)₂],

[ZA7001;OC(O)(Pip),N(CH₂CH₃)₂], [ZA7002;OC(O)(Mor),N(CH₂CH₃)₂], [ZA7003;OC(O)OCH₃,N(CH₂CH₃)₂], [ZA7004;OC(O)OCH₂CH₃,N(CH₂CH₃)₂], [ZA7005;OC(O)OCH(CH₃)₂,N(CH₂CH₃)₂], [ZA7006;OC(O)O(CH₂)₂CH₃,N(CH₂CH₃)₂], [ZA7007;OC(O)O(CH₂)₃CH₃,N(CH₂CH₃)₂], [ZA7008;OC(O)O(CH₂)₄CH₃,N(CH₂CH₃)₂], [ZA7009;OC(O)O(CH₂)₅CH₃,N(CH₂CH₃)₂], [ZA7010;OC(O)OCH₂CH=CH₂,N(CH₂CH₃)₂], [ZA7011;OC(O)OCH₂C≡CH,N(CH₂CH₃)₂], [ZA7012;OC(O)OCH₂C≡CCH₃,N(CH₂CH)₂], [ZA7013;OC(O)O-c-Pr,N(CH₂CH₃)₂], [ZA7014;OC(O)O-c-Pen,N(CH₂CH₃)₂], [ZA7015;OC(O)O-c-Hex,N(CH₂CH₃)₂], [ZA7016;OC(O)OPh,N(CH₂CH₃)₂], [ZA7017;OC(O)O(2-Py),N(CH₂CH₃)₂], [ZA7018;OC(O)O(3-Py),N(CH₂CH₃)₂], [ZA7019;OC(O)O(4-Py),N(CH₂CH₃)₂], [ZA7020;OC(O)OCF₃,N(CH₂CH₃)₂], [ZA7021;OC(O)OCH₂Ph,N(CH₂CH₃)₂], [ZA7022;OC(O)OCH₂(2-Py),N(CH₂CH₃)₂], [ZA7023;OC(O)OCH₂(3-Py),N(CH₂CH₃)₂][ZA7024;OC(O)OCH₂(4-Py),N(CH₂CH₃)₂], [ZA7025;OC(O)OCH₂CN,N(CH₂CH₃)₂], [ZA7026;OC(O)OCH₂NO₂,N(CH₂CH₃)₂], [ZA7027;OC(O)O(CH₂)₂F,N(CH₂CH₃)₂], [ZA7028;OC(O)O(CH₂)₂CN,N(CH₂CH₃)₂], [ZA7029;OC(O)O(CH₂)₂OCH₃,N(CH₂CH₃)₂], [ZA7030;OC(O)O(CH₂)₃F,N(CH₂CH₃)₂], [ZA7031;OC(O)O(CH₂)₃CN,N(CH₂CH₃)₂], [ZA7032;OC(O)O(CH₂)₃OCH₃,N(CH₂CH₃)₂], [ZA7033;OS(O)₂CH₃,N(CH₂CH₃)₂], [ZA7034;OS(O)₂CH₂CH₃,N(CH₂CH₃)₂], [ZA7035;OS(O)₂CH(CH₃)₂,N(CH₂CH₃)₂], [ZA7036;OS(O)₂(CH₂)₂CH₃,N(CH₂CH₃)₂], [ZA7037;OS(O)₂(CH₂)₃CH₃,N(CH₂CH₃)₂], [ZA7038;OS(O)₂(CH₂)₄CH₃,N(CH₂CH₃)₂], [ZA7039;OS(O)₂(CH₂)₅CH₃,N(CH₂CH₃)₂], [ZA7040;OS(O)₂-c-Pr,N(CH₂CH₃)₂], [ZA7041;OS(O)₂-c-Pen,N(CH₂CH₃)₂], [ZA7042;OS(O)₂-c-Hex,N(CH₂CH₃)₂], [ZA7043;OS(O)₂Ph,N(CH₂CH₃)₂], [ZA7044;OS(O)₂(2-Py),N(CH₂CH)₂], [ZA7045;OS(O)₂(3-Py),N(CH₂CH)₂], [ZA7046;OS(O)₂(4-Py),N(CH₂CH)₂], [ZA7047;OS(O)₂CF₃,N(CH₂CH)₂], [ZA7048;OS(O)₂CH₂Ph,N(CH₂CH)₂], [ZA7049;OH,N(CH₃)CH₂CH₃], [ZA7050;OCH₃,N(CH₃)CH₂CH₃], [ZA7051;OCH₂CH₃,N(CH₃)CH₂CH₃], [ZA7052;OCH(CH₃)₂,N(CH₃)CH₂CH₃], [ZA7053;(CH₂)₂CH₃,N(CH₃)CH₂CH₃], [ZA7054;O(CH₂)₃CH₃,N(CH₃)CH₂CH₃], [ZA7055;O(CH₂)₄CH₃,N(CH₃)CH₂CH₃], [ZA7056;O(CH₂)₅CH₃,N(CH₃)CH₂CH₃], [ZA7057;OCH₂CH=CH₂,N(CH₃)CH₂CH₃], [ZA7058;OCH₂C≡CH,N(CH₃)CH₂CH₃], [ZA7059;OCH₂C≡CCH₃,N(CH₃)CH₂CH₃], [ZA7060;O-c-Pr,N(CH₃)CH₂CH₃], [ZA7061;O-c-Pen,N(CH₃)CH₂CH₃], [ZA7062;O-c-Hex,N(CH₃)CH₂CH₃], [ZA7063;OPh,N(CH₃)CH₂CH₃], [ZA7064;OCH₂Ph,N(CH₃)CH₂CH₃], [ZA7065;OCH₂(2-Py),N(CH₃)CH₂CH₃], [ZA7066;OCH₂(3-Py),N(CH₃)CH₂CH₃], [ZA7067;OCH₂(4-Py),N(CH₃)CH₂CH₃], [ZA7068;OCH₂CN,N(CH₃)CH₂CH₃], [ZA7069;OCH₂NO₂,N(CH₃)CH₂CH₃], [ZA7070;O(CH₂)₂F,N(CH₃)CH₂CH₃], [ZA7071;(CH₂)₂CN,N(CH₃)CH₂CH₃], [ZA7072;O(CH₂)₂Ph,N(CH₃)CH₂CH₃], [ZA7073;O(CH₂)₂OCH₃,N(CH₃)CH₂CH₃], [ZA7074;O(CH₂)₃F,N(CH₃)CH₂CH₃], [ZA7075;O(CH₂)₃CN,N(CH₃)CH₂CH₃], [ZA7076;O(CH₂)₃NO₂,N(CH₃)CH₂CH₃], [ZA7077;O(CH₂)₃Ph,N(CH₃)CH₂CH₃], [ZA7078;(CH₂)₃OCH₃,N(CH₃)CH₂CH₃], [ZA7079;O(CH₂)₄F,N(CH₃)CH₂CH₃], [ZA7080;O(CH₂)₄CN,N(CH₃)CH₂CH₃], [ZA7081;(CH₂)₄NO₂,N(CH₃)CH₂CH₃], [ZA7082;O(CH₂)₄Ph,N(CH₃)CH₂CH₃], [ZA7083;O(CH₂)₄OCH₃,N(CH₃)CH₂CH₃], [ZA7084;O(CH₂)₅F,N(CH₃)CH₂CH₃], [ZA7085;O(CH₂)₅CN,N(CH₃)CH₂CH₃], [ZA7086;O(CH₂)₅NO₂,N(CH₃)CH₂CH₃], [ZA7087;O(CH₂)₅Ph,N(CH₃)CH₂CH₃], [ZA7088;(CH₂)₅OCH₃,N(CH₃)CH₂CH₃], [ZA7089;O(CH₂)₆F,N(CH₃)CH₂CH₃], [ZA7090;O(CH₂)₆CN,N(CH₃)CH₂CH₃], [ZA7091;(CH₂)₆NO₂,N(CH₃)CH₂CH₃], [ZA7092;O(CH₂)₆Ph,N(CH₃)CH₂CH₃], [ZA7093;O(CH₂)₆OCH₃,N(CH₃)CH₂CH₃], [ZA7094;OC(O)CH₃,N(CH₃)CH₂CH₃], [ZA7095;OC(O)CH₂CH₃,N(CH₃)CH₂CH₃], [ZA7096;OC(O)CH(CH₃)₂,N(CH₃)CH₂CH₃], [ZA7097;OC(O)(CH₂)₂CH₃,N(CH₃)CH₂CH₃], [ZA7098;OC(O)(CH₂)₃CH₃,N(CH₃)CH₂CH₃], [ZA7099;OC(O)(CH₂)₄CH₃,N(CH₃)CH₂CH₃], [ZA7100;OC(O)(CH₂)₅CH₃,N(CH₃)CH₂CH₃], [ZA7101;OC(O)CH₂CH=CH₂,N(CH₃)CH₂CH₃], [ZA7102;OC(O)CH₂C≡CH,N(CH₃)CH₂CH₃], [ZA7103;OC(O)CH₂C≡CCH₃,N(CH₃)CH₂CH₃], [ZA7104;OC(O)c-Pr,N(CH₃)CH₂CH₃], [ZA7105;OC(O)c-Pen,N(CH₃)CH₂CH₃], [ZA7106;OC(O)c-Hex,N(CH₃)CH₂CH₃], [ZA7107;OC(O)Ph,N(CH₃)CH₂CH₃], [ZA7108;OC(O)(2-Py),N(CH₃)CH₂CH₃], [ZA7109;OC(O)(3-Py),N(CH₃)CH₂CH₃], [ZA7110;OC(O)(4-Py),N(CH₃)CH₂CH₃], [ZA7111;OC(O)CH₂Ph,N(CH₃)CH₂CH₃], [ZA7112;OC(O)CH₂(2-Py),N(CH₃)CH₂CH₃], [ZA7113;OC(O)CH₂(3-Py),N(CH₃)CH₂CH₃], [ZA7114;OC(O)CH₂(4-Py),N(CH₃)CH₂CH₃], [ZA7115;OC(O)CH₂CN,N(CH₃)CH₂CH₃], [ZA7116;OC(O)CH₂NO₂,N(CH₃)CH₂CH₃], [ZA7117;OC(O)(CH₂)₂F,N(CH₃)CH₂CH₃], [ZA7118;OC(O)(CH₂)₂CN,

N(CH$_3$)CH$_2$CH$_3$], [ZA7119;OC(O)(CH$_2$)$_2$NO$_2$,N(CH$_3$)CH$_2$CH$_3$], [ZA7120;OC(O)(CH$_2$)$_2$ Ph,N(CH$_3$)CH$_2$CH$_3$], [ZA7121;OC(O)(CH$_2$)$_2$OCH$_3$,N(CH$_3$)CH$_2$CH$_3$], [ZA7122;OC(O)(CH$_2$)$_3$F,N(CH$_3$)CH$_2$CH$_3$], [ZA7123;OC(O)(CH$_2$)$_3$CN,N(CH$_3$)CH$_2$CH$_3$], [ZA7124;OC(O)(CH$_2$)$_3$NO$_2$,N(CH$_3$)CH$_2$CH$_3$], [ZA7125;OC(O)(CH$_2$)$_3$OCH$_3$,N(CH$_3$)CH$_2$CH$_3$], [ZA7126;OC(O)NH$_2$,N(CH$_3$)CH$_2$CH$_3$], [ZA7127;OC(O)NHCH$_3$,N(CH$_3$)CH$_2$CH$_3$], [ZA7128;OC(O)NHCH$_2$CH$_3$,N(CH$_3$)CH$_2$CH$_3$], [ZA7129;OC(O)NH(CH$_2$)$_2$ CH$_3$,N(CH$_3$)CH$_2$CH$_3$], [ZA7130;OC(O)NH(CH$_2$)$_3$CH$_3$,N(CH$_3$)CH$_2$CH$_3$], [ZA7131;OC(O)NH(CH$_2$)$_4$CH$_3$,N(CH$_3$)CH$_2$CH$_3$], [ZA7132;OC(O)NH(CH$_2$)$_5$CH$_3$,N(CH$_3$)CH$_2$CH$_3$], [ZA7133;OC(O)NHCH(CH$_3$)$_2$,N(CH$_3$)CH$_2$CH$_3$], [ZA7134;OC(O)NHCH$_2$F,N(CH$_3$)CH$_2$CH$_3$], [ZA7135;OC(O)NHCH$_2$CN,N(CH$_3$)CH$_2$ CH$_3$], [ZA7136;OC(O)NHCH$_2$OCH$_3$,N(CH$_3$)CH$_2$CH$_3$], [ZA7137;OC(O)NHCH$_2$ Ph,N(CH$_3$)CH$_2$CH$_3$], [ZA7138;OC(O)NH(CH$_2$)$_2$F,N(CH$_3$)CH$_2$CH$_3$], [ZA7139;OC(O)NH(CH$_2$)$_2$CN,N(CH$_3$)CH$_2$CH$_3$], [ZA7140;OC(O)NH(CH$_2$)$_2$OCH$_3$,N(CH$_3$)CH$_2$CH$_3$], [ZA7141;OC(O)NH(CH$_2$)$_3$F,N(CH$_3$)CH$_2$CH$_3$], [ZA7142;OC(O)NH(CH$_2$)$_3$CN,N(CH$_3$)CH$_2$CH$_3$], [ZA7143;OC(O)NH(CH$_2$)$_3$OCH$_3$,N(CH$_3$)CH$_2$CH$_3$], [ZA7144;OC(O)NH(CH$_2$)$_4$F,N(CH$_3$)CH$_2$CH$_3$], [ZA7145;OC(O)NH(CH$_2$)$_4$CN,N(CH$_3$)CH$_2$CH$_3$], [ZA7146;OC(O)NH(CH$_2$)$_4$OCH$_3$,N(CH$_3$)CH$_2$CH$_3$], [ZA7147;OC(O)NHPh,N(CH$_3$)CH$_2$CH$_3$], [ZA7148;OC(O)NH(2-Py),N(CH$_3$)CH$_2$CH$_3$], [ZA7149;OC(O)NH(3-Py),N(CH$_3$)CH$_2$ CH$_3$], [ZA7150;OC(O)NH(4-Py),N(CH$_3$)CH$_2$CH$_3$], [ZA7151;OC(O)N(CH$_3$)$_2$,N(CH$_3$)CH$_2$CH$_3$], [ZA7152;OC(O)N(CH$_3$)CH$_2$CH$_3$,N(CH$_3$)CH$_2$CH$_3$], [ZA7153;OC(O)N(CH$_3$)(CH$_2$)$_2$ CH$_3$,N(CH$_3$)CH$_2$CH$_3$], [ZA7154;OC(O)N(CH$_3$)(CH$_2$)$_3$CH$_3$,N(CH$_3$)CH$_2$CH$_3$], [ZA7155;OC(O)N(CH$_3$)CH(CH$_3$)$_2$,N(CH$_3$)CH$_2$CH$_3$], [ZA7156;OC(O)N(CH$_3$)CH$_2$F,N(CH$_3$)CH$_2$CH$_3$], [ZA7157;OC(O)N(CH$_3$)CH$_2$CN,N(CH$_3$)CH$_2$CH$_3$], [ZA7158;OC(O)N(CH$_3$)CH$_2$OCH$_3$,N(CH$_3$)CH$_2$CH$_3$], [ZA7159;OC(O)N(CH$_3$)CH$_2$ Ph,N(CH$_3$)CH$_2$CH$_3$], [ZA7160;OC(O)N(CH$_3$)(CH$_2$)$_2$F,N(CH$_3$)CH$_2$CH$_3$], [ZA7161;OC(O)N(CH$_3$)(CH$_2$)$_2$CN,N(CH$_3$)CH$_2$CH$_3$], [ZA7162;OC(O)N(CH$_3$)(CH$_2$)$_2$ OCH$_3$,N(CH$_3$)CH$_2$CH$_3$], [ZA7163;OC(O)N(CH$_3$)Ph,N(CH$_3$)CH$_2$CH$_3$], [ZA7164;OC(O)N(CH$_3$)(2-Py),N(CH$_3$)CH$_2$CH$_3$], [ZA7165;OC(O)N(CH$_3$)(3-Py),N(CH$_3$)CH$_2$CH$_3$], [ZA7166;OC(O)N(CH$_3$)(4-Py),N(CH$_3$)CH$_2$CH$_3$], [ZA7167;OC(O)N(CH(CH$_3$)$_2$,N(CH$_3$)CH$_2$CH$_3$], [ZA7168;OC(O)(Pyr),N(CH$_3$)CH$_2$CH$_3$], [ZA7169;OC(O)(Pip),N(CH$_3$)CH$_2$CH$_3$], [ZA7170;OC(O)(Mor),N(CH$_3$)CH$_2$CH$_3$], [ZA7171;OC(O)OCH$_3$,N(CH$_3$)CH$_2$CH$_3$], [ZA7172;OC(O)OCH$_2$CH$_3$,N(CH$_3$)CH$_2$CH$_3$], [ZA7173;OC(O)OCH(CH$_3$)$_2$,N(CH$_3$)CH$_2$CH$_3$], [ZA7174;OC(O)O(CH$_2$)$_2$CH$_3$,N(CH$_3$)CH$_2$CH$_3$], [ZA7175;OC(O)O(CH$_2$)$_3$CH$_3$,N(CH$_3$)CH$_2$CH$_3$], [ZA7176;OC(O)O(CH$_2$)$_4$ CH$_3$,N(CH$_3$)CH$_2$CH$_3$], [ZA7177;OC(O)O(CH$_2$)$_5$CH$_3$,N(CH$_3$)CH$_2$CH$_3$], [ZA7178;OC(O)OCH$_2$CH=CH$_2$,N(CH$_3$)CH$_2$CH$_3$], [ZA7179;OC(O)OCH$_2$C≡CH,N(CH$_3$)CH$_2$CH$_3$], [ZA7180;OC(O)OCH$_2$C≡CCH$_3$,N(CH$_3$)CH$_2$CH$_3$], [ZA7181;OC(O)O-c-Pr,N(CH$_3$)CH$_2$CH$_3$], [ZA7182;OC(O)O-c-Pen,N(CH$_3$)CH$_2$CH$_3$], [ZA7183;OC(O)O-c-Hex,N(CH$_3$)CH$_2$CH$_3$], [ZA7184;OC(O)OPh,N(CH$_3$)CH$_2$CH$_3$], [ZA7185;OC(O)O(2-Py),N(CH$_3$)CH$_2$CH$_3$], [ZA7186;OC(O)O(3-Py),N(CH$_3$)CH$_2$CH$_3$], [ZA7187;OC(O)O(4-Py),N(CH$_3$)CH$_2$CH$_3$], [ZA7188;OC(O)OCF$_3$,N(CH$_3$)CH$_2$CH$_3$], [ZA7189;OC(O)OCH$_2$Ph,N(CH$_3$)CH$_2$CH$_3$], [ZA7190;OC(O)OCH$_2$(2-Py),N(CH$_3$)CH$_2$ CH$_3$], [ZA7191;OC(O)OCH$_2$(3-Py),N(CH$_3$)CH$_2$CH$_3$], [ZA7192;OC(O)OCH$_2$ (4-Py),N(CH$_3$)CH$_2$CH$_3$], [ZA7193;OC(O)OCH$_2$CN,N(CH$_3$)CH$_2$CH$_3$], [ZA7194;OC(O)OCH$_2$NO$_2$,N(CH$_3$)CH$_2$CH$_3$], [ZA7195;OC(O)O(CH$_2$)$_2$F,N(CH$_3$)CH$_2$ CH$_3$], [ZA7196;OC(O)O(CH$_2$)$_2$CN,N(CH$_3$)CH$_2$CH$_3$], [ZA7197;OC(O)O(CH$_2$)$_2$OCH$_3$,N(CH$_3$)CH$_2$CH$_3$], [ZA7198;OC(O)O(CH$_2$)$_3$F,N(CH$_3$)CH$_2$CH$_3$], [ZA7199;OC(O)O(CH$_2$)$_3$CN,N(CH$_3$)CH$_2$CH$_3$], [ZA7200;OC(O)O(CH$_2$)$_3$OCH$_3$,N(CH$_3$)CH$_2$CH$_3$], [ZA7201;OS(O)$_2$CH$_3$,N(CH$_3$)CH$_2$CH$_3$], [ZA7202;OS(O)$_2$CH$_2$CH$_3$,N(CH$_3$)CH$_2$CH$_3$], [ZA7203;OS(O)$_2$CH(CH$_3$)$_2$,N(CH$_3$)CH$_2$CH$_3$], [ZA7204;OS(O)$_2$(CH$_2$)$_2$CH$_3$,N(CH$_3$)CH$_2$ CH$_3$], [ZA7205;OS(O)$_2$(CH$_2$)$_3$CH$_3$,N(CH$_3$)CH$_2$CH$_3$], [ZA7206;OS(O)$_2$(CH$_2$)$_4$CH$_3$,N(CH$_3$)CH$_2$CH$_3$], [ZA7207;OS(O)$_2$(CH$_2$)$_5$CH$_3$,N(CH$_3$)CH$_2$CH$_3$], [ZA7208;OS(O)$_2$-c-Pr,N(CH$_3$)CH$_2$CH$_3$], [ZA7209;OS(O)$_2$-c-Pen,N(CH)CH$_2$CH$_3$], [ZA721;OS(O)$_2$-c-Hex,N(CH$_3$)CH$_2$CH$_3$], [ZA7211;OS(O)$_2$Ph,N(CH$_3$)CH$_2$CH$_3$], [ZA7212;OS(O)$_2$ (2-Py),N(CH$_3$)CH$_2$CH$_3$], [ZA7213;OS(O)$_2$(3-Py),N(CH$_3$)CH$_2$CH$_3$], [ZA7214;OS(O)$_2$ (4-Py),N(CH$_3$)CH$_2$CH$_3$], [ZA7215;OS(O)$_2$CF$_3$,N(CH$_3$)CH$_2$CH$_3$], [ZA7216;OS(O)$_2$CH$_2$ Ph,N(CH$_3$)CH$_2$CH$_3$], [ZA7217;OH,N(CH$_3$)(CH$_2$)$_2$CH$_3$], [ZA7218;OCH$_3$,N(CH$_3$)(CH$_2$)$_2$ CH$_3$], [ZA7219;OCH$_2$CH$_3$,N(CH$_3$)(CH$_2$)$_2$CH$_3$], [ZA7220;OCH(CH$_3$)$_2$,N(CH)(CH$_2$)$_2$ CH$_3$], [ZA7221;(CH$_2$)$_2$CH$_3$,N(CH$_3$)(CH$_2$)$_2$CH$_3$], [ZA7222;O(CH$_2$)$_3$CH$_3$,N(CH$_3$)(CH$_2$)$_2$ CH$_3$], [ZA7223;O(CH$_2$)$_4$CH$_3$,N(CH$_3$)(CH$_2$)$_2$CH$_3$], [ZA7224;O(CH$_2$)$_5$CH$_3$,N(CH$_3$)(CH$_2$)$_2$ CH$_3$], [ZA7225;OCH$_2$CH=CH$_2$,N(CH$_3$)(CH$_2$)$_2$CH$_3$], [ZA7226;OCH$_2$C≡CH,N(CH$_3$)(CH$_2$)$_2$CH$_3$], [ZA7227;OCH$_2$C≡CCH$_3$,N(CH$_3$)(CH$_2$)$_2$CH$_3$], [ZA7228;O-c-Pr,N(CH$_3$)(CH$_2$)$_2$CH$_3$], [ZA7229;O-c-Pen,N(CH$_3$)(CH$_2$)$_2$CH$_3$], [ZA7230;O-c-Hex,N(CH$_3$)(CH$_2$)$_2$ CH$_3$], [ZA7231;OPh,N(CH$_3$)(CH$_2$)$_2$CH$_3$], [ZA7232;OCH$_2$ Ph,N(CH$_3$)(CH$_2$)$_2$CH$_3$], [ZA7233;OCH$_2$(2-Py),N(CH$_3$)(CH$_2$)$_2$CH$_3$], [ZA7234;OCH$_2$ (3-Py),N(CH$_3$)(CH$_2$)$_2$CH$_3$], [ZA7235;OCH$_2$(4-Py),N(CH$_3$)(CH$_2$)$_2$CH$_3$], [ZA7236;OCH$_2$ CN,N(CH$_3$)(CH$_2$)$_2$CH$_3$], [ZA7237;OCH$_2$NO$_2$,N(CH$_3$)(CH$_2$)$_2$CH$_3$], [ZA7238;(CH$_2$)$_2$ F,N(CH$_3$)(CH$_2$)$_2$CH$_3$], [ZA7239;O(CH$_2$)$_2$CN,N(CH$_3$)(CH$_2$)$_2$CH$_3$], [ZA7240;O(CH$_2$)$_2$ Ph,N(CH$_3$)(CH$_2$)$_2$CH$_3$], [ZA7241;(CH$_2$)$_2$OCH$_3$,N(CH$_3$)(CH$_2$)$_2$CH$_3$], [ZA7242;O(CH$_2$)$_3$F,N(CH$_3$)(CH$_2$)$_2$CH$_3$], [ZA7243;O(CH$_2$)$_3$CN,N(CH$_3$)(CH$_2$)$_2$CH$_3$], [ZA7244;O(CH$_2$)$_3$ NO$_2$,N(CH$_3$)(CH$_2$)$_2$CH$_3$], [ZA7245;O(CH$_2$)$_3$Ph,N(CH$_3$)(CH$_2$)$_2$CH$_3$], [ZA7246;O(CH$_2$)$_3$ OCH$_3$,N(CH$_3$)(CH$_2$)$_2$CH$_3$], [ZA7247;O(CH$_2$)$_4$F,N(CH$_3$)(CH$_2$)$_2$CH$_3$], [ZA7248;O(CH$_2$)$_4$ CN,N(CH$_3$)(CH$_2$)$_2$CH$_3$], [ZA7249;O(CH$_2$)$_4$NO$_2$,N(CH$_3$)(CH$_2$)$_2$CH$_3$], [ZA7250;O(CH$_2$)$_4$ Ph,N(CH$_3$)(CH$_2$)$_2$CH$_3$], [ZA7251;(CH$_2$)$_4$OCH$_3$,N(CH$_3$)(CH$_2$)$_2$CH$_3$], [ZA7252;O(CH$_2$)$_5$F,N(CH$_3$)(CH$_2$)$_2$CH$_3$], [ZA7253;(CH$_2$)$_5$ CN,N(CH$_3$)(CH$_2$)$_2$CH$_3$], [ZA7254;O(CH$_2$)$_5$ NO$_2$,N(CH$_3$)(CH$_2$)$_2$CH$_3$], [ZA7255;(CH$_2$)$_5$Ph,N(CH$_3$)(CH$_2$)$_2$CH$_3$], [ZA7256;(CH$_2$)$_5$ OCH$_3$,N(CH$_3$)(CH$_2$)$_2$CH$_3$], [ZA7257;O(CH$_2$)$_6$F,N(CH$_3$)(CH$_2$)$_2$CH$_3$], [ZA7258;(CH$_2$)$_6$ CN,N(CH$_3$)(CH$_2$)$_2$CH$_3$], [ZA7259;O(CH$_2$)$_6$NO$_2$,N(CH$_3$)(CH$_2$)$_2$CH$_3$], [ZA7260;O(CH$_2$)$_6$ Ph,N(CH$_3$)(CH$_2$)$_2$CH$_3$], [ZA7261;(CH$_2$)$_6$ OCH$_3$,N(CH$_3$)(CH)$_2$CH$_3$], [ZA7262;OC(O)CH$_3$,N(CH$_3$)(CH$_2$)$_2$CH$_3$], [ZA7263;OC(O)CH$_2$CH$_3$,N(CH$_3$)(CH$_2$)$_2$ CH$_3$], [ZA7264;OC(O)CH(CH$_3$)$_2$,N(CH$_3$)(CH$_2$)$_2$CH$_3$], [ZA7265;OC(O)(CH$_2$)$_2$CH$_3$,N(CH$_3$)(CH$_2$)$_2$CH$_3$], [ZA7266;OC(O)(CH$_2$)$_3$CH$_3$,N(CH$_3$)(CH$_2$)$_2$CH$_3$], [ZA7267;OC(O)(CH$_2$)$_4$ CH$_3$,N(CH$_3$)(CH$_2$)$_2$CH$_3$], [ZA7268;OC(O)(CH$_2$)$_5$CH$_3$,N(CH$_3$)(CH)$_2$CH$_3$], [ZA7269;OC(O)CH$_2$CH=CH$_2$,N(CH$_3$)(CH$_2$)$_2$CH$_3$], [ZA7270;OC(O)CH$_2$C≡CH,N(CH$_3$)(CH$_2$)$_2$CH$_3$], [ZA7271;OC(O)CH$_2$C≡CCH$_3$,N(CH$_3$)(CH$_2$)$_2$CH$_3$], [ZA7272;OC(O)c-Pr,N(CH$_3$)(CH$_2$)$_2$CH$_3$], [ZA7273;OC(O)c-Pen,N(CH$_3$)(CH$_2$)$_2$ CH$_3$], [ZA7274;OC(O)c-Hex,N(CH$_3$)(CH)$_2$CH$_3$], [ZA7275;OC(O)Ph,N(CH$_3$)(CH$_2$)$_2$CH$_3$], [ZA7276;OC(O)(2-Py),N(CH$_3$)(CH$_2$)$_2$CH$_3$], [ZA7277;OC(O)(3-Py),N(CH$_3$)(CH$_2$)$_2$CH$_3$], [ZA7278;OC(O)(4-Py),N(CH$_3$)(CH$_2$)$_2$ CH$_3$], [ZA7279;OC(O)CH$_2$Ph,N(CH$_3$)(CH$_2$)$_2$ CH$_3$], [ZA7280;OC(O)CH$_2$(2-Py),N(CH$_3$)(CH$_2$)$_2$CH$_3$], [ZA7281;

OC(O)CH₂ (3-Py),N(CH₃)(CH₂)₂CH₃], [ZA7282;OC(O)CH₂(4-Py),N(CH₃)(CH₂)₂CH₃], [ZA7283;OC(O)CH₂CN,N(CH₃)(CH₂)₂CH₃], [ZA7284;OC(O)CH₂NO₂,N(CH₃)(CH₂)₂ CH₃], [ZA7285;OC(O)(CH₂)₂F,N(CH₃)(CH₂)₂CH₃], [ZA7286;OC(O)(CH₂)₂CN,N(CH₃)(CH₂)₂CH₃], [ZA7287;OC(O)(CH₂)₂NO₂,N(CH₃)(CH₂)₂CH₃], [ZA7288;OC(O)(CH₂)₂ Ph,N(CH₃)(CH₂)₂CH₃], [ZA7289;OC(O)(CH₂)₂OCH₃,N(CH₃)(CH₂)₂CH₃], [ZA7290;OC(O)(CH₂)₃F,N(CH)(CH₂)₂CH₃], [ZA7291;OC(O)(CH₂)₃CN,N(CH₃)(CH₂)₂CH₃], [ZA7292;OC(O)(CH₂)₃NO₂,N(CH)(CH₂)₂CH₃], [ZA7293;OC(O)(CH₂)₃OCH₃,N(CH₃)(CH₂)₂CH₃], [ZA7294;OC(O)NH₂,N(CH₃)(CH₂)₂CH₃], [ZA7295;OC(O)NHCH₃,N(CH₃)(CH₂)₂CH₃], [ZA7296;OC(O)NHCH₂CH₃,N(CH₃)(CH₂)₂CH₃], [ZA7297;OC(O)NH(CH₂)₂CH₃,N(CH)(CH₂)₂CH₃], [ZA7298;OC(O)NH(CH₂)₃ CH₃,N(CH₃)(CH₂)₂CH₃], [ZA7299;OC(O)NH(CH₂)₄CH₃,N(CH₃)(CH₂)₂CH₃], [ZA7300;OC(O)NH(CH₂)₅CH₃,N(CH₃)(CH)₂CH₃], [ZA7301;OC(O)NHCH(CH₃)₂,N(CH₃)(CH₂)₂CH₃], [ZA7302;OC(O)NHCH₂F,N(CH₃)(CH₂)₂CH₃], [ZA7303;OC(O)NHCH₂CN,N(CH₃)(CH₂)₂CH₃], [ZA7304;OC(O)NHCH₂OCH₃,N(CH₃)(CH₂)₂ CH₃], [ZA7305;OC(O)NHCH₂Ph,N(CH₃)(CH₂)₂CH₃], [ZA7306;OC(O)NH(CH₂)₂F,N(CH₃)(CH₂)₂CH₃], [ZA7307;OC(O)NH(CH₂)₂CN,N(CH₃)(CH₂)₂CH₃], [ZA7308;OC(O)NH(CH₂)₂OCH₃,N(CH₃)(CH₂)₂CH₃], [ZA7309;OC(O)NH(CH₂)₃ F,N(CH₃)(CH₂)₂CH₃], [ZA731;OC(O)NH(CH₂)₃CN,N(CH₃)(CH₂)₂CH₃], [ZA7311;OC(O)NH(CH₂)₃OCH₃,N(CH₃)(CH₂)₂CH₃], [ZA7312;OC(O)NH(CH₂)₄ F,N(CH₃)(CH₂)₂CH₃], [ZA7313;OC(O)NH(CH₂)₄CN,N(CH₃)(CH₂)₂CH₃], [ZA7314;OC(O)NH(CH₂)₄OCH₃,N(CH₃)(CH₂)₂CH₃], [ZA7315;OC(O)NHPh,N(CH₃)(CH₂)₂CH₃], [ZA7316;OC(O)NH(2-Py),N(CH₃)(CH₂)₂CH₃], [ZA7317;OC(O)NH(3-Py),N(CH₃)(CH₂)₂CH₃], [ZA7318;OC(O)NH(4-Py),N(CH₃)(CH₂)₂CH₃], [ZA7319;OC(O)N(CH₃)₂,N(CH₃)(CH₂)₂CH₃], [ZA7320;OC(O)N(CH₃)CH₂CH₃,N(CH₃)(CH₂)₂CH₃], [ZA7321;OC(O)N(CH₃)(CH₂)₂CH₃,N(CH₃)(CH₂)₂CH₃], [ZA7322;OC(O)N(CH₃)(CH₂)₃CH₃,N(CH₃)(CH₂)₂CH₃], [ZA7323;OC(O)N(CH₃)CH(CH₃)₂,N(CH₃)(CH₂)₂CH₃], [ZA7324;OC(O)N(CH₃)CH₂F,N(CH₃)(CH₂)₂CH₃], [ZA7325;OC(O)N(CH₃)CH₂CN,N(CH₃)(CH₂)₂CH₃], [ZA7326;OC(O)N(CH₃)CH₂OCH₃,N(CH₃)(CH₂)₂CH₃], [ZA7327;OC(O)N(CH₃)CH₂Ph,N(CH₃)(CH₂)₂CH₃], [ZA7328;OC(O)N(CH₃)(CH₂)₂F,N(CH₃)(CH₂)₂CH₃], [ZA7329;OC(O)N(CH₃)(CH₂)₂ CN,N(CH₃)(CH₂)₂CH₃], [ZA7330; OC(O)N(CH₃)(CH₂)₂OCH₃,N(CH₃)(CH₂)₂CH₃], [ZA7331;OC(O)N(CH₃)Ph,N(CH₃)(CH₂)₂CH₃], [ZA7332;OC(O)N(CH₃)(2-Py),N(CH₃)(CH₂)₂CH₃], [ZA7333;OC(O)N(CH₃)(3-Py),N(CH₃)(CH₂)₂CH₃], [ZA7334;OC(O)N(CH₃)(4-Py),N(CH₃)(CH₂)₂CH₃], [ZA7335;OC(O)N(CH₂CH₃)₂,N(CH₃)(CH₂)₂CH₃], [ZA7336;OC(O)(Pyr),N(CH₃)(CH₂)₂CH₃], [ZA7337;OC(O)(Pip),N(CH₃)(CH₂)₂CH₃], [ZA7338;OC(O)(Mor),N(CH₃)(CH₂)₂CH₃], [ZA7339;OC(O)OCH₃,N(CH₃)(CH₂)₂CH₃], [ZA7340;OC(O)OCH₂CH₃,N(CH₃)(CH₂)₂CH₃], [ZA7341;OC(O)OCH(CH₃)₂,N(CH₃)(CH₂)₂CH₃], [ZA7342;OC(O)O(CH₂)₂CH₃,N(CH₃)(CH₂)₂CH₃], [ZA7343;OC(O)O(CH)₃CH₃,N(CH₃)(CH₂)₂CH₃], [ZA7344;OC(O)O(CH₂)₄CH₃,N(CH₃)(CH₂)₂CH₃], [ZA7345;OC(O)O(CH₂)₅CH₃,N(CH₃)(CH₂)₂CH₃], [ZA7346;OC(O)OCH₂CH=CH₂,N(CH₃)(CH₂)₂CH₃], [ZA7347;OC(O)OCH₂C≡CH,N(CH₃)(CH₂)₂CH₃], [ZA7348;OC(O)OCH₂C≡CCH₃,N(CH₃)(CH₂)₂CH₃], [ZA7349;OC(O)O-c-Pr,N(CH₃)(CH₂)₂CH₃], [ZA7350;OC(O)O-c-Pen,N(CH₃)(CH₂)₂CH₃], [ZA7351;OC(O)O-c-Hex,N(CH₃)(CH₂)₂CH₃], [ZA7352;OC(O)OPh,N(CH₃)(CH₂)₂CH₃], [ZA7353;OC(O)O(2-Py),N(CH₃)(CH₂)₂CH₃], [ZA7354;OC(O)O(3-Py),N(CH₃)(CH₂)₂CH₃], [ZA7355;OC(O)O(4-Py),N(CH₃)(CH₂)₂CH₃], [ZA7356;OC(O)OCF₃,N(CH₃)(CH₂)₂CH₃], [ZA7357;OC(O)OCH₂Ph,N(CH₃)(CH₂)₂CH₃], [ZA7358;OC(O)OCH₂ (2-Py),N(CH₃)(CH₂)₂CH₃], [ZA7359;OC(O)OCH₂(3-Py),N(CH₃)(CH₂)₂CH₃], [ZA7360;OC(O)OCH₂(4-Py),N(CH₃)(CH₂)₂CH₃], [ZA7361;OC(O)OCH₂CN,N(CH₃)(CH₂)₂CH₃], [ZA7362;OC(O)OCH₂NO₂,N(CH₃)(CH₂)₂CH₃], [ZA7363;OC(O)O(CH₂)₂ F,N(CH₃)(CH₂)₂CH₃], [ZA7364;OC(O)O(CH₂)₂CN,N(CH₃)(CH₂)₂CH₃], [ZA7365;OC(O)O(CH₂)₂OCH₃,N(CH₃)(CH₂)₂CH₃], [ZA7366;OC(O)O(CH)₃F,N(CH₃)(CH₂)₂CH₃], [ZA7367;OC(O)O(CH₂)₃CN,N(CH₃)(CH₂)₂CH₃], [ZA7368;OC(O)O(CH₂)₃OCH₃,N(CH₃)(CH₂)₂CH₃], [ZA7369;OS(O)₂CH₃,N(CH₃)(CH₂)₂CH₃], [ZA7370;OS(O)₂CH₂CH₃,N(CH₃)(CH₂)₂CH₃], [ZA7371;OS(O)₂CH(CH₃)₂,N(CH₃)(CH₂)₂CH₃], [ZA7372;OS(O)₂(CH₂)₂CH₃,N(CH₃)(CH₂)₂CH₃], [ZA7373;OS(O)₂(CH₂)₃CH₃,N(CH₃)(CH₂)₂CH₃], [ZA7374;OS(O)₂(CH₂)₄CH₃,N(CH₃)(CH₂)₂CH₃], [ZA7375;OS(O)₂(CH₂)₅CH₃,N(CH₃)(CH₂)₂CH₃], [ZA7376;OS(O)₂-c-Pr,N(CH₃)(CH₂)₂CH₃], [ZA7377;OS(O)₂-c-Pen,N(CH₃)(CH₂)₂CH₃], [ZA7378;OS(O)₂-c-Hex,N(CH₃)(CH₂)₂CH₃], [ZA7379;OS(O)₂Ph,N(CH₃)(CH₂)₂CH₃], [ZA7380;OS(O)₂(2-Py),N(CH₃)(CH₂)₂CH₃], [ZA7381;OS(O)₂(3-Py),N(CH₃)(CH₂)₂ CH₃], [ZA7382;OS(O)₂(4-Py),N(CH)(CH₂)₂ CH₃], [ZA7383;OS(O)₂CF₃,N(CH₃)(CH₂)₂CH₃], [ZA7384;OS(O)₂CH₂Ph,N(CH₃)(CH₂)₂ CH₃], [ZA7385;OH,NHPh], [ZA7386;OCH₃,NHPh], [ZA7387;OCH₂CH₃,NHPh], [ZA7388;OCH(CH₃)₂,NHPh], [ZA7389;O(CH₂)₂CH₃,NHPh], [ZA7390;O(CH₂)₃CH₃,NHPh], [ZA7391;(CH₂)₄CH₃,NHPh], [ZA7392;O(CH₂)₅CH₃,NHPh], [ZA7393;OCH₂CH=CH₂,NHPh], [ZA7394;OCH₂C≡CH,NHPh], [ZA7395;OCH₂C≡CCH₃,NHPh], [ZA7396;O-c-Pr,NHPh], [ZA7397;O-c-Pen,NHPh], [ZA7398;O-c-Hex,NHPh], [ZA7399;OPh,NHPh], [ZA7400;OCH₂Ph,NHPh], [ZA7401;OCH₂(2-Py),NHPh], [ZA7402;OCH₂(3-Py),NHPh], [ZA7403;OCH₂(4-Py),NHPh], [ZA7404;OCH₂CN,NHPh], [ZA7405;OCH₂NO₂,NHPh], [ZA7406;O(CH₂)₂F,NHPh], [ZA7407;O(CH₂)₂CN,NHPh], [ZA7408;O(CH₂)₂Ph,NHPh], [ZA7409;O(CH₂)₂OCH₃,NHPh], [ZA7410;O(CH₂)₃F,NHPh], [ZA7411;O(CH₂)₃CN,NHPh], [ZA7412;O(CH₂)₃NO₂,NHPh], [ZA7413;O(CH₂)₃Ph,NHPh], [ZA7414;O(CH₂)₃OCH₃,NHPh], [ZA7415;O(CH₂)₄F,NHPh], [ZA7416;O(CH₂)₄CN,NHPh], [ZA7417;O(CH₂)₄NO₂,NHPh], [ZA7418;O(CH₂)₄Ph,NHPh], [ZA7419;O(CH₂)₄OCH₃,NHPh], [ZA7420;O(CH₂)₅F,NHPh], [ZA7421;O(CH₂)₅CN,NHPh], [ZA7422;O(CH₂)₅NO₂,NHPh], [ZA7423;O(CH₂)₅Ph,NHPh], [ZA7424;O(CH₂)₅OCH₃,NHPh], [ZA7425;O(CH₂)₆F,NHPh], [ZA7426;O(CH₂)₆CN,NHPh], [ZA7427;O(CH₂)₆NO₂,NHPh], [ZA7428;O(CH₂)₆Ph,NHPh], [ZA7429;O(CH₂)₆OCH₃,NHPh], [ZA7430;OC(O)CH₃,NHPh], [ZA7431;OC(O)CH₂CH₃,NHPh], [ZA7432;OC(O)CH(CH₃)₂,NHPh], [ZA7433;OC(O)(CH₂)₂CH₃,NHPh], [ZA7434;OC(O)(CH₂)₃CH₃,NHPh], [ZA7435;OC(O)(CH₂)₄CH₃,NHPh], [ZA7436;OC(O)(CH₂)₅CH₃,NHPh], [ZA7437;OC(O)CH₂CH=CH₂,NHPh], [ZA7438;OC(O)CH₂C≡CH,NHPh], [ZA7439;OC(O)CH₂C≡CCH₃,NHPh], [ZA7440;OC(O)c-Pr,NHPh], [ZA7441;OC(O)c-Pen,NHPh], [ZA7442;OC(O)c-Hex,NHPh], [ZA7443;OC(O)Ph,NHPh], [ZA7444;OC(O)(2-Py),NHPh], [ZA7445;OC(O)(3-Py),NHPh], [ZA7446;OC(O)(4-Py),NHPh], [ZA7447;OC(O)CH₂Ph,NHPh], [ZA7448;OC(O)CH₂ (2-Py),NHPh], [ZA7449;OC(O)CH₂(3-Py),NHPh], [ZA7450;OC(O)CH₂(4-Py),NHPh], [ZA7451;OC(O)CH₂CN,NHPh], [ZA7452;OC(O)CH₂NO₂, NHPh], [ZA7453;OC(O)(CH₂)₂F,NHPh], [ZA7454;OC(O)(CH₂)₂CN,NHPh], [ZA7455;OC(O)(CH₂)₂NO₂,NHPh],

[ZA7456;OC(O)(CH₂)₂Ph,NHPh], [ZA7457;OC(O)(CH₂)₂OCH₃,NHPh], [ZA7458;OC(O)(CH₂)₃F,NHPh], [ZA7459;OC(O)(CH₂)₃CN,NHPh], [ZA7460;OC(O)(CH₂)₃NO₂,NHPh], [ZA7461;OC(O)(CH₂)₃OCH₃,NHPh], [ZA7462;OC(O)NH₂,NHPh], [ZA7463;OC(O)NHCH₃,NHPh], [ZA7464;OC(O)NHCH₂CH₃,NHPh], [ZA7465;OC(O)NH(CH₂)₂CH₃,NHPh], [ZA7466;OC(O)NH(CH₂)₃CH₃,NHPh], [ZA7467;OC(O)NH(CH₂)₄CH₃,NHPh], [ZA7468;OC(O)NH(CH₂)₅CH₃,NHPh], [ZA7469;OC(O)NHCH(CH₃)₂,NHPh], [ZA7470;OC(O)NHCH₂F,NHPh], [ZA7471;OC(O)NHCH₂CN,NHPh], [ZA7472;OC(O)NHCH₂OCH₃,NHPh], [ZA7473;OC(O)NHCH₂Ph,NHPh], [ZA7474;OC(O)NH(CH₂)₂F,NHPh], [ZA7475;OC(O)NH(CH₂)₂CN,NHPh], [ZA7476;OC(O)NH(CH₂)₂OCH₃,NHPh], [ZA7477;OC(O)NH(CH₂)₃F,NHPh], [ZA7478;OC(O)NH(CH₂)₃CN,NHPh], [ZA7479;OC(O)NH(CH₂)₃OCH₃,NHPh], [ZA7480;OC(O)NH(CH₂)₄F,NHPh], [ZA7481;OC(O)NH(CH₂)₄CN,NHPh], [ZA7482;OC(O)NH(CH₂)₄OCH₃,NHPh], [ZA7483;OC(O)NHPh,NHPh], [ZA7484;OC(O)NH(2-Py),NHPh], [ZA7485;OC(O)NH(3-Py),NHPh], [ZA7486;OC(O)NH(4-Py),NHPh], [ZA7487;OC(O)N(CH₃)₂,NHPh], [ZA7488;OC(O)N(CH₃)CH₂CH₃,NHPh], [ZA7489;OC(O)N(CH₃)(CH₂)₂CH₃,NHPh], [ZA7490;OC(O)N(CH₃)(CH₂)₃CH₃,NHPh], [ZA7491;OC(O)N(CH₃)CH(CH₃)₂,NHPh], [ZA7492;OC(O)N(CH₃)CH₂F,NHPh], [ZA7493;OC(O)N(CH₃)CH₂CN,NHPh], [ZA7494;OC(O)N(CH₃)CH₂OCH₃,NHPh], [ZA7495;OC(O)N(CH₃)CH₂Ph,NHPh], [ZA7496;OC(O)N(CH₃)(CH₂)₂F,NHPh], [ZA7497;OC(O)N(CH₃)(CH₂)₂CN,NHPh], [ZA7498;OC(O)N(CH₃)(CH₂)₂OCH₃,NHPh], [ZA7499;OC(O)N(CH₃)Ph,NHPh], [ZA7500;OC(O)N(CH₃)(2-Py),NHPh],

[ZA7501;OC(O)N(CH₃)(3-Py),NHPh], [ZA7502;OC(O)N(CH₃)(4-Py),NHPh], [ZA7503;OC(O)N(CH₂CH₃)₂,NHPh], [ZA7504;OC(O)(Pyr),NHPh], [ZA7505;OC(O)(Pip),NHPh], [ZA7506;OC(O)(Mor),NHPh], [ZA7507;OC(O)OCH₃,NHPh], [ZA7508;OC(O)OCH₂CH₃,NHPh], [ZA7509;OC(O)OCH(CH₃)₂,NHPh], [ZA7510;OC(O)O(CH₂)₂CH₃,NHPh], [ZA7511;OC(O)O(CH₂)₃CH₃,NHPh], [ZA7512;OC(O)O(CH₂)₄CH₃,NHPh], [ZA7513;OC(O)O(CH₂)₅CH₃,NHPh], [ZA7514;OC(O)OCH₂CH=CH₂,NHPh], [ZA7515;OC(O)OCH₂C≡CH,NHPh], [ZA7516;OC(O)OCH₂C≡CCH₃,NHPh], [ZA7517;OC(O)O-c-Pr,NHPh], [ZA7518;OC(O)O-c-Pen,NHPh], [ZA7519;OC(O)O-c-Hex,NHPh], [ZA7520;OC(O)OPh,NHPh], [ZA7521;OC(O)O(2-Py),NHPh], [ZA7522;OC(O)O(3-Py),NHPh], [ZA7523;OC(O)O(4-Py),NHPh], [ZA7524;OC(O)OCF₃,NHPh], [ZA7525;OC(O)OCH₂Ph,NHPh], [ZA7526;OC(O)OCH₂(2-Py),NHPh], [ZA7527;OC(O)OCH₂(3-Py),NHPh], [ZA7528;OC(O)OCH₂(4-Py),NHPh], [ZA7529;OC(O)OCH₂CN,NHPh], [ZA7530;OC(O)OCH₂NO₂,NHPh], [ZA7531;OC(O)O(CH₂)₂F,NHPh], [ZA7532;OC(O)O(CH₂)₂CN,NHPh], [ZA7533;OC(O)O(CH₂)₂OCH₃,NHPh], [ZA7534;OC(O)O(CH₂)₃F,NHPh], [ZA7535;OC(O)O(CH₂)₃CN,NHPh], [ZA7536;OC(O)O(CH₂)₃OCH₃,NHPh], [ZA7537;OS(O)₂CH₃,NHPh], [ZA7538;OS(O)₂CH₂CH₃,NHPh], [ZA7539;OS(O)₂CH(CH₃)₂,NHPh], [ZA7540;OS(O)₂(CH₂)₂CH₃,NHPh], [ZA7541;OS(O)₂(CH₂)₃CH₃,NHPh], [ZA7542;OS(O)₂(CH₂)₄CH₃,NHPh], [ZA7543;OS(O)₂(CH₂)₅CH₃,NHPh], [ZA7544;OS(O)₂-c-Pr,NHPh], [ZA7545;OS(O)₂-c-Pen,NHPh], [ZA7546;OS(O)₂-c-Hex,NHPh], [ZA7547;OS(O)₂Ph,NHPh], [ZA7548;OS(O)₂(2-Py),NHPh], [ZA7549;OS(O)₂(3-Py),NHPh], [ZA7550;OS(O)₂(4-Py),NHPh], [ZA7551;OS(O)₂CF₃,NHPh], [ZA7552;OS(O)₂CH₂Ph,NHPh], [ZA7553;OH,NHCH₂Ph], [ZA7554;OCH₃,NHCH₂Ph], [ZA7555;OCH₂CH₃,NHCH₂Ph], [ZA7556;OCH(CH₃)₂,NHCH₂Ph], [ZA7557;O(CH₂)₂CH₃,NHCH₂Ph], [ZA7558;O(CH₂)₃CH₃,NHCH₂Ph], [ZA7559;O(CH₂)₄CH₃,NHCH₂Ph], [ZA7560;O(CH)₅CH₃,NHCH₂Ph], [ZA7561;OCH₂CH=CH₂,NHCH₂Ph], [ZA7562;OCH₂C≡CH,NHCH₂Ph], [ZA7563;OCH₂C≡CCH₃,NHCH₂Ph], [ZA7564;O-c-Pr,NHCH₂Ph], [ZA7565;O-c-Pen,NHCH₂Ph], [ZA7566;O-c-Hex,NHCH₂Ph], [ZA7567;OPh,NHCH₂Ph], [ZA7568;OCH₂Ph,NHCH₂Ph], [ZA7569;OCH₂(2-Py),NHCH₂Ph], [ZA7570;OCH₂(3-Py),NHCH₂Ph], [ZA7571;OCH₂(4-Py),NHCH₂Ph], [ZA7572;OCH₂CN,NHCH₂Ph], [ZA7573;OCH₂NO₂,NHCH₂Ph], [ZA7574;O(CH₂)₂F,NHCH₂Ph], [ZA7575;O(CH₂)₂CN,NHCH₂Ph], [ZA7576;O(CH₂)₂Ph,NHCH₂Ph], [ZA7577;O(CH₂)₂OCH₃,NHCH₂Ph], [ZA7578;(CH₂)₃F,NHCH₂Ph], [ZA7579;O(CH₂)₃CN,NHCH₂Ph], [ZA7580;O(CH₂)₃NO₂,NHCH₂Ph], [ZA7581;O(CH₂)₃Ph,NHCH₂Ph], [ZA7582;O(CH₂)₃OCH₃,NHCH₂Ph], [ZA7583;O(CH₂)₄F,NHCH₂Ph], [ZA7584;O(CH₂)₄CN,NHCH₂Ph], [ZA7585;O(CH₂)₄NO₂,NHCH₂Ph], [ZA7586;O(CH₂)₄Ph,NHCH₂Ph], [ZA7587;O(CH₂)₄OCH₃,NHCH₂Ph], [ZA7588;O(CH₂)₅F,NHCH₂Ph], [ZA7589;O(CH₂)₅CN,NHCH₂Ph], [ZA7590;O(CH₂)₅NO₂,NHCH₂Ph], [ZA7591;(CH₂)₅Ph,NHCH₂Ph], [ZA7592;O(CH₂)₅OCH₃,NHCH₂Ph], [ZA7593;O(CH₂)₆F,NHCH₂Ph], [ZA7594;O(CH₂)₆CN,NHCH₂Ph], [ZA7595;O(CH₂)₆NO₂,NHCH₂Ph], [ZA7596;O(CH₂)₆Ph,NHCH₂Ph], [ZA7597;O(CH₂)₆OCH₃,NHCH₂Ph], [ZA7598;OC(O)CH₃,NHCH₂Ph], [ZA7599;OC(O)CH₂CH₃,NHCH₂Ph], [ZA7600;OC(O)CH(CH₃)₂,NHCH₂Ph], [ZA7601;OC(O)(CH₂)₂CH₃,NHCH₂Ph], [ZA7602;OC(O)(CH₂)₃CH₃,NHCH₂Ph], [ZA7603;OC(O)(CH₂)₄CH₃,NHCH₂Ph], [ZA7604;OC(O)(CH₂)₅CH₃,NHCH₂Ph], [ZA7605;OC(O)CH₂CH=CH₂,NHCH₂Ph], [ZA7606;OC(O)CH₂C≡CH,NHCH₂Ph], [ZA7607;OC(O)CH₂C≡CCH₃,NHCH₂Ph], [ZA7608;OC(O)c-Pr,NHCH₂Ph], [ZA7609;OC(O)c-Pen,NHCH₂Ph], [ZA761;OC(O)c-Hex,NHCH₂Ph], [ZA7611;OC(O)Ph,NHCH₂Ph], [ZA7612;OC(O)(2-Py),NHCH₂Ph], [ZA7613;OC(O)(3-Py),NHCH₂Ph], [ZA7614;OC(O)(4-Py),NHCH₂Ph], [ZA7615;OC(O)CH₂Ph,NHCH₂Ph], [ZA7616;OC(O)CH₂(2-Py),NHCH₂Ph], [ZA7617;OC(O)CH₂(3-Py),NHCH₂Ph], [ZA7618;OC(O)CH₂(4-Py),NHCH₂Ph], [ZA7619;OC(O)CH₂CN,NHCH₂Ph], [ZA7620;OC(O)CH₂NO₂,NHCH₂Ph], [ZA7621;OC(O)(CH₂)₂F,NHCH₂Ph], [ZA7622;OC(O)(CH₂)₂CN,NHCH₂Ph], [ZA7623;OC(O)(CH₂)₂NO₂,NHCH₂Ph], [ZA7624;OC(O)(CH₂)₂Ph,NHCH₂Ph], [ZA7625;OC(O)(CH₂)₂OCH₃,NHCH₂Ph], [ZA7626;OC(O)(CH₂)₃F,NHCH₂Ph], [ZA7627;OC(O)(CH₂)₃CN,NHCH₂Ph], [ZA7628;OC(O)(CH₂)₃NO₂,NHCH₂Ph], [ZA7629;OC(O)(CH₂)₃OCH₃,NHCH₂Ph], [ZA7630;OC(O)NH₂,NHCH₂Ph], [ZA7631;OC(O)NHCH₃,NHCH₂Ph], [ZA7632;OC(O)NHCH₂CH₃,NHCH₂Ph], [ZA7633;OC(O)NH(CH₂)₂CH₃,NHCH₂Ph], [ZA7634;OC(O)NH(CH₂)₃CH₃,NHCH₂Ph], [ZA7635;OC(O)NH(CH₂)₄CH₃,NHCH₂Ph], [ZA7636;OC(O)NH(CH₂)₅CH₃,NHCH₂Ph], [ZA7637;OC(O)NHCH(CH₃)₂,NHCH₂Ph], [ZA7638;OC(O)NHCH₂F,NHCH₂Ph], [ZA7639;OC(O)NHCH₂CN,NHCH₂Ph], [ZA7640;OC(O)NHCH₂OCH₃,NHCH₂Ph], [ZA7641;OC(O)NHCH₂Ph,NHCH₂Ph], [ZA7642;OC(O)NH(CH₂)₂F,NHCH₂Ph], [ZA7643;OC(O)NH(CH₂)₂CN,NHCH₂Ph], [ZA7644;OC(O)NH(CH₂)₂OCH₃,NHCH₂Ph], [ZA7645;OC(O)NH(CH₂)₃F,NHCH₂Ph], [ZA7646;OC(O)NH(CH₂)₃CN,NHCH₂Ph], [ZA7647;OC(O)NH(CH₂)₃OCH₃,NHCH₂Ph], [ZA7648;OC(O)NH(CH)₄F,NHCH₂Ph], [ZA7649;OC(O)NH(CH₂)₄CN,NHCH₂Ph], [ZA7650;OC(O)NH(CH₂)₄OCH₃,NHCH₂Ph], [ZA7651;OC(O)NHPh,NHCH₂Ph], [ZA7652;OC(O)NH(2-Py),NHCH₂Ph], [ZA7653;OC(O)NH(3-Py),NHCH₂Ph],

[ZA7654;OC(O)NH(4-Py),NHCH$_2$Ph], [ZA7655;OC(O)N(CH$_3$)$_2$,NHCH$_2$Ph], [ZA7656;OC(O)N(CH$_3$)CH$_2$CH$_3$,NHCH$_2$Ph], [ZA7657;OC(O)N(CH$_3$)(CH$_2$)$_2$CH$_3$,NHCH$_2$Ph], [ZA7658;OC(O)N(CH$_3$)(CH$_2$)$_3$CH$_3$,NHCH$_2$Ph], [ZA7659;OC(O)N(CH$_3$)CH(CH$_3$)$_2$,NHCH$_2$Ph], [ZA7660;OC(O)N(CH$_3$)CH$_2$F,NHCH$_2$Ph], [ZA7661;OC(O)N(CH$_3$)CH$_2$CN,NHCH$_2$Ph], [ZA7662;OC(O)N(CH$_3$)CH$_2$OCH$_3$,NHCH$_2$Ph], [ZA7663;OC(O)N(CH)CH$_2$Ph,NHCH$_2$Ph], [ZA7664;OC(O)N(CH$_3$)(CH$_2$)$_2$F,NHCH$_2$Ph], [ZA7665;OC(O)N(CH$_3$)(CH$_2$)$_2$CN,NHCH$_2$Ph], [ZA7666;OC(O)N(CH$_3$)(CH$_2$)$_2$OCH$_3$,NHCH$_2$Ph], [ZA7667;OC(O)N(CH$_3$)Ph,NHCH$_2$Ph], [ZA7668;OC(O)N(CH$_3$)(2-Py),NHCH$_2$Ph], [ZA7669;OC(O)N(CH$_3$)(3-Py),NHCH$_2$Ph], [ZA7670;OC(O)N(CH$_3$)(4-Py),NHCH$_2$Ph], [ZA7671;OC(O)N(CH$_2$CH$_3$)$_2$,NHCH$_2$Ph], [ZA7672;OC(O)(Pyr),NHCH$_2$Ph], [ZA7673;OC(O)(Pip),NHCH$_2$Ph], [ZA7674;OC(O)(Mor),NHCH$_2$Ph], [ZA7675;OC(O)OCH$_3$,NHCH$_2$Ph], [ZA7676;OC(O)OCH$_2$CH$_3$,NHCH$_2$Ph], [ZA7677;OC(O)OCH(CH$_3$)$_2$,NHCH$_2$Ph], [ZA7678;OC(O)O(CH$_2$)$_2$CH$_3$,NHCH$_2$Ph], [ZA7679;OC(O)O(CH$_2$)$_3$CH$_3$,NHCH$_2$Ph], [ZA7680;OC(O)O(CH$_2$)$_4$CH$_3$,NHCH$_2$Ph], [ZA7681;OC(O)O(CH$_2$)$_5$CH$_3$,NHCH$_2$Ph], [ZA7682;OC(O)OCH$_2$CH=CH$_2$,NHCH$_2$Ph], [ZA7683;OC(O)OCH$_2$C≡CH,NHCH$_2$Ph], [ZA7684;OC(O)OCH$_2$C≡CCH$_3$,NHCH$_2$Ph], [ZA7685;OC(O)O-c-Pr,NHCH$_2$Ph], [ZA7686;OC(O)O-c-Pen,NHCH$_2$Ph], [ZA7687;OC(O)O-c-Hex,NHCH$_2$Ph], [ZA7688;OC(O)OPh,NHCH$_2$Ph], [ZA7689;OC(O)O(2-Py),NHCH$_2$Ph], [ZA7690;OC(O)O(3-Py),NHCH$_2$Ph], [ZA7691;OC(O)O(4-Py),NHCH$_2$Ph], [ZA7692;OC(O)OCF$_3$,NHCH$_2$Ph], [ZA7693;OC(O)OCH$_2$Ph,NHCH$_2$Ph], [ZA7694;OC(O)OCH$_2$(2-Py),NHCH$_2$Ph], [ZA7695;OC(O)OCH$_2$(3-Py),NHCH$_2$Ph], [ZA7696;OC(O)OCH$_2$(4-Py),NHCH$_2$Ph], [ZA7697;OC(O)OCH$_2$CN,NHCH$_2$Ph], [ZA7698;OC(O)OCH$_2$NO$_2$,NHCH$_2$Ph], [ZA7699;OC(O)O(CH$_2$)$_2$F,NHCH$_2$Ph], [ZA7700;OC(O)O(CH$_2$)$_2$CN,NHCH$_2$Ph], [ZA7701;OC(O)O(CH)$_2$OCH$_3$,NHCH$_2$Ph], [ZA7702;OC(O)O(CH$_2$)$_3$F,NHCH$_2$Ph], [ZA7703;OC(O)O(CH$_2$)$_3$CN,NHCH$_2$Ph], [ZA7704;OC(O)O(CH$_2$)$_3$OCH$_3$,NHCH$_2$Ph], [ZA7705;OS(O)$_2$CH$_3$,NHCH$_2$Ph], [ZA7706;OS(O)$_2$CH$_2$CH$_3$,NHCH$_2$Ph], [ZA7707;OS(O)$_2$CH(CH$_3$)$_2$,NHCH$_2$Ph], [ZA7708;OS(O)$_2$(CH$_2$)$_2$CH$_3$,NHCH$_2$Ph], [ZA7709;OS(O)$_2$(CH$_2$)$_3$CH$_3$,NHCH$_2$Ph], [ZA771;OS(O)$_2$(CH$_2$)$_4$CH$_3$,NHCH$_2$Ph], [ZA7711;OS(O)$_2$(CH$_2$)$_5$CH$_3$,NHCH$_2$Ph], [ZA7712;OS(O)$_2$-c-Pr,NHCH$_2$Ph], [ZA7713;OS(O)$_2$-c-Pen,NHCH$_2$Ph], [ZA7714;OS(O)$_2$-c-Hex,NHCH$_2$Ph], [ZA7715;OS(O)$_2$Ph,NHCH$_2$Ph], [ZA7716;OS(O)$_2$(2-Py),NHCH$_2$Ph], [ZA7717;OS(O)$_2$(3-Py),NHCH$_2$Ph], [ZA7718;OS(O)$_2$(4-Py),NHCH$_2$Ph], [ZA7719;OS(O)$_2$CF$_3$,NHCH$_2$Ph], [ZA7720;OS(O)$_2$CH$_2$Ph,NHCH$_2$Ph], [ZA7721;OH,N(CH$_3$)Ph], [ZA7722;OCH$_3$,N(CH$_3$)Ph], [ZA7723;OCH$_2$CH$_3$,N(CH$_3$)Ph], [ZA7724;OCH(CH$_3$)$_2$,N(CH$_3$)Ph], [ZA7725;O(CH$_2$)$_2$CH$_3$,N(CH$_3$)Ph], [ZA7726;O(CH$_2$)$_3$CH$_3$,N(CH$_3$)Ph], [ZA7727;O(CH$_2$)$_4$CH$_3$,N(CH$_3$)Ph], [ZA7728;O(CH$_2$)$_5$CH$_3$,N(CH$_3$)Ph], [ZA7729;OCH$_2$CH=CH$_2$,N(CH$_3$)Ph], [ZA7730;OCH$_2$C≡CH,N(CH$_3$)Ph], [ZA7731;OCH$_2$C≡CCH$_3$,N(CH$_3$)Ph], [ZA7732;O-c-Pr,N(CH$_3$)Ph], [ZA7733;O-c-Pen,N(CH$_3$)Ph], [ZA7734;O-c-Hex,N(CH$_3$)Ph], [ZA7735;OPh,N(CH$_3$)Ph], [ZA7736;OCH$_2$Ph,N(CH$_3$)Ph], [ZA7737;OCH$_2$(2-Py),N(CH$_3$)Ph], [ZA7738;OCH$_2$(3-Py),N(CH$_3$)Ph], [ZA7739;OCH$_2$(4-Py),N(CH$_3$)Ph], [ZA7740;OCH$_2$CN,N(CH$_3$)Ph], [ZA7741;OCH$_2$NO$_2$,N(CH$_3$)Ph], [ZA7742;O(CH$_2$)$_2$F,N(CH$_3$)Ph], [ZA7743;O(CH$_2$)$_2$CN,N(CH$_3$)Ph], [ZA7744;O(CH$_2$)$_2$Ph,N(CH$_3$)Ph], [ZA7745;O(CH$_2$)$_2$OCH$_3$,N(CH$_3$)Ph], [ZA7746;O(CH$_2$)$_3$F,N(CH$_3$)Ph], [ZA7747;O(CH$_2$)$_3$CN,N(CH$_3$)Ph], [ZA7748;O(CH$_2$)$_3$NO$_2$,N(CH$_3$)Ph], [ZA7749;O(CH$_2$)$_3$Ph,N(CH$_3$)Ph], [ZA7750;O(CH$_2$)$_3$OCH$_3$,N(CH$_3$)Ph], [ZA7751;(CH$_2$)$_4$F,N(CH$_3$)Ph], [ZA7752;O(CH$_2$)$_4$CN,N(CH$_3$)Ph], [ZA7753;(CH$_2$)$_4$NO$_2$,N(CH$_3$)Ph], [ZA7754;O(CH$_2$)$_4$Ph,N(CH$_3$)Ph], [ZA7755;(CH$_2$)$_4$OCH$_3$,N(CH$_3$)Ph], [ZA7756;(CH$_2$)$_5$F,N(CH$_3$)Ph], [ZA7757;O(CH$_2$)$_5$CN,N(CH$_3$)Ph], [ZA7758;(CH$_2$)$_5$NO$_2$,N(CH$_3$)Ph], [ZA7759;O(CH$_2$)$_5$Ph,N(CH$_3$)Ph], [ZA7760;O(CH$_2$)$_5$OCH$_3$,N(CH$_3$)Ph], [ZA7761;(CH$_2$)$_6$F,N(CH$_3$)Ph], [ZA7762;O(CH$_2$)$_6$CN,N(CH$_3$)Ph], [ZA7763;O(CH$_2$)$_6$NO$_2$,N(CH$_3$)Ph], [ZA7764;O(CH$_2$)$_6$Ph,N(CH$_3$)Ph], [ZA7765;O(CH$_2$)$_6$OCH$_3$,N(CH$_3$)Ph], [ZA7766;OC(O)CH$_3$,N(CH$_3$)Ph], [ZA7767;OC(O)CH$_2$CH$_3$,N(CH$_3$)Ph], [ZA7768;OC(O)CH(CH$_3$)$_2$,N(CH$_3$)Ph], [ZA7769;OC(O)(CH$_2$)$_2$CH$_3$,N(CH$_3$)Ph], [ZA7770;OC(O)(CH$_2$)$_3$CH$_3$,N(CH$_3$)Ph], [ZA7771;OC(O)(CH$_2$)$_4$CH$_3$,N(CH$_3$)Ph], [ZA7772;OC(O)(CH$_2$)$_5$CH$_3$,N(CH$_3$)Ph], [ZA7773;OC(O)CH$_2$CH=CH$_2$,N(CH$_3$)Ph], [ZA7774;OC(O)CH$_2$C≡CH,N(CH$_3$)Ph], [ZA7775;OC(O)CH$_2$C≡CCH$_3$,N(CH$_3$)Ph], [ZA7776;OC(O)c-Pr,N(CH$_3$)Ph], [ZA7777;OC(O)c-Pen,N(CH$_3$)Ph], [ZA7778;OC(O)c-Hex,N(CH$_3$)Ph], [ZA7779;OC(O)Ph,N(CH$_3$)Ph], [ZA7780;OC(O)(2-Py),N(CH$_3$)Ph], [ZA7781;OC(O)(3-Py),N(CH$_3$)Ph], [ZA7782;OC(O)(4-Py),N(CH$_3$)Ph], [ZA7783;OC(O)CH$_2$Ph,N(CH$_3$)Ph], [ZA7784;OC(O)CH$_2$(2-Py),N(CH$_3$)Ph], [ZA7785;OC(O)CH$_2$(3-Py),N(CH$_3$)Ph], [ZA7786;OC(O)CH$_2$(4-Py),N(CH$_3$)Ph], [ZA7787;OC(O)CH$_2$CN,N(CH$_3$)Ph], [ZA7788;OC(O)CH$_2$NO$_2$,N(CH$_3$)Ph], [ZA7789;OC(O)(CH$_2$)$_2$F,N(CH$_3$)Ph], [ZA7790;OC(O)(CH$_2$)$_2$CN,N(CH$_3$)Ph], [ZA7791;OC(O)(CH$_2$)$_2$NO$_2$,N(CH$_3$)Ph], [ZA7792;OC(O)(CH$_2$)$_2$Ph,N(CH$_3$)Ph], [ZA7793;OC(O)(CH$_2$)$_2$OCH$_3$,N(CH$_3$)Ph], [ZA7794;OC(O)(CH$_2$)$_3$F,N(CH$_3$)Ph], [ZA7795;OC(O)(CH$_2$)$_3$CN,N(CH$_3$)Ph], [ZA7796;OC(O)(CH$_2$)$_3$NO$_2$,N(CH$_3$)Ph], [ZA7797;OC(O)(CH$_2$)$_3$OCH$_3$,N(CH$_3$)Ph], [ZA7798;OC(O)NH$_2$,N(CH$_3$)Ph], [ZA7799;OC(O)NHCH$_3$,N(CH$_3$)Ph], [ZA7800;OC(O)NHCH$_2$CH$_3$,N(CH$_3$)Ph], [ZA7801;OC(O)NH(CH$_2$)$_2$CH$_3$,N(CH$_3$)Ph], [ZA7802;OC(O)NH(CH$_2$)$_3$CH$_3$,N(CH$_3$)Ph], [ZA7803;OC(O)NH(CH$_2$)$_4$CH$_3$,N(CH$_3$)Ph], [ZA7804;OC(O)NH(CH$_2$)$_5$CH$_3$,N(CH$_3$)Ph], [ZA7805;OC(O)NHCH(CH$_3$)$_2$,N(CH$_3$)Ph], [ZA7806;OC(O)NHCH$_2$F,N(CH$_3$)Ph], [ZA7807;OC(O)NHCH$_2$CN,N(CH$_3$)Ph], [ZA7808;OC(O)NHCH$_2$OCH$_3$,N(CH$_3$)Ph], [ZA7809;OC(O)NHCH$_2$Ph,N(CH$_3$)Ph], [ZA7810;OC(O)NH(CH$_2$)$_2$F,N(CH$_3$)Ph], [ZA7811;OC(O)NH(CH$_2$)$_2$CN,N(CH$_3$)Ph], [ZA7812;OC(O)NH(CH$_2$)$_2$OCH$_3$,N(CH$_3$)Ph], [ZA7813;OC(O)NH(CH$_2$)$_3$F,N(CH$_3$)Ph], [ZA7814;OC(O)NH(CH$_2$)$_3$CN,N(CH$_3$)Ph], [ZA7815;OC(O)NH(CH$_2$)$_3$OCH$_3$,N(CH$_3$)Ph], [ZA7816;OC(O)NH(CH$_2$)$_4$F,N(CH$_3$)Ph], [ZA7817;OC(O)NH(CH$_2$)$_4$CN,N(CH$_3$)Ph], [ZA7818;OC(O)NH(CH$_2$)$_4$OCH$_3$,N(CH$_3$)Ph], [ZA7819;OC(O)NHPh,N(CH$_3$)Ph], [ZA7820;OC(O)NH(2-Py),N(CH$_3$)Ph], [ZA7821;OC(O)NH(3-Py),N(CH$_3$)Ph], [ZA7822;OC(O)NH(4-Py),N(CH$_3$)Ph], [ZA7823;OC(O)N(CH$_3$)$_2$,N(CH$_3$)Ph], [ZA7824;OC(O)N(CH$_3$)CH$_2$CH$_3$,N(CH$_3$)Ph], [ZA7825;OC(O)N(CH$_3$)(CH$_2$)$_2$CH$_3$,N(CH$_3$)Ph], [ZA7826;OC(O)N(CH$_3$)(CH$_2$)$_3$CH$_3$,N(CH$_3$)Ph], [ZA7827;OC(O)N(CH$_3$)CH(CH$_3$)$_2$,N(CH$_3$)Ph], [ZA7828;OC(O)N(CH$_3$)CH$_2$F,N(CH$_3$)Ph], [ZA7829;OC(O)N(CH$_3$)CH$_2$CN,N(CH$_3$)Ph], [ZA7830;OC(O)N(CH$_3$)CH$_2$OCH$_3$,N(CH$_3$)Ph], [ZA7831;OC(O)N(CH$_3$)CH$_2$Ph,N(CH$_3$)Ph], [ZA7832;OC(O)N(CH$_3$)(CH$_2$)$_2$F,N(CH$_3$)Ph], [ZA7833;OC(O)N(CH$_3$)(CH$_2$)$_2$CN,N(CH$_3$)Ph], [ZA7834;OC(O)N(CH$_3$)(CH$_2$)$_2$OCH$_3$,N(CH$_3$)Ph], [ZA7835;OC(O)N(CH$_3$)Ph,N(CH$_3$)Ph], [ZA7836;OC(O)N(CH$_3$)(2-Py),N(CH$_3$)Ph], [ZA7837;OC(O)N(CH$_3$)(3-Py),N(CH$_3$)Ph], [ZA7838;OC(O)N(CH$_3$)(4-Py),N(CH$_3$)Ph], [ZA7839;OC(O)N(CH$_2$CH$_3$)$_2$,N(CH$_3$)Ph], [ZA7840;OC(O)(Pyr),N(CH$_3$)Ph], [ZA7841;OC(O)(Pip),N(CH$_3$)Ph], [ZA7842;OC(O)(Mor),N(CH$_3$)Ph], [ZA7843;OC(O)OCH$_3$,

N(CH₃)Ph], [ZA7844;OC(O)OCH₂CH₃,N(CH₃)Ph], [ZA7845;OC(O)OCH(CH₃)₂,N(CH₃)Ph], [ZA7846;OC(O)O(CH₂)₂CH₃,N(CH₃)Ph], [ZA7847;OC(O)O(CH₂)₃CH₃,N(CH₃)Ph], [ZA7848;OC(O)O(CH₂)₄CH₃,N(CH₃)Ph], [ZA7849;OC(O)O(CH₂)₅CH₃,N(CH₃)Ph], [ZA7850;OC(O)OCH₂CH=CH₂,N(CH₃)Ph], [ZA7851;OC(O)OCH₂C=CH,N(CH₃)Ph], [ZA7852;OC(O)OCH₂C≡CCH₃,N(CH₃)Ph], [ZA7853;OC(O)O-c-Pr,N(CH₃)Ph], [ZA7854;OC(O)O-c-Pen,N(CH₃)Ph], [ZA7855;OC(O)O-c-Hex,N(CH₃)Ph], [ZA7856;OC(O)OPh,N(CH₃)Ph], [ZA7857;OC(O)O(2-Py),N(CH₃)Ph], [ZA7858;OC(O)O(3-Py),N(CH₃)Ph], [ZA7859;OC(O)O(4-Py),N(CH₃)Ph], [ZA7860;OC(O)OCF₃,N(CH₃)Ph], [ZA7861;OC(O)OCH₂Ph,N(CH₃)Ph], [ZA7862;OC(O)OCH₂(2-Py),N(CH₃)Ph], [ZA7863;OC(O)OCH₂(3-Py),N(CH₃)Ph], [ZA7864;OC(O)OCH₂(4-Py),N(CH₃)Ph], [ZA7865;OC(O)OCH₂CN,N(CH₃)Ph], [ZA7866;OC(O)OCH₂NO₂,N(CH₃)Ph], [ZA7867;OC(O)O(CH₂)₂F,N(CH₃)Ph], [ZA7868;OC(O)O(CH₂)₂CN,N(CH₃)Ph], [ZA7869;OC(O)O(CH₂)₂OCH₃,N(CH₃)Ph], [ZA7870;OC(O)O(CH₂)₃F,N(CH₃)Ph], [ZA7871;OC(O)O(CH₂)₃CN,N(CH₃)Ph], [ZA7872;OC(O)O(CH₂)₃OCH₃,N(CH₃)Ph], [ZA7873;OS(O)₂CH₃,N(CH₃)Ph], [ZA7874;OS(O)₂CH₂CH₃,N(CH₃)Ph], [ZA7875;OS(O)₂CH(CH₃)₂,N(CH₃)Ph], [ZA7876;OS(O)₂(CH₂)₂CH₃,N(CH₃)Ph], [ZA7877;OS(O)₂(CH₂)₃CH₃,N(CH₃)Ph], [ZA7878;OS(O)₂(CH₂)₄CH₃,N(CH₃)Ph], [ZA7879;OS(O)₂(CH₂)₅CH₃,N(CH₃)Ph], [ZA7880;OS(O)₂-c-Pr,N(CH₃)Ph], [ZA7881;OS(O)₂-c-Pen,N(CH₃)Ph], [ZA7882;OS(O)₂-c-Hex,N(CH₃)Ph], [ZA7883;OS(O)₂Ph,N(CH₃)Ph], [ZA7884;OS(O)₂(2-Py),N(CH₃)Ph], [ZA7885;OS(O)₂(3-Py),N(CH₃)Ph], [ZA7886;OS(O)₂(4-Py),N(CH₃)Ph], [ZA7887;OS(O)₂CF₃,N(CH₃)Ph], [ZA7888;OS(O)₂CH₂Ph,N(CH₃)Ph], [ZA7889;OH,N(CH₃)CH₂Ph], [ZA7890;OCH₃,N(CH₃)CH₂Ph], [ZA7891;OCH₂CH₃,N(CH₃)CH₂Ph], [ZA7892;OCH(CH₃)₂,N(CH₃)CH₂Ph], [ZA7893;O(CH₂)₂CH₃,N(CH₃)CH₂Ph], [ZA7894;O(CH)₃CH₃,N(CH₃)CH₂Ph], [ZA7895;O(CH₂)₄CH₃,N(CH₃)CH₂Ph], [ZA7896;O(CH₂)₅CH₃,N(CH₃)CH₂Ph], [ZA7897;OCH₂CH=CH₂,N(CH₃)CH₂Ph], [ZA7898;OCH₂C≡CH,N(CH₃)CH₂Ph], [ZA7899;OCH₂C≡CCH₃,N(CH₃)CH₂Ph], [ZA7900;O-c-Pr,N(CH₃)CH₂Ph], [ZA7901;O-c-Pen,N(CH₃)CH₂Ph], [ZA7902;O-c-Hex,N(CH₃)CH₂Ph], [ZA7903;OPh,N(CH₃)CH₂Ph], [ZA7904;OCH₂Ph,N(CH₃)CH₂Ph], [ZA7905;OCH₂(2-Py),N(CH₃)CH₂Ph], [ZA7906;OCH₂(3-Py),N(CH₃)CH₂Ph], [ZA7907;OCH₂(4-Py),N(CH₃)CH₂Ph], [ZA7908;OCH₂CN,N(CH₃)CH₂Ph], [ZA7909;OCH₂NO₂,N(CH₃)CH₂Ph], [ZA7910;(CH₂)₂F,N(CH₃)CH₂Ph], [ZA7911;O(CH₂)₂CN,N(CH₃)CH₂Ph], [ZA7912;O(CH₂)₂Ph,N(CH₃)CH₂Ph], [ZA7913;O(CH₂)₂OCH₃,N(CH₃)CH₂Ph], [ZA7914;O(CH₂)₃F,N(CH₃)CH₂Ph], [ZA7915;O(CH₂)₃CN,N(CH₃)CH₂Ph], [ZA7916;O(CH₂)₃NO₂,N(CH₃)CH₂Ph], [ZA7917;O(CH₂)₃Ph,N(CH₃)CH₂Ph], [ZA7918;O(CH₂)₃OCH₃,N(CH₃)CH₂Ph], [ZA7919;O(CH₂)₄F,N(CH₃)CH₂Ph], [ZA7920;O(CH₂)₄CN,N(CH₃)CH₂Ph], [ZA7921;(CH₂)₄NO₂,N(CH₃)CH₂Ph], [ZA7922;O(CH₂)₄Ph,N(CH₃)CH₂Ph], [ZA7923;O(CH₂)₄OCH₃,N(CH₃)CH₂Ph], [ZA7924;O(CH₂)₅F,N(CH₃)CH₂Ph], [ZA7925;O(CH₂)₅CN,N(CH₃)CH₂Ph], [ZA7926;O(CH₂)₅NO₂,N(CH₃)CH₂Ph], [ZA7927;O(CH₂)₅Ph,N(CH₃)CH₂Ph], [ZA7928;O(CH₂)₅OCH₃,N(CH₃)CH₂Ph], [ZA7929;O(CH₂)₆F,N(CH₃)CH₂Ph], [ZA7930;O(CH₂)₆CN,N(CH₃)CH₂Ph], [ZA7931;(CH₂)₆NO₂,N(CH₃)CH₂Ph], [ZA7932;O(CH₂)₆Ph,N(CH₃)CH₂Ph], [ZA7933;O(CH₂)₆OCH₃,N(CH₃)CH₂Ph], [ZA7934;OC(O)CH₃,N(CH₃)CH₂Ph], [ZA7935;OC(O)CH₂CH₃,N(CH₃)CH₂Ph], [ZA7936;OC(O)CH(CH₃)₂,N(CH₃)CH₂Ph], [ZA7937;OC(O)(CH₂)₂CH₃,N(CH₃)CH₂Ph], [ZA7938;OC(O)(CH₂)₃CH₃,N(CH₃)CH₂Ph], [ZA7939;OC(O)(CH₂)₄CH₃,N(CH₃)CH₂Ph], [ZA7940;OC(O)(CH₂)₅CH₃,N(CH₃)CH₂Ph], [ZA7941;OC(O)CH₂CH=CH₂,N(CH₃)CH₂Ph], [ZA7942;OC(O)CH₂C≡CH,N(CH₃)CH₂Ph], [ZA7943;OC(O)CH₂C≡CCH₃,N(CH₃)CH₂Ph], [ZA7944;OC(O)c-Pr,N(CH₃)CH₂Ph], [ZA7945;OC(O)c-Pen,N(CH₃)CH₂Ph], [ZA7946;OC(O)c-Hex,N(CH₃)CH₂Ph], [ZA7947;OC(O)Ph,N(CH₃)CH₂Ph], [ZA7948;OC(O)(2-Py),N(CH₃)CH₂Ph], [ZA7949;OC(O)(3-Py),N(CH₃)CH₂Ph], [ZA7950;OC(O)(4-Py),N(CH₃)CH₂Ph], [ZA7951;OC(O)CH₂Ph,N(CH₃)CH₂Ph], [ZA7952;OC(O)CH₂(2-Py),N(CH₃)CH₂Ph], [ZA7953;OC(O)CH₂(3-Py),N(CH₃)CH₂Ph], [ZA7954;OC(O)CH₂(4-Py),N(CH₃)CH₂Ph], [ZA7955;OC(O)CH₂CN,N(CH₃)CH₂Ph], [ZA7956;OC(O)CH₂NO₂,N(CH₃)CH₂Ph], [ZA7957;OC(O)(CH₂)₂F,N(CH₃)CH₂Ph], [ZA7958;OC(O)(CH₂)₂CN,N(CH₃)CH₂Ph], [ZA7959;OC(O)(CH₂)₂NO₂,N(CH₃)CH₂Ph], [ZA7960;OC(O)(CH₂)₂Ph,N(CH₃)CH₂Ph], [ZA7961;OC(O)(CH₂)₂OCH₃,N(CH₃)CH₂Ph], [ZA7962;OC(O)(CH₂)₃F,N(CH₃)CH₂Ph], [ZA7963;OC(O)(CH₂)₃CN,N(CH₃)CH₂Ph], [ZA7964;OC(O)(CH₂)₃NO₂,N(CH₃)CH₂Ph], [ZA7965;OC(O)(CH₂)₃OCH₃,N(CH₃)CH₂Ph], [ZA7966;OC(O)NH₂,N(CH₃)CH₂Ph], [ZA7967;OC(O)NHCH₃,N(CH₃)CH₂Ph], [ZA7968;OC(O)NHCH₂CH₃,N(CH₃)CH₂Ph], [ZA7969;OC(O)NH(CH₂)₂CH₃,N(CH₃)CH₂Ph], [ZA7970;OC(O)NH(CH₂)₃CH₃,N(CH₃)CH₂Ph], [ZA7971;OC(O)NH(CH₂)₄CH₃,N(CH₃)CH₂Ph], [ZA7972;OC(O)NH(CH₂)₅CH₃,N(CH₃)CH₂Ph], [ZA7973;OC(O)NHCH(CH)₂,N(CH₃)CH₂Ph], [ZA7974;OC(O)NHCH₂F,N(CH₃)CH₂Ph], [ZA7975;OC(O)NHCH₂CN,N(CH₃)CH₂Ph], [ZA7976;OC(O)NHCH₂OCH₃,N(CH₃)CH₂Ph], [ZA7977;OC(O)NHCH₂Ph,N(CH₃)CH₂Ph], [ZA7978;OC(O)NH(CH₂)₂F,N(CH₃)CH₂Ph], [ZA7979;OC(O)NH(CH₂)₂CN,N(CH₃)CH₂Ph], [ZA7980;OC(O)NH(CH₂)₂OCH₃,N(CH₃)CH₂Ph], [ZA7981;OC(O)NH(CH₂)₃F,N(CH₃)CH₂Ph], [ZA7982;OC(O)NH(CH₂)₃CN,N(CH₃)CH₂Ph], [ZA7983;OC(O)NH(CH₂)₃OCH₃,N(CH₃)CH₂Ph], [ZA7984;OC(O)NH(CH₂)₄F,N(CH₃)CH₂Ph], [ZA7985;OC(O)NH(CH₂)₄CN,N(CH₃)CH₂Ph], [ZA7986;OC(O)NH(CH₂)₄OCH₃,N(CH₃)CH₂Ph], [ZA7987;OC(O)NHPh,N(CH₃)CH₂Ph], [ZA7988;OC(O)NH(2-Py),N(CH)CH₂Ph], [ZA7989;OC(O)NH(3-Py),N(CH₃)CH₂Ph], [ZA7990;OC(O)NH(4-Py),N(CH₃)CH₂Ph], [ZA7991;OC(O)N(CH₃)₂,N(CH₃)CH₂Ph], [ZA7992;OC(O)N(CH₃)CH₂CH₃,N(CH₃)CH₂Ph], [ZA7993;OC(O)N(CH₃)(CH₂)₂CH₃,N(CH₃)CH₂Ph], [ZA7994;OC(O)N(CH₃)(CH₂)₃CH₃,N(CH₃)CH₂Ph], [ZA7995;OC(O)N(CH₃)CH(CH₃)₂,N(CH₃)CH₂Ph], [ZA7996;OC(O)N(CH₃)CH₂F,N(CH₃)CH₂Ph], [ZA7997;OC(O)N(CH)CH₂CN,N(CH₃)CH₂Ph], [ZA7998;OC(O)N(CH₃)CH₂OCH₃,N(CH₃)CH₂Ph], [ZA7999;OC(O)N(CH₃)CH₂Ph,N(CH₃)CH₂Ph], [ZA8000;OC(O)N(CH₃)(CH₂)₂F,N(CH₃)CH₂Ph], [ZA8001;OC(O)N(CH₃)(CH₂)₂CN,N(CH₃)CH₂Ph], [ZA8002;OC(O)N(CH₃)(CH₂)₂OCH₃,N(CH₃)CH₂Ph], [ZA8003;OC(O)N(CH₃)Ph,N(CH₃)CH₂Ph], [ZA8004;OC(O)N(CH₃)(2-Py),N(CH₃)CH₂Ph], [ZA8005;OC(O)N(CH₃)(3-Py),N(CH₃)CH₂Ph], [ZA8006;OC(O)N(CH₃)(4-Py),N(CH₃)CH₂Ph], [ZA8007;OC(O)N(CH₂CH₃)₂,N(CH₃)CH₂Ph], [ZA8008;OC(O)(Pyr),N(CH₃)CH₂Ph], [ZA8009;OC(O)(Pip),N(CH₃)CH₂Ph], [ZA8010;OC(O)(Mor),N(CH₃)CH₂Ph], [ZA8011;OC(O)OCH₃,N(CH₃)CH₂Ph], [ZA8012;OC(O)OCH₂CH₃,N(CH₃)CH₂Ph], [ZA8013;OC(O)OCH(CH₃)₂,N(CH₃)CH₂Ph], [ZA8014;OC(O)O(CH₂)₂CH₃,N(CH₃)CH₂Ph], [ZA8015;OC(O)O(CH₂)₃CH₃,N(CH₃)CH₂Ph], [ZA8016;OC(O)O(CH₂)₄CH₃,N(CH₃)CH₂Ph], [ZA8017;OC(O)O(CH₂)₅CH₃,N(CH₃)CH₂Ph], [ZA8018;OC(O)OCH₂CH=CH₂,N(CH₃)CH₂Ph], [ZA8019;OC(O)OCH₂C≡CH,N(CH₃)CH₂Ph], [ZA8020;OC(O)OCH₂C≡CCH₃,N(CH₃)CH₂Ph], [ZA8021;OC(O)O- c-Pr,N(CH$_3$)CH$_2$Ph], [ZA8022;OC(O)O-c-Pen,N(CH$_3$)CH$_2$Ph], [ZA8023;OC(O)O-c-Hex,N(CH$_3$)CH$_2$Ph], [ZA8024;OC(O)OPh,N(CH$_3$)CH$_2$Ph], [ZA8025;OC(O)O(2-Py),N(CH$_3$)CH$_2$Ph], [ZA8026;OC(O)O(3-Py),N(CH$_3$)CH$_2$Ph], [ZA8027;OC(O)O(4-Py),N(CH$_3$)CH$_2$Ph], [ZA8028;OC(O)OCF$_3$,N(CH$_3$)CH$_2$Ph], [ZA8029;OC(O)OCH$_2$Ph,N(CH$_3$)CH$_2$Ph], [ZA8030;OC(O)OCH$_2$(2-Py),N(CH$_3$)CH$_2$Ph], [ZA8031;OC(O)OCH$_2$(3-Py),N(CH$_3$)CH$_2$Ph], [ZA8032;OC(O)OCH$_2$(4-Py),N(CH$_3$)CH$_2$Ph], [ZA8033;OC(O)OCH$_2$CN,N(CH$_3$)CH$_2$Ph], [ZA8034;OC(O)OCH$_2$NO$_2$,N(CH$_3$)CH$_2$Ph], [ZA8035;OC(O)O(CH$_2$)$_2$F,N(CH$_3$)CH$_2$Ph], [ZA8036;OC(O)O(CH$_2$)$_2$CN,N(CH$_3$)CH$_2$Ph], [ZA8037;OC(O)O(CH$_2$)$_2$OCH$_3$,N(CH$_3$)CH$_2$Ph], [ZA8038;OC(O)O(CH$_2$)$_3$F,N(CH$_3$)CH$_2$Ph], [ZA8039;OC(O)O(CH$_2$)$_3$CN,N(CH$_3$)CH$_2$Ph], [ZA8040;OC(O)O(CH$_3$)$_3$OCH$_3$,N(CH$_3$)CH$_2$Ph], [ZA8041;OS(O)$_2$CH$_3$,N(CH$_3$)CH$_2$Ph], [ZA8042;OS(O)$_2$CH$_2$CH$_3$,N(CH$_3$)CH$_2$Ph], [ZA8043;OS(O)$_2$CH(CH$_3$)$_2$,N(CH$_3$)CH$_2$Ph], [ZA8044;OS(O)$_2$(CH$_2$)$_2$CH$_3$,N(CH$_3$)CH$_2$Ph], [ZA8045;OS(O)$_2$(CH$_2$)$_3$CH$_3$,N(CH$_3$)CH$_2$Ph], [ZA8046;OS(O)$_2$(CH$_2$)$_4$CH$_3$,N(CH$_3$)CH$_2$Ph], [ZA8047;OS(O)$_2$(CH$_2$)$_5$CH$_3$,N(CH$_3$)CH$_2$Ph], [ZA8048;OS(O)$_2$-c-Pr,N(CH$_3$)CH$_2$Ph], [ZA8049;OS(O)$_2$-c-Pen,N(CH$_3$)CH$_2$Ph], [ZA8050;OS(O)$_2$-c-Hex,N(CH$_3$)CH$_2$Ph], [ZA8051;OS(O)$_2$Ph,N(CH$_3$)CH$_2$Ph], [ZA8052;OS(O)$_2$(2-Py),N(CH$_3$)CH$_2$Ph], [ZA8053;OS(O)$_2$(3-Py),N(CH$_3$)CH$_2$Ph], [ZA8054;OS(O)$_2$(4-Py),N(CH$_3$)CH$_2$Ph], [ZA8055;OS(O)$_2$CF$_3$,N(CH$_3$)CH$_2$Ph], [ZA8056;OS(O)$_2$CH$_2$Ph,N(CH$_3$)CH$_2$Ph], [ZA8057;OH,Pyr], [ZA8058;OCH$_3$,Pyr], [ZA8059;OCH$_2$CH$_3$,Pyr], [ZA8060;OCH(CH$_3$)$_2$,Pyr], [ZA8061;(CH$_2$)$_2$CH$_3$,Pyr], [ZA8062;O(CH$_2$)$_3$CH$_3$,Pyr], [ZA8063;O(CH$_2$)$_4$CH$_3$,Pyr], [ZA8064;O(CH$_2$)$_5$CH$_3$,Pyr], [ZA8065;OCH$_2$CH=CH$_2$,Pyr], [ZA8066;OCH$_2$C≡CH,Pyr], [ZA8067;OCH$_2$C≡CCH$_3$,Pyr], [ZA8068;O-c-Pr,Pyr], [ZA8069;O-c-Pen,Pyr], [ZA8070;O-c-Hex,Pyr], [ZA8071;OPh,Pyr], [ZA8072;OCH$_2$Ph,Pyr], [ZA8073;OCH$_2$(2-Py),Pyr], [ZA8074;OCH$_2$(3-Py),Pyr], [ZA8075;OCH$_2$(4-Py),Pyr], [ZA8076;OCH$_2$CN,Pyr], [ZA8077;OCH$_2$NO$_2$,Pyr], [ZA8078;O(CH$_2$)$_2$F,Pyr], [ZA8079;O(CH$_2$)$_2$CN,Pyr], [ZA8080;O(CH$_2$)$_2$Ph,Pyr], [ZA8081;(CH$_2$)$_2$OCH$_3$,Pyr], [ZA8082;O(CH$_2$)$_3$F,Pyr], [ZA8083;O(CH$_2$)$_3$CN,Pyr], [ZA8084;O(CH$_2$)$_3$NO$_2$,Pyr], [ZA8085;O(CH$_2$)$_3$Ph,Pyr], [ZA8086;O(CH$_2$)$_3$OCH$_3$,Pyr], [ZA8087;O(CH$_2$)$_4$F,Pyr], [ZA8088;O(CH$_2$)$_4$CN,Pyr], [ZA8089;O(CH$_2$)$_4$NO$_2$,Pyr], [ZA8090;O(CH$_2$)$_4$Ph,Pyr], [ZA8091;(CH$_2$)$_4$OCH$_3$,Pyr], [ZA8092;O(CH$_2$)$_5$F,Pyr], [ZA8093;O(CH$_2$)$_5$CN,Pyr], [ZA8094;O(CH$_2$)$_5$NO$_2$,Pyr], [ZA8095;O(CH$_2$)$_5$Ph,Pyr], [ZA8096;O(CH$_2$)$_5$OCH$_3$,Pyr], [ZA8097;O(CH$_2$)$_6$F,Pyr], [ZA8098;O(CH$_2$)$_6$CN,Pyr], [ZA8099;O(CH$_2$)$_6$NO$_2$,Pyr], [ZA8100;O(CH$_2$)$_6$Ph,Pyr], [ZA8101;O(CH$_2$)$_6$OCH$_3$,Pyr], [ZA8102;OC(O)CH$_3$,Pyr], [ZA8103;OC(O)CH$_2$CH$_3$,Pyr], [ZA8104;OC(O)CH(CH$_3$)$_2$,Pyr], [ZA8105;OC(O)(CH$_2$)$_2$CH$_3$,Pyr], [ZA8106;OC(O)(CH$_2$)$_3$CH$_3$,Pyr], [ZA8107;OC(O)(CH$_2$)$_4$CH$_3$,Pyr], [ZA8108;OC(O)(CH$_2$)$_5$CH$_3$,Pyr], [ZA8109;OC(O)CH$_2$CH=CH$_2$,Pyr], [ZA8110;OC(O)CH$_2$C≡CH,Pyr], [ZA8111;OC(O)CH$_2$C≡CCH$_3$,Pyr], [ZA8112;OC(O)c-Pr,Pyr], [ZA8113;OC(O)c-Pen,Pyr], [ZA8114;OC(O)c-Hex,Pyr], [ZA8115;OC(O)Ph,Pyr], [ZA8116;OC(O)(2-Py),Pyr], [ZA8117;OC(O)(3-Py),Pyr], [ZA8118;OC(O)(4-Py),Pyr], [ZA8119;OC(O)CH$_2$Ph,Pyr], [ZA8120;OC(O)CH$_2$(2-Py),Pyr], [ZA8121;OC(O)CH$_2$(3-Py),Pyr], [ZA8122;OC(O)CH$_2$(4-Py),Pyr], [ZA8123;OC(O)CH$_2$CN,Pyr], [ZA8124;OC(O)CH$_2$NO$_2$,Pyr], [ZA8125;OC(O)(CH$_2$)$_2$F,Pyr], [ZA8126;OC(O)(CH$_2$)$_2$CN,Pyr], [ZA8127;OC(O)(CH$_2$)$_2$NO$_2$,Pyr], [ZA8128;OC(O)(CH$_2$)$_2$Ph,Pyr], [ZA8129;OC(O)(CH$_2$)$_2$OCH$_3$,Pyr], [ZA8130;OC(O)(CH$_2$)$_3$F,Pyr], [ZA8131;OC(O)(CH$_2$)$_3$CN,Pyr], [ZA8132;OC(O)(CH$_2$)$_3$NO$_2$,Pyr], [ZA8133;OC(O)(CH$_2$)$_3$OCH$_3$,Pyr], [ZA8134;OC(O)NH$_2$,Pyr], [ZA8135;OC(O)NHCH$_3$,Pyr], [ZA8136;OC(O)NHCH$_2$CH$_3$,Pyr], [ZA8137;OC(O)NH(CH$_2$)$_2$CH$_3$,Pyr], [ZA8138;OC(O)NH(CH$_2$)$_3$CH$_3$,Pyr], [ZA8139;OC(O)NH(CH$_2$)$_4$CH$_3$,Pyr], [ZA8140;OC(O)NH(CH$_2$)$_5$CH$_3$,Pyr], [ZA8141;OC(O)NHCH(CH$_3$)$_2$,Pyr], [ZA8142;OC(O)NHCH$_2$F,Pyr], [ZA8143;OC(O)NHCH$_2$CN,Pyr], [ZA8144;OC(O)NHCH$_2$OCH$_3$,Pyr], [ZA8145;OC(O)NHCH$_2$Ph,Pyr], [ZA8146;OC(O)NH(CH$_2$)$_2$F,Pyr], [ZA8147;OC(O)NH(CH$_2$)$_2$CN,Pyr], [ZA8148;OC(O)NH(CH$_2$)$_2$OCH$_3$,Pyr], [ZA8149;OC(O)NH(CH$_2$)$_3$F,Pyr], [ZA8150;OC(O)NH(CH$_2$)$_3$CN,Pyr], [ZA8151;OC(O)NH(CH$_2$)$_3$OCH$_3$,Pyr], [ZA8152;OC(O)NH(CH$_2$)$_4$F,Pyr], [ZA8153;OC(O)NH(CH$_2$)$_4$CN,Pyr], [ZA8154;OC(O)NH(CH$_2$)$_4$OCH$_3$,Pyr], [ZA8155;OC(O)NHPh,Pyr], [ZA8156;OC(O)NH(2-Py),Pyr], [ZA8157;OC(O)NH(3-Py),Pyr], [ZA8158;OC(O)NH(4-Py),Pyr], [ZA8159;OC(O)N(CH$_3$)$_2$,Pyr], [ZA8160;OC(O)N(CH$_3$)CH$_2$CH$_3$,Pyr], [ZA8161;OC(O)N(CH$_3$)(CH$_2$)$_2$CH$_3$,Pyr], [ZA8162;OC(O)N(CH$_3$)(CH$_2$)$_3$CH$_3$,Pyr], [ZA8163;OC(O)N(CH$_3$)CH(CH$_3$)$_2$,Pyr], [ZA8164;OC(O)N(CH$_3$)CH$_2$F,Pyr], [ZA8165;OC(O)N(CH$_3$)CH$_2$CN,Pyr], [ZA8166;OC(O)N(CH$_3$)CH$_2$OCH$_3$,Pyr], [ZA8167;OC(O)N(CH$_3$)CH$_2$Ph,Pyr], [ZA8168;OC(O)N(CH$_3$)(CH$_2$)$_2$F,Pyr], [ZA8169;OC(O)N(CH$_3$)(CH$_2$)$_2$CN,Pyr], [ZA8170;OC(O)N(CH$_3$)(CH$_2$)$_2$OCH$_3$,Pyr], [ZA8171;OC(O)N(CH$_3$)Ph,Pyr], [ZA8172;OC(O)N(CH$_3$)(2-Py),Pyr], [ZA8173;OC(O)N(CH$_3$)(3-Py),Pyr], [ZA8174;OC(O)N(CH$_3$)(4-Py),Pyr], [ZA8175;OC(O)N(CH$_2$CH$_3$)$_2$,Pyr], [ZA8176;OC(O)(Pyr),Pyr], [ZA8177;OC(O)(Pip),Pyr], [ZA8178;OC(O)(Mor),Pyr], [ZA8179;OC(O)OCH$_3$,Pyr], [ZA8180;OC(O)OCH$_2$CH$_3$,Pyr], [ZA8181;OC(O)OCH(CH$_3$)$_2$,Pyr], [ZA8182;OC(O)O(CH$_2$)$_2$CH$_3$,Pyr], [ZA8183;OC(O)O(CH$_2$)$_3$CH$_3$,Pyr], [ZA8184;OC(O)O(CH$_2$)$_4$CH$_3$,Pyr], [ZA8185;OC(O)O(CH$_2$)$_5$CH$_3$,Pyr], [ZA8186;OC(O)OCH$_2$CH=CH$_2$,Pyr], [ZA8187;OC(O)OCH$_2$C≡CH,Pyr], [ZA8188;OC(O)OCH$_2$C≡CCH$_3$,Pyr], [ZA8189;OC(O)O-c-Pr,Pyr], [ZA8190;OC(O)O-c-Pen,Pyr], [ZA8191;OC(O)O-c-Hex,Pyr], [ZA8192;OC(O)OPh,Pyr], [ZA8193;OC(O)O(2-Py),Pyr], [ZA8194;OC(O)O(3-Py),Pyr], [ZA8195;OC(O)O(4-Py),Pyr], [ZA8196;OC(O)OCF$_3$,Pyr], [ZA8197;OC(O)OCH$_2$Ph,Pyr], [ZA8198;OC(O)OCH$_2$(2-Py),Pyr], [ZA8199;OC(O)OCH$_2$(3-Py),Pyr], [ZA8200;OC(O)OCH$_2$(4-Py),Pyr], [ZA8201;OC(O)OCH$_2$CN,Pyr], [ZA8202;OC(O)OCH$_2$NO$_2$,Pyr], [ZA8203;OC(O)O(CH$_2$)$_2$F,Pyr], [ZA8204;OC(O)O(CH)$_2$CN,Pyr], [ZA8205;OC(O)O(CH$_2$)$_2$OCH$_3$,Pyr], [ZA8206;OC(O)O(CH$_2$)$_3$F,Pyr], [ZA8207;OC(O)O(CH$_2$)$_3$CN,Pyr], [ZA8208;OC(O)O(CH$_2$)$_3$OCH$_3$,Pyr], [ZA8209;OS(O)$_2$CH$_3$,Pyr], [ZA8210;OS(O)$_2$CH$_2$CH$_3$,Pyr], [ZA8211;OS(O)$_2$CH(CH$_3$)$_2$,Pyr], [ZA8212;OS(O)$_2$(CH$_2$)$_2$CH$_3$,Pyr], [ZA8213;OS(O)$_2$(CH$_2$)$_3$CH$_3$,Pyr], [ZA8214;OS(O)$_2$(CH$_2$)$_4$CH$_3$,Pyr], [ZA8215;OS(O)$_2$(CH$_2$)$_5$CH$_3$,Pyr], [ZA8216;OS(O)$_2$-c-Pr,Pyr], [ZA8217;OS(O)$_2$-c-Pen,Pyr], [ZA8218;OS(O)$_2$-c-Hex,Pyr], [ZA8219;OS(O)$_2$Ph,Pyr], [ZA822;OS(O)$_2$(2-Py),Pyr], [ZA8221;OS(O)$_2$(3-Py),Pyr], [ZA8222;OS(O)$_2$(4-Py),Pyr], [ZA8223;OS(O)$_2$CF$_3$,Pyr], [ZA8224;OS(O)$_2$CH$_2$Ph,Pyr], [ZA8225;OH,Pip], [ZA8226;OCH$_3$,Pip], [ZA8227;OCH$_2$CH$_3$,Pip], [ZA8228;OCH(CH$_3$)$_2$,Pip], [ZA8229;O(CH$_2$)$_2$CH$_3$,Pip], [ZA8230;O(CH$_2$)$_3$CH$_3$,Pip], [ZA8231;(CH$_2$)$_4$CH$_3$,Pip], [ZA8232;O(CH$_2$)$_5$CH$_3$,Pip], [ZA8233;OCH$_2$CH=CH$_2$,Pip], [ZA8234;OCH$_2$C≡CH,Pip], [ZA8235;OCH$_2$C≡CCH$_3$,Pip], [ZA8236;O-c-Pr,Pip], [ZA8237;O-c-Pen,Pip], [ZA8238;O-c-Hex,Pip], [ZA8239;OPh,Pip], [ZA8240;OCH$_2$Ph,Pip], [ZA8241;OCH$_2$(2-Py),Pip], [ZA8242;OCH$_2$(3-Py),Pip], [ZA8243;OCH$_2$(4-Py),Pip], [ZA8244;OCH$_2$CN,Pip], [ZA8245;OCH$_2$NO$_2$,Pip], [ZA8246;O(CH$_2$)$_2$F,Pip], [ZA8247;O(CH$_2$)$_2$CN,Pip], [ZA8248;O(CH$_2$)$_2$Ph,Pip],

[ZA8249;O(CH₂)₂OCH₃,Pip], [ZA8250;O(CH₂)₃F,Pip], [ZA8251;(CH₂)₃CN,Pip], [ZA8252;O(CH₂)₃NO₂,Pip], [ZA8253;O(CH₂)₃Ph,Pip], [ZA8254;O(CH₂)₃OCH₃,Pip], [ZA8255;O(CH₂)₄F,Pip], [ZA8256;O(CH₂)₄CN,Pip], [ZA8257;O(CH₂)₄NO₂,Pip], [ZA8258;(CH₂)₄Ph,Pip], [ZA8259;O(CH₂)₄OCH₃,Pip], [ZA8260;O(CH₂)₅F,Pip], [ZA8261;(CH₂)₅CN,Pip], [ZA8262;O(CH₂)₅NO₂,Pip], [ZA8263;O(CH₂)₅Ph,Pip], [ZA8264;O(CH₂)₅OCH₃,Pip], [ZA8265;O(CH₂)₆F,Pip], [ZA8266;O(CH₂)₆CN,Pip], [ZA8267;O(CH₂)₆NO₂,Pip], [ZA8268;O(CH₂)₆Ph,Pip], [ZA8269;O(CH₂)₆OCH₃,Pip], [ZA8270;OC(O)CH₃,Pip], [ZA8271;OC(O)CH₂CH₃,Pip], [ZA8272;OC(O)CH(CH₃)₂,Pip], [ZA8273;OC(O)(CH₂)₂CH₃,Pip], [ZA8274;OC(O)(CH₂)₃CH₃,Pip], [ZA8275;OC(O)(CH₂)₄CH₃,Pip], [ZA8276;OC(O)(CH₂)₅CH₃,Pip], [ZA8277;OC(O)CH₂CH=CH₂,Pip], [ZA8278;OC(O)CH₂C≡CH,Pip], [ZA8279;OC(O)CH₂C≡CCH₃,Pip], [ZA8280;OC(O)c-Pr,Pip], [ZA8281;OC(O)c-Pen,Pip], [ZA8282;OC(O)c-Hex,Pip], [ZA8283;OC(O)Ph,Pip], [ZA8284;OC(O)(2-Py),Pip], [ZA8285;OC(O)(3-Py),Pip], [ZA8286;OC(O)(4-Py),Pip], [ZA8287;OC(O)CH₂Ph,Pip], [ZA8288;OC(O)CH₂(2-Py),Pip], [ZA8289;OC(O)CH₂(3-Py),Pip], [ZA8290;OC(O)CH₂(4-Py),Pip], [ZA8291;OC(O)CH₂CN,Pip], [ZA8292;OC(O)CH₂NO₂,Pip], [ZA8293;OC(O)(CH₂)₂F,Pip], [ZA8294;OC(O)(CH₂)₂CN,Pip], [ZA8295;OC(O)(CH₂)₂NO₂,Pip], [ZA8296;OC(O)(CH₂)₂Ph,Pip], [ZA8297;OC(O)(CH₂)₂OCH₃,Pip], [ZA8298;OC(O)(CH₂)₃F,Pip], [ZA8299;OC(O)(CH₂)₃CN,Pip], [ZA8300;OC(O)(CH)₃NO₂,Pip], [ZA8301;OC(O)(CH₂)₃OCH₃,Pip], [ZA8302;OC(O)NH₂,Pip], [ZA8303;OC(O)NHCH₃,Pip], [ZA8304;OC(O)NHCH₂CH₃,Pip], [ZA8305;OC(O)NH(CH₂)₂CH₃,Pip], [ZA8306;OC(O)NH(CH₂)₃CH₃,Pip], [ZA8307;OC(O)NH(CH₂)₄CH₃,Pip], [ZA8308;OC(O)NH(CH₂)₅CH₃,Pip], [ZA8309;OC(O)NHCH(CH₃)₂,Pip], [ZA831;OC(O)NHCH₂F,Pip], [ZA8311;OC(O)NHCH₂CN,Pip], [ZA8312;OC(O)NHCH₂OCH₃,Pip], [ZA8313;OC(O)NHCH₂Ph,Pip], [ZA8314;OC(O)NH(CH₂)₂F,Pip], [ZA8315;OC(O)NH(CH₂)₂CN,Pip], [ZA8316;OC(O)NH(CH₂)₂OCH₃,Pip], [ZA8317;OC(O)NH(CH₂)₃F,Pip], [ZA8318;OC(O)NH(CH₂)₃CN,Pip], [ZA8319;OC(O)NH(CH₂)₃OCH₃,Pip], [ZA8320;OC(O)NH(CH₂)₄F,Pip], [ZA8321;OC(O)NH(CH₂)₄CN,Pip], [ZA8322;OC(O)NH(CH₂)₄OCH₃,Pip], [ZA8323;OC(O)NHPh,Pip], [ZA8324;OC(O)NH(2-Py),Pip], [ZA8325;OC(O)NH(3-Py),Pip], [ZA8326;OC(O)NH(4-Py),Pip], [ZA8327;OC(O)N(CH₃)₂,Pip], [ZA8328;OC(O)N(CH₃)CH₂CH₃,Pip], [ZA8329;OC(O)N(CH₃)(CH₂)₂CH₃,Pip], [ZA8330;OC(O)N(CH₃)(CH₂)₃CH₃,Pip], [ZA8331;OC(O)N(CH₃)CH(CH₃)₂,Pip], [ZA8332;OC(O)N(CH₃)CH₂F,Pip], [ZA8333;OC(O)N(CH₃)CH₂CN,Pip], [ZA8334;OC(O)N(CH)CH₂OCH₃,Pip], [ZA8335;OC(O)N(CH₃)CH₂Ph,Pip], [ZA8336;OC(O)N(CH₃)(CH₂)₂F,Pip], [ZA8337;OC(O)N(CH₃)(CH₂)₂CN,Pip], [ZA8338;OC(O)N(CH)(CH₂)₂OCH₃,Pip], [ZA8339;OC(O)N(CH₃)Ph,Pip], [ZA8340;OC(O)N(CH₃)(2-Py),Pip], [ZA8341;OC(O)N(CH₃)(3-Py),Pip], [ZA8342;OC(O)N(CH₃)(4-Py),Pip], [ZA8343;OC(O)N(CH₂CH₃)₂,Pip], [ZA8344;OC(O)(Pyr),Pip], [ZA8345;OC(O)(Pip),Pip], [ZA8346;OC(O)(Mor),Pip], [ZA8347;OC(O)OCH₃,Pip], [ZA8348;OC(O)OCH₂CH₃,Pip], [ZA8349;OC(O)OCH(CH₃)₂,Pip], [ZA8350;OC(O)O(CH₂)₂CH₃,Pip], [ZA8351;OC(O)O(CH₂)₃CH₃,Pip], [ZA8352;OC(O)O(CH₂)₄CH₃,Pip], [ZA8353;OC(O)O(CH₂)₅CH₃,Pip], [ZA8354;OC(O)OCH₂CH=CH₂,Pip], [ZA8355;OC(O)OCH₂C≡CH,Pip], [ZA8356;OC(O)OCH₂C≡CCH₃,Pip], [ZA8357;OC(O)O-c-Pr,Pip], [ZA8358;OC(O)O-c-Pen,Pip], [ZA8359;OC(O)O-c-Hex,Pip], [ZA8360;OC(O)OPh,Pip], [ZA8361;OC(O)O(2-Py),Pip], [ZA8362;OC(O)O(3-Py),Pip], [ZA8363;OC(O)O(4-Py),Pip], [ZA8364;OC(O)OCF₃,Pip], [ZA8365;OC(O)OCH₂Ph,Pip], [ZA8366;OC(O)OCH₂(2-Py),Pip], [ZA8367;OC(O)OCH₂(3-Py),Pip], [ZA8368;OC(O)OCH₂(4-Py),Pip], [ZA8369;OC(O)OCH₂CN,Pip], [ZA8370;OC(O)OCH₂NO₂,Pip], [ZA8371;OC(O)O(CH₂)₂F,Pip], [ZA8372;OC(O)O(CH₂)₂CN,Pip], [ZA8373;OC(O)O(CH₂)₂OCH₃,Pip], [ZA8374;OC(O)O(CH₂)₃F,Pip], [ZA8375;OC(O)O(CH₂)₃CN,Pip], [ZA8376;OC(O)O(CH₂)₃OCH₃,Pip], [ZA8377;OS(O)₂CH₃,Pip], [ZA8378;OS(O)₂CH₂CH₃,Pip], [ZA8379;OS(O)₂CH(CH₃)₂,Pip], [ZA8380;OS(O)₂(CH₂)₂CH₃,Pip], [ZA8381;OS(O)₂(CH₂)₃CH₃,Pip], [ZA8382;OS(O)₂(CH₂)₄CH₃,Pip], [ZA8383;OS(O)₂(CH₂)₅CH₃,Pip], [ZA8384;OS(O)₂-c-Pr,Pip], [ZA8385;OS(O)₂-c-Pen,Pip], [ZA8386;OS(O)₂-c-Hex,Pip], [ZA8387;OS(O)₂Ph,Pip], [ZA8388;OS(O)₂(2-Py),Pip], [ZA8389;OS(O)₂(3-Py),Pip], [ZA8390;OS(O)₂(4-Py),Pip], [ZA8391;OS(O)₂CF₃,Pip], [ZA8392;OS(O)₂CH₂Ph,Pip], [ZA8393;OH,Mor], [ZA8394;OCH₃,Mor], [ZA8395;OCH₂CH₃,Mor], [ZA8396;OCH(CH₃)₂,Mor], [ZA8397;O(CH₂)₂CH₃,Mor], [ZA8398;O(CH₂)₃CH₃,Mor], [ZA8399;O(CH₂)₄CH₃,Mor], [ZA8400;O(CH₂)₅CH₃,Mor], [ZA8401;OCH₂CH=CH₂,Mor], [ZA8402;OCH₂C≡CH,Mor], [ZA8403;OCH₂C≡CCH₃,Mor], [ZA8404;O-c-Pr,Mor], [ZA8405;O-c-Pen,Mor], [ZA8406;O-c-Hex,Mor], [ZA8407;OPh,Mor], [ZA8408;OCH₂Ph,Mor], [ZA8409;OCH₂(2-Py),Mor], [ZA841;OCH₂(3-Py),Mor], [ZA8411;OCH₂(4-Py),Mor], [ZA8412;OCH₂CN,Mor], [ZA8413;OCH₂NO₂,Mor], [ZA8414;O(CH₂)₂F,Mor], [ZA8415;O(CH₂)₂CN,Mor], [ZA8416;O(CH₂)₂Ph,Mor], [ZA8417;O(CH₂)₂OCH₃,Mor], [ZA8418;O(CH₂)₃F,Mor], [ZA8419;O(CH₂)₃CN,Mor], [ZA8420;O(CH₂)₃NO₂,Mor], [ZA8421;(CH₂)₃Ph,Mor], [ZA8422;O(CH₂)₃OCH₃,Mor], [ZA8423;O(CH₂)₄F,Mor], [ZA8424;O(CH₂)₄CN,Mor], [ZA8425;O(CH₂)₄NO₂,Mor], [ZA8426;O(CH₂)₄Ph,Mor], [ZA8427;O(CH₂)₄OCH₃,Mor], [ZA8428;O(CH₂)₅F,Mor], [ZA8429;O(CH₂)₅CN,Mor], [ZA8430;O(CH₂)₅NO₂,Mor], [ZA8431;(CH₂)₅Ph,Mor], [ZA8432;O(CH₂)₅OCH₃,Mor], [ZA8433;O(CH₂)₆F,Mor], [ZA8434;O(CH₂)₆CN,Mor], [ZA8435;O(CH₂)₆NO₂,Mor], [ZA8436;O(CH₂)₆Ph,Mor], [ZA8437;O(CH₂)₆OCH₃,Mor], [ZA8438;OC(O)CH₃,Mor], [ZA8439;OC(O)CH₂CH₃,Mor], [ZA8440;OC(O)CH(CH₃)₂,Mor], [ZA8441;OC(O)(CH₂)₂CH₃,Mor], [ZA8442;OC(O)(CH₂)₃CH₃,Mor], [ZA8443;OC(O)(CH₂)₄CH₃,Mor], [ZA8444;OC(O)(CH₂)₅CH₃,Mor], [ZA8445;OC(O)CH₂CH=CH₂,Mor], [ZA8446;OC(O)CH₂C≡CH,Mor], [ZA8447;OC(O)CH₂C≡CCH₃,Mor], [ZA8448;OC(O)c-Pr,Mor], [ZA8449;OC(O)c-Pen,Mor], [ZA8450;OC(O)c-Hex,Mor], [ZA8451;OC(O)Ph,Mor], [ZA8452;OC(O)(2-Py),Mor], [ZA8453;OC(O)(3-Py),Mor], [ZA8454;OC(O)(4-Py),Mor], [ZA8455;OC(O)CH₂Ph,Mor], [ZA8456;OC(O)CH₂(2-Py),Mor], [ZA8457;OC(O)CH₂(3-Py),Mor], [ZA8458;OC(O)CH₂(4-Py),Mor], [ZA8459;OC(O)CH₂CN,Mor], [ZA8460;OC(O)CH₂NO₂,Mor], [ZA8461;OC(O)(CH₂)₂F,Mor], [ZA8462;OC(O)(CH₂)₂CN,Mor], [ZA8463;OC(O)(CH₂)₂NO₂,Mor], [ZA8464;OC(O)(CH₂)₂Ph,Mor], [ZA8465;OC(O)(CH₂)₂OCH₃,Mor], [ZA8466;OC(O)(CH₂)₃F,Mor], [ZA8467;OC(O)(CH₂)₃CN,Mor], [ZA8468;OC(O)(CH₂)₃NO₂,Mor], [ZA8469;OC(O)(CH₂)₃OCH₃,Mor], [ZA8470;OC(O)NH₂,Mor], [ZA8471;OC(O)NHCH₃,Mor], [ZA8472;OC(O)NHCH₂CH₃,Mor], [ZA8473;OC(O)NH(CH₂)₂CH₃,Mor], [ZA8474;OC(O)NH(CH₂)₃CH₃,Mor], [ZA8475;OC(O)NH(CH₂)₄CH₃,Mor], [ZA8476;OC(O)NH(CH₂)₅CH₃,Mor], [ZA8477;OC(O)NHCH(CH₃)₂,Mor], [ZA8478;OC(O)NHCH₂F,Mor], [ZA8479;OC(O)NHCH₂CN,Mor], [ZA8480;OC(O)NHCH₂OCH₃,Mor], [ZA8481;OC(O)NHCH₂Ph,Mor], [ZA8482;OC(O)NH(CH₂)₂F,Mor], [ZA8483;OC(O)NH(CH₂)₂CN,Mor], [ZA8484;OC(O)NH (CH₂)₂OCH₃,Mor], [ZA8485;OC(O)NH(CH₂)₃F,Mor], [ZA8486;OC(O)NH(CH₂)₃CN,Mor], [ZA8487;OC(O)NH(CH)₃OCH₃,Mor], [ZA8488;OC(O)NH(CH₂)₄F,Mor], [ZA8489;OC(O)NH(CH₂)₄CN,Mor], [ZA8490;OC(O)NH(CH₂)₄OCH₃,Mor], [ZA8491;OC(O)NHPh,Mor], [ZA8492;OC(O)NH(2-Py),Mor], [ZA8493;OC(O)NH(3-Py),Mor], [ZA8494;OC(O)NH(4-Py),Mor], [ZA8495;OC(O)N(CH₃)₂,Mor], [ZA8496;OC(O)N(CH₃)CH₂CH₃,Mor], [ZA8497;OC(O)N(CH₃)(CH₂)₂CH₃,Mor], [ZA8498;OC(O)N(CH₃)(CH₂)₃CH₃,Mor], [ZA8499;OC(O)N(CH₃)CH(CH₃)₂,Mor], [ZA8500;OC(O)N(CH₃)CH₂F,Mor],

[ZA8501;OC(O)N(CH₃)CH₂CN,Mor], [ZA8502;OC(O)N(CH₃)CH₂OCH₃,Mor], [ZA8503;OC(O)N(CH₃)CH₂Ph,Mor], [ZA8504;OC(O)N(CH₃)(CH₂)₂F,Mor], [ZA8505;OC(O)N(CH₃)(CH₂)₂CN,Mor], [ZA8506;OC(O)N(CH₃)(CH₂)₂OCH₃,Mor], [ZA8507;OC(O)N(CH₃)Ph,Mor], [ZA8508;OC(O)N(CH₃)(2-Py),Mor], [ZA8509;OC(O)N(CH₃)(3-Py),Mor], [ZA8510;OC(O)N(CH₃)(4-Py),Mor], [ZA8511;OC(O)N(CH₂CH₃)₂,Mor], [ZA8512;OC(O)(Pyr),Mor], [ZA8513;OC(O)(Pip),Mor], [ZA8514;OC(O)(Mor),Mor], [ZA8515;OC(O)OCH₃,Mor], [ZA8516;OC(O)OCH₂CH₃,Mor], [ZA8517;OC(O)OCH(CH₃)₂,Mor], [ZA8518;OC(O)O(CH₂)₂CH₃,Mor], [ZA8519;OC(O)O(CH₂)₃CH₃,Mor], [ZA8520;OC(O)O(CH₂)₄CH₃,Mor], [ZA8521;OC(O)O(CH₂)₅CH₃,Mor], [ZA8522;OC(O)OCH₂CH=CH₂,Mor], [ZA8523;OC(O)OCH₂C≡CH,Mor], [ZA8524;OC(O)OCH₂C≡CCH₃,Mor], [ZA8525;OC(O)O-c-Pr,Mor], [ZA8526;OC(O)O-c-Pen,Mor], [ZA8527;OC(O)O-c-Hex,Mor], [ZA8528;OC(O)OPh,Mor], [ZA8529;OC(O)O(2-Py),Mor], [ZA8530;OC(O)O(3-Py),Mor], [ZA8531;OC(O)O(4-Py),Mor], [ZA8532;OC(O)OCF₃,Mor], [ZA8533;OC(O)OCH₂Ph,Mor], [ZA8534;OC(O)OCH₂(2-Py),Mor], [ZA8535;OC(O)OCH₂(3-Py),Mor], [ZA8536;OC(O)OCH₂(4-Py),Mor], [ZA8537;OC(O)OCH₂CN,Mor], [ZA8538;OC(O)OCH₂NO₂,Mor], [ZA8539;OC(O)O(CH₂)₂F,Mor], [ZA8540;OC(O)O(CH₂)₂CN,Mor], [ZA8541;OC(O)O(CH₂)₂OCH₃,Mor], [ZA8542;OC(O)O(CH₂)₃F,Mor], [ZA8543;OC(O)O(CH₂)₃CN,Mor], [ZA8544;OC(O)O(CH₂)₃OCH₃,Mor], [ZA8545;OS(O)₂CH₃,Mor], [ZA8546;OS(O)₂CH₂CH₃,Mor], [ZA8547;OS(O)₂CH(CH₃)₂,Mor], [ZA8548;OS(O)₂(CH₂)₂CH₃,Mor], [ZA8549;OS(O)₂(CH₂)₃CH₃,Mor], [ZA8550;OS(O)₂(CH₂)₄CH₃,Mor], [ZA8551;OS(O)₂(CH₂)₅CH₃,Mor], [ZA8552;OS(O)₂-c-Pr,Mor], [ZA8553;OS(O)₂-c-Pen,Mor], [ZA8554;OS(O)₂-c-Hex,Mor], [ZA8555;OS(O)₂Ph,Mor], [ZA8556;OS(O)₂(2-Py),Mor], [ZA8557;OS(O)₂(3-Py),Mor], [ZA8558;OS(O)₂(4-Py),Mor], [ZA8559;OS(O)₂CF₃,Mor], [ZA8560;OS(O)₂CH₂Ph,Mor], [ZA8561;OH,S(O)CH₃], [ZA8562;OCH₃,S(O)CH₃], [ZA8563;OCH₂CH₃,S(O)CH₃], [ZA8564;OCH(CH₃)₂,S(O)CH₃], [ZA8565;O(CH₂)₂CH₃,S(O)CH₃], [ZA8566;O(CH₂)₃CH₃,S(O)CH₃], [ZA8567;O(CH₂)₄CH₃,S(O)CH₃], [ZA8568;O(CH₂)₅CH₃,S(O)CH₃], [ZA8569;OCH₂CH=CH₂,S(O)CH₃], [ZA8570;OCH₂C≡CH,S(O)CH₃], [ZA8571;OCH₂C≡CCH₃,S(O)CH₃], [ZA8572;O-c-Pr,S(O)CH₃], [ZA8573;O-c-Pen,S(O)CH₃], [ZA8574;O-c-Hex,S(O)CH₃], [ZA8575;OPh,S(O)CH₃], [ZA8576;OCH₂Ph,S(O)CH₃], [ZA8577;OCH₂(2-Py),S(O)CH₃], [ZA8578;OCH₂(3-Py),S(O)CH₃], [ZA8579;OCH₂(4-Py),S(O)CH₃], [ZA8580;OCH₂CN,S(O)CH₃], [ZA8581;OCH₂NO₂,S(O)CH₃], [ZA8582;O(CH₂)₂F,S(O)CH₃], [ZA8583;O(CH₂)₂CN,S(O)CH₃], [ZA8584;O(CH₂)₂Ph,S(O)CH₃], [ZA8585;O(CH₂)₂OCH₃,S(O)CH₃], [ZA8586;O(CH₂)₃F,S(O)CH₃], [ZA8587;O(CH₂)₃CN,S(O)CH₃], [ZA8588;O(CH₂)₃NO₂,S(O)CH₃], [ZA8589;O(CH₂)₃Ph,S(O)CH₃], [ZA8590;O(CH₂)₃OCH₃,S(O)CH₃], [ZA8591;(CH₂)₄F,S(O)CH₃], [ZA8592;O(CH₂)₄CN,S(O)CH₃], [ZA8593;O(CH₂)₄NO₂,S(O)CH₃], [ZA8594;O(CH₂)₄Ph,S(O)CH₃], [ZA8595;O(CH₂)₄OCH₃,S(O)CH₃], [ZA8596;O(CH₂)₅F,S(O)CH₃], [ZA8597;O(CH₂)₅CN,S(O)CH₃], [ZA8598;O(CH₂)₅NO₂,S(O)CH₃], [ZA8599;O(CH₂)₅Ph,S(O)CH₃], [ZA8600;O(CH₂)₅OCH₃,S(O)CH₃], [ZA8601;(CH₂)₆F,S(O)CH₃], [ZA8602;O(CH₂)₆CN,S(O)CH₃], [ZA8603;O(CH₂)₆NO₂,S(O)CH₃], [ZA8604;O(CH₂)₆Ph,S(O)CH₃], [ZA8605;O(CH₂)₆OCH₃,S(O)CH₃], [ZA8606;OC(O)CH₃,S(O)CH₃], [ZA8607;OC(O)CH₂CH₃,S(O)CH₃], [ZA8608;OC(O)CH(CH₃)₂,S(O)CH₃], [ZA8609;OC(O)(CH₂)₂CH₃,S(O)CH₃], [ZA861;OC(O)(CH₂)₃CH₃,S(O)CH₃], [ZA8611;OC(O)(CH₂)₄CH₃,S(O)CH₃], [ZA8612;OC(O)(CH₂)₅CH₃,S(O)CH₃], [ZA8613;OC(O)CH₂CH=CH₂,S(O)CH₃], [ZA8614;OC(O)CH₂C≡CH,S(O)CH₃], [ZA8615;OC(O)CH₂C≡CCH₃,S(O)CH₃], [ZA8616;OC(O)c-Pr,S(O)CH₃], [ZA8617;OC(O)c-Pen,S(O)CH₃], [ZA8618;OC(O)c-Hex,S(O)CH₃], [ZA8619;OC(O)Ph,S(O)CH₃], [ZA8620;OC(O)(2-Py),S(O)CH₃], [ZA8621;OC(O)(3-Py),S(O)CH₃], [ZA8622;OC(O)(4-Py),S(O)CH₃], [ZA8623;OC(O)CH₂Ph,S(O)CH₃], [ZA8624;OC(O)CH₂(2-Py),S(O)CH₃], [ZA8625;OC(O)CH₂(3-Py),S(O)CH₃], [ZA8626;OC(O)CH₂(4-Py),S(O)CH₃], [ZA8627;OC(O)CH₂CN,S(O)CH₃], [ZA8628;OC(O)CH₂NO₂,S(O)CH₃], [ZA8629;OC(O)(CH₂)₂F,S(O)CH₃], [ZA8630;OC(O)(CH₂)₂CN,S(O)CH₃], [ZA8631;OC(O)(CH₂)₂NO₂,S(O)CH₃], [ZA8632;OC(O)(CH₂)₂Ph,S(O)CH₃], [ZA8633;OC(O)(CH₂)₂OCH₃,S(O)CH₃], [ZA8634;OC(O)(CH₂)₃F,S(O)CH₃], [ZA8635;OC(O)(CH₂)₃CN,S(O)CH₃], [ZA8636;OC(O)(CH₂)₃NO₂,S(O)CH₃], [ZA8637;OC(O)(CH₂)₃OCH₃,S(O)CH₃], [ZA8638;OC(O)NH₂,S(O)CH₃], [ZA8639;OC(O)NHCH₃,S(O)CH₃], [ZA8640;OC(O)NHCH₂CH₃,S(O)CH₃], [ZA8641;OC(O)NH(CH)₂CH₃,S(O)CH₃], [ZA8642;OC(O)NH(CH₂)₃CH₃,S(O)CH₃], [ZA8643;OC(O)NH(CH₂)₄CH₃,S(O)CH₃], [ZA8644;OC(O)NH(CH₂)₅CH₃,S(O)CH₃], [ZA8645;OC(O)NHCH(CH₃)₂,S(O)CH₃], [ZA8646;OC(O)NHCH₂F,S(O)CH₃], [ZA8647;OC(O)NHCH₂CN,S(O)CH₃], [ZA8648;OC(O)NHCH₂OCH₃,S(O)CH₃], [ZA8649;OC(O)NHCH₂Ph,S(O)CH₃], [ZA8650;OC(O)NH(CH₂)₂F,S(O)CH₃], [ZA8651;OC(O)NH(CH₂)₂CN,S(O)CH₃], [ZA8652;OC(O)NH(CH)₂OCH₃,S(O)CH₃], [ZA8653;OC(O)NH(CH₂)₃F,S(O)CH₃], [ZA8654;OC(O)NH(CH₂)₃CN,S(O)CH₃], [ZA8655;OC(O)NH(CH₂)₃OCH₃,S(O)CH₃], [ZA8656;OC(O)NH(CH₂)₄F,S(O)CH₃], [ZA8657;OC(O)NH(CH₂)₄CN,S(O)CH₃], [ZA8658;OC(O)NH(CH₂)₄OCH₃,S(O)CH₃], [ZA8659;OC(O)NHPh,S(O)CH₃], [ZA8660;OC(O)NH(2-Py),S(O)CH₃], [ZA8661;OC(O)NH(3-Py),S(O)CH₃], [ZA8662;OC(O)NH(4-Py),S(O)CH₃], [ZA8663;OC(O)N(CH₃)₂,S(O)CH₃], [ZA8664;OC(O)N(CH₃)CH₂CH₃,S(O)CH₃], [ZA8665;OC(O)N(CH₃)(CH₂)₂CH₃,S(O)CH₃], [ZA8666;OC(O)N(CH₃)(CH₂)₃CH₃,S(O)CH₃], [ZA8667;OC(O)N(CH₃)CH(CH₃)₂,S(O)CH₃], [ZA8668;OC(O)N(CH₃)CH₂F,S(O)CH₃], [ZA8669;OC(O)N(CH₃)CH₂CN,S(O)CH₃], [ZA8670;OC(O)N(CH₃)CH₂OCH₃,S(O)CH₃], [ZA8671;OC(O)N(CH₃)CH₂Ph,S(O)CH₃], [ZA8672;OC(O)N(CH₃)(CH₂)₂F,S(O)CH₃], [ZA8673;OC(O)N(CH₃)(CH₂)₂CN,S(O)CH₃], [ZA8674;OC(O)N(CH₃)(CH₂)₂OCH₃,S(O)CH₃], [ZA8675;OC(O)N(CH₃)Ph,S(O)CH₃], [ZA8676;OC(O)N(CH₃)(2-Py),S(O)CH₃], [ZA8677;OC(O)N(CH₃)(3-Py),S(O)CH₃], [ZA8678;OC(O)N(CH₃)(4-Py),S(O)CH₃], [ZA8679;OC(O)N(CH₂CH₃)₂,S(O)CH₃], [ZA8680;OC(O)(Pyr),S(O)CH₃], [ZA8681;OC(O)(Pip),S(O)CH₃], [ZA8682;OC(O)(Mor),S(O)CH₃], [ZA8683;OC(O)OCH₃,S(O)CH₃], [ZA8684;OC(O)OCH₂CH₃,S(O)CH₃], [ZA8685;OC(O)OCH(CH₃)₂,S(O)CH₃], [ZA8686;OC(O)O(CH₂)₂CH₃,S(O)CH₃], [ZA8687;OC(O)O(CH₂)₃CH₃,S(O)CH₃], [ZA8688;OC(O)O(CH₂)₄CH₃,S(O)CH₃], [ZA8689;OC(O)O(CH₂)₅CH₃,S(O)CH₃], [ZA8690;OC(O)OCH₂CH=CH₂,S(O)CH₃],

[ZA8691;OC(O)OCH₂C≡CH,S(O)CH₃], [ZA8692;OC(O)OCH₂C≡CCH₃,S(O)CH₃], [ZA8693;OC(O)O-c-Pr,S(O)CH₃], [ZA8694;OC(O)O-c-Pen,S(O)CH₃], [ZA8695;OC(O)O-c-Hex,S(O)CH₃], [ZA8696;OC(O)OPh,S(O)CH₃], [ZA8697;OC(O)O(2-Py),S(O)CH₃], [ZA8698;OC(O)O(3-Py),S(O)CH₃], [ZA8699;OC(O)O(4-Py),S(O)CH₃], [ZA8700;OC(O)OCF₃,S(O)CH₃], [ZA8701;OC(O)OCH₂Ph,S(O)CH₃], [ZA8702;OC(O)OCH₂(2-Py),S(O)CH₃], [ZA8703;OC(O)OCH₂(3-Py),S(O)CH₃], [ZA8704;OC(O)OCH₂(4-Py),S(O)CH₃], [ZA8705;OC(O)OCH₂CN,S(O)CH₃], [ZA8706;OC(O)OCH₂NO₂,S(O)CH₃], [ZA8707;OC(O)O(CH₂)₂F,S(O)CH₃], [ZA8708;OC(O)O(CH₂)₂CN,S(O)CH₃], [ZA8709;OC(O)O(CH₂)₂OCH₃,S(O)CH₃], [ZA871;OC(O)O(CH₂)₃F,S(O)CH₃], [ZA8711;OC(O)O(CH₂)₃CN,S(O)CH₃], [ZA8712;OC(O)O(CH₂)₃OCH₃,S(O)CH₃], [ZA8713;OS(O)₂CH₃,S(O)CH₃], [ZA8714;OS(O)₂CH₂CH₃,S(O)CH₃], [ZA8715;OS(O)₂CH(CH₃)₂,S(O)CH₃], [ZA8716;OS(O)₂(CH₂)₂CH₃,S(O)CH₃], [ZA8717;OS(O)₂(CH₂)₃CH₃,S(O)CH₃], [ZA8718;OS(O)₂(CH₂)₄CH₃,S(O)CH₃], [ZA8719;OS(O)₂(CH₂)₅CH₃,S(O)CH₃], [ZA8720;OS(O)₂-c-Pr,S(O)CH₃], [ZA8721;OS(O)₂-c-Pen,S(O)CH₃], [ZA8722;OS(O)₂-c-Hex,S(O)CH₃], [ZA8723;OS(O)₂Ph,S(O)CH₃], [ZA8724;OS(O)₂(2-Py),S(O)CH₃], [ZA8725;OS(O)₂(3-Py),S(O)CH₃], [ZA8726;OS(O)₂(4-Py),S(O)CH₃], [ZA8727;OS(O)₂CF₃,S(O)CH₃], [ZA8728;OS(O)₂CH₂Ph,S(O)CH₃], [ZA8729;OH,S(O)₂CH₃], [ZA8730;OCH₃,S(O)₂CH₃], [ZA8731;OCH₂CH₃,S(O)₂CH₃], [ZA8732;OCH(CH₃)₂,S(O)₂CH₃], [ZA8733;O(CH₂)₂CH₃,S(O)₂CH₃], [ZA8734;O(CH₂)₃CH₃,S(O)₂CH₃], [ZA8735;O(CH₂)₄CH₃,S(O)₂CH₃], [ZA8736;O(CH₂)₅CH₃,S(O)₂CH₃], [ZA8737;OCH₂CH=CH₂,S(O)₂CH₃], [ZA8738;OCH₂C≡CH,S(O)₂CH₃], [ZA8739;OCH₂C≡CCH₃,S(O)₂CH₃], [ZA8740;O-c-Pr,S(O)₂CH₃], [ZA8741;O-c-Pen,S(O)₂CH₃], [ZA8742;O-c-Hex,S(O)₂CH₃], [ZA8743;OPh,S(O)₂CH₃], [ZA8744;OCH₂Ph,S(O)₂CH₃], [ZA8745;OCH₂(2-Py),S(O)₂CH₃], [ZA8746;OCH₂(3-Py),S(O)₂CH₃], [ZA8747;OCH₂(4-Py),S(O)₂CH₃], [ZA8748;OCH₂CN,S(O)₂CH₃], [ZA8749;OCH₂NO₂,S(O)₂CH₃], [ZA8750;O(CH₂)₂F,S(O)₂CH₃], [ZA8751;(CH₂)₂CN,S(O)₂CH₃], [ZA8752;O(CH₂)₂Ph,S(O)₂CH₃], [ZA8753;O(CH₂)₂OCH₃,S(O)₂CH₃], [ZA8754;O(CH₂)₃F,S(O)₂CH₃], [ZA8755;O(CH₂)₃CN,S(O)₂CH₃], [ZA8756;O(CH₂)₃NO₂,S(O)₂CH₃], [ZA8757;O(CH₂)₃Ph,S(O)₂CH₃], [ZA8758;(CH₂)₃OCH₃,S(O)₂CH₃], [ZA8759;O(CH₂)₄F,S(O)₂CH₃], [ZA8760;O(CH)₄CN,S(O)₂CH₃], [ZA8761;(CH₂)₄NO₂,S(O)₂CH₃], [ZA8762;O(CH₂)₄Ph,S(O)₂CH₃], [ZA8763;O(CH₂)₄OCH₃,S(O)₂CH₃], [ZA8764;O(CH₂)₅F,S(O)₂CH₃], [ZA8765;O(CH₂)₅CN,S(O)₂CH₃], [ZA8766;O(CH₂)₅NO₂,S(O)₂CH₃], [ZA8767;O(CH₂)₅Ph,S(O)₂CH₃], [ZA8768;O(CH₂)₅OCH₃,S(O)₂CH₃], [ZA8769;O(CH₂)₆F,S(O)₂CH₃], [ZA8770;O(CH₂)₆CN,S(O)₂CH₃], [ZA8771;(CH₂)₆NO₂,S(O)₂CH₃], [ZA8772;O(CH₂)₆Ph,S(O)₂CH₃], [ZA8773;O(CH₂)₆OCH₃,S(O)₂CH₃], [ZA8774;OC(O)CH₃,S(O)₂CH₃], [ZA8775;OC(O)CH₂CH₃,S(O)₂CH₃], [ZA8776;OC(O)CH(CH₃)₂,S(O)₂CH₃], [ZA8777;OC(O)(CH₂)₂CH₃,S(O)₂CH₃], [ZA8778;OC(O)(CH₂)₃CH₃,S(O)₂CH₃], [ZA8779;OC(O)(CH₂)₄CH₃,S(O)₂CH₃], [ZA8780;OC(O)(CH₂)₅CH₃,S(O)₂CH₃], [ZA8781;OC(O)CH₂CH=CH₂,S(O)₂CH₃], [ZA8782;OC(O)CH₂C≡CH,S(O)₂CH₃], [ZA8783;OC(O)CH₂C≡CCH₃,S(O)₂CH₃], [ZA8784;OC(O)c-Pr,S(O)₂CH₃], [ZA8785;OC(O)c-Pen,S(O)₂CH₃], [ZA8786;OC(O)c-Hex,S(O)₂CH₃], [ZA8787;OC(O)Ph,S(O)₂CH₃], [ZA8788;OC(O)(2-Py),S(O)₂CH₃], [ZA8789;OC(O)(3-Py),S(O)₂CH₃], [ZA8790;OC(O)(4-Py),S(O)₂CH₃], [ZA8791;OC(O)CH₂Ph,S(O)₂CH₃], [ZA8792;OC(O)CH₂(2-Py),S(O)₂CH₃], [ZA8793;OC(O)CH₂(3-Py),S(O)₂CH₃], [ZA8794;OC(O)CH₂(4-Py),S(O)₂CH₃], [ZA8795;OC(O)CH₂CN,S(O)₂CH₃], [ZA8796;OC(O)CH₂NO₂,S(O)₂CH₃], [ZA8797;OC(O)(CH₂)₂F,S(O)₂CH₃], [ZA8798;OC(O)(CH₂)₂CN,S(O)₂CH₃], [ZA8799;OC(O)(CH₂)₂NO₂,S(O)₂CH₃], [ZA8800;OC(O)(CH₂)₂Ph,S(O)₂CH₃], [ZA8801;OC(O)(CH₂)₂OCH₃,S(O)₂CH₃], [ZA8802;OC(O)(CH)₃F,S(O)₂CH₃], [ZA8803;OC(O)(CH₂)₃CN,S(O)₂CH₃], [ZA8804;OC(O)(CH₂)₃NO₂,S(O)₂CH₃], [ZA8805;OC(O)(CH₂)₃OCH₃,S(O)₂CH₃], [ZA8806;OC(O)NH₂,S(O)₂CH₃], [ZA8807;OC(O)NHCH₃,S(O)₂CH₃], [ZA8808;OC(O)NHCH₂CH₃,S(O)₂CH₃], [ZA8809;OC(O)NH(CH₂)₂CH₃,S(O)₂CH₃], [ZA8810;OC(O)NH(CH₂)₃CH₃,S(O)₂CH₃], [ZA8811;OC(O)NH(CH₂)₄CH₃,S(O)₂CH₃], [ZA8812;OC(O)NH(CH₂)₅CH₃,S(O)₂CH₃], [ZA8813;OC(O)NHCH(CH₃)₂,S(O)₂CH₃], [ZA8814;OC(O)NHCH₂F,S(O)₂CH₃], [ZA8815;OC(O)NHCH₂CN,S(O)₂CH₃], [ZA8816;OC(O)NHCH₂OCH₃,S(O)₂CH₃], [ZA8817;OC(O)NHCH₂Ph,S(O)₂CH₃], [ZA8818;OC(O)NH(CH₂)₂F,S(O)₂CH₃], [ZA8819;OC(O)NH(CH₂)₂CN,S(O)₂CH₃], [ZA8820;OC(O)NH(CH₂)₂OCH₃,S(O)₂CH₃], [ZA8821;OC(O)NH(CH₂)₃F,S(O)₂CH₃], [ZA8822;OC(O)NH(CH₂)₃CN,S(O)₂CH₃], [ZA8823;OC(O)NH(CH₂)₃OCH₃,S(O)₂CH₃], [ZA8824;OC(O)NH(CH)₄F,S(O)₂CH₃], [ZA8825;OC(O)NH(CH₂)₄CN,S(O)₂CH₃], [ZA8826;OC(O)NH(CH₂)₄OCH₃,S(O)₂CH₃], [ZA8827;OC(O)NHPh,S(O)₂CH₃], [ZA8828;OC(O)NH(2-Py),S(O)₂CH₃], [ZA8829;OC(O)NH(3-Py),S(O)₂CH₃], [ZA8830;OC(O)NH(4-Py),S(O)₂CH₃], [ZA8831;OC(O)N(CH₃)₂,S(O)₂CH₃], [ZA8832;OC(O)N(CH₃)CH₂CH₃,S(O)₂CH₃], [ZA8833;OC(O)N(CH₃)(CH₂)₂CH₃,S(O)₂CH₃], [ZA8834;OC(O)N(CH₃)(CH₂)₃CH₃,S(O)₂CH₃], [ZA8835;OC(O)N(CH₃)CH(CH₃)₂,S(O)₂CH₃], [ZA8836;OC(O)N(CH₃)CH₂F,S(O)₂CH₃], [ZA8837;OC(O)N(CH₃)CH₂CN,S(O)₂CH₃], [ZA8838;OC(O)N(CH₃)CH₂OCH₃,S(O)₂CH₃], [ZA8839;OC(O)N(CH₃)CH₂Ph,S(O)₂CH₃], [ZA8840;OC(O)N(CH₃)(CH₂)₂F,S(O)₂CH₃], [ZA8841;OC(O)N(CH₃)(CH₂)₂CN,S(O)₂CH₃], [ZA8842;OC(O)N(CH₃)(CH₂)₂OCH₃,S(O)₂CH₃], [ZA8843;OC(O)N(CH₃)Ph,S(O)₂CH₃], [ZA8844;OC(O)N(CH₃)(2-Py),S(O)₂CH₃], [ZA8845;OC(O)N(CH₃)(3-Py),S(O)₂CH₃], [ZA8846;OC(O)N(CH₃)(4-Py),S(O)₂CH₃], [ZA8847;OC(O)N(CH₂CH₃)₂,S(O)₂CH₃], [ZA8848;OC(O)(Pyr),S(O)₂CH₃], [ZA8849;OC(O)(Pip),S(O)₂CH₃], [ZA8850;OC(O)(Mor),S(O)₂CH₃], [ZA8851;OC(O)OCH₃,S(O)₂CH₃], [ZA8852;OC(O)OCH₂CH₃,S(O)₂CH₃], [ZA8853;OC(O)OCH(CH₃)₂,S(O)₂CH₃], [ZA8854;OC(O)O(CH₂)₂CH₃,S(O)₂CH₃], [ZA8855;OC(O)O(CH₂)₃CH₃,S(O)₂CH₃], [ZA8856;OC(O)O(CH₂)₄CH₃,S(O)₂CH₃], [ZA8857;OC(O)O(CH₂)₅CH₃,S(O)₂CH₃], [ZA8858;OC(O)OCH₂CH=CH₂,S(O)₂CH₃], [ZA8859;OC(O)OCH₂C≡CH,S(O)₂CH₃], [ZA8860;OC(O)OCH₂C≡CCH₃,S(O)₂CH₃], [ZA8861;OC(O)O-c-Pr,S(O)₂CH₃], [ZA8862;OC(O)O-c-Pen,S(O)₂CH₃], [ZA8863;OC(O)O-c-Hex,S(O)₂CH₃], [ZA8864;OC(O)OPh,S(O)₂CH₃], [ZA8865;OC(O)O(2-Py),S(O)₂CH₃], [ZA8866;OC(O)O(3-Py),S(O)₂CH₃], [ZA8867;OC(O)O(4-Py),S(O)₂CH₃], [ZA8868;OC(O)OCF₃,S(O)₂CH₃], [ZA8869;OC(O)OCH₂Ph,S(O)₂CH₃], [ZA8870;OC(O)OCH₂(2-Py),S(O)₂CH₃], [ZA8871;OC(O)OCH₂(3-Py),S(O)₂CH₃], [ZA8872;OC(O)OCH₂(4-Py),S(O)₂CH₃], [ZA8873;OC(O)OCH₂CN,S(O)₂CH₃], [ZA8874;OC(O)OCH₂NO₂,S(O)₂CH₃], [ZA8875;OC(O)O(CH₂)₂F,S(O)₂CH₃], [ZA8876;OC(O)O(CH₂)₂CN,S(O)₂CH₃], [ZA8877;OC(O)O(CH₂)₂OCH₃,S(O)₂CH₃], [ZA8878;OC(O)O(CH₂)₂F,S(O)₂CH₃], [ZA8879;OC(O)O(CH₂)₃CN,S(O)₂CH₃], [ZA8880;OC(O)O(CH₂)₃OCH₃,S(O)₂CH₃], [ZA8881;OS(O)₂CH₃,S(O)₂CH₃], [ZA8882;OS(O)₂CH₂CH₃,S(O)₂CH₃], [ZA8883;OS(O)₂CH(CH₃)₂,S(O)₂CH₃], [ZA8884;OS(O)₂(CH₂)₂CH₃,S(O)₂CH₃], [ZA8885;OS(O)₂(CH₂)₃CH₃,S(O)₂CH₃],

[ZA8886;OS(O)$_2$(CH$_2$)$_4$CH$_3$,S(O)$_2$CH$_3$], [ZA8887;OS(O)$_2$(CH$_2$)$_5$CH$_3$,S(O)$_2$CH$_3$], [ZA8888;OS(O)$_2$-c-Pr,S(O)$_2$CH$_3$], [ZA8889;OS(O)$_2$-c-Pen,S(O)$_2$CH$_3$], [ZA8890;OS(O)$_2$-c-Hex,S(O)$_2$CH$_3$], [ZA8891;OS(O)$_2$Ph,S(O)$_2$CH$_3$], [ZA8892; OS(O)$_2$ (2-Py),S(O)$_2$CH$_3$], [ZA8893;OS(O)$_2$(3-Py),S(O)$_2$CH$_3$], [ZA8894;OS(O)$_2$(4-Py),S(O)$_2$ CH$_3$], [ZA8895;OS(O)$_2$CF$_3$,S(O)$_2$CH$_3$], [ZA8896;OS(O)$_2$CH$_2$Ph,S(O)$_2$CH$_3$]

For example, the Present compound ZA2 indicates the compound represented by formula (T1) wherein the Substituent number is ZA2, and represents the compound represented by formula (T1) wherein $E^Z$ represents a methoxy group and $A^Z$ represents a hydrogen atom represented by the following formula.

[Chem.35]

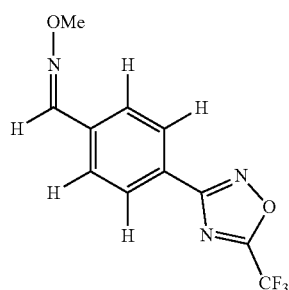

(ZA2)

The compound represented by formula (T2)

[Chem.36]

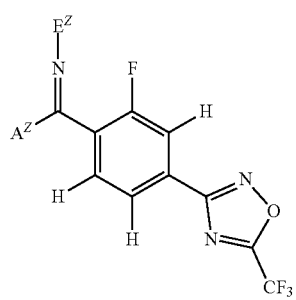

(T2)

wherein the combination of $E^Z$ and $A^Z$ is any one combination described in the Substituent numbers ZA1 to ZA8896 (hereinafter the compounds represented by formula (T2) wherein the Substituent numbers are ZA1 to ZA8896 are referred to as "Present compounds ZB1 to ZB8896", and the "Present compounds ZB1 to ZB8896" are collectively referred to as "Present compound SX2") may be prepared according to the above processes.

For example, the Present compound ZB2 indicates the compound represented by formula (T2) wherein the Substituent number is ZA2, and represents the compound represented by formula (T2) wherein $E^Z$ represents a methoxy group and $A^Z$ represents a hydrogen atom represented by the following formula.

[Chem.37]

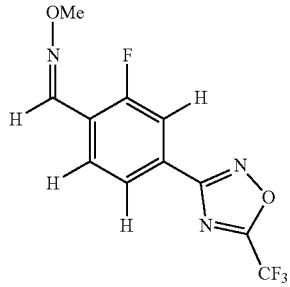

(ZB2)

The compound represented by formula (T3)

[Chem.38]

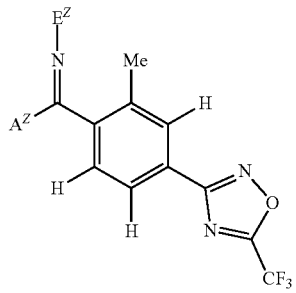

(T3)

wherein the combination of $E^Z$ and $A^Z$ is any one combination described in the Substituent numbers ZA1 to ZA8896 (hereinafter the compounds represented by formula (T3) wherein the Substituent numbers are ZA1 to ZA8896 are referred to as "Present compounds ZC1 to ZC8896", and the "Present compounds ZC1 to ZC8896" are collectively referred to as "Present compound SX3") may be prepared according to the above processes.

For example, the Present compound ZC2 indicates the compound represented by formula (T3) wherein the Substituent number is ZA2, and represents the compound represented by formula (T3) wherein $E^Z$ represents a methoxy group and $A^Z$ represents a hydrogen atom represented by the following formula.

[Chem.39]

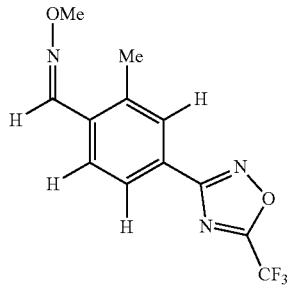

(ZC2)

The compound represented by formula (T4)

[Chem.40]

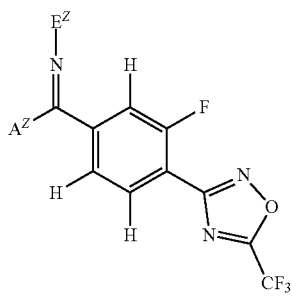

(T4)

wherein the combination of $E^Z$ and $A^Z$ is any one combination described in the Substituent numbers ZA1 to ZA8896 (hereinafter the compounds represented by formula (T4) wherein the Substituent numbers are ZA1 to ZA8896 are referred to as "Present compounds ZD1 to ZD8896", and the "Present compounds ZD1 to ZD8896" are collectively referred to as "Present compound SX4") may be prepared according to the above processes.

For example, the Present compound ZD2 indicates the compound represented by formula (T4) wherein the Substituent number is ZA2, and represents the compound represented by formula (T4) wherein $E^Z$ represents a methoxy group and $A^Z$ represents a hydrogen atom represented by the following formula.

[Chem.41]

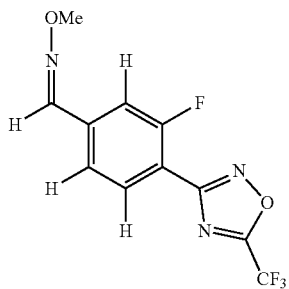

(ZD2)

The compound represented by formula (T5)

[Chem.42]

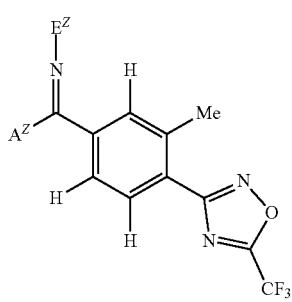

(T5)

wherein the combination of $E^Z$ and $A^Z$ is any one combination described in the Substituent numbers ZA1 to ZA8896 (hereinafter the compounds represented by formula (T5) wherein the Substituent numbers are ZA1 to ZA8896 are referred to as "Present compounds ZE1 to ZE8896", and the "Present compounds ZE1 to ZE8896" are collectively referred to as "Present compound SX5") may be prepared according to the above processes.

For example, the Present compound ZE2 indicates the compound represented by formula (T5) wherein the Substituent number is ZA2, and represents the compound represented by formula (T5) wherein $E^Z$ represents a methoxy group and $A^Z$ represents a hydrogen atom represented by the following formula.

[Chem.43]

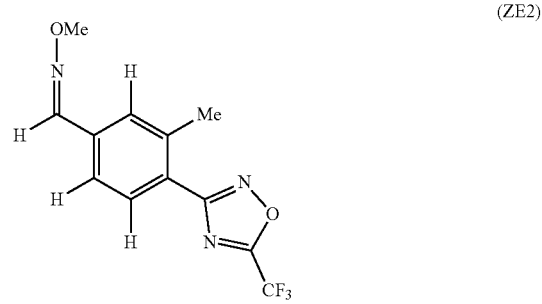

(ZE2)

The compound represented by formula (T6)

[Chem.44]

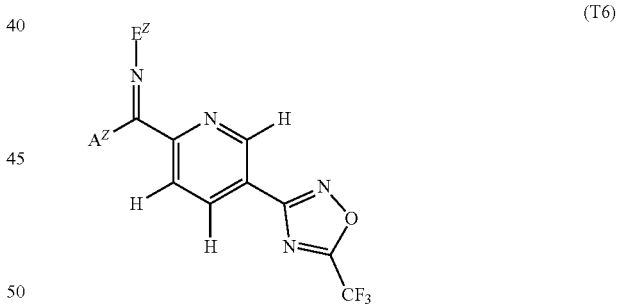

(T6)

wherein the combination of $E^Z$ and $A^Z$ is any one combination described in the Substituent numbers ZA1 to ZA8896 (hereinafter the compounds represented by formula (T6) wherein the Substituent numbers are ZA1 to ZA8896 are referred to as "Present compounds ZF1 to ZF8896", and the "Present compounds ZF1 to ZF8896" are collectively referred to as "Present compound SX6") may be prepared according to the above processes.

For example, the Present compound ZF2 indicates the compound represented by formula (T6) wherein the Substituent number is ZA2, and represents the compound represented by formula (T6) wherein $E^Z$ represents a methoxy group and $A^Z$ represents a hydrogen atom represented by the following formula.

[Chem.45]

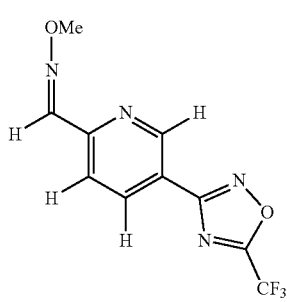

(ZF2)

The compound represented by formula (T7)

[Chem.46]

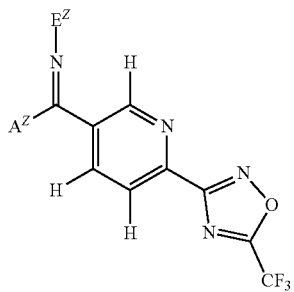

(T7)

wherein the combination of $E^Z$ and $A^Z$ is any one combination described in the Substituent numbers ZA1 to ZA8896 (hereinafter the compounds represented by formula (T7) wherein the Substituent numbers are ZA1 to ZA8896 are referred to as "Present compounds ZG1 to ZG8896", and the "Present compounds ZG1 to ZG8896" are collectively referred to as "Present compound SX7") may be prepared according to the above processes.

For example, the Present compound ZG2 indicates the compound represented by formula (T7) wherein the Substituent number is ZA2, and represents the compound represented by formula (T7) wherein $E^Z$ represents a methoxy group and $A^Z$ represents a hydrogen atom represented by the following formula.

[Chem.47]

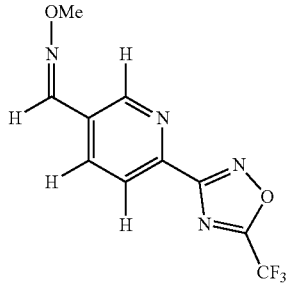

(ZG2)

The compound represented by formula (T8)

[Chem.48]

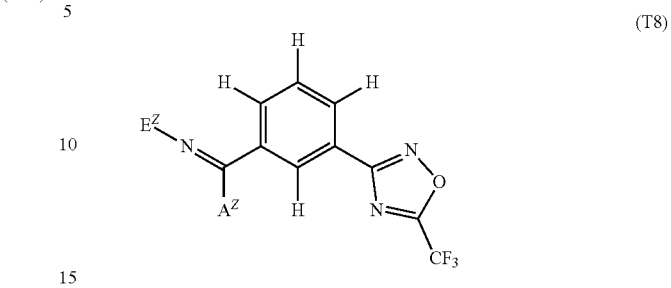

(T8)

wherein the combination of $E^Z$ and $A^Z$ is any one combination described in the Substituent numbers ZA1 to ZA8896 (hereinafter the compounds represented by formula (T8) wherein the Substituent numbers are ZA1 to ZA8896 are referred to as "Present compounds ZH1 to ZH8896", and the "Present compounds ZH1 to ZH8896" are collectively referred to as "Present compound SX8") may be prepared according to the above processes.

For example, the Present compound ZH2 indicates the compound represented by formula (T8) wherein the Substituent number is ZA2, and represents the compound represented by formula (T8) wherein $E^Z$ represents a methoxy group and $A^Z$ represents a hydrogen atom represented by the following formula.

[Chem.49]

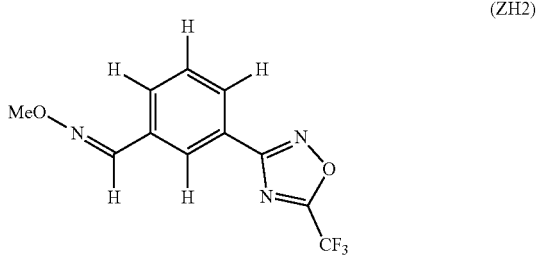

(ZH2)

The compound represented by formula (T9)

[Chem.50]

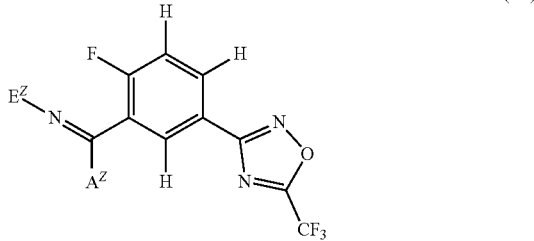

(T9)

wherein the combination of $E^Z$ and $A^Z$ is any one combination described in the Substituent numbers ZA1 to ZA8896 (hereinafter the compounds represented by formula (T9) wherein the Substituent numbers are ZA1 to ZA8896 are referred to as "Present compounds ZI1 to ZI8896", and the "Present compounds ZI1 to ZI8896" are collectively referred to as "Present compound SX9") may be prepared according to the above processes.

For example, the Present compound ZI2 indicates the compound represented by formula (T9) wherein the Substituent number is ZA2, and represents the compound represented by formula (T9) wherein $E^Z$ represents a methoxy group and $A^Z$ represents a hydrogen atom represented by the following formula.

[Chem.51]

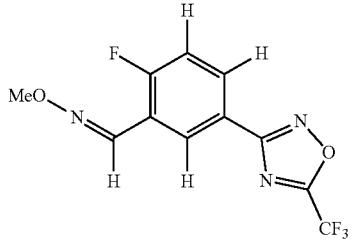

(ZI2)

The compound represented by formula (T10)

[Chem.52]

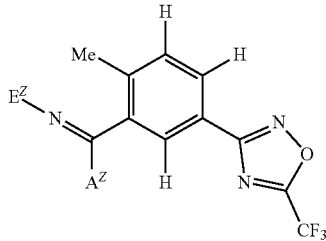

(T10)

wherein the combination of $E^Z$ and $A^Z$ is any one combination described in the Substituent numbers ZA1 to ZA8896 (hereinafter the compounds represented by formula (T10) wherein the Substituent numbers are ZA1 to ZA8896 are referred to as "Present compounds ZJ1 to ZJ8896", and the "Present compounds ZJ1 to ZJ8896" are collectively referred to as "Present compound SX10") may be prepared according to the above processes.

For example, the Present compound ZJ2 indicates the compound represented by formula (T10) wherein the Substituent number is ZA2, and represents the compound represented by formula (T10) wherein $E^Z$ represents a methoxy group and $A^Z$ represents a hydrogen atom represented by the following formula.

[Chem.53]

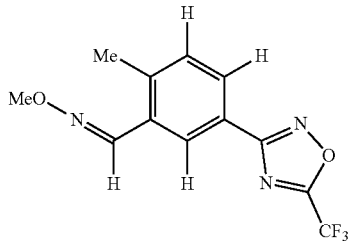

(ZJ2)

The compound represented by formula (T11)

[Chem.54]

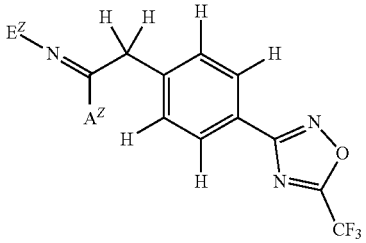

(T11)

wherein the combination of $E^Z$ and $A^Z$ is any one combination described in the Substituent numbers ZA1 to ZA8896 (hereinafter the compounds represented by formula (T11) wherein the Substituent numbers are ZA1 to ZA8896 are referred to as "Present compounds ZK1 to ZK8896", and the "Present compounds ZK1 to ZK8896" are collectively referred to as "Present compound SX11") may be prepared according to the above processes.

For example, the Present compound ZK2 indicates the compound represented by formula (T11) wherein the Substituent number is ZA2, and represents the compound represented by formula (T11) wherein $E^Z$ represents a methoxy group and $A^Z$ represents a hydrogen atom represented by the following formula.

[Chem.55]

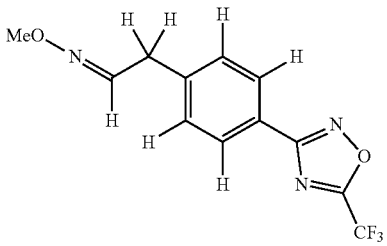

(ZK2)

The compound represented by formula (T12)

[Chem.56]

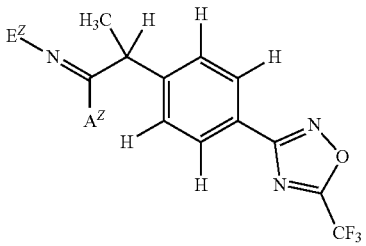

(T12)

wherein the combination of $E^Z$ and $A^Z$ is any one combination described in the Substituent numbers ZA1 to ZA8896 (hereinafter the compounds represented by formula (T12) wherein the Substituent numbers are ZA1 to ZA8896 are referred to as "Present compounds ZL1 to ZL8896", and the "Present compounds ZL1 to ZL8896" are collectively referred to as "Present compound SX12") may be prepared according to the above processes.

For example, the Present compound ZL2 indicates the compound represented by formula (T12) wherein the Substituent number is ZA2, and represents the compound represented by formula (T12) wherein $E^Z$ represents a methoxy group and $A^Z$ represents a hydrogen atom represented by the following formula.

[Chem.57]

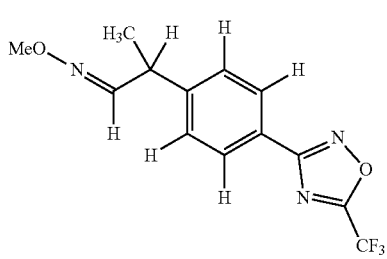

(ZL2)

The compound represented by formula (T13)

[Chem.58]

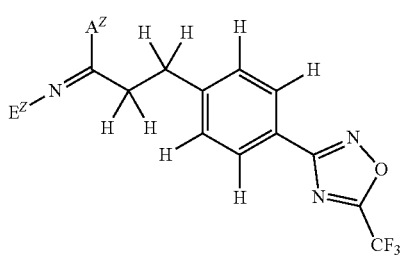

(T13)

wherein the combination of $E^Z$ and $A^Z$ is any one combination described in the Substituent numbers ZA1 to ZA8896 (hereinafter the compounds represented by formula (T13) wherein the Substituent numbers are ZA1 to ZA8896 are referred to as "Present compounds ZM1 to ZM8896", and the "Present compounds ZM1 to ZM8896" are collectively referred to as "Present compound SX13") may be prepared according to the above processes.

For example, the Present compound ZM2 indicates the compound represented by formula (T13) wherein the Substituent number is ZA2, and represents the compound represented by formula (T13) wherein $E^Z$ represents a methoxy group and $A^Z$ represents a hydrogen atom represented by the following formula.

[Chem.59]

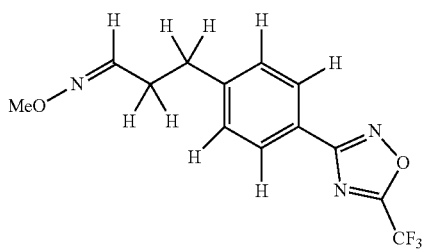

(ZM2)

The compound represented by formula (T14)

[Chem.60]

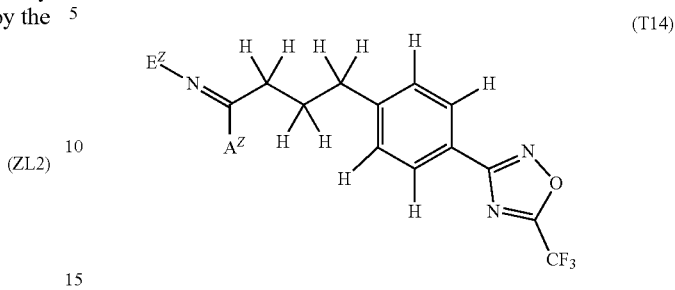

(T14)

wherein the combination of $E^Z$ and $A^Z$ is any one combination described in the Substituent numbers ZA1 to ZA8896 (hereinafter the compounds represented by formula (T14) wherein the Substituent numbers are ZA1 to ZA8896 are referred to as "Present compounds ZN1 to ZN8896", and the "Present compounds ZN1 to ZN8896" are collectively referred to as "Present compound SX14") may be prepared according to the above processes.

For example, the Present compound ZN2 indicates the compound represented by formula (T14) wherein the Substituent number is ZA2, and represents the compound represented by formula (T14) wherein $E^Z$ represents a methoxy group and $A^Z$ represents a hydrogen atom represented by the following formula.

[Chem.61]

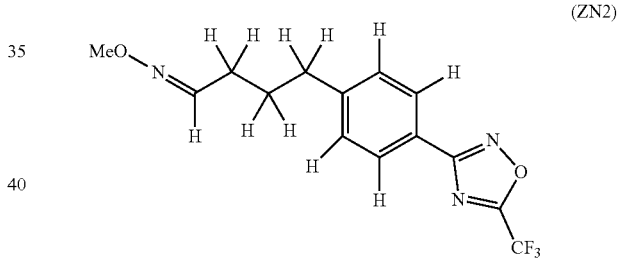

(ZN2)

The present compound can be mixed with or used in combination with a fungicidal active ingredient, an insecticidal active ingredient, a miticidal active ingredient, a nematicidal active ingredient, a plant growth regulatory component, or a synergist (hereinafter each active ingredient is referred to as "Present active ingredient"). Hereinafter, examples of the combination of the Present compound and the Present active ingredient are described. The abbreviation of "SX" indicates any one compound selected from the Present compounds SX1 to SX14. Also, the number in parentheses represents the CAS registration number.

tebuconazole+SX, prothioconazole+SX, metconazole+SX, ipconazole+SX, triti-conazole+SX, difenoconazole+SX, imazalil+SX, triadimenol+SX, tetraconazole+SX, flutriafol+SX, bromuconazole+SX, propiconazole+SX, mefentrifluconazole+SX, ipfentrifluconazole+SX, epoxiconazole+SX, cyproconazole+SX, mandestrobin+SX, azoxystrobin+SX, pyraclostrobin+SX, trifloxystrobin+SX, fluoxastrobin+SX, pi-coxystrobin+SX, fenamidone+SX, dimoxystrobin+SX, metominostrobin+SX, pyribencarb+SX, sedaxane+SX, penflufen+SX, fluxapyroxad+SX, fluopyram+SX, benzovindiflupyr+SX, boscalid+SX, carboxin+SX, penthiopyrad+SX, flutolanil+SX, bixafen+SX, pydiflumetofen+SX, 3-(difluoromethyl)-N-(7-fluoro-1,1,3-trimethylindan-4-yl)-1-methylpyrazole-4-carboxamide (1383809-87-7)+SX, N-cy-clopropyl-3-(difluoromethyl)-5-fluoro-N-(5-chloro-2-isopropylbenzyl)-1-methyl-1H-pyrazole-4-carboxamide (1255734-28-1)+SX, 3-(difluoromethyl)-1-methyl-N-(1,1,3-trimethylindan-4-yl) pyrazole-4-carboxamide (141573-94-6)+SX, 3-(difluoromethyl)-1-methyl-N-[(3R)-1,1,3-trimethylindan-4-yl] pyrazole-4-carboxami de (1352994-67-2)+SX, metalaxyl+SX, metalaxyl-M+SX, metrafenone+SX, cyflufenamid+SX, proquinazid+SX, 3-chloro-5-phenyl-6-methyl-4-(2,6-difluorophenyl) pyridazine (1358061-55-8)+SX, 1-[2-({[1-(4-chlorophenyl)-1H-pyrazol-3-yl]oxy}methyl)-3-methylphenyl]-3-methyl-4,5-dihydrotetrazol-5-one (1472649-01-6)+SX, 4-(2-bromo-4-fluorophenyl)-N-(2-chloro-6-fluorophenyl)-1,3-dimethyl-1H-pyrazol-5-amine (1362477-26-6)+SX, (3S,6S,7R,8R)-8-benzyl-3-[({3-[(isobutyryloxy)methoxy]-4-methoxypyridin-2-yl}carb onyl)amino]-6-methyl-4,9-dioxo-1,5-dioxonan-7-yl-2-methylpropionate (517875-34-2)+SX, N'-(2,5-dimethyl-4-phenoxyphenyl)-N-ethyl-N-methyl-methanimidamide (1052688-31-9)+SX, isotianil+SX, oxolinic acid+SX, ferimzone+SX, phthalide+SX, kasugamycin+SX, tebufloquin+SX, quinofumelin+SX, fenpyrazamine+SX, pro-cymidone+SX, fludioxonil+SX, tolclofos-methyl+SX, thiabendazole+SX, ethaboxam+SX, picarbutrazox+SX, oxathiapiprolin+SX, iminoctadine triacetate+SX, iminoctadine albesilate+SX, fenpropimorph+SX, fenpropidin+SX, spiroxamine+SX, chlorothalonil+SX, folpet+SX, captan+SX, thiram+SX, silthiofam+SX, mancozeb+SX, cartap+SX, clothianidin+SX, thiamethoxam+SX, imidacloprid+SX, thiacloprid+SX, flupyradifurone+SX, sulfoxaflor+SX, triflumezopyrim+SX, di-cloromezotiaz+SX, beta-cyfluthrin+SX, tefluthrin+SX, fipronil+SX, chlo-rantraniliprole+SX, cyantraniliprole+SX, tetraniliprole+SX, thiodicarb+SX, carbofuran+SX, fluxametamide+SX, afoxolaner+SX, fluralaner+SX, broflanilide+SX, abamectin+SX, fluensulfone+SX, fluazaindolizine+SX, tioxazafen+SX, the compound represented by the following formula:

[Chem.62]

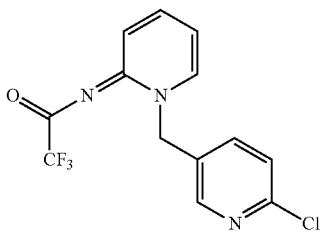

(1689566-03-7)+SX, Mycorrhiza Fungi+SX, *Bacillus firmus*+SX, *Bacillus amyloliquefaciens*+SX, *Pasteuria nishizawae*+SX, and *Pasteuria penetrans*+SX.

Examples of the mixture ratio of the Present compound and the Present active ingredient include, but are not limited to, 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10 in the ratio by weight (Present compound:Present active ingredient).

Applying the Present compound to a plant achieves efficacies for promoting the plant growth such as the increase in the rate of seedling establishment, increase in the number of healthy leaves, increase in the height of the plant, increase in the weight of the plant, increase in the leaf area, increase in the number or weight of seeds or fruits, increase in the number of occasion of flower setting or fruit setting, and promoted growth of a root. Also, applying the Present compound to a plant achieves the improvement in tolerance to abiotic stresses such as temperature stresses (for example, high-temperature stress and low-temperature stress), water stresses (for example, drought stress and excess water stress), and salt stresses.

Next, the Formulation examples are shown below. In the Formulation examples, the "part(s)" represents "part(s) by weight".

Formulation Example 1

Fifty (50) parts of SX, 3 parts of calcium lignin sulfonate, 2 parts of magnesium lauryl sulfate, and 45 parts of synthetic hydrated silicon oxide are fully ground and mixed to obtain each formulation.

Formulation Example 2

Twenty (20) parts of SX, 1.5 parts of sorbitan trioleate, and 28.5 parts of an aqueous solution comprising 2 parts of polyvinyl alcohol are mixed and finely ground by a wet grinding method, and then 40 parts of an aqueous solution comprising 0.05 parts of xanthane gum and 0.1 part of aluminum magnesium silicate is added thereto, and 10 parts of propylene glycol is further added thereto, and the resulting mixture is mixed with stirring to obtain each formulation.

Formulation Example 3

Two (2) parts of SX, 88 parts of kaolin clay, and 10 parts of talc are fully ground and mixed to obtain each formulation.

Formulation Example 4

Five (5) parts of SX, 14 parts of polyoxyethylene styryl phenyl ether, 6 parts of calcium dodecylbenzenesulfonate, and 75 parts of xylene are fully mixed to obtain each formulation.

Formulation Example 5

Two (2) parts of SX, 1 part of synthetic hydrated silicon oxide, 2 parts of calcium lignin sulfonate, 30 parts of bentonite, and 65 parts of kaolin clay are fully ground and mixed, and then water is added thereto, and the resulting mixture is fully kneaded, and granulated and dried to obtain each formulation.

Formulation Example 6

Thirty-five (35) parts of a mixture of polyoxyethylene alkyl ether sulfate ammonium salt and white carbon (weight ratio 1:1), 20 parts of SX, and 45 parts of water are fully mixed to obtain each formulation.

Next, Test examples are used to show efficacies of the Present compounds on controlling pests.

Test Example 1: Test for Controlling *Septoria tritici*

The Present compound 1, 2, 6, 12, 13, 18, 22, 23, 24, 25, 30, 33, 34, 35, or 38 was diluted with dimethyl sulfoxide such that each concentration of the Present compound was 1500 ppm. The resultant dilute solution was dispensed into a microtiter plate (with 96 wells) in 1 µL portion thereof per well. Thereto was then dispensed 150 µL of a potato dextrose broth medium (PDB medium) to which spores of *Septoria tritici* were inoculated in advance. This plate was cultured at 18° C. for five days, thereby allowing *Septoria tritici* to undergo proliferation, and the absorbance at 550 nm of each well of the microtiter plate was then measured, and the obtained value was used as the degree of growth of *Septoria tritici*. From the test results, each degree of growth in the group treated with the Present compound 1, 2, 6, 12, 13, 18, 22, 23, 24, 25, 30, 33, 34, 35, or 38 was 50% or less as compared to the degree of growth in the untreated group.

Test Example 2: Test for Controlling *Cladosporium fulvum*

The Present compound 1, 2, 5, 6, 20, 21, 23, 24, 25, 30, 33, 34, 35, or 38 was diluted with dimethyl sulfoxide such that each concentration of the Present compound was 1500 ppm. The resultant dilute solution was dispensed into a microtiter plate (with 96 wells) in 1 µL portion thereof per well. Thereto was then dispensed 150 µL of a potato dextrose broth medium (PDB medium) to which spores of *Cladosporium fulvum* (QoI resistance strain in which the base sequence of the gene encoding cytochrome b was mutated such that the amino acid residue 129 in cytochrome b was replaced from phenylalanine with leucine) were inoculated in advance. This plate was cultured at 18° C. for five days, thereby allowing *Cladosporium fulvum* to undergo proliferation, and the absorbance at 550 nm of each well of the microtiter plate was then measured, and the obtained value was used as the degree of growth of *Cladosporium fulvum*. From the test results, each degree of growth in the group treated with the Present compound 1, 2, 5, 6, 20, 21, 23, 24, 25, 30, 33, 34, 35, or 38 was 50% or less as compared to the degree of growth in the untreated group.

Test Example 3: Test for Controlling *Colletotrichum truncatum*

The Present compound 6, 17, 21, 23, 24, 25, or 33 was diluted with dimethyl sulfoxide such that each concentration of the Present compound was 1500 ppm. The resultant dilute solution was dispensed into a microtiter plate (with 96 wells) in 1 µL portion thereof per well. Thereto was then dispensed 150 µL of a potato dextrose broth medium (PDB medium) to which spores of *Colletotrichum truncatum* were inoculated in advance. This plate was cultured at 18° C. for four days, thereby allowing *Colletotrichum truncatum* to undergo proliferation, and the absorbance at 550 nm of each well of the microtiter plate was then measured, and the obtained value was used as the degree of growth of *Colletotrichum truncatum*. From the test results, each degree of growth in the group treated with the Present compound 6, 17, 21, 23, 24, 25, or 33 was 50% or less as compared to the degree of growth in the untreated group.

Test Example 4: Test for Controlling Soybean Rust (*Phakopsora pachyrhizi*) on Soybean A plastic pot was filled with soil, and thereto soybeans (cultivar. Kurosengoku) were seeded, and the soybeans were cultivated in a greenhouse for ten days, and an aqueous suspension of uredospores of *Phakopsora pachyrhizi* was inoculated by spraying thereto. After the inoculation, the soybeans were placed at 23° C. in daytime and at 20° C. in nighttime in a greenhouse under humid condition for one day, and then cultivated in a greenhouse for two days. Separately, the Present compound 1, 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 38 formulated according to the process described in the Formulation example 6 was mixed with water such that each concentration of the Present compound was 200 ppm. Said mixture was sprayed to the foliar parts so as to adhere adequately onto the surfaces of leaves of the above soybeans. After spraying the mixture, the soybeans were air-dried, and cultivated in a greenhouse for eight days, and then the lesion area was examined. From the test results, each lesion area in the group of soybeans treated with the Present compound 1, 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 38 was 30% or less as compared to the lesion area in the untreated group of soybeans.

Test Example 5: Test for Controlling Soybean Rust (*Phakopsora pachyrhizi*) on Soybean A plastic pot was filled with soil, and thereto soybeans (cultivar. Kurosengoku) were seeded, and the soybeans were cultivated in a greenhouse for thirteen days. Separately, the Present compound 1, 2, 6, 7, 9, 10, 11, 12, 13, 14, 15, 16, 17, 18, 19, 20, 21, 22, 23, 24, 26, 27, 28, 29, 30, 31, 32, 33, 34, 35, 36, or 38 formulated according to the process described in the Formulation example 6 was mixed with water such that each concentration of the Present compound was 200 ppm. Said mixture was sprayed to the foliar parts so as to adhere adequately onto the surfaces of leaves of the above soybeans. After spraying the mixture, the soybeans were air-dried, and four days after the application, an aqueous suspension of spores of *Phakopsora pachyrhizi* was inoculated by spraying thereto. After the inoculation, the soybeans were placed at 23° C. in daytime and at 20° C. in nighttime in a greenhouse under humid condition for one day, and then cultivated in a greenhouse for ten days, and then the lesion area was examined. From the test results, each lesion area in the group of soybeans treated with the Present compound 1, 2, 6, 7, 9, 10, 11, 12, 13, 14, 15, 16, 17, 18, 19, 20, 21, 22, 23, 24, 26, 27, 28, 29, 30, 31, 32, 33, 34, 35, 36, or 38 was 30% or less as compared to the lesion area in the untreated group of soybeans.

Test Example 6: Test for Controlling *Septoria* Leaf Blotch (*Septoria tritici*) on Wheat A plastic pot was filled with soil, and thereto wheat (cultivar. Apogee) was seeded, and the wheat was cultivated in a greenhouse for ten days. Separately, the Present compound 2, 10, 24, 26, 28, 29, 30, 31, 32, 33, 34, 35, or 38 formulated according to the process described in the Formulation example 6 was mixed with water such that each concentration of the Present compound was 200 ppm. Said mixture was sprayed to the foliar parts so as to adhere adequately onto the surfaces of leaves of the above wheat. After spraying the mixture, the wheat was air-dried, and four days after the application, an aqueous suspension of spores of *Septoria tritici* was inoculated by spraying thereto. After the inoculation, the wheat was placed at 18° C. under humid condition for three days and then cultivated under lighting for fourteen to eighteen days, and then the lesion area was examined. From the test results, each lesion area in the group of wheat treated with the Present compound 2, 10, 24, 26, 28, 29, 30, 31, 32, 33, 34, 35, or 38 was 30% or less as compared to the lesion area in the untreated group of wheat.

Test Example 7: Test for Controlling Rust (*Puccinia recondita*) on Wheat

A plastic pot was filled with soil, and thereto wheat (cultivar. Shirogane) was seeded, and the wheat was cultivated in a greenhouse for nine days. Separately, the Present compound 2, 10, 17, 24, 26, 28, 29, 30, 31, 32, 33, 34, 35, 36, or 38 formulated according to the process described in the Formulation example 6 was mixed with water such that each concentration of the Present compound was 200 ppm. Said mixture was sprayed to the foliar parts so as to adhere adequately onto the surfaces of leaves of the above wheat. After spraying the mixture, the wheat was air-dried, and cultivated at 20° C. under lighting for five days, and then spores of *Puccinia recondita* were inoculated by dusting thereto. After the inoculation, the wheat was placed at 23° C. under dark and humid condition for one day, and then cultivated at 20° C. under lighting for eight days, and the lesion area was examined. From the test results, each lesion area in the group of wheat treated with the Present compound 2, 10, 17, 24, 26, 28, 29, 30, 31, 32, 33, 34, 35, 36, or 38 was 30% or less as compared to the lesion area in the untreated group of wheat.

Test Example 8: Test for Controlling Rice Blast (*Magnaporthe grisea*) on Rice

A plastic pot was filled with soil, and thereto rice (cultivar. Hinohikari) was seeded, and the rice was cultivated in a greenhouse for twenty days. Separately, the Present compound 2, 26, 28, 29, 32, 34, 36, or 38 formulated according to the process described in the Formulation example 6 was mixed with water such that each concentration of the Present compound was 500 ppm. Said mixture was sprayed to the foliar parts so as to adhere adequately onto the surfaces of leaves of the above rice. After spraying the mixture, the rice was air-dried, and the above spray-treated rice was placed at 24° C. in daytime and at 20° C. in nighttime under humid condition for six days in contact with rice seedlings (cultivar. Hinohikari) infected with *Magnaporthe grisea*, and then the lesion area was examined. From the test results, each lesion area in the group of rice treated with the Present compound 2, 26, 28, 29, 32, 34, 36, or 38 was 30% or less as compared to the lesion area in the untreated group of rice.

Test Example 9: Test for Controlling Rice Blast (*Magnaporthe grisea*) on Rice

A plastic pot was filled with soil, and thereto rice (cultivar. Hinohikari) was seeded, and the rice was cultivated in a greenhouse for twenty days. Separately, the Present compound 11, 26, 32, 35, or 38 formulated according to the process described in the Formulation example 6 was mixed with water such that each concentration of the Present compound was 200 ppm. Said mixture was sprayed to the foliar parts so as to adhere adequately onto the surfaces of leaves of the above rice. After spraying the mixture, the rice was air-dried, and the above spray-treated rice was placed at 24° C. in daytime and at 20° C. in nighttime under humid condition for six days in contact with rice seedlings (cultivar. Hinohikari) infected with *Magnaporthe grisea*, and then the lesion area was examined. From the test results, each lesion area in the group of rice treated with the Present compound 11, 26, 32, 35, or 38 was 30% or less as compared to the lesion area in the untreated group of rice.

Test Example 10: Test for Controlling Barley Scald (*Rhynchosporium secalis*) on Barley A plastic pot was filled with soil, and thereto barley (cultivar. Nishinohoshi) was seeded, and the barley was cultivated in a greenhouse for seven days. Separately, the Present compound 2, 10, 24, or 30 formulated according to the process described in the Formulation example 6 was mixed with water such that each concentration of the Present compound was 200 ppm. Said mixture was sprayed to the foliar parts so as to adhere adequately onto the surfaces of leaves of the above barley. After spraying the mixture, the barley was air-dried, and one day after the application, an aqueous suspension of spores of *Rhynchosporium secalis* was inoculated by spraying thereto. After the inoculation, the barley was placed at 15° C. under humid condition for three days, and then cultivated in a greenhouse for fourteen days, and then the lesion area was examined. From the test results, each lesion area in the group of barley treated with the Present compound 2, 10, 24, or 30 was 30% or less as compared to the lesion area in the untreated group of barley.

Test Example 11: Test for Controlling *Septoria* Leaf Blotch (*Septoria tritici*) on Wheat A plastic pot was filled with soil, and thereto wheat (cultivar. Apogee) was seeded, and the wheat was cultivated in a greenhouse for ten days. Separately, the Present compound 6, 23, 26, 27, 28, 29, 30, 31, 32, 34, 35, 36, 37, or 38 formulated according to the process described in the Formulation example 6 was mixed with water such that each concentration of the Present compound was 500 ppm. Said mixture was sprayed to the foliar parts so as to adhere adequately onto the surfaces of leaves of the above wheat. After spraying the mixture, the wheat was air-dried, and four days after the application, an aqueous suspension of spores of *Septoria tritici* was inoculated by spraying thereto. After the inoculation, the wheat was placed at 18° C. under humid condition for three days and then cultivated under lighting for fourteen to eighteen days, and then the lesion area was examined. From the test results, each lesion area in the group of wheat treated with the Present compound 6, 23, 26, 27, 28, 29, 30, 31, 32, 34, 35, 36, 37, or 38 was 30% or less as compared to the lesion area in the untreated group of wheat.

Test Example 12: Test for Controlling Rust (*Puccinia recondita*) on Wheat

A plastic pot was filled with soil, and thereto wheat (cultivar. Shirogane) was seeded, and the wheat was cultivated in a greenhouse for nine days. Separately, the Present compound 6, 19, 20, 21, 22, 23, 24, 26, 27, 28, 29, 30, 31, 32, 34, 35, 36, 37, or 38 formulated according to the process described in the Formulation example 6 was mixed with water such that each concentration of the Present compound was 500 ppm. Said mixture was sprayed to the foliar parts so as to adhere adequately onto the surfaces of leaves of the above wheat. After spraying the mixture, the wheat was air-dried, and cultivated at 20° C. under lighting for five days, and then spores of *Puccinia recondita* were inoculated by dusting thereto. After the inoculation, the wheat was placed at 23° C. under dark and humid condition for one day, and then cultivated at 20° C. under lighting for eight days, and the lesion area was examined. From the test results, each lesion area in the group of wheat treated with the Present compound 6, 19, 20, 21, 22, 23, 24, 26, 27, 28, 29, 30, 31, 32, 34, 35, 36, 37, or 38 was 30% or less as compared to the lesion area in the untreated group of wheat.

Test Example 13: Test for Controlling Net Blotch (*Pyrenophora teres*) on Barley A plastic pot was filled with soil, and thereto barley (cultivar. Nishinohoshi) was seeded, and the barley was cultivated in a greenhouse for seven days. Separately, the Present compound 6, 19, 28, 32, 36, or 38 formulated according to the process described in the Formulation example 6 was mixed with water such that each concentration of the Present compound was 500 ppm. Said mixture was sprayed to the foliar parts so as to adhere adequately onto the surfaces of leaves of the above barley. After spraying the mixture, the barley was air-dried, and two days after the application, an aqueous suspension of spores of *Pyrenophora teres* was inoculated by spraying thereto. After the inoculation, the barley was placed at 23° C. in daytime and at 20° C. in nighttime in a greenhouse under humid condition for three days, and then cultivated in a greenhouse for seven days, and then the lesion area was examined. From the test results, each lesion area in the group of barley treated with the Present compound 6, 19, 28, 32, 36, or 38 was 30% or less as compared to the lesion area in the untreated group of barley.

Test Example 14: Test for Controlling Powdery Mildew (*Microsphaera diffusa*) on Soybean A plastic pot was filled with soil, and thereto soybeans (cultivar. Kurosengoku) were seeded, and the soybeans were cultivated in a greenhouse for ten days, and then spores of soybean seedlings (cultivar. Kurosengoku) infected with *Microsphaera diffusa* were inoculated by dusting thereto. The soybeans were cultivated at 24° C. in daytime and at 20° C. in nighttime in a greenhouse for two days. Separately, the Present compound 13, 23, 24, 26, 27, 32, 34, 35, or 36 formulated according to the process described in the Formulation example 6 was mixed with water such that each concentration of the Present compound was 200 ppm. Said mixture was sprayed to the foliar parts so as to adhere adequately onto the surfaces of leaves of the above soybeans. After spraying the mixture, the soybeans were air-dried, and cultivated in a greenhouse for nine days, and then the lesion area was examined. From the test results, each lesion area in the group of soybeans treated with the Present compound 13, 23, 24, 26, 27, 32, 34, 35, or 36 was 30% or less as compared to the lesion area in the untreated group of soybeans.

Test Example 15: Test for Controlling Powdery Mildew (*Microsphaera diffusa*) on Soybean A plastic pot was filled with soil, and thereto soybeans (cultivar. Kurosengoku) were seeded, and the soybeans were cultivated in a greenhouse for thirteen days. Separately, the Present compound 11, 13, 34, or 35 formulated according to the process described in the Formulation example 6 was mixed with water such that each concentration of the Present compound was 200 ppm. Said mixture was sprayed to the foliar parts so as to adhere adequately onto the surfaces of leaves of the above soybeans. After spraying the mixture, the soybeans were air-dried, and one day after the application, spores of soybean seedlings (cultivar. Kurosengoku) infected with *Microsphaera diffusa* were inoculated by dusting thereto. After the inoculation, the soybeans were cultivated at 24° C. in daytime and at 20° C. in nighttime in a greenhouse for eleven days, and then the lesion area was examined. From the test results, each lesion area in the group of soybeans treated with the Present compound 11, 13, 34, or 35 was 30% or less as compared to the lesion area in the untreated group of soybeans.

Test Example 16

The Present compound 19, 21, or 29 formulated according to the process described in the Formulation example 6 was mixed with water such that each concentration of the Present compound was 500 ppm. Said mixed solution was sprayed to the foliar parts of cabbage seedlings (on the developmental stage of the second to the third true leaf) planted in a container so as to adhere adequately onto the surfaces of leaves of the above cabbage seedlings. After spraying the mixture, the cabbage seedlings were air-dried, and the stem and leaf parts of these seedlings were cut out, and placed in a container lined with a filter paper. Five heads of cabbage moth (*Plutella xylostella*) at the second instar larval stages were released into the container. After five days, the number of the surviving insects was counted, and the mortality of insects was calculated by the following equation.

Mortality of insects (%)=(1−the number of the surviving insects/5)×100

From the test results, each mortality of insects treated with the Present compound 19, 21, or 29 was 80% or more.

INDUSTRIAL APPLICABILITY

The compound of the present invention has excellent efficacies for controlling pests and useful as an active ingredient of an agent for controlling pests.

The invention claimed is:
1. A compound represented by formula (I):

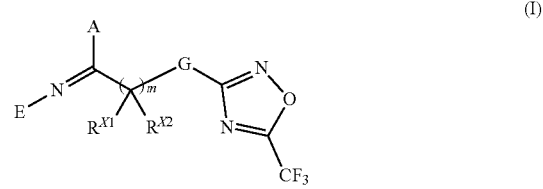

wherein:
G represents a benzene ring, a thiophene ring, a furan ring, a pyrazole ring, an imidazole ring, an oxazole ring, an isoxazole ring, a thiazole ring, an oxadiazole ring, a thiadiazole ring, a pyridine ring, a pyrazine ring, a pyrimidine ring, or a pyridazine ring, wherein said benzene ring, said thiophene ring, said furan ring, said pyrazole ring, said imidazole ring, said oxazole ring, said isoxazole ring, said thiazole ring, said pyridine ring, said pyrazine ring, said pyrimidine ring, and said pyridazine ring may optionally have one or more substituents selected from Group A;
A represents a C2-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, a C1-C6 alkoxy group optionally having one or more substituents selected from Group C, a C1-C6 alkylthio group optionally having one or more substituents selected from Group C, a C1-C6 alkylsulfinyl group optionally having one or more substituents selected from Group C, a C1-C6 alkylsulfonyl group optionally having one or more substituents selected from Group C, a cyano group, or a $NR^1R^2$;

m represents 0, 1, 2, or 3;

$R^{X1}$ and $R^{X2}$ represent each independently a hydrogen atom, a halogen atom, a cyano group, a C1-C6 chain hydrocarbon group optionally having one or more substituents selected from Group B, a C1-C6 alkoxy group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, or a C3-C6 cycloalkyl group optionally having one or more substituents selected from Group C, wherein when m represents 2 or 3, two or more $R^{X1}$ and $R^{X2}$ may be identical to or different from each other;

E represents a $OR^3$, a $OC(O)R^4$, a $OC(X^1)NR^5R^6$, a $OC(X^2)OR^7$, a $OS(O)_2R^8$, a $NR^9R^{10}$, or a $S(O)_nR^{11}$;

n represents 1 or 2;

$R^1$, $R^5$, and $R^9$ represent each independently a hydrogen atom or a C1-C6 chain hydrocarbon group optionally having one or more substituents selected from Group B;

$R^2$ represents a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, a C6-C10 aryl group optionally having one or more substituents selected from Group G, or a C1-C6 alkoxy group optionally having one or more substituents selected from Group C;

$R^3$, $R^6$, and $R^{10}$ represent each independently a hydrogen atom, a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, or a C6-C10 aryl group optionally having one or more substituents selected from Group G;

$R^4$, $R^7$, $R^8$, and $R^{11}$ represent each independently a C1-C6 chain hydrocarbon group optionally having one or more substituents selected from Group B, a C3-C6 cycloalkyl group optionally having one or more substituents selected from Group C, a 3 to 8 membered nonaromatic heterocyclic group optionally having one or more substituents selected from Group C, a 5 to 6 membered aromatic heterocyclic group optionally having one or more substituents selected from Group G, or a C6-C10 aryl group optionally having one or more substituents selected from Group G;

$R^1$ and $R^2$ may be combined with the nitrogen atom to which $R^1$ and $R^2$ are attached to form a 4 to 7 membered nonaromatic heterocyclic group, wherein said 4 to 7 membered nonaromatic heterocyclic group may optionally have one or more substituents selected from Group C;

$R^5$ and $R^6$ may be combined with the nitrogen atom to which $R^5$ and $R^6$ are attached to form a 4 to 7 membered nonaromatic heterocyclic group, wherein said 4 to 7 membered nonaromatic heterocyclic group may optionally have one or more substituents selected from Group C;

$R^9$ and $R^{10}$ may be combined with the nitrogen atom to which $R^9$ and $R^{10}$ are attached to form a 4 to 7 membered nonaromatic heterocyclic group, wherein said 4 to 7 membered nonaromatic heterocyclic group may optionally have one or more substituents selected from Group C;

$X^1$ and $X^2$ represent each independently an oxygen atom or a sulfur atom;

Group A is selected from the group consisting of a C1-C6 alkyl group optionally having one or more substituents selected from Group D, a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a C1-C6 alkylsulfonyloxy group optionally having one or more halogen atoms, a halogen atom, a cyano group, and a nitro group;

Group B is selected from the group consisting of a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, a C6-C10 aryl group optionally having one or more substituents selected from Group H, a $OR^{12}$, a $S(X^3)_rR^{13}$, a $C(X^4)R^{14}$, a $C(X^5)OR^{15}$, a $OC(X^6)R^{16}$, a $C(X^7)NR^{17}R^{18}$, a $S(X^8)_rNR^{19}R^{20}$, a $SC(O)R^{21}$, a $NR^{22}R^{23}$, a $NR^{24}C(X^9)R^{25}$, a $NR^{26}S(X^{10})_rR^{27}$, a $NR^{28}C(X^{11})OR^{29}$, a $OC(X^{12})NR^{30}R^{31}$, a $NR^{32}C(X^{13})NR^{33}R^{34}$, a $OC(X^{14})OR^{35}$, a $SC(X^{15})OR^{36}$, a $NC(O)R^{37}$, a $NC(O)OR^{38}$, a $NR^{39}$, a $NOR^{40}$, a $NR^{41}NR^{42}R^{43}$, a $NNR^{44}R^{45}$, a NCN, a $NNO_2$, an oxo group, a thioxo group, a halogen atom, a cyano group, a nitro group, a sulfanyl group, and a carboxy group;

Group C is selected from the group consisting of a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, a C6-C10 aryl group optionally having one or more substituents selected from Group H, a OR$^{12}$, a S(X$^3$)$_t$R$^{13}$, a C(X$^4$)R$^{14}$, a C(X$^5$)OR$^{15}$, a OC(X$^6$)R$^{16}$, a C(X$^7$)NR$^{17}$R$^{18}$, a S(X$^8$)$_t$NR$^{19}$R$^{20}$, a SC(O)R$^{21}$, a NR$^{22}$R$^{23}$, a NR$^{24}$C(X$^9$)R$^{25}$, a NR$^{26}$S(X$^{10}$)$_t$R$^{27}$, a NR$^{28}$C(X$^{11}$)OR$^{29}$, a OC(X$^{12}$)NR$^{30}$R$^{31}$, a NR$^{32}$C(X$^{13}$) NR$^{33}$R$^{34}$, a OC(X$^{14}$)OR$^{35}$, a SC(X$^{15}$)OR$^{36}$, a NC(O)R$^{37}$, a NC(O)OR$^{38}$, a NR$^{39}$, a NOR$^{40}$, a NR$^{41}$NR$^{42}$R$^{43}$, a NNR$^{44}$R$^{45}$, a NCN, a NNO$_2$, an oxo group, a thioxo group, a halogen atom, a cyano group, a nitro group, a sulfanyl group, and a carboxy group;

Group D is selected from the group consisting of a halogen atom, a cyano group, a nitro group, and a C1-C6 alkoxy group optionally having one or more halogen atoms;

Group E is selected from the group consisting of a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a halogen atom, an oxo group, a thioxo group, a cyano group, a nitro group, a hydroxy group, an amino group, a sulfanyl group, and a carboxy group;

Group F is selected from the group consisting of a C1-C3 chain hydrocarbon group optionally having one or more halogen atoms, a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a halogen atom, an oxo group, a thioxo group, a cyano group, a nitro group, a hydroxy group, an amino group, a sulfanyl group, and a carboxy group;

Group G is selected from the group consisting of a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, a C6-C10 aryl group optionally having one or more substituents selected from Group H, a OR$^{12}$, a S(X$^3$)$_t$R$^{13}$, a C(X$^4$)R$^{14}$, a C(X$^5$)OR$^{15}$, a OC(X$^6$)R$^{16}$, a C(X$^7$)NR$^{17}$R$^{18}$, a S(X$^8$)$_t$NR$^{19}$R$^{20}$, a SC(O)R$^{21}$, a NR$^{22}$R$^{23}$, a NR$^{24}$C(X$^9$)R$^{25}$, a NR$^{26}$S(X$^{10}$)$_t$R$^{27}$, a NR$^{28}$C(X$^{11}$)OR$^{29}$, a OC(X$^{12}$)NR$^{30}$R$^{31}$, a NR$^{32}$C(X$^{13}$) NR$^{33}$R$^{34}$, a OC(X$^{14}$)OR$^{35}$, a SC(X$^{15}$)OR$^{36}$, a NC(O)R$^{37}$, a NC(O)OR$^{38}$, a NR$^{39}$, a NOR$^{40}$, a NR$^{41}$NR$^{42}$R$^{43}$, a NNR$^{44}$R$^{45}$, a NCN, a NNO$_2$, a halogen atom, a cyano group, a nitro group, a sulfanyl group, and a carboxy group;

Group H is selected from the group consisting of a C1-C3 chain hydrocarbon group optionally having one or more halogen atoms, a C3-C6 cycloalkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylthio group optionally having one or more halogen atoms, a halogen atom, a cyano group, a nitro group, a hydroxy group, an amino group, a sulfanyl group, and a carboxy group;

R$^{12}$, R$^{17}$, R$^{18}$, R$^{19}$, R$^{20}$, R$^{22}$, R$^{23}$, R$^{24}$, R$^{26}$, R$^{28}$, R$^{30}$, R$^{31}$, R$^{32}$, R$^{33}$, R$^{34}$, and R$^{40}$ represent each independently a hydrogen atom, a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, or a C6-C10 aryl group optionally having one or more substituents selected from Group H;

R$^{13}$, R$^{14}$, R$^{15}$, R$^{16}$, R$^{21}$, R$^{25}$, R$^{27}$, R$^{29}$, R$^{35}$, and R$^{36}$ represent each independently a C1-C6 chain hydrocarbon group optionally having one or more substituents selected from Group E, a C3-C6 cycloalkyl group optionally having one or more substituents selected from Group F, a 3 to 8 membered nonaromatic heterocyclic group optionally having one or more substituents selected from Group F, a 5 to 6 membered aromatic heterocyclic group optionally having one or more substituents selected from Group H, or a C6-C10 aryl group optionally having one or more substituents selected from Group H;

R$^{37}$, R$^{38}$, and R$^{39}$ represent each independently a C1-C6 chain hydrocarbon group optionally having one or more substituents selected from Group E or a C3-C6 cycloalkyl group optionally having one or more substituents selected from Group F;

R$^{41}$, R$^{42}$, R$^{43}$, R$^{44}$, and R$^{45}$ represent each independently a hydrogen atom, a C1-C6 chain hydrocarbon group optionally having one or more substituents selected from Group E, or a C3-C6 cycloalkyl group optionally having one or more substituents selected from Group F;

t represents 0, 1, or 2;

X$^4$, X$^5$, X$^6$, X$^7$, X$^9$, X$^{11}$, X$^{12}$, X$^{13}$, X$^{14}$, and X$^{15}$ represent each independently an oxygen atom or a sulfur atom;

X$^3$, X$^8$, and X$^{10}$ represent each independently an oxygen atom, a NCN, a NNO$_2$, a NC(O)R$^{46}$, a NC(O)OR$^{47}$, or a NV, wherein when t represents 2, two X$^3$, two X$^8$, and two X$^{10}$ may be identical to or different from each other;

R$^{47}$ represents a C1-C3 chain hydrocarbon group optionally having one or more halogen atoms;

R$^{46}$ and R$^{48}$ represent each independently a hydrogen atom or a C1-C3 chain hydrocarbon group optionally having one or more halogen atoms;

R$^{17}$ and R$^{18}$ may be combined with the nitrogen atom to which R$^{17}$ and R$^{18}$ are attached to form a 4 to 7 membered nonaromatic heterocyclic group, wherein said 4 to 7 membered nonaromatic heterocyclic group may optionally have one or more substituents selected from Group F;

R$^{19}$ and R$^{20}$ may be combined with the nitrogen atom to which R$^9$ and R$^{20}$ are attached to form a 4 to 7 membered nonaromatic heterocyclic group, wherein said 4 to 7 membered nonaromatic heterocyclic group may optionally have one or more substituents selected from Group F;

R$^{22}$ and R$^{23}$ may be combined with the nitrogen atom to which R$^{22}$ and R$^{23}$ are attached to form a 4 to 7 membered nonaromatic heterocyclic group, wherein said 4 to 7 membered nonaromatic heterocyclic group may optionally have one or more substituents selected from Group F;

$R^{30}$ and $R^{31}$ may be combined with the nitrogen atom to which $R^{30}$ and $R^{31}$ are attached to form a 4 to 7 membered nonaromatic heterocyclic group, wherein said 4 to 7 membered nonaromatic heterocyclic group may optionally have one or more substituents selected from Group F;

$R^{33}$ and $R^{34}$ may be combined with the nitrogen atom to which $R^{33}$ and $R^{34}$ are attached to form a 4 to 7 membered nonaromatic heterocyclic group, wherein said 4 to 7 membered nonaromatic heterocyclic group may optionally have one or more substituents selected from Group F;

$R^{42}$ and $R^{43}$ may be combined with the nitrogen atom to which $R^{42}$ and $R^{43}$ are attached to form a 4 to 7 membered nonaromatic heterocyclic group, wherein said 4 to 7 membered nonaromatic heterocyclic group may optionally have one or more substituents selected from Group F; and $R^{44}$ and $R^{45}$ may be combined with the nitrogen atom to which $R^{44}$ and $R^{45}$ are attached to form a 4 to 7 membered nonaromatic heterocyclic group, wherein said 4 to 7 membered nonaromatic heterocyclic group may optionally have one or more substituents selected from Group F.

2. The compound according to claim 1, wherein

G represents a benzene ring;

$(CR^{X1}R^{X2})_m C(A)=N-E$ is attached to G at the meta position or the para position relative to the oxadiazole ring;

m represents 0 or 1;

$R^{X1}$ and $R^{X2}$ represent each independently a hydrogen atom; and

A represents a C2-C6 alkyl group, a phenyl group, a C1-C6 alkoxy group, a C1-C6 alkylthio group, a cyano group, an amino group, a C1-C6 alkylamino group, a di(C1-C6 alkyl)amino group, or a 5 to 6 membered nonaromatic heterocyclic group.

3. The compound according to claim 1, wherein

G represents a benzene ring optionally having one or more substituents selected from the group consisting of a fluorine atom and a methyl group;

$(CR^{X1}R^{X2})_m C(A)=N-E$ is attached to G at the meta position or the para position relative to the oxadiazole ring;

m represents 0; and

A represents a C2-C6 alkyl group, a C3-C6 cycloalkyl group, a phenyl group, a C1-C6 alkoxy group, a C1-C6 alkylthio group, a cyano group, an amino group, a C1-C6 alkylamino group, or a di(C1-C6 alkyl)amino group.

4. The compound according to claim 3, wherein

G represents a benzene ring;

$((CR^{X1}R^{X2})_m C(A)=N-E$ is attached to G at the para position relative to the oxadiazole ring; and A represents a methoxy group, a methylthio group, a cyano group, an amino group, a methylamino group, or a dimethylamino group.

5. The compound according to claim 4, wherein A represents a methoxy group, a cyano group, an amino group, a methylamino group, or a dimethylamino group.

6. The compound according to claim 1, wherein

E represents a $OR^3$, a $OC(O)R^4$, a $OC(X^1)NR^5R^6$, or a $OS(O)_2R^8$;

$R^3$ represents a hydrogen atom or a C1-C6 chain hydrocarbon group optionally having one or more substituents selected from Group D;

$R^4$ represents a C1-C6 alkyl group optionally having one or more substituents selected from Group D, a phenyl group optionally having one or more substituents selected from Group D, or a 5 to 6 membered aromatic heterocyclic group optionally having one or more substituents selected from Group D;

$R^5$ represents a hydrogen atom or a C1-C6 alkyl group optionally having one or more substituents selected from Group D;

$R^6$ represents a phenyl group or a C1-C6 alkyl group optionally having one or more substituents selected from Group D;

$R^8$ represents a C1-C6 alkyl group optionally having one or more substituents selected from Group D; and $X^1$ represents an oxygen atom.

7. The compound according to claim 1, wherein

E represents a $OR^3$, a $OC(O)R^4$, or a $OC(X^1)NR^5R^6$;

$R^3$ represents a C1-C6 chain hydrocarbon group optionally having one or more substituents selected from the group consisting of a cyano group and a C1-C6 alkoxy group, or a hydrogen atom;

$R^4$ represents a C1-C6 alkyl group;

$R^5$ and $R^6$ represent each independently a C1-C6 alkyl group; and $X^1$ represents an oxygen atom.

8. An agent for controlling a pest comprising the compound according to claim 1.

9. A method for controlling a pest, the method comprising applying an effective amount of the compound according to claim 1 to a plant or a soil.

* * * * *